US010441185B2

(12) United States Patent
Rogers et al.

(10) Patent No.: US 10,441,185 B2
(45) Date of Patent: Oct. 15, 2019

(54) FLEXIBLE AND STRETCHABLE ELECTRONIC SYSTEMS FOR EPIDERMAL ELECTRONICS

(75) Inventors: John A. Rogers, Champaign, IL (US); Dae-Hyeong Kim, Champaign, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 1304 days.

(21) Appl. No.: 13/492,636

(22) Filed: Jun. 8, 2012

(65) Prior Publication Data
US 2013/0041235 A1 Feb. 14, 2013

Related U.S. Application Data

(63) Continuation-in-part of application No. 12/968,637, filed on Dec. 15, 2010.
(Continued)

(51) Int. Cl.
*A61B 5/0408* (2006.01)
*A61B 5/00* (2006.01)
(Continued)

(52) U.S. Cl.
CPC ........ *A61B 5/04085* (2013.01); *A61B 5/0422* (2013.01); *A61B 5/076* (2013.01); *A61B 5/1107* (2013.01); *A61B 5/4875* (2013.01); *A61B 5/6867* (2013.01); *A61N 1/0472* (2013.01); *A61N 1/05* (2013.01); *A61N 1/36* (2013.01); *H01L 23/3192* (2013.01); *H05K 1/0283* (2013.01); *H05K 1/189* (2013.01); *A61B 5/0478* (2013.01); *A61B 5/0492* (2013.01); *A61B 5/04284* (2013.01); *A61B 5/0537* (2013.01);
(Continued)

(58) Field of Classification Search
CPC combination set(s) only.
See application file for complete search history.

(56) References Cited

U.S. PATENT DOCUMENTS 3,949,410 A 4/1976 Bassous
4,058,418 A 11/1977 Lindmayer
(Continued)

FOREIGN PATENT DOCUMENTS

CN 1222758 7/1999
CN 1454045 11/2003
(Continued)

OTHER PUBLICATIONS

Office Action dated Aug. 7, 2015 corresponding to U.S. Appl. No. 12/968,637.
(Continued)

*Primary Examiner* — Christian Jang
*Assistant Examiner* — Karen E Toth
(74) *Attorney, Agent, or Firm* — Leydig, Voit & Mayer, Ltd.

(57) ABSTRACT

Provided herein are skin-mounted biomedical devices and methods of making and using biomedical devices for sensing and actuation applications. For example, flexible and/or stretchable biomedical devices are provided, including electronic devices useful for establishing conformal contact with the skin of a subject. Devices disclosed herein can comprise a plurality of sensing and/or actuating devices provided as part of a skin-mounted flexible or stretchable electronic circuit.

58 Claims, 138 Drawing Sheets

Related U.S. Application Data

(60) Provisional application No. 61/286,921, filed on Dec. 16, 2009, provisional application No. 61/313,397, filed on Mar. 12, 2010, provisional application No. 61/388,529, filed on Sep. 30, 2010, provisional application No. 61/495,623, filed on Jun. 10, 2011.

(51) Int. Cl.

| | | |
|---|---|---|
| *A61N 1/05* | (2006.01) | |
| *A61B 5/042* | (2006.01) | |
| *A61B 5/07* | (2006.01) | |
| *A61N 1/36* | (2006.01) | |
| *H01L 23/31* | (2006.01) | |
| *H05K 1/02* | (2006.01) | |
| *H05K 1/18* | (2006.01) | |
| *A61N 1/04* | (2006.01) | |
| *A61B 5/11* | (2006.01) | |
| *H01L 29/786* | (2006.01) | |
| *H01L 27/12* | (2006.01) | |
| *H05K 1/14* | (2006.01) | |
| *H05K 3/32* | (2006.01) | |
| *A61B 5/053* | (2006.01) | |
| *A61B 5/0428* | (2006.01) | |
| *A61B 5/0478* | (2006.01) | |
| *A61B 5/0492* | (2006.01) | |

(52) U.S. Cl.
CPC ......... *A61B 5/1104* (2013.01); *A61B 2562/02* (2013.01); *A61B 2562/029* (2013.01); *A61B 2562/0261* (2013.01); *A61B 2562/0271* (2013.01); *A61B 2562/046* (2013.01); *A61B 2562/066* (2013.01); *A61B 2562/12* (2013.01); *A61B 2562/164* (2013.01); *A61N 1/0587* (2013.01); *H01L 23/3121* (2013.01); *H01L 27/1218* (2013.01); *H01L 29/7869* (2013.01); *H01L 29/78603* (2013.01); *H01L 2924/0002* (2013.01); *H01L 2924/12044* (2013.01); *H01L 2924/19041* (2013.01); *H01L 2924/3011* (2013.01); *H01L 2924/3025* (2013.01); *H05K 1/147* (2013.01); *H05K 3/323* (2013.01); *H05K 2201/09263* (2013.01)

(56) References Cited

U.S. PATENT DOCUMENTS

| | | |
|---|---|---|
| 4,392,451 A | 7/1983 | Mickelsen et al. |
| 4,471,003 A | 9/1984 | Cann |
| 4,487,162 A | 12/1984 | Cann |
| 4,663,828 A | 5/1987 | Hanak |
| 4,715,235 A * | 12/1987 | Fukui .................. G01D 5/16 338/114 |
| 4,761,335 A | 8/1988 | Aurichio et al. |
| 4,766,670 A | 8/1988 | Gazdik et al. |
| 4,784,720 A | 11/1988 | Douglas |
| 4,855,017 A | 8/1989 | Douglas |
| 5,041,973 A | 8/1991 | Lebron et al. |
| 5,086,785 A | 2/1992 | Gentile et al. |
| 5,118,400 A | 6/1992 | Wollam |
| 5,178,957 A | 1/1993 | Kolpe et al. |
| 5,204,144 A | 4/1993 | Cann et al. |
| 5,313,094 A | 5/1994 | Beyer et al. |
| 5,316,017 A | 5/1994 | Edwards et al. |
| 5,339,180 A | 8/1994 | Katoh |
| 5,403,700 A | 4/1995 | Heller et al. |
| 5,427,096 A | 6/1995 | Bogusiewicz et al. |
| 5,434,751 A | 7/1995 | Cole, Jr. et al. |
| 5,455,178 A | 10/1995 | Fattnger |
| 5,469,845 A | 11/1995 | Delonzor et al. |
| 5,501,893 A | 3/1996 | Laermer et al. |
| 5,525,815 A | 6/1996 | Einset |
| 5,545,291 A | 8/1996 | Smith et al. |
| 5,625,471 A | 4/1997 | Smith |
| 5,648,148 A | 7/1997 | Simpson |
| 5,678,737 A | 10/1997 | White |
| 5,687,737 A | 11/1997 | Branham et al. |
| 5,691,245 A | 11/1997 | Bakhit |
| 5,753,529 A | 5/1998 | Chang et al. |
| 5,757,081 A | 5/1998 | Chang et al. |
| 5,767,578 A | 6/1998 | Chang et al. |
| 5,772,905 A | 6/1998 | Chou |
| 5,783,856 A | 7/1998 | Smith et al. |
| 5,790,151 A | 8/1998 | Mills |
| 5,817,242 A | 10/1998 | Biebuyck et al. |
| 5,824,186 A | 10/1998 | Smith et al. |
| 5,904,545 A | 5/1999 | Smith et al. |
| 5,907,189 A | 5/1999 | Mertol |
| 5,915,180 A | 6/1999 | Hara et al. |
| 5,917,534 A | 6/1999 | Rajeswaran |
| 5,928,001 A | 7/1999 | Gilette et al. |
| 5,955,781 A | 9/1999 | Joshi et al. |
| 5,976,683 A | 11/1999 | Liehrr et al. |
| 5,998,291 A | 12/1999 | Bakhit et al. |
| 6,024,702 A | 2/2000 | Iverson |
| 6,057,212 A | 5/2000 | Chan et al. |
| 6,077,228 A * | 6/2000 | Schonberger .......... A61B 5/015 374/100 |
| 6,080,608 A | 6/2000 | Nowak |
| 6,097,984 A | 8/2000 | Douglas |
| 6,165,391 A | 12/2000 | Vedamuttu |
| 6,171,730 B1 | 1/2001 | Kuroda et al. |
| 6,197,420 B1 * | 3/2001 | Takamizawa ......... B44C 1/1758 428/143 |
| 6,225,149 B1 | 5/2001 | Gan et al. |
| 6,236,883 B1 | 5/2001 | Ciaccio et al. |
| 6,265,326 B1 | 7/2001 | Ueno |
| 6,267,775 B1 | 8/2001 | Schulte |
| 6,274,508 B1 | 8/2001 | Jacobsen et al. |
| 6,276,775 B1 | 8/2001 | Schulte |
| 6,277,712 B1 | 8/2001 | Kang et al. |
| 6,281,038 B1 | 8/2001 | Jacobsen et al. |
| 6,284,418 B1 | 9/2001 | Trantolo |
| 6,291,896 B1 | 9/2001 | Smith |
| 6,316,278 B1 | 11/2001 | Jacobsen et al. |
| 6,316,283 B1 | 11/2001 | Saurer |
| 6,317,175 B1 | 11/2001 | Salerno et al. |
| 6,322,895 B1 | 11/2001 | Canham |
| 6,334,960 B1 | 1/2002 | Wilson et al. |
| 6,380,729 B1 | 4/2002 | Smith |
| 6,403,397 B1 | 6/2002 | Katz |
| 6,413,790 B1 | 6/2002 | Duthaler et al. |
| 6,417,025 B1 | 7/2002 | Gengel |
| 6,420,266 B1 | 7/2002 | Smith et al. |
| 6,433,401 B1 | 8/2002 | Clark et al. |
| 6,451,191 B1 | 9/2002 | Bentsen et al. |
| 6,459,418 B1 | 10/2002 | Comiskey et al. |
| 6,468,638 B2 | 10/2002 | Jacobsen et al. |
| 6,479,395 B1 | 11/2002 | Smith et al. |
| 6,487,906 B1 | 12/2002 | Hock |
| 6,517,995 B1 | 2/2003 | Jacobson et al. |
| 6,555,408 B1 | 4/2003 | Jacobsen et al. |
| 6,527,964 B1 | 5/2003 | Smith et al. |
| 6,559,905 B1 | 5/2003 | Akiyama |
| 6,566,744 B2 | 5/2003 | Gengel |
| 6,580,151 B2 | 6/2003 | Vandeputte et al. |
| 6,586,338 B2 | 7/2003 | Smith et al. |
| 6,590,346 B1 | 7/2003 | Hadley et al. |
| 6,606,079 B1 | 8/2003 | Smith |
| 6,606,247 B2 | 8/2003 | Credelle et al. |
| 6,608,370 B1 | 8/2003 | Chen et al. |
| 6,623,579 B1 | 9/2003 | Smith et al. |
| 6,639,578 B1 | 10/2003 | Comiskey et al. |
| 6,655,286 B2 | 12/2003 | Rogers |
| 6,657,289 B1 | 12/2003 | Craig et al. |
| 6,661,037 B2 | 12/2003 | Pan et al. |
| 6,665,044 B1 | 12/2003 | Jacobsen et al. |
| 6,666,821 B2 | 12/2003 | Keimel |
| 6,683,663 B1 | 1/2004 | Hadley et al. |
| 6,693,384 B1 | 2/2004 | Vicentini et al. |
| 6,706,402 B2 | 3/2004 | Ruecks et al. |

(56) References Cited

U.S. PATENT DOCUMENTS

| | | | |
|---|---|---|---|
| 6,720,469 B1 | 4/2004 | Curtis et al. | |
| 6,723,576 B2 | 4/2004 | Nozawa et al. | |
| 6,730,990 B2 | 5/2004 | Kondo et al. | |
| 6,731,353 B1 | 5/2004 | Credelle et al. | |
| 6,743,982 B2 | 6/2004 | Biegelsen et al. | |
| 6,780,696 B1 | 8/2004 | Schatz | |
| 6,784,450 B2 | 8/2004 | Pan et al. | |
| 6,814,898 B1 | 11/2004 | Deeman et al. | |
| 6,816,380 B2 | 11/2004 | Credelle et al. | |
| 6,844,673 B1 | 1/2005 | Bernkopf | |
| 6,848,162 B2 | 2/2005 | Arneson et al. | |
| 6,850,312 B2 | 2/2005 | Jacobsen et al. | |
| 6,856,830 B2 | 2/2005 | He | |
| 6,863,219 B1 | 3/2005 | Jacobsen et al. | |
| 6,864,435 B2 | 3/2005 | Hermanns et al. | |
| 6,864,570 B2 | 3/2005 | Smith | |
| 6,872,645 B2 | 3/2005 | Duan et al. | |
| 6,878,871 B2 | 4/2005 | Scher et al. | |
| 6,881,979 B2 | 4/2005 | Starikov et al. | |
| 6,887,450 B2 | 5/2005 | Chen et al. | |
| 6,900,094 B2 | 5/2005 | Hammond et al. | |
| 6,917,061 B2 | 7/2005 | Pan et al. | |
| 6,936,181 B2 | 8/2005 | Bulthaup et al. | |
| 6,949,199 B1 | 9/2005 | Gauzner et al. | |
| 6,949,206 B2 | 9/2005 | Whiteford | |
| 6,950,220 B2 | 9/2005 | Abramson et al. | |
| 6,984,934 B2 | 1/2006 | Moller et al. | |
| 6,989,285 B2 | 1/2006 | Ball | |
| 7,029,951 B2 | 4/2006 | Chen et al. | |
| 7,033,961 B1 | 4/2006 | Smart et al. | |
| 7,067,903 B2 | 6/2006 | Tachibana et al. | |
| 7,116,318 B2 | 10/2006 | Amundson et al. | |
| 7,132,313 B2 | 11/2006 | O'Connor et al. | |
| 7,148,512 B2 | 12/2006 | Leu et al. | |
| 7,158,277 B2 | 1/2007 | Berggren et al. | |
| 7,169,546 B2 | 1/2007 | Suzuki et al. | |
| 7,169,669 B2 | 1/2007 | Blakers et al. | |
| 7,170,164 B2 | 1/2007 | Chen et al. | |
| 7,186,624 B2 | 3/2007 | Welser et al. | |
| 7,190,051 B2 | 3/2007 | Mech et al. | |
| 7,195,733 B2 | 3/2007 | Rogers et al. | |
| 7,223,609 B2 | 5/2007 | Anvar et al. | |
| 7,253,442 B2 | 8/2007 | Huang et al. | |
| 7,255,919 B2 | 8/2007 | Sakata et al. | |
| 7,291,540 B2 | 11/2007 | Mech et al. | |
| 7,374,968 B2 | 5/2008 | Kornlivich et al. | |
| 7,408,187 B2 * | 8/2008 | Kim | H01L 51/0525 257/295 |
| 7,425,523 B2 | 9/2008 | Ikemizu et al. | |
| 7,521,292 B2 | 4/2009 | Rogers et al. | |
| 7,557,367 B2 | 7/2009 | Rogers et al. | |
| 7,622,367 B1 | 11/2009 | Nuzzo et al. | |
| 7,629,691 B2 | 12/2009 | Roush et al. | |
| 7,635,755 B2 | 12/2009 | Kaplan et al. | |
| 7,648,925 B2 | 1/2010 | Moro et al. | |
| 7,674,882 B2 | 3/2010 | Kaplan et al. | |
| 7,700,402 B2 | 4/2010 | Wild et al. | |
| 7,704,684 B2 | 4/2010 | Rogers et al. | |
| 7,705,280 B2 | 4/2010 | Nuzzo et al. | |
| 7,709,961 B2 | 5/2010 | Greenberg et al. | |
| 7,727,575 B2 | 6/2010 | Kaplan et al. | |
| 7,799,699 B2 | 9/2010 | Nuzzo et al. | |
| 7,842,780 B2 | 11/2010 | Kaplan et al. | |
| 7,896,807 B2 | 3/2011 | Clancy et al. | |
| 7,932,123 B2 | 4/2011 | Rogers et al. | |
| 7,943,491 B2 | 5/2011 | Nuzzo et al. | |
| 7,972,875 B2 | 7/2011 | Rogers et al. | |
| 7,982,296 B2 | 7/2011 | Nuzzo et al. | |
| 8,039,847 B2 | 10/2011 | Nuzzo et al. | |
| 8,198,621 B2 | 6/2012 | Rogers et al. | |
| 8,217,381 B2 | 7/2012 | Rogers et al. | |
| 8,367,035 B2 | 2/2013 | Rogers et al. | |
| 8,394,706 B2 | 3/2013 | Nuzzo et al. | |
| 8,440,546 B2 | 5/2013 | Rogers et al. | |
| 8,470,701 B2 | 6/2013 | Rogers et al. | |
| 8,552,299 B2 | 10/2013 | Rogers et al. | |
| 8,562,095 B2 | 10/2013 | Alleyne et al. | |
| 2001/0003043 A1 | 6/2001 | Metspalu et al. | |
| 2002/0004251 A1 | 1/2002 | Roberts et al. | |
| 2002/0021445 A1 | 2/2002 | Boxhevolnyi et al. | |
| 2002/0110766 A1 | 8/2002 | Tsai et al. | |
| 2003/0006527 A1 | 1/2003 | Rabolt et al. | |
| 2003/0032892 A1 | 2/2003 | Erlach et al. | |
| 2003/0082889 A1 | 5/2003 | Maruyama et al. | |
| 2003/0087476 A1 | 5/2003 | Oohata et al. | |
| 2003/0138704 A1 | 7/2003 | Mei et al. | |
| 2003/0149456 A1 | 8/2003 | Rottenberg et al. | |
| 2003/0178316 A1 | 9/2003 | Jacobs et al. | |
| 2003/0222282 A1 | 12/2003 | Fjelstad et al. | |
| 2003/0227116 A1 | 12/2003 | Halik et al. | |
| 2004/0005723 A1 | 1/2004 | Empedocles et al. | |
| 2004/0026684 A1 | 2/2004 | Empedocles et al. | |
| 2004/0079464 A1 | 4/2004 | Kumakura | |
| 2004/0081384 A1 | 4/2004 | Datesman et al. | |
| 2004/0095658 A1 | 5/2004 | Buretea et al. | |
| 2004/0112964 A1 | 6/2004 | Empedocles et al. | |
| 2004/0129937 A1 | 7/2004 | Hirai | |
| 2004/0136866 A1 | 7/2004 | Pontis et al. | |
| 2004/0146560 A1 | 7/2004 | Whiteford et al. | |
| 2004/0155290 A1 | 8/2004 | Mech et al. | |
| 2004/0178390 A1 | 9/2004 | Whiteford | |
| 2004/0192082 A1 | 9/2004 | Wagner et al. | |
| 2004/0114459 A1 | 10/2004 | Suenaga et al. | |
| 2004/0200734 A1 | 10/2004 | Co et al. | |
| 2004/0206448 A1 | 10/2004 | Dubrow | |
| 2004/0211458 A1 | 10/2004 | Gui et al. | |
| 2004/0250950 A1 | 12/2004 | Dubrow | |
| 2004/0252559 A1 | 12/2004 | Gupta | |
| 2005/0020094 A1 | 1/2005 | Forbes et al. | |
| 2005/0233546 A1 | 1/2005 | Oohata et al. | |
| 2005/0038498 A1 | 2/2005 | Dubrow et al. | |
| 2005/0082526 A1 | 4/2005 | Bedell et al. | |
| 2005/0124712 A1 | 6/2005 | Anderson et al. | |
| 2005/0133954 A1 | 6/2005 | Homola | |
| 2005/0214962 A1 | 9/2005 | Daniels et al. | |
| 2005/0227389 A1 | 10/2005 | Bhattacharya et al. | |
| 2005/0238967 A1 | 10/2005 | Rogers et al. | |
| 2005/0255686 A1 | 11/2005 | Yamano et al. | |
| 2005/0260706 A1 | 11/2005 | Kaplan et al. | |
| 2005/0261561 A1 | 11/2005 | Jones et al. | |
| 2006/0038182 A1 | 2/2006 | Rogers et al. | |
| 2006/0049485 A1 | 3/2006 | Pan et al. | |
| 2006/0052678 A1 * | 3/2006 | Drinan | A61B 5/0531 600/301 |
| 2006/0084012 A1 | 4/2006 | Nuzzo et al. | |
| 2006/0085976 A1 | 4/2006 | Eldridge et al. | |
| 2006/0102525 A1 | 5/2006 | Volkel et al. | |
| 2006/0119853 A1 | 6/2006 | Baumberg et al. | |
| 2006/0127817 A1 | 6/2006 | Ramanujan et al. | |
| 2006/0129056 A1 | 6/2006 | Leuthardt et al. | |
| 2006/0132025 A1 | 6/2006 | Gao et al. | |
| 2006/0134893 A1 | 6/2006 | Savage et al. | |
| 2006/0159837 A1 | 7/2006 | Kaplan et al. | |
| 2006/0169989 A1 | 8/2006 | Bhatacharya | |
| 2006/0173364 A1 * | 8/2006 | Clancy | A61B 5/04 600/485 |
| 2006/0177479 A1 | 8/2006 | Giachelli et al. | |
| 2006/0178655 A1 | 8/2006 | Santini et al. | |
| 2006/0205180 A1 * | 9/2006 | Henley | B81C 1/00357 438/458 |
| 2006/0244105 A1 | 11/2006 | Forbes et al. | |
| 2006/0255341 A1 | 11/2006 | Pinnington et al. | |
| 2006/0273279 A1 | 12/2006 | Kaplan et al. | |
| 2006/0279191 A1 | 12/2006 | Gehegan et al. | |
| 2006/0286488 A1 | 12/2006 | Rogers et al. | |
| 2006/0286785 A1 | 12/2006 | Rogers et al. | |
| 2007/0009968 A1 | 1/2007 | Cunningham et al. | |
| 2007/0031607 A1 | 2/2007 | Dubson et al. | |
| 2007/0032089 A1 | 2/2007 | Nuzzo et al. | |
| 2007/0043416 A1 | 2/2007 | Callas et al. | |
| 2007/0058254 A1 | 3/2007 | Kim | |
| 2007/0073130 A1 | 3/2007 | Finch et al. | |
| 2007/0085078 A1 * | 4/2007 | Kuroda | G11C 29/50 257/40 |

(56) References Cited

U.S. PATENT DOCUMENTS

| | | |
|---|---|---|
| 2007/0100219 A1* | 5/2007 | Sweitzer .............. A61B 5/0002 600/323 |
| 2007/0123963 A1 | 5/2007 | Krulevitch |
| 2007/0187862 A1 | 8/2007 | Kaplan et al. |
| 2007/0212730 A1 | 9/2007 | Vepari et al. |
| 2007/0227586 A1 | 10/2007 | Zapalac |
| 2007/0233208 A1 | 10/2007 | Kurtz et al. |
| 2007/0257821 A1 | 11/2007 | Son et al. |
| 2008/0038236 A1 | 2/2008 | Gimble et al. |
| 2008/0055581 A1 | 3/2008 | Rogers et al. |
| 2008/0085272 A1 | 4/2008 | Kaplan et al. |
| 2008/0090322 A1 | 4/2008 | Mech et al. |
| 2008/0102096 A1 | 5/2008 | Molin et al. |
| 2008/0108171 A1 | 5/2008 | Rogers et al. |
| 2008/0146958 A1* | 6/2008 | Guillory .............. A61B 5/0476 600/544 |
| 2008/0152281 A1 | 6/2008 | Lundquist et al. |
| 2008/0000871 A1 | 7/2008 | Suh et al. |
| 2008/0157235 A1 | 7/2008 | Rogers et al. |
| 2008/0170982 A1* | 7/2008 | Zhang ................... B82Y 10/00 423/447.3 |
| 2008/0183076 A1 | 7/2008 | Witte et al. |
| 2008/0203431 A1* | 8/2008 | Garcia ................ G01N 27/4141 257/192 |
| 2008/0212102 A1 | 9/2008 | Nuzzo et al. |
| 2008/0239755 A1 | 10/2008 | Parker et al. |
| 2008/0253085 A1* | 10/2008 | Soffer ...................... G06F 1/18 361/679.4 |
| 2008/0280360 A1 | 11/2008 | Kaplan et al. |
| 2008/0284710 A1* | 11/2008 | Kimura .............. G02F 1/13454 345/98 |
| 2008/0288037 A1 | 11/2008 | Neysmith et al. |
| 2008/0293919 A1 | 11/2008 | Kaplan et al. |
| 2009/0004737 A1 | 1/2009 | Borenstein et al. |
| 2009/0012533 A1 | 1/2009 | Barbagli et al. |
| 2009/0028910 A1 | 1/2009 | Desimone et al. |
| 2009/0078990 A1 | 3/2009 | Yasuda |
| 2009/0085214 A1 | 4/2009 | Wada et al. |
| 2009/0149930 A1 | 6/2009 | Schecnk |
| 2009/0198293 A1 | 8/2009 | Cauller et al. |
| 2009/0199960 A1 | 8/2009 | Nuzzo et al. |
| 2009/0202614 A1 | 8/2009 | Kaplan et al. |
| 2009/0208555 A1 | 8/2009 | Kuttler et al. |
| 2009/0221896 A1 | 9/2009 | Rickert et al. |
| 2009/0232963 A1 | 9/2009 | Kaplan et al. |
| 2009/0234026 A1 | 9/2009 | Kaplan et al. |
| 2009/0289246 A1 | 11/2009 | Schneider et al. |
| 2009/0293664 A1 | 12/2009 | Aabloo et al. |
| 2009/0294803 A1* | 12/2009 | Nuzzo ................... B82Y 10/00 257/213 |
| 2010/0002402 A1 | 1/2010 | Rogers et al. |
| 2010/0028451 A1 | 2/2010 | Kaplan et al. |
| 2010/0046902 A1 | 2/2010 | Kaplan et al. |
| 2010/0052112 A1 | 3/2010 | Rogers et al. |
| 2010/0055438 A1 | 3/2010 | Kaplan et al. |
| 2010/0059863 A1 | 3/2010 | Rogers et al. |
| 2010/0063404 A1 | 3/2010 | Kaplan et al. |
| 2010/0065784 A1 | 3/2010 | Kaplan et al. |
| 2010/0068740 A1 | 3/2010 | Kaplan et al. |
| 2010/0070068 A1 | 3/2010 | Kaplan et al. |
| 2010/0072577 A1 | 3/2010 | Nuzzo et al. |
| 2010/0096763 A1 | 4/2010 | Kaplan et al. |
| 2010/0120116 A1 | 5/2010 | Kaplan et al. |
| 2010/0121420 A1 | 5/2010 | Fiset et al. |
| 2010/0141407 A1 | 6/2010 | Heubel et al. |
| 2010/0178304 A1 | 7/2010 | Wang et al. |
| 2010/0191328 A1 | 7/2010 | Kaplan et al. |
| 2010/0196447 A1 | 8/2010 | Kaplan et al. |
| 2010/0200752 A1 | 8/2010 | Lee et al. |
| 2010/0203226 A1 | 8/2010 | Kaplan et al. |
| 2010/0279112 A1 | 11/2010 | Kaplan et al. |
| 2010/0283069 A1 | 11/2010 | Rogers et al. |
| 2010/0289124 A1 | 11/2010 | Nuzzo et al. |
| 2010/0317132 A1 | 12/2010 | Rogers et al. |
| 2011/0054583 A1* | 3/2011 | Litt ...................... A61N 5/0601 607/116 |
| 2011/0071439 A1 | 3/2011 | Bach-y-Rita et al. |
| 2011/0129158 A1 | 6/2011 | Sato |
| 2011/0147715 A1 | 6/2011 | Rogers et al. |
| 2011/0168403 A1 | 7/2011 | Patel |
| 2011/0170225 A1 | 7/2011 | Rogers et al. |
| 2011/0171813 A1 | 7/2011 | Rogers et al. |
| 2011/0187798 A1 | 8/2011 | Rogers et al. |
| 2011/0220890 A1 | 9/2011 | Nuzzo et al. |
| 2011/0230747 A1 | 9/2011 | Rogers et al. |
| 2011/0266561 A1 | 11/2011 | Rogers et al. |
| 2011/0276112 A1 | 11/2011 | Simon et al. |
| 2011/0277813 A1 | 11/2011 | Rogers et al. |
| 2011/0316120 A1 | 12/2011 | Rogers et al. |
| 2012/0157804 A1 | 6/2012 | Rogers et al. |
| 2012/0165759 A1 | 6/2012 | Rogers et al. |
| 2012/0261551 A1 | 10/2012 | Rogers et al. |
| 2012/0320581 A1 | 12/2012 | Rogers et al. |
| 2012/0327608 A1 | 12/2012 | Rogers et al. |
| 2013/0036928 A1 | 2/2013 | Rogers et al. |
| 2013/0072775 A1 | 3/2013 | Rogers et al. |
| 2013/0100618 A1 | 4/2013 | Rogers et al. |
| 2013/0140649 A1 | 6/2013 | Rogers et al. |

FOREIGN PATENT DOCUMENTS

| | | |
|---|---|---|
| CN | 101772348 A | 7/2010 |
| DE | 4241045 C1 | 5/1994 |
| DE | 19748173 | 5/1999 |
| EP | 0929097 | 7/1999 |
| EP | 1357773 | 10/2003 |
| EP | 1 467 224 | 10/2004 |
| EP | 1 477 230 | 11/2004 |
| EP | 1 498 456 | 1/2005 |
| EP | 1 511 096 | 3/2005 |
| EP | 1 558 444 | 8/2005 |
| EP | 1 613 796 | 1/2006 |
| EP | 1 773 240 | 4/2007 |
| EP | 1 915 436 | 4/2008 |
| EP | 1 726 329 | 8/2009 |
| EP | 2 086 749 | 8/2009 |
| EP | 2 101 975 | 9/2009 |
| EP | 2 107 964 | 10/2009 |
| EP | 2 109 634 | 10/2009 |
| EP | 2 129 772 | 12/2009 |
| EP | 2 206 017 | 7/2010 |
| EP | 2 211 876 | 8/2010 |
| EP | 2 249 886 | 11/2010 |
| JP | 06-118441 | 4/1994 |
| JP | 6-163365 | 6/1994 |
| JP | 11-026344 | 1/1999 |
| JP | 11-142878 | 5/1999 |
| JP | 2001-007340 | 1/2001 |
| JP | 2002092984 | 3/2002 |
| JP | 2006-504450 | 2/2006 |
| JP | 2006-186294 | 7/2006 |
| JP | 2007-515391 | 6/2007 |
| JP | 2007-167636 | 7/2007 |
| JP | 2008-502739 | 1/2008 |
| JP | 2010-508852 | 3/2010 |
| JP | 2010-509593 | 3/2010 |
| JP | 2010-509644 | 3/2010 |
| JP | 2010-509645 | 3/2010 |
| JP | 2010-522583 | 7/2010 |
| JP | 2010-529230 | 8/2010 |
| KR | 10-2008-0069553 | 7/2008 |
| TW | 367570 | 8/1999 |
| TW | 494257 | 7/2002 |
| TW | 200836353 | 9/2008 |
| TW | 200913345 | 3/2009 |
| WO | WO 98/49936 | 11/1998 |
| WO | WO 99/45860 | 9/1999 |
| WO | WO 00/046854 | 8/2000 |
| WO | WO 00/049421 | 8/2000 |
| WO | WO 00/049658 | 8/2000 |
| WO | WO 00/055915 | 9/2000 |
| WO | WO 00/055916 | 9/2000 |
| WO | WO 01/31082 | 5/2001 |

(56) References Cited

FOREIGN PATENT DOCUMENTS

| | | |
|---|---|---|
| WO | WO 01/033621 | 5/2001 |
| WO | WO 01/066833 | 9/2001 |
| WO | WO 01/098838 | 12/2001 |
| WO | WO 02/027701 | 4/2002 |
| WO | WO 02/043032 | 5/2002 |
| WO | WO 02/073699 | 9/2002 |
| WO | WO 02/092778 | 11/2002 |
| WO | WO 02/097724 | 12/2002 |
| WO | WO 04/099068 | 12/2002 |
| WO | WO 03/030194 | 4/2003 |
| WO | WO 03/032240 | 4/2003 |
| WO | WO 03/049201 | 6/2003 |
| WO | WO 03/063211 | 7/2003 |
| WO | WO 03/085700 | 10/2003 |
| WO | WO 03/085701 | 10/2003 |
| WO | WO 03/092073 | 11/2003 |
| WO | WO 2004/000915 | 12/2003 |
| WO | WO 2004/001103 | 12/2003 |
| WO | WO 04/003535 | 1/2004 |
| WO | WO 04/022637 | 3/2004 |
| WO | WO 04/022714 | 3/2004 |
| WO | WO 04/023527 | 3/2004 |
| WO | WO 04/024407 | 3/2004 |
| WO | WO 04/027822 | 4/2004 |
| WO | WO 04/032190 | 4/2004 |
| WO | WO 04/032191 | 4/2004 |
| WO | WO 04/032193 | 4/2004 |
| WO | WO 04/034025 | 4/2004 |
| WO | WO 2004/062697 | 7/2004 |
| WO | WO 04/086289 | 10/2004 |
| WO | WO 04/094303 | 11/2004 |
| WO | WO 04/100252 | 11/2004 |
| WO | WO 04/105456 | 12/2004 |
| WO | WO 05/005679 | 1/2005 |
| WO | WO 2005/000483 | 1/2005 |
| WO | WO 05/015480 | 2/2005 |
| WO | WO 05/017962 | 2/2005 |
| WO | WO 2005/012606 | 2/2005 |
| WO | WO 05/022120 | 3/2005 |
| WO | WO 2005/029578 | 3/2005 |
| WO | WO 2005/054119 | 6/2005 |
| WO | WO 2005/104756 | 11/2005 |
| WO | WO 02/097708 | 12/2005 |
| WO | WO 05/122285 | 12/2005 |
| WO | WO 2005/123114 | 12/2005 |
| WO | WO 2006/028996 | 3/2006 |
| WO | WO 2006/042287 | 4/2006 |
| WO | WO 2006/076711 | 7/2006 |
| WO | WO 2006/104069 | 10/2006 |
| WO | WO 2006/130721 | 12/2006 |
| WO | WO 2007/000037 | 1/2007 |
| WO | WO 2007/016524 | 2/2007 |
| WO | WO 2007/028003 | 3/2007 |
| WO | WO 2007/056183 | 5/2007 |
| WO | WO 2007/126412 | 11/2007 |
| WO | WO 2008/030666 | 3/2008 |
| WO | WO 2008/030960 | 3/2008 |
| WO | WO 2008/036837 | 3/2008 |
| WO | WO 08/055054 | 5/2008 |
| WO | WO 2008/085904 | 7/2008 |
| WO | WO 2008/103464 | 8/2008 |
| WO | WO 2008/106485 | 9/2008 |
| WO | WO 2008/108838 | 9/2008 |
| WO | WO 2008/118133 | 10/2008 |
| WO | WO 2008/118211 | 10/2008 |
| WO | WO 2008/127401 | 10/2008 |
| WO | WO 2008/127402 | 10/2008 |
| WO | WO 2008/127403 | 10/2008 |
| WO | WO 2008/127404 | 10/2008 |
| WO | WO 2008/127405 | 10/2008 |
| WO | WO 2008/140562 | 11/2008 |
| WO | WO 2008/143635 | 11/2008 |
| WO | WO 2008/150861 | 12/2008 |
| WO | WO 2009/011709 | 1/2009 |
| WO | WO 2009/023615 | 2/2009 |
| WO | WO 2009/061823 | 5/2009 |
| WO | WO 2009/075625 | 6/2009 |
| WO | WO 2009/076088 | 6/2009 |
| WO | WO 2009/090398 | 7/2009 |
| WO | WO 2009/100280 | 8/2009 |
| WO | WO 2009/111641 | 9/2009 |
| WO | WO 2009/114115 | 9/2009 |
| WO | WO 2009/114689 | 9/2009 |
| WO | WO 2009/118678 | 10/2009 |
| WO | WO 2009/126689 | 10/2009 |
| WO | WO 2009/140588 | 11/2009 |
| WO | WO 2009/155397 | 12/2009 |
| WO | WO 2010/005707 | 1/2010 |
| WO | WO 2010/036807 | 4/2010 |
| WO | WO 2010/036992 | 4/2010 |
| WO | WO 2010/040528 | 4/2010 |
| WO | WO 2010/042798 | 4/2010 |
| WO | WO 2010/049881 | 5/2010 |
| WO | WO 2010/057142 | 5/2010 |
| WO | WO 2010/065957 | 6/2010 |
| WO | WO 2010/081989 | 7/2010 |
| WO | WO 2010/126640 | 11/2010 |
| WO | WO 2010/132552 | 11/2010 |
| WO | WO 2010/141133 | 12/2010 |
| WO | WO 2011/005381 | 1/2011 |
| WO | WO 2011/006133 | 1/2011 |
| WO | WO 2011/008842 | 1/2011 |
| WO | WO 2011/011347 | 1/2011 |
| WO | WO 2011/026101 | 3/2011 |
| WO | WO 2011/038401 | 3/2011 |
| WO | WO 2011/041395 | 4/2011 |
| WO | WO 2011/046652 | 4/2011 |
| WO | WO 2011/084450 | 7/2011 |
| WO | WO 2011/112931 | 9/2011 |
| WO | WO 2011/115643 | 9/2011 |
| WO | WO 2012/167096 | 12/2012 |
| WO | WO 2013/149181 | 10/2013 |

OTHER PUBLICATIONS

Alanen et al. (2004) "Measurement of Hydration in the Stratum Corneum with the Moisturemeter and Comparison with the Corneometer," *Skin Research and Technology*. 10:32-37.

Alekseev, et al. (2008) "Millimeter Wave Reflectivity Used for Measurement of Skin Hydration with Different Moisturizers," *Skin Res. Technol*, 14:390-396.

Al-Hardan et al. (2010) "The Effect of Oxygen Ratio on the Crystallography and Optical Emission Properties of Reactive RF Sputtered ZnO Films," *Physica B*. 405:1081.

Andosca et al. (2012) "Experimental and Theoretical Studies on MEMS Piezoelectric Vibrational Energy Harvesters with Mass Loading," *Sensors and Actuators A*. 178:76.

Arumugam et al. (1994) "Effect of Strain Rate on the Fracture Behaviour of Skin," *J. Bioscience*. 19(3):307-313.

Attas et al. (2002) "Near-IR Spectroscopic Imaging for Skin Hydration: The Long and the Short of it," *Biopolymers*. 67:96-106.

Bach-y-Rita et al. (2003) "Seeing with the Brain," *Int. J. Hum-Comput. Int*. 15:285-296.

Barel et al. (1997) *In Vitro* Calibration of the Capacitance Method (Corneometer CM 825) and Conductance Method (Skicon-200) for the Evaluation of the Hydration State of the Skin, *Skin Research and Technology*. 3:107-113.

Barfield et al. (1995) "Comparison of Human Sensory Capabilities with Technical Specifications for Virtual Environment Equipment," *Presence-Teleoperators and Virtual Environments*. 4:329-356.

Baskoutas et al. (2011) "Transition in the Optical Emission Polarization of ZnO Nanorods," *J. Phys. Chem. C*. 115:15862.

Berger (1929) "Über das Elektrenkephalogram des. Menschen." *Arch Psychiatr Nervenkr*. 87:527-570.

Bernardini et al. (1997) "Spontaneous Polarization and Piezoelectric Constants of III—V nitrides," *Physics Review B*. 56:10024.

Bettinger et al. (2010) "Biomaterials-Based Organic Electronic Devices," *Polym. Int*. 59:563.

Bettinger et al. (2010) "Organic Thin-Film Transistors Fabricated on Resorbable Biomaterial Substrates," *Adv. Mater*. 22:651.

(56) References Cited

OTHER PUBLICATIONS

Biot. (1963) "Surface Instability of Rubber in Compression," *Appl. Sci. Res. A.* 12:168-182.
Blichmann et al. (1987) "Hydration Studies on Scaly Hand Eczema," *Contact Dermatitis.* 16:155-159.
Blom et al. (1990) "Thin-film ZnO as Micromechanical Actuator at Low Frequencies," *Sensors and Actuators.* 21:226.
Boguniewicz, et al. (2008) "A Multidisciplinary Approach to Evaluation and Treatment of Atopic Dermatitis," *Seminars in Cutaneous Medicine and Surgery.* 27:115-127.
Briscoe (2012) "Measured Efficiency of a ZnO Nanostructured Diode Piezoelectric Energy Harvesting Device," *Appl. Phys. Lett.* 101:093902.
Camacho et al. (2011) "Structural, Optical and Electrical Properties of ZnO Thin Films Grown by Radio Frequency (Rf) Sputtering in Oxygen Atmosphere," *International Journal of Physical Sciences.* 6:6660.
Carcia et al. (2006) "High-Performance ZnO Thin-Film Transistors on Gate Dielectrics Grown by Atomic Layer Deposition," *Appl. Phys. Lett.* 88:123509.
Chang et al. (2010) "Direct-Write Piezoelectric Polymeric Nanogenerator with High Energy Conversion Efficiency," *Nano Lett.* 10:726.
Chaudhury et al. (1991) "Direct Measurement of Interfacial Interactions Between Semispherical Lenses and Flat Sheets of Poly(Dimethylsiloxane) and their Chemical Derivatives," *Langmuir.* 7:1013-1025.
Chen et al. (2005) "Humidity Sensors: A Review of Materials and Mechanisms," *Sensor Letters.* 3:274-295.
Choi-Yim et al. (1998) "The Effect of Silicon on the Glass Forming Ability of the $Cu_{47}Ti_{34}Zr_{11}Ni_8$ Bulk Metallic Glass Forming Alloy During Processing of Composites," *J. Appl. Phys.* 83:7993.
Clarys et al. (1999) "Non-Invasive Electrical Measurements for the Evaluation of the Hydration State of the Skin: Comparison Between Three Conventional Instruments—Corneometer®, the Skicon® and the Nova DPM®," *Skin Research and Technology.* 5:14-20.
Csutak et al. (2002) "CMOS-Compatible High-Speed Planar Silicon Photodiodes Fabricated on SOI Substrates," IEEE *Journal of Quantum Electronics.* 38:193-196.
Czekalla et al. (2008) "Spatial Fluctuations of Optical Emission from Single ZnO/MgZnO Nanowire Quantum Wells," *International Journal of Nanotechnology.* 19:115202.
Dagdeviren et al. (published online Apr. 19, 2013) "Transient, Biocompatible Electronics and Energy Harvesters Based on ZnO," *Small.* e-publication.
Danckwerts (1950) "Absorption by Simultaneous Diffusion and Chemical Reaction," *Transactions of the Faraday Society.* 46:300.
Danilova et al. (2008) "Dipole Analysis of Event-Related Oscillations in Anticipation Processes," *International Journal of Psychophysiology.* 69:161-162.
David et al. (2012) "Dissolution Kinetics and Solubility of ZnO Nanoparticles Followed by AGNES," *J. Phys. Chem.* 116:11758.
Dobrev (2000) "Use of Cutometer to Assess Epidermal Hydration," *Skin Research and Technology.* 6:239-244.
Ducéré et al. (2005) "A Capacitive Humidity Sensor Using Cross-Linked Cellulose Acetate Butyrate," *Sensors and Actuators B: Chemical.* 106:331-334.
Fan et al. (2009) "Three Dimensional Nanopillar Array Photovoltaics on Low Cost and Flexible Substrates," *Nature Materials.* 8:648-653.
Fluhr et al. (1999) "Comparative Study of Five Instruments Measuring Stratum Corneum Hydration (Corneometer CM 820 and CM 825, Skicon 200, Nova DPM 9003, DermaLab). Part I. *In vitro*," *Skin Research and Technology.* 5:161-170.
Fox et al. (1976) "Transcutaneous Electrical Stimulation and Acupuncture: Comparison of Treatment for Low-Back Pain," *Pain.* 2:141-148.
Frodin et al. (1988) "Hydration of Human Stratum Corneum Studied *In Vivo* by Optothermal Infrared Spectrometry, Electrical Capacitance Measurement, and Evaporimetry," *Acta Derm Venereol.* 68:461-7.

Fulati et al. (2009) "Miniaturized pH Sensors Based on Zinc Oxide Nanotubes/Nanorods," *Sensors.* 9:8911-8923.
Geerligs et al. (2011) "*In Vivo* Indentation to Determine the Mechanical Properties of Epidermis," *J. Biomech.* 44:1176-1181.
Gerischer et al. (1992) "Chemical dissolution of zinc oxide crystals in aqueous electrolytes—An analysis of the kinetics," *Electrochimica Acta.* 37:827.
Gonzalez et al. (2008) "Design of Metal Interconnects for Stretchable Electronic Circuits," *Microelectronics Reliability.* 48:825-832.
Griss et al. (2002) "Characterization of Micromachined Spiked Biopotential Electrodes," *IEEE Trans. Biomed. Eng.* 49:597-604.
Grosjean et al. (2006) "Hydrolysis of Mg-salt and MgH2-Salt Mixtures Prepared by Ball Milling for Hydrogen Production," *Journal of Alloys and Compounds.* 416:296.
Guimerà et al. (2008) "Method and Device for Bio-Impedance Measurement with Hard-Tissue Applications," *Physiological Measurement.* 29:S279.
Gullapalli et al. (2010) "Flexible Piezoelectric ZnO—Paper Nanocomposite Strain Sensor," *Small.* 6:1641.
Gupta et al. (2010) "Development of Gas Sensors Using ZnO Nanostructures," *J. Chem. Sci.* 122:57.
Hamed et al. (Dec. 2012) "Construction, *In Vitro* and *In Vivo* Evaluation of an In-House Conductance Meter for Measurement of Skin Hydration," *Medical Engineering & Physics.* 34:1471-1476.
Hardyck et al. (1966) "Feedback of Speech Muscle Activity During Silent Reading: Rapid Extinction," *Science.* 154:1467-1468.
Hendriks, et al. (2004) "Influence of Hydration and Experimental Length Scale on the Mechanical Response of Human Skin *In Vivo*, Using Optical Coherence Tomography," *Skin Research and Technology.* 10: 231-241.
Hoffman et al. (2003) "ZnO-Based Transparent Thin-Film Transistors," *Appl. Phys. Lett.* 82:733.
Hua et al. (1993) "Finite Element Modeling of Electrode-Skin Contact Impedance in Electrical Impedance Tomography," *IEEE Transactions on Biomedical Engineering.* 40:335-343.
Huang et al. (2011) "A Flexible pH Sensor Based on the Iridium Oxide Sensing Film," *Sensors and Actuators A: Physical.* 169:1-11.
Huang et al. (Dec. 2012) "Epidermal Differential Impedance Sensor for Conformal Skin Hydration Monitoring," *Biointerphases.* 7:52.
Hudson et al. (2008) "The Biocompatibility of Mesoporous Silicates," *Biomaterials.* 29:4045.
Hwang et al. (2012) "A Physically Transient Form of Silicon Electronics," *Science.* 337:1640.
Ilican et al. (2008) "Preparation and Characterization of ZnO Thin Films Deposited by Sol-Gel Coating Method," *Journal of Optoelectronics and Advanced Materials.* 10:2578.
International Search Report and Written Opinion corresponding to International Patent Application No. PCT/US2013/034667.
Irimia-Vladu (2010) "Biocompatible and Biodegradable Materials for Organic Field-Effect Transistors," *Adv. Funct. Mater.* 20:4069.
Ives et al. (2007) "Miniaturized, On-Head, Invasive Electrode Connector Integrated EEG Data Acquisition System," *Clinical Neurophysiol.* 118:1633-1638.
Jeon et al. (2007) "Low-Voltage Zinc-Oxide Thin-Film Transistors on a Conventional $SiO_2$ Gate Insulator Grown by Radio-Frequency Magnetron Sputtering at Room Temperature," *J. of the Korean Physical Society* 51:1999.
Jiang et al. (2008) "Post-Buckling Anlysis for the Precisely Controlled Buckling of Thin Film Encapsulated by Elastomeric Substrates," *Int. J. Solids Struct.* 45, 2014-2023.
Jones (2008) Tactile Displays: Guidance for Their Design and Application,: *Human Factors.* 50:90-111.
Kaczmarek et al. (1991) "Electrotactile and Vibrotactile Displays for Sensory Substitution Systems," *IEEE Transactions on Biomedical Engineering.* 38:1-16.
Kaczmarek et al. (2003) "Pattern Identification and Perceived Stimulus Quality as a Function of Stimulation Waveform on a Fingertip-Scanned Electrotactile Display," *IEEE Transactions on Neural Systems and Rehabilitation Engineering.* 11:9-16.
Kadlec et al. (2008) "Assessing Skin Hydration Status in Haemodialysis Patients Using Terahertz Spectroscopy: A Pilot/Feasibility Study," *Physics in Medicine and Biology.* 53:7063.

(56) References Cited

OTHER PUBLICATIONS

Kaneko et al. (2005) "The Influence of Age on Pressure Perception of Static and Moving Two-Point Discrimination in Normal Subjects," *J. Hand Ther*. 18:421-424.
Keplinger et al. (2010) "Röntgen's Electrode-Free Elastomer Actuators without Electromechanical Pull-In Instability," *Proc. Natl. Acad. Sci. USA*. 107:4505-4510.
Kim et al. (2011) "Epidermal Electronics," *Science*. 333(6044):838-843.
Kim et al. (2011) "Materials for Multifunctional Balloon Catheters With Capabilities in Cardiac Electrophysiological Mapping and Ablation Therapy," *Nat. Mater*. 10:316.
Kim et al. (May 2013) "Deterministic Assembly of Releasable Single Crystal Silicon-Metal Oxide Field-Effect Devices Formed From Bulk Wafers," *Applied Physics Letters*. 102:182104.
Kleiner (1999) "Water: An Essential But Overlooked Nutrient," *Journal of the American Dietetic Association*. 99:200-206.
Klode et al. (2011) "Investigation of Adhesion of Modern Wound Dressings: A Comparative Analysis of 56 Different Wound Dressings," *J. Eur. Acad. Dermatol*. 25(8):933-939.
Kubo et al. (2010) "Stretchable Microfluidic Radiofrequency Antennas," *Adv. Mater*. 22:2749-2752.
Kumar et al. (2006) "Ultrasensitive DNA Sequence Detection Using Nanoscale ZnO Sensor Arrays," *Nanotechnology*. 17:2875.
Kumar et al. (2011) "ZnO Nanoparticle as Catalyst for Efficient Green One-Pot Synthesis of Coumarins through Knoevenagel Condensation," *J. Chem. Sci*. 123:615.
Kurzweil (2009) "Metal Oxides and Ion-Exchanging Surfaces as pH Sensors in Liquids: State-of-the-Art and Outlook," *Sensors (Basel)*. 9:4955-85.
Kuwazuru et al. (2008) "Mechanical Approach to Aging and Wrinkling of Human Facial Skin Based on the Multistage Buckling Theory," *Med. Eng. Physics*. 30:516-522.
Legnani et al. (2008) "Bacterial Cellulose Membrane as Flexible Substrate for Organic Light Emitting Devices," *Thin Film Solids*. 517:1016.
Li et al. (2008) "Cellular Level Biocompatibility and Biosafety of ZnO Nanowires," *J. Phys. Chem. C*. 112:20114.
Lipomi et al. (2011) "Skin-Like Sensors of Pressure and Strain Enabled by Transparent, Elastic Films of Carbon Nanotubes," *Nature Nanotech*. 6:788-792.
Loo et al. (2008) "Progress and Challenges in Commercialization of Organic Electronics," *MRS Bull*. 33:653-662.
Lozano (2009) "Electrotactile Stimulation on the Tongue: Intensity Perception, Discrimination, and Cross-Modality Estimation," *Somatosens. Mot. Res*. 26:50-63.
Ma et al. (2010) "A Stretchable Electrode Array for Non-Invasive, Skin-Mounted Measurement of Electrocardiography (ECG), Electromyography (EMG) and Electroencephalography (EEG)," In; Engineering in Medicine and Biology Society (EMBC), 2010 Annual International Conference of the IEEE. Buenos Aires, Arentina. pp. 6405-6408.
Mannsfeld et al. (2010) "Highly Sensitive Flexible Pressure Sensors with Microstructured Rubber Dielectric Layers," *Nat. Mater*. 9:859-864.
Martinez-Boubeta et al. (2010) "Self-Assembled Multifunctional Fe/MgO Nanospheres for Magnetic Resonance Imaging and Hyperthermia," *Nanomedicine: Nanotechnology, Biology, and Medicine*. 6:362.
Martinsen, et al. (1999) "Measuring depth depends on frequency in electrical skin impedance measurements," *Skin Research and Technology*. 5:179-181.
Masuda et al. (2003) "Transparent Thin Film Transistors Using Zno as an Active Channel Layer and Their Electrical Properties," *J. Appl. Phys*. 93:1624.
Matteau et al. (2010) "Beyond Visual, Aural and Haptic Movement Perception: hMT+ is Activated by Electrotactile Motion Stimulation of the Tongue in Sighted and in Congenitally Blind Individuals," *Brain Research Bulletin*. 82:264-270.

Matthie (2008) "Bioimpedance Measurements of Human Body Composition: Critical Analysis and Outlook," *Expert Rev. Med. Devices*. 5:239-261.
Menard et al. (2007) "Micro- and Nanopatterning Techniques for Organic Electronic and Optoelectronic Systems," *Chem. Rev*. 107:1117-1160.
Michalske et al. (1985) "Closure and Repropagation of Healed Cracks in Silicate Glass," *J. Am. Ceram. Soc*. 68:586-590.
Miyamoto et al. (2004) "High-Electron-Mobility ZnO epilayers Grown by Plasma-Assisted Molecular Beam Epitaxy," *Journal of Crystal Growth*. 265:34.
Mondal et al. (2008) "Preparation of Al-doped ZnO (AZO) Thin Film by SILAR," *Journal of Physical Sciences*. 12:221.
Moore et al. (1959) "II. Diffusion of Zinc and Oxygen in Zinc Oxide," *Discussions of the Faraday Society*. 28:86.
Moravej et al. (2011) "Biodegradable Metals for Cardiovascular Stent Application: Interests and New Opportunities," *Int. J. Mol. Sci*. 12:4250.
Mudunkotuwa et al. (2012) "Dissolution of ZnO Nanoparticles at Circumeutral pH: A Study of Size Effects in the Prescencse and Asbsence of Citric Acid," *Langmuir*. 28:396.
Ondo-Ndong et al. (2003) "Electrical Properties of Zinc Oxide Sputtered Thin Films," *Microelectronics Journal*. 34:1087.
Pailler-Mattei et al. (2008) "*In Vivo* Measurements of the Elastic Mechanical Properties of Human Skin by Indentation Tests," *Med. Eng. Phys*. 30:599-606.
Panilaitis et al. (2003) "Macrophage Activation in Response to Silk," *Biomaterials*. 24:3079.
Park et al. (2008) "Theoretical and Experimental Studies in Bending of Inorganic Electronic Materials on Plastic Substrates," *Adv. Funct. Mater*. 18:2673.
Park et al. (2009) "The Effects of Rapid Thermal Annealing on the Performance of ZnO Thin-Film Transistors," *Journal of the Korean Physical Society*. 55:1925.
Patolsky et al. (2006) "Detection, Stimulation, and Inhibition of Neuronal Signals with High-Density Nanowire Transistor Arrays," *Science*. 313:1100-1104.
Paye et al. (1995) "Corneometiy Measurements to Evaluate Skin Dryness in the Modified Soap Chamber Test," *Skin Research and Technology*. 1:123-127.
Reed et al. (2012) "Solubility of Nano-Zinc Oxide in Environmentally and Biologically Important Matrices," *Environ. Toxicol. Chem*. 31:93.
Richter et al. (2008) "Review on Hydrogel-based pH Sensors and Microsensors," *Sensors*. 8:561-581.
Rodriguez et al. (2007) "Dual-Frequency Resonance-Tracking Atomic Force Microscopy," *Nanotechnology*. 18:475504.
Rogers et al. (2009) "A Curvy, Stretchy Future for Electronics," *Proc. Natl. Acad. Sci. U. S. A*. 106:16889.
Rogers et al. (2010) "Materials and Mechanics for Stretchable Electronics," Science. 327:1603-1607.
Rogers et al. (Sep. 1, 2011) "Synthesis, Assembly and Applications of Semiconductor Nanomembranes," *Nature*. 477:45-53.
Saad et al. (2010) "Characterization of Various Zinc Oxide Catalysts and Their Activity in the Dehydration-Dehydrogenation of Isobutanol" *J. Serb. Chem. Soc*. 73:997.
Searle et al. (2000) "A Direct Comparison of Wet, Dry and Insulating Bioelectric Recording Electrodes," *Physiol. Meas*. 21:271.
Sharma et al. (1986) "Influence of Heat-Stress Induced Dehydration on Mental Functions," *Ergonomics*. 29:791-799.
Shen et al. (2007) "Submicron Particles of SBA-15 Modified with MgO as Carriers for Controlled Drug Delivery," *Chem. Pharm. Bull*. 55:985.
Shimizu et al. (2012) "Letter: Zinc Oxide Paste as Sunscreen in the Postoperative Period," *Dermatologic Surgery* 38:965.
Song et al. (2003) "Understanding Magnesium Corrosion—A Framework for Improved Alloy Performance," *Advanced Engineering Materials*. 5:837.
Sparks et al. (1978) "Investigating the MESA (multipoint electrotactile speech aid): the transmission of segmental features of speech," *Journal of the acoustical Society of America*. 63:246-257.
Staiger et al. (2006) "Magnesium and its Alloys as Orthopedic Biomaterials: A Review," *Biomaterials*. 27:1728.

(56) References Cited

OTHER PUBLICATIONS

Stroop (1935) "Studies of Interference in Serial Verbal Reactions," *Journal of Experimental Psychology.* 18:643-662.
Su et al. (2012) "Postbuckling Analysis and its Application to Stretchable Electronics," *Journal of the Mechanics and Physics of Solids.* 60:487.
Tagami et al. (1980) "Evaluation of the Skin Surface Hydration In Vivo by Electrical Measurement," *J. Investig. Dermatol.* 75:500-507.
Takei et al. (2010) "Nanowire Active-Matrix Circuitry for Low-Voltage Macroscale Artificial Skin," *Nat. Mater.* 9:821.
Tan et al. (1999) "Information Transmission with a Multifinger Tactual Display," *Perception & Psychophysics.* 61:993-1008.
Tchvialeva et al. (2010) "Skin Roughness Assessment," In; *New Developments in Biomedical Engineering.* D. Campolo: Eds. *In Tech.* p. 341-358.
Trewyn et al. (2008) "Biocompatible Mesoporous Silica Nanoparticles with Different Morphologies for Animal Cell Membrane Penetration," *Chemical Engineering Journal.* 137:23.
Valtiner et al. (2008) "Stabilization and acidic dissolution mechanism of single crystalline ZnO(0001) surfaces in electrolytes studied by in-situ AFM imaging and ex-situ LEED," *Langmuir.* 24:5350.
Vidal-Verdu et al. (2007) "Graphical Tactile Displays for Visually-Impaired People," *IEEE Transactions on Neural Systems and Rehabilitation Engineering.* 15:119-130.
Viventi et al. (2011) "Flexible, Foldable, Actively Multiplexing, High Density Electrode Array for Mapping Brain Activity In Vivo," *Nature Neuroscience.* 14:1599-1605.
Vuillerme et al. (2008) "Sensory Supplementation System Based on Electrotactile Tongue Biofeedback of Head Position for Balance Control," *Neurosci. Lett.* 431:206-210.
Wales et al. (2003) "Stationary Points and Dynamics in High-Dimensional Systems," *J. Chem. Phys.* 119:12409.
Wang (May 2012) "Mechanics of Epidermal Electronics," *Journal of Applied Mechanics.* 79:031022.
Wang et al. (1999) "Electromechanical Coupling and Output Efficiency of Piezoelectric Bending Actuators," *IEEE transactions on Ultrasonics, Ferroelectrics and Frequency Control.* 46:638.
Warren et al. (2008) "Receptive Field Characteristics Under Electrotactile Stimulation of the Fingertip," *IEEE Transactions on Neural Systems and Rehabilitation Engineering.* 16:410-415.
Wegnera et al. (2006) "In situ formation and hydrolysis of Zn nanoparticles for $H_2$ Production by the 2-Step ZnO/Zn Water-Splitting Thermochemical Cycle," *International Journal of Hydrogen Energy.* 31:55.
Won et al. (2011) "Piezoresitive Strain Sensors and Multiplexed Arrays Using Assemblies of Single-Crystalline Silicon Nanoribbons on Plastic Substrates," *IEEE Transactions on Electron Devices.* 58:4074-4078.
Woo et al. (1992) "Skin Impedance Measurements Using Simple and Compound Electrodes," *Medical & Biological Engineering & Computing.* 30:97-102.
Yeo et al. (Feb. 26, 2013) "Multifunctional Epidermal Electronics Printed Directly Onto the Skin," *Advanced Materials.* 25:2773-2778.
Ying et al. (Mar. 27, 2012) "Silicon Nanomembranes for Fingertip Electronics," *Nanotechnology.* 23: 344004.
Yu et al. (2007) "Micropatterning Metal Electrode of Organic Light Emitting Devices Using Rapid Polydimethylsiloxane Lift-Off," *Appl. Phys. Lett.* 91:043102.
Yu et al. (2009) "A Microfabricated Electrode with Hollow Microneedles for ECG Measurement," *Sens. Actuators A.* 151:17-22.
Zhang et al. (2010) "Fabrication and Comparative Study of Top-Gate and Bottom-Gate ZnO-TFTs with Various Insulator Layers," *J. Mater. Sci: Mater. Electron.* 21:671.
Zhao et al. (2004) "Piezoelectric Characterization of Individual Zinc Oxide Nanobelt Probed by Piezoresponse Force Microscopy," *Nano Lett.* 4:587.

Zheng et al. (2009) "In Vitro and In Vivo Biocompatibility Studies of ZnO Nanoparticles," *International Journal of Modern Physics B.* 23:1566.
Zhou et al. (2006) "Dissolving Behavior and Stability of ZnO Wires in Biofluids: A Study on Biodegradability and Biocompatibility of ZnO Nanostructures," *Adv. Mater.* 18:2432.
Zhou et al. (2013) "Fast Flexible Electronics with Strained Silicon Nanomembranes," *Scientific Reports.* 3:1291.
Zhu et al. (2010) "Flexible High-Output Nanogenerator Based on Lateral ZnO Nanowire Array," *Nano Lett.* 10:3151.
Abbaschian et al. (Dec. 2005) "High Pressure-High Temperature Growth of Diamond Crystals Using Split Sphere Apparatus," *Diamond Relat. Mater.* 14(11-12):1916-1919.
Adachi et al (1982) "Chemical Etching of InGaAsP/InP DH Wafer," *J. Electrochem. Soc.* 129:1053-1062.
Adachi et al. (1983) "Chemical Etching Characteristics of (001)GaAs," *J. Electrochem. Soc.* 130:2427-2435.
Adrega et al. (2010) "Stretchable Gold Conductors Embedded in PDMS and Patterned by Photolithography: Fabrication and Electromechanical Characterization," *J. Micromech. Microeng.* 20:055025.
Ago et al. (2005) "Aligned Growth of Isolated Single-Walled Carbon Nanotubes Programmed by Atomic Arrangement of Substrate Surface," *Chem. Phys. Lett.* 408:433-438.
Ago et al. (2006) "Synthesis of Horizontally-Aligned Single-Walled Carbon Nanotubes with Controllable Density on Sapphire Surface and Polarized Raman Spectroscopy," *Chem. Phys. Lett.* 421:399-403.
Ahmed et al. (Web Release Oct. 11, 2005) "Extending the 3ω-Method to the MHz Range for Thermal Conductivity Measurements of Diamond Thin Films," *Diamond Relat. Mater.* 15(2-3):389-393.
Ahn et al. (2007) "Bendable Integrated Circuits on Plastic Substrates by Use of Printed Ribbons of Single-Crystalline Silicon," *Appl. Phys. Lett.* 90:213501.
Ahn et al. (Dec. 15, 2006) "Heterogeneous Three-Dimensional Electronics by Use of Printed Semiconductor Nanomaterials," *Science* 314:1754-1757.
Ahn et al. (Jun. 2006) "High-Speed Mechanically Flexible Single-Crystal Silicon Thin-Film Transistors on Plastic Substrates," *IEEE Electron Dev. Lett.* 27(6):460-462.
Al-Halhouli et al. (2008) "Nanoindentation Testing of SU-8 Photoresist Mechanical Properties," *Microelectronic Eng.* 85:942-944.
Aliot, E. M. et al. (2009) "EHRA/HRS Expert Consensus on Catheter Ablation of Ventricular Arrhythmias: Developed in a partnership with the European Heart Rhythm Association (EHRA), a Registered Branch of the European Society of Cardiology (ESC), and the Heart Rhythm Society (HRS); in collaboration with the American College of Cardiology (ACC) and the American Heart Association (AHA)," *Europace* 11:771-817.
Alivisatos et al. (1996) "Semiconductor Clusters, Nanocrystals, and Quantum Dots," *Science* 271:933-937.
Alivisatos et al. (1998) "From Molecules to Materials: Current Trends and Future Directions," *Adv. Mater.* 10:1297-1336.
Allen et al. (Feb. 20, 2006) "Nanomaterial Transfer Using Hot Embossing for Flexible Electronic Devices," *Appl. Phys. Lett.* 88:083112.
Al-Sarawi et al. (Feb. 1998) "A Review of 3-D Packaging Technology," *IEEE Trans. Comp. Packag. Manufac. Technol. B* 21(1):2-14.
Altman et al. (2003) "Silk-Based Biomaterials," *Biomaterials* 24:401-416.
Amano et al. (Feb. 3, 1986) "Metalorganic Vapor Phase Epitaxial Growth of a High Quality GaN Film Using an AlN Buffer Layer," *Appl. Phys. Lett.* 48(5):353-355.
Ambrosy et al. (1996) "Silicon Motherboards for Multichannel Optical Modules," *IEEE Trans. Compon. Pack. A* 19:34-40.
Amir et al. (2000) "The Influence of Helium-Neon Irradiation on the Viability of Skin Flaps in the Rat," *Br. J. Plast. Surg.* 53:58-62.
Amsden et al. (Nov. 9, 2009) "Spectral Analysis of Induced Color Change on Periodically Nanopatterned Silk Films," *Opt. Express* 17(23):21271-21279.
Andersen et al. (2004) "Selecting the Signals for a Brain—Machine Interface," *Curr. Opin. Neurobiol.* 14:720-726.

(56) References Cited

OTHER PUBLICATIONS

Andersson et al. (Oct. 16, 2002) "Active Matrix Displays Based on All-Organic Electrochemical Smart Pixels Printed on Paper," *Adv. Mater.* 14:1460-1464.
Ando et al. (2004) "Self-Aligned Self-Assembly Process for Fabricating Organic Thin-Film Transistors," *Appl. Phys. Lett.* 85:1849-1851.
Angadi et al. (Web Release Jun. 1, 2006) "Thermal Transport and Grain Boundary Conductance in Ultrananocrystalline Diamond Thin Films," *J. Appl. Phys.* 99:114301.
Aoki et al. (2003) "Microassembly of Semiconductor Three Dimensional Photonic Crystals," *Nat. Mater.* 2:117-121.
Arnold et al. (2003) "Field-Effect Transistors Based on Single Semiconducting Oxide Nanobelts," *J. Phys. Chem. B* 107(3):659-663.
Ayón et al. (Jan. 1999) "Characterization of a Time Multiplexed Inductively Coupled Plasma Etcher," *J. Electrochem. Soc.* 146(1):339-349.
Baca et al. (2008) "Semiconductor Wires and Ribbons for High-Performance Flexible Electronics," *Angew. Chem. Int. Ed.* 47:5524-5542.
Bachtold et al. (Nov. 9, 2001) "Logic Circuits with Carbon Nanotube Transistors," *Science* 294:1317-1320.
Bae et al. (Jul. 1, 2002) "Single-Crystalline Gallium Nitride Nanobelts," *Appl. Phys. Lett.* 81(1):126-128.
Ball et al. (2004) "Towards an Implantable Brain-Machine Interface Based on Epicortical Field Potentials," *Biomed. Tech.* 49:756-759.
Balmer et al. (2005) "Diffusion of Alkanethiols in PDMS and Its Implications on Microcontact Printing (μCP)," *Langmuir* 21(2):622-632.
Banerjee et al. (May 2001) "3-D ICs: A Novel Chip Design for Improving Deep-Submicrometerinterconnect Performance and Systems-on-Chip Integration," *Proc. IEEE* 89(5):602-633.
Bao et al. (1997) "High-Performance Plastic Transistors Fabricated by Printing Techniques," *Chem. Mater.* 9:1299-1301.
Bao et al. (1999) "Printable Organic and Polymeric Semiconducting Materials and Devices," *J. Mater. Chem.* 9:1895-1904.
Barquins, M. (1992) "Adherence, Friction and Wear of Rubber-Like Materials," *Wear* 158:87-117.
Bates, F.S. (1991) "Polymer-Polymer Phase Behavior," *Science* 251:898-905.
Battaglia et al. (2003) "Colloidal Two-Dimensional Systems: CdSe Quantum Shells and Wells," *Angew. Chem. Int. Ed.* 442:5035-5039.
Bauer et al. (2004) "Biological Applications of High Aspect Ratio Nanoparticles," *J. Mater. Chem.* 14:517-526.
Berg et al. (2003) "Tailored Micropatters Through Weak Polyelectrolyte Stamping," *Langmuir* 19:2231-2237.
Bernard et al. (1998) "Printing Patterns of Proteins," *Langmuir* 14(9):2225--2229.
Bett et al. (Aug. 1999) "III-V Compounds for Solar Cell Applications," *Appl. Phys. A. Mater. Sci.* 69(2):119-129.
Bhunia et al. (2004) "Free-Standing and Vertically Aligned InP Nanowires Grown by Metalorganic Vapor Phase Epitaxy," *Physica E* 21:583-587.
Bhushan et al. (Nov. 2004) "Multiwalled Carbon Nanotube AFM Probes for Surface Characterization of Micro/Nanostructures," *Microsyst. Technol.* 10(8-9):633-639.
Bietsch et al. (Oct. 1, 2000) "Conformal Contact and Pattern Stability of Stamps Used for Soft Lithography," *J. Appl. Phys.* 88(7):4310-4318.
BIOFLEX—Biocompatible Flexible Electronic Circuits. Available at http://tfcg.elis.ugent.be/projects/bioflex. Accessed Feb. 8, 2012.
Bishay et al. (2000) "Temperature Coefficient of the Surface Resistivity of Two-Dimensional Island Gold Films," *J. Phys. D. Appl. Phys.* 33(18):2218-2222.
Blanchet et al. (2003) "Large Area, High Resolution, Dry Printing of Conducting Polymers for Organic Electronics," *Appl. Phys. Lett.* 82:463-465.
Blanchet et al. (2003) "Printing Techniques for Plastic Electronics," *J. Imag. Sci. Tech.* 47(4):296-303.

Blazdell et al. (Nov. 1999) "Preparation of Ceramic Inks for Solid Freeforming Using a Continuous Jet Printer," *J. Mat. Syn. Process.* 7(6):349-356.
Boltau et al. (1998) "Surface-Induced Structure Formation of Polymer Blends on Patterned Substrates," *Nature* 391:877-879.
Boncheva et al. (Mar. 15, 2005) "Magnetic Self-Assembly of Three-Dimensional Surfaces from Planar Sheets," *Proc. Natl. Acad. Sci. USA* 102(11):3924-3929.
Boncheva et al. (Mar. 8, 2005) "Templated Self-Assembly: Formation of Folded Structures by Relaxation of Pre-Stressed, Planar Tapes," *Adv. Mater.* 17(5):553-557.
Bourzac, K. (May/Jun. 2010) "TR10: Implantable Electronics," *Technology Review*, Published by MIT, http://www.technologyreview.com/biomedicine/25086/?a=f.
Bowden et al. (1997) "Self Assembly of Mesoscale Objects into Ordered Two-Dimensional Arrays," *Science* 276:233-235.
Bowden et al. (1998) "Spontaneous Formation of Ordered Structures in Thin Films of Metals Supported on an Elastomeric Polymer," *Nature* 393:146-149.
Bowden et al. (2001) "Molecule-Mimetic Chemistry and Mesoscale Self-Assembly," *Acc. Chem. Res.* 34:231-238.
Bracher et al. (2009) "Shaped Films of Ionotropic Hydrogels Fabricated Using Templates of Patterns Paper," *Adv. Mater.* 21:445-450.
Bradley et al. (2003) "Flexible Nanotube Electronics," *Nano Lett.*, vol. 3, No. 10, pp. 1353-1355.
Braun et al. (1999) "Electrochemically Grown Photonic Crystals," *Nature* 402:603-604.
Britton et al. (Web Release Oct. 25, 2005) "Microstructural Defect Characterization of a Si:H Deposited by Low Temperature HW-CVD on Paper Substrates," *Thin Solid Films* 501(1-2):79-83.
Brown et al. (2005) "Evaluation of Polydimethylsiloxane Scaffolds with Physiologically-Relevant Elastic Moduli: Interplay of Substrate Mechanics and Surface Chemistry Effects on Vascular Smooth Muscle Cell Response," *Biomaterials* 26:3123-3129.
Brown et al. (Dec. 19, 2001) "Heterogeneous Materials Integration: Compliant Substrates to Active Device and Materials Packaging," *Mater. Sci. Eng. B* 87(3):317-322.
Brown, H.R. (1991) "The Adhesion Between Polymers," *Ann. Rev. Mater. Sci.* 21:463-489.
Bruschi et al. (2001) "Micromachined Silicon Suspended Wires With Submicrometric Dimensions," *Microelectron. Eng.* 57-58:959-965.
Buma et al. (2001) "High-Frequency Ultrasound Array Element Using Thermoelastic Expansion in an Elastomeric Film," *Appl. Phys. Lett.* 79:548-550.
Burdinski et al. (2005) "Single Etch Patterning of Stacked Silver and Molybdenum Alloy Layers on Glass Using Microcontat Wave Printing," *J. Am. Chem. Soc.* 127(31):10786-10787.
Burdinski, D. (non-dated) "Soft Lithography and Microcontact Wave Printing," http://www.research.philips.com/technologies/light_dev_microsys/softlitho/index.html, Downloaded May 23, 2007.
Burge et al. (Jun. 25, 1997) "X-Ray Holography for VLSI Using Synthetic Bilevel Holograms," *Proc. Int. Soc. Opt. Eng.* 3183:2-13.
Burgin et al. (2000) "Large Area Submicrometer Contact Printing Using a Contact Aligner," *Langmuir* 16:5371-5375.
Burns et al. (2003) "Printing of Polymer Thin-Film Transistors for Active-Matrix-Display Applications," *J. Soc. Inf. Display* 11:599-604.
Campbell et al. (2000) "Fabrication of Photonic Crystals for the Visible Spectrum by Holographic Lithography," *Nature* 404:53-56.
Cao et al. (2006) "Bilayer Organic-Inorganic Gate Dielectrics for High-Performance, Low-Voltage, Single-Walled Carbon Nanotube Thin-Film Transistors, Complementary Logic Gates, and p-n Diodes on Plastic Substrates," *Adv. Funct. Mater.* 16:2355-2362.
Cao et al. (2006) "Highly Bendable,Transparent Thin-Film Transistors That Use Carbon-Nanotube-Based Conductors and Semiconductors with Elastomeric Delectrics," *Adv. Mater.* 18(3):304-309.
Cao et al. (2006) "Transparent flexible organic thin-film transistors that use printed single-walled carbon nanotube electrodes," *Applied Physics Letters* 88:113511.

(56) References Cited

OTHER PUBLICATIONS

Cao et al. (Jan. 5, 2009) "Ultrathin Films of Single-Walled Carbon Nanotubes for Electronics and Sensors: A Review of Fundamental and Applied Aspects," *Adv. Mater.* 21(1):29-53.
Cao et al. (Jul. 24, 2008) "Medium-Scale Carbon Nanotube Thin-Film Integrated Circuits on Flexible Plastic Substrates," *Nature* 454:495-500.
Carr et al. (1998) "Measurement of Nanomechanical Resonant Structures in Single-Crystal Silicon," *J. Vac. Sci. Technol. B* 16:3821-3824.
Chadhury et al. (1991) "Direct Measurement of Interfacial Interactions Between Semispherical Lenses and Flat Sheets of Poly(dimethylsiloxane) and their Chemical Derivatives," *Langmuir* 7:1013-1025.
Chang et al. (1994) "Process Techniques," "Lithography," and "Device-Related Physics and Principles," In; *GaAs High-Speed Devices: Physics, Technology and Circuit Application*, John Wiley and Sons, New York, pp. 115-278.
Chen et al. (2003) "Characterization of Pd-GaAs Schottly Diodes Prepared by the Electrodes Plating Technique," *Semiconductor. Sci. Technol.* 18:620-626.
Chen et al. (2003) "Electronic Paper: Flexible Active-Matrix Electronics Ink Display," *Nature* 423:136.
Chen et al. (2005) "InGaN Nanorings and Nanodots by Selective Area Epitaxy," *Appl. Phys. Lett.* 87:143111.
Chen et al. (2005) "The Role of Metal-Nanotube Caontact in the Performance of Carbon Nanotube Field-Effect Transistors," *Nano Lett.* 5(7):1497-1502.
Chen et al. (Feb. 27, 2006) "Complementary Carbon Nanotube-Gated Carbon Nanotube Thin-Fim Transistor," *Appl. Phys. Lett.* 88:093502.
Chen et al. (Jun. 2002) Effect of Process Parameters on the Surface Morphology and Mechanical Performance of Silicon Structures After Deep Reactive Ion Etching (DRIE) *J. Microelectromech. Syst.* 11(3):264-275.
Chen et al. (Mar. 2004) "A Family of Herringbone Patterns in Thin Films," *Scr. Mater.* 50(6):797-801.
Chen et al. (Mar. 24, 2006) "An Integrated Logic Crcuit Assembled on a Single Carbon Nanotube," *Science* 311:1735.
Chen et al. (Sep. 2004) "Herringbone Buckling Patterns of Compressed Thin Films on Compliant Substrates," *J. Appl. Mech.* 71:597-603.
Cheng et al. (2005) "Ink-Jet Printing, Self-Assembled Polyelectrolytes, and Electroless Plating: Low Cost Fabrication of Circuits on a Flexible Substrate at Room Temperature," *Macromol. Rapid Commun.* 26:247-264.
Childs et al. (2002) "Decal Transfer Microlithography: A New Soft-Lithographic Patterning Method," *J. Am. Chem. Soc.* 124:13583-13596.
Childs et al. (2005) "Masterless Soft-Lithography: Patterning UV/Ozone-Induced Adhesion on Poly(dimethylsiloxane) Surfaces," *Langmuir* 21:10096-10105.
Childs et al. (Aug. 14, 2004) "Patterning of Thin-Film Microstructures on Non-Planar Substrate Surfaces Using Decal Transfer Lithography," *Adv. Mater.* 16(15):1323-1327.
Choi et al. (2007) "Biaxially Stretchable 'Wavy' Silicon Nanomembranes," *Nano Lett.* 7(6):1655-1663.
Choi et al. (Web Release Jan. 25, 2005) "Simple Detachment Patterning of Organic Layers and Its Applications to Organic Light-Emitting Diodes," *Adv. Mater.* 17(2):166-171.
Chou et al. (2004) "An Orientation-Controlled Pentacene Film Aligned by Photoaligned Polyimide for Organic Thin-Film Transistor Applications," *Adv. Func. Mater.* 14:811-815.
Chou et al. (Jun. 8, 1999) "Micromachining on (111)-Oriented Silicon," *Sens. Actuators A* 75(3):271-277.
Chu et al. (2005) "High-Performance Organic Thin-Film Transistors with Metal Oxide/Metal Bilayer Electrode," *Appl. Phys. Lett.* 87:193508.
Chung et al. (2000) Silicon Nanowire Devices *Appl. Phys. Lett.* 76(15):2068-2070.

Chung et al. (Jul. 1, 2003) "A Study on Formation of Al and $Al_2O_3$ on the Porous Paper by DC Magnetron Sputtering," *Surf. Coat. Technol.* 171(1-3):65-70.
Clerc, L. (1976) "Directional Differences of Impulse Spread in Trabecular Muscle from Mammalian Heart," *J. Physiol.* 255:335-346.
Cohen-Karni et al. (2009) "Flexible Electrical Recording from Cells Using Nanowire Transistor Arrays," *Proc. Natl. Acad. Sci. USA* 106:7309-7313.
Cole et al. (2008) "Patterned Growth and Transfer of ZnO Micro- and Nanocrystals with Size and Location Control," *Adv. Mater.* 20:1474-1478.
Collins et al. (Apr. 27, 2001) "Engineering Carbon Nanotubes and Nanotube Circuits Using Electrical Breakdown," *Science* 292:706-709.
Corazza et al. (2007) "Photobiomodulation on the Angiogenesis of Skin Wounds in Rats Using Different Light Sources," *Photomedicine Laser Surg.* 25:102-106.
Cox, H. L. (1952) "The Elasticity and Strength of Paper and Other Fibrous Materials," *Br. J. Appl. Phys.* 3:72-79.
Creagh et al. (2003) "Design and Performance of Inkjet Print Heads for Non-Graphic-Arts Applications," *MRS Bull.* 28:807-811.
Crone et al. (Feb. 3, 2000) "Large-Scale Complementary Integrated Circuits Based on Organic Transistors," *Nature* 403:521-523.
Crowder et al. (1998) "Low-Temperature Single-Crystal Si TFTs Fabricated on Si Films Processed via Sequential Lateral Solidification," *IEEE Electron. Dev. Lett.* 19:306-308.
Cui et al. (2001) "Nanowire Nanosensors for Highly Sensitive and Selective Detection of Biological and Chemical Species," *Science* 293:1289-1292.
Dai et al. (2002) "Gallium Oxide Nanoribbons and Nanosheets," *J. Phys. Chem. B* 106(5):902-904.
Dai et al. (2003) "Novel Nanostructures of Functional Oxides Synthesized by Thermal Evaporation," *Adv. Funct. Mater.* 13:9-24.
Davidson et al. (2004) "Supercritical Fluid-Liquid-Solid Synthesis of Gallium Arsenide Nanowires Seeded by Alkanethiol-Stabilized Gold Nanocrystals," *Adv. Mater.* 16:646-649.
De Gans (2004) "Inkjet Printing of Polymers: State of the Art and Future Developments," *Adv. Mater.* 16(3):203-213.
De Sio et al. (Web Release May 18, 2005) "Electro-Optical Response of a Single-Crystal Diamond Ultraviolet Photoconductor in Transverse Configuration," *Appl. Phys. Lett.* 86:213504.
DeBoer et al. (2004) "Organic Single-Crystal Field-Effect Transistors," *Phys. Stat. Sol.* 201:1302-1331.
Deen et al. (2004) "Electrical Characterization of Polymer-Based FETs Fabricated by Spin-Coating Poly(3-alkylthiophene)s," *IEEE Trans. Electron Devices* 51:1892-1901.
Delmerche et al. (1997) "Stability of Molded Polydimethylsiloxane Microstructures," *Adv. Mat.* 9:741-746.
Deruelle et al. (1995) "Adhesion at the Solid-Elastomer Interface: Influence of Interfacial Chains," *Macromol.* 28:7419-7428.
Derycke et al. (Sep. 2001) "Carbon Nanotube Inter- and Intramolecular Logic Gates," *Nano Lett.* 1(9):453-456.
Desai et al. (Feb. 1999) "Nanopore Technology for Biomedical Applications," *Biomed. Microdevices* 2(1):11-40.
Dick et al. (Jun. 2004) "Synthesis of Branched 'Nanotrees' by Controlled Seeding of Multiples Branching Events," *Nat. Mater.* 3:380-384.
Dimroth et al. (Mar. 2007) "High Efficiency Multijunction Solar Cells," *MRS Bull.* 32:230-235.
Ding et al. (Oct. 4, 2004) "Self Catalysis and Phase Transformation in the Formation of CdSe Nanosaws," *Adv. Mater.* 16(19):1740-1743.
Dinsmore et al. (2002) "Colloidosomes: Selectively Permeable Capsules Composed of Colloidal Particles," *Science* 298:1006-1009.
Divliansky et al. (2003) "Fabrication of Three-Dimensional Polymer Photonic Crystal Structures Using Single Diffraction Element Interference Lithography," *Appl. Phys. Lett.* 82(11):1667-1669.
Dodabalapur A. (Apr. 2006) "Organic and Polymer Transistors for Electronics," *Mater Today* 9(4):24-30.

(56) References Cited

OTHER PUBLICATIONS

Dodabalapur et al. (1995) "Organic Transistors: Two-Dimensional Transport and Improved Electrical Characteristics," *Science* 268:270-271.
Duan et al. (2000) "General Synthesis of Compound Semiconductor Nanowires," *Adv. Mater.* 12(4):298-302.
Duan et al. (2003) "High-performance Thin-Film Transistors Using Semiconductor Nanowires and Nanoribbons," *Nature* 425:274-278.
Duan X, (2003) "Semiconductor Nanowires: From Nanoelectronics to Macroelectronics," Abstract from a presentation given at the 11$^{th}$ Foresight Conference on Molecular Nanotechnology, Oct. 10-20, Burlingame, CA.
Duboz et al. (1998) "Transistors and Detectors Based on GaN-Related Materials," In; Group III Nitride Semiconductor Compounds, Gill, B. ed., Clarendon, Oxford, pp. 343-387.
Duesberg et al. (2000) "Polarized Raman Spectroscopy on Isolated Single-Wall Carbon Nanotubes," *Phys. Rev. Lett.*, vol. 85, No. 25, pp. 5436-5439.
Duffy et al. (1998) "Rapid Prototyping of Microfluidic Systems in Poly(dimethylsiloxane)," *Anal. Chem.* 70:4974-4984.
Dupuis et al. (2008) "History, Development, and Applications of High-Brightness Visible Light-Emitting Diodes," *IEEE J. Lightwave Tech.* 26:1154-1171.
Durkop et al. (2004) "Extraordinary Mobility in Semiconducting Carbon Nanotube," *Nano Lett.* 4(1):35-39.
Eder et al. (Apr. 5, 2004) "Organic Electronics on Paper," *Appl. Phys. Lett.* 84(14):2673-2675.
Edrington et al. (2001) "Polymer-Based Photonic Crystals," *Adv. Mater.* 13:421-425.
Efimenko et al. (Oct. 15, 2002) "Surface Modification of Sylgard-184 Poly(dimethyl Siloxane) Networks by Ultraviolet and Ultraviolet/Ozone Treatment," *J. Colloid Interface Sci.* 254(2):306-315.
Eftekhari, G. (1993) "Variation in the Effective Richardson Constant of Metal-GaAs and Metal-InP Contacta Due to the Effect of Processing Parameters," *Phys. Status Solid A-Appl. Res.* 140:189-194.
Ensell, G. (1995) "Free Standing Single-Crystal Silicon Microstructures," *J. Micromech. Microeng.* 5:1-4.
Exam Report, Written Opinion and Response to Written Opinion, Corresponding to Singapore Patent Application No. 2007/18082-1, dated Jan. 15, 2009.
Examination Report and Response, Corresponding to Malaysian Patent Application No. PI 20062672, dated Aug. 28, 2009.
Examination Report, Corresponding to European Application No. EP 05 756 327.2, dated Jan. 20, 2010.
Examination Report, Corresponding to Malaysian Patent Application No. PI 20092343, dated Jun. 15, 2010.
Examination Report, Corresponding to Malaysian Patent Publication No. PI 20052553, dated Mar. 13, 2009.
Examination Report, Corresponding to Singapore Patent Application No. 200608359-6, Completed on Aug. 27, 2008.
Examination Report, Response and Search Report, Corresponding to Malaysian Patent Application No. PI 20062537, dated Nov. 20, 2009.
Faez et al. (1999) "An Elastomeric Conductor Based on Poluaniline Prepared by Mechanical Mixing," *Polymer* 40:5497-5503.
Felgner et al. (1996) "Flexural Rigidity of Microtubules Measured with the Use of Optical Tweezers," *J. Cell Sci.* 109:509-516.
Fink et al. (1999) "Block Copolymers as Photonic Bandgap Materials," *J. Lightwave Tech.* 17:1963-1969.
Flewitt et al. (2005) "Low-Temperature Deposition of Hydrogenated Amorphous Silicon in an Electron Cyclotron Resonance Reactor for Flexible Displays," *Proc. IEEE* 93:1364-1373.
Folch et al. (1999) "Wafer-Level In-Registry Microstamping," *J. Microelectromech. Syst.* 8:85-89.
Forment et al. (2004) "Influence of Hydrogen Treatment and Annealing Processes Upon the Schottky Barrier Height of Au/n—GaAs and Ti/n—GaAs Diodes," *Semicond. Sci. Technol.* 19:1391-1396.

Forrest et al. (2004) "The Path to Ubiquitous and Low-Cost Organic Electronic Appliances on Plastic," *Nature* 428:911-918.
Fortunato et al. (2005) "Flexible a-Si: H Position-Sensitive Detectors," *Proc. IEEE* 93:1281-1286.
Fortunato et al. (Sep. 2008) "High-Performance Flexible Hybrid Field-Effect Transistors Based on Cellulose Fiber Paper," *IEEE Electron. Dev. Lett.* 29(9):988-990.
Freeman et al. (2000) "Spatial Spectral Analysis of Human Electrocardiograms Including the Alpha and Gamma Bands," *J. Neurosci. Methods* 95:111-121.
Freire et al. (1999) "Thermal Stability of Polyethylene Terephthalate (PET): Oligomer Distribution and Formation of Volatiles," *Packag. Technol. Sci.* 12:29-36.
Freund, L.B. (2000) "The Mechanics of Electronic Materials," *Int. J. Solids Struct.* 37:185-196.
Friedman et al. (2005) "High-Speed Integrated Nanowire Circuits," *Nature* 434:1085.
Fu et al. (Jan. 10, 2003) "Patterning of Diamond Microstructures on Si Substrate by Bulk and Surface Micromachining," *J. Mater. Process. Technol.* 132(1-3):73-81.
Furneaux et al. (1989) "The Formation of Controlled-Porosity Membranes from Anodically Oxidized Aluminum," *Nature* 337:147-149.
Gan et al. (2002) "Preparation of Thin-Film Transostros With Chemical Bath Deposited CdSe and CdS Thin Films," *IEEE Trans. Electron. Dev.* 49:15-18.
Gao et al. (Sep. 9, 2005) "Conversion of Zinc Oxide Nanobelts into Superlattice-Structures Nanohelices," *Science* 309:1700-1704.
Garcia et al. (2004) "Etchant Anisotropy Controls the Step Bunching Instability in KOH Etching of Silicon," *Phys. Rev. Lett.* 93(16):166102.
Gardner et al. (1965) "Physical Aspects of the Internal Water Relations of Plant Leaves," *Plant Physiol.* 40:705-710.
Garnier et al. (1994) "All-Polymer Field-Effect Transistor Realized by Printing Techniques," *Science* 265:1684-1686.
Geim et al. (Mar. 2007) "The Rise of Graphene," *Nature Mater.* 6:183-191.
Geissler et al. (2003) "Fabrication of Metal Nanowires Using Microcontact Printing," *Langmuir* 19(15):6301-6311.
Geissler et al. (Jun. 2003) "Selective Wet-Etching of Microcontact-Printed Cu Substrates with Control Over the Etch Profile," *Microelec. Eng.* 67-68:326-332.
Gelinck et al. (2000) "High-Performance All-Polymer Integrated Circuits," *Appl. Phys. Lett.* 77:1487-1489.
Gelinck et al. (2004) "Fleible Active-Matrix Displays and Shift Registers Based on Solution-Processed Organic Transistors," *Nat. Mater.* 3:106-110.
Georgakilas et al. (2002) "Wafer-Scale Integration of GaAs Optoelectronic Devices with Standard Si Integrated Circuits Using a Low-Temperature Bonding Procedure," *Appl. Phys. Lett.* 81:5099-5101.
Givargizov, E.I. (1991) "Applications," In; *Oriented Crystallization on Amorphous Substrates*, Plenum Press, New York, pp. 341-363.
Goetting et al. (1999) "Microcontact Printing of Alkanephosphonic Acids on Aluminum: Pattern Transfer by Wet Chemical Etching," *Langmuir* 15:1182-1191.
Goldman et al. (1996) "Correlation of Buffer Strain Relaxation Modes with Transport Properties of Two-Dimensional Electron Gases," *J. Apple. Phys.* 80:6849-6854.
Goldmann et al. (2004) "Hole Mobility in Organic Single Crystals Measured by a "Flip-Crystal" Field-Effect Technique," *J. Appl. Phys.* 96:2080-2086.
Goldsmith, T.H. (Sep. 1990) "Optimization, Constraint, and History in the Evolution of Eyes," *Quart. Rev. Biol.* 65(3):281-322.
Gratz et al. (1991) "Atomic Force Microscopy of Atomic-Scale Ledges and Etch Pits Formed During Dissolution of Quartz," *Science*, 251:1343-1346.
Gray et al. (Dec. 2001) "Screen Printed Organic Thin Film Transistors (OTFTs) on a Flexible Substrate," *Proc. SPIE* 4466:89-94.
Gray et al. (Mar. 5, 2004) "High-Conductivity Elastomeric Electronics," *Adv. Mater.* 16(5):393-397.
Grayson, T. (2002) "Curved Focal Plane Wide Field of View Telescope Design," *Proc. SPIE* 4849:269-274.

(56) References Cited

OTHER PUBLICATIONS

Gruen et al. (Mar. 21, 1994) "Fullerenes as Precursors for Diamond Film Growth Without Hydrogen or Oxygen Additions," *Appl. Phys. Lett.* 65(12):1502-1504.
Gudiksen et al. (Web Release Apr. 18, 2001) "Synthetic Control of the Diameter and Length of Single Crystal Semiconductor Nanowires," *J. Phys. Chem. B* 105:40624064.
Guo et al. (Aug. 19, 2002) "Metal-Insulator-Semiconductor Electrostatics of Carbon Nanotubes," *Appl. Phys. Lett.* 81(8):1486-1488.
Gur et al. (2005) "Air-Stable All-Inorganic Nanocrystal Solar Cells Processed from Solution," *Science* 310:462-465.
Gurbuz et al. (Jul. 2005) "Diamond Semiconductor Technology for RF Device Applications." *Solid State Electron.* 49(7):1055-1070.
Haisma et al. (2002) "Contact Bonding, Including Direct-Bonding in a Historical and Recent Context of Materials Science and Technology, Physics and Chemistry," *Mater. Sci Eng.* 37:1-60.
Halik et al. (2004) "Low-Voltage Organic Transistors with an Amorphous Molecular Gate Dielectric," *Nature* 431:963-966.
Hamedi et al. (May 2007) "Towards Woven Logic from Organic Electronic Fibres," *Nat. Mater.* 6:357-362.
Hamilton et al. (2004) "Field-Effect Mobility of Organic Polymer Thin-Film Transistors," *Chem. Mater.* 16:4699-4704.
Han et al. (2005) "Template-Free Directional Growth of Single-Walled Carbon Nanotues on a- and r-Plane Sapphire," *J. Am. Chem. Soc.* 127:5294-5295.
Harada et al. (2001) "Catalytic Amplification of the Soft Lithographic Patterning of Si. Nonelectrochemical Orthogonal Fabrication of Photoluminescent Porous Si Pixel Arrays," *J. Am. Chem. Soc.* 123:8709-8717.
Harkonen et al. (Jun. 8, 2006) "4 W Single-Transverse Mode VECSEL Utilizing Intra-Cavity Diamond Heat Spreader," *Electron Lett.* 42(12):693-694.
Hayase et al. (2001) "Photoangioplasty with Local Motexafin Lutetium Delivery Reduces Macrophages in a Rabbit Post-Balloon Injury Model," *Cardiovascular Res.* 49:449-455.
He et al. (2005) "Si Nanowire Bridges in Microtrenches: Integration of Growth into Device Fabrication," *Adv. Mater.* 17:2098-2102.
Heffelfinger et al. (1997) "Steps and the structure of the (0001) α-alumina surface," *Surf. Sci.*, 370:L168-L172.
Hillbrog et al. (Web Release Dec. 30, 2003) "Nanoscale Hydrophobic Recovery: A Chemical Force Microscopy Study of UV/Ozone-Treated Cross-Linker Poly(dimethylsiloxane)," *Langmuir* 20(3):785-794.
Hines et al. (2005) "Nanotransfer Printing of Organic and Carbon Nanotube Thin-Film Transistors on Plastic Substrates," *Appl. Phys. Lett.* 86:163101.
Hollenberg et al. (2006) "A MEMS Fabricated Flexible Electrode Array for Recording Surface Field Potentials," *J. Neurosci. Methods* 153:147-153.
Holmes et al. (Feb. 25, 2000) "Control of Thickness and Orientation of Solution-Grown Silicon Nanowires," *Science* 287:1471-1473.
Horan et al. (Jun. 2005) "In Vitro Degradation of Silk Fibroin," *Biomaterials* 26(17):3385-3393.
Horn et al. (1992) "Contact Electrification and Adhesion Between Dissimilar Materials," *Science* 256:362-364.
Hoyer, P. (1996) "Semiconductor Nanotube Formation by a Two-Step Template Process," *Adv. Mater.* 8:857-859.
Hsia et al. (2005) "Collapse of Stamps for Soft Lithography Due to Interfacial Adhesion," *Appl. Phys. Lett.* 86:154106.
Hsu et al. (2002) "Amorphous Si TFTs on Plastically Deformed Spherical Domes," *J. Non-Crystalline Solids* 299-302:1355-1359.
Hsu et al. (2003) "Nature of Electrical Contacts in a Metal—Molecule—Semiconductor System," *J. Vac. Sci. Technol. B* 21(4):1928-1935.
Hsu et al. (Jan. 15, 2004) "Spherical Deformation of Compliant Substrates with Semiconductor Device Islands," *J. Appl. Phys.* 95(2):705-712.
Hsu et al. (Mar. 2004) "Effects of Mechanical Strain on TFT's on Spherical Domes," *IEEE Trans. Electron Dev.* 51(3):371-377.

Hu et al. (1997) "Using Soft Lithography to Fabricate GaAs/AlGaAs Heterostructure Field Effect Transistors," *Appl. Phys. Lett.* 71:2020-2022.
Hu et al. (1999) Chemistry and Physics in One Dimension: Synthesis and Properties of Nanowires and Nanotubes, *Acc. Chem. Res.* 32:435-445.
Hu et al. (2004) "Percolation in Transparent and Conducting Carbon Nanotube Networks," *Nano Lett.*, vol. 4, No. 12, pp. 2513-2517.
Hu et al. (2009) "Highly Conductive Paper for Energy-Storage Devices," *Proc. Natl. Acad. Sci. USA* 106:21490-21494.
Hu et al. (2010) "Stretchable, Porous, and Conductive Energy Textiles," *Nano Lett.* 10:708-714.
Huang et al. (2001) "Directed Assembly of One-Dimensional Nanostructures into Functional Networks," *Science* 291:630-633.
Huang et al. (2001) "Room-Temperature Ultraviolet Nanowire Nanolasers," *Science* 292:1897-1899.
Huang et al. (2003) "Growth of Millimeter-Long and Horizontally Aligned Single-Walled Carbon Nanotubes on Flat Substrates," *J. Am. Chem. Soc.*, 125:5636-5637.
Huang et al. (2004) "Long and Oriented Single-Walled Carbon Nanotubes Grown by Ethanol Chemical Vapor Deposition," *J. Phys. Chem. B.* 108:16451-16456.
Huang et al. (2004) "Self-Organizing High-Density Single-Walled Carbon Nanotube Arrays from Surfactant Suspensions," *Nanotechnol.* 15:1450-1454.
Huang et al. (2005) "Nanomechanical Architecture of Strained Bilayer Thin Films: From Design Principles to Experimental Fabrication," *Adv. Mater.* 17(23):2860-2864.
Huang et al. (2005) "Nanowires for Integrated Multicolor Nanophotonics," *Small* 1(1):142-147.
Huang et al. (2005) "Nonlinear Analyses of Wrinkles in a Film Bonded to a Compliant Substrate," *J. Mech. Phys. Solids* 53:2101-2118.
Huang et al. (2005) "Stamp Collapse in Soft Lithography," *Langmuir* 21:8058-8068.
Huang et al. (Jan. 16, 2001) "Catalytic Growth of Zinc Oxide Nanowires by Vapor Transport," *Adv. Mater.* 13(2):113-116.
Huck et al. (2000) "Ordering of Spontaneously Formed Buckles on Planar Surfaces," *Langmuir* 16:3497-3501.
Huie, J.C. (2003) "Guided Molecular Self Assembly: A review of Recent Efforts," *Smart Mater. Struct.* 12:264-271.
Huitema et al. (2001) "Plastic Transistors in Active-Matrix Displays," *Nature* 414:599.
Hur et al. (2005) "Printed thin-film transistors and complementary logic gates that use polymer-coated single-walled carbon nanotube networks," *J. Appl. Phys.*, 98, 114302.
Hur et al. (205) "Organic Nanodelectrics for Low Voltage Carbon Nanotube Thin Film Transistors and Complementary Logc Gates," *J. Am. Chem. Soc.* 127:13808-13809.
Hur et al. (Dec. 2004) "Nanotransfer Printing by Use of Noncovalent Surface Forces: Applications to Thin-Film Transistors that Use Single-Walled Carbon Nanotube Networks and Semiconducting Polymers," *Appl. Phys. Lett.* 85(23):5730-5732.
Hur etal. (Jun. 13, 2005) "Extreme Bendability of Single Walled Carbon Nanotube Networks Transferred From High-Temperature Growth Substrates to Plastic and Their Use in Thin-Film Transistors," *Appl. Phys. Lett.* 243502.
Hutchinson et al. (1992) "Mixed Mode Cracking in Layered Materials," *Adv. Appl. Mech.* 29:63-191.
Imparato et al. (2005) "Excimer Laser Induced Crystallization of Amorphous Silicon on Flexible Polymer Substrates," *Thin Solid Films* 487:58-62.
International Search Report and Written Opinion, Corresponding to International Application No. PCT/US2006/032125, dated Mar. 21, 2008.
International Search Report and Written Opinion, Corresponding to International Application No. PCT/US2009/058231, dated Nov. 17, 2009.
International Search Report and Written Opinion, Corresponding to International Application No. PCT/2005/014449, dated Jul. 3. 2008.
International Search Report and Written Opinion, Corresponding to International PCT Application No. PCT/US05/19354, dated Apr. 18, 2007.

(56) References Cited

OTHER PUBLICATIONS

International Search Report and Written Opinion, Corresponding to International PCT Application No. PCT/US2007/079070, dated Apr. 23, 2008.
International Search Report and Written Opinion, Corresponding to International PCT Application No. PCT/US2007/077759, dated Apr. 11, 2008.
International Search Report and Written Opinion, Corresponding to International PCT Application No. PCT/US2007/022959, dated Oct. 14, 2008.
International Search Report and Written Opinion, Corresponding to International PCT Application No. PCT/US2006/021161, dated Feb. 28, 2008.
International Search Report and Written Opinion, Corresponding to International Application No. PCT/US2009/036192, dated Jul. 6, 2009.
International Search Report and Written Opinion, Corresponding to International Application No. PCT/US2010/034520, dated Sep. 24, 2010.
International Search Report and Written Opinion, Corresponding to International Application No. PCT/US07/74293, dated Jul. 24, 2008.
International Search Report and Written Opinion, Corresponding to International Application No. PCT/US07/82633, dated May 16, 2008.
International Search Report and Written Opinion, Corresponding to International Application No. PCT/US07/77217, dated Jun. 3, 2008.
International Search Report and Written Opinion, Corresponding to International Application No. PCT/US09/47442, dated Sep. 21, 2009.
International Search Report and Written Opinion, Corresponding to International Application No. PCT/US04/40192, dated Jul. 6, 2005.
International Search Report and Written Opinion, Corresponding to International Application no. PCT/US10/50468, dated Jan. 6, 2011.
International Search Report and Written Opinion, Corresponding to International Application no. PCT/US10/60425, dated May 25, 2011.
International Search Report and Written Opinion, Corresponding to International Application No. PCT/US2011/028094, dated Jul., 14, 2011.
International Search Report and Written Opinion, Corresponding to International Application No. PCT/US2010/042585, dated May 25, 2011.
Isberg et al. (Sep. 6, 2002) "High Carrier Mobility in Single-Crystal Plasma-Deposited Diamond," *Science* 297:1670-1672.
Islam et al. (Jan. 16, 2003) "High Weight Fraction Surfactant Solubilization of Single-Wall Carbon Nanotubes in Water," *Nano Lett.* 3(2):269-273.
Ismach et al. (2004) "Atomic-Step-Templated Formation of Single Wall Carbon Nanotube Patters," *Angew. Chem. Int. Ed.* 43:6140-6143.
Itoh et al. (1991) "Cathodoluminescence Properties of Undoped and Zn-Doped $Al_xGa_{1-x}N$ Grown by Metaloganic Vapor Phase Epitaxy," *Jap. J. Appl. Phys.* 30:1604-1608.
Jabbour et al. (2001) "Screen Printing for the Fabrication of Organic Light-Emitting Devices," *IEEE J. Select. Top. Quantum. Electron.* 7:769-773.
Jackman et al. (Aug. 4, 1995) "Fabrication of Submicrometer Features on Curved Substrates by Microcontact Printing," *Science* 269:664-666.
Jacobs et al. (2001) "Submicrometer Patterning of Charge in Thin-Film Electrets," *Science* 291:1763-1766.
Jacobs et al. (2002) "Fabrication of a Cylindrical Display by Patterned Assembly," *Science* 296:323-325.
Jain et al. (2000) "III-Nitrides: Growth, Characterization, and Properties," *J. Appl. Phys.* 87:965-1006.
Jain et al. (2005) "Flexible Electronics and Displays: High-Resolution, Roll-to-Roll, Projection Lithography and Photoblation processing Technologies for Hiogh-Throughput Production," *Proc. IEEE* 93:1500-1510.

James et al. (1998) "Patterned Protein Layers on Solid Substrates by This Stamp Microcontact Printing," *Langmuir* 14:742-744.
Jang et al. (2003) "Lateral Growth of Aligned Multiwalled Carbon Nanotubes Under Electric Fiels," *Solid State Commun.* 126:305-308.
Jang et al. (2006) "Low-Voltage and High-Field-Effect Mobility Organic Transistors with a Polymer Insulator," *Appl. Phys. Lett.* 88:072101.
Javey et al. (2002) "High-K Dielectrics for Advanced Carbon-Nanotube Transistors and Logic Gates," *Nature Mater.* 1:241-246.
Javey et al. (2005) "High Performance n-Type Carbon Nanotube Field-Effect Transistors with Chemically Doped Contacts," *Nano Lett.*, vol. 5, No. 2, pp. 345-348.
Javey et al. (Aug. 7, 2003) "Ballistic Carbon Nanotube Field-Effect Transistors," *Nature* 424:654-657.
Jenkins et al. (1994) "Gallium Arsenide Transistors: Realization Through a Molecularly Designs Insulator," *Science* 263:1751-1753.
Jeon et al. (1995) "Patterning of Dielectric Oxide Thin Layers by Microcontact Printing of Self-Assembled Monolayers," *J. Mater. Res.* 10:2996-2999.
Jeon et al. (2003) "Structural and Mechanical Properties of Woven Fabrics Employing Peirce's Model," *Textile Res. J.* 73:929-933.
Jeon et al. (2004) "Fabricating Complex Three-Dimensional Nanostructures with High Resolution Conformable Phase Masks," *Proc. Natl. Acad. Sci. USA* 101:12428-12433.
Jeon et al. (2004) "Three Dimensional Nanofabrication with Arubber Stamps and Conformable Photomasks," *Adv. Mater.* 16:593-600.
Jeon et al. (Aug. 4, 2004) "Three Dimensional Nanofabrication with Rubber Stamps and Conformable Photomasks," *Adv. Mater.* 16(15):1369-1375.
Jiang et a. (Oct. 2, 2007) "Finite Deformation Mechanics in Buckled Thin Films on Compliant Supports," *Proc. Natl. Acad. Sci. USA* 104(40):15607-15612.
Jiang et al. (1999) "Preparation of Macroporous Metal Films from Colloidal Crystals," *J. Am. Chem. Soc.* 121:7957-7958.
Jiang et al. (2002) "Polymer-on-Polymer Stamping: Universal Approaches to Chemically Patterned Surfaces," *Langmuir* 18:2607-2615.
Jiang et al. (2007) "Mechanical Properties of Robust Ultrathin Silk Fibroin Films," *Adv. Funct. Mater.* 17:2229-2237.
Jin et al. (2004) "Scalable Interconnection and Integration of Nanowire Devices Without Registration," *Nano Lett.* 4:915-919.
Jin et al. (2004) "Soft Lithographic Fabrication of an Image Sensor Array on a Curved Substrate," *J. Vac. Sci. Technol. B* 22(5):2548-2551.
Jin et al. (Aug. 2005) "Water-Stable Silk Films with Reduced β-Sheet Content," *Adv. Funct. Mater.* 15(8):1241-1247.
Jin et al. (Web Release Jan. 23, 2004) "Biomaterial Films of *Bombyx mori* Silk Fibroin with Poly(ethylene oxide)," *Biomacromolecules* 5(3):711-717.
Jiyun, C.H. (2003) "Guided Molecular Self-Assembly: A Review of Recent Efforts," *Smart Mater. Struct.* 12:264-271.
Joachim et al. (Nov. 30, 2000) "Electronics Using Hybrid-Molecular and Mono-Molecular Devices," *Nature* 408:541-548.
Johnson et al. (1999) "Ordered Mesoporous Polymers of Tunable Pore Size from Colloidal Silica Templates," *Science* 283:963-965.
Jones et al. (Jul./Aug. 2004) "Stretchable Wavy Metal Interconnects," *J. Vac. Sci. Technol. A* 22(4):1723-1725.
Joo et al. (2006) "Low-Temperature Solution-Phase Synthesis of Quantum Well Structures CdSe Nanoribbons," *J. Am. Chem. Soc.* 128(17):5632-5633.
Jortner et al. (2002) "Nanostructured Advanced Materials Perspectives and Directions," *Pure Appl. Chem.* 74(9):1491-1506.
Joselevich (2002) "Vectorial Growth of Metallic and Semiconducting Single-Wall Carbon Nanotubes," *Nano Lett.*, vol. 2, No. 10, pp. 1137-1141.
Kadish et al. (1988) "Interaction of Fiber Orientation and Direction of Impulse Propagation with Anatomic Barriers in Anisotropic Canine Myocardium," *Circulation.* 78:1478-1494.
Kagan (1999) "Organic-Inorganic Hybrid Materials as Semiconducting Channels in Thin-Film Field-Effect Transistors," *Science* 286:945-947.

(56) References Cited

OTHER PUBLICATIONS

Kagan et al. (2001) "Patterning Organic—Inorganic Thin-Film Transistors Using Microcontact Printed Templates," *Appl. Phys Lett.* 79(21):3536-3538.

Kagan et al. (2003) *Thin Film Transistors*, Dekker, New York, pp. 1-34.

Kane et al. (2000) "Analog and Digital Circuits Using Organic Thin-Film Transistors on Polyester Substrates," *IEEE Electron. Dev. Lett.* 21:534-536.

Kang et al. (2007) "Printed Multilayer Superstructures of Aligned Single-Walled Carbon Nanotubes for Electronic Applications," *Nano Lett.* 7(11):3343-3348.

Kang et al. (Apr. 2007) "High-Performance Electronics Using Dnese, Perfectly aligned Arrays of Single-Walled Carbon Nanotubes," *Nat. Nanotechnol.* 2(4):230-236.

Kar et al. (2005) "Controlled Synthesis and Photoluminescence Properties of ZnS Nanowires and Nanoribbons," *J. Phys. Chem. B* 109(8):3298-3302.

Kar et al. (2005) "Synthesis and Optical Properties of CdS Nanoribbons," *J. Phys. Chem B.* 109(41):19134-19138.

Kar et al. (2006) "Shape Selective Growth of CdS One-Dimensional Nanostructures by a Thermal Evaporation Process," *J. Phys. Chem. B.* 110(10):4542-4547.

Karnik et al. (2003) "Lateral Polysilicon $p^+$-p-$n^+$ and $p^+$-n-$n^+$ Diodes," *Solid-State Electronics* 47:653-659.

Karnik et al. (2003) "Multiple Lateral Polysilicon Diodes as Temperature Sensors for Chemical Microreaction Systems," *Jpn. J. Appl. Phys.* 42:1200-1205.

Kato et al. (2004) The Characteristic Improvement of Si(111) Metal-Oxide-Semiconductor Field-Effect Transistor by Long-Time Hydrogen Annealing, *Jpn. J. Appl. Phys.* 43(10):6848-6853.

Katz et al. (2001) "Synthetic Chemistry for Ultrapure, Processable, and High-Mobility Organic Transistor Semiconductors," *Acc. Chem. Res.* 34:359-369.

Katz, H.E. (2004) "Recent Advances in Semiconductor Performance and Printing Processes for Organic Transistor-Based Electronics," *Chem. Mater.* 16:4748-4756.

Kawata et al. (2001) "Finer Features for Functional Microdevices," *Nature* 412:697-698.

Kellis et al. (2009) "Human Neocortical Electrical Activity Recorded on Nonpenetrating Microwire Arrays: Applicability for Neuroprostheses," *Neurosurg. Focus* 27(1):E9.

Kendall, D.L. (1979) "Vertical Etching of Silicon at Very High Apect Ratios," *Ann. Rev. Mater. Sci.* 9:373-403.

Khakani et al. (2006) "Lateral Growth of Single Wall Carbon Nanotubes on Various Substrates by Means of an 'All-Laser' Synthesis Approach," *Diamond Relat. Mater.* 15:1064-1069.

Khan et al. (1993) "High Electron Mobility Transistor Based on a GaN—$Al_xGa_{1-x}$N Heterojunction," *Appl. Phys. Lett.* 63:1214-1215.

Khang et al. (2006) "A Stretchable Form of Single-Crystal Silicon for High-Performance Electronics on Rubber Substraights," *Science* 311:208-212.

Kilby, J.S. (1976) "Invention of the Integrated Circuit," *IEEE Trans. Electron. Dev.* 23:648-654.

Kim et al. (2000) "Field Emission from Carbon Nanotubes for Displays," *Diamond and Related Mater.* 9(3-6):1184-1189.

Kim et al. (2002) "Nanolithography Based on Patterned Metal Transfer and Its Application to Organic Electronic Devices," *Appl. Phys. Lett.* 80:4051-4053.

Kim et al. (2003) "Epitaxial Self-Assembly of Block Copolymers on Lithographically Defined Nanopatterned Substrates," *Nature* 424:411-414.

Kim et al. (2008) "Stretchable Electronics: Materials Strategies and Devices," *Adv. Mater.* 20:4887-4892.

Kim et al. (2009) "Integrated Wireless Neural Interface Based on the Utah Electrode array," *Biomed. Microdevices* 11:453-466.

Kim et al. (2009) "Optimized Structural Designs for Stretchable Silicon Integrated Circuits," *Small* 5(24):2841-2847.

Kim et al. (Apr. 25, 2008) "Stretchable and Foldable Silicon Integrated Circuits," *Science* 320:507-511.

Kim et al. (Dec. 2, 2008) "Materials and Noncoplanar Mesh Designs for Integrated Circuits with Linear Elastic Responses to Extreme Mechanical Deformations," *Proc. Natl. Acad. Sci. USA* 105(48):18675-18680.

Kim et al. (Jan. 2008) "Complementary Logic Gates and Ring Oscillators Plastic Substrates by Use of Printed Ribbons Single-Crystalline Silicon," *IEEE Electron. Dev. Lett.* 29(1):73-76.

Kim et al. (Nov. 15, 1999) "Direct Observation of Electron Emission Site on Boron-Doped Polycrystalline Diamond Thin Films Using an Ultra-High-Vacuum Scanning Tunneling Microscope," *Appl. Phys. Lett.* 75(20):3219-3221.

Kim et al. (Oct. 17, 2010) "Waterproof AllnGaP optoelectronics on stretchable substrates with applications in biomedicine and robotics," *Nature Materials* 9:929-937.

Kim et al. (Oct. 2004) "Organic TFT Array on a Paper Substrate," *IEEE Electron. Dev. Lett.* 25(10):702-704.

Kim et al. (Web Release Apr. 18, 2010) "Dissolvable Films of Silk Fibroin for Ultrathin Conformal Bio-Integrated Electronics," *Nature Materials* 9:511-517.

Kim et al. (Web Release Feb. 29, 2008) "Highly Emissive Self-Assembled Organic Nanoparticles Having Dual Color Capacity for Targeted Immunofluorescence Labeling," *Adv. Mater.* 20(6):1117-1121.

Kim et al. (Web Release Jul. 31, 2008) "Complementary Metal Oxide Silicon Integrated Circuits Incorporating Monolithically Integrated Stretchable Wavy Interconnects," *Appl. Phys. Lett.* 93(4):044102.

Kim et al. (Web Release Jul. 6, 2009) "Ultrathin Silicon Circuits with Strain-Isolation Layers and Mesh Layouts for High-Performance Electronics on Fabric, Vinyl, Leather and Paper," *Adv. Mater.* 21(36):3703-3707.

Kim et al. (Web Release Sep. 29, 2009) "Silicon Electronics on Silk as a Path to Bioresorbable, Implantable Devices," *Appl. Phys. Lett.* 95:133701-133703.

Kim, Y.S. (Web Release Aug. 9, 2005) "Microheater-Integrated Single Gas Sensor Array Chip Fabricated on Flexible Polyimide Substrate," *Sens. Actuators B* 114(1)410-417.

Klauk et al. (2002) "High-Mobility Polymer Gate Dielectric Pentacene Thin Film Transistors," *J. Appl. Phys.* 92:5259-5263.

Klein-Wiele et al. (2003) "Fabrication of Periodic Nanostructures by Phase-Controlled Multiple-Beam Interference," *Appl. Phys. Lett.* 83(23):4707-4709.

Knipp et al. (2003) "Pentacine Thin Film Transistors on Inorganic Dielectrics: Morphology, Structural Properties, and Electronic Transport," *Appl. Phys. Lett.* 93:347-355.

Ko et al. (2006) "Bulk Quantities of Single-Crystal Silicon Micro-/Nanoribbons Generated from Bulk Wafers," *Nano Lett.* 6(10):2318-2324.

Ko et al. (2010) "Flexible Carbon Nanofiber Connectors with Anisotropic Adhesion Properties," *Small* 6:22-26.

Ko et al. (Aug. 7, 2008) "A Hemispherical Electronic Eye Camera Based on Compressible Silicon Optoelectronics," *Nature* 454:748-753.

Ko et al. (Web Release Oct. 28, 2009) "Curvilinear Electronics Formed Using Silicon Membrane Circuits and Elastomeric Transfer Elements," *Small* 5(23):2703-2709.

Kocabas et al. (2004) "Aligned Arrays of Single-Walled Carbon Nanotubes Generated from Random Networks by Orientationally Selective Laser Ablation," *Nano Lett.*, vol. 4, No. 12, pp. 2421-2426.

Kocabas et al. (2005) "Guided Growth of Large-Scale, Horizontally Aligned Arrays of Single-Walled Carbon Nanotubes and Their Use in Thin-Film Transstors," *Small* 1(11):1110-1116.

Kocabas et al. (2006) "Large Area Aligned Arrays of SWNTs for High Performance Thin Film Transistors," American Physical Society, APS March Meeting, Mar. 13-17, Abstract # W31.004.

Kocabas et al. (2006) "Spatially Selective Guided Growth of High-Coverage Arrays and Random Networks of Single-Walled Carbon Nanotbes and Thir Integration into Electronic Devices," *J. Am. Chem. Soc.* 128:4540-4541.

Kocabas et al. (2007) "Experimental and Theoretical Studies of Transport Through Large Scale, Partially Aligned Arrays of Single-Walled Carbon Nanotubes ni Thin Film Type Transistors," *Nano Lett.* 7(5):1195-1202.

(56) References Cited

OTHER PUBLICATIONS

Kocabas et al. (Feb. 5, 2008) "Radio Frequency Analog Electronics Based on Carbon Nanotube Transistors," *Proc. Natl. Acad. Sci. USA* 105(5):1405-1409.
Kodambaka et al. (2006) "Control of Si Nanowire Growth by Oxygen," *Nano Lett.* 6(6):1292-1296.
Koide et al. (2000) "Patterned Luminescence of Organic Light-Emitting Diodes by Hot Microcontact Printing (H$\mu$CP) of Self-Assembled Monolayers," *J. Am. Chem. Soc.* 122:11266-11267.
Konagai et al. (1978) "High Efficiency GaAs Thin Film Solar Cells by Peeled Film Technology," *J. Cryst. Growth* 45:277-280.
Kong et al. (2004) "Single-Crystal Nanorings Formed by Epitaxial Self0Coating of Polar Nanobelts," *Science* 303:1348-1351.
Kong et al. (Jan. 28, 2000) "Nanotube Molecular Wires as Chemical Sensors," *Science* 287:622-625.
Kong et al. (Oct. 2003) "Structure of Indium Oxide Nanobelts," *Solid State Commun.* 128(1):1-4.
Kong et al. (Oct. 29, 1998) "Synthesis of Individual Single-Walled Carbon Nonotubes on Patterned Silicon Wafers," *Nature* 395:878-881.
Kudo et al. (Web Release Jun. 13, 2006) "A Flexible and Wearable Glucose Sensor Based on Functional Polymers with Soft-Mems Techniques," *Biosens. Bioelectron.* 22:558-562.
Kulkarni et al. (2002) "Mesoscale Organization of Metal Nanocrystals," *Pure Appl. Chem* 74(9):1581-1591.
Kumar et al. (1993) "Features of Gold Having Micrometer to Centimeter Dimensions can be Formed Through a Combination of Stamping with an Elastomeric Stamp and an Alkanethiol "Ink" Followed by Chemical Etching," *Appl. Phys. Lett.* 63(4):2002-2004.
Kumar et al. (1994) "Patterning Self-Assembled Monolayers: Applications in Materials Science," *Langmuir* 10:1498-1511.
Kumar et al. (2002) "Thermally-Stable Low-Resistance Ti/Al/Mo/Au Multilayer Ohmic Contacts on n-GaN," *J. Appl. Phys.* 92:1712-1714.
Kumar et al. (2005) "Percolating in Finite Nanotube Networks," *Phys. Rev. Lett.*, 95, 066802.
Kuo et al. (1985) "Effect of Mismatch Strain on Band Gap in III-V Semiconductors," *J. Appl. Phys.* 57:5428-5432.
Kuykendall et al. (Aug. 2004) "Crystallographic Alignment of High Density Gallium Nitride Nanowire Arrays," *Nat. Mater.* 3:524-528.
Lacour et al. (2005) "Stretchable Interconnects for Elastic Electronic Surfaces," *Proc. IEEE* 93:1459-1467.
Lacour et al. (2010) "Flexible and Stretchable Micro-Electrodes for in Vitro and n Vivo Neural Interfaces," *Med. Biol. Eng. Comput.* 48:945-954.
Lacour et al. (Apr. 14, 2003) "Stretchable Gold Conductors on Elastomeric Substrates," *Appl. Phys. Lett.* 82(15):2404.
Lacour et al. (Apr. 2004) "Design and Performance of Thin Metal Film Interconnects for Skin-Like Electronic Circuits," *IEEE Electron. Dev. Lett.* 25(4):179-181.
Lacour et al. (Dec. 2004) "An Elastically Stretchable TFT Circuit," *IEEE Electron Dev. Lett.* 25(12):792-794.
Lacour et al. (Web Release Jul. 14, 2006) "Stiff Subcircuit Islands of Diamondlike Carbon for Stretchable Electronics," *J. Appl. Phys.* 100:014913.
Lacour et al. (Web Release May 16, 2006) "Mechanisms of Reversible Stretchability of Thin Metal Films on Elastomeric Substrates," *Appl. Phys. Lett.* 88:204103.
Laimer et al. (Mar. 1997) "Diamond Growth in a Direct-Current Low-Pressure Supersonic Plasmajet," *Diamond Relat. Mater.* 6:406-410.
Lambacher et al. (2004) "Electrical Imaging of Neuronal Activity by Multi-Transistor-Array (MTA) Recording at 7.8 μm Resolution," *Appl. Phys. A* 79:1607-1611.
Landes et al. (2002) "Some Properties of Spherical and Rod-Shaped Semiconductor and Metal Nanocrystals," *Pure Appl. Chem.* 74(9):1675-1692.
Law et al. (2004) "Semiconductor Nanowires and Nanotubes," *Ann. Rev. Mater. Res.* 34:83-122.
Law et al. (Aug. 27, 2004) "Nanoribbon Waveguides for Subwavelength Photonics Integration," *Science* 305:1269-1273.
Lawrence et al. (2008) "Bioactive Silk Protein Biomaterial Systems for Optical Devices," *Biomacromolecules* 9:1214-1220.
Lay et al. (2004) "Simple Route to Large-Scale Ordered Arrays of Liquid-Deposited Carbon Nanotubes," *Nano Lett.*, vol. 4, No. 4, pp. 603-606.
Leclercq et al. (1998) "III-V Micromachined Devices for Microsystems," *Microelectronics J.* 29:613-619.
Lecomte et al. (Apr. 2006) "Degradation Mechanism of Diethylene Glycol Units in a Terephthalate Polymer," *Polym. Degrade. Stab.* 91(4):681-689.
Lee et al. (2000) "Thin Film Transistors for Displays on Plastic Substrates," *Solid State Electron.* 44:1431-1434.
Lee et al. (2003) "High-Performance Poly-Si TFTs on Plastic Substrates Using a Nano-Structured Separation Layer Approach," *IEEE Elec. Dev. Lett.* 24:19-21.
Lee et al. (2004)"Organic Light-Emitting Diodes Formed by Soft Contact Lamination," *Proc. Natl. Acad. Sci. USA* 101(2):429-433.
Lee et al. (2005) "A Printable Form of Single-Crystalline Gallium Nitride for Flexable Optoelectronic Systems," *Small* 1:1164-1168.
Lee et al. (2005) "Large-Area, Selective Transfer of Microstructured Silicon (μs-Si): A Printing-Based Approach to High-Performance Thin0Film Transistors Supported on Flexible Substraights," *Adv. Mater.* 17:2332-2336.
Lee et al. (2006) "Micron and Submicron Patterning of Polydimethylsiloxane Resists on Electronic Materials by Decal Transfer Lithography and Reactive Ion-Beam Etching: Application to the Fabrication of High-Mobility, Thin-Film Transistors," *Appl. Phys. Lett.* 100:084907/1-7.
Lee et al. (Apr. 2005) "Fabrication of Stable Metallic Patterns Embedded in Poly(dimethylsiloxane) and Model Applications in Non-Planar Electronic and Lab-on-a-Chip Device Patterning," *Adv. Funct. Mater.* 15(4):557-566.
Lee et al. (Dec. 1999) "The Surface/Bulk Micromachining (SBM) Process: A New Method for Fabricating Released MEMS in Single Crystal Silicon," *J. Microelectromech. Syst.* 8(4):409-416.
Lee et al. (Feb. 2001) "Application of Carbon Nanotubes to Field Emission Displays," *Diamond and Related Mater.* 10(2):265-270.
Lee et al. (Feb. 2005) "Weave Patterned Organic Transistors on Fiber for E-Textiles," *IEEE Trans. Electron. Dev.* 52(2):269-275.
Leong et al. (2009) "Tetherless Thermobiochemicall Actuated Microgrippers," *Proc. Natl. Acad. Sci. USA* 106:703-709.
Létant et al. (Jun. 2003) "Functionalized Silicon Membranes for Selective Bio-Organisms Capture," *Nat. Mater.* 2:391-395.
Li et al. (2002) "High-Resolution Contact Printing with Dendrimers," *Nano Lett.* 2(4):347-349.
Li et al. (2003) "Ultrathin Single-Crystalline-Silicon Cantilever Resonators: Fabrication Technology and Significant Specimen Size effect on Young's Modulus," *Appl. Phys. Lett.* 83:3081-3083.
Li et al. (2004) "Electrospinning of Nanofibers: Reinventing the Wheel," *Adv. Mater.* 16(14):1151-1170.
Li et al. (2006) "Catalyst-Assisted Formation of Nanocantilever Arrays on ZnS Nanoribbons by Post-Annealing Treatment," *J. Phys. Chem. B* 110(13):6759-6762.
Li et al. (Dec. 2005) "Compliant Thin Film Patterns of Stiff Materials as Platforms for Stretchable Electronics," *J. Mater. Res.* 20(12):3274-3277.
Li et al. (Jul. 1, 2002) "ZnO Nanobelts Grown on Si Substrate," *Appl. Phys. Lett.* 81:144-146.
Lieber, C. (2001) "The Incredible Shrinking Circuit," *Sci. Am.* 285(3):58-64.
Lieber, C.M. (2003) "Nanoscale Science and Technology: Building a Bog Future from Small Things," *MRS. Bull.* 28:486-491.
Lim et al. (2005) "Flexible Membrane Pressure Sensor," *Sens. Act. A* 119:332-335.
Lima et al. (2007) "Creating Micro- and Nanostructures on Tubular and Spherical Surfaces," *J. Vac. Sci. Technol. B* 25(6):2412-2418.
Lin et al. (Sep. 2005) "High-Performance Carbon Nanotube Field-Effect Transistor With Tunable Polarities," *IEEE Trans. Nano* 4(5):481-489.

(56) References Cited

OTHER PUBLICATIONS

Linder et al. (1994) "Fabrication Technology for Wafer Through-Hole Interconnections and Three-Dimensional Stacks of Chips and Wafers," *Proc. IEEE Micro. Electro Mech. Syst.* 349-354.
Ling et al. (2004) "Thin Film Deposition, Patterning, and Printing in Organic Thin Film Transistors," *Chem. Mater.* 16:4824-4840.
Liu et al. (1999) "Controlled deposition of individual single-walled carbon nanotubes on chemically functionalized templates," *Chem. Phys. Lett.*, 303:125-129.
Long et al. (1990) "Heterostructure FETs and Bipolar Transistors," In; *Gallium Arsenide Digital Integrated Circuit Design*, McGraw-Hill, New York, pp. 58-69.
Loo et al. (2002) "Additive, Nanoscale Patterning of Metal Films with a Stamp and A Surface Chemistry Mediated Transfer Process: Applications in Plastic Electronics," *Appl. Phys. Lett.* 81:562-564.
Loo et al. (2002) "High-Resolution Transfer Printing on GaAs Surfaces Using Alkane Dithiol Monolayers," *J. Vac. Sci. Technol. B* 20(6):2853-2856.
Loo et al. (2002) "Interfacial Chemistries for Nanoscale Transfer Printing," *J. Am. Chem. Soc.* 124:7654-7655.
Loo et al. (2002) "Soft, Conformable Electrical Contacts for Organic Semiconductors: High-Resolution Plastic Circuits by Lamination," *Proc. Natl. Acad. Sci. USA* 99(16):10252-10256.
Loo et al. (2003) "Electrical Contacts to Molecular Layers by Nanotransfer Printing," *Nano Lett.* 3(7):913-917.
Lopes et al. (Sep. 2004) "Thermal Conductivity of PET/(LDPE/Al) Composites Determined by MDSC," *Polym. Test.* 23(6):637-643.
Lu et al. (Apr. 2010) "Water-Insoluble Silk Films with Silk I Structure," *Acta Biomater.* 6(4):1380-1387.
Lu et al. (Dec. 2006) "Electronic Materials-Buckling Down for Flexible Electronics," *Nat. Nanotechnol.* 1:163-164.
Lu et al. (Jul. 19, 2005) "One Dimensional Hole Gas in Germanium/Silicon Nanowire Heterostructures," *Proc. Nat. Acad. Sci. USA* 102(29):10046-10051.
Lu et al. (Nov. 2008) "Nanowire Transistor Performance Limits and Applications," *IEEE Trans Electron Dev.* 55(11):2859-2876.
Luan et al. (1992) "An Experimental Study of the Source/Drain Parasitic Resistance Effects in Amorphous Silicon Thin Film Transistors," *J. Appl. Phys.* 72:766-772.
Ma et al. (2004) "Single-Crystal CdSe Nanosaws," *J. Am. Chem. Soc.* 126(3):708-709.
Mack et al. (2006) "Mechanically Flexible Thin-Film Transistors that Use Ultrathin Ribbons of Silicon Derived from Bulk Wafers," *Appl. Phys. Lett.* 88:213101.
Madou, M. (1997) "Etch-Stop Techniques," In; *Fundamentals of Microfabrication*, CRC Press, New York, pp. 193-199.
Maikap et al. (2004) "Mechanically Strained-Si NMOSFETs," *IEEE Electron. Dev. Lett.* 25:40-42.
Maldovan et al. (2004) "Diamond-Structured Photonic Crystals," *Nature Materials* 3:593-600.
Mandlik et al. (Aug. 2006) "Fully Elastic Interconnects on Nanopatterned Elastomeric Substrates," *IEEE Electron Dev. Lett.* 27(8):650-652.
Manna et al. (Web Release May 25, 2003) "Controlled Growth of Tetrapod-Branched Inorganic Nanocrystals," *Nat. Mater.* 2:382-385.
Markovich et al. (1999) "Architectonic Quantum Dot Solids," *Acc. Chem. Res.* 32:415-423.
Marquette et al. (2004) "Conducting Elastomer Surface Texturing: A Path to Electrode Spotting Application to the Biochip Production," *Biosens. Bioelectron.* 20:197-203.
Martensson et al. (2004) "Nanowire Arrays Defined by Nanoimprint Lithography," *Nano Lett.* 4:699-702.
Martin, C.R. (1995) "Template Synthesis of Electronically Conductive Polymer Nanostructures," *Acc. Chem. Res.* 28:61-68.
Mas-Torrent et al. (2006) "Large Photoresponsivity in High-Mobility Single-Crystal Organic Field-Effect Phototransistors," *ChemPhysChem* 7:86-88.
Masuda et al. (2000) "Fabrication of Ordered Diamonds/Metal Nanocomposite Structures," *Chem. Lett.* 10:1112-1113.

Matsunaga et al. (2003) "An Improved GaAs Device Model for the Simulation of Analog Integrated Circuit," *IEEE Trans. Elect. Dev.* 50:1194-1199.
McAlpine et al. (2003) "High-Performance Nanowire Electronics and Photonics on Glass and Plastic Substrates," *Nano Lett.* 3:1531-1535.
McAlpine et al. (2005) "High-Performance Nanowire Electronics and Photonics and Nanoscale Patterning on Flexible Plastic Substrates," *Proc. IEEE* 93:1357-1363.
McCaldin et al. (1971) "Diffusivity and Solubility of Si in the Al Metallization of Integrated Circuits," *Appl. Phys. Lett.* 19:524-517.
Mehring C. et al. (2003) Inference of hand movements from local field potentials in monkey motor cortex. *Nature Neurosci.* 6, 1253-1254.
Meisel et al. (2004) "Three-Dimensional Photonic Crystals by Holographic Lithography Using the Umbrella Configuration: Symmetries and Complete Photonic Band Gaps," *Phys. Rev. B.* 70:165101:1-10.
Meitl et al. (2004) "Solution Casting and Transfer Printing Single-Walled Carbon Nanotube Films," *Nano Lett.* 4:1643-1947.
Meitl et al. (2006) "Transfer Printing by Kinetic Control of Adhesion to an Elastomeric Stamp," *Nat. Mater.* 5:33-38.
Meitl et al. (Web Release Feb. 22, 2007) "Stress Focusing for Controlled Fracture in Microelectromechanical Systems," *Appl. Phys. Lett.* 90:083110.
Melosh et al. (2003) "Ultrahigh-Density Nanowire Lattices and Circuits," *Science* 300:112-115.
Menard et al. (2004) "A Printable Form of Silicon for High Performance Thin Film Transistors on Plastic Substrates," *Appl. Phys. Lett.* 84:5398-5400.
Menard et al. (2004) "Improved Surface Chemistries, Thin Film Deposition Techniques, and Stamp Designs for Nanotransfer Printing," *Langmuir* 20:6871-6878.
Menard et al. (2004) "High-Performance n- and p-Type Single-Crystal Organic Transistors with Free-Space Gate Dielectrics," *Adv. Mat.* 16:2097-2101.
Menard et al. (2005) "Bendable Single Crystal Silicon Thin Film Transistors Formed by Printing on Plastic Substrates," *Appl. Phys. Lett.* 86(093507):1-3.
Miao et al. (2003) "Micromachining of Three-Dimensional GaAs Membrane Structures Using High-Energy Nitrogen Implantation," *J. Micromech. Microeng.* 13:35-39.
Michel et al. (2001) Printing Meets Lithography: Soft Approaches to High-Resolution Printing, *IBM J. Res. Dev.* 45:697-719.
Miller et al. (2002) "Direct Printing of Polymer Microstructures on Flat and Spherical Surfaces Using a Letterpress Technique," *J. Vac. Sci. Technol. B* 20(6):2320-2327.
Milliron et al. (2004) "Colloidal Nanocrystal Heterostructures with Linear and Branched Topology," *Nature* 430:190-195.
Min, G. (Apr. 4, 2003) "Plastic Electronics and Their Packaging Technologies," *Syn. Metals.* 135:141-143.
Minev et al. (2010) "Impedance Spectroscopy on Stretchable Microelectrode Arrays," *Appl. Phys. Lett.* 97:043707.
Mirkin et al. (2001) "Emerging Methods for Micro- and Nanofabrication," *MRS Bulletin* 26(7):506-507.
Misewich et al. (May 2, 2003) "Electronically Induced Optical Emission from a Carbon Nanotube FET," *Science* 300:783-786.
Mishra et al. (2002) "AlGaN/GaN HEMTs—an Overview of Device Operation and Applications," *Proc. IEEE* 90:1022-1031.
Mitzi et al. (2004) "High-Mobility Ulltrathin Semiconducting Films Prepared by Spin Coating," *Nature* 428:299-303.
Moon et al. (2002) "Ink-Jet Printing of Binders for Ceramic Components," *J. Am. Ceram. Soc.* 85:755-762.
Moore et al. (Sep. 9, 2003) "Individually Suspended Single-Walled Carbon Nanotubes in Various Surfactants," *Nano Lett.* 3(10):1379-1382.
Morales et al. (Jan. 9, 1998) "A Laser Ablation Method for the Synthesis of Crystalline Semiconductor Nanowires," *Science* 279:208-211.
Morent et al. (2007) "Adhesion Enhancement by a Dielectric Barrier Discharge of PDMS used for Flexible and Stretchable Electronics," *J. Phys. D. Appl. Phys.* 40:7392-7401.

(56) References Cited

OTHER PUBLICATIONS

Mori et al. (1978) "A New Etching Solution System, $H_3PO_4$—$H_2O_2$—$H_2O$, for GaAs and Its Kinetics," *J. Electrochem. Soc.* 125:1510-1514.
Morkoc et al. (1995) "High-Luminosity Blue and Blue-Green Gallium Nitride Light-Emitting Diodes," *Science* 267:51-55.
Morkved et al. (1994) "Mesoscopic Self-Assembly of Gold Islands on Diblock-Copolymer Films," *Appl. Phys. Lett.* 64:422-424.
Morra et al. (1990) "On the Aging of Oxygen Plasma-Treated Polydimthylsiloxane Surfaces," *J. Colloid Interface Sci.* 137:11-24.
Murakami et al. (2005) "Polarization Dependence of the Optical Absorption of Single-Walled Carbon Nanotubes," *Phys. Rev. Lett.*, 94, 087402.
Murphy et al. (2008) "Modification of Silk Fibroin Using Diazonium Coupling Chemistry and the Effects on hMSC Proliferation and Differentiation," *Biomaterials* 29:2829-2838.
Namazu et al. (2000) "Evaluation of Size Effect on Mechanical Properties of Single Crystal Silicon by Nanoscale Bending Test Using AFM," *J. MEMS* 9:450-459.
Nath et al. (2002) "Nanotubes of the Disulfides of Groups 4 and 5 Metals," *Pure Appl. Chem.* 74(9):1545-1552.
Nathan et al. (2000) "Amorphous Silicon Detector and Thin Film Transistor Technology for Large-Area Imaging of X-Rays,." *Microelectron J.* 31:883-891.
Nathan et al. (2002) "Amorphous Silicon Technology for Large Area Digital X-Ray and Optical Imaging," *Microelectronics Reliability* 42:735-746.
Newman et al. (2004) "Introduction to Organic Thin Film Transistors and Design of n-Channel Organic Semiconductors," *Chem. Mater.* 16:4436-4451.
Nirmal et al. (1999) "Luminescence Photophysics in Semiconductor Nanocrystals," *Acc. Chem. Res.* 32:407-414.
Noda et al. (1996) "New Realization Method for Three-Dimensional Photonic Crystal in Optical Wavelength Region," *Jpn. J. Appl. Phys.* 35:L909-L912.
Nomura et al. (2004) "Room-Temperature Fabrication of Transparent Flexible Thin-Film Transistors Using Oxide Semiconductors," *Nature* 432:488-492.
Novoselov et al. (Oct. 22, 2004) "Electric Field Effect in Atomically Thin Carbon Films," *Science* 306:666-669.
O'Connell et al. (Jul. 26, 2002) "Bang Gap Fluorescence from Individual Single-Walled Caarbon Nanotubes," *Science* 297:593-596.
O'Riordan et al. (2004) "Field Configured Assembly: Programmed Manipulation and Self-Assembly at the Mesoscale," *Nano Lett.* 4:761-765.
Odom et al. (2002) "Improved Pattern Transfer in Soft Lithography Using Composite Stamps," *Langmuir* 18(13):5314-5320.
Office Action and Response, Corresponding to Malaysian Patent Publication No. PI 20052553, dated Mar. 13, 2009 and Dec. 8, 2009.
Office Action and Response, Corresponding to U.S. Appl. No. 11/423,287, dated Feb. 13, 2008.
Office Action and Response, Corresponding to U.S. Appl. No. 11/421,654, dated Sep. 29, 2009.
Office Action and Response, Corresponding to U.S. Appl. No. 11/858,788, dated Jan. 28, 2011.
Office Action Corresponding to Chinese Patent Application No. 200780049982.1, dated May 12, 2010.
Office action Corresponding to Korean Patent Application No. 10-2006-7010632, Completed Nov. 22, 2007.
Office Action Corresponding to U.S. Appl. No. 11/851,182, dated Apr. 1, 2010.
Office Action, Corresponding to Chinese Patent Application No. 200780048002.6, dated Apr. 13, 2010.
Office Action, Corresponding to Chinese Patent Application No. 200580013574.1, dated May 11, 2010.
Office Action, Corresponding to Taiwan Patent Application No. 095121212, dated May 7, 2010.
Office Action, Corresponding to U.S. Appl. No. 11/981,380, dated Sep. 23, 2010.
Office Actions and Responses, Corresponding to U.S. Appl. No. 11/145,542, dated Apr. 5, 2007 and Dec. 23, 2008.
Office Actions and Responses, Corresponding to U.S. Appl. No. 11/981,380, dated Sep. 23, 2010.
Office Actions Corresponding to Chinese Patent Application No. 200480035731.4, dated Mar. 27, 2009 and Dec. 3, 2010.
Office Actions, Corresponding to Chinese Patent Application No. 200580018159.5, dated Jan. 23, 2009 and Feb. 12, 2010.
Office Action Corresponding to Chinese Patent Application No. 200780041127.6, dated Apr. 8, 2011.
Office Action Corresponding to Chinese Patent Application No. 201010519400.5 dated Nov. 3, 2011.
Ohzono et al. (2004) "Ordering of Microwrinkle Patterns by Compressive Strain," *Phys. Rev. B* 69(13):132202.
Ohzono et al. (Web Release Jul. 7, 2005) "Geometry-Dependent Stripe Rearrangement Processes Induced by Strain on Preordered Microwrinkle Patterns," *Langmuir* 21(16):7230-7237.
Omenetto et al. (2008) "A New Route for Silk," *Nature Photon.* 2:641-643.
Ong et al. (2004) "High-Performance Semiconducting Poolythiophenes for Organic Thin-Film Transistors," *J. Am. Chem. Soc.* 126:3378-3379.
Ong et al. (2005) "Design of High-Performance Regioreular Polythiophenes for Organic Thin-Film Transistors," *Proc. IEEE* 93:1412-1419.
Origin Energy (May 2004) "Fact Sheet—Sliver Cells,".
Ouyang et al. (2002) "High-Performance, Flexible Polymer Light-Emitting Diodes Fabricated by a Continuous Polymer Coating Process," *Adv. Mat.* 14:915-918.
Ouyang et al. (2008) "High Frequency Properties of Electro-Textiles for Wearable Antenna Applications," *IEEE Trans. Antennas Propag.* 56(2):381-389.
Ouyang et al. (Web Release Mar. 20, 2000) "Conversion of Some Siloxane Polymers to Silicon Oxide by UV/Ozone Photochemical Processes," *Chem. Mater.* 12(6):1591-1596.
Overholt et al. (2005) "Photodynamic Therapy for Esophageal Cancer using a 180° Windowed Esophageal Balloon," *Lasers in Surg. Med.* 14:27-33.
Pan et al. (2001) "Nanobelts of Semiconducting Oxides," *Science* 291:1947-1949.
Panev et al. (2003) "Sharp Excitation from Single InAs Quantum Dots in GaAs Nanowires," *Appl. Phys. Lett.* 83:2238-2240.
Pardo et al. (2000) "Application of Screen Printing in the Fabrication of Organic Ligh-Emitting Devices," *Adv. Mater.* 12(17):1249-1252.
Park et al. (1997) "Block Copolymer Lithography: Periodic Arrays of ~$10^{11}$ Holes in 1 Square Centimeter," *Science* 276:1401-1404.
Park et al. (1998) "Fabrication of Three-Dimensional Macroporous Membranes with Assemblies of Microspheres as templates," *Chem. Mater.* 10:1745-1747.
Park et al. (Aug. 2009) "Printed Assemblies of Inorganic Light-Emitting Diodes for Deformable and Semitransparent Displays," *Science* 325:977-981.
Park et al. (Web Release Feb. 22, 2009) "Biodegradable Luminescent Porous Silicon Nanoparticles for *in Vivo* Applications," *Nature Mater.* 8:331-336.
Parker et al. (2009) "Biocompatible Silk Printed Optical Waveguides," *Adv. Mater.* 21:2411-2415.
Patolsky et al. (2006) "Stimulation, and Inhibition of Neuronal Signals with High-Density Nanowire Transistor Arrays," *Science* 313:1100-1104.
Patton et al. (Mar. 1998) "Effect of Diamond like Carbon Coating and Surface Topography on the Performance of Metal Evaporated Magnetic Tapes," *IEEE Trans Magn.* 34(2):575-587.
Paul et al. (Apr. 2003) "Patterning Spherical Surfaces at the Two Hundred Nanometer Scale Using Soft Lithography," *Adv. Func. Mater.* 13(4):259-263.
Pearton et al. (1999) "GaN: Processing, Defects, and Devices," *J. Appl. Phys.* 86:1-78.
Peng et al. (Mar. 2, 2000) "Shape Control of CdSe Nanocrystals," *Nature* 404:59-61.

(56) References Cited

OTHER PUBLICATIONS

Perry et al. (2008) "Nano- and Micropatterning of Optically Transparent, Mechanically Robust, Biocompatible Silk Fibroin Films," *Adv. Mater.* 20:3070-3072.
Piazza et al. (2005) "Protective Diamond-Like Carbon Coatings for Future Optical Storage Disks," *Diamond Relat. Mater.* 14:994-999.
Pimparkar et al. (Feb. 2007) "Current-Voltage Characteristics of Long-Channel Nanobundle Thin-Film Transistors: A 'Bottom-Up' Perspective," *IEEE Electron Dev. Lett.* 28(2):157-160.
Podzorov et al. (2005) "Hall Effect in the Accumulation Layers on the Surface of Orgaic Semiconductors," *Phys. Rev. lett.* 95:226601.
Pushpa et al. (2002) "Stars and Stripes. Nanoscale Misfit Dislocation Patterns on Surfaces," *Pure Appl. Chem.* 74(9):1663-1671.
Qian et al. (2006) "Scaling Effects of Wet Adhesion in Biological Attachment Systems," *Acta Biomaterialia* 2:51-58.
Quake et al (2000) "From Micro- to Nanofabrication with Soft Materials," *Science* 290:1536-1540.
Radtke et al. (Feb. 5, 2007) "Laser-Lithography on Non-Planar Surfaces," *Opt. Exp.* 15(3):1167-1174.
Raman et al. (1989) "Study of Mesa Undercuts Produced in GaAs with $H_3PO_4$-Based Etchants," *J. Electrochem. Soc.* 136:2405-2410.
Randall et al. (2005) "Permeation-driven flow in poly(dimethylsiloxane) microfluidic devices," *Proc. Nat. Acad. Sci. USA* 102(31):10813-10818.
Rao et al. (2003) "Large-scale assembly of carbon nanotubes," *Nature*, 425:36-37.
Razavi et al. (2009) "Three Dimensional Nanopillar Array Photovoltaics on Low Cost and Flexible Substrates," *Nature Materials* 8:648-653.
Razeghi et al. (1994) "High-Power Laser Diode Based on in GaAsP Alloys," *Nature* 369:631-633.
Razouk et al. (Sep. 1979) "Dependence of Interface State Density on Silicon Thermal Oxidation Process Variables," *J. Electrochem. Soc.* 126(9):1573-1581.
Reuss et al. (Jul. 2005) "Macroelectronics: Perspectives on Technology and Applications," *Proc. IEEE* 93(7):1239-1256.
Reuss et al. (Jun. 2006) "Macroelectronics," *MRS Bull.* 31:447-454.
Ribas et al. (1998) "Bulk Micromachining Characterization of 1.2 μm HEMT MMIC Technology for GaAs MEMS Design," *Mater. Sci. Eng. B* 51:267-273.
Ridley et al. (1999) "All-Inorganic Field Effect Transistors Fabricated by Printing," *Science* 286:746-749.
Roberts et al. (1979) "Looking at Rubber Adhesion," *Rubber Chem. Technol.* 52:23-42.
Roberts et al. (Mar. 2006) "Elastically Relaxed Free-Standing Strained-Silicon Nanomembranes," *Nat. Mater.* 5:388-393.
Robinson et al. (1983) "GaAs Readied for High-Speed Microcircuits," *Science* 219:275-277.
Roelkens et al. (Dec. 2005) "Integration of InP/InGaAsP Photodetectors onto Silicon-on-Insulator Waveguide Circuits," *Optics Express* 13(25):10102-10108.
Rogers et al. (1997) "Using an Elastomeric Phase Mask for Sub-100 nm Photolithography in the Optical Near Field," *Appl. Phys. Lett.* 70:2658-2660.
Rogers et al. (1998) "Generating ~90 Nanometer Features Using Near Field Contact Mode Photolithography with an Elastomeric Phase Mask," *J. Vac. Sci. Technol.* 16(1):59-68.
Rogers et al. (1998) "Quantifying Distortions in Soft Lithography," *J. Vac. Sci. Technol.* 16:88-97.
Rogers et al. (1998) "Using Printing and Molding Techniques to Produce Distributed Feedback and Bragg Reflector Resonators for Plastic Lasers," *Appl. Phys. Lett.* 73:1766-1768.
Rogers et al. (1999) "Printing Process Sutable for Reel-to-Reel Production of High-Performance Organic Transistors and Circuits," *Adv. Mater.* 11(9):741-745.
Rogers et al. (2002) "Paper-Like Electronic Displays: Large-Area Rubber-Stamped Plastic Sheets of Electronics and Microencazpsulated Electrophoretic Inks," *Proc. Nat. Acad. Sci. USA* 98:4835-4840.
Rogers et al. (2002) "Printed Plastic Electronics and Paperlike Displays," *J. Polym. Sci. Part A. Polym. Chem.* 40:3327-3334.

Rogers et al. (Mar. 2000) "Organic Smart Pixels and Complementary Inverter Circuits Formed on Plastic Substrates by Casting and Rubber Stamping," *IEEE Electron Dev. Lett.* 21(3):100-103.
Rogers, J.A. (2001) "Rubber Stamping for Plastic Electronics and Fiber Optics," *MRS Bulletin* 26(7):530-534.
Rogers, J.A. (2001) "Toward Paperlike Displays," *Science* 291:1502-1503.
Rogjers, J. (Jul. 9, 2010) "Farewell to Flatland," *Science* 329:139-139.
Rosenblatt et al. (2002) "High Performance Electrolyte Gated Carbon Nanotube Transistors," *Nano Lett.* 2(8):869-872.
Rotkin et al. (2003) "Universal Description of Channel Conductivity for Nanotube and Nanowire Transistors," *Appl. Phys. Lett.* 83:1623-1625.
Roundy et al. (2003) "Photonic Crystal Structure with Square Symetry within Each Layer and a Three-Dimensional Band Gap," *Appl. Phys Lett.* 82:3835-3837.
Rubehn et al. (2009) "A MEMS based Flexible Multichannel ECoG-Electrode Array," *J. Neural Eng.* 6:036003.
Ruchehoeft et al. (2000) "Optimal Strategy for Controlling Linewidth on Spherical Focal Surface Arrays," *J. Vac. Sci. Technol. B* 18(6):3185-3189.
Ryu et al. (2009) "Human Cortical Prostheses: Lost in Translation?" *Neurosurg Focus* 27(1):E5.
Samuelson et al. (2004) "Semiconductor Nanowires for Novel One-Dimensional Devices," *Physica E* 21:560-567.
Sangwal et al. (1997) "Nature of multilayer steps on the {100} cleavage planes of MgO single crystals," *Surf. Sci.*, 383:78-87.
Santin et al. (1999) "*In vitro* Evaluation of the Inflammatory Potential of the Silk Fibroin," *J. Biomed. Mater. Res.* 46:382-389.
Sanyal et al. (2002) "Morphology of Nanostructures Materials," *Pure Appl. Chem.* 74(9):1553-1570.
Sazonov et al. (2005) "Low-Temperature Materials and Thin-Film Transistors for Flexible Electronics," *Proc. IEEE* 93:1420-1428.
Scherlag et al. (1969) "Catheter Technique for Recording His Bundle Activity in Man," *Circulation* 39:13-18.
Schermer et al. (Web Release Apr. 28, 2005) "Thin-Film GaAs Epitaxial Lift-Off Solar Cells for Space Applications," *Prog. Photovoltaics: Res. Applic.* 13:587-596.
Schermer et al. (Web Release Jan. 19, 2006) "Photon Confinement in High-Efficiency, Thin-Film III-V Solar Cells Obtained by Epitaxial Lift-Off," *Thin Solid Films* 511-512:645-653.
Schindl et al. (2003) "Direct Stimulatory Effect of Low-Intensity 670-nm Laser Irradiation on Human Endothelial Cell Proliferation," *Br. J. Dermatol.* 148:334-336.
Schlegel et al. (2002) "Structures of quartz (1010)- and (1011)-water interfaces determined by X-ray reflectivity and atomic force microscopy of natural growth surfaces," *Geochim. Cosmochim. Acta*, vol. 66, No. 17, pp. 3037-3054.
Schmid et al. (2003) "Preparation of metallic Films on Elastomeric Stamps and Their Application on Contact Processing and Contact Printing," *Adv. Funct. Mater.* 13:145153.
Schmid et al. (Mar. 25, 2000) "Siloxane Polymers for High-Resolution, High-Accuracy Soft Lithography," *Macromolecules* 33(8):3042-3049.
Schmid et al. (May 11, 1998) "Light0 Coupling Masks for Lensless, Sub-wavelength Optical Lithography," *Appl. Phys. Lett.* 72(19):2379-2381.
Schmidt et al. (Mar. 8, 2001) "Thin Solid Films Roll up into Nanotubes," *Nature* 410:168.
Schneider et al. (2008) "Mechanical Properties of Silicones for MEMS," *J. Micromech. Microeng.* 18:065008.
Schon et al. (1995) "Ambipolar Pentacene Field-Effect Transistors and Inverters," *Science* 287:1022-1023.
Schrieber et al. (1998) "The Effectiveness of Silane Adhesion Promotors in the Performance of Polyurethane Adhesives," *J. Adhesion* 68:31-44.
Scnable et al. (1969) "Aluminum Metallization; Advantages and Limitations for Integrated Circuit Applications," *IEEE* 57:1570-1580.
Scorzoni et al. (Oct. 4, 2004) "On the Relationship Between the Temperature coefficient of Resistance and the Thermal Conductance of Integrated Metal Resistors," *Sens Actuators A* 116(1):137-144.

(56) References Cited

OTHER PUBLICATIONS

Search and Examination Report, Corresponding to Singapore Application No. 200904208-6, dated Dec. 17, 2010.
Search Report and Examination Report Corresponding to Singapore Patent Application No. 200901178-4, Completed Mar. 13, 2010.
Search Report and First Written Opinion, Corresponding to Singapore Patent Application No. 200902530-5, dated Sep. 23, 2010.
Search Report and Written Opinion, Corresponding to Singapore Application No. 200901451-5, dated Dec. 22, 2010.
Search Report Corresponding to Singapore Patent Application No. SG 200607372-0, dated Oct. 17, 2007.
Search Report Corresponding to Taiwanese Patent Application No. 095121212, Completed Oct. 8, 2010.
Search Report, Corresponding to Republic of China (Taiwan) Patent Application No. 094118507, dated Feb. 24, 2007.
Seidel et al. (2004) "High-Current Nanotube Transistors," *Nano Lett.*, vol. 4, No. 5, pp. 831-834.
Sekitani et al. (2005) "Bending Experiment on Pentacene Fiield-Effect Transistors on Plastic Films," *Appl. Phys. Lett.* 86:073511.
Sekitani et al. (2009) "Stretchable Active-Matrix Organic Light-Emitting Diode Display Using Printable Elastic Conductors," *Nature Mater.* 8:494-499.
Sekitani et al. (Sep. 12, 2008) "A Rubberlike Stretchable Active Matrix Using Elastic Conductors," *Science* 321:1468-1472.
Sen et al. (2002) "Nonequilibrium Processes for Generating Silicon Nanostructures in Single-Crystalline Silicon," *Pure Appl. Chem.* 74(9):1631-1641.
Serikawa et al. (May 1, 2000) "High-Mobility Poly-Si Thin Film Transistors Fabricated on Stainless-Steel Foils by Low-Temperature Processes Using Sputter-Depositions," *Jpn. J. Appl. Phys.* 39:L393-L395.
Servanti et al. (2005) "Functional Pixel Circuits for Elastic AMOLED displays," *Proc. IEEE* 93:1257-1264.
Service, R.F. (Aug. 15, 2003) "Electronic Textiles Charge Ahead," *Science* 301:909- 911.
Shan et al. (2004) "From Si Source Gas Directly to Positioned, Electrically Contained Si Nanowires: The Self-Assembling 'Grow-in-Place' Approach," *Nano Lett.* 4(11):2085-2089.
Sharp et al. (2003) "Holographic Photonic Crystals with Diamond Symmetry," *Phys. Rev. B* 68:205102/1-205102/6.
Sheraw et al. (2002) "Organic Thin-Film Transistor-Driven Polymer-Dispersed Liquid Crystal Displays on Flexible Polymeric Substrates," *Appl. Phys. Lett.* 80:1088-1090.
Shetty et al. (2005) "Formation and Characterization of Silicon Films on Flexible Polymer Substrates," *Mater. Lett.* 59:872-875.
Shi et al. (2001) "Free-Standing Single Crystal Silicon Nanoribbons," *J. Am. Chem. Soc.* 123(44):11095-11096.
Shi et al. (Sep. 2000) "Synthesis of Large Areas of Highly Oriented, Very Long Silicon Nanowires," *Adv. Mater.* 12(18):1343-1345.
Shin et al. (2003) "PDMS-Based Micro PCR Chip with Parylene Coating," *J. Micromech. Microeng.* 13:768-774.
Shtein et al. (Oct. 15, 2004) "Direct Mask-Free Patterning of Molecular Organic Semiconductors Using Organic Vapor Jet Printing," *J. Appl. Phys.* 96(8):4500-4507.
Shull et al. (1998) "Axisymmetric Adhesion Tests of Soft Materials," *Macromol. Chem. Phys.* 199:489-511.
Siegel et al. (2009) "lightweight, Foldable Thermochromic Displays on Paper," *Lab Chip* 9:2775-2781.
Siegel et al. (2010) "Foldable Printed Circuit Boards on Paper Substrates," *Adv. Funct. Mater.* 20:28-35.
Siegel et al. (Web Release Feb. 7, 2007) "Microsolidics: Fabrication of Three-Dimensional Metallic Microstructures in Poly(dimethylsiloxane)," *Adv. Mater.* 19(5):727-733.
Sim et al. (1993) "An Analytical Back-Gate Bias Effect Model for Ultrathin SOI CMOS Devices," *IEEE Trans. Elec. Dev.* 40:755-765.
Sirringhaus et al. (2003) "Inkjet Printing of Functional Materials," *MRS Bull.* 28:802-806.
Sirringhaus et al. (Dec. 15, 2000) "High-Resolution Inkjet Printing of All-Polymer Transistor Circuits," *Science* 290:2123-2126.
Sirringhaus, H. (2005) "Device Physics of Solution-Processed Organic Field-Effect Transistors," *Adv. Mater.* 17:2411-2425.
Smay et al. (2002) "Colloidal Inks for Directed Assembly of 3-D Periodic Structures," *Langmuir* 18:5429-5437.
Smith et al. (2000) "Electric-Field Assisted Assembly and Alignment of Metallic Nanowires," *Appl. Phys. Lett.* 77(9):1399-1401.
Snow et al. (2003) "Random networks of carbon nanotubes as an electronic material," *Appl. Phys. Lett.*, vol. 82, No. 13, pp. 2145-2147.
Snow et al. (2005) "High-mobility carbon-nanotube transistors on a polymeric substrate," *Appl. Phys. Lett.*, 86, 033105.
So et al. (2008) Organic Light-Emitting Devices for Solid-State Lighting, *MRS Bull.* 33:663-669.
Sofia et al. (2001) "Functionalized Silk-Based Biomaterials for Bone Formation," *J. Biomed. Mater. Res.* 54:139-148.
Someya et al. (2005) "Conformable, Flexible, Large-Area Networks of Pressure and Thermal Sensors with Organic Transistor Active Matrixes," *Proc. Nat. Acad. Sci. USA* 102:12321-12325.
Someya et al. (2005) "Integration of Organic FETs with Organic Photodiodes for a Large Area, Flexible, and Lightweight Sheet Image Scanners," *IEEE Trans. Electron Devices* 52:2502-2511.
Someya et al. (Jul. 6, 2004) "A Large-Area, Flexible, Pressure Sensor Matric with Organic Field-Effect Transistors for Artificial Skin Applications," *Proc. Nat. Acad. Sci. USA* 101(27):9966-9970.
Someya, T. (Aug. 7, 2008) "Electronic Eyeballs," *Nature* 454:703-704.
Soole et al. (Mar. 1991) "InGaAs Metal-Semiconductor-Metal Photodetectors for Long Wavelength Optical Communications," *IEEE J. Quantum Electron.* 27(3):737752.
Soong et al. (1984) "Adverse Reactions to Virgin Silk Sutures in Cataract Surgery," *Ophthalmology* 91:479-483.
Srinivasan et al. (Web Release Mar. 26, 2007) "Piezoelectric/Ultrananocrystalline Diamond Heterostructures for High-Performance Multifunctional Micro/Nanoelectromechanical Systems," *Appl. Phys. Lett.* 90:134101.
Stafford et al. (Aug. 2004) "A Buckling-Based Metrology for Measureing the Elastic Moduli of Polymeric Thin Films," *Nature Mater.* 3:545-550.
Star et al. (2004) "Nanotube Optoelectric Memory Devices," *Nano Lett.*, vol. 4, No. 9, pp. 1587-1591.
Stella Project—Stretchable Electronics for Large-Area Applications. Available at www.stella-project.de. Accessed Feb. 8, 2012.
Storm et al. (Aug. 2003) "Fabrication of Solid-State Nanopores with Single-Nanometre Precision," *Nat. Mater.* 2:537-540.
Streetman et al. (2000) "Intrinsic Material," In; *Solid State Electronic Devices*, 5$^{th}$ Ed., Prentice Hall; Upper Saddle River, NJ; pp. 74-75.
Strukov et al. (2005) "CMOL FPGA: A Reconfigurable Architecture for Hybrid Digital Circuits with Two-Terminal Nanodevices," *Nanotechnology* 16:888-900.
Su et al. (2000) "Lattice-Oriented Growth of Single-Walled Carbon Nanotubes," *J. Phys. Chem. B* 104(28):6505-6508.
Sum et al. (2009) "Near-Infrared Spectroscopy for the Detection of Lipid Core Coronary Plaques," *Curr. Cardiovasc. Imag. Rep.* 2:307-315.
Sumant et al. (Apr. 2005) "Toward the Ultimate Tribological Interface: Surface Chemistry and Nanotribology of Ultrananocrystalline Diamond," *Adv. Mater.* 17(8):1039-1045.
Sun et al. (2004) "Fabricating Semiconductor Nano/Microwires and Transfer Printing Ordered Arrays of Them onto Plastic Substrates," *Nano Lett.* 4:1953-1959.
Sun et al. (2005) "Advances in Organic Field-Effect Transistors," *J. Mater. Chem.* 15:53-65.
Sun et al. (2005) "Bendable GaAs Metal-Semiconductor Field-Effect Transistors Formed with a Printed GaAs Wire Arrays on Plastic Substrates," *Appl. Phys. Lett.* 87:083501.
Sun et al. (2005) "Photolithographic Route to the Fabrication of Micro/Nanowires of III-V Semiconductors," *Adv. Fuct. Mater.* 15:30-40.
Sun et al. (2007) "Controlled Buckling of Semiconductor Nanoribbons for Stretchable Electronics," *Nat. Nanotechnol.* 1:201-207.
Sun et al. (2007) "Inorganic Semiconductors for Flexible Electronics," *Adv. Mater.* 19:1897-1916.

(56) References Cited

OTHER PUBLICATIONS

Sun et al. (2007) "Structural Forms of Single Crystal Semiconductor Nanoribbons for High-Performance Stretchable Electronics," *J. Mater Chem.* 17:832-840.
Sun et al. (Aug. 2007) "Inorganic Semiconductors for Flexible Electronics," *Adv. Mater.* 19(15):1897-1916.
Sun et al. (Nov. 2006) "Buckled and Wavy Ribbons of GaAs for High-Performance Electronics on Elastomeric Substrates," *Adv. Mater.* 18(21):2857-2862.
Sundar et al. (2004) "Elastomeric Transistor Stamps: Reversible Probing of CHaarge Transport in Organic Crystals," *Science* 303:1644-1646.
Suo et al. (Feb. 22, 1999) "Mechnics of Rollable and Foldable Film-on-Foil Electronics," *Appl. Phys. Lett.* 74(8):1177-1179.
Supplementary European Search Report, Corresponding to European Application No. 05 75 6327, Completed Sep. 25, 2009.
Supplementary European Search Report, Corresponding to European Application No. 04 81 2651, Completed Oct. 19, 2010.
Supplementary European Search Report Corresponding to European Patent Application No. 07 84 1968, Completed Mar. 31, 2011.
Supplementary European Search Report Corresponding to European Patent Application No. 10 842 518, Completed Aug. 9, 2013.
Swain et al. (2004) "Curved CCD Detector Devices and Arrays for Multi-Spectral Astrophysical Application and Terrestrial Stereo Panoramic Cameras," *Proc. SPIE* 5499:281-301.
Sweet: Stretchable and Washable Electronics for Embedding Textiles. Available at http://tfcg.elis.ugent.be/projects/sweet. Accessed Feb. 8, 2012.
Sze et al. (1985) *Semiconductor Devices, Physics and Technology*, $2^{nd}$ ed., Wiley, New York, pp. 190-192.
Sze, S. (1985) *Semiconductor Devices: Physics and Technology*, New York: Wiley, pp. 428-467.
Sze, S. (1988) *VLSI Technology*, Mcgraw-Hill, 327-374, 566-611.
Sze, S. (1994) *Semiconductor Sensors*, John Wiley and Sons: New York, pp. 17-95.
Takamoto et al. (Jan. 20, 1997) "Over 30% Efficient InGaP/GaAs Tandem Solar Cells," *Appl. Phys. Lett.* 70(3):381-383.
Talapin et al. (Oct. 7, 2005) "PbSe Nanocrystal Solids for n- and p-Channel Thin Film Field-Effect Transistors," *Science* 310:86-89.
Tan et al. (Apr. 12, 2004) "Performance Enhancement of InGaN Light Emitting Diodes by Laser-Lift-off and Transfer from Sapphire to Copper Substrate," *Appl. Phys. Lett.* 84(15):2757-2759.
Tanase et al. (2002) "Magnetic Trapping and Self-Assembly of Multicomponent Nanowires," *J. Appl. Phys.* 91:8549-8551.
Tang et al. (2005) "One-Dimensional Assemblies of Nanoparticles: Preparation, Properties, and Promise," *Adv. Mater.* 17:951-962.
Tao et al. (2003) "Langmuir-Blodgett Silver Nanowire Monolayers for Molecular Sensing Using Surface-Enhanced Raman Spectroscopy," *Nano Lett.* 3:1229-1233.
Tate et al. (2000) "Anodization and Microcontact Printing on Electroless Silver: Solution-Based Fabrication Procedures for Low-Voltage Electronic Systems with Organic Active Components," *Langmuir* 16:6054-6060.
Teshima et al. (2001) "Room-Temperature Deposition of High-Purity Silicon Oxide Films by RF Plasma-Enhanced CVD," *Surf. Coat. Technol.* 146-147:451-456.
Theiss et al. (1998) "PolySilicon Thin Film Transistors Fabricated at 100° C on a Flexible Plastic Substrate," *IEDM* 98:257-260.
Thornwood et al. (Oct. 1, 1990) "Utilizing Olptical Lithography in the Sub-Micron Dimensional Regime," *IBM Tech. Disc. Bull.* 33(5):187-188.
Timko et al. (2009) "Electrical Recording from Hearts with Flexible Nanowire Device Arrays," *Nano Lett.* 9:914-918.
Toader et al. (2004) "Photonic Band Gap Architectures for Holographic Lithography," *Phy. Rev. Lett.* 043905/1-043905/4.
Toader et al. (2004) "Photonic Band Gaps Based on Tetragonal Lattices of Slanted Pores," *Phys. Rev. Lett.* 90:233901/1-233901/4.
Tong (1999) *Semiconductor Wafer Bonding: Science and Technology*, John Wiley;.New York, pp. 187-221.

Trau et al. (1997) "Microscopic Patterning of Orientated Mesoscopic Silica Through Guided Growth," *Nature* 390:674-676.
Trentler et al. (1995) "Solution-Liquid-Solid Growth of Crytalline III-V Semiconductors: An Analogy to Vapor-Liquid-Solid Growth," *Science* 270:1791-1794.
Tseng et al. (Web Release Dec. 19, 2003) "Monolithic Integration of Carbon Nanotube Devices with Silicon MOS Technology" *Nano Lett.* 4(1):123-127.
Ucjikoga, S. (2002) "Low-Temperature Polycrystalline Silicon Thin-Film Transistor Technologies ofr System-on-Glass Displays," *MRS Bull.* 27:881.
Urruchi et al. (2000) "Etching of DLC Films Using a Low Intensity Oxygen Plasma Jet," *Diamond Relat. Mater.* 9:685-688.
J. Vanfleteren. SWEET: Stretchable and Washable Electronics for Embedding Textiles. Available at ftp://ftp.cordis.europa.eu/pub/ist/docs/mnd/ws-sfit_en.pdf. Accessed Feb. 8, 2012.
Vanhollenbeke et al. (2000) "Compliant Substrate Technology: Integration of Mismatched Materials for Opto-Electronic Applications," *Prog. Cryst. Growth Charact. Mater.* 41(1-4):1-55.
Velev et al. (1997) "Porous silica via colloidal crystallization," *Nature* 389:447-448.
Vepari et al. (Aug. Sep. 2007) "Silk as a Biomaterial," *Prog. Polym. Sci.* 32(8-9):991-1007.
Vilan et al. (2000) "Molecular Control Over Au/GaAs Diodes," *Nature* 404:166-168.
Vinck et al. (2003) "Increased Fibroblast Proliferation Induced by Light Emitting Diode and Low Power Laser Irradiation," *Lasers Med. Sci.* 18:95-99.
Viventi et al. (Mar. 2010) "A Conformal, Bio-Interfaced Class of Silicon Electronics for Mapping Cardiac Electrophysiology," *Sci. Trans. Med.* 2(24):24ra22.
Vlasov et al. (2001) "On-Chip Natural Assembly of Silicon Photonic Bandgap Crystals," *Nature* 414:289-293.
Voss, D. (2000) "Cheap and Cheerful Circuits," *Nature* 407:442-444.
Wagner et al. (2003) "Silicon for Thin-Film Transistors," *Thin Solid Films* 430:15-19.
Wagner et al. (2005) "Electronic Skin: Architecture and Components," *Physica E* 25:326-334.
Wagner et al. (Mar. 1, 1964) "Vapor-Liquid-Solid Mechanism of Single Crystal Growth," *Appl. Phys. Lett.* 4(5):89-90.
Waksman et al.(2008) "Photopoint Photodynamic Therapy Promotes Stabilization of Atherosclerotic Plaques and Inhibits Plaque Progression," *J. Am. Coll. Cardiol.* 52:1024-1032.
Wang et al. (2003) "A Solution-Phase, Precursor Route to Polycrystalline $SnO_2$ Nanowores that can be Used for Gas Sensing under Ambient Conditions," *J. Am. Chem. Soc.* 125:16176-16177.
Wang et al. (2005) "Electronically Selective Chemical Functionalization of Carbon Nanotubes: Correlation between Raman Spectral and Electrical Responses," *J. Am. Chem. Soc.*, 127:11460-11468.
Wang et al. (2005) "Oxidation Resistant Germanium Nanowires: Bulk Synthesis, Long Chain Alkanethiol Functionalization, and Langmuir-Blodgett Assembly," *J. Am. Chem. Soc.* 127(33):11871-11875.
Wang et al. (2006) "Direct Synthesis and Characterization of CdS Nanobelts," *Appl. Phys. Lett.* 89:033102.
Wang et al. (Aug.-Sep. 2008) "*In Vivo* Degradation of Three-Dimensional Silk Fibroin Scaffolds," *Biomaterials* 29(24-25):3415-3428.
Waxman et al. (2009) "In vivo Validation of a Catheter-Based Near-Infrared Spectroscopy System for Detection of Lipid Core Coronary Plaques: Initial Results of the Spectacl Study," *J. Am. Coll. Cardiol. Img.* 2:858-868.
Waxman, S. (2008) "Near-Infrared Spectroscopy for Plaque Characterization," *J. Interv. Cardiol.* 21:452-458.
Weber et al. (Jan. 2004) "A Novel Low-Cost, High Efficiency Micromachined Silicon Solar Cell," *IEEE Electron Device Lett.* 25(1):37-39.
Wen et al. (Web Release Dec. 4, 2004) "Controlled Growth of Large-Area, Uniform, Vertically Aligned Arrays of $\alpha$-$Fe_2O_3$ Nanobelts and Nanowires," *J. Phys. Chem. B* 109(1):215-220.

(56) References Cited

OTHER PUBLICATIONS

Whang et al. (2003) "Large-Scale Hierarchical Organization of Nanowire Arrays for Integrated Nanosystems," *Nano Lett.* 3(9):1255-1259.
Williams et al. (Oct. 2006) "Growth and Properties of Nanocrystalline Diamond Films," *Phys. Stat. Sol. A* 203(13):3375-3386.
Williams et al. (Web Release Jan. 23, 2006) "Comparison of the Growth and Properties of Ultranocrystalline Diamond and Nanocrystalline Diamond," *Diamond Relat. Mater.* 15:654-658.
Willner et al. (2002) "Functional Nanoparticle Architectures for Senoric, Optoelectronic, and Bioelectronic Applications," *Pure Appl. Chem.* 74(9):1773-1783.
Wilson et al. (2006) "ECoG Factors Underlying Multimodal Control of a Brain—Computer Interface," *IEEE Trans. Neural Syst. Rehabil. Eng.* 14:246-250.
Wind et al. (May 20, 2002) "Vertical Scaling of Carbon Nanotube-Field-Effect Transitors Using Top Gate Electrodes," *Appl. Phys. Lett.* 80(20):3871-3819.
Wise et al. (Jul. 2008) "Microelectrodes, Microelectronics, and Implantable Neural Microsystems," *Proc. IEEE* 96(7):1184-1202.
Won et al. (2004) "Effect of Mechanical and Electrical Stresses on the Performance of an a-Si:H TFT on Plastic Substrate," *J. Electrochem. Soc.* 151:G167-G170.
Wong-Riley et al. (2005) "Photobiomodulation Directly Benefits Primary Neurons Functionally Inactivated by Toxins," *J. Biol. Chem.* 280:4761-4771.
Woodburn et al. (1996) "Phototherapy of Cancer and Atheromatous Plaque with Texaphyrins," *J. Clin. Laser Med. Surg.* 14:343-348.
Wu et al. (2001) "Amorphous Silicon Crystallization and Polysilicon Thin Film Transistors on SiO2 Passivated Steel Foil Substrates," *Apple. Surf. Sci* 175-176:753758.
Wu et al. (2001) "Direct Observation of Vapor-Liquid-Solid Nanowire Growth," *J. Am. Chem. Soc.* 123(13):3165-3166.
Wu et al. (2001) "Thermal Oxide of Polycrystalline Silicon on Steel Foil as a Thin-Film Transitor Gate Dielectric," *Appl. Phys. Lett.* 78:3729-2731.
Wu et al. (2002) "Block-by-Block Growth of Single-Crystalline Si/SiGe Superlattice Nanowires," *Nano Lett.* 2(2):83-86.
Wu et al. (2002) "Growth of Au-Catalyzed Ordered GaAs Nanowire Arrays by Molecular-Beam Epitaxy," *Appl. Phys. Lett.* 81:5177-5179.
Wu et al. (2002) "Inorganic Semiconductor Nanowires: Rational Growth, Assembly, and Novel Properties," *Chem. Eur. J.* 8(6):1261-1268.
Wu et al. (2003) "Growth, Branching, and Kinking of Molecular-Beam Epitaxial (110) GaAs Nanowires," *Appl. Phys. Lett.* 83:3368-3370.
Wu et al. (Jul. 1, 2004) "Single-Crystal Metallic Nanowires and Metal/Semiconductor Nanowire Heterostructures," *Nature* 430:61-65.
Wu et al. (Nov. 2002) "Complementary Metal-Oxide-Semiconductor Thin-Film Transistor Circuits from a High-Temperature Polycrystalline Silicon Process on Steel Foil Substrates," *IEEE Trans. Electr. Dev.* 49(11):1993-2000.
Xia (1998) "Soft Lithography" *Angew. Chem. Int. Ed.* 37:551-575.
Xia et al. (1996) "Shadowed Sputtering of Gold on V-Shaped Microtrenches Etched in Silicon and Applications in Microfabrication," *Adv. Mater.* 8(9):765-768.
Xia et al. (1998) "Soft Lithography," *Annu. Rev. Mater. Sci.* 28:153-184.
Xia et al. (1999) "Unconventional Methods for Fabricating and Patterning Nanostructures," *Chem. Rev.* 99:1823-1848.
Xia et al. (2003) "One-Dimensional Nanostructures: Synthesis, Characterization and Applications," *Adv. Mater.* 15:353-389.
Xia et al. (Jul. 19, 1996) "Complex Optical Surfaces Formed by Replica Molding Against Elastomeric Masters," *Science* 273:347-349.
Xiang et al. (Mar. 25, 2006) "Ge/Si Nanowire Heterostructures as High-Performance Field-Effect Transistors," *Nature* 441:489-493.

Xiao et al. (2003) "High-mobility thin-film transistors based on aligned carbon nanotubes," *Appl. Phys. Lett.*, vol. 83, No. 1, pp. 150-152.
Xie et al. (May 2003) "Polymer-Controlled Growth of $Sb_2Se_3$ Nanoribbons via a Hydrothermal Process," *J. Cryst. Growth* 252(4):570-574.
Xin et al. (Jun. 2005) "Evaluation of Polydimethylsiloxane Scaffolds with Physiologically-Relevant Elastic Moduli: Interplay of Substrate Mechanics and Surface Chemistry Effects on Vascular Smooth Muscle Cell Response," *Biomaterials* 26(16):3123-3129.
Yang et al. (1997) "Mesoporous Silica with Micrometer-Scale Desgns," *Adv. Mater.* 9:811-814.
Yang et al. (2000) "Stability of Low-Temperature Amorphous Silicon Thin Film Transistors Formed on Glass and Transparent Plastic Substrates," *J. Vac. Sci. Technol. B* 18:683-689.
Yang et al. (2002) "Creating Periodic Three-Dimensional Structures by Multibeam Interface of Visible Laser," *Chem. Mater.* 14:2831-2833.
Yang et al. (Dec. 2007) "RFID Tag and RF Structures on a Paper Substrate Using Inkjet-Printing Technology," *IEEE Trans. Microw. Theory Tech.* 55(12):2894-2901.
Yang, P. (2005) "The Chemistry and Physics of Semiconductor Nanowires," *MRS Bull.* 30:85.
Yanina et al. (2002) "Terraces and ledges on (001) spinel surfaces," *Surf. Sci.*, 513:L402-L412.
Yao et al. (2008) "Seeing Molecules by Eye: Surface Plasmon Resonance Imaging at Visible Wavelengths with High Spatial Resolution and Submonolayer Sensitivity," *Angew. Chem.* 47:5013-5017.
Yao et al. (2010) "Functional Nanostructured Plasmonic Materials," *Adv. Mater.* 22:1102-1110.
Yao et al. (Mar. 2000) "High-Field Effect Electrical Transport in Single-Walled Carbon Nanotubes," *Phys. Rev. Lett.* 84(13):2941-2944.
Yeager et al. (Aug. 30, 2008) "Characterization of Flexible ECoG Electrode Arrays for Chronic Recording in Awake Rats," *J. Neurosci. Methods* 173(2):279-285.
Yeh et al. (1994) "Fluidic Self-Assembly for the Integration of GaAs Light Emitting Diodes on Si Substrates," *IEEE Photon. Techn. Lett.* 6:706-708.
Yin et al. (2000) "A Soft Lithography Approach to the Fabrication of Nanostructures of Single Crystalline Silicon with Well-Defined Dimensions and Shapes," *Adv. Mater.* 12:1426-1430.
Yin et al. (2005) "Colloidal Nanocrystal Synthesis and the Organic-Inorganic Interface," *Nature* 437:664-670.
Yoon et al. (2005) "Low-Voltage Organic Field-Effect Transistors and Inverters Enabled by Ultrathin Cross-Linked Polymers as Gate Dielectrics," *J. Am. Chem. Soc.* 127:10388-10395.
Yu et al. (2000) "Silicon Nanowires: Preparation, Device Fabrication, and Transport Properties," *J. Phys. Chem. B* 104(50):11864-11870.
Yu et al. (2003) "Solution-Liquid-Solid Growth of Soluble GaAs Nanowires," *Adv. Mater.* 15:416-419.
Yu et al. (2003) Two-Versus Three-Dimensional Quantum Confinement in Indium Phosphide Wires and Dots, *Nat. Mater.* 2:517-520.
Yu et al. (2004) "The Yield Strength of Thin Copper Films on Kapton," *J. Appl. Phys.* 95:2991-2997.
Yuan et al. (2006) "High-Speed Strained-Single-Crystal-Silicon Thin-Film Transistors on Flexible Polymers," *J. Appl. Phys.* 100:013708.
Yurelki et al. (Jul. 24, 2004) "Small-Angle Neutron Scattering from Surfactant-Assisted Aqueous Dispersions of Carbon Nanotubes," *J. Am. Chem. Soc.* 126(32):9902-9903.
Zakhidov et al. (1998) "Carbon Structure with Three-Dimensional Periodicity at Optical Wavelengths," *Science* 282:897-901.
Zaumseil et al. (2003) "Nanoscale Organic Transistors that use Source/Drain Electrodes Supported by High Resolution Rubber Stamps," *Appl. Phys. Lett.* 82(5):793-795.
Zaumseil et al. (2003) "Three-Dimensional and Multilayer Nanostructures Formed by Nanotransfer Printing," *Nano Lett.* 3(9):1223-1227.
Zhang et al. (2001) "Electric-field-directed growth of aligned single-walled carbon nanotubes," *Appl. Phys. Lett.*, vol. 79, No. 19. pp. 3155-3157.

(56) References Cited

OTHER PUBLICATIONS

Zhang et al. (2005) "Low-Temperature Growth and Photoluminescence Property of ZnS Nanoribbons," *J. Phys. Chem. B* 109(39):18352-18355.

Zhang et al. (2006) "Anomalous Coiling of SiGe/Si and SiGe/Si/Cr Helical Nanobelts," *Nano Lett.* 6(7):1311-1317.

Zhang et al. (Apr. 2003) "Oxide-Assisted Growth of Semiconducting Nanowires," *Adv. Mater.* 15(7-8):635-640.

Zhang et al. (Apr. 5, 2004) "Structure and Photoiluminescence of ZnSe Nanoribbons Grown by Metal Organic Chemical Vapor Deposition," *Appl. Phys. Lett.* 84(14):26412643.

Zhang et al. (Feb. 9, 2006) "Electronic Transport in Nanometre-Scale Silicon-on-Insulator Membranes," *Nature* 439:703-706.

Zhao et al. (Mar. 2007) "Improved Field Emission Properties from Metal-Coated Diamond Films," *Diamond Relat Mater.* 16(3):650-653.

Zheng et al. (1998) "Sudden Cardiac Death in the United States, 1989 to 1998," *Circulation* 104, 2158-2163 (1998.

Zheng et al. (2004) "Shape-and Solder-Directed Self-Assembly to Package Semiconductor Device Segments," *Appl. Phys. Lett.* 85:3635-3637.

Zheng et al. (Aug. 31, 2004) "Sequential Shape-and-Solder-Directed Self Assembly of Functional Microsystems," *Proc. Natl. Acad. Sci. USA* 101(35):12814-12817.

Zhou et al. (2002) "An Efficient Two-Photon-Generated Photoacid Applied to Positive-Tone 3D Microfabrication," *Science* 296:1106-1109.

Zhou et al. (2004) "p-Channel, n-Channel Thin Film Transistors and p-n Diodes Based on Single Wall Carbon Nanotube Networks," *Nano Lett.* 4:2031-2035.

Zhou et al. (2005) "Band Structure, Phonon Scattering, and the Performance Limit of Single-Walled Carbon Nanotube Transistors," *Phys. Rev. Lett.* 95:146805.

Zhou et al. (2005) "Mechanism for Stamp Collapse in Soft Lithography," *Appl. Phys. Lett.* 87:251925.

Zhu et al. (2005) "Spin on Dopants for High-Performance Single Crystal Silicon Transistors on Flexible Plastic Substrates," *Appl. Phys. Lett.* 86(133507)1-3.

Zipes et al. (2006) "ACC/AHA/ESC 2006 Guidelines for Management of Patients With Ventricular Arrhythmias and the Prevention of Sudden Cardiac Death: A Report of the American College of Cardiology/American Heart Association Task Force and the European Society of Cardiology Committee for Practice Guidelines (Writing Committee to Develop Guidelines for Management of Patients With Ventricular Arrhythmias and the Prevention of Sudden Cardiac Death," *Circulation* 114:385-484.

Notice of Reasons for Rejection Corresponding to Japanese Patent Application No. P2012-544735, Dispatched Sep. 9, 2014 (includes English translation).

Office Action dated Oct. 18, 2017 corresponding to U.S. Appl. No. 12/968,637.

Office Action dated Oct. 2, 2017 corresponding to Taiwanese Patent Application No. 105106567.

* cited by examiner

*

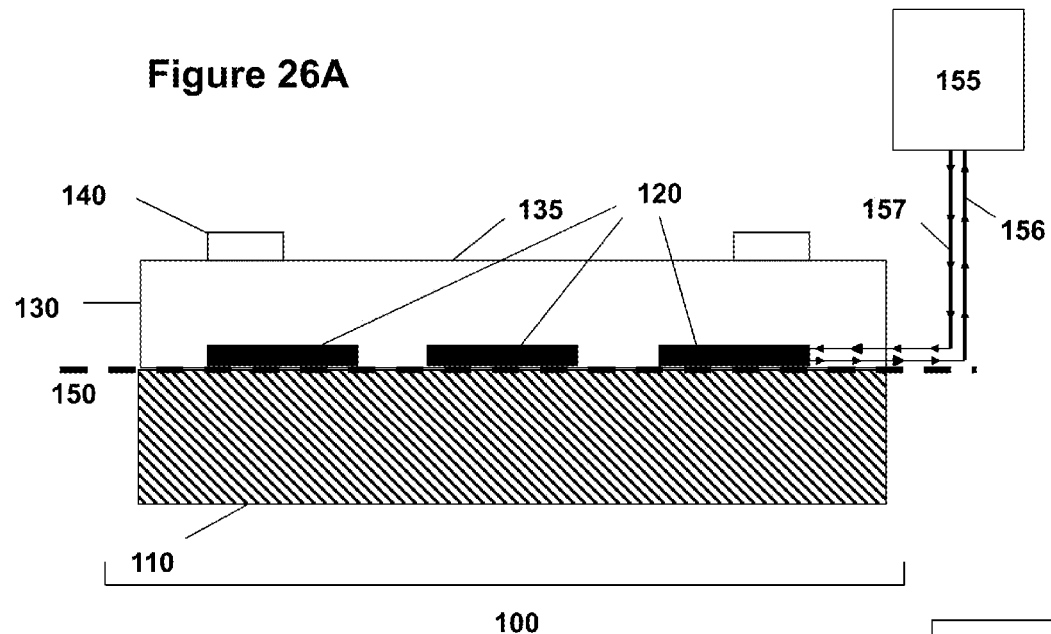
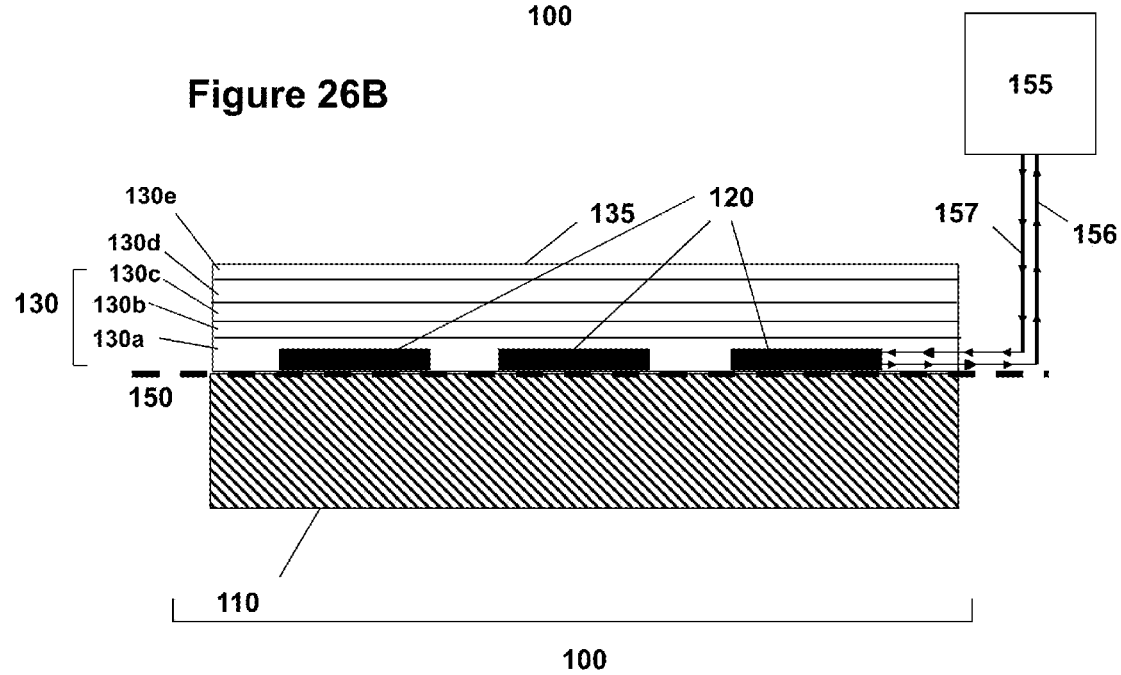

1st layer On | 2nd layer On | Two layers On

Figure 34a
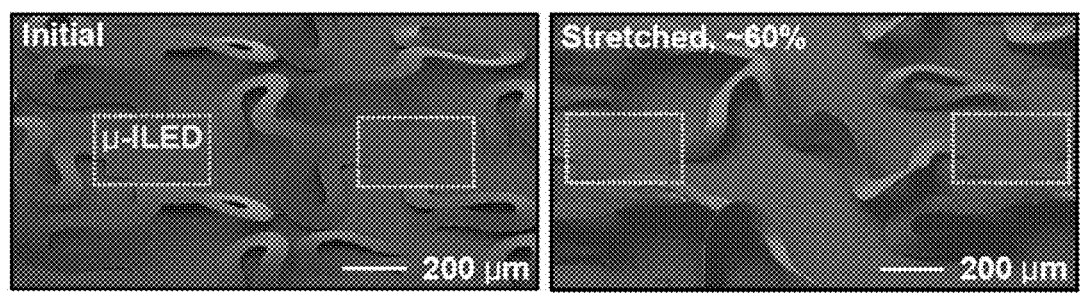
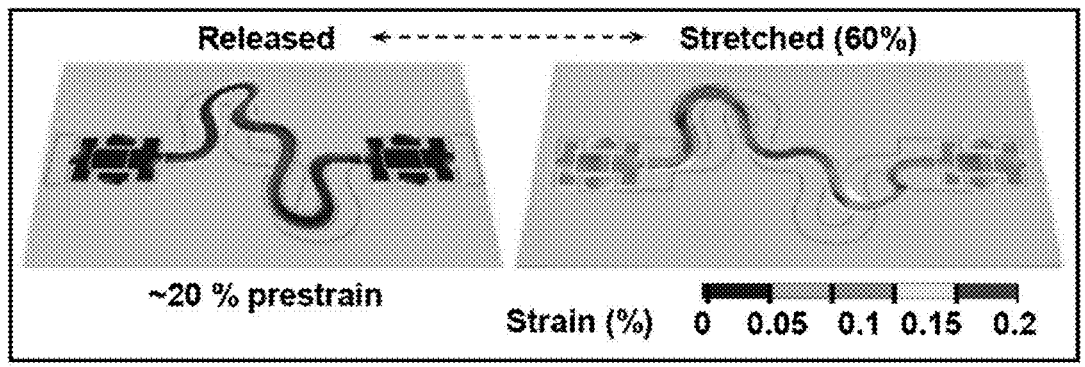
Figure 34b

Figure 35a
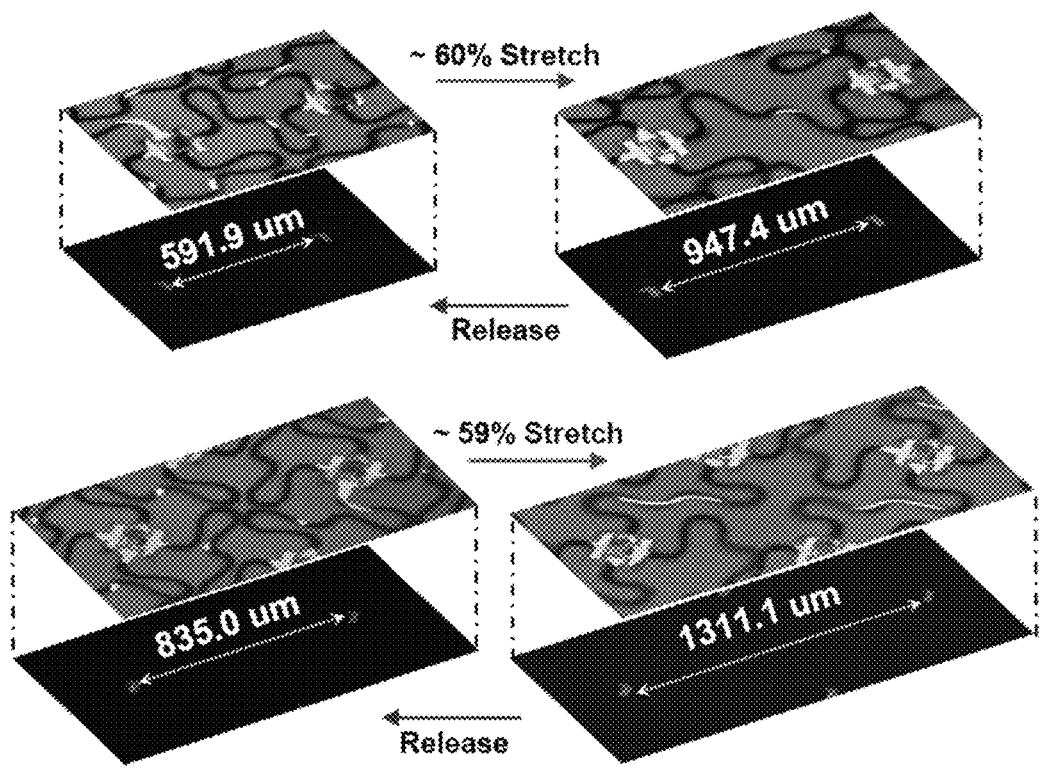
Figure 35b
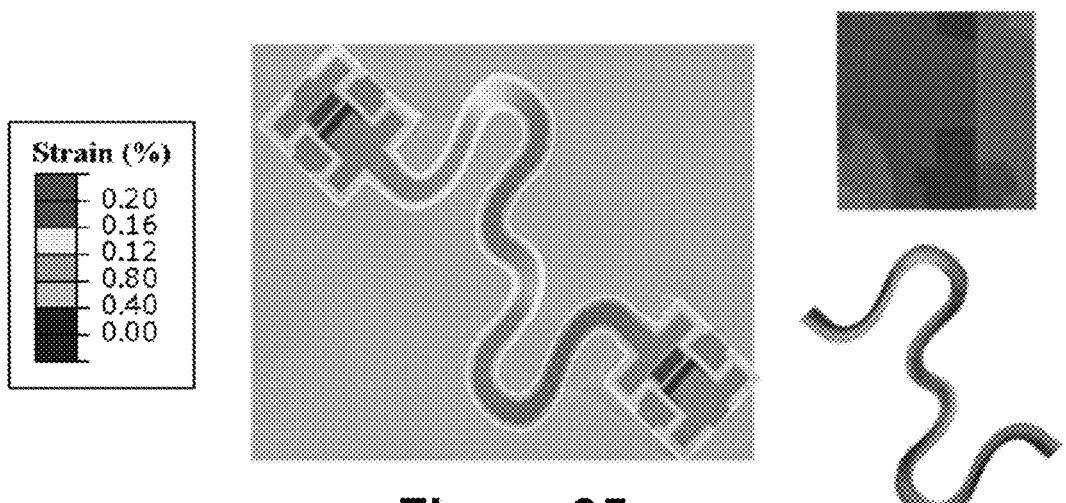
Figure 35c

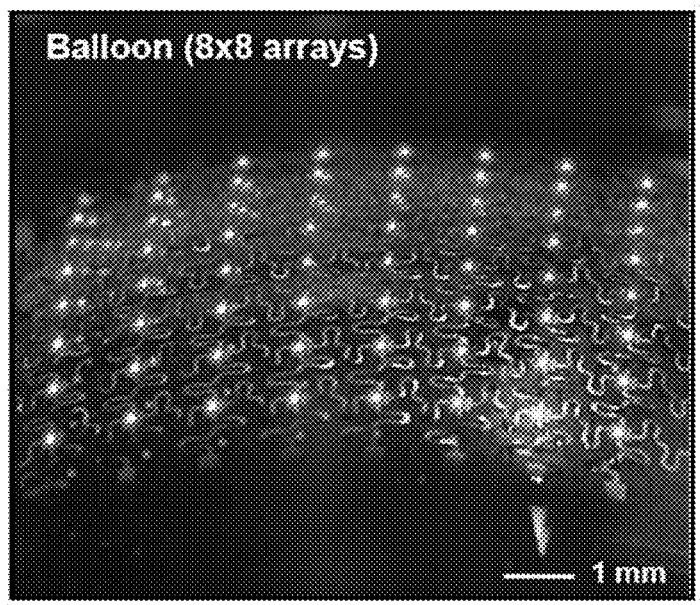
Figure 37a
Figure 37b
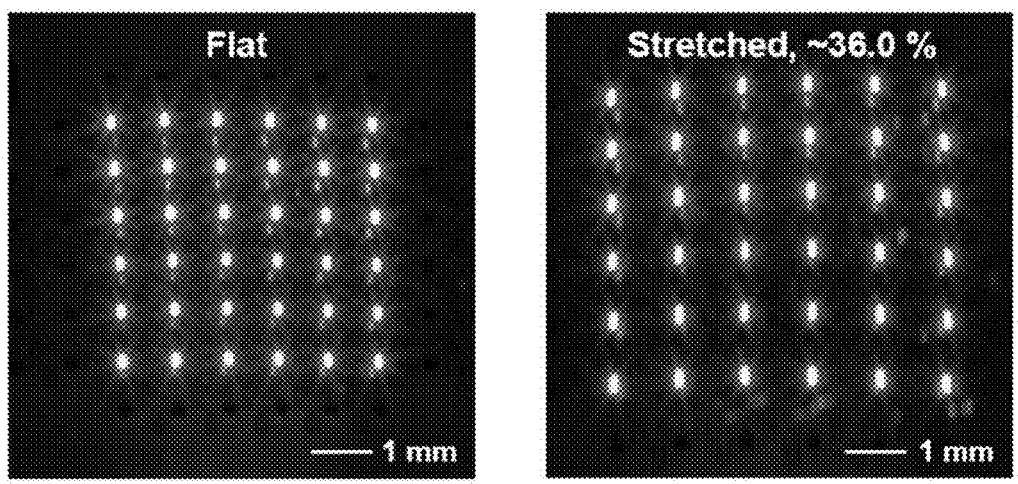
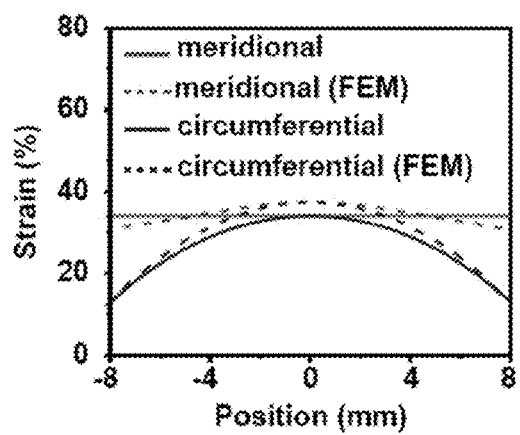
Figure 37c

Figure 38a
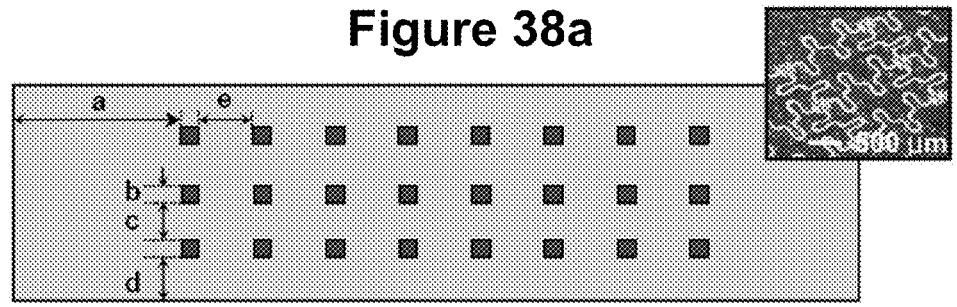
a = 5 mm / b = 277 um / c = 695.5 um / d = ~ 1.5 mm / e = 1.2676 mm
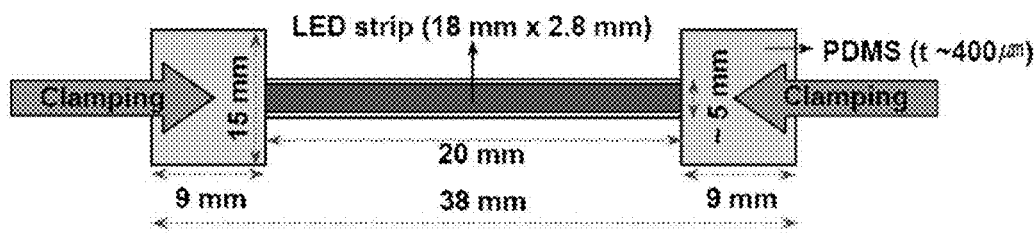
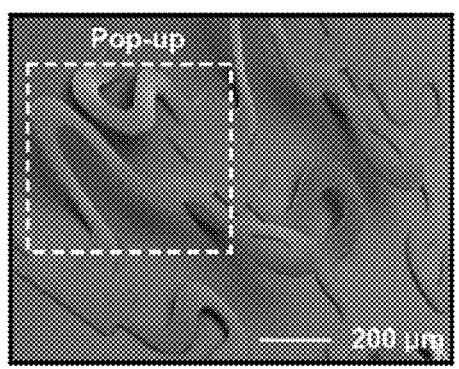
Figure 38b
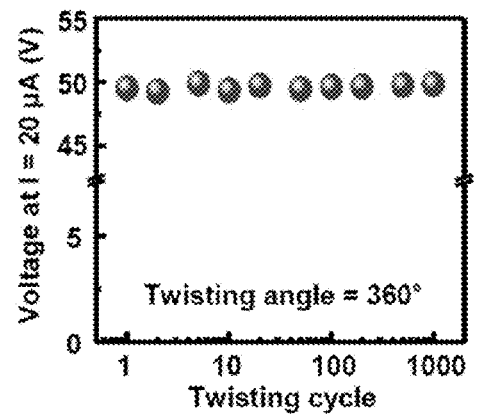
Figure 38c Figure 44c
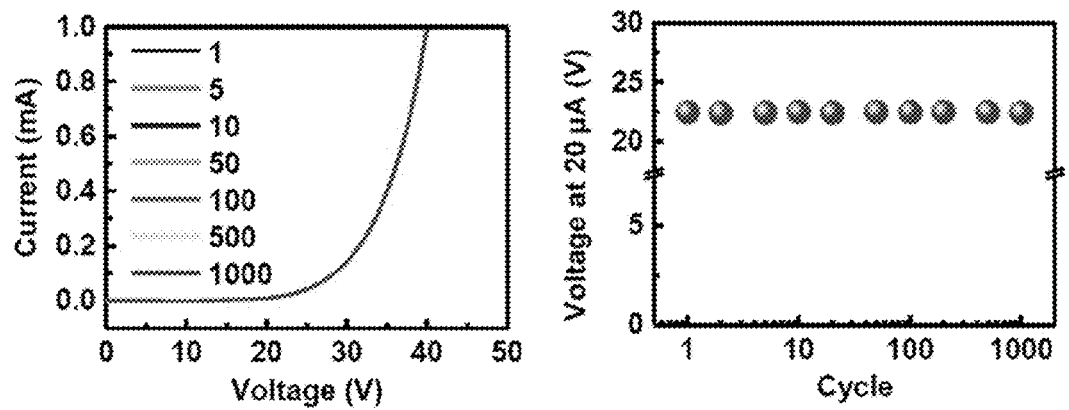
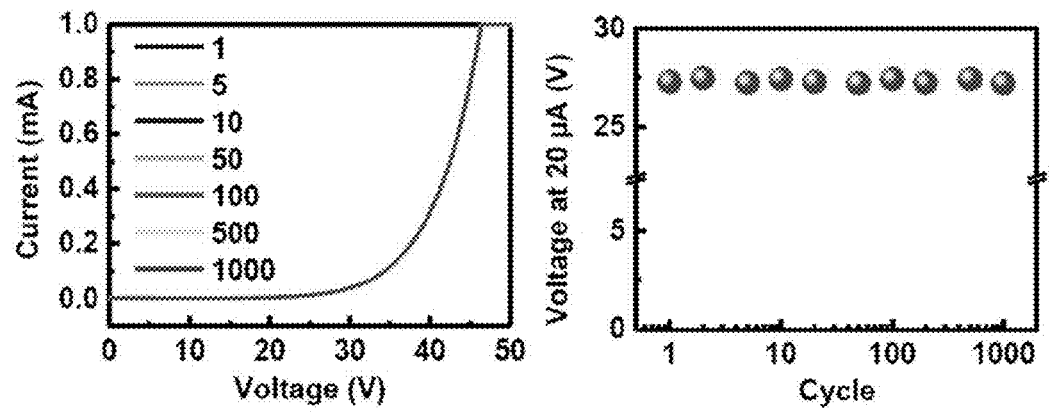
Figure 44d Figure 45a
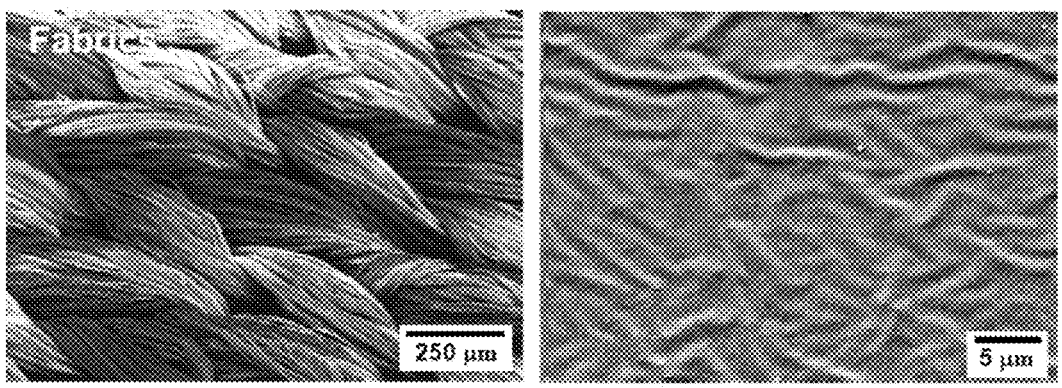
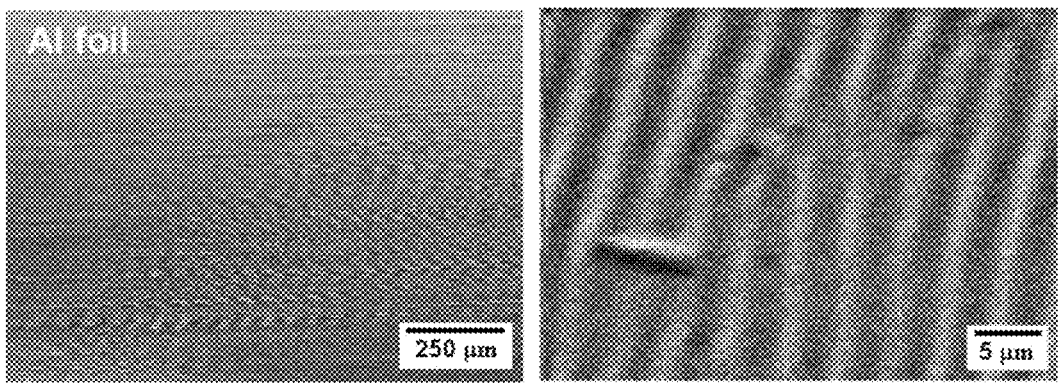
Figure 45b Figure 45c
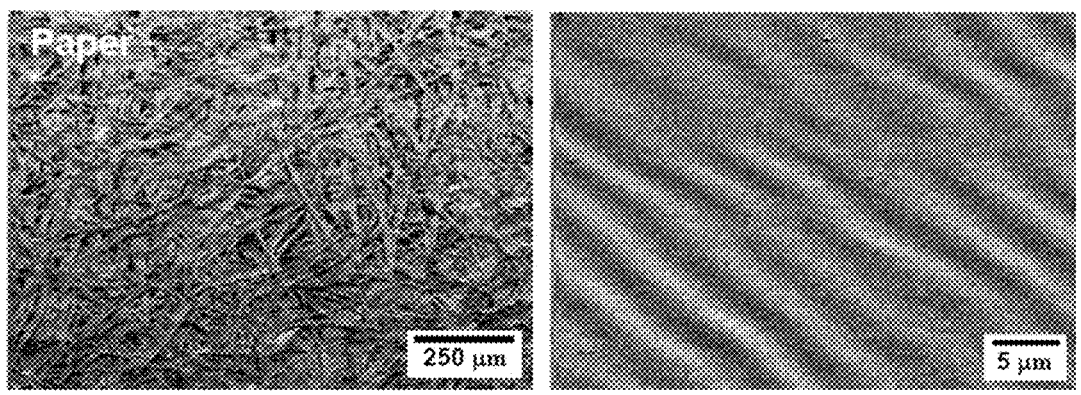
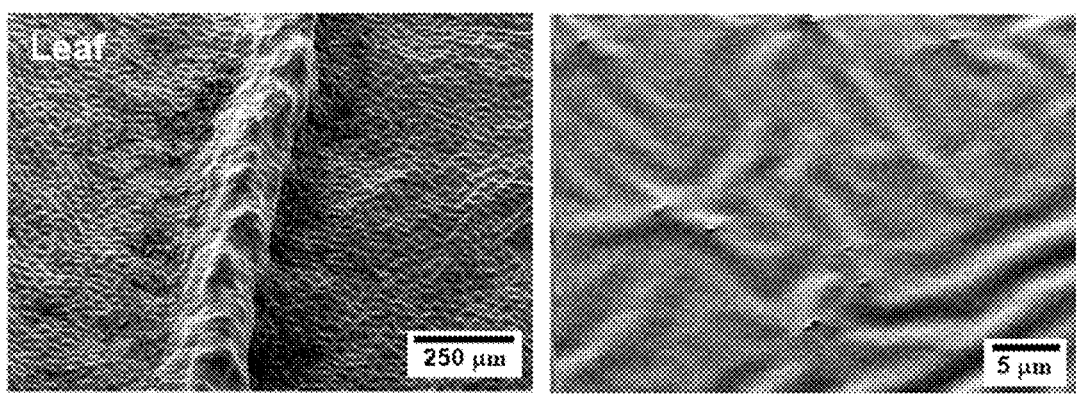
Figure 45d transfer to ecoflex/PVA apply to skin dissolve backing PVA conform to deformed skin

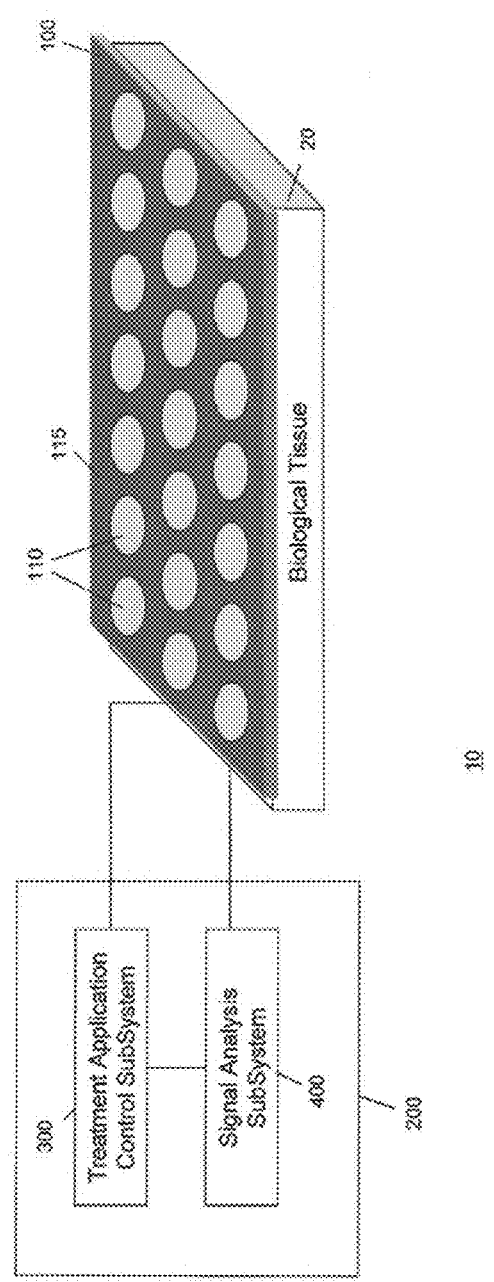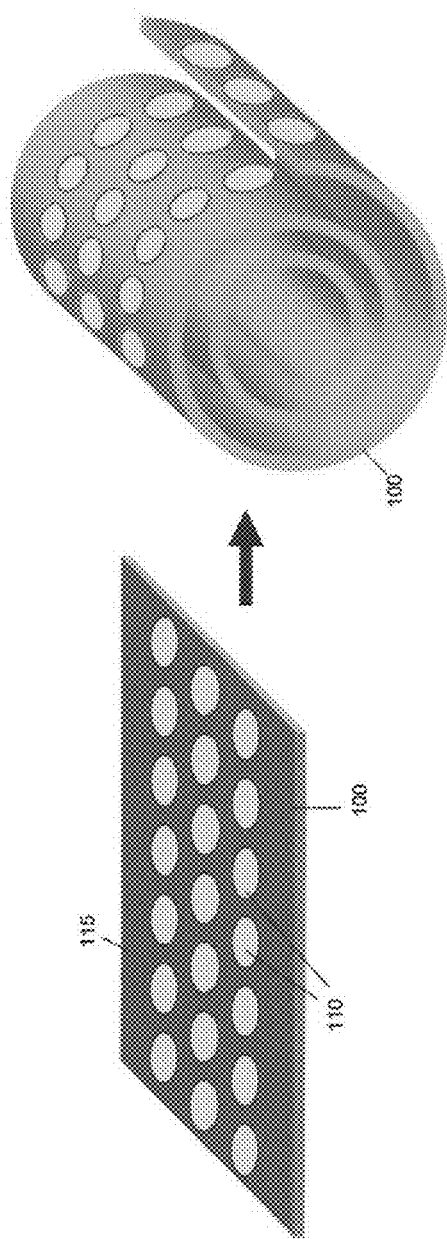
Figure 55
Figure 56

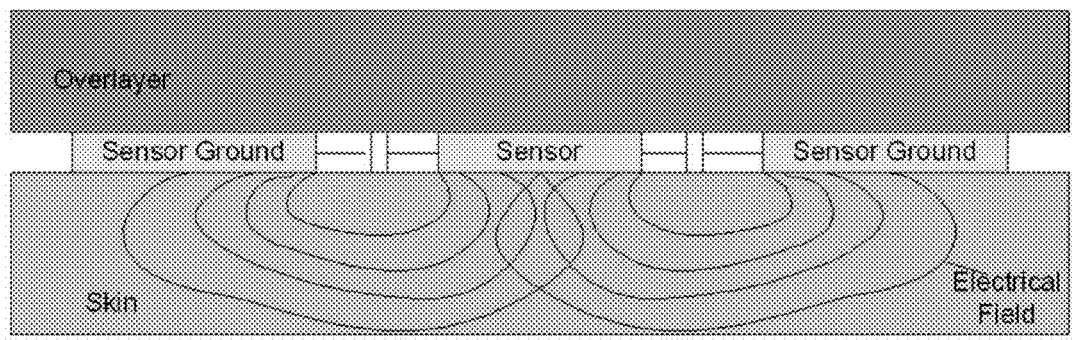
Figure 92
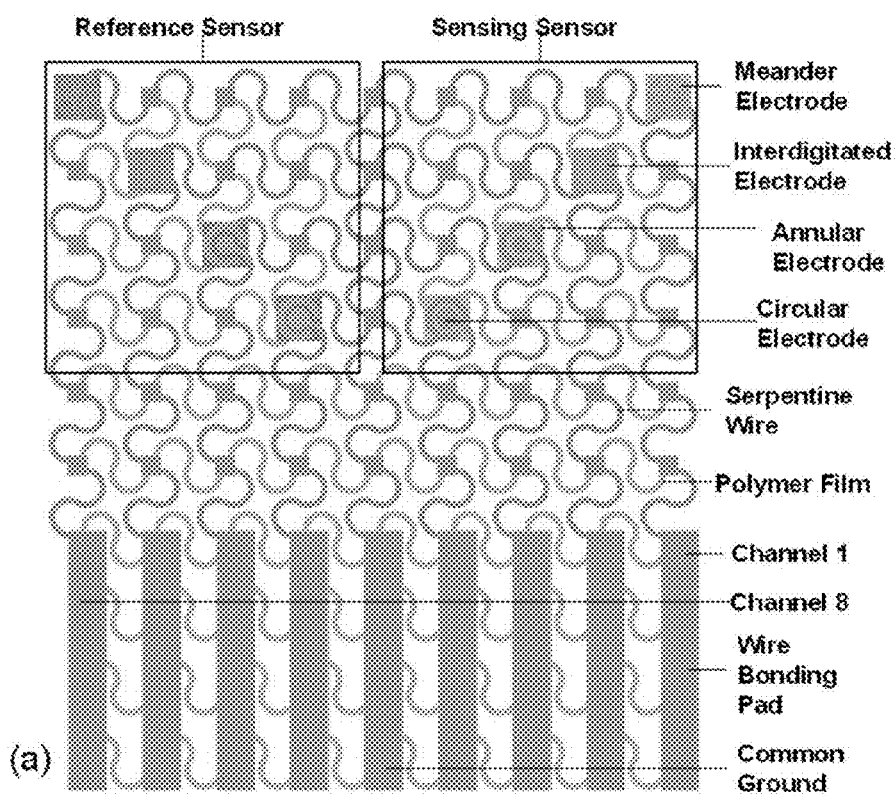
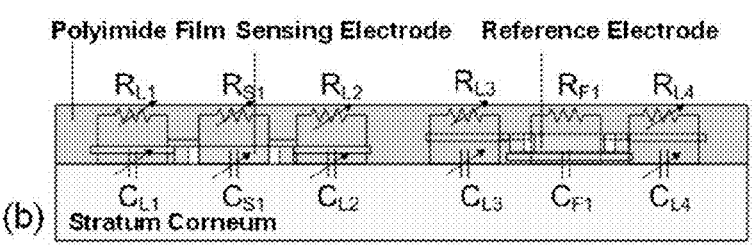
Figure 93

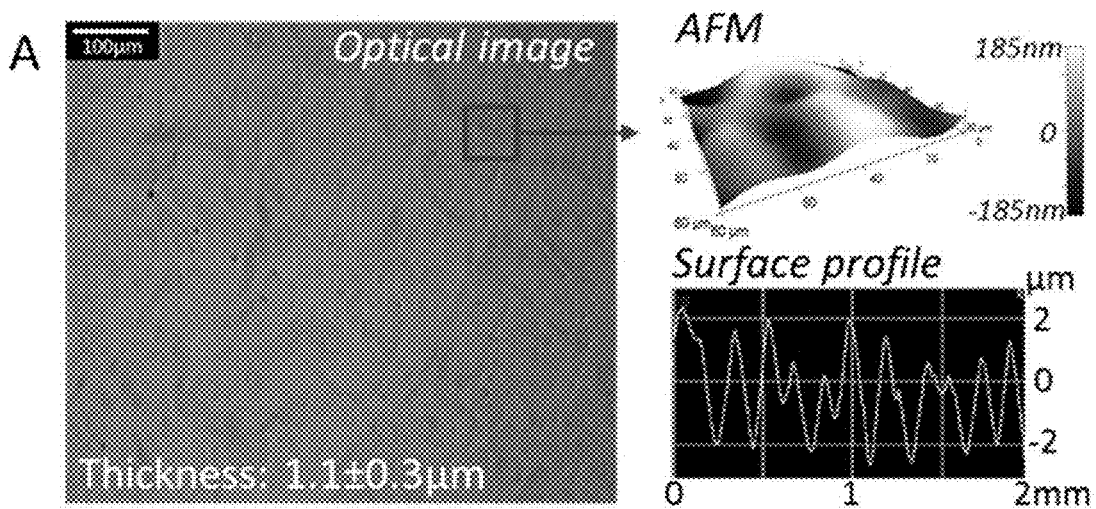
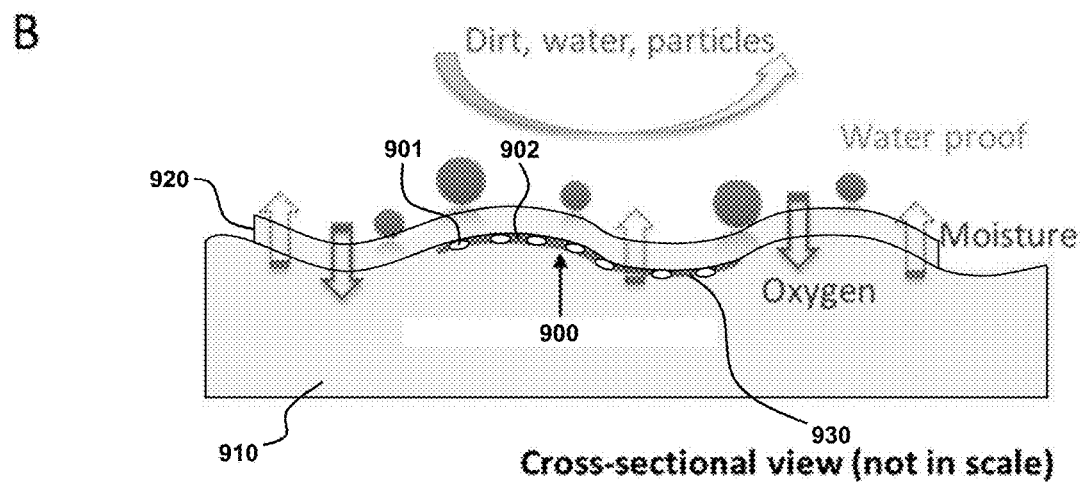
Figure 113

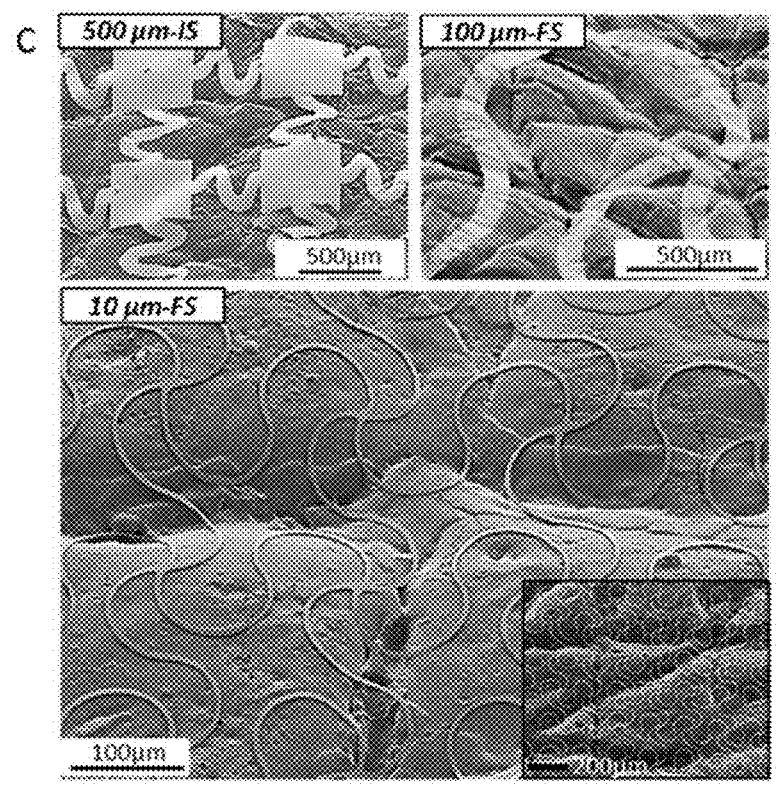
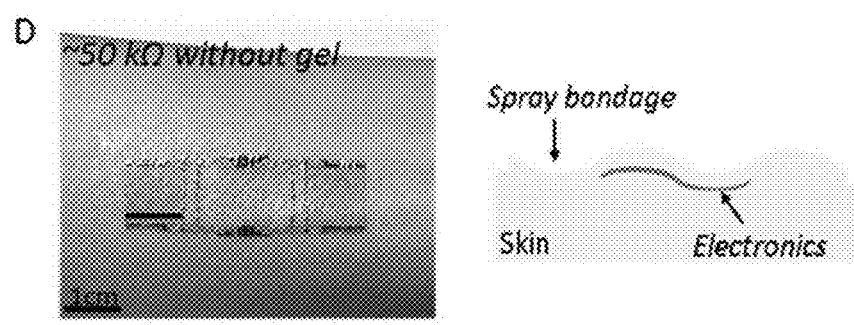
Skin-like electronics
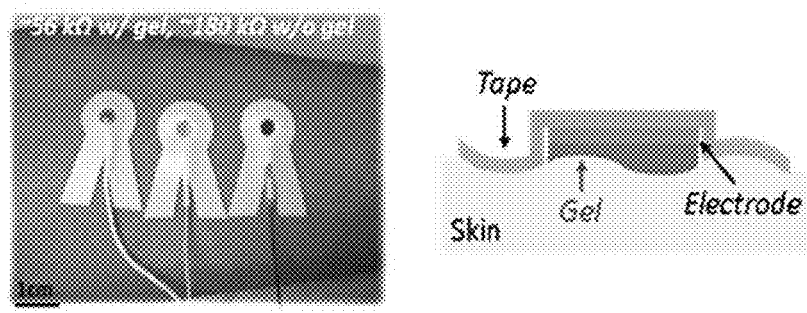
Conventional electronics
Figure 114 (cont'd)

FLEXIBLE AND STRETCHABLE ELECTRONIC SYSTEMS FOR EPIDERMAL ELECTRONICS

CROSS REFERENCE TO RELATED APPLICATIONS

This application is a continuation-in-part of U.S. patent application Ser. No. 12/968,637 filed Dec. 15, 2010, which claims the benefit of, and priority to, U.S. Provisional Patent Application Nos. 61/286,921, 61/313,397 and 61/388,529 filed Dec. 16, 2009, Mar. 12, 2010, and Sep. 30, 2010, respectively; and this application claims the benefit of U.S. Provisional Patent Application No. 61/495,623 filed Jun. 10, 2011, all of which are incorporated by reference to the extent not inconsistent with the disclosure herein.

STATEMENT REGARDING FEDERALLY SPONSORED RESEARCH OR DEVELOPMENT

This invention was made with United States governmental support from the U.S. Department of Energy under Award No. DEFG02-91ER45439, the National Science Foundation under grant DMI-0328162, the U.S. Department of Energy under Award No. DE-FG02-07ER46453 and DE-FG02-07ER46471, the U.S. Army Research Laboratory and the U.S. Army Research Office under contract number W911 NF-07-1-0618, the National Institute of Neurological Disorders and Stroke (NINDS) under Award Nos. RO1-NS041811-04 and RO1-NS48598-01 and by the DARPA-DSO and the National Institutes of Health P41 Tissue Engineering Resource Center under award number P41 EB002520. The U.S. Government has certain rights in the invention.

BACKGROUND

Physiological measurement and stimulation techniques that exploit interfaces to the skin have been of interest for more than 40 years, the former beginning in as early as 1966 with electromyography of laryngeal muscles. Despite much progress over this time, nearly all associated device technologies continue to rely on conceptually old designs. Typically, small numbers of bulk electrodes are mounted on the skin via adhesive tapes, mechanical clamps/straps and/or penetrating needles, often mediated by conductive gels, with terminal connections to separate boxes that house collections of rigid circuit boards, power supplies and communication components. These systems have many important capabilities, but they are poorly suited for practical application outside of research labs or clinical settings, due to difficulties in establishing long-lived, robust electrical contacts that do not irritate the skin, and in achieving integrated systems with overall sizes, weights and shapes that do not cause discomfort during prolonged use.

Recently, a number of patents and publications have disclosed flexible, resilient and implantable electrode arrays. For example, U.S. Patent Application Publication US 2007/0043416 discloses an implantable flexible elastic support with a plurality of electrodes held in contact with a target tissue. Similarly, International Patent Application Publication WO 98/49936 discloses a resilient electrode array for sensing signals associated (mapping) and ablating heart tissue. U.S. Pat. No. 5,678,737 discloses an electrophysiology mapping system for displaying a 3D model of epicardial and endocardial surfaces with dynamic display of potential distribution data.

U.S. Patent Application Publication US 2003/0149456 discloses a multi-electrode cardiac lead adapter which incorporates a multiplexing circuit allowing for control by a conventional single lead cardiac pacing pulse generator. Similarly, U.S. Patent Application Publication US 2006/0173364 discloses a multichannel electrophysiology acquisition system which utilizes a digital multiplexing circuit build on a conventional integrated circuit. U.S. Pat. No. 6,666,821 discloses an implantable sensor array system with an associated protective member which prevents the sensors from interacting with the surrounding environment until it is disabled.

International Application Publication WO 2009/114689, which is hereby incorporated by reference in its entirety, discloses flexible and scalable sensor arrays for recording and modulating physiologic activity. US Patent Application Publication Nos. US 2008/0157235, US 2008/0108171, US 2010/0002402 and U.S. Pat. No. 7,557,367 issued Jul. 7, 2009, all of which are hereby incorporated by reference in their entireties, disclose multilayer stretchable, foldable and printable semiconductor devices.

SUMMARY OF THE INVENTION

Provided herein are skin-mounted biomedical devices and methods of making and using biomedical devices for sensing and actuation applications. For example, flexible and/or stretchable biomedical devices are provided, including electronic devices useful for establishing conformal contact with the skin of a subject. Devices disclosed herein can comprise a plurality of sensing and/or actuating devices provided as part of a skin-mounted flexible or stretchable electronic circuit.

In one aspect, the invention provides devices for interfacing with a tissue in a biological environment including conformable devices. Devices of this aspect are useful, for example, for sensing and/or actuating a tissue in a biological environment. When placed in a biological environment, devices of an aspect of the invention optionally establish conformal contact with a target tissue(s), thereby providing contact useful for sensing or actuation of the tissue. Further, devices of this aspect optionally maintain conformal contact and/or electrical contact and/or optical communication with the surface of a tissue as the tissue moves and/or as the device is moved across a surface of the tissue. Devices and related methods provided herein are particularly suited for long-term mounting to the skin without adverse biological events typically associated with long-term wear, including undue surface irritation, cell death. Long-term refers to continuous wear of the device on the order of days or weeks, including about 7 days or longer.

In an embodiment, a device for establishing an interface with a skin of a subject is provided, the device comprising: (1) a flexible or stretchable substrate having an average modulus less than or equal to 1 MPa; (2) a flexible or stretchable electronic circuit supported by the flexible or stretchable substrate, wherein the flexible or stretchable electronic circuit comprises a plurality of sensors, actuators or both sensors and actuators provided in an array including one or more inorganic semiconductor circuit elements or electrodes, or a combination of inorganic semiconductor circuit elements and electrodes; and (3) a barrier layer encapsulating at least a portion of the flexible or stretchable electronic circuit, the flexible or stretchable substrate, or both the flexible or stretchable electronic circuit and the flexible or stretchable substrate; wherein the flexible or stretchable substrate, barrier layer and the electronic circuit provide a net bending stiffness, thickness, effective elastic modulus, and areal mass density of the device such that the device establishes conformal contact with the skin of the subject.

In an aspect, the device is a skin mounted tissue sensor, a skin mounted tissue actuator, or an array of skin mounted tissue sensors or skin mounted tissue actuators. In another aspect, the device does not include an adhesive layer between the skin of the subject and the flexible or stretchable electronic circuit. In another aspect, any of the flexible or stretchable electronic circuits or devices are mounted on the skin without a flexible or stretchable substrate. In this aspect, the transfer is mediated via a transfer substrate such as transfer stamp that picks up the circuit from a donor substrate and transfers the circuit to the skin. Optionally, a contact layer facilitates transfer from the transfer substrate to the skin.

In an embodiment, the device has a modulus and a thickness within a factor of 2 of a modulus and a thickness of an epidermal layer of the skin of the subject at the interface, optionally within a factor of 1.5, optionally within a factor of 1.0, optionally within a factor of 0.5. In an aspect, the device has an average modulus less than or equal to 500 kPa, optionally less than 250 kPa. In an aspect, the device has an average modulus less than or equal to 100 kPa. In an aspect, the device has an average modulus less than or equal to 50 kPa. In another aspect, the device has an average modulus selected over the range of 0.5 kPa to 100 kPa, optionally selected over the range of 0.5 kPa to 250 kPa, optionally selected over the range of 1 kPa to 250 kPa, optionally over the range of 5 kPa to 500 kPa. In an aspect, the device has an average modulus equal to or less than 50 times the average modulus of the skin of the subject at the interface, optionally equal to or less than 25 times, optionally less than or equal to or less than 15 times.

In an embodiment, the device has an average thickness less than or equal to 500 microns, optionally less than or equal to 250 microns, optionally less than or equal to 150 microns. In an aspect, the device has an average thickness less than or equal to 100 microns. In another aspect, the device has an average thickness less than or equal to 50 microns. In an aspect, the device has an average thickness selected over the range of 1 to 500 microns, optionally 10 to 250 microns, optionally 1 to 150 microns.

In an embodiment, the device has a net bending stiffness less than or equal to 1 nN m, optionally less than or equal to 0.5 nN m. In an aspect, the device has a net bending stiffness selected over the range of 0.1 to 1 nN m, optionally 0.1 to 0.5 nN m, optionally 0.2 nN m to 1 nNm. In another embodiment, the device has an areal mass density less than or equal to 10 mg cm$^{-2}$, optionally less than or equal to 5 mg cm$^{-2}$, optionally less than or equal to 1 mg cm$^{-2}$. In an aspect, the device has an areal mass density selected over the range of 0.5 mg cm$^{-2}$ to 10 mg cm$^{-2}$, optionally 0.5 mg cm$^{-2}$ to 5 mg cm$^{-2}$.

In an embodiment, the flexible or stretchable substrate is a low modulus polymer. In an aspect, the flexible or stretchable substrate has an average modulus less than or equal to 500 kPa, optionally less than or equal to 250 kPa, optionally less than or equal to 150 kPa, optionally less than or equal to 100 kPa, optionally less than or equal to 50 kPa. In an aspect, the flexible or stretchable substrate has an average modulus selected over the range of 1 kPa to 500 kPa, optionally 10 kPa to 500 kPa, optionally 1 kPa to 250 kPa, optionally 25 kPa to 500 kPa, optionally 1 kPa to 150 kPa. In an aspect, the flexible or stretchable substrate is a low modulus rubber material or a low modulus silicone material.

In an aspect, the flexible or stretchable substrate comprises a low modulus rubber material or a low modulus silicone material. In an aspect, the flexible or stretchable substrate is Ecoflex® plastic (BASF). In an aspect, the flexible or stretchable substrate is a bioinert or biocompatible material. In an aspect, the flexible or stretchable substrate comprises a bioinert or biocompatible material. In an aspect, the flexible or stretchable substrate comprises a gas-permeable elastomeric sheet. In an aspect, the flexible or stretchable substrate is applied to the electronic circuit after the circuit is mounted to the skin, such as by application of a sprayable liquid bandage.

In an embodiment, the flexible or stretchable electronic circuit comprises one or more electrodes, transistors, inducers, LEDs, capacitors, oscillators, photodiodes, diodes or any combinations of these. In an aspect, the flexible or stretchable electronic circuit comprises one or more amplifiers, strain gauges, temperature sensors, wireless power coils, solar cells, inductive coils, high frequency inductors, high frequency capacitors, high frequency oscillators, high frequency antennae, multiplex circuits, electrocardiography sensors, electromyography sensors, electroencephalography sensors, electrophysiological sensors, thermistors, transistors, diodes, resistors, capacitive sensors, light emitting diodes, or any combinations of these. In an aspect, the flexible or stretchable is a hydration sensor that measures hydration level of a biological tissue, including skin. In an aspect, the hydration sensor determines hydration level by measuring impedance of the biological tissue. In an aspect, a map of hydration levels is provided over a surface area and/or as a function of depth from the tissue surface.

In an embodiment, the plurality of sensors, actuators or both sensors and actuators of the device are provided in an array, wherein the sensors, actuators, or both are separated by less than or equal to 2.0 mm, optionally 1.0 mm, optionally 0.75 mm, optionally 0.5 mm. In an embodiment, the plurality of sensors, actuators or both sensors and actuators of the device are provided in an array, wherein the sensors, actuators, or both are separated by a distance selected over the range of 0.005 mm to 5.0 mm, optionally 0.1 mm to 2.0 mm, optionally 0.1 to 1.0 mm, optionally 0.1 mm to 0.75 mm, optionally 0.1 to 0.5 mm. In an aspect, the plurality of sensors, actuators or both sensors and actuators of the device are provided in an array, wherein the array is a one dimensional array, optionally a two dimensional array, optionally a three dimensional array.

In an embodiment, the flexible or stretchable electronic circuit has an average thickness less than or equal to 100 microns, optionally less than or equal to 75 microns, optionally less than or equal to 50 microns, optionally less than or equal to 25 microns. In an aspect, the flexible or stretchable electronic circuit has an average thickness less than or equal to 10 microns, optionally less than or equal to 5 microns.

In an embodiment, the flexible or stretchable electronic circuit comprises one or more single crystalline inorganic semiconductor structures. In an embodiment, the flexible or stretchable electronic circuit is positioned proximate to a neutral mechanical plane of the device.

In an embodiment, the flexible or stretchable electronic circuit comprises a plurality of stretchable electronic devices or device components. In an aspect, the flexible or stretchable electronic circuit comprises one or more electronic devices or device components having a curved, serpentine, bent, wavy or buckled geometry. In an aspect, the flexible or stretchable electronic circuit comprises one or more electronic devices or device components comprising structures having a curved geometry, wherein the one or more electronic devices or device components exhibit one or more curves positioned within a plane parallel to a receiving surface of the flexible or stretchable substrate supporting the flexible or stretchable electronic circuit. In an aspect, the flexible or stretchable electronic circuit comprises one or more electronic devices or device components having the wavy geometry comprising structures characterized by a plurality of maxima and minima, wherein the maxima and minima are positioned within a plane parallel to a receiving surface of the flexible or stretchable substrate supporting the flexible or stretchable electronic circuit.

In an embodiment, the flexible or stretchable electronic circuit comprises one or more nanoribbons, micromembranes or nanomembranes. In an aspect, the nanoribbons, micromembranes or nanomembranes are provided in a wavy geometry characterized by a plurality of maxima and minima. In an aspect, adjacent maxima and minima of the wavy geometry are separated by a distance less than or equal to 10 microns, optionally less than or equal to 5 microns. In an aspect, adjacent maxima and minima of the wavy geometry are separated by a distance selected over the range of 0.1 micron to 10 microns, optionally 1 micron to 8 microns, optionally 1 micron to 5 microns, optionally 2 microns to 10 microns.

In an embodiment, the wavy geometry is characterized by a periodic structure. In an aspect, wavy geometry is characterized by an amplitude of less than 10 microns, optionally less than 8 microns, optionally less than 5 microns. In an aspect, the wavy geometry is characterized by a periodic structure. In an aspect, wavy geometry is characterized by an amplitude selected over the range of 0.1 micron to 10 microns, optionally 1 micron to 10 microns, optionally 1 micron to 8 microns.

In an embodiment, the wavy geometry is characterized by a radius of curvature less than or equal to 1 mm, optionally 0.5 mm, optionally 0.1 mm. In an aspect, the wavy geometry is characterized by a radius of curvature selected over the range of 0.01 mm to 1 mm, optionally 0.02 mm to 1 mm, optionally 0.1 mm to 1 mm.

In an embodiment, the wavy geometry is a serpentine geometry. In an aspect, the serpentine geometry is characterized by a repeating s-shaped feature.

In an embodiment, local displacement of the nanoribbons, micromembranes or nanomembranes within the plane parallel to the receiving surface of the flexible or stretchable substrate supporting the flexible or stretchable electronic circuit reduces an overall state of strain of the device.

In an embodiment, the nanoribbons, micromembranes or nanomembranes comprise metallic structures. In an aspect, the nanoribbons, micromembranes or nanomembranes comprise single crystalline semiconductor structures. In another aspect, the nanoribbons, micromembranes or nanomembranes comprise hybrid structures comprising one or more metallic structures connected to one or more single crystalline semiconductor structures.

In an embodiment, the flexible or stretchable electronic circuit comprises one or more island and bridge structures. In an aspect, the island structures comprise one or more semiconductor circuit elements. In an aspect, the island structures correspond to electrodes. In another aspect, the bridge structures comprise one or more flexible or stretchable electrical interconnections.

In an embodiment, the flexible or stretchable electronic circuit is assembled on the flexible or stretchable substrate or directly to the biological tissue via contact printing.

In an embodiment, the device further comprises a transfer substrate supporting the flexible or stretchable substrate, the flexible or stretchable electronic circuit, or both the flexible or stretchable substrate and the flexible or stretchable electronic circuit. In an aspect, the transfer substrate is in physical contact with the flexible or stretchable substrate. In an aspect, the transfer substrate is in physical contact with the flexible or stretchable electronic circuit. In this aspect, the transfer substrate functions as a supporting substrate during the transfer of the flexible or stretchable electronic circuit to the tissue surface. In an aspect, the transfer substrate is a removable substrate and the transfer substrate is partially or completely removed upon providing the device in contact with the skin of the subject. In an aspect, the transfer substrate is a dissolvable substrate and wherein the transfer substrate is partially or completely dissolved after the device is provided in contact with the skin of the subject. In another aspect, the transfer substrate is a polymer. In an aspect, the transfer substrate is polyvinyl acetate.

In an aspect, the flexible or stretchable substrate, the electronic circuit and the barrier layer provide a net flexural rigidity of the device less than or equal to $1 \times 10^{-4}$ N m, optionally $5 \times 10^{-5}$ N m, optionally $2.5 \times 10^{-5}$ N m. In an aspect, the flexible or stretchable substrate, the electronic circuit and the barrier layer provide a net flexural rigidity of the device selected over the range of $5 \times 10^{-6}$ N m to $1 \times 10^{-4}$ N m, optionally $1 \times 10^{-5}$ N m to $1 \times 10^{-4}$ N m.

In an embodiment, the barrier layer comprises a material selected from the group consisting of: a polymer, an inorganic polymer, an organic polymer, an elastomer, a biopolymer, a ceramic, and any combination of these. In an aspect, the barrier layer comprises polyvinylpyrrolidone, pyroxylin, nitrocellulose, poly(methylacrylate-isobutene-monoisopropylmaleate), pyroxylin, an acrylate polymer, a siloxane polymer, a cyanoacrylate, an octylcyanoacrylate, an acrylate copolymer, 2-octyl cyanoacrylate, ethyl cyanoacrylate, n-Butyl cyanoacrylate, an acrylate terpolymer, polyethylene, polydimethylsiloxane, a liquid bandage composition, or any combination thereof. In an aspect, the barrier layer comprises an elastomer. In an aspect, the barrier layer comprises PDMS, polyimide, SU-8, parylene, parylene C, silicon carbide (SiC), or $Si_3N_4$. In an aspect, the barrier layer is a biocompatible material or a bioinert material. In an aspect, the barrier layer comprises a biocompatible material or a bioinert material. In an aspect, any of the barrier layers provided herein is a cover layer. In an aspect, the barrier layer is applied as a liquid, wherein upon evaporation of solvent, a polymer layer is left behind that covers the electronic circuit.

In an embodiment, a method of interfacing an electronic device with a skin of a subject is provided, the method comprising: (1) providing the skin of the subject; (2) providing a conformable electronic device, the device comprising: (i) a flexible or stretchable substrate having an average modulus less than or equal to 1 MPa; (ii) a flexible or stretchable electronic circuit supported by the flexible or stretchable substrate, wherein the flexible or stretchable electronic circuit comprises a plurality of sensors, actuators or both sensors and actuators provided in an array including one or more inorganic semiconductor circuit elements or electrodes, or a combination of inorganic semiconductor circuit elements and electrodes; (iii) a barrier layer encapsulating at least a portion of the flexible or stretchable electronic circuit, the flexible or stretchable substrate, or both the flexible or stretchable electronic circuit and the flexible or stretchable substrate; and (iv) a transfer substrate supporting the flexible or stretchable substrate, the flexible or stretchable electronic circuit, or both the flexible or stretchable substrate and the flexible or stretchable electronic circuit; (3) contacting the conformable electronic device to a receiving surface of the skin of the subject, wherein upon contact the flexible or stretchable electronic circuit is positioned between the skin and the a flexible or stretchable substrate; and (4) at least partially removing the transfer substrate; wherein the flexible or stretchable substrate, barrier layer and the flexible or stretchable electronic circuit provide a net bending stiffness of the conformable electronic device low enough that the conformable electronic device establishes conformal contact with the skin of the subject upon at least partial removal of the transfer substrate, thereby interfacing the conformable electronic device with the skin of the subject.

In an embodiment, the step of at least partially removing the transfer substrate comprises entirely removing the transfer substrate. In an aspect, the step of at least partially removing the transfer substrate comprises dissolving the transfer substrate after the step of contacting the conformable electronic device to a receiving surface of the skin of the subject.

In an embodiment, the method further comprises sensing and/or actuating a tissue of the subject. In an aspect, the tissue of the subject is skin, heart, muscle or brain tissue of the subject. In an aspect, impedance of skin is measured, such as by a plurality of electrodes and impedance is used to determine hydration.

In an embodiment, the method further comprises making electrocardiography measurements, electromyography measurements or electroencephalography measurements of the subject. In an embodiment, the method further comprises providing electromagnetic radiation to the tissue of the subject. In an embodiment, the method further comprises measuring a temperature of the tissue of the subject. In an embodiment, the method further comprises comprising making one or more voltage measurements, current measurements, impedance measurements, electromagnetic radiation intensity or power measurements, temperature measurements, pressure measurements, tissue acceleration measurements, or tissue movement measurements of the tissue of the subject. In an aspect, any of those measures provide a distribution over a region or a "map". Such spatial monitoring is referred herein as "mapping". The mapping may further by measured as a time course, with the map changing over time. In this manner, localized regions within a larger monitoring area can be further studied and examined.

In an embodiment, the conformal device contacts an area of the skin of the subject selected from the range of 1000 $\mu m^2$ to 1000 $cm^2$, optionally 5000 $\mu m^2$ to 1000 $cm^2$, optionally 1000 $\mu m^2$ to 500 $cm^2$, optionally 5000 $\mu m^2$ to 500 $cm^2$.

In an embodiment, the flexible or stretchable electronic circuit is positioned proximate to a neutral mechanical plane of the device. In an embodiment, the substrate, the electronic circuit and the barrier layer provide a net flexural rigidity of the device less than or equal to $1\times10^{-4}$ N m, optionally $5\times10^{-5}$ N m, optionally $1\times10^{-5}$ N m.

In an embodiment, the method further comprises measuring a temperature of the tissue of the subject. In an aspect, the method further comprises making one or more voltage measurements, current measurements, electromagnetic radiation intensity or power measurements, temperature measurements, pressure measurements, tissue acceleration measurements, or tissue movement measurements of the tissue of the subject. In an aspect, the conformal device contacts an area of the skin of the subject selected from the range of 1000 $\mu m^2$ to 1000 $cm^2$, optionally 5000 $\mu m^2$ to 500 $cm^2$, optionally 5000 $\mu m^2$ to 1000 $cm^2$, optionally 1 $cm^2$ to 100 $cm^2$.

In an embodiment, the invention provides a device for interfacing with a tissue in a biological environment comprising: (1) a flexible or stretchable substrate; (2) a flexible or stretchable electronic circuit comprising one or more inorganic semiconductor circuit elements supported by the flexible or stretchable substrate; and (3) a barrier layer encapsulating at least a portion of the flexible or stretchable electronic circuit. The materials, physical dimensions and mechanical properties of the device, and components thereof, are selected in some embodiments to provide device attributes useful for a range of biomedical applications, including sensing and actuation of tissue. In an embodiment, for example, the flexible or stretchable substrate, the flexible or stretchable electronic circuit and the barrier layer have compositions, physical dimensions and/or geometries providing a net bending stiffness and/or flexural rigidity of the device low enough that the device establishes conformal contact with the tissue in the biological environment. In certain embodiments, the barrier layer is a moisture barrier, a thermal barrier, an electromagnetic radiation barrier, an electrical barrier, an optical barrier, a magnetic barrier, a selectively permeable or impermeable barrier or any combination of these. In an embodiment, for example, the substrate is a flexible substrate and the electronic circuit is a flexible electronic circuit. In an embodiment, for example, the substrate is a stretchable substrate and the electronic circuit is a stretchable electronic circuit.

In an embodiment, the invention provides a device for interfacing with a tissue in a biological environment, the device comprising: a flexible or stretchable substrate; a flexible or stretchable electronic circuit supported by the flexible or stretchable substrate, wherein the flexible or stretchable electronic circuit comprises a plurality of sensors, actuators or both sensors and actuators provided in an array and one or more inorganic semiconductor circuit elements; a controller in communication with the flexible or stretchable electronic circuit, the controller configured to receive input signals from the flexible or stretchable electronic circuit and provide output signals to the flexible or stretchable electronic circuit, wherein the controller receives and analyzes input signals corresponding to one or more measurements from the sensors and generates output signals that control or provide one or more sensing or actuation parameter to the flexible or stretchable electronic circuit; and a barrier layer encapsulating at least a portion of the flexible or stretchable electronic circuit; wherein the substrate, the electronic circuit and the barrier layer provide a net bending stiffness of the device low enough that the device establishes conformal contact with the tissue in the biological environment. In an embodiment, the controller receives input signals corresponding to measurements by the sensors of tissue properties, such as composition, structure and physiological properties, and uses the input signals to control sensing and/or actuation of the tissue, for example, via a closed-loop feedback algorithm. In an embodiment, the controller receives input signals corresponding to measurements by the sensors of tissue properties, such as composition, structure and physiological properties, as a function of time and uses the input signals as a function of time to adjust and/or optimize sensing and/or actuation of the tissue. In an embodiment, the controller receives input signals corresponding to measurements by the sensors of tissue properties, such as composition, structure and physiological properties, and uses the input signals to control removal of at least a portion of the tissue, for example, via tissue ablation methods.

The materials, physical dimensions and mechanical properties of the device, and components thereof, are selected in some embodiments to provide complete or partial electronic, optical, chemical and/or thermal isolation of the device from the tissue and/or biological environment useful for avoiding damage of the tissue during use. In an embodiment, for example, the barrier layer and the flexible or stretchable substrate limit a net leakage current from the electronic circuit to an amount which does not adversely affect the tissue. In an embodiment, for example, the barrier layer and the flexible or stretchable substrate limits heat transfer from the electronic circuit to the tissue in the biological environment to an amount that does not adversely affect the tissue in the biological environment.

The materials, physical dimensions and mechanical properties of the device, and components thereof, are selected in some embodiments to provide access of the device to the tissue and/or biological environment useful for biomedical applications, including sensing and/or actuation of tissue. In an embodiment, for example, the barrier layer is patterned so as to selectively modulate physical contact, thermal contact, optical communication or electrical communication between the electronic circuit and the tissue in the biological environment. In an embodiment, for example, the barrier layer is patterned so as to provide one or more permeable regions that are selectively permeable to one or more target molecules to allow transport of the target molecules from the biological environment to the electronic circuit or from the electronic circuit to the biological environment. In an embodiment, for example, the barrier layer is patterned so as to provide one or more impermeable regions that are impermeable to one or more target molecules to prevent transport of the target molecules from the biological environment to the electronic circuit or from the electronic circuit to the biological environment. In an embodiment, for example, the barrier layer is patterned to provide one or more transparent regions, wherein the transparent regions transmit to or from the electronic circuit ultraviolet, visible or near-infrared electromagnetic radiation having a preselected wavelength distribution. In an embodiment, for example, the barrier layer is patterned to provide one or more opaque regions that substantially prevent transmission to or from the electronic circuit of electromagnetic radiation having a preselected distribution of wavelengths in the ultraviolet, visible or near-infrared regions of the electromagnetic spectrum.

As used in this context, the term "patterned" refers to selective variation of the physical properties, chemical composition, physical dimensions and/or geometry of a device or component thereof, for example via openings, channels, pores, contact regions, permeable regions, impermeable regions, transmissive regions, conductive regions and/or opaque regions. In an embodiment, the barrier layer is patterned to have one or more contact regions, such as openings or passages allowing physical contact between components of the electronic circuit (e.g., electrodes or sensors) and the tissue. In an embodiment, the barrier layer is patterned to have one or more transmissive regions, such as windows allowing optical communication between components (e.g., sensors, optical sources, LEDs, laser, photodiodes, etc.) of the electronic circuit and the tissue. In an embodiment, the barrier layer is patterned to have one or more chemically permeable regions, such as pores or channels allowing selective transport of target molecules between with electronic circuit and the tissue. Patterned in this context may refer to a device component, such as a barrier layer, that is patterned via a microprocessing technique such as optical lithography, soft lithography, etching, e-beam writing and/or laser ablation.

Devices of the present invention are applicable to a wide range of tissues and biological environments, including implant environments and exposed tissue environments, such as skin. In an embodiment, for example, the biological environment is an in-vivo biological environment. In an embodiment, for example, the biological environment comprises a conductive ionic solution, such as a biological fluid including blood, a component of blood, pericardial fluid, peritoneal fluid, cerumen, and cerebrospinal fluid. In an embodiment, for example, the tissue in the biological environment comprises heart tissue, brain tissue, muscle tissue, skin, nervous system tissue, epithelial tissue, retina tissue, ear drum, tumor tissue, digestive system structures, circulatory system structures and/or vascular tissue. In an embodiment, the device establishes conformal contact with the tissue in situ when the device is placed in physical contact with the tissue in the biological environment, and wherein the conformal contact with the tissue in the biological environment is maintained as the tissue or the device moves. In an embodiment, the device is in electrical contact with the tissue in the biological environment, wherein the electrical contact with the tissue in the biological environment is maintained as the tissue or the device moves. In some embodiments, the device of the invention is applied via establishing physical contact with the tissue and/or biological environment, for example by implanting the device or contacting a surface of the tissue with the device.

The invention provides devices having physical and chemical properties useful for a wide range of biomedical applications including cardiac monitoring, sensing and actuation of brain tissue, vascular therapies and skin mounted sensing. In an embodiment, for example, the substrate, the electronic circuit and the barrier layer provide a net bending stiffness of the device less than or equal to $1\times10^8$ GPa µm$^4$, optionally for some applications less than or equal to $1\times10^7$ GPa µm$^4$, and optionally for some applications less than or equal to $1\times10^6$ GPa µm$^4$. In an embodiment, for example, the substrate, the electronic circuit and the barrier layer provide a net bending stiffness of the device selected over the range of $1\times10^8$ GPa µm$^4$-$1\times10^5$ GPa µm$^4$, and optionally for some applications selected over the range of $1\times10^7$ GPa µm$^4$-$1\times10^{-5}$ GPa µm$^4$, and optionally for some applications selected over the range of $1\times10^6$ GPa µm$^4$-$1\times10^5$ GPa µm$^4$. In an embodiment, for example, the substrate, the electronic circuit and the barrier layer provide a net flexural rigidity of the device less than or equal to $1\times10^{-4}$ Nm, and optionally for some embodiments less than or equal to $1\times10^{-5}$ Nm. In an embodiment, for example, the substrate, the electronic circuit and the barrier layer provide a net flexural rigidity of the device selected from the range of $1\times10^{-4}$ Nm to $1\times10^{-7}$ Nm, and optionally for some applications device selected from the range of $1\times10^{-5}$ Nm to $1\times10^{-7}$ Nm. For certain embodiments, devices of this aspect have and/or are capable of having a bending radius for all and/or portions of the device of 100 µm. For example, devices of this aspect can adopt a radius of curvature of 100 µm without undergoing damage to the device or device components, such as mechanical fracture, device failure or interruption of electrical interconnections.

The invention includes devices having a multilayer geometry, including a geometry wherein independently any of the substrate, electronic circuit and barrier layer components (and/or components of these) are provided in a series of stacked layers, including layers and/or thin films that are provided in direct contact with each other in the series of layers or in a series having one or more intermediate layers (e.g., adhesive layers, contact layers, cover layers, spacer layers, NMP layers, etc.) provided between device layers of the series. The positioning of device components in multi-layer geometries of the present devices may be selected to provide enhanced mechanical attributes or device functionality. In an embodiment, for example, the device has a neutral mechanical plane and at least a portion of the inorganic semiconductor circuit elements are positioned proximate to the neutral mechanical plane. In an embodiment, for example, a thickness of the barrier layer and a thickness of the flexible or stretchable substrate are selected so as to position at least a portion, or optionally all, of the inorganic semiconductor circuit elements proximate to the neutral mechanical plane. In some embodiments, proximate to the neutral mechanical plane refers to device geometries wherein a device component, such as an electronic circuit component is positioned within 10 microns, and optionally for some applications, within 1 micron, to the overall neutral mechanical plane at a specific position of the device.

Any of the barrier layers of any of the devices may function to completely or partially encapsulate one or more other device components such as flexible or stretchable electronic circuit components and or the flexible or stretchable substrate. In some embodiments, the electronic circuit component is completely encapsulated by, and in physical contact with, the barrier layer and/or flexible or stretchable substrate. In an embodiment, for example, the barrier layer and/or flexible or stretchable substrate encapsulates at least 50% of the electronic circuit component of the device, optionally at least 90% of the electronic circuit component of the device, and optionally all of the electronic circuit component of the device. In an embodiment, the barrier layer partially or completely encapsulates the flexible or stretchable substrate. In an embodiment, for example, the barrier layer encapsulates at least 50% of the flexible or stretchable substrate of the device, optionally at least 90% of the flexible or stretchable substrate of the device, and optionally all of the flexible or stretchable substrate of the device. In an aspect, a cover layer is provided that is functionally similar to a barrier layer. Cover layer refers to the aspect where a layer is provided after any of the devices disclosed herein are applied to the tissue, such as skin. In an aspect where the application is to skin having a contact layer, the cover layer effectively encapsulates the device from the surrounding environment. As necessary or desired, the cover layer may be periodically reapplied, such as daily, to facilitate long term use. A plurality of cover layers may be applied, including cover layers having different compositions for different functionality. For example, one cover layer may provide exceptional waterproofing and another exceptional durability. In this manner, the cover layer may be a composite cover layer to achieve better functional outcome.

Selection of the composition and physical properties of the barrier, contact or cover layer is an important aspect of the invention for controlling and/or selectively modulating the interface of the device and the tissue and/or biological environment. In an embodiment, for example, the barrier, contact or cover layer has an average thickness over at least a portion of the electronic circuit less than or equal to 1000 µm, optionally for some applications less than or equal to 100 µm, optionally for some applications less than or equal to 10 µm, and optionally for some embodiments applications less than or equal to 1 µm. In an embodiment, for example, the barrier, contact or cover layer has a thickness over at least a portion of the electronic circuit selected over the range of 0.25 µm to 1000 µm, and optionally for some applications selected over the range of 0.5 µm to 500 µm, and optionally for some applications selected over the range of 1 µm to 25 µm. In an embodiment, the ratio of the average thickness of the barrier layer to the average thickness of the flexible or stretchable substrate is selected over the range of 0.1 to 10, and optionally for some applications 0.5 to 2.

In some embodiments, the barrier layer comprises a low modulus material. The invention includes, for example, devices wherein the barrier layer has an average modulus less than or equal to 10 GPa, an average modulus less than or equal to 1 GPa optionally for some embodiments less than or equal to 100 MPa, optionally for some embodiments less than or equal to 10 MPa, and optionally for some embodiments less than or equal to 1 MPa. In an embodiment, for example, the barrier layer has an average modulus selected over the range of 0.5 KPa to 10 GPa, optionally for some application selected over the range of 1 KPa to 1 GPa, and optionally for some application selected over the range of 1 KPa to 100 MPa. In an embodiment, for example, the barrier layer has an average modulus equal to or less than 50 times the average modulus of the skin of the subject at the tissue interface. As will be generally understood by one skilled in the art, use of a barrier layer with a relatively high modulus (e.g., greater than 1 GPa) in some embodiments may require a small thickness (e.g., less than 100 microns or optionally less than 10 microns) to provide net device mechanical properties (e.g., bending stiffness or flexural rigidity) useful for establishing conformal contact with the tissue.

A range of materials are useful for barrier layers of the devices of the invention. In an embodiment, for example, the barrier layer comprises a material selected from the group consisting of: a polymer, an inorganic polymer, an organic polymer, an elastomer, a biopolymer (e.g., polypeptide, protein, polynucleotide, oligonucleotide, carbohydrate, etc.), a ceramic, and any combination of these. Barrier layers of the invention include composite materials. In an embodiment, for example, the barrier layer comprises an elastomer. In an embodiment, for example, the barrier layer comprises PDMS, SU-8, $Si_3N_4$, $SiO_2$, polyurethane, polyimide, parylene, parylene C, silicon carbide (SiC), BCB, NOA, and any combination of these. In an embodiment, for example, the barrier layer is a biocompatible material and/or a bioinert material.

In an embodiment, for example, the barrier layer is patterned to have one or more nanostructured or microstructured optically transmissive regions, optically opaque regions or selectively permeable regions that are permeable to one or more target molecules, for example, to provide 1 to 1000 of such nanostructured or microstructured regions, and optionally 10-50 of such nanostructured or microstructured regions. As used herein, the term "microstructured" refers to a structure having at least one physical dimension selected over the range of 1 micron to 1000 microns, such as one or more lateral dimensions (e.g., length or width) selected over the range of 1 micron to 1000 microns. The term "nanostructured" refers to a structure having at least one physical dimension selected over the range of 10 nanometers to 1000 nanometers, such as one or more lateral dimensions (e.g., length or width) selected over the range of 10 nanometers to 1000 nanometers. Microstructured and/or nanostructured regions of the barrier layer include a variety of structures including channels, pores, openings, windows, electrodes, permeable regions, recessed features, relief features (e.g., raised features), transparent regions, opaque regions and the like. In an embodiment, the microstructured or nanostructured region(s) of the barrier layer is one or more openings, pores or channels in the barrier layer so as to provide physical contact between selected regions of the electronic circuit and the tissue or biological environment. In an embodiment, the microstructured or nanostructured region(s) of the barrier layer is one or more optically transparent windows in the barrier layer so as to provide optical communication between selected regions of the electronic circuit and the tissue and/or biological environment, for example, to allow transmission of electromagnetic radiation having a preselected wavelength distribution, such as light in the visible, ultra violet and/or near infrared regions of the electromagnetic spectrum. In an embodiment, the microstructured or nanostructured region(s) of the barrier layer is one or more electrodes in the barrier layer so as to provide electrical contact between selected regions of the electronic circuit and the tissue and/or biological environment.

In an embodiment, the barrier and/or cover layer comprises a multilayer structure, for example, comprising 2 to 50 individual layers and optionally 2-20 individual layers. In some embodiments, for example, a barrier layer of the invention comprises a sequence of layers, wherein layers in the sequence are selected from the group consisting of metal layers, inorganic layers (e.g., inorganic dielectrics such as oxides, carbides or nitrides, etc.) and polymer layers. In an embodiment, the layers of the sequence are thin film layers having thicknesses ranging from 10 nanometers to 10 microns. This aspect of the invention is beneficial for providing barrier layers having useful chemical, electronic or thermal properties, such as providing low leakage currents for long periods of time. In an embodiment, for example, the barrier layer is a multilayer structure comprising one or more metal layers separated by one or more inorganic layers or polymer layers. In an embodiment, for example, the barrier layer is a multilayer structure comprising one or more inorganic layers separated by one or more metal layers or polymer layers. In an embodiment, for example, the barrier layer is a multilayer structure comprising one or more polymer layers separated by one or more metal layers or inorganic layers. Use of polymer layers in barrier or cover layers comprising multilayer structures is useful in some embodiments for filling in cracks and/or pinholes in metal and/or inorganic layers and filling in open areas of the flexible and stretchable electronic circuit, thereby facilitating long-term use. In an embodiment, a barrier layer of the invention comprises a multilayer structure having a total thickness less than 500 microns, optionally for some applications less than 100 microns, and optionally for some applications less than 10 microns.

Selection of the composition and physical properties of the flexible or stretchable substrate is an important aspect of the invention for providing useful device properties. In an embodiment, for example, the flexible or stretchable substrate has an average thickness less than or equal to 1000 µm, optionally for some applications less than or equal to 100 µm, and optionally for some applications less than or equal to 10 µm. In an embodiment, for example, the flexible or stretchable substrate has an average thickness selected over the range of 0.25 µm to 1000 µm, optionally for some embodiments selected over the range of 10 µm to 500 µm and optionally for some embodiments selected over the range of 10 µm to 100 µm. Substrates of certain devices of the invention have a substantially uniform thickness (e.g., deviations from an average thickness less than 10% and optionally less than 5% and optionally less than 1%). Alternatively, the invention includes substrates having a thickness that varies selectively along one or more lateral dimension (e.g. length or width) over the electronic circuit. In some embodiments, for example, the substrate is thicker in certain regions, such as regions supporting or in physical contact with components of the electronic circuit, than in other regions of the substrate that are not supporting or in physical contact with components of the electronic circuit. In some embodiments, for example, the substrate is absent in certain regions, such as regions of the substrate that are not supporting or in physical contact with components of the electronic circuit.

In some embodiments, the device of the invention comprises a substrate having one or more microstructured and/or nanostructured features, including recessed features, relief (e.g. raised) features, openings, passages and/or channels. In an embodiment, at least a portion of, and optionally all of, the electronic circuit component of the device is supported by a flexible or stretchable substrate having a mesh structure. Use of a substrate having a mesh structure is beneficial in the invention for providing a structurally supporting layer allowing for efficient handling and administration of the device, while at the same time providing mechanical properties (e.g., flexibility, deformability, bendability, stretchability, etc.) useful for establishing conformal contact with the target tissue. In an embodiment, for example, a mesh structure refers to a layer or other structural component that occupies a portion of, but not all, the foot print area of the device, for example, occupying a portion of, but not all of, the area of the device that interfaces the target tissue. In an embodiment, for example, the foot print area of the device is an area corresponding to the perimeter of the device that establishes the interface with a target tissue, and the mesh structure of the substrate occupies a portion, but not all of the, foot print area. Mesh structures in some embodiments, occupy 75% or less than the foot print area and/or tissue interface area of the device, and optionally 50% or less than the foot print area and/or tissue interface area; and optionally 25% or less than the foot print area and/or tissue interface area of the device. In an embodiment, for example, the substrate has a mesh structure that is a lattice structure, a perforated structure or a tentacle structure. In an embodiment, for example, the substrate is a mesh structure having structural regions at least partially supporting, or optionally in physical contact with, one or more of the components of the electronic circuit, such as inorganic semiconductor components or electrodes, wherein structural regions of the substrate are separated from each other by voids, cut outs or other openings where the substrate is not present. In such embodiments, therefore, the presence of the void regions, cut outs or other openings provides a mesh structured substrate occupying less than the foot print area of the device. In an embodiment, for example, the substrate having a mesh structure is a discontinuous layer, as opposed to a continuous layer, such as a continuous film or sheet.

In an embodiment, for example, the flexible or stretchable substrate comprises a low modulus material. For example, the invention includes devices having a flexible or stretchable substrate with an average modulus less than or equal to 10 GPa, optionally for some embodiments less than or equal to 100 MPa, optionally for some embodiments less than or equal to 10 MPa, and optionally for some embodiments less than or equal to 1 MPa and optionally less than 0.1 MPa. In an embodiment, for example, the flexible or stretchable substrate has an average modulus selected over the range of 0.5 KPa to 5 GPa, optionally for some application selected over the range of 1K to 1 GPa, and optionally for some application selected over the range of 1 KPa to 100 MPa. In an embodiment, for example, the flexible or stretchable substrate has an average modulus equal to or less than 50 times the average modulus of the skin of the subject at the tissue interface. As will be generally understood by one skilled in the art, use of a flexible or stretchable substrate layer with a relatively high modulus (e.g., greater than 1 GPa) in some embodiments may require a small thickness (e.g., less than 100 microns or optionally less than 10 microns) to provide net device mechanical properties (e.g., bending stiffness or flexural rigidity) useful for establishing conformal contact with the tissue.

A range of materials are useful for flexible or stretchable substrates of the devices of the invention. In an embodiment, for example, the flexible or stretchable substrate comprises a material selected from the group consisting of: a polymer, an inorganic polymer, an organic polymer, a biopolymer (e.g., polypeptide, protein, polynucleotide, oligonucleotide, carbohydrate, etc.), a plastic, an elastomer, a thermoset, rubber, fabric, paper, a composite material and any combination of these. In an embodiment, for example, the flexible or stretchable substrate comprises PDMS, parylene or polyimide. In an embodiment, for example, the flexible or stretchable substrate comprises a low modulus rubber or a low modulus silicone material, such as Ecoflex®. In an embodiment, for example, the flexible or stretchable substrate is a biocompatible material or a bioinert material. In an embodiment, for example, the flexible or stretchable substrate and the barrier each comprise the same material, such as the same polymer or elastomer material Flexible or stretchable electronic circuit components of the invention include a range of electronic devices, or components thereof, including semiconductor devices, active electronic devices, passive electronic devices, optoelectronic devices, optical devices, and electronic device arrays. Electronic circuits of the invention include, for example, an inorganic semiconductor component, such as a single crystalline inorganic semiconductor structure, doped single crystalline inorganic semiconductor structure, high purity single crystalline inorganic semiconductor structure. This aspect of the invention is particularly useful for accessing devices exhibiting very high electronic device performance, such as devices having transistor components exhibiting useful field effect mobilities and/or on/off ratios.

In an embodiment, for example, the flexible or stretchable electronic circuit comprises one or more flexible or stretchable inorganic semiconductor structures. In an embodiment, for example, the flexible or stretchable inorganic semiconductor structures of the electronic circuit component comprise a single crystalline inorganic semiconductor, such as single crystalline silicon or a single crystalline iii-v semiconductor structure. To provide useful flexibility in some embodiments, the semiconductor structures of the electronic circuit of the invention are thin semiconductor structures. In an embodiment, for example, the flexible or stretchable inorganic semiconductor structures have an average thickness less than or equal to 500 microns, optionally for some applications less than or equal to 100 microns, optionally for some applications less than or equal to 10 microns, optionally for some applications less than or equal to 1 micron, and optionally for some applications less than or equal to 500 nanometers. In an embodiment, for example, the flexible or stretchable inorganic semiconductor structures have an average thickness selected from the range of 100 nanometers to 1000 microns, optionally for some embodiments selected from the range of 500 nm to 500 microns, optionally for some embodiments selected from the range of 1 micron to 100 microns. In an embodiment, for example, the flexible or stretchable inorganic semiconductor structures have an average thickness selected from the range of 250 nanometers to 100 microns. In an embodiment, for example, the flexible or stretchable inorganic semiconductor structures are ultrathin structures. In an embodiment, for example, each of the flexible or stretchable inorganic semiconductor structures has a net flexural rigidity less than or equal to less than or equal to $1\times10^{-4}$ Nm. In an embodiment, for example, each of the flexible or stretchable inorganic semiconductor structures has a net bending stiffness less than or equal to $1\times10^{8}$ GPa $\mu m^4$, optionally for some applications less than or equal to $1\times10^{7}$ GPa $\mu m^4$, and optionally for some applications less than or equal to $1\times10^{6}$ GPa $\mu m^4$. In an embodiment, for example, each of the flexible or stretchable inorganic semiconductor structures is independently a flexible or stretchable semiconductor nanoribbon, semiconductor membrane, semiconductor nanowire or any combination of these. In an embodiment, for example, the flexible or stretchable inorganic semiconductor structures are assembled on the flexible or stretchable substrate via a transfer printing technique, such as dry transfer contact printing and/or transfer printing process using an elastomeric transfer device.

In an embodiment, the flexible or stretchable electronic circuit further comprises one or more additional device components in physical or electronic contact with the inorganic semiconductor structures. In an embodiment, for example, the flexible or stretchable electronic circuit further comprises one or more flexible or stretchable dielectric structures, wherein at least a portion of the flexible or stretchable inorganic semiconductor structures is in physical contact with one or more of the dielectric structures. A range of dielectric structures are useful in this aspect of the invention including flexible or stretchable dielectric structures having a thickness equal to or less than 100 microns. In an embodiment, for example, the flexible or stretchable electronic circuit further comprises one or more flexible or stretchable electrodes, wherein at least a portion of the flexible or stretchable inorganic semiconductor structures or a portion of the dielectric structures is in electrical contact with one or more of the electrodes. A range of electrodes are useful in this aspect of the invention including flexible or stretchable electrodes having a thickness equal to or less than 500 microns.

The invention includes devices wherein the flexible or stretchable electronic circuit comprises a plurality of electronically interconnected island and bridge structures. This aspect of the invention is useful for providing highly conformal and optionally stretchable devices. In an embodiment, for example, the island structures comprise one or more semiconductors, including flexible or rigid semiconductor structures and/or semiconductor electronic devices, semiconductor and dielectric structures, semiconductor and electrode structures, transistors, photodiodes, light emitting diodes, lasers, diodes, integrated circuits, multiplexer circuits, and amplifier circuits. In an embodiment, for example, the bridge structures comprise one or more flexible or stretchable electrical interconnections, such as electrical interconnections having a serpentine, meander, buckled, or bent geometry. In an embodiment, for example, the flexible or stretchable electrical interconnections are encapsulated structures (e.g. encapsulated in polymer or elastomer). In some embodiments, at least a portion of the island structures comprising semiconductor structures are in electrical contact with one or more flexible or stretchable interconnects.

The invention includes devices wherein the flexible or stretchable electronic circuit is selected from the group consisting of: a flexible or stretchable transistor, a flexible or stretchable diode, a flexible or stretchable amplifier, a flexible or stretchable multiplexer, a flexible or stretchable light emitting diode, a flexible or stretchable laser, a flexible or stretchable photodiode, a flexible or stretchable integrated circuit and any combination and arrays thereof. In some embodiments, for example, the flexible or stretchable electronic circuit is a CMOS integrated circuit or a logic gate circuit. In an embodiment, the flexible or stretchable electronic circuit further comprises a plurality of sensing or actuating elements spatially arranged over the flexible or stretchable substrate, wherein each sensing or actuating element is in electrical communication with at least one of the plurality of flexible semiconductor circuit elements, for example, wherein at least one of the plurality of sensing or actuating elements is in electrical communication with the tissue when the device is in conformal contact with the tissue in the biological environment. In an embodiment, for example, the actuating elements comprise circuit elements selected from the group consisting of: electrode elements, electromagnetic radiation emitting elements, heating elements, ablation elements and any combination of these. In an embodiment, for example, the flexible or stretchable electronic circuit includes one or more sensing electrode elements, chemical or biological sensor elements, pH sensors, optical sensors, temperature sensors, capacitive sensors, strain sensors, acceleration sensors, movement sensors, displacement sensors and any combination of these. In an embodiment, for example, the flexible or stretchable electronic circuit comprises one or more sensors using a capacitance type circuit. In an embodiment, for example, at least a portion of the sensing or actuating elements is encapsulated by the barrier layer and/or the flexible or stretchable substrate. In some embodiments, at least one sensing element is positioned at the surface of the barrier layer, in electrical communication with a tissue in a biological environment, optical communication with a tissue in a biological environment and/or in physical contact with a tissue in a biological environment.

In an embodiment, the flexible or stretchable electronic circuit comprises an active circuit, such as an amplifier circuit, multiplexing circuit or a logic gate. In an embodiment, for example, the multiplexing circuit of the flexible or stretchable electronic device is configured to individually address each of a plurality of sensing or actuating circuit elements spatially arranged over the flexible or stretchable substrate, such as a plurality of electrodes in an array. In an embodiment, the flexible or stretchable electronic circuit comprises a current limiting circuit, for example, a current limiting circuit that limits net leakage current from the electronic device to 10 µA or less, optionally for some applications 5 µA or less or optionally for some applications 1 µA or less.

Devices of this aspect optionally have a neutral mechanical plane wherein at least a portion of the flexible or stretchable electronic circuit, or components thereof, are positioned proximate to the neutral mechanical plane, or wherein optionally all of the components of the flexible or stretchable electronic circuit are positioned proximate to the neutral mechanical plane. In some embodiments, device components, such as flexible semiconductor circuit components, provided proximate to the neutral mechanical plane are within 100 microns of the neutral mechanical plane, optionally for some embodiments within 10 microns of the neutral mechanical plane, optionally for some embodiments within 5 microns of the neutral mechanical plane, and optionally for some embodiments within 1 micron of the neutral mechanical plane. Thicknesses of the device components, such as the flexible substrate and the barrier layer are optionally be selected in some embodiments so as to position the neutral mechanical plane of the device proximate to one or more flexible semiconductor circuit elements.

In an aspect, the invention provides a conformable device for biomedical sensing applications. In a device of this aspect, the flexible or stretchable electronic circuit is a stretchable or flexible electrode array comprising a plurality of individually addressable electrodes, multiplex circuitry and amplification circuitry. Devices of this aspect include conformable high density electrode arrays for making high-speed and high resolution electrophysiology measurements, for example in cardiac tissue, brain tissue and skin environments. In an embodiment, the stretchable or flexible electrode array comprises 2 to 500,000 electrodes, optionally for some applications 2 to 50,000 electrodes and optionally for some applications 2 to 5,000 electrodes, wherein the electrodes of the array are each optionally individually addressable electrodes. In an aspect, the device is for assessing hydration in a tissue by electrical impedance measurement by the array of electrodes.

In an embodiment, for example, the stretchable or flexible electrode array comprises 20 or more electrode unit cells, optionally 50 or more electrode unit cells, and optionally 100 or more electrode unit cells. In an embodiment, for example, adjacent electrodes of the electrode array are separated from each other by a distance less than or equal to 50 µm, optionally for some applications a distance less than or equal to 500 µm, and optionally for some applications a distance less than or equal to 2000 µm. In an embodiment, for example, the electrode unit cells of the electrode array are disposed on an area of the flexible or stretchable substrate ranging from 10 mm$^2$ to 10000 mm$^2$, optionally for some applications 10 mm$^2$ to 1000 mm$^2$, and optionally for some applications 100 mm$^2$ to 1000 mm$^2$. In some embodiments, the density of electrodes in the stretchable or flexible electrode array is selected over the range of 0.1 electrode mm$^{-2}$ to 50 electrodes mm$^{-2}$, and optionally for some application selected over the range of 1 electrode mm$^{-2}$ to 20 electrodes mm$^{-2}$.

In an embodiment, for example, the stretchable or flexible electrode array comprises a plurality of electrode unit cells, for example, a plurality of electrode unit cells comprising a contact pad, amplifier and multiplexer, wherein the contact pad provides an electrical interface to the tissue and is in electrical communication with the amplifier and multiplexer. In an embodiment, for example, the amplifier and multiplexer of the unit cell comprises a plurality of transistors, for example, 2 to 50 transistors, and optionally for some applications 2 to 10 transistors. In an embodiment, for example, each of the unit cells of the flexible or stretchable electrode array comprises a multilayer structure comprising one or more semiconductor layers, one or more dielectric layers and one or more metal layers provided in a multilayer stacked geometry, for example, a stacked geometry wherein the semiconductor layers, dielectric layers and metal layers are provided in series, wherein adjacent layers are in physical contact with each other or separated by intermediate layers, such as adhesive, spacer and/or boundary layers. In an embodiment, for example, the semiconductor layers of the multilayer structure are positioned proximate to the neutral mechanical plane of the flexible or stretchable electronic circuit.

In an aspect, the invention provides a device for optical applications, including sensing and providing a local source of electromagnetic radiation at the tissue site. In a device of this aspect, the flexible or stretchable electronic circuit is a stretchable or flexible array of light emitting diodes comprising a plurality of light emitting diodes in electrical communication with a plurality of stretchable or flexible electrical interconnects. Devices of this aspect include high density LED arrays, including implantable LED arrays, stretchable LED arrays and LED arrays for interfacing with tissue including epithelial tissue. Devices of this aspect include large area light emitting diode arrays, for example wherein LEDs of the array are disposed on an area of the flexible or stretchable substrate ranging from 100 mm$^2$ to 10,000 mm$^2$, and optionally for some embodiments ranging from 1000 mm$^2$ to 10,000 mm$^2$.

In an embodiment of this aspect, the stretchable or flexible array of light emitting diodes is an island-bridge structure, wherein the light emitting diodes provide islands of the island-bridge structure and the stretchable or flexible electrical interconnects provide bridge structures of the island-bridge structure. In an embodiment, the electrical interconnects and the light emitting diodes are entirely encapsulated by the barrier layer, the flexible or stretchable substrate or both the barrier layer and the flexible or stretchable substrate. In an embodiment, for example, the light emitting diodes comprise the one or more inorganic semiconductor circuit elements of the flexible or stretchable electronic circuit. In an embodiment, for example, each of the stretchable or flexible electrical interconnects comprise a metal film encapsulated in a polymer layer, for example a thin metal film (e.g., thickness equal to or less than 500 microns) encapsulated in PDMS. In an embodiment, for example, the metal film is positioned proximate to the neutral mechanical plane of the stretchable interconnect. In an embodiment, for example, the device further comprises additional bridge structures physically connecting light emitting diodes of the array, wherein the additional bridge structures comprise a polymer layer. In an embodiment, for example, at least a portion of the stretchable or flexible electrical interconnects have a serpentine, bent or buckled geometry. In an embodiment, electrical interconnects or electrodes of the invention comprise a conductive metal such as copper, silver, gold, aluminum and the like, and alloys thereof.

In a device of this aspect, the stretchable or flexible array of light emitting diodes of this aspect comprises a multilayer structure comprising a plurality of individually encapsulated LED array layers provided in a multilayer stacked geometry. In an embodiment, for example, the stretchable or flexible array of light emitting diodes comprises 2 to 1000 individually encapsulated LED array layers provided in a multilayer stacked geometry, an optionally 10 to 1000 individually encapsulated LED array layers provided in a multilayer stacked geometry. The multilayer geometry of this aspect of the invention is beneficial for providing high LED densities and fill factors which maintaining a useful degree of conformability and stretchability. In an embodiment, for example, the individually encapsulated LED array layers are combined to provide a density equal to or greater than 1 LED mm$^{-2}$, and optionally equal to or greater than 100 LEDs mm$^{-2}$. In an embodiment, for example, the individually encapsulated LED array layers provide a density selected from the range of 1 LEDs mm$^{-2}$ to 1000 LEDs mm$^{-2}$. In an embodiment, for example, the individually encapsulated LED array layers are laterally offset so as to provide a fill factor greater than or equal to $1\times10^{-6}$, or optionally provide a fill factor selected over the range of $1\times10^{-6}$ to $1\times10^{-3}$. As used herein, the expression "laterally offset" refers to a multilayer geometry wherein at least a portion of the LEDs in different layers of the device are positioned such that they do not reside on top of each other. As used in this context, the term "fill factor" refers to the fraction of the area of the footprint of the device that is occupied by the LED structures.

In some embodiments, barrier layers and flexible or stretchable substrates limit a net leakage current from the electronic device to an amount which does not adversely affect a tissue in a biological environment. Barrier layers of the invention include moisture barriers. In one embodiment, the barrier layer is configured to limit a net leakage current from the electronic device to the biological environment to less than 10 µA, optionally for some applications less than 5 µA and optionally for some applications less than 1 µA, and optionally for some applications less than 0.1 µA. In some embodiments, the barrier layer prevents leakage current from being concentrated to small areas so to prevent tissue damage caused by current leakage from the device. In an embodiment, for example, the barrier layer is configured to limit leakage current from the device to the biological environment to 0.1 µA/cm$^2$; less, and for some applications 0.01 µA/cm$^2$ or less, and for some applications 0.001 µA/cm$^2$ or less. In some embodiments, barrier layers of the invention have an electrical resistivity of $10^{14}$ Ω·m or greater, for example an electrical resistivity selected over the range of $10^{15}$ to $10^{17}$ Ω·m. In some embodiments, the barrier layer prevents the rate at which charge is leaked from the electronic device; for example, one barrier layer embodiment limits electrical discharge from a device to 10 µC or less over a period of 1 second. In some embodiments, the barrier layer limits leakage current or average leakage current from the device to 10 µA or less or 5 µA or less over a long period of time, such as 3 hours or more or 5 hours or more.

In some embodiments, a barrier and/or cover layer is configured to prevent moisture from reaching the flexible or stretchable electronic circuit and limit leakage current therefrom, for example to less than 10 µA optionally for some applications less than 5 µA and optionally for some applications less than 1 µA. Useful moisture barriers, for example, include those configured for protecting tissue in contact with electronic device embodiments from damage due to leakage current. Further, useful moisture barriers include those configured for protecting electronic devices from damage due to leakage current.

In an embodiment, the barrier layer is patterned so as to selectively modulate physical, thermal, optical, electromagnetic and/or electrical contact and/or communication between flexible semiconductor circuit elements and the tissue in the biological environment. Optionally, a barrier layer comprises multiple layers. For example, a barrier layer comprises at least one organic polymer layer and at least one inorganic dielectric layer. In specific embodiments, the net thickness of a barrier layer comprising multiple layers is selected over the range of 1 µm to 25 µm or over the range of 1 µm to 100 µm.

In some embodiments, the barrier layer includes one or more via structures. As used herein, a via structure refers to a recessed region which is at least partially filled with a conducting material. Via structures are useful in a barrier layer for providing electrical communication between electronic circuit components encapsulated by a barrier layer (e.g., semiconductor device such as a transistor, amplifier or multiplexer) and electronic circuit components not encapsulated by a barrier layer and in contact with the tissue or fluid in contact with the tissue (e.g., an electrode). In a specific embodiment, the barrier layer comprises multiple layers and includes multiple offset via structures; for example, one via structure in a lower barrier layer and one via structure in an upper barrier layer in electrical communication with the first via structure. In embodiments, barrier layers including multiple layers with offset via structures are useful as moisture barriers.

Depending on the application, the barrier layer can have a variable thickness; that is, for certain applications, the barrier layer has a thickness that is spatially variable (i.e., relatively thicker in some regions and relatively thinner in other regions). In embodiments where a sensing element does not need to be exposed and/or in direct contact with or electrical communication with a tissue in a biological environment, barrier layers of spatially varying thickness are useful; for example, when a sensing element is positioned close to the surface (e.g., within 5 µm or less) of the barrier layer but still encapsulated by the barrier layer.

In embodiments, an electronic device of this aspect further comprises a plurality of actuating elements spatially arranged over the flexible substrate. Optionally, each actuating element is positioned in electrical communication with at least one flexible semiconductor circuit element. Optionally, one or more via structures are configured to and/or positioned in the barrier layer to provide electrical communication between an actuating element and a flexible semiconductor circuit element. In some embodiments, one or more actuating elements are encapsulated by the barrier layer. Useful actuating elements include, but are not limited to, electrode elements, electromagnetic radiation emitting elements, light emitting diodes, lasers, and heating elements. In some embodiments, at least one actuating element is positioned at the surface of the barrier layer, in electrical communication with a tissue in a biological environment, in optical communication with a tissue in a biological environment and/or in physical contact with a tissue in a biological environment. In some embodiments an actuating element is a sensing element.

"Spatially arranged over the flexible substrate" as used herein, refers to a distribution of elements over the surface area of a flexible substrate such that each element is located at a different position. Inter element spacing can be uniform or variable. In some embodiments, the elements are spatially arranged in a regular array pattern with equal inter element spacing, for example in a 2D array or 3D array. In some embodiments, the elements are spatially arranged in a line (e.g., a 1D array). Useful spatial arrangements include regular and irregular distributions of elements.

Modulation of physical, optical, thermal and/or electrical contact and/or communication is achieved in some embodiments by selective variation of the physical dimensions (e.g., thickness, etc.), shape, and/or composition of the barrier layer. In some embodiments, for example, the physical dimensions and/or shape of the barrier layer provides a preselected pattern of openings in the barrier layer that expose preselected circuit elements to the tissue and/or biological environment, particularly when the device is provided in conformal contact with the tissue. In some embodiments, for example, the physical dimensions, shape or composition of the barrier layer provide a preselected pattern of electrically conductive and/or optically or electromagnetically transparent regions of the barrier, particularly when the device is provided in conformal contact with the tissue. Barrier layers include, but are not limited to, barrier layers having a plurality of contact regions that expose a components of the electronic circuit (e.g., electrodes, sensors, etc.) to the tissue and/or biological environment. Barrier layers of some embodiments of this aspect provide patterned physical contact between preselected circuit elements, such as electrode and/or sensor components, and the tissue and/or biological environment. Barrier layers include, but are not limited to, barrier layers having a plurality of contact regions that electronically couple a preselected subset of flexible semiconductor circuit elements and the tissue and/or biological environment. Barrier layers of some embodiments of this aspect provide patterned electrical contact between preselected circuit elements, such as electrode and/or sensor components, and the tissue and/or biological environment. Barrier layers include, but are not limited to, barrier layers having a plurality of contact regions that optically couple a preselected subset of flexible semiconductor circuit elements and the tissue and/or biological environment. Barrier layers of some embodiments of this aspect provide patterned optical communication (e.g., a pattern of optically transmissive regions and optically opaque regions) between preselected circuit elements, such as optical source (e.g., laser, LED, fiber optic, etc.) components and photodetector (e.g., photodiode, diode array. etc.) components, and the tissue and/or biological environment. In an embodiment, for example, at least a portion of the barrier layer is opaque or substantially blocks electromagnetic radiation having a preselected range of wavelengths.

In an embodiment, a barrier layer limits heat transfer from the electronic device to the tissue in the biological environment to an amount that does not adversely affect the tissue. In an embodiment, the barrier layer, or components thereof, have a thermal conductivity of 0.3 W/m·K or less, 0.1 W/m·K or less, 0.01 W/m·K or less, 0.001 W/m·K or less or selected over the range of 0.001 W/m·K to 0.3 W/m·K and/or portions having a thermal resistivity of 3 m·K/W or more, 10 m·K/W or more, 100 m·K/W or more, 1000 m·K/W or more selected over the range of 1 to 1000 m·K/W. In an embodiment, a barrier layer comprises a thermal insulator and/or a heat spreader. Certain device embodiments further include active cooling components; for example active cooling components positioned in thermal communication with the barrier layer and/or in thermal communication with one or more flexible semiconductor circuit elements. In some embodiments, the barrier layer comprises active cooling components, such as thermoelectric cooling devices.

In an embodiment, a barrier layer includes portions which are at least partially transparent to electromagnetic radiation. In an embodiment, a device comprises a barrier layer patterned to provide one or more transparent regions and one or more non-transparent regions, wherein the transparent regions transmit electromagnetic radiation have wavelengths in the ultraviolet, visible or near-infrared regions of the electromagnetic spectrum having a preselected wavelength distribution, wherein the non-transparent regions substantially prevent transmission of electromagnetic radiation in the in the ultraviolet, visible or near-infrared regions of the electromagnetic spectrum. In an embodiment, a barrier layer includes portions which are opaque or block electromagnetic radiation. In another embodiment, a barrier layer includes portions which are at least partially transparent to electromagnetic radiation and portions which are opaque or block electromagnetic radiation. For example, portions of the barrier layer can be partially or fully transparent to electromagnetic radiation of a selected wavelength or over a selected region of the electromagnetic spectrum. For example, selected over the range of 100 nm to 2000 nm, 1 µm to 2000 µm, 400 nm to 2000 nm or in the UV, visible, IR, near IR, or microwave portions of the spectrum. In embodiments, a barrier layer is selectively patterned to provide one or more transparent regions and one or more opaque regions. In embodiments, a barrier layer is selectively patterned to provide one or more optical components or structures, such as lenses, microlenses, lens arrays, optical filters, reflectors, reflective coatings, and antireflective coatings.

Transparent or partially transparent barrier layers are useful, for example, when an optical sensor, such as a photodiode, is encapsulated within the barrier layer and/or it is desired to detect electromagnetic radiation. A transparent or partially transparent can also be useful, for example, when a source of electromagnetic radiation, such as a light emitting diode and/or a laser, is encapsulated within the barrier layer and/or it is desired to permit electromagnetic radiation to pass through the barrier layer.

In an embodiment, a barrier layer includes portions which serve as an electrical, electrostatic and/or magnetic barrier. In specific embodiments, a barrier layer blocks electric fields and/or magnetic fields, for example, blocking fields external to the electronic circuit from interacting with the electronic circuit or blocking fields generated by the electronic circuit from interacting with the tissue and/or biological environment. In various embodiments of this aspect, the barrier layer comprises a Faraday cage, an electrical insulator and/or magnetic shielding. In a specific embodiment, a barrier layer comprises material having an electrical resistivity of $10^{14}$ $\Omega \cdot m$ or larger or selected over the range of $10^{15}$ to $10^{17}$ $\Omega \cdot m$.

In an embodiment, a barrier layer is patterned so as to provide one or more selectively permeable regions that are selectively permeable to one or more target molecules. In some embodiments, the barrier layer provides a plurality of spatially patterned regions which are selectively permeable to one or more target molecules comprising biomolecules, analytes, liquids or gases. In another aspect, a barrier layer comprises a plurality of spatially patterned impermeable regions which are selectively impermeable to one or more target molecules, such as one or more biomolecules, analytes, liquids or gases. For example, portions of the barrier layer can be selectively permeable to one or more target chemicals, molecules or biomolecules while being impermeable to other chemicals, molecules or biomolecules, such as solvents or aqueous solutions. Optionally, the barrier layer is impermeable to water and salts dissolved therein and is selectively permeable to one or more proteins, organic compounds or biomolecules (e.g., nucleic acids). A selectively permeable barrier layer is useful, for example, when a chemical or biochemical sensor is encapsulated within the barrier layer and it is desired to detect and/or collect a target chemical, molecule or biomolecule. Target molecules useful in the embodiments of the present devices and methods include, but are not limited to: polypeptides, polynucleotides, carbohydrates, proteins, steroids, glycopeptides, lipids, metabolites, drugs or drug precursors.

In an embodiment, a device of the present invention further comprises a controller in communication with the flexible or stretchable electronic circuit. Controllers of this aspect of the invention are useful for providing device control, signal processing and measurement analysis functionality. In an embodiment, the controller receives input signals from the flexible or stretchable electronic circuit that serves the basis of closed-loop control of the electronic device, for example, providing real-time adjustment of sensing and actuation of the tissue. In an embodiment, for example, the controller provides closed-loop control of sensing and/or actuation based on signals received from the electronic circuit corresponding to measurements of tissue properties.

For example, the invention includes a controller configured to provide an output signal to the flexible or stretchable electronic circuit, receive an input signal from the flexible or stretchable electronic circuit, or to provide an output signal to the flexible or stretchable electronic circuit and receive an input signal to the flexible or stretchable electronic circuit. As used in this context, the expression "in communication" refers to a configuration of devices or device components such that a signal can be exchanged, and includes one way communication and two way communication between the controller and the flexible or stretchable electronic circuit. In an embodiment, for example, the controller is in electrical communication or wireless communication with the flexible or stretchable electronic circuit. In an embodiment, for example, the output signal provides an input to the flexible or stretchable electronic circuit so as to control actuation or sensing of the tissue in the biological environment. In an embodiment, for example, the output signal provides a sensing or actuation parameter from the controller to the flexible or stretchable electronic circuit, for example, a parameter relating to the timing of a measurement or actuation, the magnitude of a sensing or actuation variable (e.g., voltage, current, power, intensity, temperature, etc.). In an embodiment, for example, the input signal provides a measurement parameter from the flexible or stretchable electronic circuit to the controller, for example a measurement parameter corresponding to a time, voltage, current, impedance, intensity, power, or temperature. In an embodiment, for example, the input signal provides a measurement parameter corresponding to a plurality of voltage measurements, current measurements, electromagnetic radiation intensity or power measurements, temperature measurements, pressure measurements, tissue acceleration measurements, tissue movement measurements, target molecule concentration measurements, time measurements, position measurements, acoustic measurements or any combination of these. In an embodiment, for example, the controller receives and analyzes the input signal from the flexible or stretchable electronic circuit and generates an output signal that controls or provides a sensing or actuation parameter(s) to the flexible or stretchable electronic circuit, for example via a closed-loop control algorithm that adjusts the sensing or actuation parameter(s) based on one or more tissue measurements. A wide range of controllers are useful in the present devices and methods, including a microprocessor, microcontroller, digital signal processor, computer or fixed logic device. Controllers of this aspect include implantable controllers, controllers that are administered to the tissue site along with the flexible or stretchable electronic circuit and controllers that are ex vivo.

In an aspect, a device of the invention further comprises a transfer substrate supporting the flexible or stretchable substrate, the flexible or stretchable electronic circuit or both. Transfer substrates of some devices of the invention function to facilitate administration of the device to a tissue site, for example, by providing net mechanical properties and/or physical dimensions of the device to allow effective handling, transfer and/or deployment to the tissue interface in a manner that does not damage or modify the properties of the other components of the device (e.g., substrate, barrier layer or electronic circuit components). Transfer layers of some embodiments also function as sacrificial layers that are at least partially removed upon administration to the tissue, for example, via dissolution or delamination (e.g., peel back) processes. In an embodiment, the invention provides a method of administrating, or otherwise using, a device of the invention having a transfer layer, the method further comprising the step of at least partially removing the transfer substrate, for example, via dissolving the transfer substrate or separating the transfer substrate from the flexible or stretchable substrate (e.g., via a delamination process). In a method of the invention, for example, partial or complete removal of the transfer substrate results in the device establishing conformal contact with the tissue in the biological environment.

In some embodiments, the transfer substrate is in physical contact with, and/or optionally bonded to, the flexible or stretchable substrate. In an embodiment, the transfer substrate is bound to the flexible or stretchable substrate via one or more adhesive layers. In an embodiment, the transfer substrate is a removable substrate, wherein the transfer substrate is partially or completely removed after the device establishes conformal contact with the tissue in the biological environment. In an embodiment, for example, the removable substrate is a dissolvable substrate, wherein the removable substrate is partially or completely dissolved after the device is provided in contact with the tissue in the biological environment, for example via washing or rinsing with one or more solvents (e.g., water). In an embodiment, for example, the removable substrate is configured so as to be able to be separated from the flexible or stretchable substrate after administration, for example, via a delamination process.

In some embodiments, the transfer substrate comprises a bioinert or biocompatible material, for example, to minimize or avoid inflammation or unwanted immune responses upon administration of the device to a tissue in a biological environment. In an embodiment, for example, the transfer substrate is a polymer layer such as a polyvinyl acetate layer. In an embodiment, for example, the transfer substrate has a thickness selected from the range of 100 µm to 100 mm. in an embodiment, for example, the transfer substrate has a composition and physical dimensions that allowed the device to be handled and/or administered by hand, for example, during a surgical procedure.

In an aspect, the invention provides a device for collecting electrophysiology data from a tissue in a biological environment, the device comprising: (1) a flexible or stretchable substrate; (2) a flexible or stretchable electrode array comprising one or more inorganic semiconductor circuit elements and a plurality of electrode elements positioned in electrical communication with at least a portion of the semiconductor circuit elements, wherein the one or more inorganic semiconductor circuit elements include multiplex circuitry and amplification circuitry, and wherein the electrode array is supported by the flexible or stretchable substrate; (3) a barrier and/or cover layer encapsulating at least a portion of the flexible or stretchable electrode array to limit a net leakage current from the flexible or stretchable electrode array to an amount that does not adversely affect the tissue; wherein the flexible or stretchable substrate, the flexible or stretchable electrode array and the barrier layer provide a net bending stiffness of the device low enough that the device establishes conformal contact with the tissue in the biological environment, thereby, positioning at least one of the plurality of electrode elements in electrical communication with the tissue in the biological environment. In an embodiment, for example, the electrode array comprises a plurality of electrode unit cells, wherein each unit cell comprises a contact pad, amplifier and multiplexer. In some embodiments, the contact pad provides an electrical interface to the tissue and is in electrical contact with the amplifier and multiplexer. In an embodiment, for example, each of the unit cells of the flexible or stretchable electrode array comprises a multilayer structure comprising one or more semiconductor layers, one or more dielectric layers and one or more metal layers provided in a multilayer stacked geometry. In an embodiment, for example, the semiconductor layers of the multilayer structure are positioned proximate to the neutral mechanical plane of the flexible or stretchable electronic circuit.

In an aspect, the invention provides a method of collecting electrophysiology data from a tissue in a biological environment, the method comprising the steps of: (1) providing a conformable electronic device comprising: (i) a flexible or stretchable substrate; (ii) a flexible or stretchable electrode array comprising one or more inorganic semiconductor circuit elements and a plurality of electrode elements positioned in electrical communication with at least a portion of the semiconductor circuit elements, wherein the one or more inorganic semiconductor circuit elements include multiplex circuitry and amplification circuitry, and wherein the electrode array is supported by the flexible or stretchable substrate; (iii) a barrier and/or cover layer encapsulating at least a portion of the flexible or stretchable electrode array to limit a net leakage current from the flexible or stretchable electrode array to an amount that does not adversely affect the tissue; wherein the flexible or stretchable substrate, the flexible or stretchable electrode array and the barrier layer provide a net bending stiffness of the device low enough that the device establishes conformal contact with the tissue in the biological environment; (2) contacting the tissue with the conformable electronic device, thereby establishing the conformal contact such that at least one of the plurality of electrode elements is positioned in electrical communication with the tissue in the biological environment; and (3) measuring one or more voltages associated with the tissue in the biological environment on at least a portion of the plurality of electrode elements. In an embodiment, for example, the voltages associated with the tissue have a spatial arrangement corresponding to a spatial arrangement of the electrode elements. Methods of the invention may include the steps of administering the conformable device to a subject (e.g., a patient), and/or removal of the conformable device from the subject (e.g., a patient). In an embodiment, the step of contacting the conformable device with the tissue of the subject is carried out by physically contacting one or more surfaces of the tissue with a contact surface of the conformable device.

In an aspect, the invention provides a device for interfacing with a tissue in a biological environment, the device comprising: (1) a flexible or stretchable substrate; (2) a stretchable or flexible array of light emitting diodes comprising a plurality of light emitting diodes in electrical communication with a plurality of stretchable or flexible electrical interconnects, the stretchable or flexible array of light emitting diodes supported by the flexible or stretchable substrate; and (3) a barrier layer encapsulating at least a portion of the stretchable or flexible array of light emitting diodes to limit a net leakage current from the stretchable or flexible array of light emitting diodes to the tissue to an amount that does not adversely affect the tissue; wherein the flexible or stretchable substrate, stretchable or flexible array of light emitting diodes and the barrier layer provide a net bending stiffness of the device low enough that the device establishes conformal contact with the tissue in the biological environment. In an embodiment, the device of this aspect is an implantable or skin mounted array of light emitting diodes. In an embodiment, for example, the stretchable or flexible array of light emitting diodes comprises a multilayer structure comprising a plurality of individually encapsulated LED array layers provided in a multilayer stacked geometry, for example, wherein 2 to 50 individually encapsulated LED array layers provided in a multilayer stacked geometry.

In an embodiment, the invention provides a method of interfacing an array of light emitting diodes with a tissue of a subject, the method comprising the steps of: (1) providing a conformable device for interfacing with a tissue in a biological environment, the device comprising: (i) a flexible or stretchable substrate; (ii) a stretchable or flexible array of light emitting diodes comprising a plurality of light emitting diodes in electrical communication with a plurality of stretchable or flexible electrical interconnects, the stretchable or flexible array of light emitting diodes supported by the flexible or stretchable substrate; and (iii) a barrier layer encapsulating at least a portion of the stretchable or flexible array of light emitting diodes to limit a net leakage current from the stretchable or flexible array of light emitting diodes to the tissue to an amount that does not adversely affect the tissue, wherein the flexible or stretchable substrate, stretchable or flexible array of light emitting diodes and the barrier layer provide a net bending stiffness of the device low enough that the device establishes conformal contact with the tissue in the biological environment; and (2) contacting the conformable device with the tissue of the subject, thereby establishing the conformal contact with the tissue in the biological environment. Methods of the invention may include the steps of administering the conformable device to a subject (e.g., a patient), and/or removal of the conformable device from the subject (e.g., a patient). In an embodiment, the step of contacting the conformable device with the tissue of the subject is carried out by physically contacting one or more surfaces of the tissue with a contact surface of the conformable device.

The invention provides a range of bioanalytical and therapeutic methods including diagnostic and therapeutic methods. As will be appreciated by one of skill in the art, methods of the invention may utilize any of the device configurations disclosed herein. Devices of this aspect are useful, for example, for making electrophysiology measurements of a tissue in a biological environment. In embodiments, the biological environment is an in-vivo biological environment. In certain embodiments, the biological environment comprises an ionic solution, such as saline. Devices of this aspect are useful for making measurements and/or actuating tissues including, but not limited to, heart tissue, brain tissue, muscle tissue, skin, nervous system tissue, vascular tissue, epithelial tissue, retina tissue, ear drum, tumor tissue, digestive system structures and any combination of these.

In an embodiment, the invention provides a method of sensing or actuating a tissue in a biological environment; the method comprising: (1) providing a subject having the tissue in the biological environment; (2) providing a conformable device, the device comprising: (i) a flexible or stretchable substrate; (ii) a flexible or stretchable electronic circuit supported by the flexible or stretchable substrate, wherein the flexible or stretchable electronic circuit comprises an plurality of sensors, actuators or both sensors and actuators provided in an array, wherein said sensors or actuators comprise one or more inorganic semiconductor circuit elements; and (iii) a barrier layer encapsulating at least a portion of the flexible or stretchable electronic circuit; wherein the barrier layer and the flexible or stretchable substrate limit a net leakage current from the flexible or stretchable electronic circuit to an amount which does not adversely affect the tissue or the barrier layer is patterned so as to selectively modulate physical contact, thermal contact, optical communication or electrical communication between the flexible or stretchable electronic circuit and the tissue in the biological environment; wherein the flexible or stretchable substrate, the flexible or stretchable electronic circuit and the barrier layer provide a net bending stiffness of the device low enough that the conformable device establishes conformal contact with the tissue in the biological environment; (3) contacting the tissue with the conformable device, thereby establishing the conformal contact such that at least a portion of the plurality of sensors, actuators or both sensors and actuators of the array is provided in physical contact, electrical communication, optical communication, fluid communication or thermal communication with the tissue in the biological environment; and (4) sensing or actuating the tissue in contact with the conformable device. In an embodiment, for example, the biological environment is an in-vivo biological environment. In an embodiment, for example, the tissue in the biological environment comprises heart tissue, brain tissue, muscle tissue, skin, nervous system tissue, vascular tissue, epithelial tissue, retina tissue, ear drum, tumor tissue, a digestive system structure or any combination of these. In an embodiment, for example, the step of contacting the tissue with the conformable device establishes conformal contact between one or more contact surfaces of the conformable device and an area of the tissue selected from the range of from 10 mm$^2$ to 10,000 mm$^2$. In an embodiment, for example, the method further comprising the step of moving the conformable device along a surface of the tissue in the biological environment.

In an embodiment, the step of sensing or actuating the tissue in contact with the conformable device comprises: generating one or more voltages at a plurality of different regions on a surface of the tissue; sensing one or more voltages at a plurality of different regions on a surface of the tissue; or sensing one or more voltages at a plurality of different regions on a surface of the tissue and generating one or more voltages at a plurality of different regions on the surface of the tissue. In a method, for example for sensing applications, the voltages are selected from the range of −100 mV to 100 mV, optionally for some applications from the range of −50 mV to 50 mV, and optionally for some applications from the range of −20 mV to 20 mV. In a method, for example for stimulation and actuation applications, the voltages are selected from the range of −100 V to 100 V, optionally for some applications from the range of −5 V to 5 V, and optionally for some applications from the range of −1 V to 1 V.

In an embodiment, the step of sensing or actuating the tissue in contact with the conformable device comprises: generating one or more currents at a plurality of different regions on a surface of the tissue; sensing one or more currents at a plurality of different regions on a surface of the tissue; or sensing one or more currents at a plurality of different regions on a surface of the tissue and generating one or more currents at a plurality of different regions on the surface of the tissue.

In an embodiment, the step of sensing or actuating the tissue in contact with the conformable device comprises: sensing electromagnetic radiation at a surface of the tissue; generating electromagnetic radiation at a surface of the tissue; or sensing electromagnetic radiation at a surface of the tissue and generating electromagnetic radiation at the surface of the tissue. In a method, for example, the electromagnetic radiation has a distribution of wavelengths in the ultraviolet, visible, near infrared, microwave and/or radio-wave regions of the electromagnetic spectrum. In a method, for example, the step of sensing or actuating the tissue in contact with the conformable device comprises ablating at least a portion of the tissue, such as a portion of the tissue comprising a lesion or tumor.

In an embodiment, the step of sensing or actuating the tissue in contact with the conformable device comprises: transporting a target molecule from a surface of the tissue to the flexible or stretchable electronic circuit; transporting a target molecule from the flexible or stretchable electronic circuit to a surface of the tissue; or transporting a target molecule from a surface of the tissue to the flexible or stretchable electronic circuit and transporting a target molecule from the flexible or stretchable electronic circuit to a surface of the tissue. In a methods, for example, the target molecule is selected from the group consisting of polypeptides, polynucleotides, carbohydrates, proteins, steroids, glycopeptides, lipids, metabolites and drugs, including photoactive drugs such as Type 1 or Type 2 phototherapy agents.

In an embodiment, the step of sensing or actuating the tissue in contact with the conformable device comprises: sensing or changing a temperature of a region of the tissue; sensing or changing a pressure of a region of the tissue; sensing or changing a position of the tissue; sensing or generating an electrical field at a region of the tissue; or sensing or generating a magnetic field at a region of the tissue.

In an embodiment, a method of this aspect further comprises administering to the subject a therapeutic agent, wherein the therapeutic agent localizes at the tissue, wherein the step of sensing or actuating the tissue in contact with the conformable device comprises activating the therapeutic agent at the tissue or specific region thereof (e.g., a tumor or lesion). Methods and devices of the invention are capable of a range of activation techniques, including optical activation, electronic activation, acoustic activation or thermal activation.

In an embodiment, the step of sensing or actuating the tissue in contact with the conformable device comprises measuring an electrophysiological signal from the tissue, measuring an intensity of electromagnetic radiation from the tissue, measuring a change in the concentration of a target molecule at the target tissue, measuring an acceleration of the tissue, measuring a movement of the tissue, measuring a position of the tissue or region thereof or measuring a temperature of the tissue. In a method, for example, the tissue is heart tissue, and wherein the step of sensing or actuating the tissue in contact with the conformable device comprises simultaneously applying multiple pacing stimuli to the heart tissue, such as applying a plurality of voltages to different areas of the tissue at the same or different times. In an embodiment of this aspect, the tissue is epicardium tissue.

In an embodiment, the step of contacting the tissue with the conformable device is carried out via a surgical technique. In a method, for example, the step of contacting the tissue with the conformable device is carried out using a catheter. In a method, for example, the conformable device is collapsed, rolled or wrapped on itself and inserted into the catheter, and wherein the catheter is subsequently positioned at the tissue and the conformable device is released from the catheter, thereby delivering the conformable device to a surface of the tissue. In a method, for example, the conformable device changes conformation upon release from the catheter so as to establish conformal contact with one or more surfaces of the tissue, for example by unrolling or unwrapping.

In an embodiment, a method of the invention comprises a diagnostic or therapeutic procedure, for example a surgical diagnostic or therapeutic procedure. In a method, for example, the diagnostic or therapeutic procedure is selected from the group consisting of anatomic mapping, physiologic mapping and resynchronization therapy. In a method, for example, the diagnostic or therapeutic procedure comprises measuring cardiac contractility, myocardial wall displacement, myocardial wall stress, myocardial movement or ischemic changes. In a method, for example, the diagnostic or therapeutic procedure comprises cardiac mapping or cardiac resynchronization therapy. In a method, for example, the diagnostic or therapeutic procedure comprises cardiac ablation therapy.

In an embodiment, for example, the flexible or stretchable electronic circuit comprises a plurality of sensors for determination and/or discrimination of tissue properties and one or more actuators that is an ablation source for ablating one or more regions of the tissue. In a method, for example, the sensors for determination and/or discrimination of tissue properties distinguish one or more components of the tissue selected from the group consisting of a lesion, a tumor, epicardial muscle, myocardial tissue, epicardial fat, a coronary artery, and a nerve. In a method, for example, the ablation source selectively ablates the lesion or tumor component of the tissue.

In another embodiment, any of the devices and methods disclosed herein relate to a skin-mounted device that does not, at least initially, have a flexible or stretchable substrate. Instead, the substrate may functionally correspond to a transfer substrate that picks up the flexible or stretchable electronic circuit, applies it to the skin, and the transfer substrate removed with the flexible or stretchable electronic circuit left connected to the skin, including in conformal contact. Optionally, a contact layer is applied to the skin to facilitate receipt, placement, and long-term use of the device connected to the skin. Removal of the transfer substrate or stamp leaves behind a free-standing flexible or stretchable electronic circuit in conformal contact without a flexible or stretchable substrate (other than the skin and optionally contact layer). The exposed surface of the flexible or stretchable electronic circuit is covered with a cover layer, such as by application of a polymer layer by a liquid bandage application. Repeated cover layer application ensures the device is adequately protected from the surrounding environment. In this manner, long-term and comfortable wearability is achieved. Such long-term function may be described quantitatively in terms of continued conformal contact maintained, such as over at least 90% or 95%, continued sensor or actuator functionality, and lack of unduly adverse biological response.

In another embodiment, provided herein is a device for establishing an interface with a skin of a subject, the device comprising a flexible or stretchable electronic circuit comprising an array of sensors, actuators, or sensors and actuators, wherein elements of the array are interconnected by serpentine interconnects, the flexible or stretchable electronic circuit configured for conformal contact with the skin of a subject. A contact layer is positioned between the flexible or stretchable electronic circuit and the skin to provide conformal contact between the flexible or stretchable electronic circuit and the skin. A cover layer covers the flexible or stretchable electronic circuit when the device is in conformal contact with skin. In an aspect, the cover layer and contact layer is a polymer layer from a spray liquid bandage. In an aspect, the device has a plurality of cover layers, such as from between 2 and 10, or about 4. In an aspect, the cover layers are applied at different time points, such as on the order of every few hours or about every day.

In an embodiment, the contact layer is a polymer layer formed from a spray bandage applied to the skin and the cover layer is a polymer layer formed from a spray bandage applied to the flexible or stretchable electronic circuit in conformal contact with the skin. In this manner, the device is for long-term monitoring, wherein the sensors measure and transmit information about a physical parameter of the skin over a maximum time period that is at least seven days.

Also provided are related methods of interfacing an electronic device with a skin of a subject by applying a liquid bandage on the skin to form a contact layer on the skin and contacting a conformable electronic device with the contact layer on the skin to establish conformal contact between the conformable electronic device and the underlying skin. In an embodiment, the conformable electronic device comprises a plurality of sensors interconnected by serpentine interconnects. A liquid bandage is applied over the conformable electronic device in conformal contact with the skin to provide a cover layer. Any of the methods disclosed herein further comprise wirelessly transmitting data from the plurality of sensors to a receiver. Any of the devices and methods are for an interfacing duration that is at least seven days without substantial degradation of conformal contact, conformal electronic device performance, or adverse biological response of the skin underlying the conformal electronic device. In this context "adverse biological response" refers to unduly large responses attributed to the device including user-selected percentage of cell death or turnover compared to normal without the device, rash, itchiness, or other dermatological response.

Without wishing to be bound by any particular theory, there can be discussion herein of beliefs or understandings of underlying principles relating to the invention. It is recognized that regardless of the ultimate correctness of any mechanistic explanation or hypothesis, an embodiment of the invention can nonetheless be operative and useful.

BRIEF DESCRIPTION OF THE DRAWINGS

FIG. 3c also provides a spatial map of electrophysiology data measured by a conformable device showing individual layers of a multilayer device geometry.

FIG. 26A provides a schematic illustration of a cross sectional view of a conformal electronic device embodiment. FIG. 26B provides a schematic illustration of a cross sectional view of a conformal electronic device having a barrier layer comprising a multilayer structure.

FIG. 27. Device layouts of μ-ILED arrays and their responses to uniaxial and balloon-shape biaxial stretching.

FIG. 28. Responses of μ-ILED arrays to twisting and stretching on sharp tips.

FIG. 29. Multilayer laminated configurations of arrays of μ-ILEDs for high effective area coverage and integration on various unusual substrates. FIG. 29c, Optical images of a two layer stack of 8×8 arrays, with different layers in operation. The inset shows the device in a bent state (bending radius ~2 mm) with both layers on.

(b) Schematic illustration (left frame) and corresponding microscope (top right frame) and optical (bottom right frame) images of a 6×6 μ-ILEDs array which is picked up with a PDMS stamp for transfer printing. A shadow mask for selective deposition of Cr/SiO$_2$ (thickness: 3 nm/30 nm) covers the retrieved array on a soft elastomeric PDMS stamp. (c) Schematic illustration of transfer printing to a pre-strained thin (thickness: ~400 μm) PDMS substrate (left frame) and microscope (top right frame) and SEM (bottom right frame) images of the transferred μ-ILEDs array on a prestrained thin PDMS substrate. Prestrain value was ~20%.

Figure 33A:
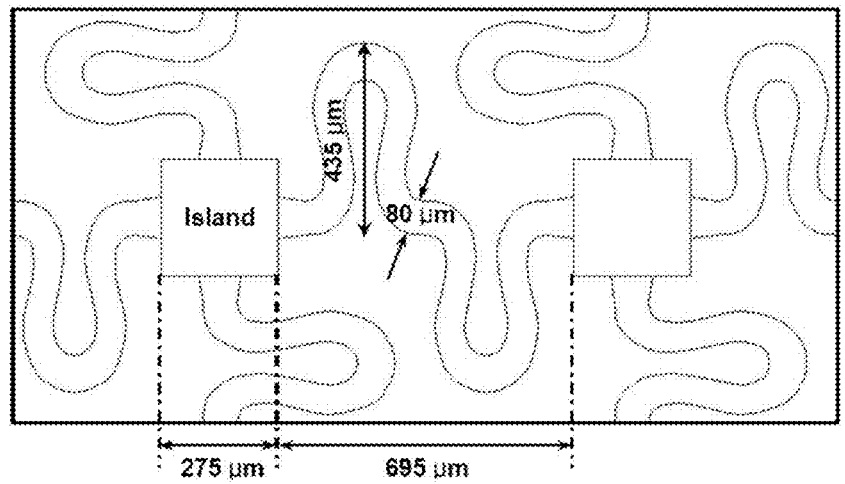
Figure 33B:
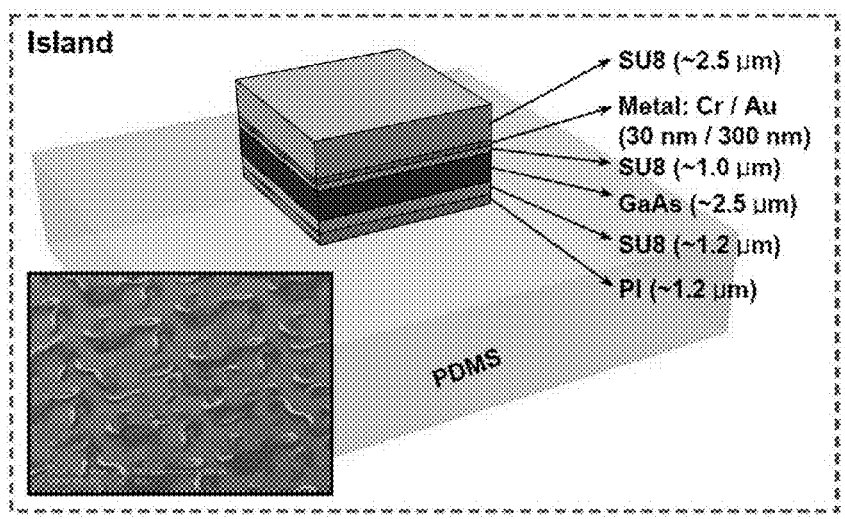
Figure 33C:
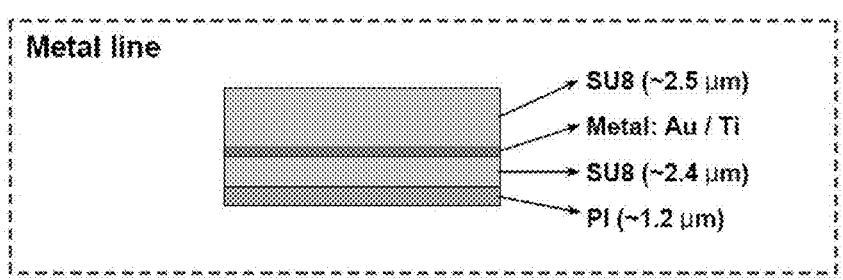

FIG. 33. (a) Schematic illustration of top encapsulation layers indicating some of the key dimensions. (b) Schematic illustration of the cross sectional structure at an island, with approximate thicknesses for each layer. The inset corresponds to an SEM image of a μ-ILEDs array after transfer printing to a thin PDMS substrate with prestrain of ~20%. (c) Schematic illustration of the cross sectional structure at metal interconnection bridges, with approximate thicknesses of each layer.

FIG. 34. (a) Tilted view SEM images of adjacent μ-ILEDs (yellow dashed boxes) before (left, formed with ~20% pre-strain) and after (right) stretching along the horizontal direction (red arrows). (b) Strain distributions determined by 3D-FEM for the cases corresponding to frames in (a). The black outlines indicate the positions of the devices and the serpentines before relaxing the pre-strain.

FIG. 35. (a) Optical microscope images of two pixels in a μ-ILEDs array with a serpentine bridge design before (left frame) and after (right frame) external stretching along the horizontal direction. The upper and lower images show optical micrographs in emission light off (upper) and on (lower) states. The distance between adjacent pixels appears in the lower images and used for calculation of applied strains. The lower images were obtained without external illumination. (b) Optical micrograph images of two pixels in a μ-ILEDs array before (left frame) and after (right frame) external stretching along the diagonal direction. (c) FEM simulation under external stretching along the diagonal direction (left frame), and strain contours in the GaAs active island (top right frame) and the metal bridge (bottom right frame).

Figure 36:
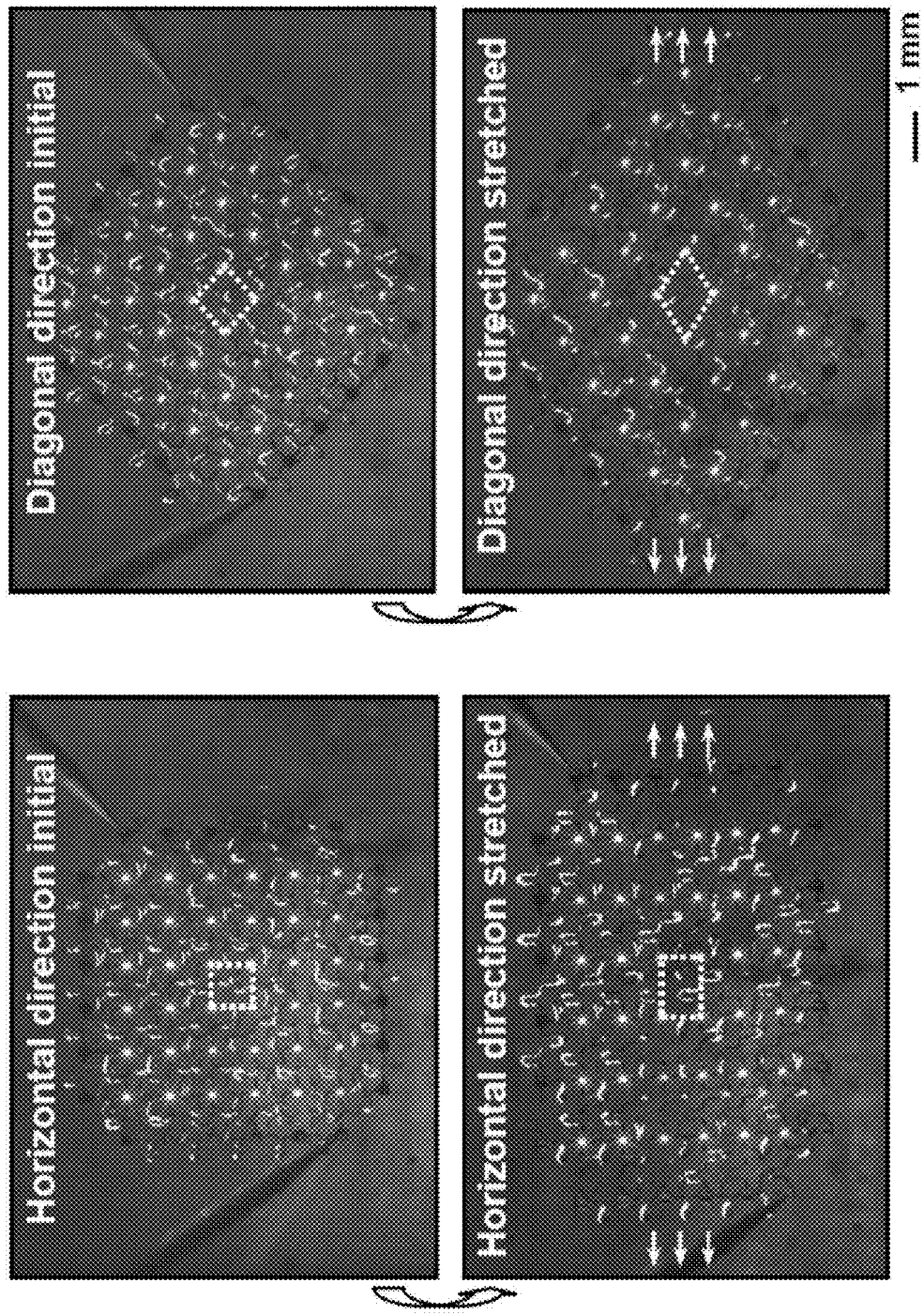

FIG. 36. Optical images of a 6×6 μ-ILEDs array with a serpentine mesh design with external illumination under the same strain circumstances as FIG. 27b.

FIG. 37. (a) Optical image of an 8×8 μ-ILEDs array on a thin PDMS substrate in its on state, which is under the same kind of deformed condition as bottom left frame of FIG. 27d. (b) Top view optical images of same array as FIG. 27d in its 'flat' (left frame) and 'inflated' state (right frame) without external illumination. (c) Spatial distribution of FEM results of the right frame of FIG. 27d and analytical solutions calculated from Equations (S1) and (S2).

FIG. 38. (a) Schematic illustrations of a 3×8 μ-ILEDs array integrated on a thin PDMS substrate with detailed dimensions (upper frame: registrations of the μ-ILEDs on a PDMS donor substrate, lower frame: entire view of the printed 3×8 μ-ILEDs array). The inset on top represents an optical microscope image of this μ-ILEDs array on a handle glass substrate before transfer printing. (b) Magnified view of the SEM image in FIG. 28b. The white dotted rectangle highlights the non-coplanar bridge structures. (c) Voltage at 20 μA current for each twisting cycle of 360°.

Figure 39:
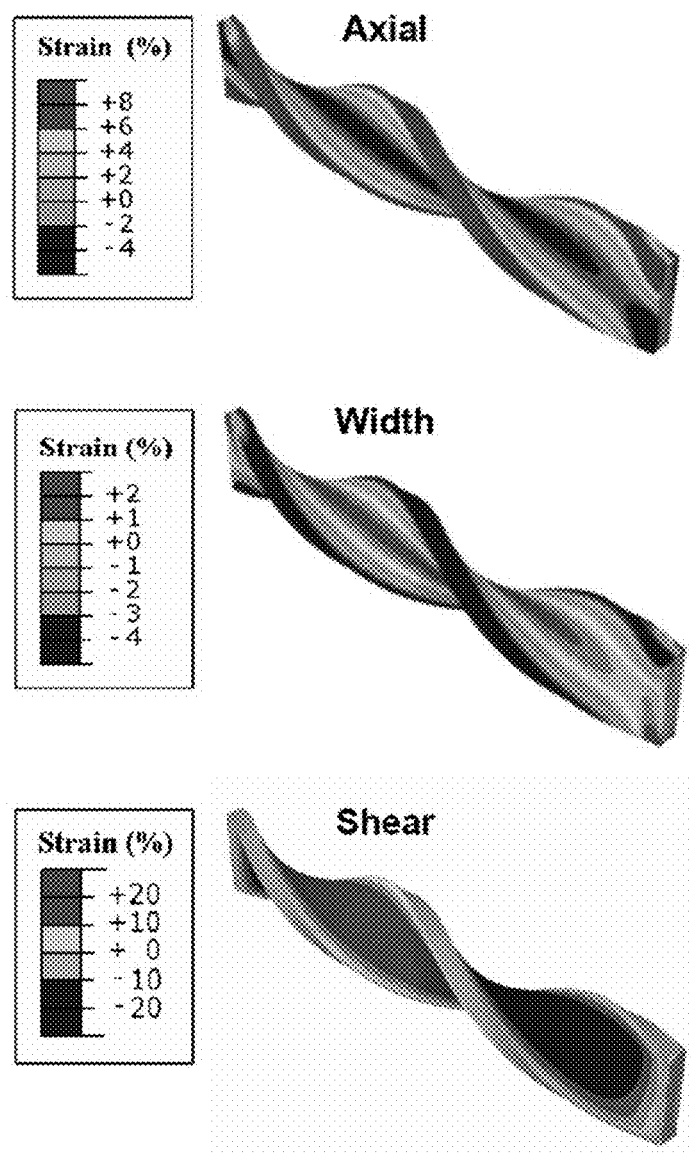

FIG. 39. FEM strain contours of axial (top), width (center), and shear (bottom) strains for 360° twisted PDMS substrate.

Figure 28A:
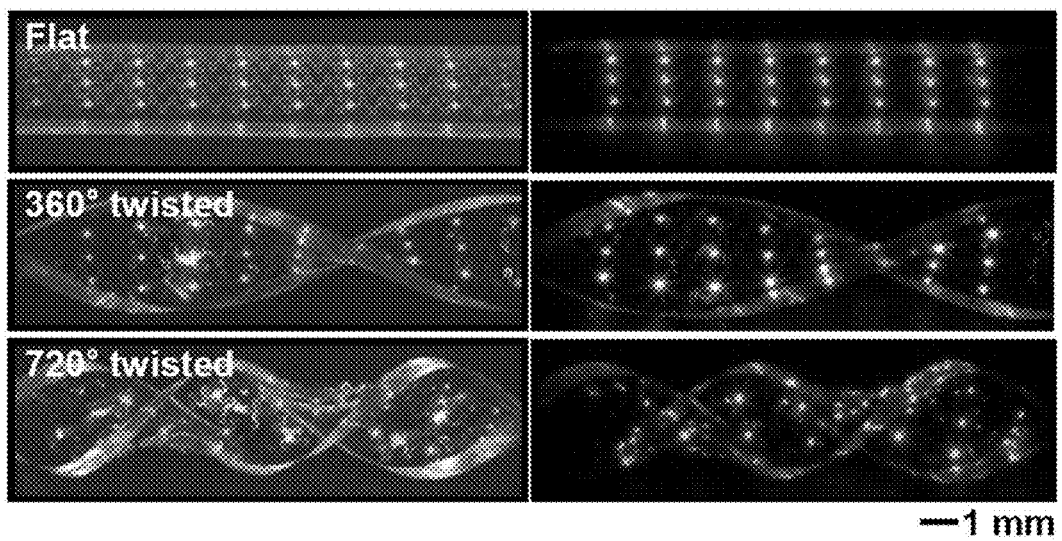
FIG. 28a, Optical images of an array of μ-ILEDs (3×8) on a band of PDMS twisted to different angles (0° (flat), 360°, and 720° from top to bottom), collected with (left) and without (right) external illumination.
Figure 28B:
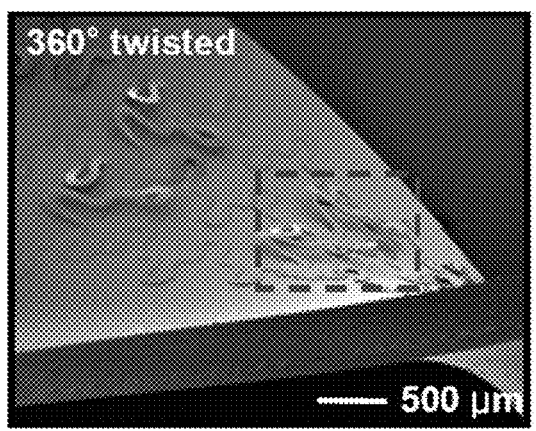
FIG. 28b, SEM image of the array when twisted to 360°. The serpentine interconnects move out of the plane (red box) to accommodate the induced strains.
Figure 28C:
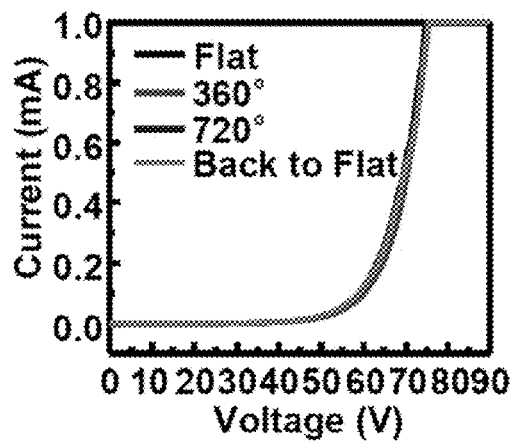
FIG. 28c, I-V characteristics of the array twisted by various amounts (0 (flat), 360 and 720°).
Figure 28D:
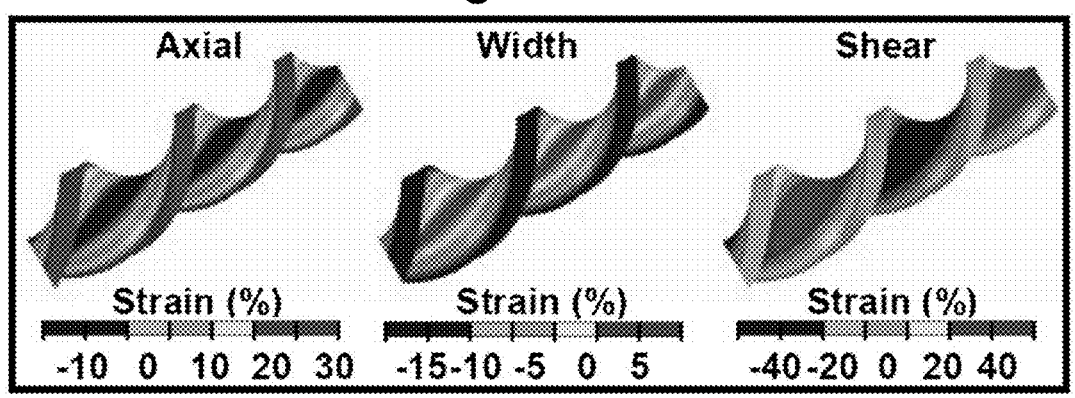
FIG. 28d, Distributions of axial (left), width (center) and shear (right) strain determined by 3D-FEM for twisting to 720°.
Figure 28E:
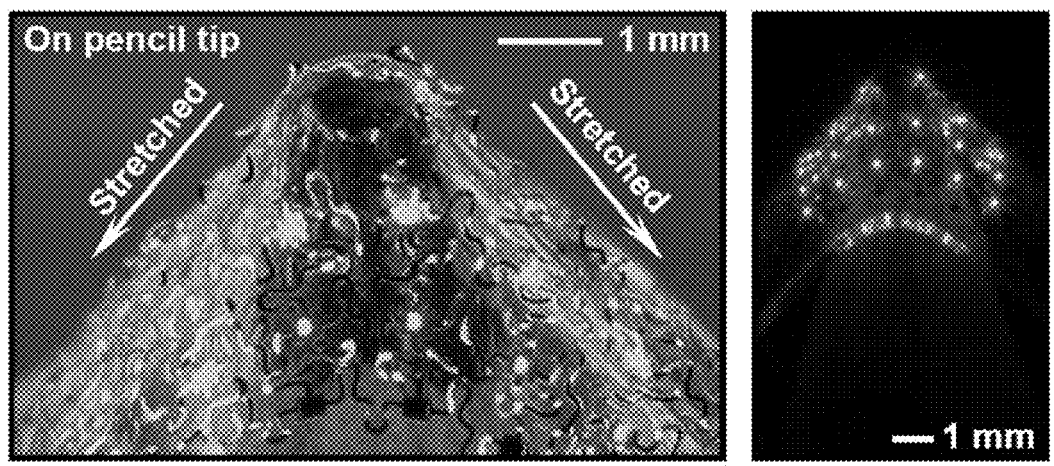
FIG. 28e, Optical images of an array of μ-ILEDs (6×6), tightly stretched on the sharp tip of a pencil, collected with (left) and without (right) external illumination. The white arrows indicate the direction of stretching. The inset image was obtained without external illumination.
Figure 40A:
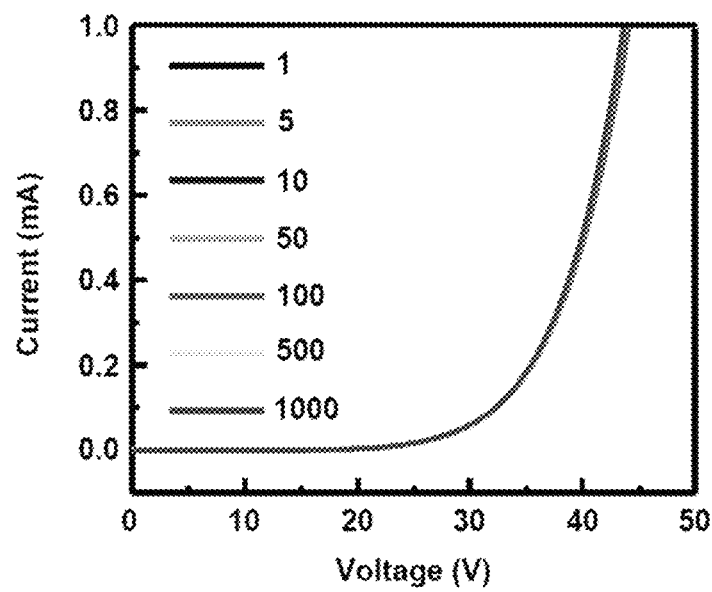
Figure 40B:
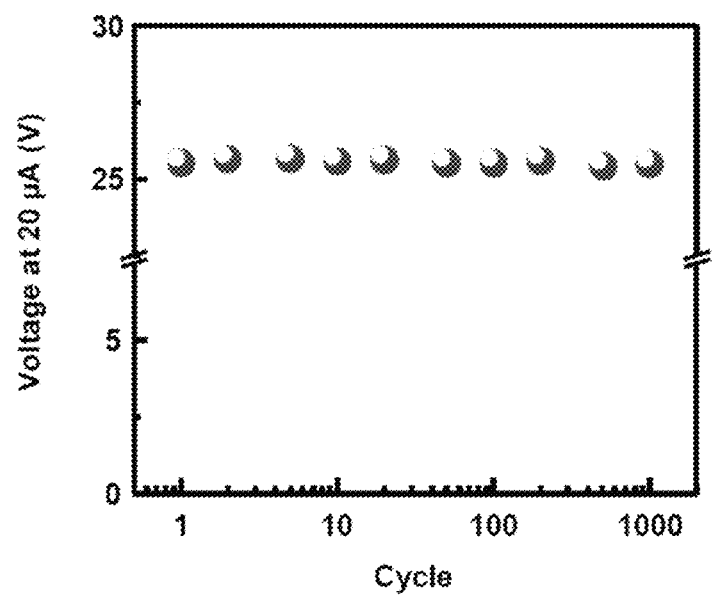

FIG. 40. Fatigue test result of a 6×6 µ-ILEDs array as shown in FIG. 28e. (a) Plot of I-V characteristics of a 6×6 µ-ILEDs array as a function of deformation cycles. (b) Plot of voltage needed to generate a current of 20 µA measured after deformation cycles up to 1000 times. Each deformed state is approximately same as shown in FIG. 28e.

Figure 29A:
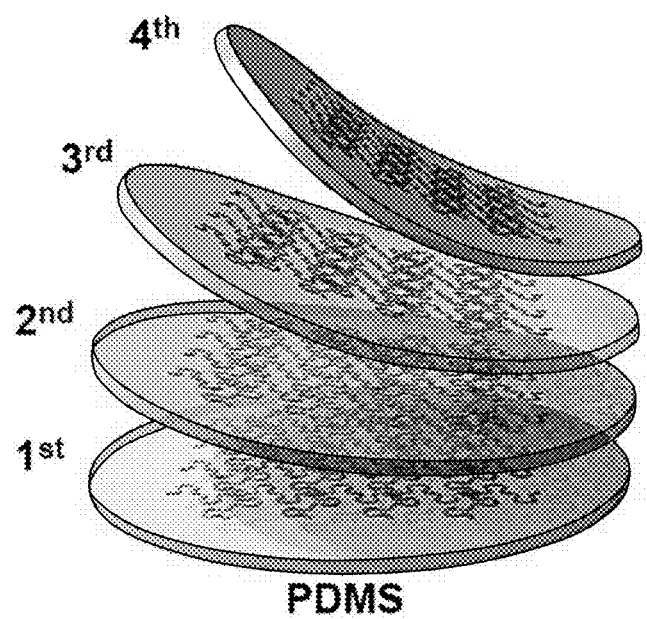
FIG. 29a, Schematic, exploded view illustration for a stacked device formed by multilayer lamination.
Figure 29B:
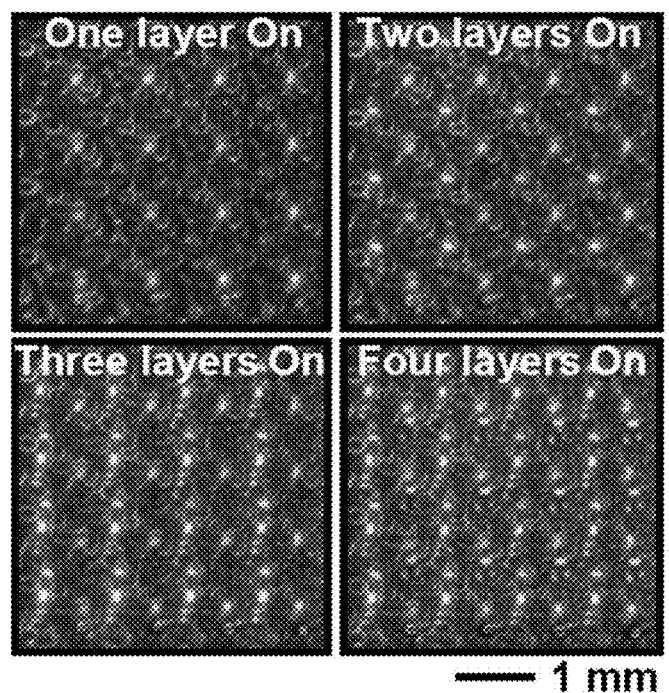
FIG. 29b, Optical images of a four layer stack of 4×4 arrays with layer-to-layer offsets designed to minimize overlap of interconnect lines with positions of the μ-ILEDs. The images show emission with different numbers of layers in operation (1st layer on, 1st and 2nd layers on, 1st, 2nd and 3rd layers on, and 1st, 2nd, 3rd and 4th layers on).
Figure 41A:
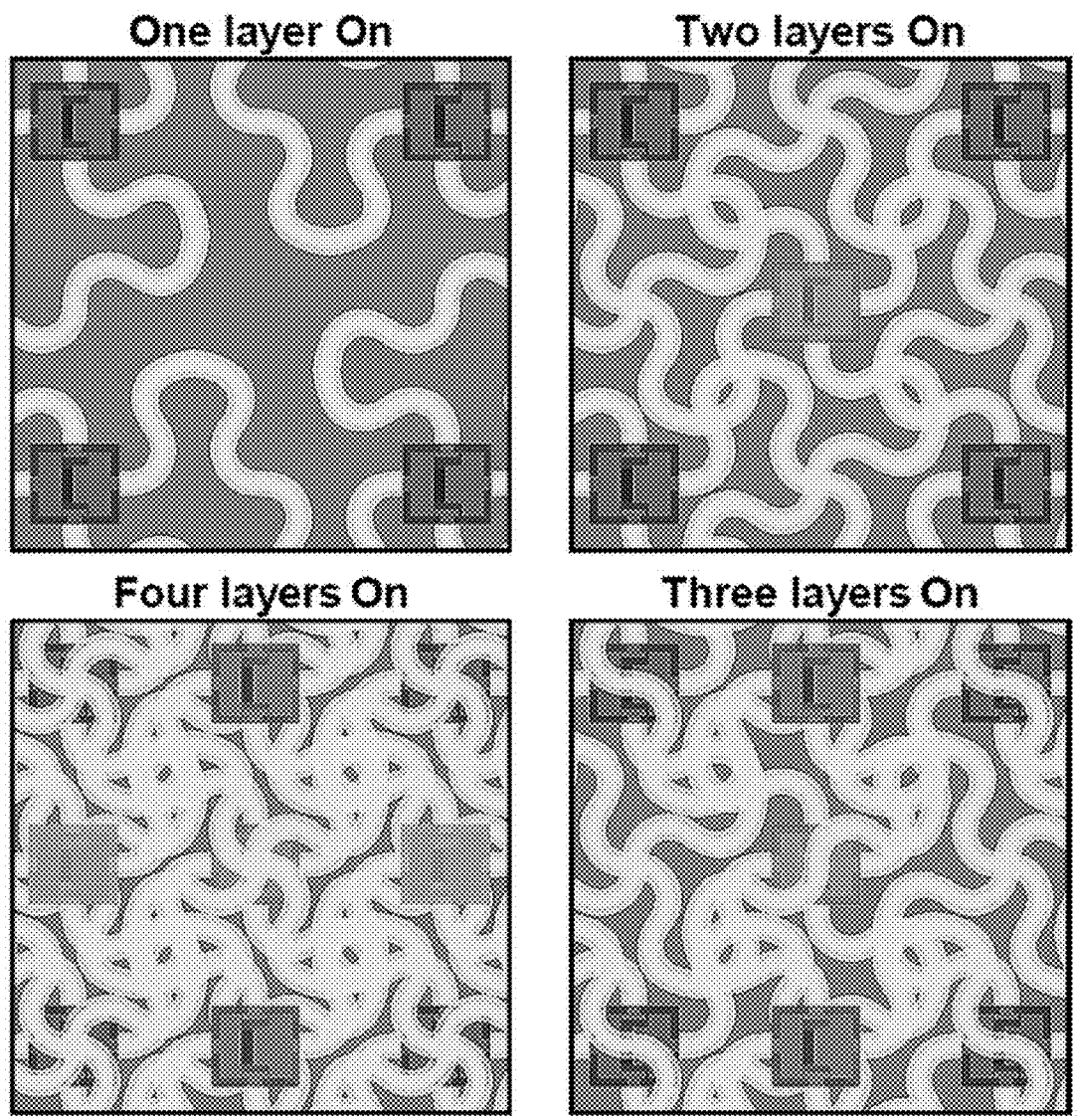

FIG. 41. (a) Schematic illustration of stacked devices describing states of FIG. 29b. (b) Optical images of stacked devices as shown in FIG. 29b, collected without external illumination.

Figure 29C:
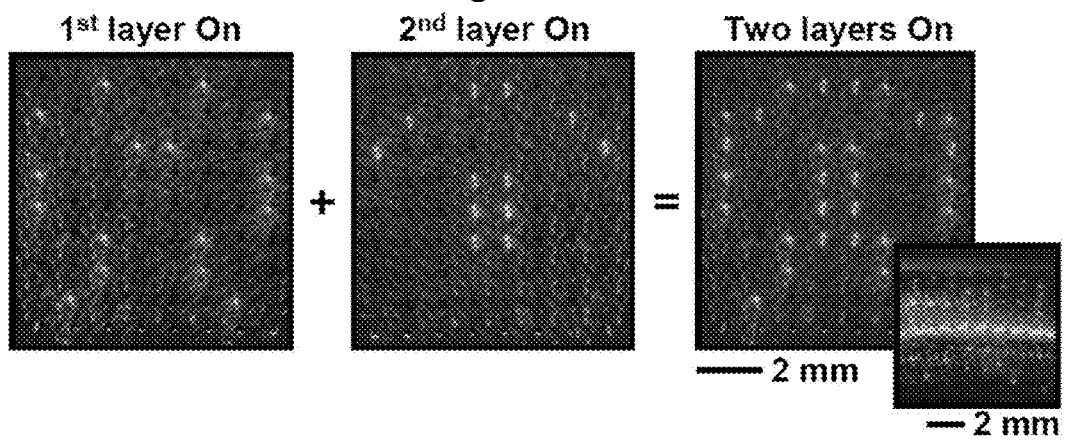
Figure 42A:
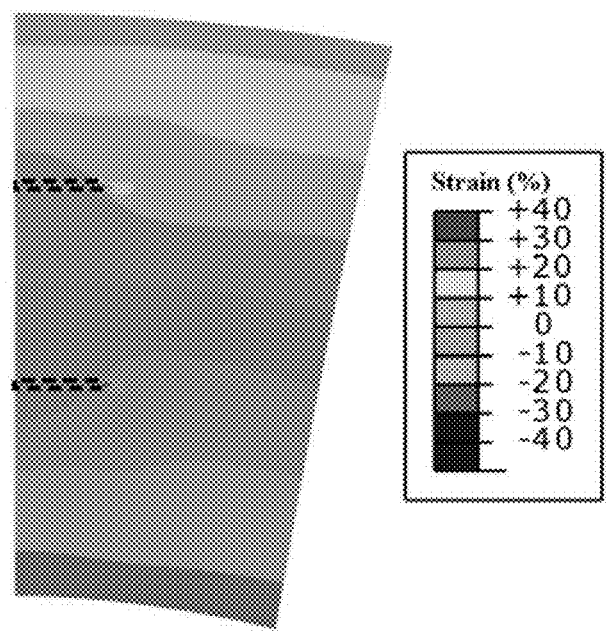
Figure 42B:
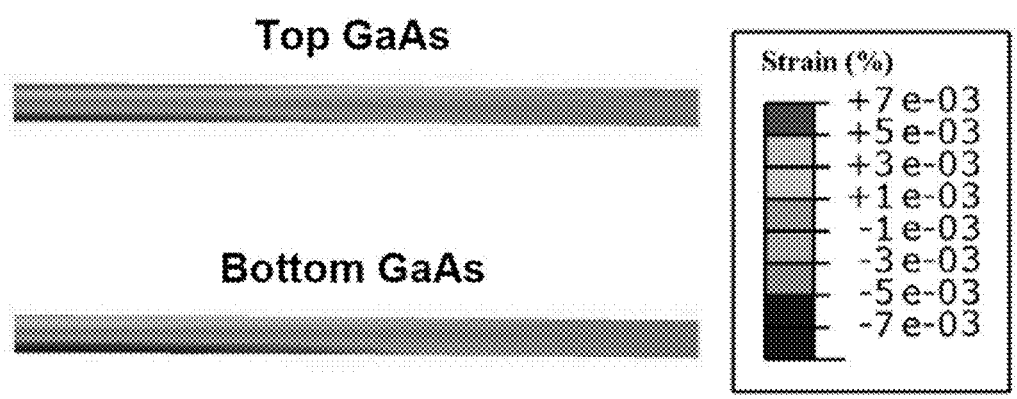

FIG. 42. (a) The strain distribution of the two-layer system in the stacked array bent to a radius of curvature 2 mm, as shown in FIG. 29c. The black dashed rectangles demonstrate the positions of µ-ILEDs. (b) The strain distribution in GaAs layers in the µ-ILEDs island.

Figure 29D:
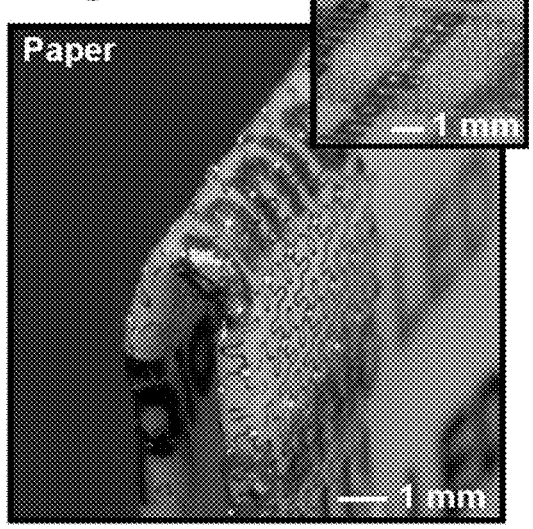
FIG. 29d, Optical image of an array of μ-ILEDs (8×8) on a piece of paper, in a folded state (bending radius ~400 μm) during operation. The inset shows the device in its flat state.
Figure 29E:
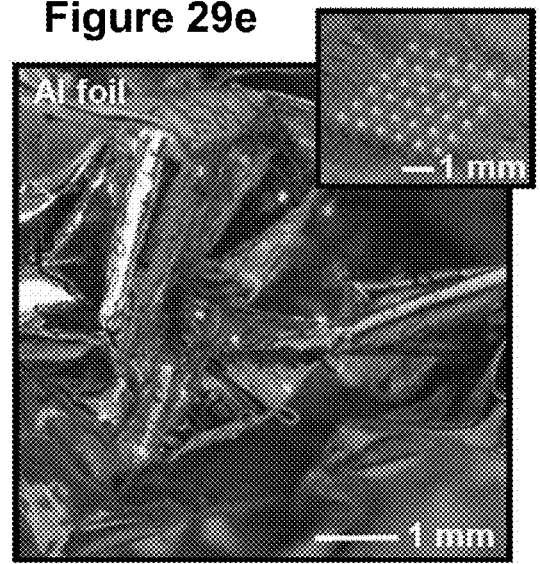
FIG. 29e, Image of a 6×6 array on a sheet of aluminum foil under crumpled state. The inset shows the device in its flat state.

FIG. 43. (a) Optical image of a 6×6 µ-ILEDs array with serpentine metal interconnects, integrated on fabrics, in its bent and on state (bending radius ~4.0 mm). The inset shows the device in its flat and off state. (b) Plot of I-V characteristics of this array in its bent state. Inset provides a graph of the voltage needed to generate a current of 20 µA, measured after different numbers of cycles of bending deformation. (c) Optical image of an 8×8 µ-ILEDs array with a human pattern, integrated on a fallen leaf, in its bent and on state. The inset image was collected with external illumination. (d) Plot of I-V characteristics in the bent state as shown in FIG. 43c. (e) Optical image of a µ-ILEDs array integrated on a paper in its folded and on state. (f) Optical image of the same µ-ILEDs array as shown in FIG. 29e in its mildly crumbled state. Inset represents microscope image of adjacent four pixels in their on states.

Figure 43B:
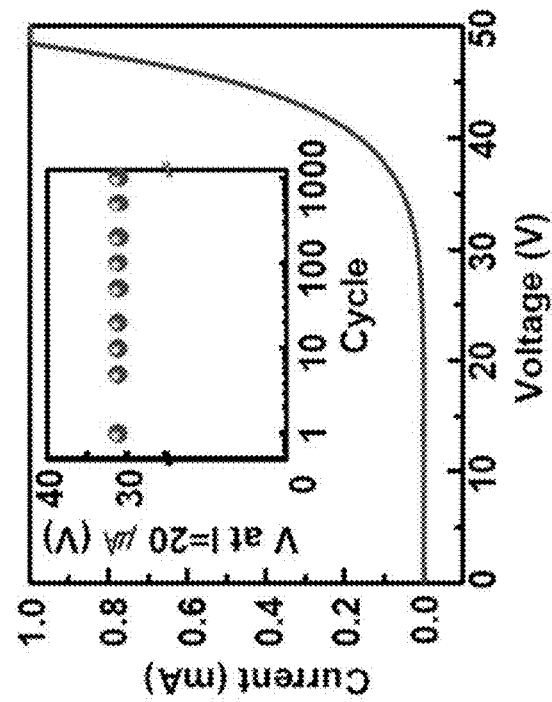
Figure 43A:
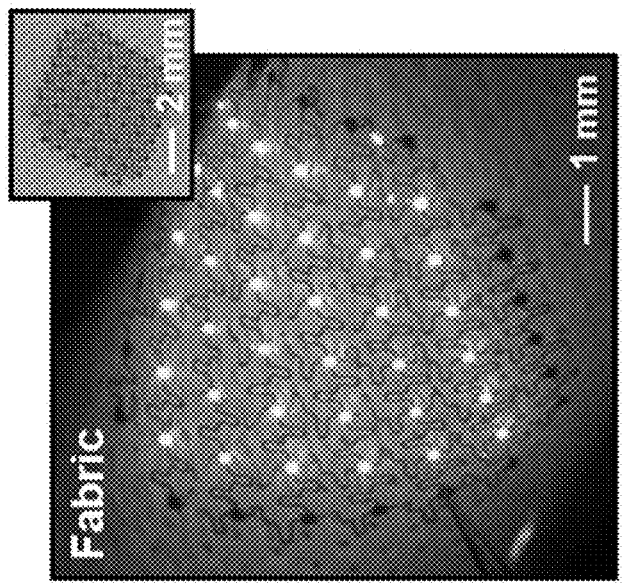
Figure 43D:
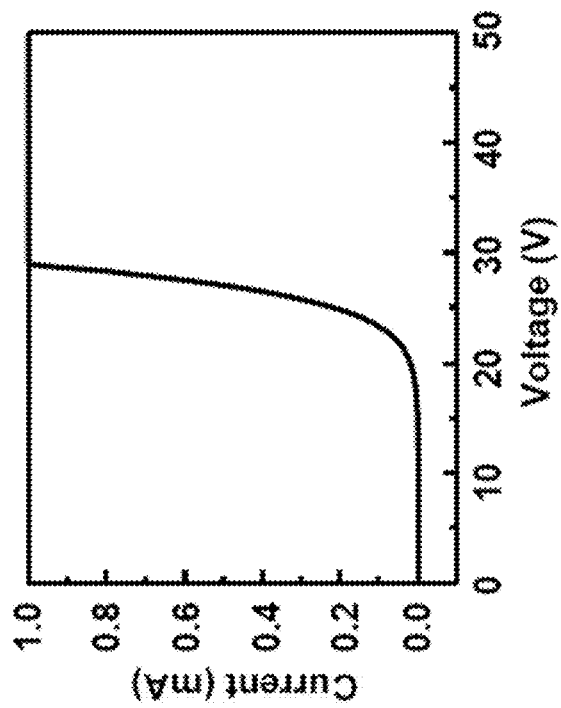
Figure 43C:
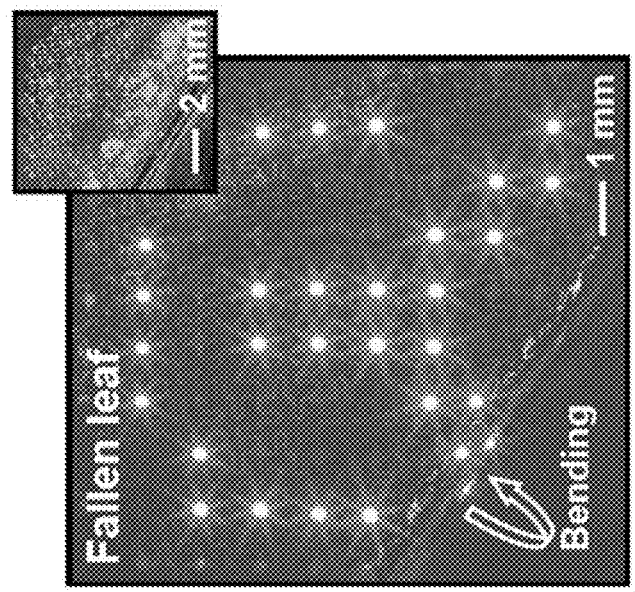
Figure 43F:
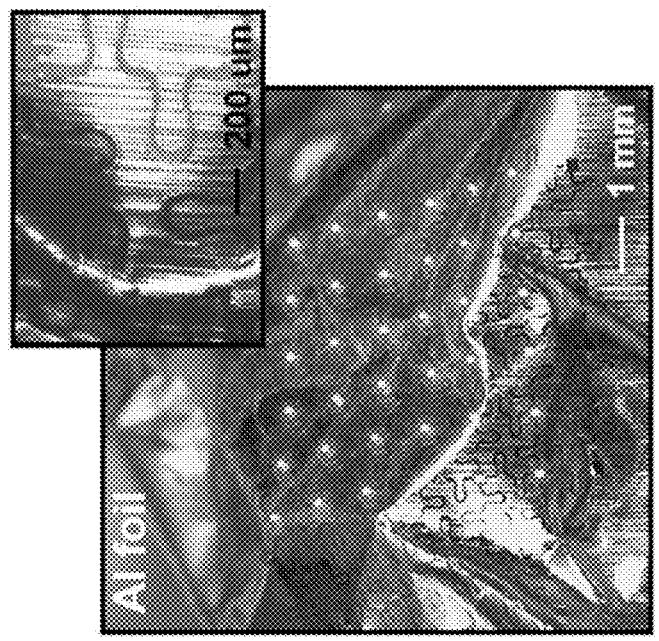
Figure 43E:
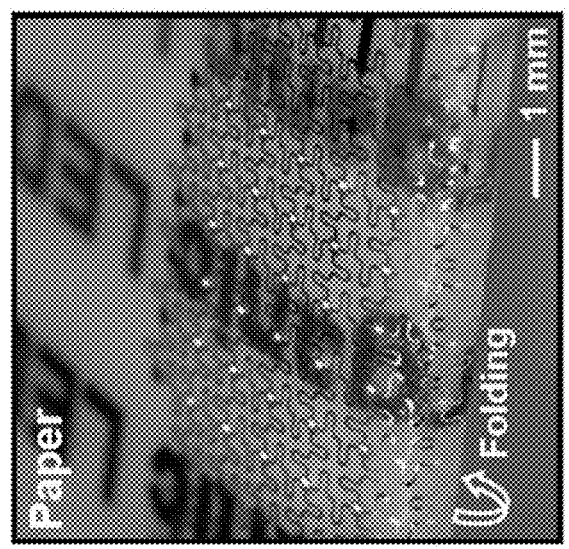
Figure 44A:
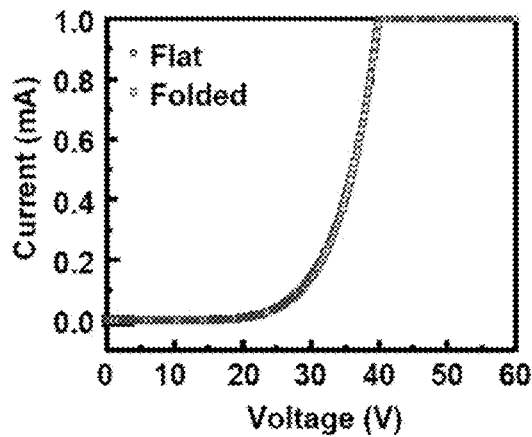
Figure 44B:
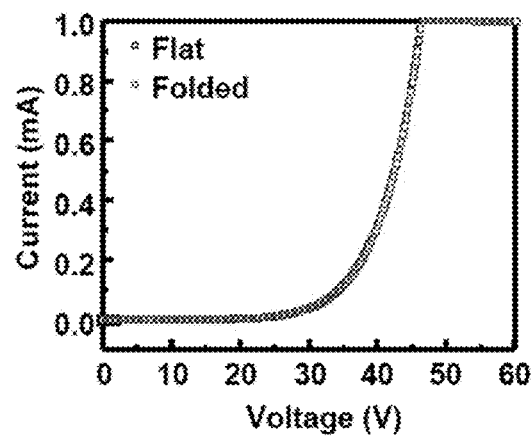

FIG. 44. (a) Plot of I-V characteristics of a 6×6 µ-ILEDs array integrated on paper in its flat (FIG. 29d inset) and folded (FIG. 29d) state. (b) Plot of I-V characteristics of a 6×6 µ-ILEDs array integrated on aluminum foil in its flat (FIG. 29e inset) and crumbled (the center frame of FIG. 29e) state. (c) Fatigue tests of arrays of 6×6 µ-ILEDs as shown in FIG. 43e. Plot of I-V characteristics of a µ-ILEDs array integrated on paper as a function of deformation cycles (left frame). Plot of voltage needed to generate a current of 20 µA measured after deformation cycles up to 1000 times (right frame). (d) Fatigue tests of arrays of 6×6 µ-ILEDs as shown in FIG. 43f. Plot of I-V characteristics of a µ-ILEDs array integrated on aluminum foil as a function of deformation cycles (left frame). Plot of voltage needed to generate a current of 20 µA measured after deformation cycles up to 1000 times (right frame).

FIG. 45. SEM images of various substrate such as fabrics (a), Al foils (b), paper (c), and fallen leaves (d) before (left frame) and after (right frame) coating of thin layer of PDMS.

Figure 46:
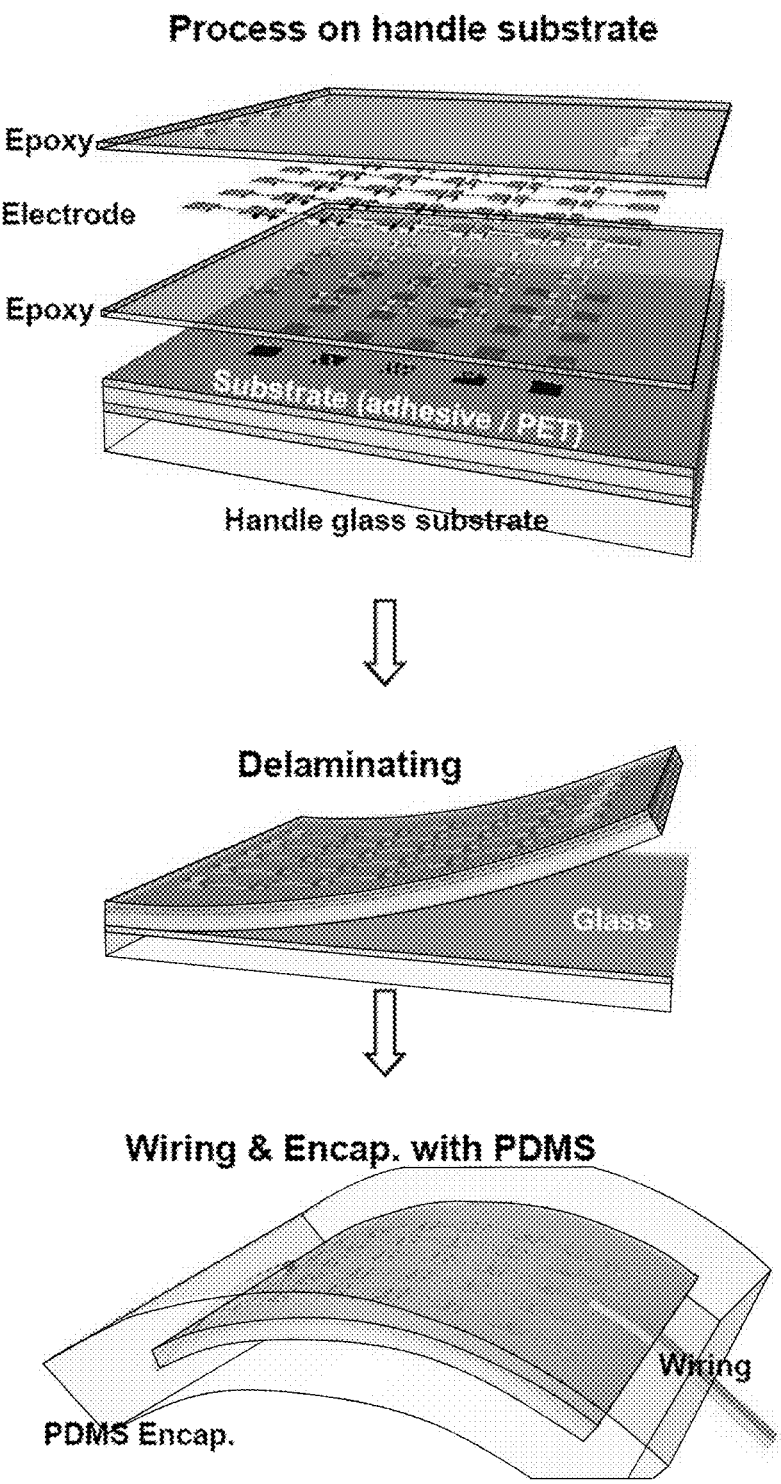

FIG. 46. Schematic illustration of the encapsulation of an implantable array of µ-ILEDs as described in FIGS. 30a and 30b.

FIG. 47. (a) Result of Luminance (L)-Current (I)-Voltage (V) measurement of an individual pixel with and without applied ohmic contacts. (b) Applied voltage to generate a current of 20 µA, measured after different operation time. The inset provides I-V characteristics with different operation time.

FIG. 48. (a) Schematic illustration of analytical model for the inflation and printing-down of PDMS film. (b) FEM contours of meridional (upper left) and circumferential (lower left) strains of the inflated state and its comparison with analytical solutions calculated from Equations (S1) and (S2). (c) FEM contours of meridional (upper left) and circumferential (lower left) strains of the as-printed state and its comparison with analytical solutions Equations (S3) and (S4) (right frame).

Figure 49:
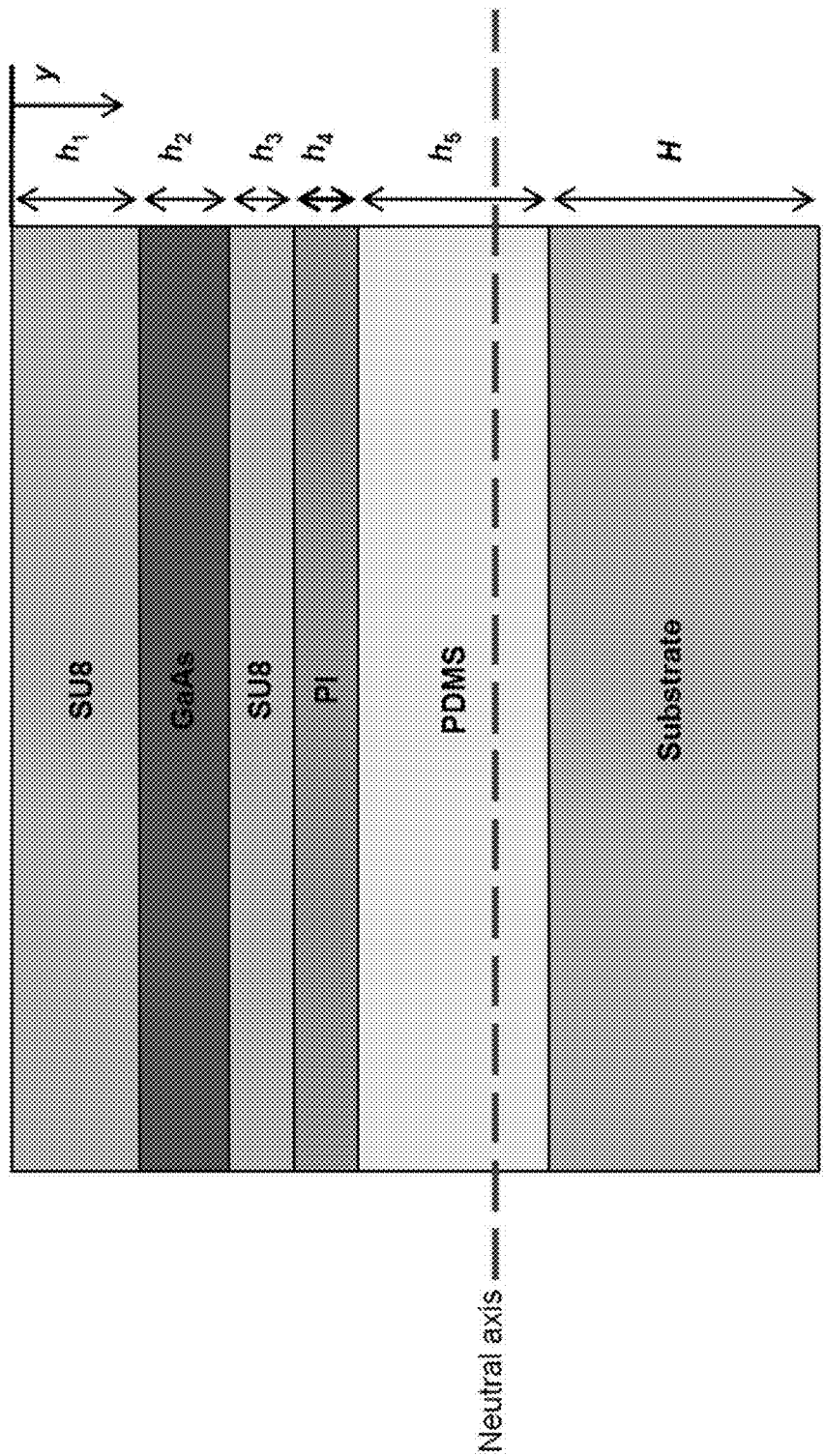

FIG. 49. Schematic illustration of the cross section of µ-ILEDs on a substrate.

FIG. 50 provides: (a) Four frames of the electrode array transfer printed onto thin, low modulus ecoflex. On skin (left top), partially peeled off state (right top), magnified view of each top frame (bottom). Blue dotted boxes correspond to the magnified images at the bottom frame. The modulus and thickness of ecoflex substrate is ~50 kPa and ~30 um, respectively. The electrode array is facing down to skin, sandwiched by the skin and ecoflex substrate. (b) Schematic view of application procedures of skin patch to the skin. The electrode array is transfer printed onto ecoflex, coated on the PVA film, and water dissolvable and biocompatible film. The transferred electrode array is positioned onto the right location of skin. Some water can be applied to the backside of PVA film to dissolve it away. Thin, low modulus skin patch conforms very well to skin, like a tattoo. (c) Deformed images of skin patch on skin to four different directions and their magnified views. The highly conformal skin patch follows the wrinkles on skin very well. (d) Electrode array transfer printed at the backside of the commercial temporary tattoo. It is applied to the skin. Instead of ecoflex thin film, a temporary tattoo can be used for the purpose of camouflage or cover-up. (e) A schematic diagram illustrating a cross-sectional view of a skin-mounted conformal device of the invention having a polyimide encapsulating barrier layer.

Figure 51A:
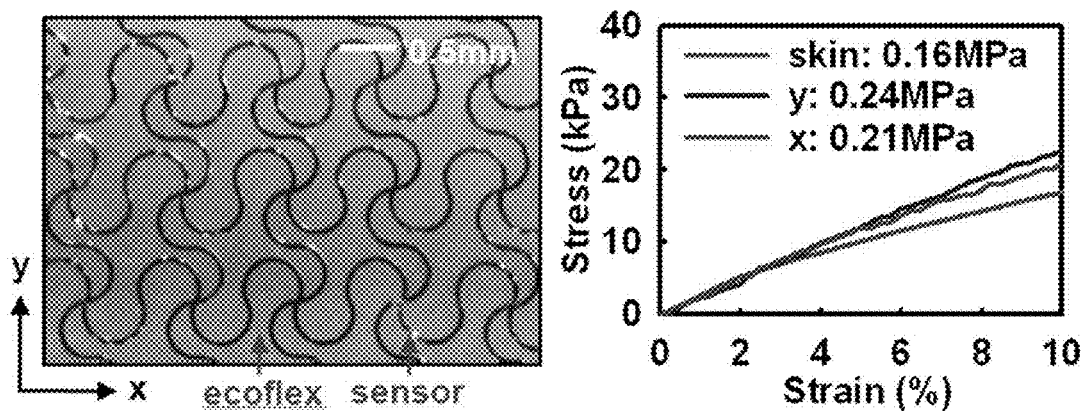
Figure 51B:
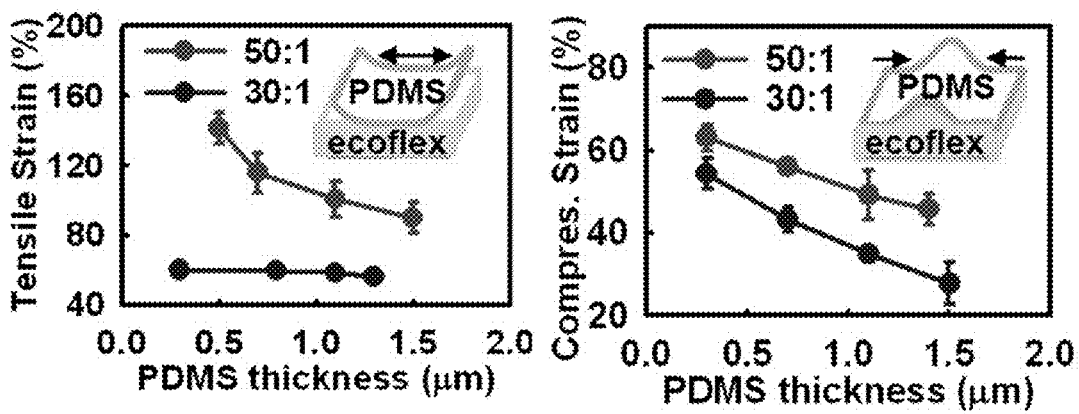
Figure 51C:
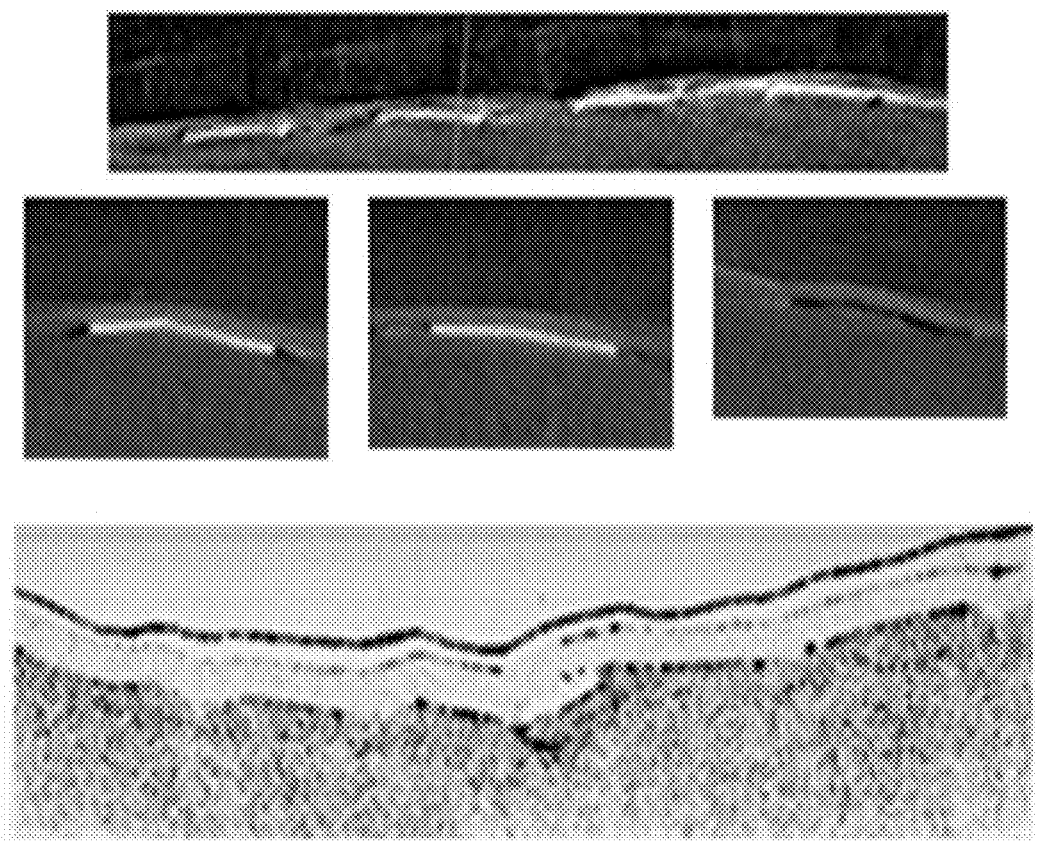
Figure 52A:
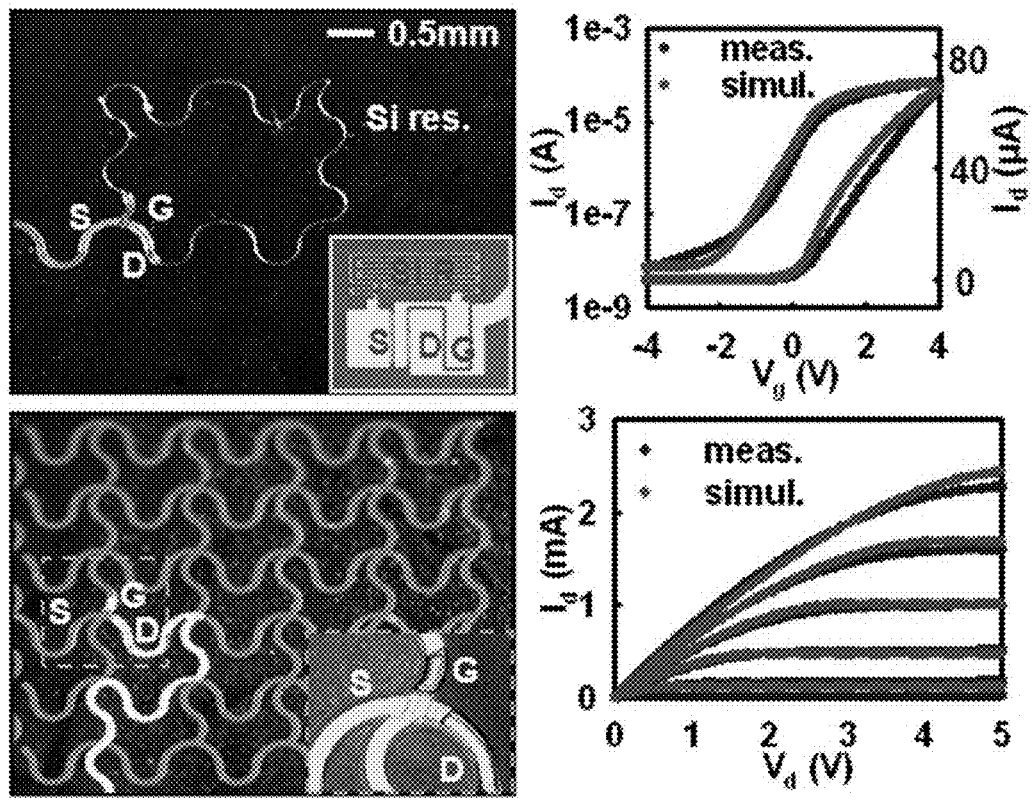
Figure 52B:
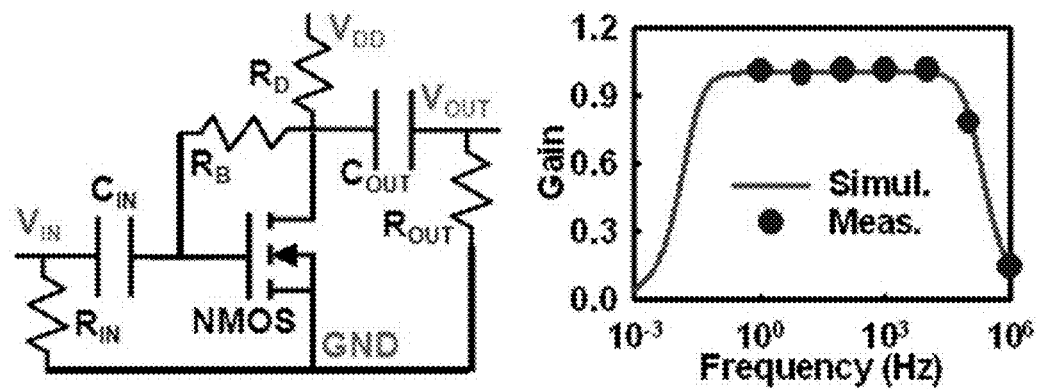
Figure 52C:
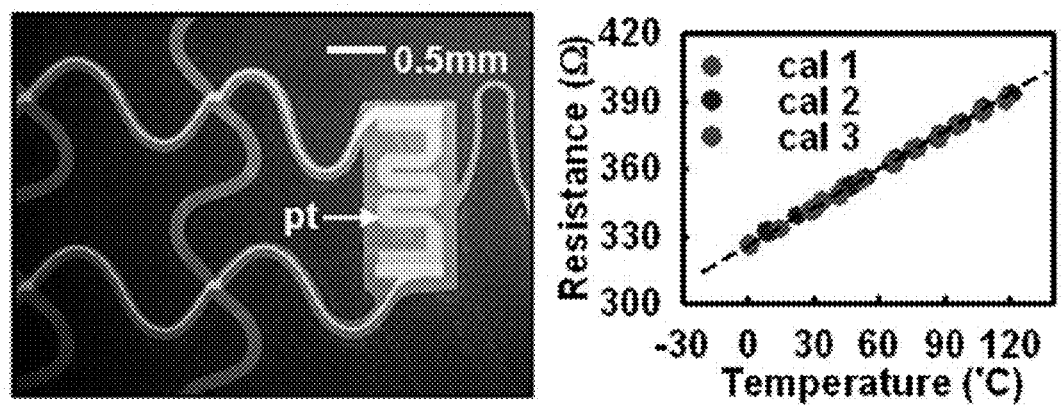
Figure 52D:
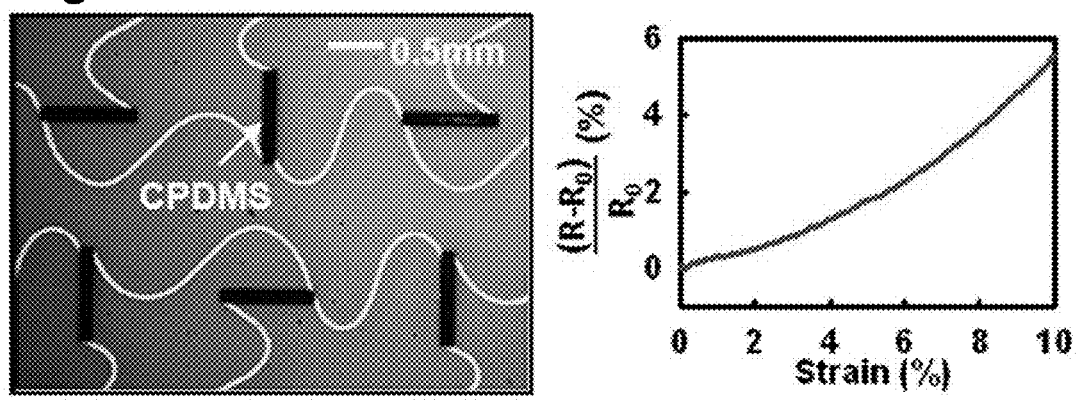
Figure 52E:
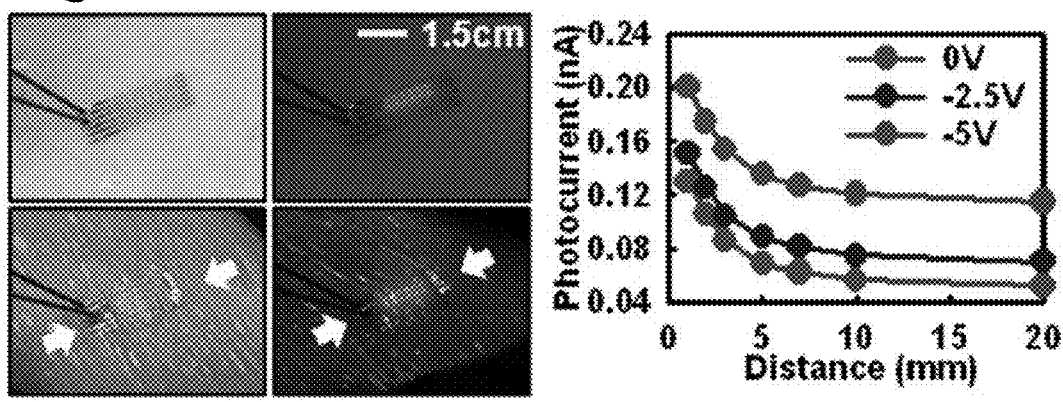
Figure 52F:
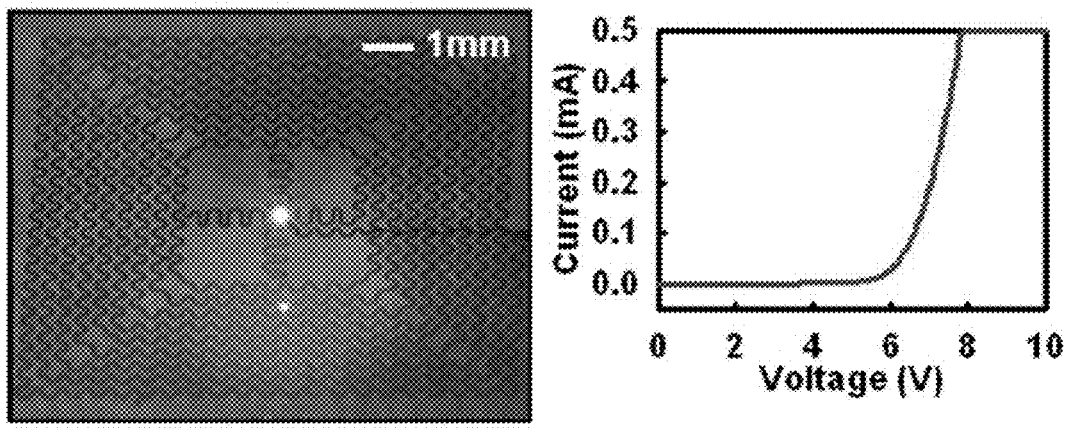
Figure 52G:
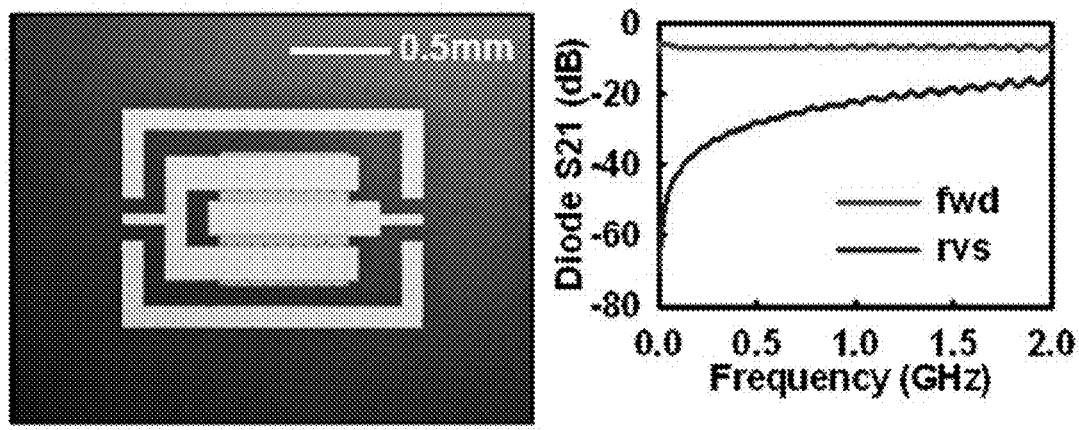
Figure 52H:
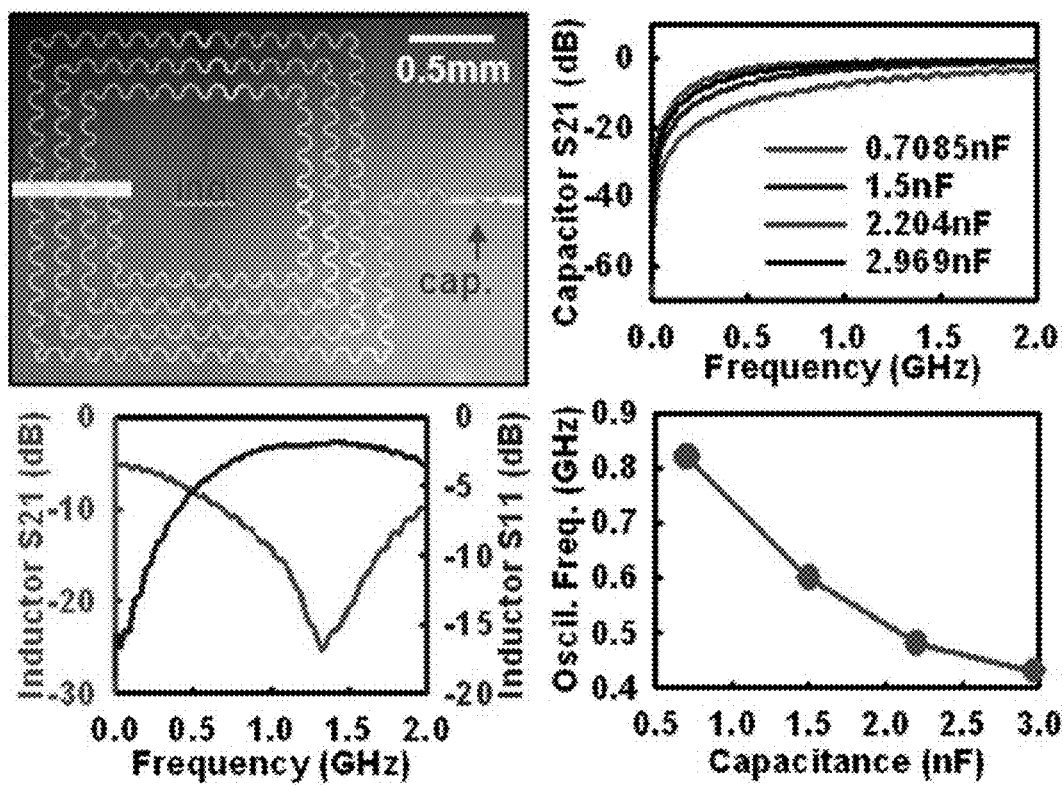

FIG. 51 provides (a) Mechanically optimized fully serpentine electrode array (left). The right frame shows the stress-strain relationship from which the modulus in the plot was calculated. The optimized design shows comparable modulus with the bare skin. (b) Debonding experiment results under tension (left) and compression (right). As the modulus and thickness decrease, the debonding happens at larger strain. (c) Cross-sectional image (X-ray) of skin electronic devices located on the pig skin.

FIG. 52 provides (a) Serpentine shape active EMG/EKG sensor. Left top frame shows source, drain and gate of nmos transistor and silicon drain to gate feedback resistor. Inset shows conventional shape active EMG/EKG sensor. Left bottom image shows the final device image for serpentine shape device and its magnified view (inset). Right top and bottom frame shows transfer and IV curve for the transistor. (b) Circuit diagram for active EMG/EKG sensor and the frequency response of active sensor (common source amplifier). (c) Microscope image of temperature sensor using platinum resistor and gold serpentine wires. Right frame shows the calibration curve, showing different resistances of temperature sensor at different temperatures. (d) Microscope image of strain gauge using conductive PDMS (CPDMS). Right frame shows the calibration curve of the strain gauge. (e) Microscope images of proximity sensor using forward and reverse biased LED array. Forward biased LED array radiates light and reverse biased LED array detects the reflected light from the object. As the distance between the object and LED array decreases, the reflectance increases and thereby the photocurrent increases, as shown in the right frame. (f) A single LED pixel powered by wireless power transmission coil. Right frame shows the IV curve of LED pixel. (g) Microscope image of PN diodes (left) and it S21 value measured at different frequencies in radio frequency range. (h) Microscope image of inductor and capacitor pair (left top). Right top plot shows S21 value of capacitor at various RF frequencies and left bottom plot shows S21 and S11 values of inductor at RF frequencies. Right bottom plot shows the estimated oscillation frequencies for different capacitors.

Figure 53A:
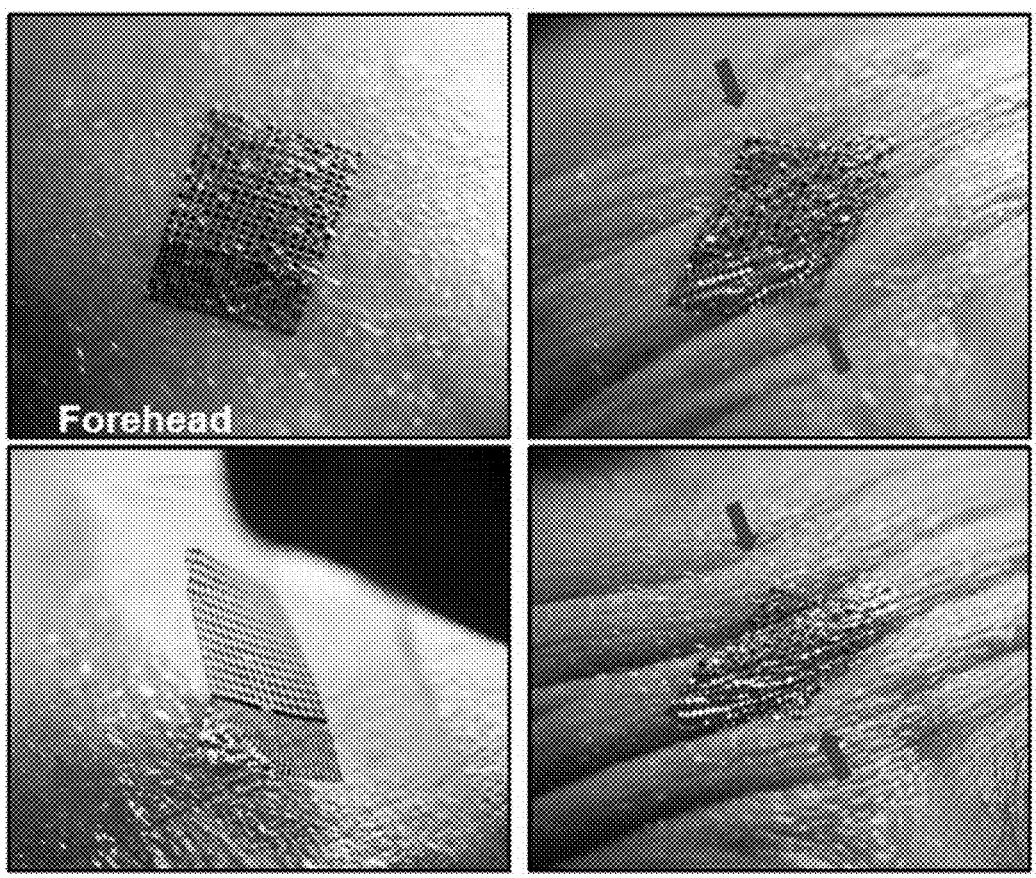
Figure 53B:
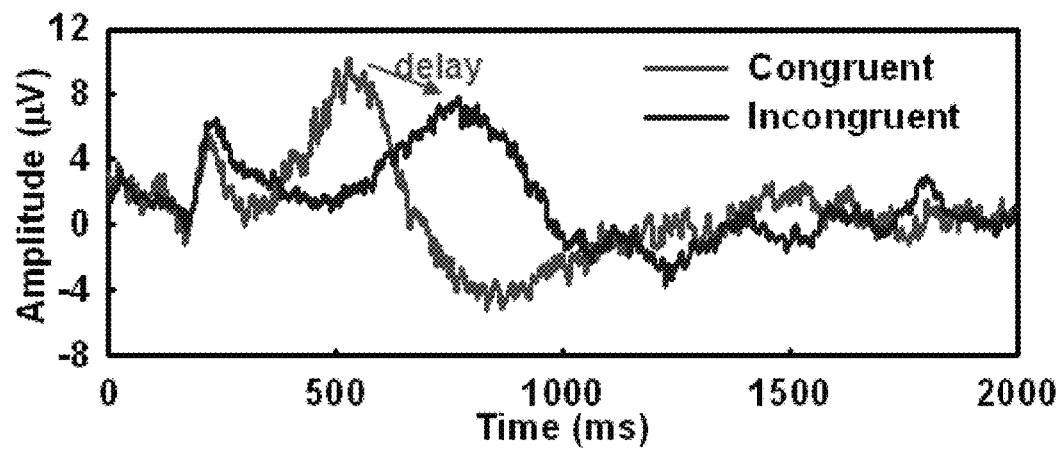
Figure 53C:
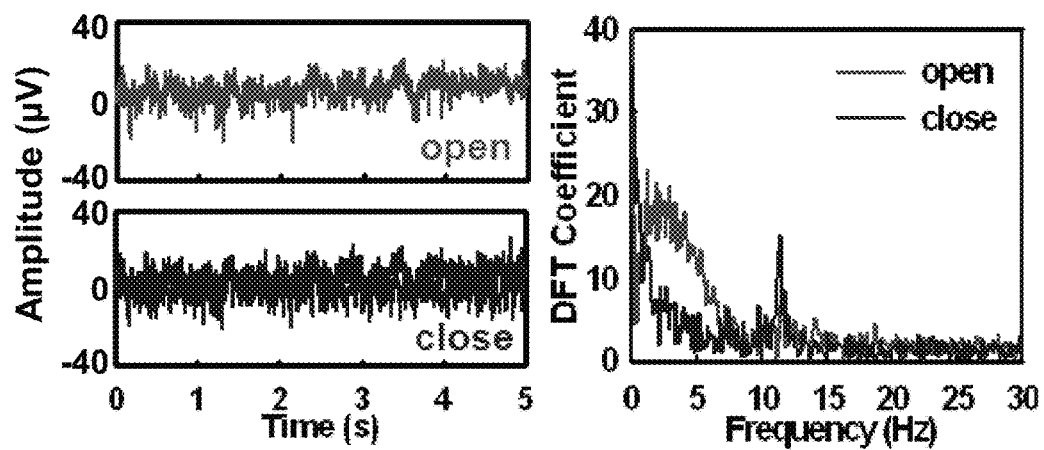
Figure 54A:
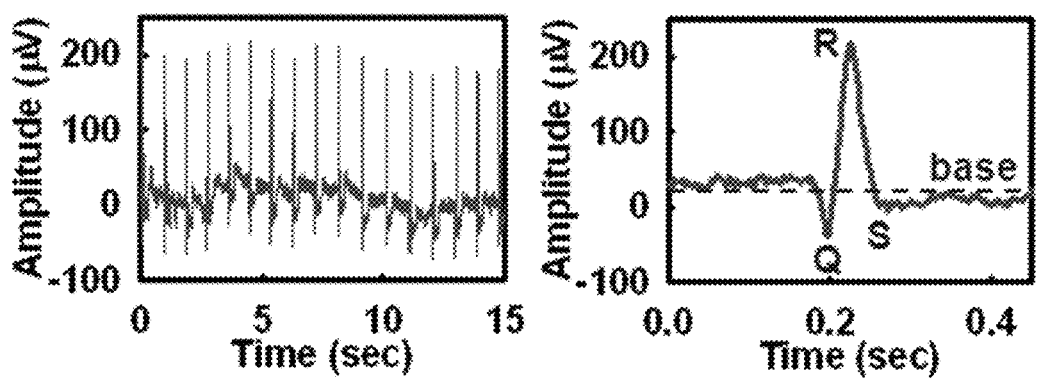
Figure 54B:
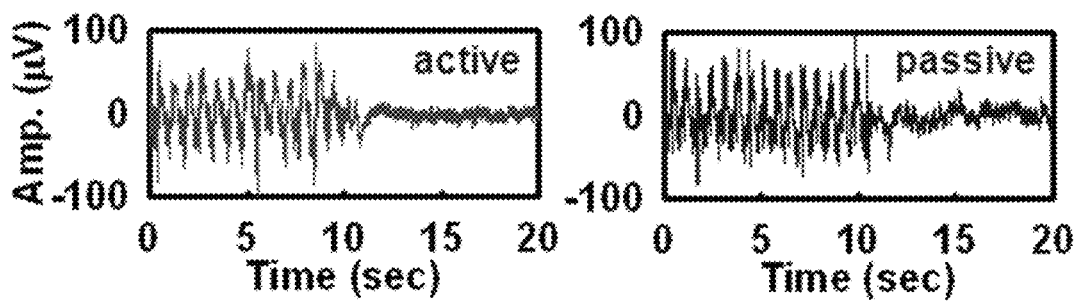
Figure 54C:
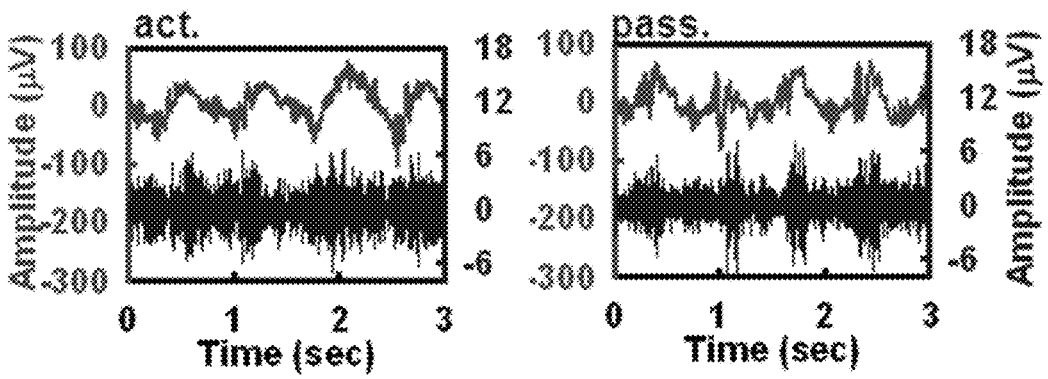
Figure 54D:
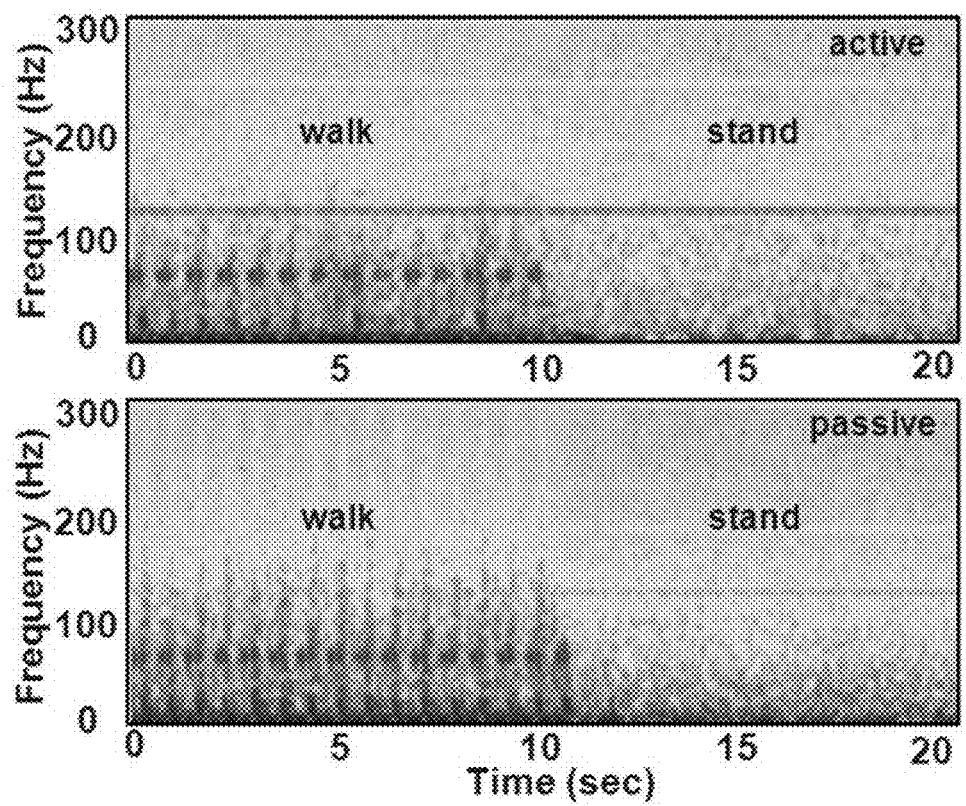
Figure 54E:
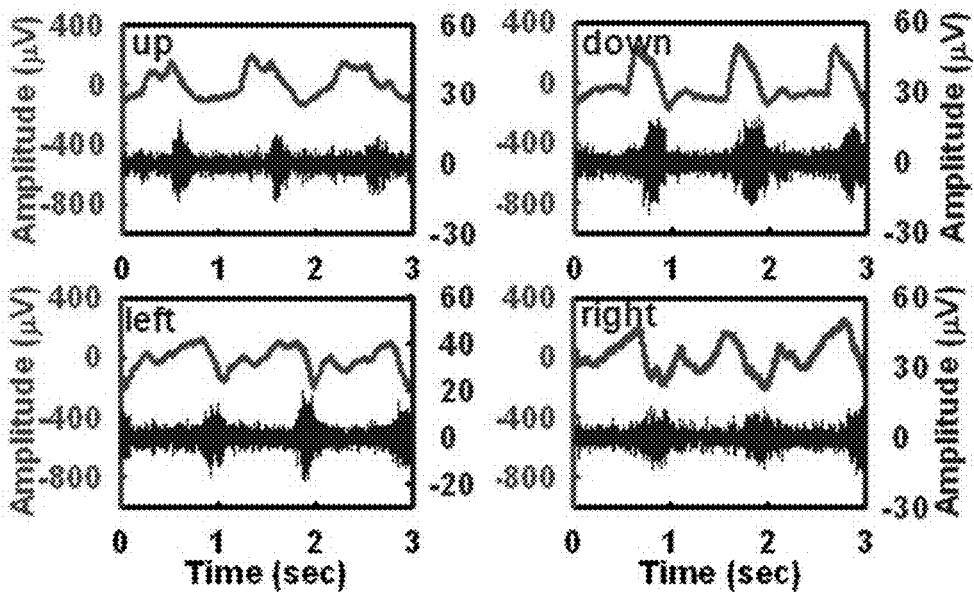
Figure 54F:
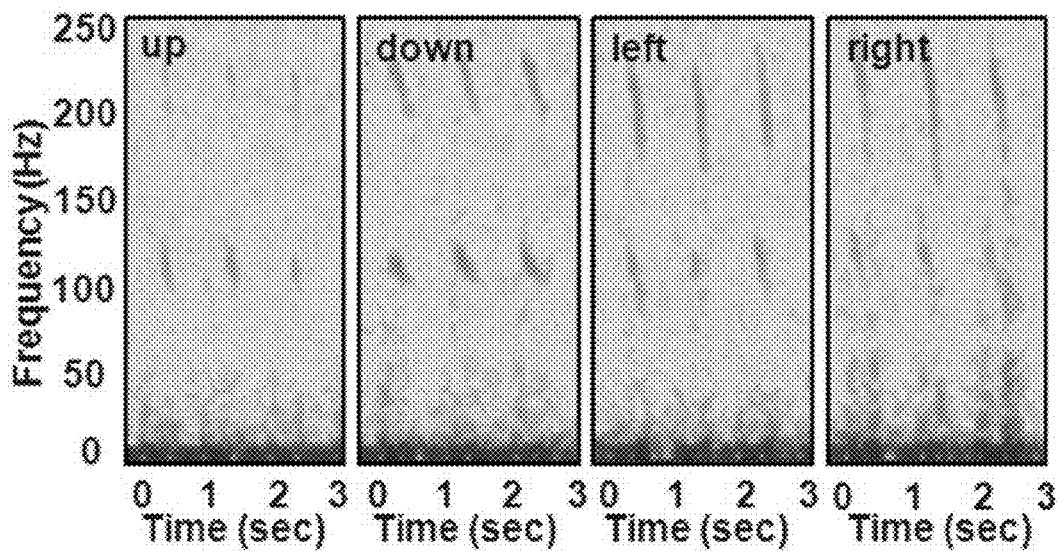
Figure 54G:
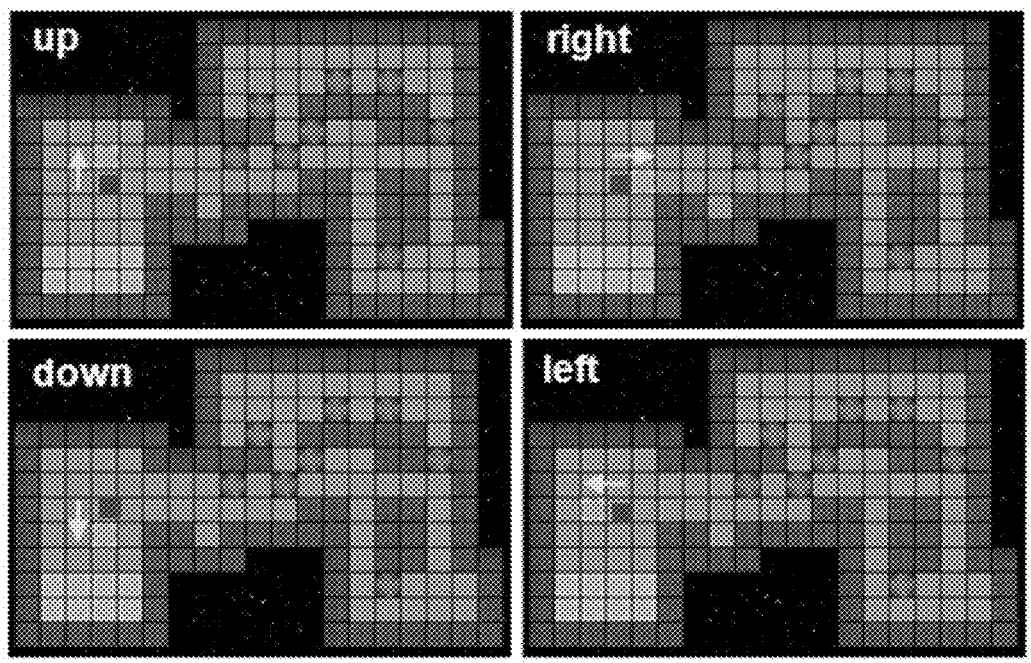

FIG. 53 provides (a) Passive electrode array on forehead for undeformed (left top) and deformed (right top and bottom) state. Left bottom image shows the partially peeled off state. (b) EEG measurement results for Stroop test. When the target letter matches with the highlighted letter (congruent case) the response speed is faster than unmatched (incongruent case) case. (c) EEG measurement results for eye open and eye close case. Left plot shows raw EEG and right plot shows results after Fourier transformation.

FIG. 54 provides (a) EKG measurement result measured with active EKG sensor (left) and magnified view of single heartbeat (right). (b) EMG measurement result from a right leg during walking (from 0 sec to 10 sec) and standing (from 10 sec to 20 sec) measured with active EMG sensor (left) and conventional passive EMG sensor with conductive gel (right). (c) Magnified view of EMG signal of (b). (d) Corresponding spectrogram for each electrode. (e) EMG measurement result from neck for four different words, "up", "down", "left" and "right". (f) Corresponding spectrogram for four words. (g) Video game control using recorded EMG signal.

FIG. 55 is block diagram of a system for a wide range of biological sensing and therapeutic treatment applications.

FIG. 56 is a diagram depicting the collapsible nature of a flexible high-density micro-array device that can be deployed to a tissue site.

Figure 57:
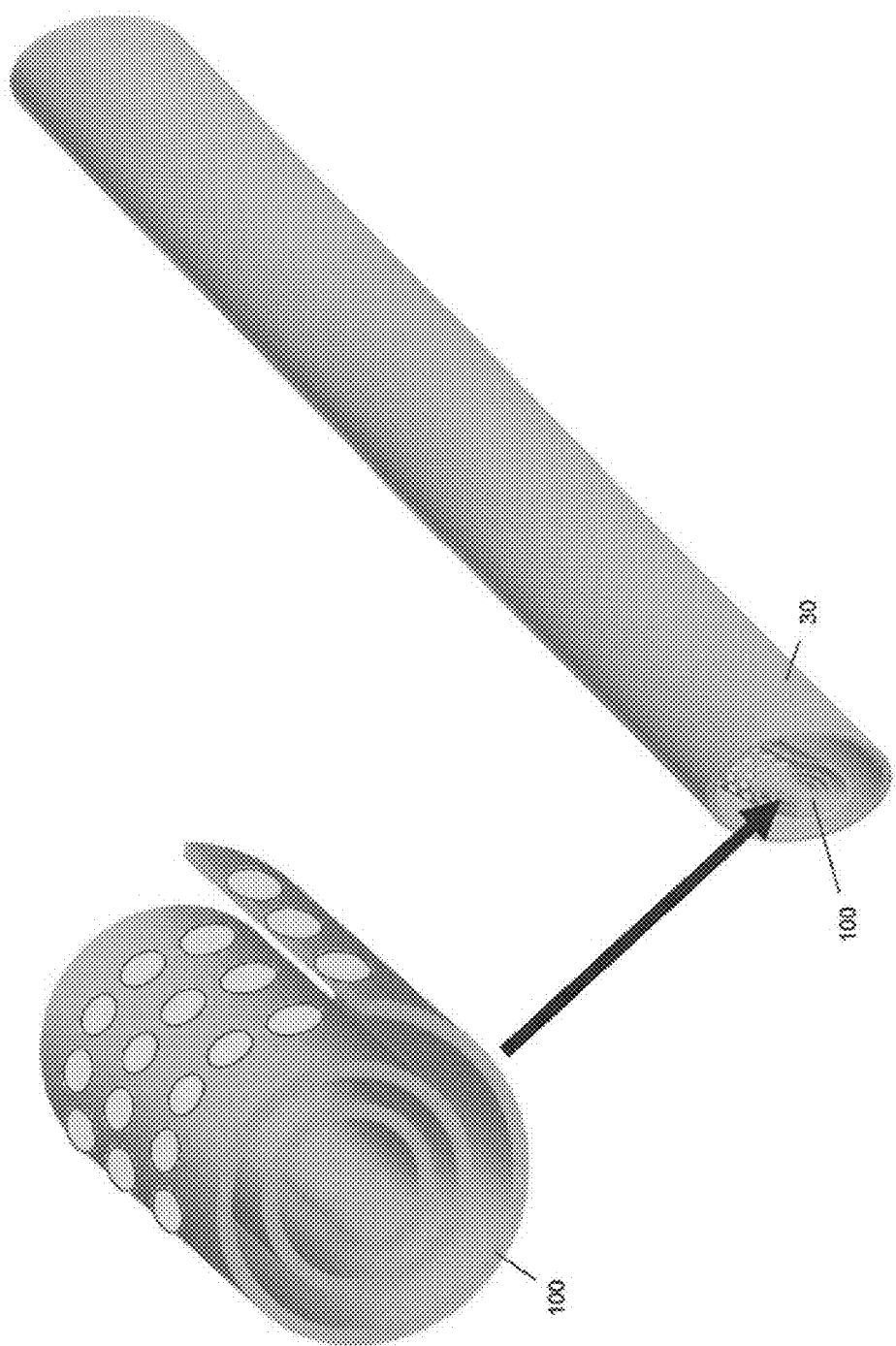

FIG. 57 is a diagram depicting insertion of the array device into a sheath for introduction into a patient.

Figure 58:
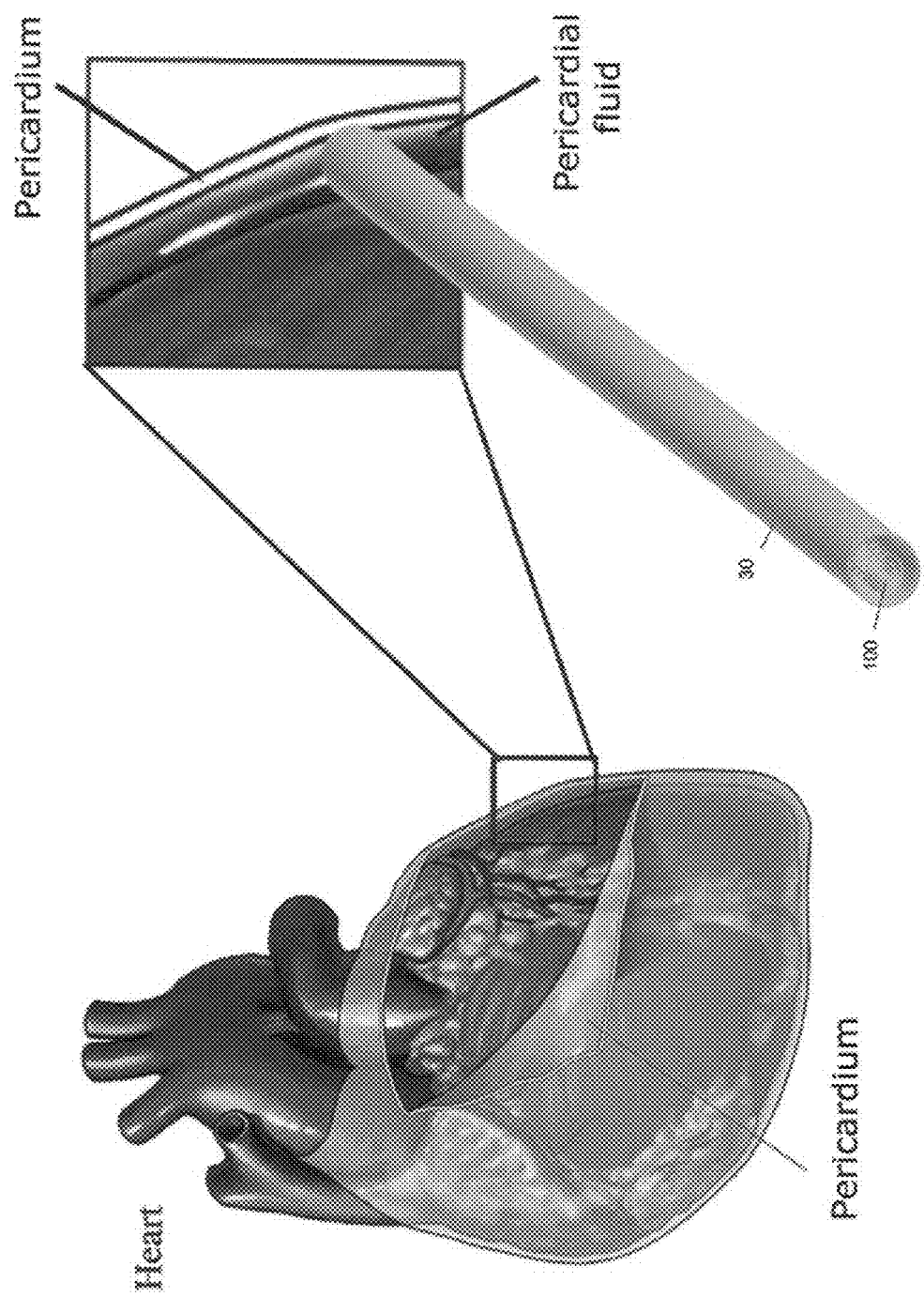

FIG. 58 is a diagram depicting deployment of the array device from a sheath to a tissue surface.

Figure 59:
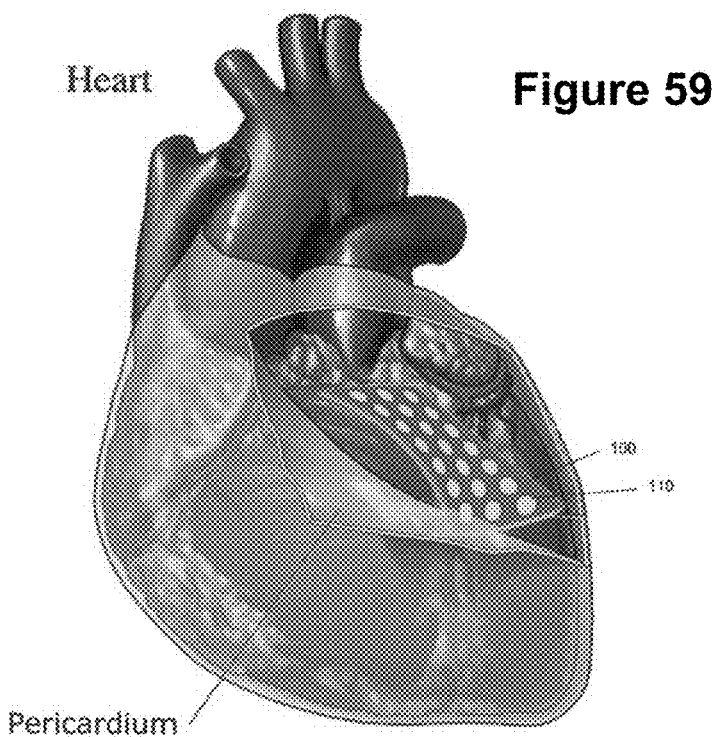

FIG. 59 is a diagram of the array device deployed on the surface of the heart.

Figure 60:
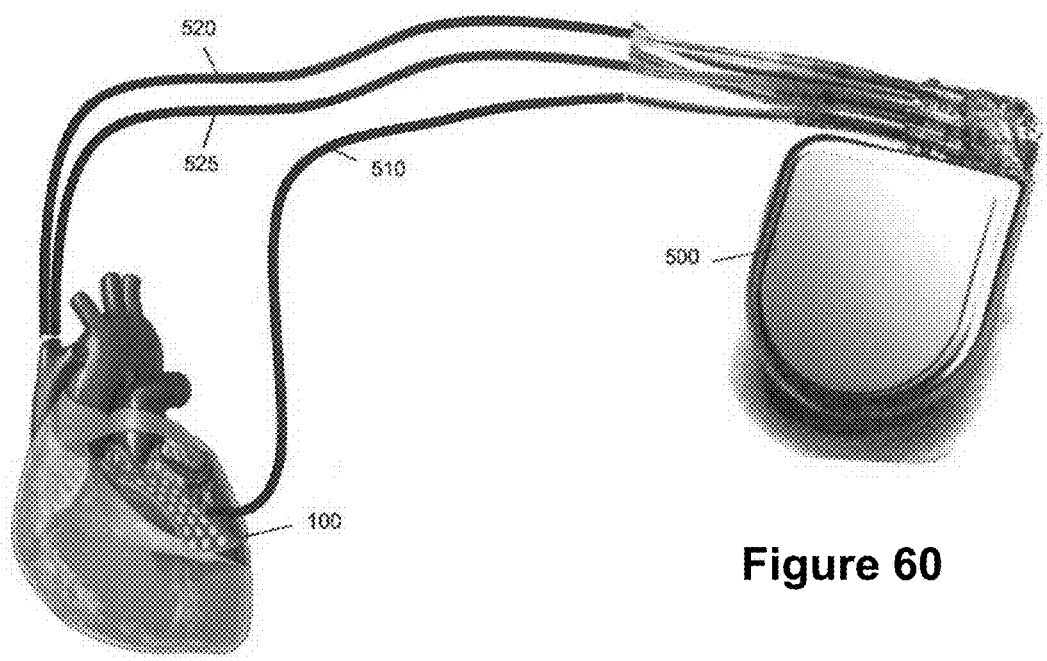
Figure 61:
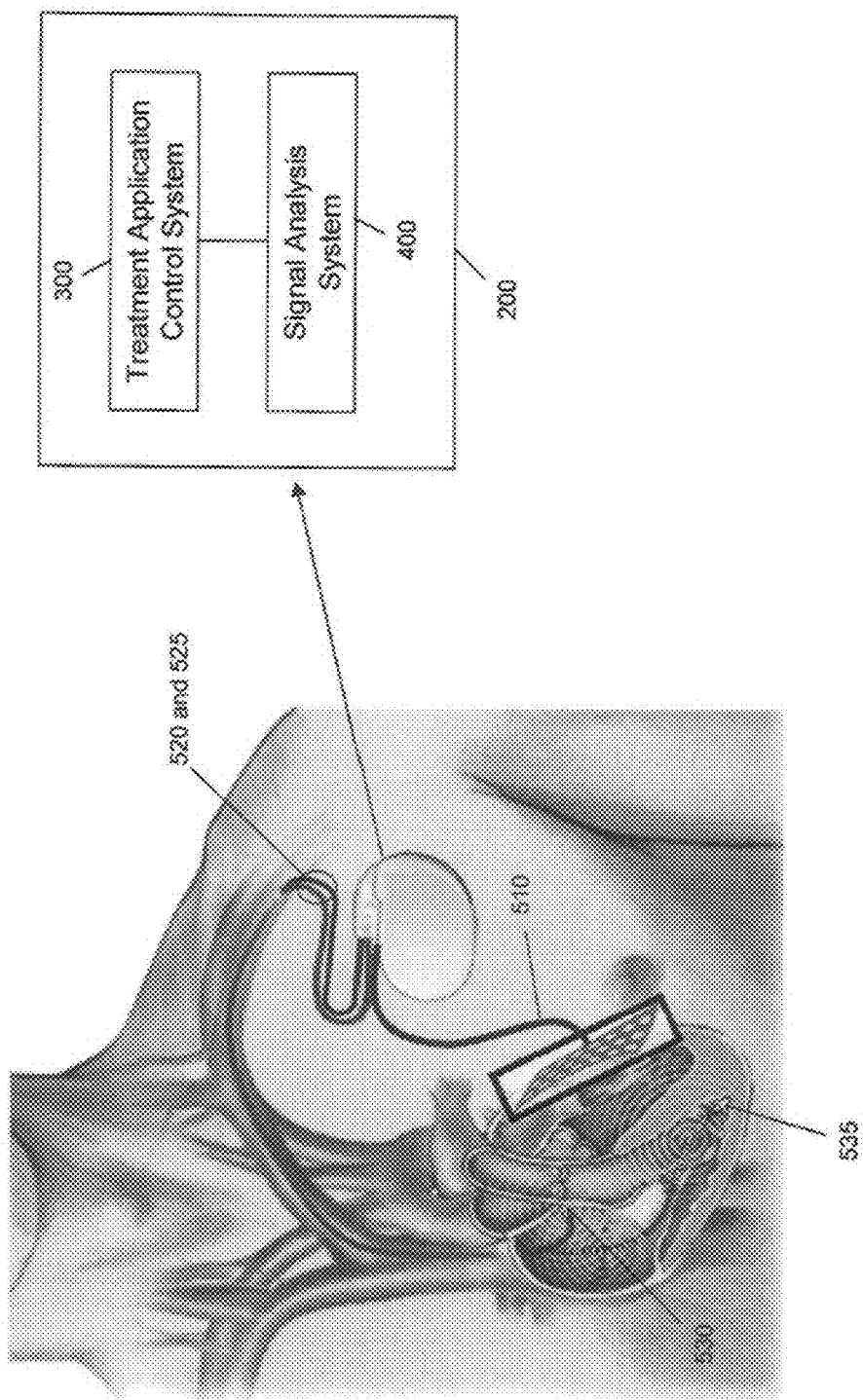

FIGS. 60 and 61 are diagrams showing connection of the array device to an implantable electronics unit.

Figure 62:
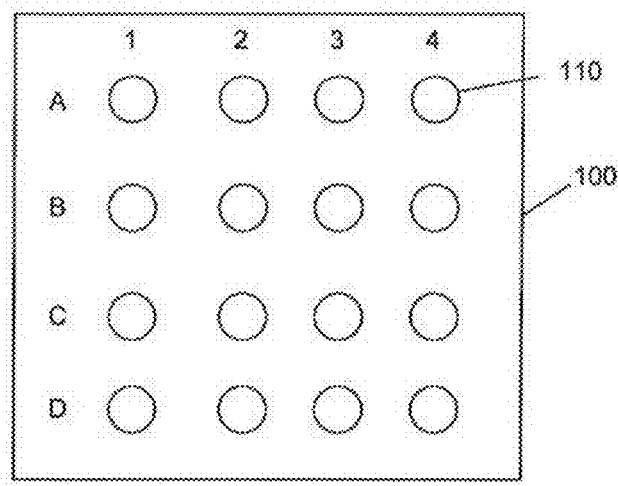

FIG. 62 is a diagram showing a specific example of elements on the array device.

Figure 63:
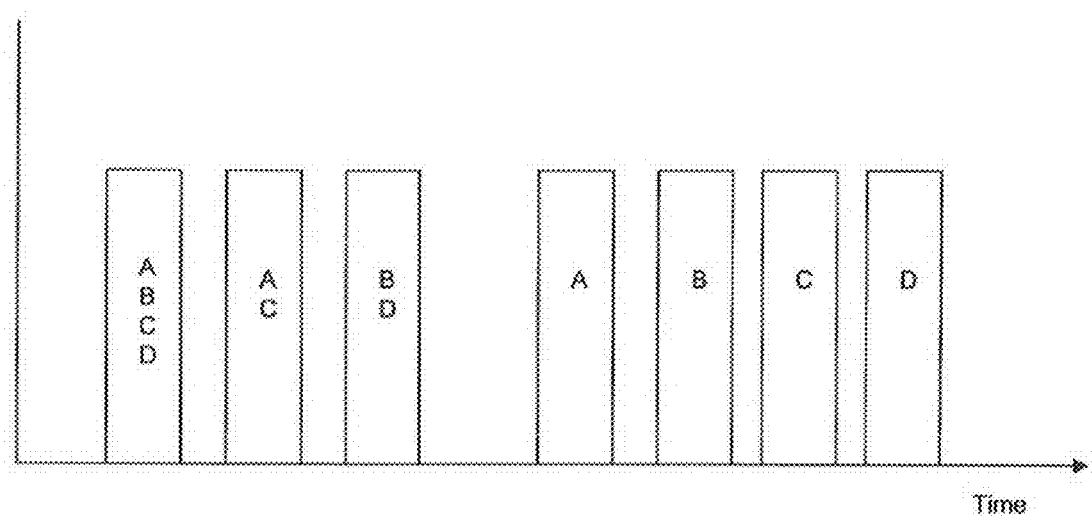

FIG. 63 is a timing diagram showing examples of stimulation timing schemes to groups of elements on the array device.

Figure 64:
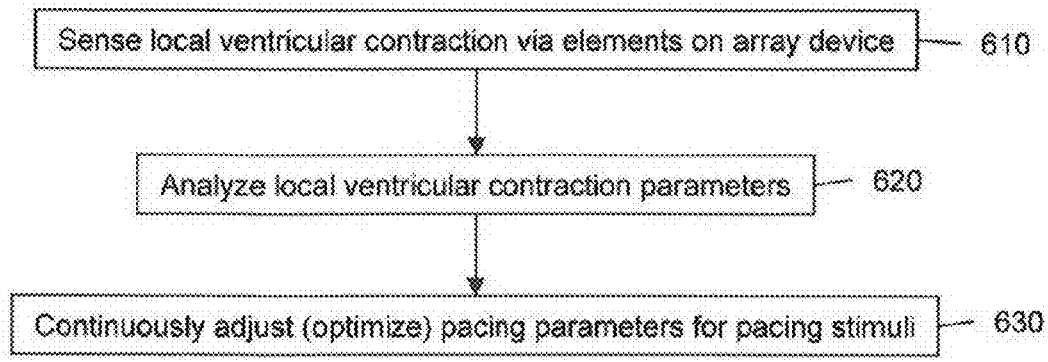

FIG. 64 is a flow chart of a continuously adjustable stimulation process using the array device.

Figure 65:
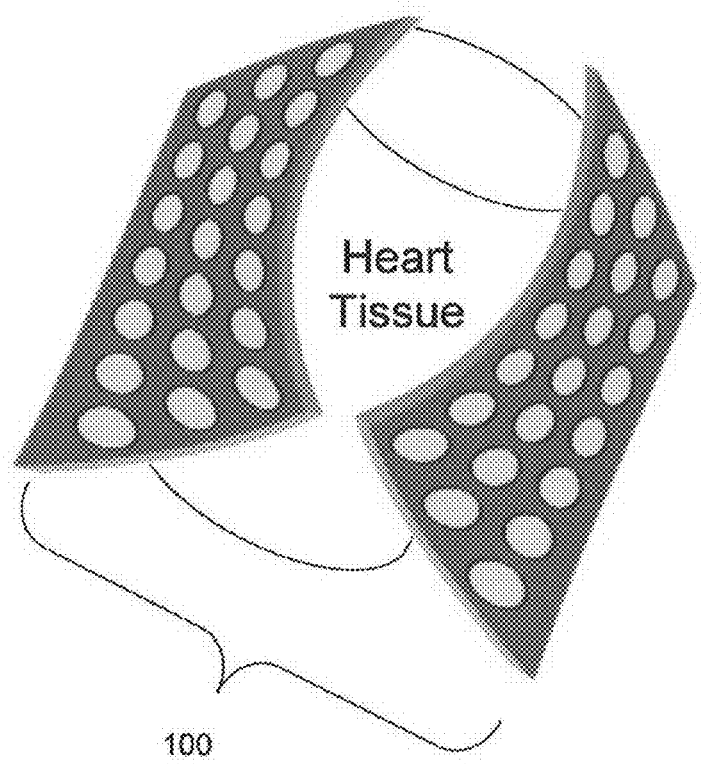

FIG. 65 is a diagram showing a configuration of the array device suitable for providing mechanical support to a portion of the heart.

Figure 66:
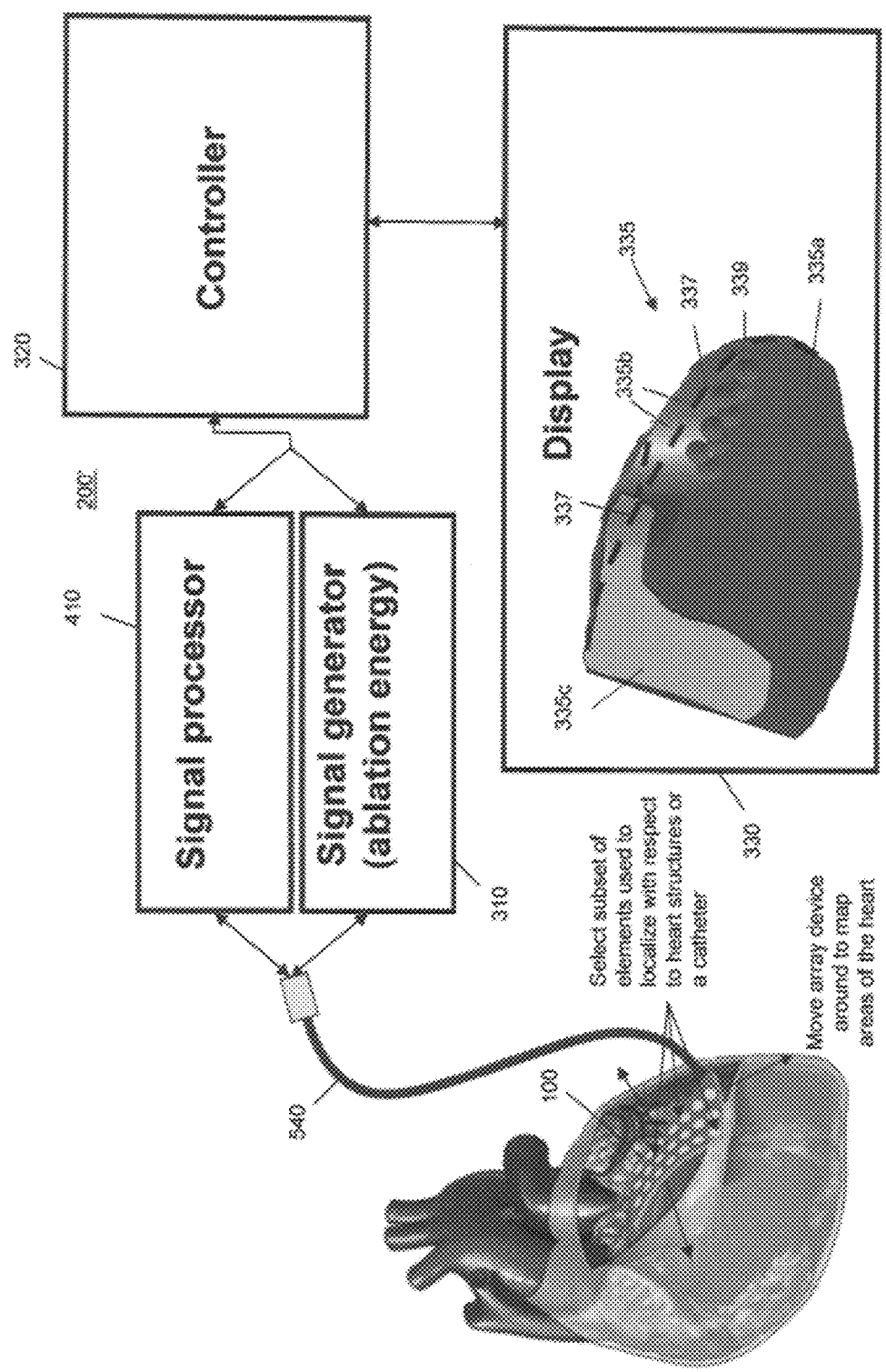

FIG. 66 is a block diagram showing the array device used in a cardiac mapping and ablation system configuration.

Figure 67A:
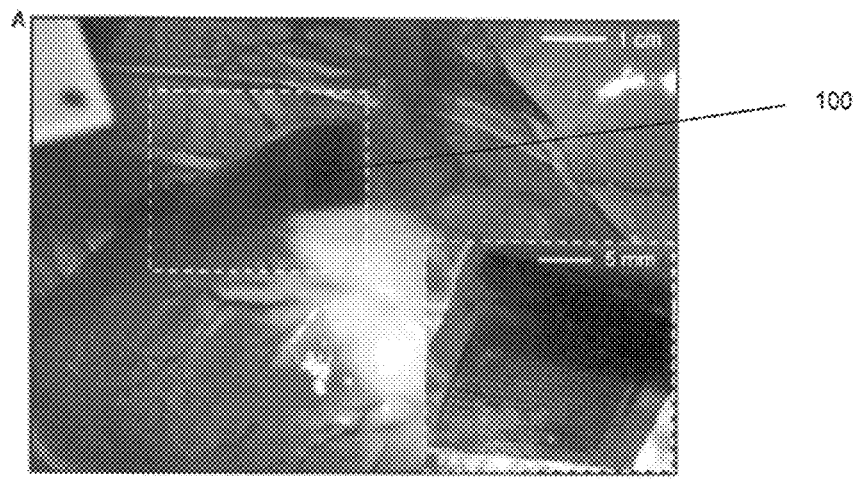
Figure 67B:
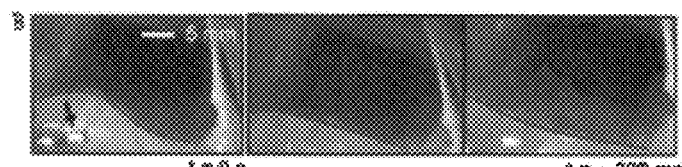
Figure 67C:
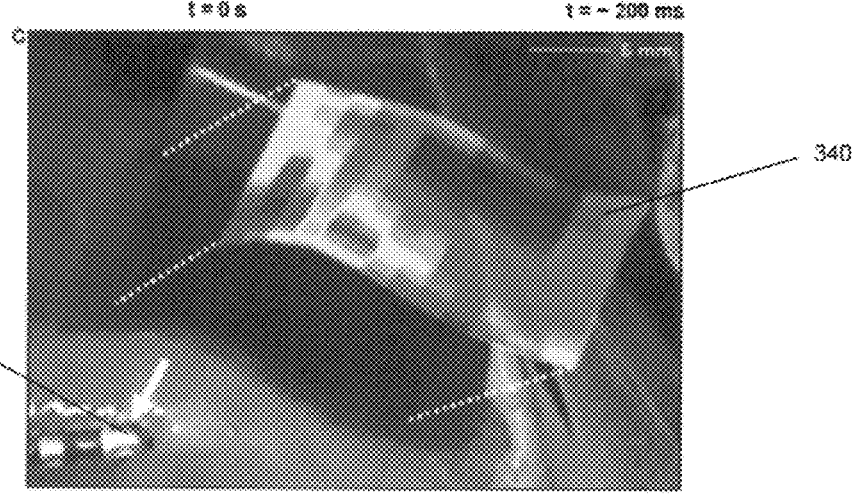

FIGS. 67A and 67B are diagrams showing photos of actual deployment of the array device on the surface of a heart. FIG. 67C is a diagram depicting the mapping data that can be obtained from the array device in the environment shown in FIGS. 67A and 67B.

Figure 68:
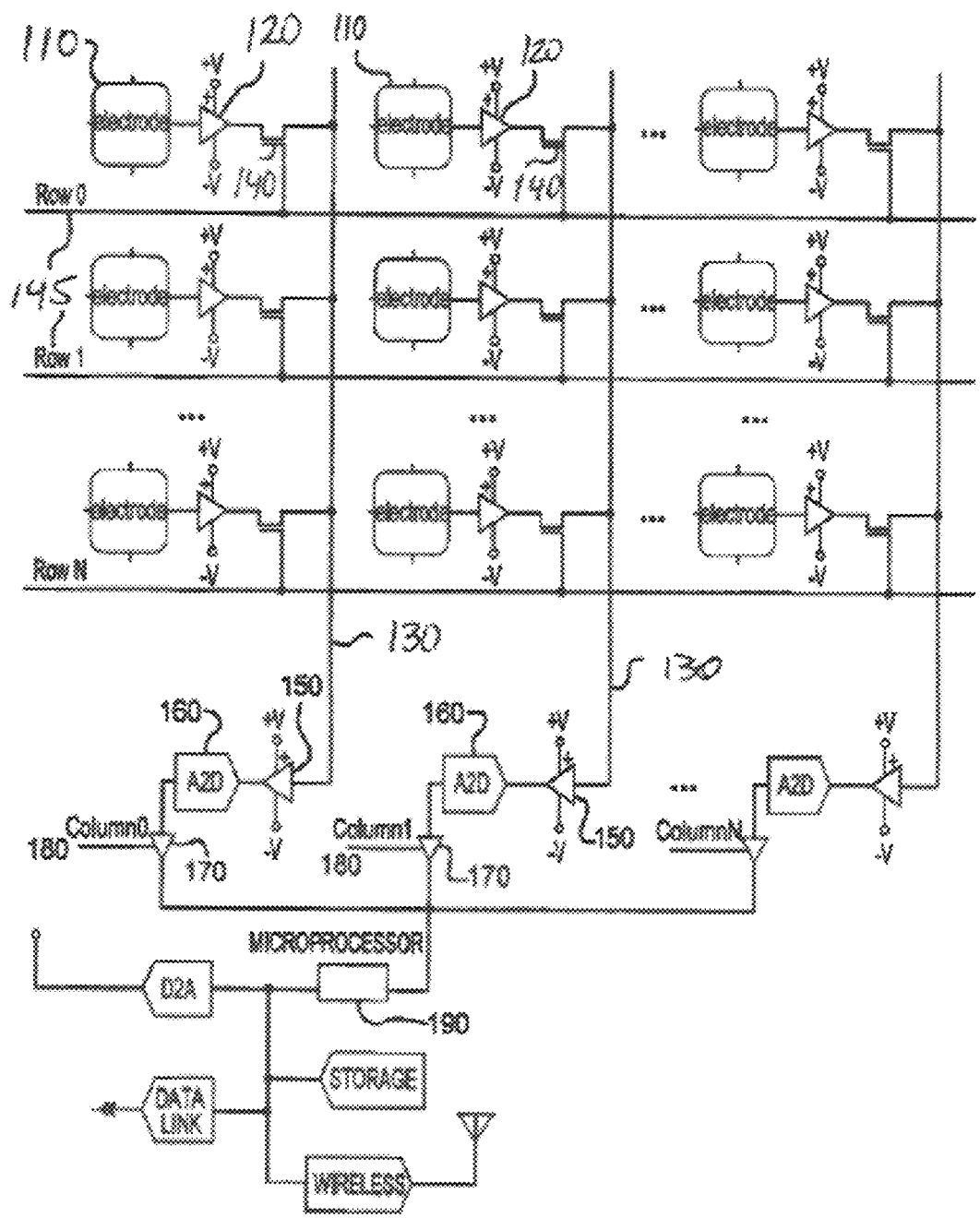

FIG. 68 illustrates an example of the array device 100.

Figure 69:
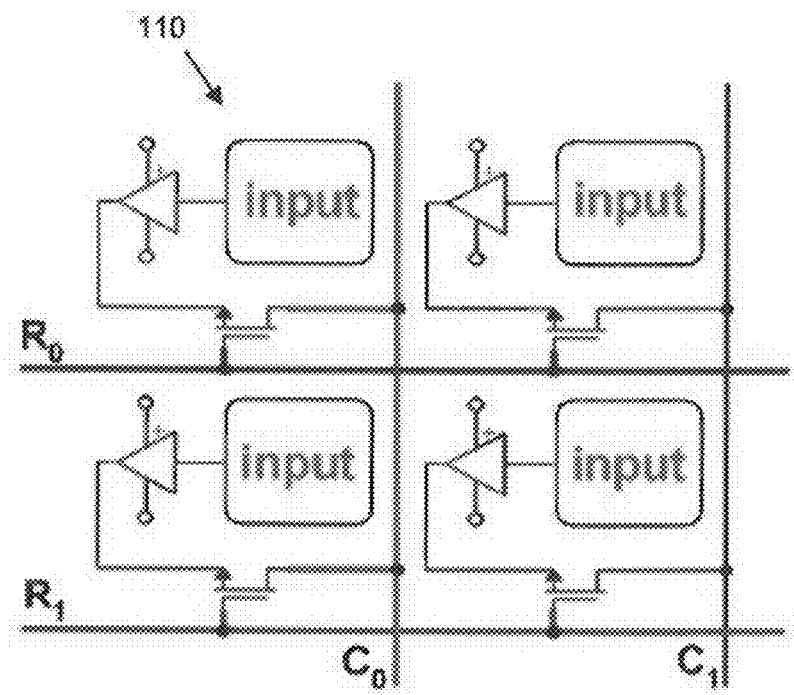

FIG. 69 is a schematic diagram that illustrates how unit cells connect to other unit cells to create a multiplexed signal output, for example for sensing from one of the elements 110 that is configured to operate as a sensor electrode.

Figure 70:
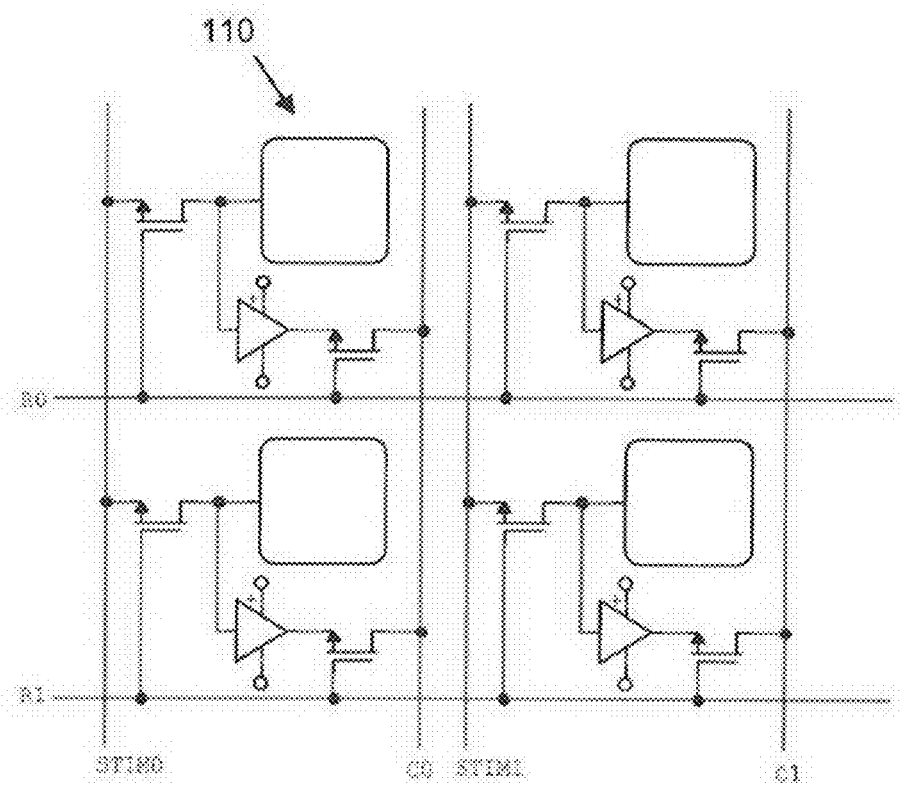

FIG. 70 is similar to FIG. 69, but adds stimulation control capability. In this example, the stimulation input lines STIM0, STIM1, etc., are provided.

Figure 71:
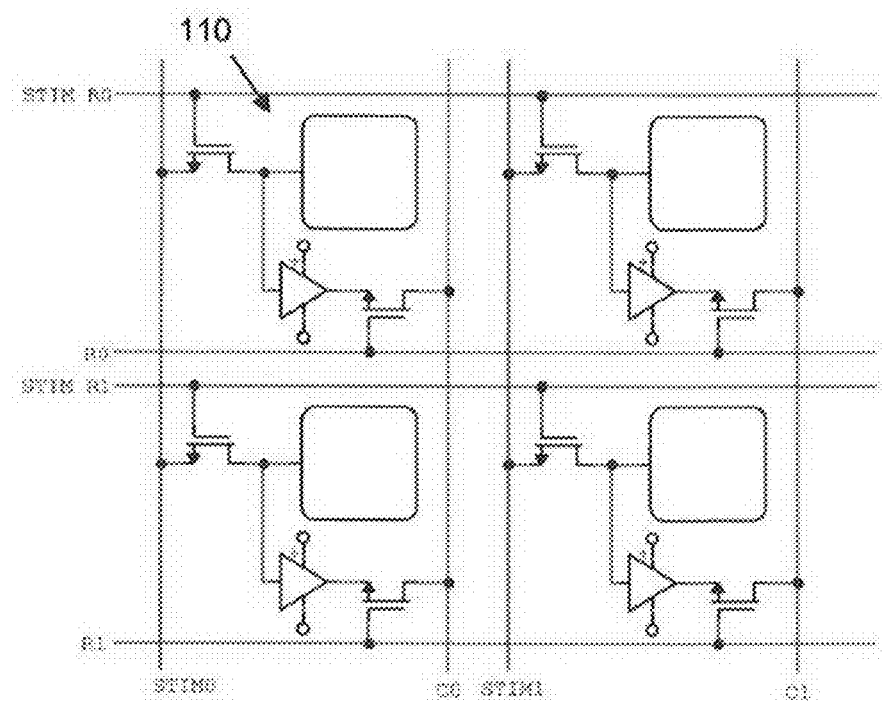

FIG. 71 illustrates a schematic diagram that is similar to FIG. 70, but uses independent stimulation row select signals.

Figure 72:
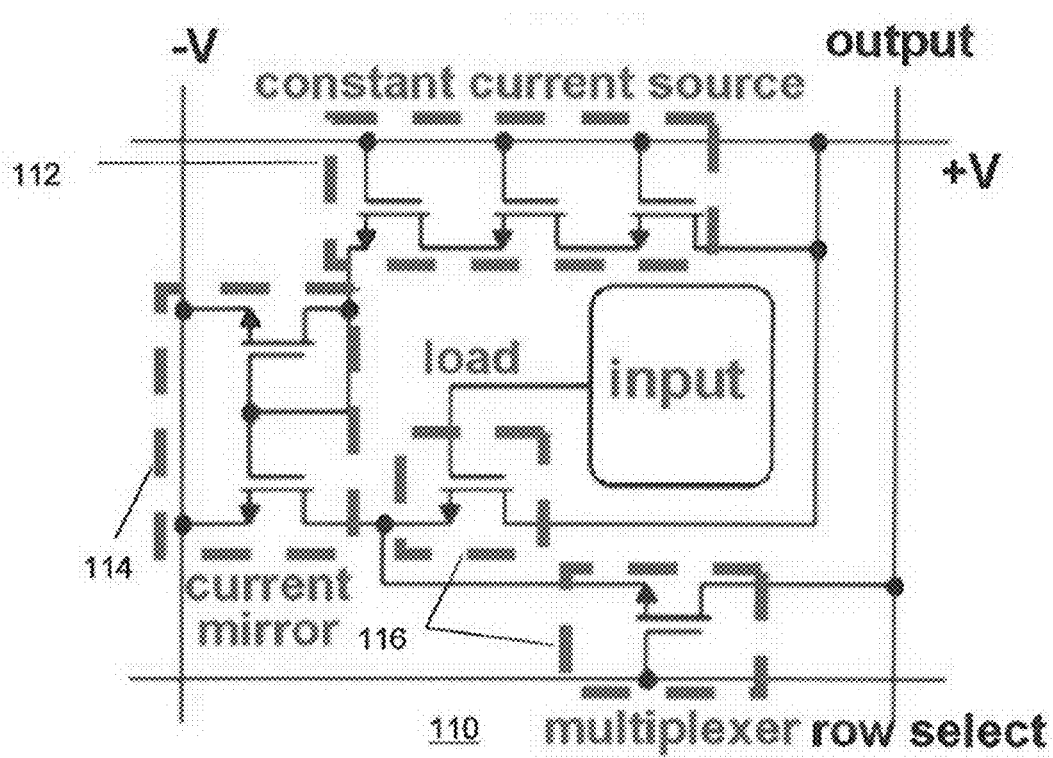

FIG. 72 shows an example transistor level schematic for an element 110 in a sensing configuration. There is a constant current source 112, a current mirror 114 and a multiplexer 116.

Figure 73:
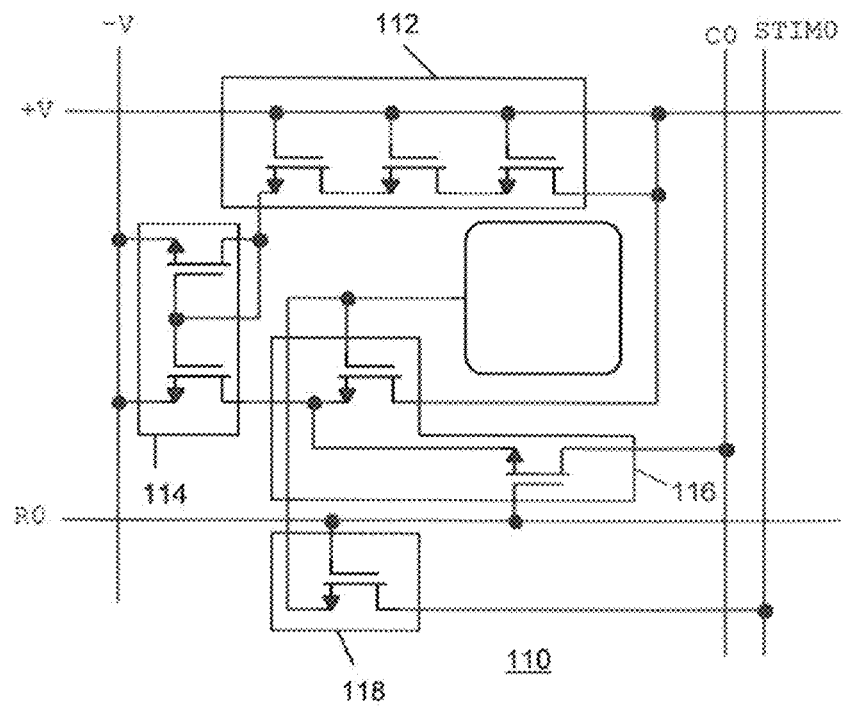

FIG. 73 shows an example transistor level layout for an element 110 with stimulation control according to that described above in connection with FIG. 70.

Figure 74:
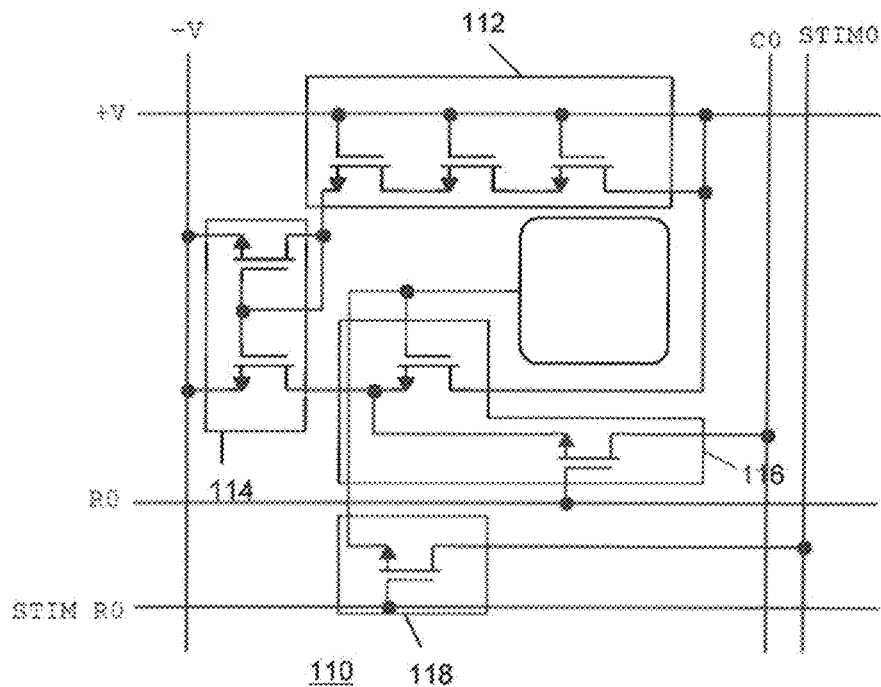

FIG. 74 shows an example transistor level layout for an element 110 with row independent selectable stimulation control according to that described above in connection with FIG. 71.

Figure 75:
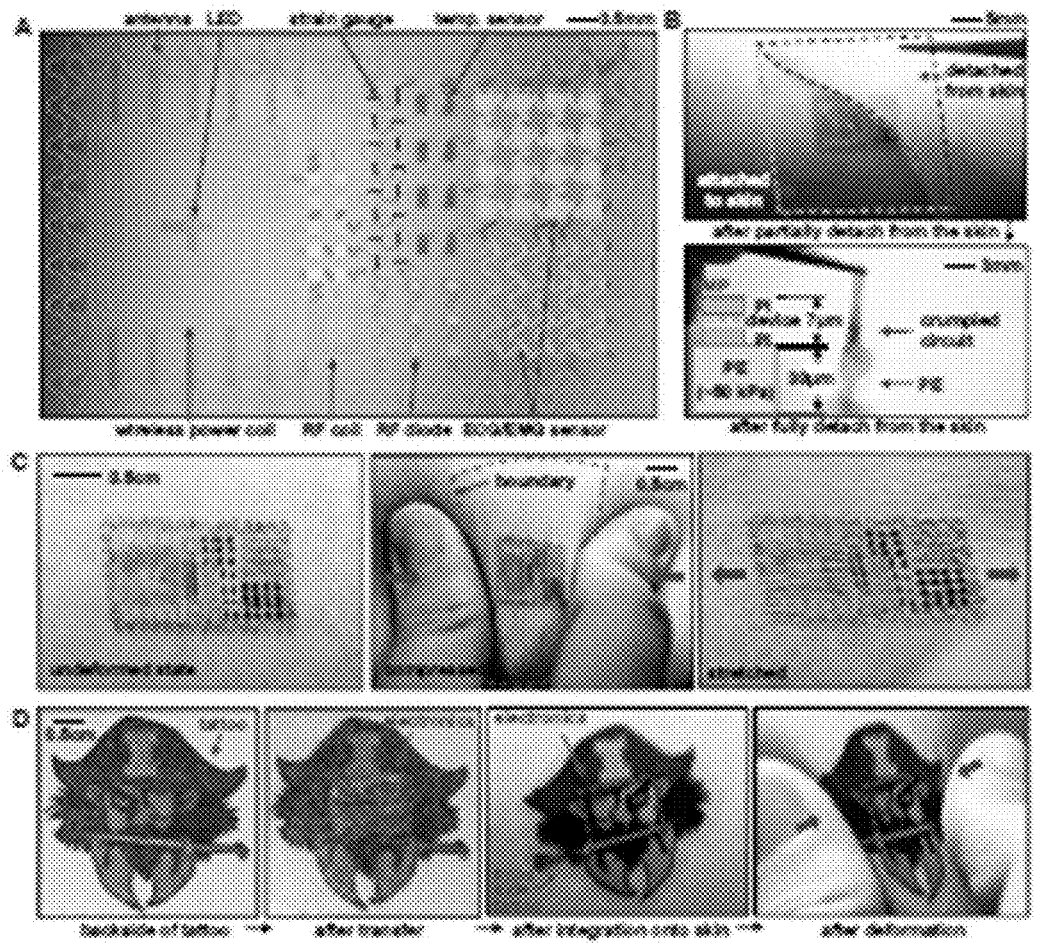

FIG. 75 provides: (A) Image of a multifunctional, 'skin-like' electronic system that serves as a demonstration platform for electrophysiological and temperature sensors, strain gauges, LEDs, wireless power coils, RF inductors, capacitors, diodes and oscillators, and a wireless transmit/receive antenna. Mounting this device on a sacrificial, water-soluble film of PVA, placing the entire structure against the skin, with electronics facing down, dissolving the PVA and then drying to remove the remaining water leaves the device conformally attached to the skin, in an overall procedure similar to that used for a temporary transfer tattoo. The elastic moduli, thickness and other physical properties of the device match the epidermis; we refer to the technology as an epidermal electronic system (EES). Adequate adhesion is possible through van der Waals forces alone, in a format that imposes negligible mass or mechanical loading effects on the skin; (B) EES partially (top frame) and fully (bottom frame) peeled away from the skin. The inset shows a representative cross-sectional illustration of the structure, with the neutral mechanical plane (NMP) defined by a red dashed line; (C) Multifunctional EES on skin: undeformed (first frame), compressed (middle frame) and stretched (right frame); (D) A commercial temporary transfer tattoo provides an alternative to PE/PVA for the substrate; in this case, the system includes an adhesive to improve bonding to the skin. Images of the backside of a tattoo (first frame), electronics integrated onto this surface (second frame) and attached to skin with electronics facing down in undeformed (third frame) and compressed (fourth frame) states.

Figure 76:
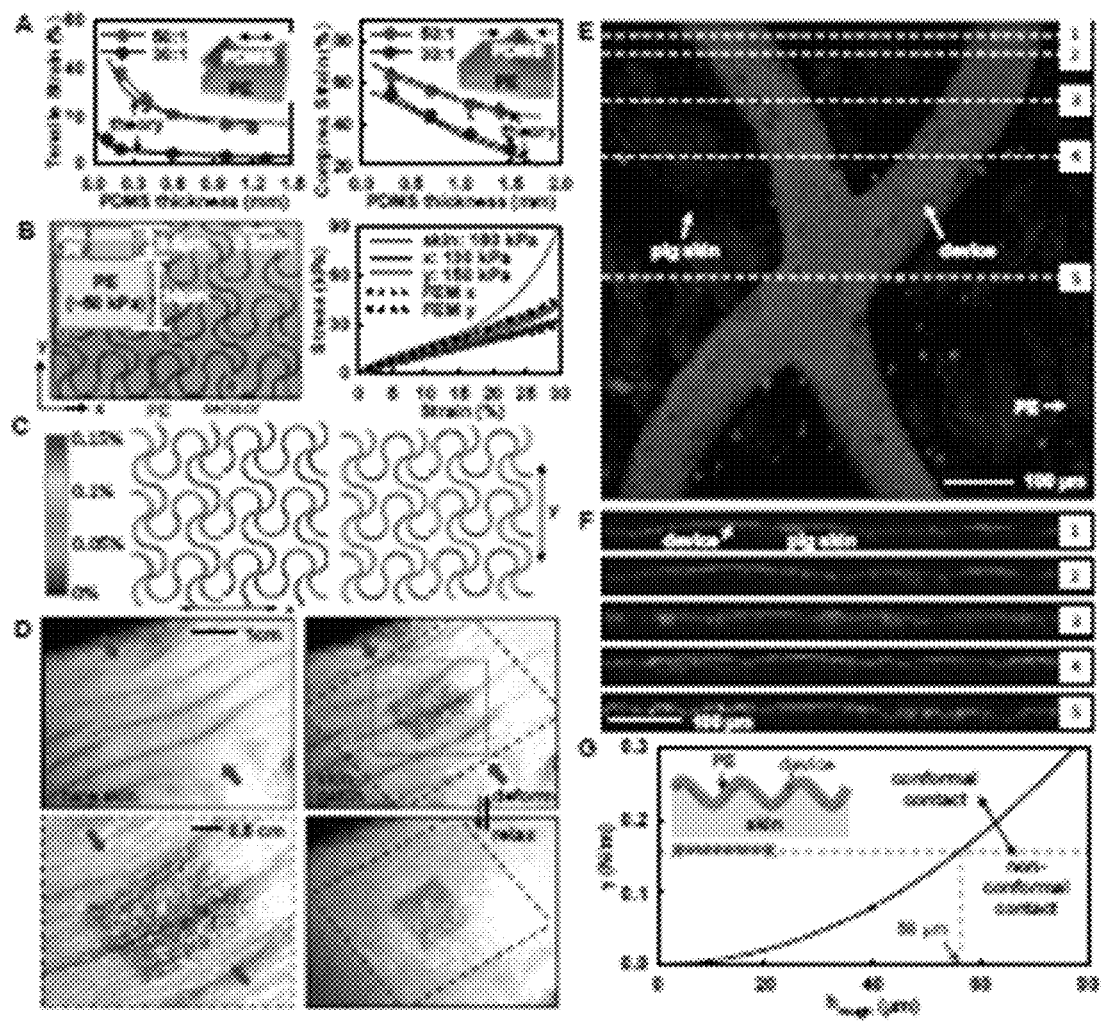

FIG. 76 provides: (A) Plots of critical tensile (left frame) and compressive (right frame) strains for delamination of a test structure consisting of films of PDMS on substrates of PE, designed to model the EES/skin system. Data for formulations of PDMS with two different moduli are shown (red: 19 kPa; blue: 145 kPa). The results indicate that the critical strains increase as the PDMS thickness and modulus decrease, consistent with modeling results (lines). (B) Optical micrograph of an EES with filamentary serpentine (FS) design (left frame). The plot in the right frame shows the stress-strain data from uniaxial tensile measurements on an FS-EES, for two orthogonal directions. Data collected from a sample of pig skin are also presented. The FS-EES has modulus comparable to or less than the skin, over the range of strains shown here. The dashed lines correspond to calculations by finite element modeling. (C) Contour plots of strain distributions computed by FEM, for 30% tensile strains along x (left) and y (right). The results indicate maximum principle strains of less than 0.2% in the FS structures. (D) Skin of the forehead before (top left frame) and after integration of a representative FS-EES, at various magnifications and states of deformation. The dashed blue boxes in the right frames highlight the outer boundary of the device. The red arrows indicate the direction of compressive strains, generated by contraction of facial muscles. The red dashed box in the upper right frame corresponds to the field of view of the image in the lower left. (E) Confocal microscope image (top view) of the contacting interface between an FS-EES and a sample of pig skin. The FS structure and the skin are dyed with red and blue fluorophores, respectively. (F) Cross-sectional confocal images, at locations corresponding to the numbered, white dashed lines shown in the top view frame above. The results indicate intimate, conformal contact, to within the resolution of the microscope. (G) Mechanics analysis of the condition for conformal contact as a function of tattoo-skin adhesion and skin roughness.

Figure 77:
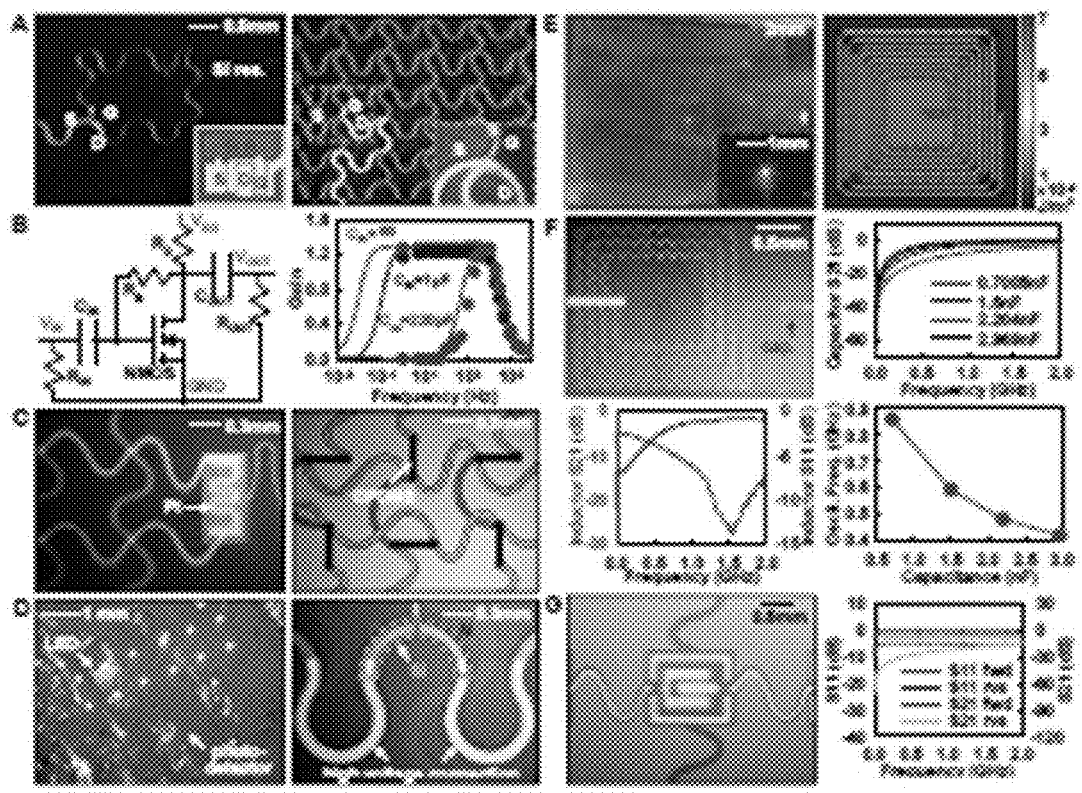

FIG. 77 provides: (A) Optical micrographs of an active electrophysiological (EP) sensor with local amplification, as part of an FS-EES. The left frame shows the source, drain and gate of a silicon MOSFET and a silicon feedback resistor before connection to sensor electrodes, all in FS layouts. The right image shows the final device, after metallization for the interconnects and sensor electrodes, with magnified view (inset). (B) Circuit diagram for the amplified EP sensor shown above (left frame). The right frame shows measured and simulated frequency response for different input capacitance ($C_{IN}=\infty$, 1 µF, 220 pF). (C) Optical micrograph of a temperature sensor that uses a platinum resistor with FS interconnects (left frame) and a strain gauge that uses electrically conductive silicone (CPDMS; right frame). (D) Image of an array of microscale AlInGaP LEDs and photodetectors, in an interconnected array integrated on skin, under compressive deformation, (left frame) and of a FS silicon solar cell (right frame). (E) Image of a FS wireless coil, connected to a microscale AlGaN LED, powered by inductive coupling to a separate transmission coil (not in the field of view). The right frame shows electromagnetic simulations of the behavior of the FS coil. (F) Optical micrograph of an interconnected pair of FS inductors and capacitors designed for RF operation (left top frame). The plot in the upper right shows the value of S21 measured on a set of FS capacitors as a function of frequency. The plot in the lower left frame shows the frequency dependence of S21 and S11 for an FS inductor. The graph on the bottom right shows resonant frequencies for LC oscillators built with different FS capacitors. (G) Image of a silicon RF diode (left frame) and the frequency dependence of S11 and S21 (right frame).

Figure 78:
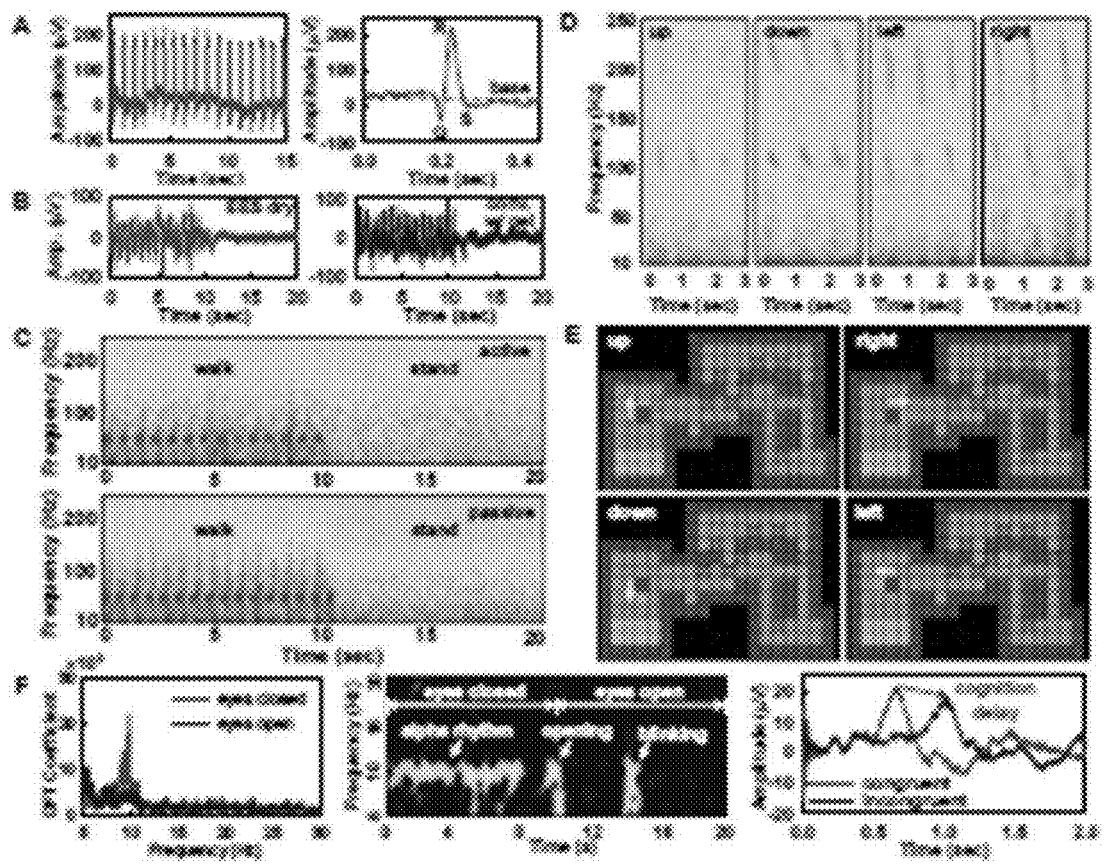

FIG. 78 provides: (A) ECG signals measured with an EES integrated on the chest using an active EP sensor (left frame), and magnified view of data corresponding to a single heartbeat (right frame). (B) The left frame shows the results of EMG measurement using a similar device, mounted on the right leg during simulated walking (from 0 sec to 10 s) and standing (from 10 s to 20 s). The right frame shows similar data recorded using a conventional EMG sensor based on a tin electrode coupled to the skin with a conductive gel and affixed using adhesive tape. (C) Frequency spectral (i.e. spectrogram) representation of the data in (B), for each electrode type. (D) EMG spectrograms measured using an EES mounted on the neck during vocalization of four different words: "up", "down", "left" and "right". (E) Simulated video game control using pattern recognition algorithms applied to EMG data recorded with an EES on the neck. The yellow arrows indicate the direction of motion of the player icon from an initial position (red) to a final one (green). (F) The left frame shows discrete Fourier transform (DFT) coefficient associated with EES recordings of EEG from the forehead, showing expected alpha rhythms at ~10 Hz when the eyes are closed. (See below for DFT definition.) The center frame shows a spectrogram representation of the alpha rhythm measurement. The first and next 10 seconds correspond to periods when the eyes were closed and open, respectively. The right frame shows results that demonstrate expected Stroop effects in data measured with the same type of EES used for the alpha rhythms.

Figure 79:
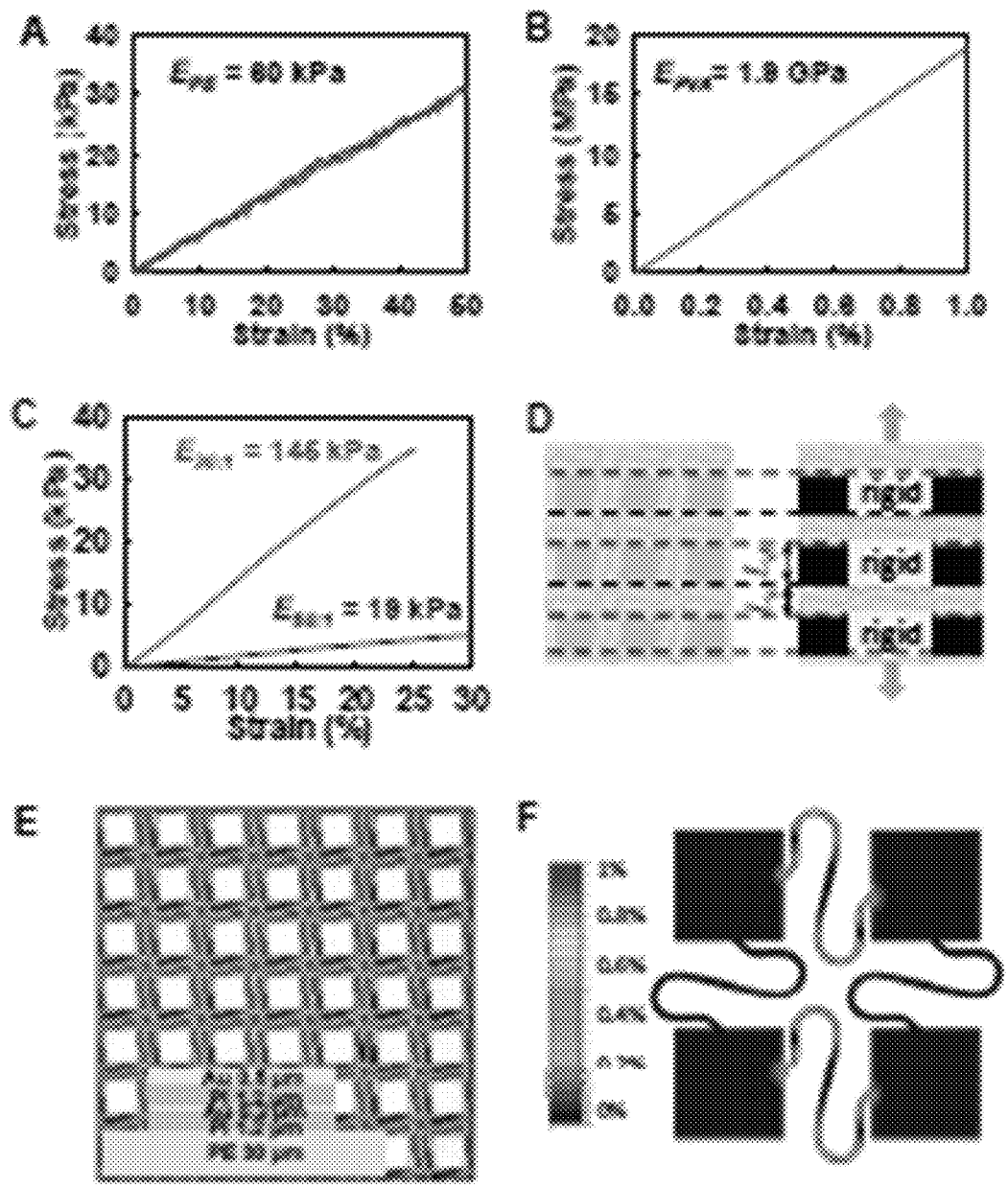

FIG. 79 provides: (A) Stress-strain curve for a 30 m thick free-standing PE film. The Young's modulus is 60 kPa. (B) Stress-strain curve for PVA. The Young's modulus is 1.9 GPa. (C) Stress-strain curve for 30:1 and 50:1 PDMS, with Young's moduli of 145 kPa and 19 kPa respectively. (D) Schematic illustration for a device island with size $L_d$ and a serpentine span $L_s$. (E) Top view and cross-sectional schematic illustrations of an island-plus-serpentine sample. (F) Contour plot of strain in an island-plus-serpentine sample after stretching by 30%, computed using FEM.

Figure 80:
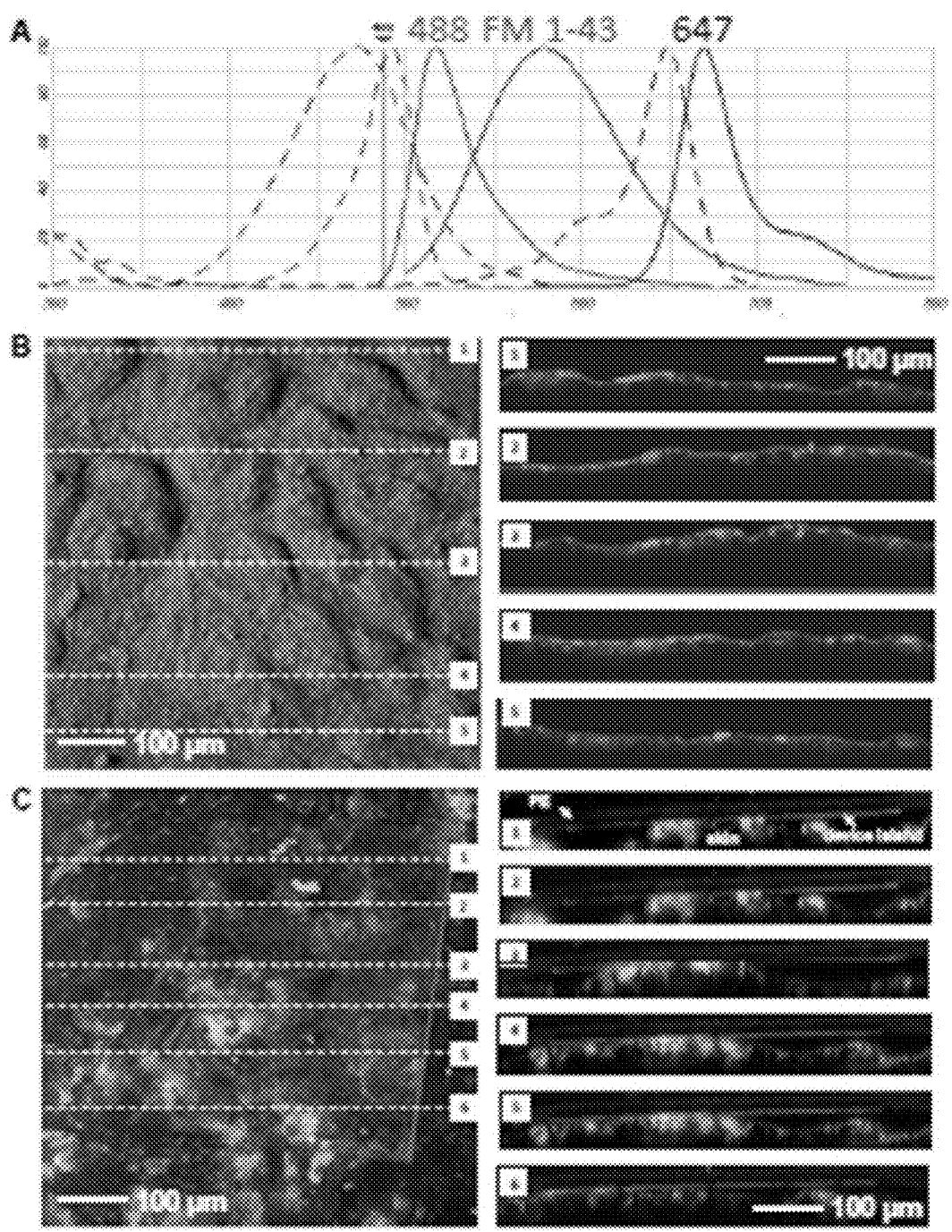

FIG. 80 provides: (A) Excitation and emission spectrum of fluorescent dyes used for confocal microscopy. Alexa Fluor 488 is used to stain PE substrate and Alexa Fluor 647 is used to stain polyimide, which is patterned into the layout of electrodes. Pig skin is stained by FM 1-43, which labels cell membrane. (B) Top and cross-sectional view of bare pig skin. (C) Top and cross-sectional view of EES with island mounted on pig skin.

Figure 81:
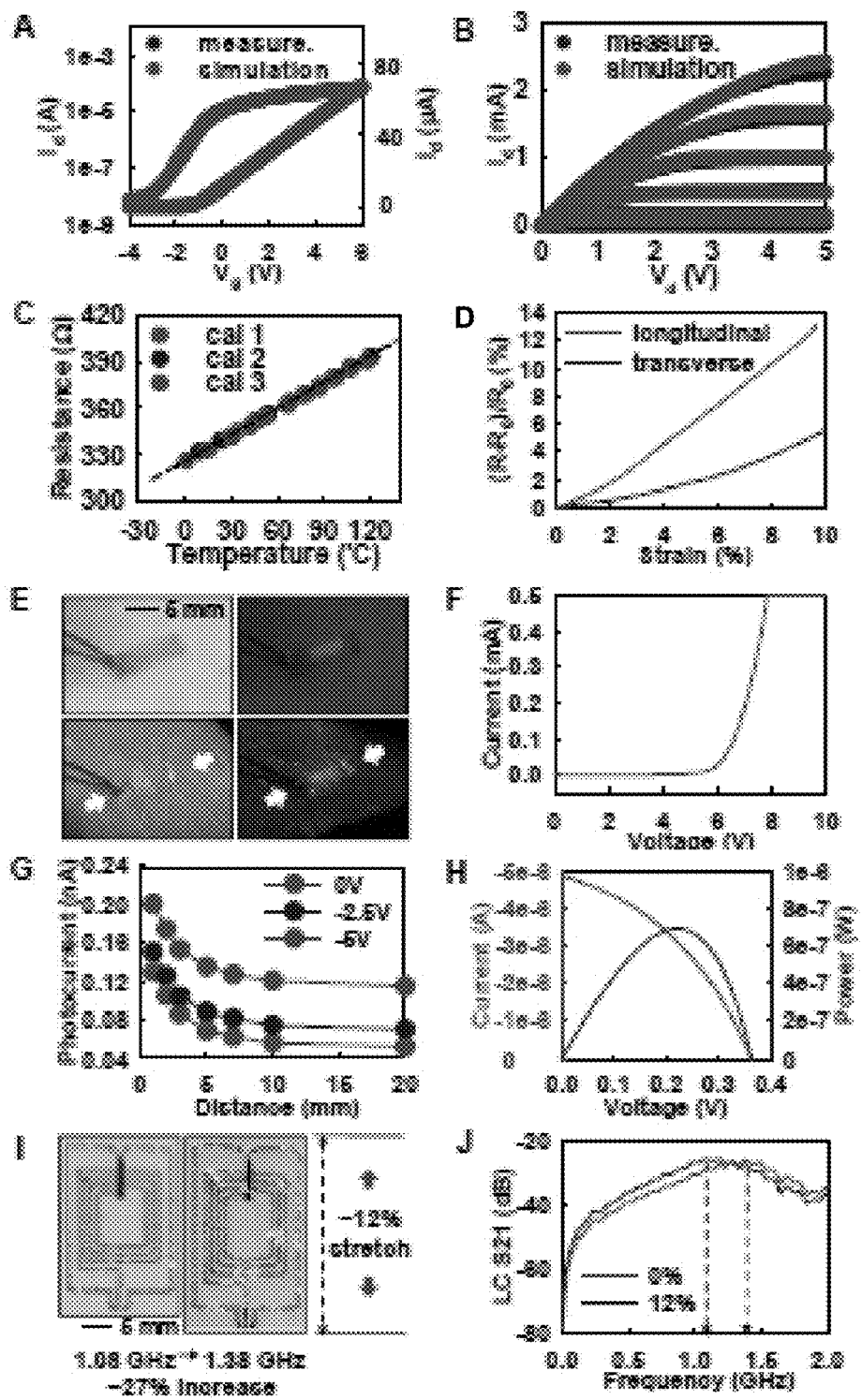

FIG. 81 provides: (A) Transfer curve and (B) IV curve of an Si MOSFET in FS geometry. (C) Calibration curve of a temperature sensor. (D) Percentage change in resistance of the strain gauge as a function of uniaxial tensile strain. Gauge factors for the longitudinal and transverse strain gauges are 1.3 and 0.5 respectively. (E) Proximity sensor and optical measurement system on skin using a combined LED-photodetector array with forward and reverse biases before (top frame) and after (bottom frame) deforming the skin with (left frame) and without (right frame) external illumination. (F) Current-voltage characteristics of a single LED. (G) Measured photocurrent from reverse biased diodes at different distances between the sensor and the external object. (H) Current and power of a FS Si photovoltaic cell at different voltages. (I) Images of an LC (inductor-capacitor) oscillator at 0% (left frame) and ~12% (right frame) tensile strain. (J) S21 of an LC oscillator as a function of frequency. The resonant frequency changes from 1.08 GHz (0% strain) to 1.38 GHz (~12% strain) due to tensile deformation.

Figure 82:
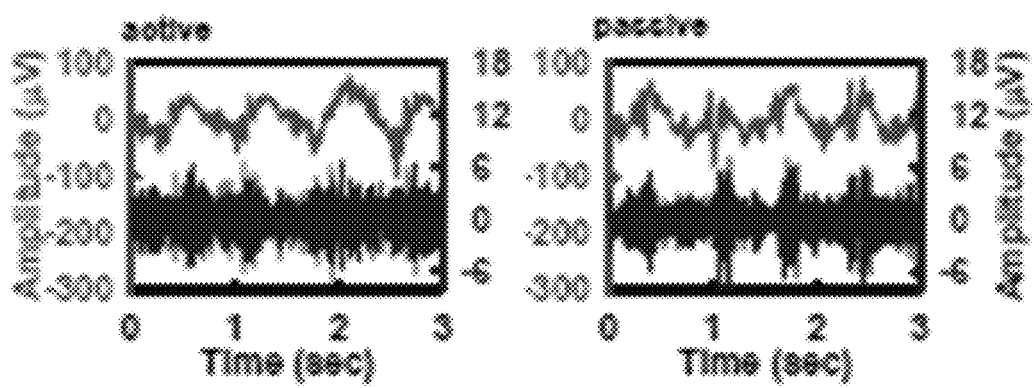

FIG. 82 provides a magnified view of the EMG signal of FIG. 78 (B). Red and blue plots correspond to raw and high pass filtered data, respectively.

Figure 83:
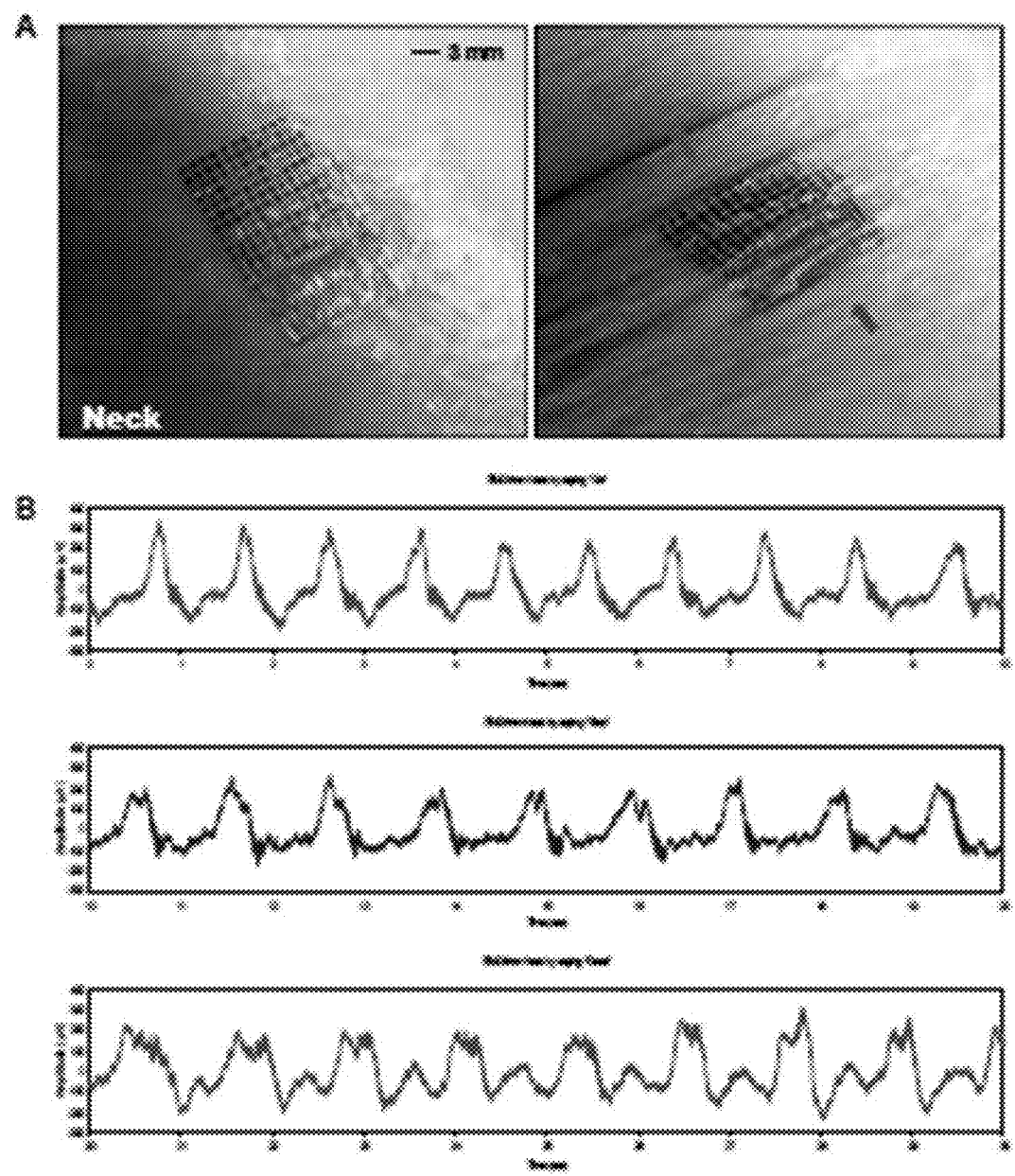

FIG. 83 provides: (A) Images of an active EES-based EMG sensor on the neck without (left frame) and with (right frame) skin deformation. (B) Raw recordings from neck using a similar sensor for different words. "Go" (top frame), "Stop" (middle frame) and "Great" (bottom frame).

Figure 84:
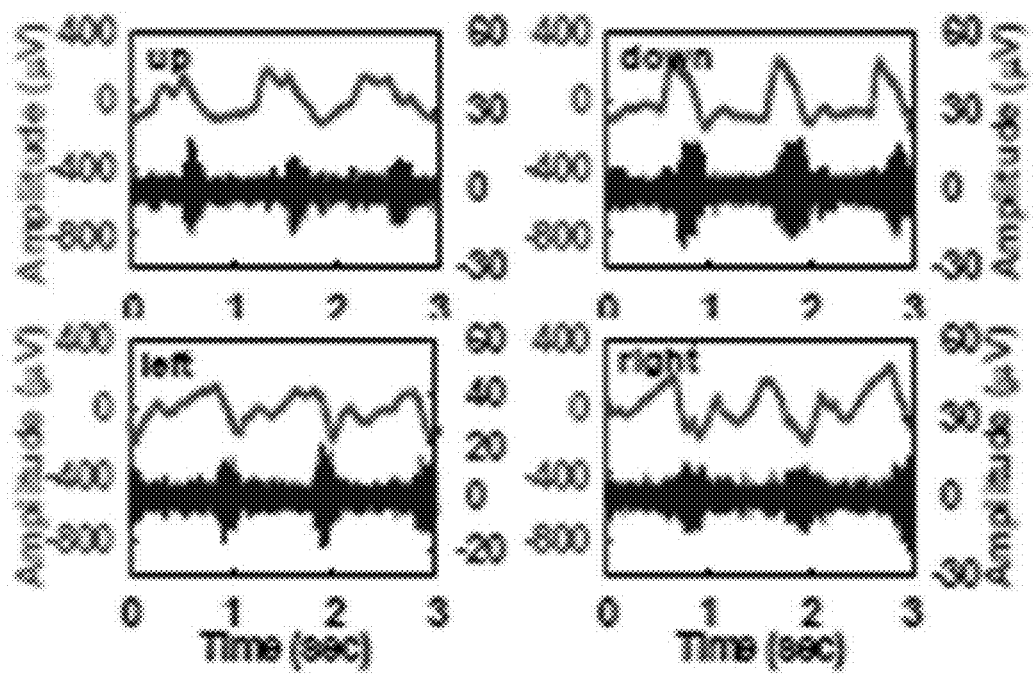

FIG. 84 provides a plot showing an EES EMG measurement from the neck for four different words, "up", "down", "left" and "right". Red and blue plots correspond to raw and high pass filtered data, respectively.

Figure 85:
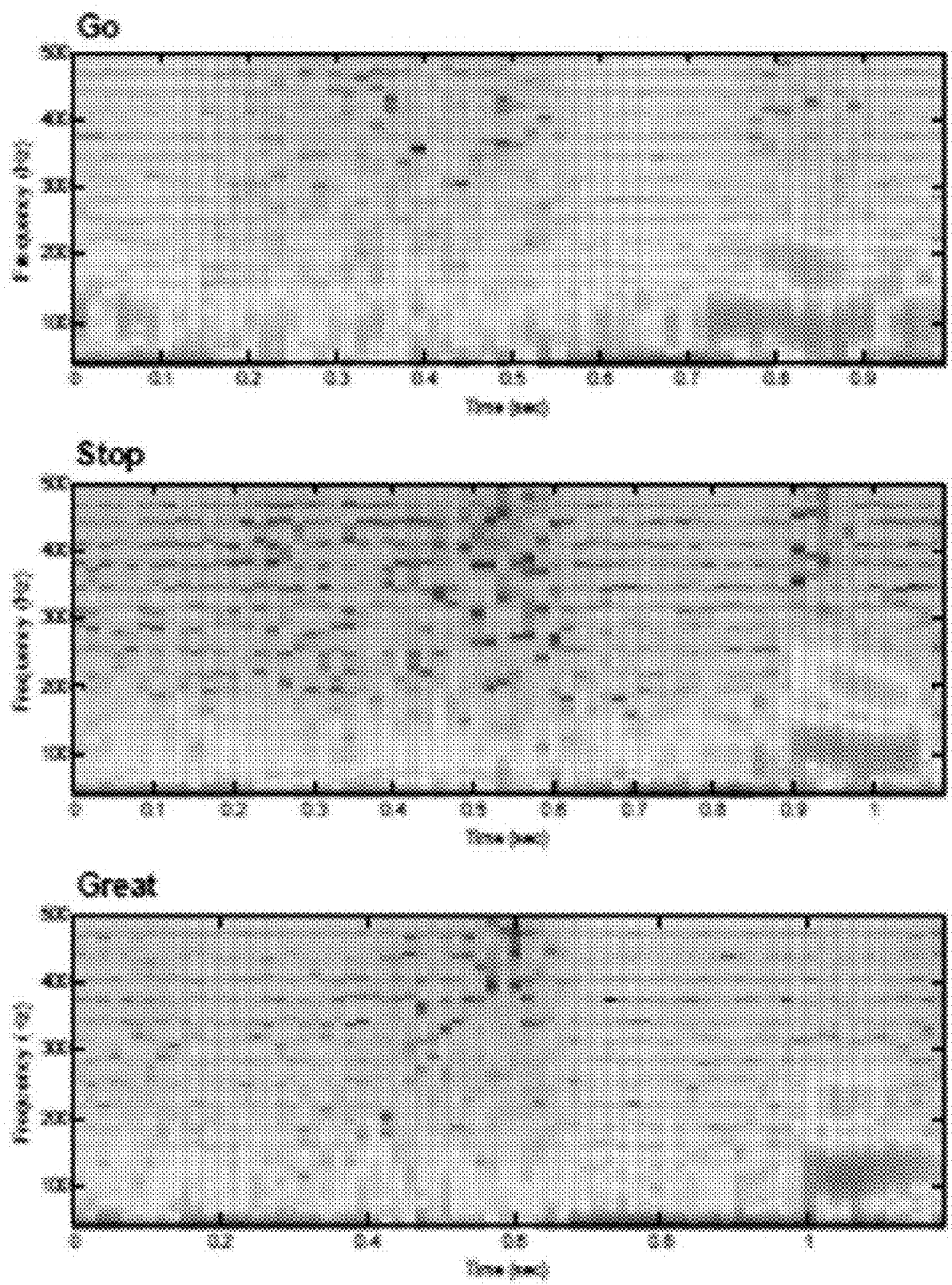

FIG. 85 provides spectrograms of EES EMG measurements from the neck for four different words, "Go" (top frame), "Stop" (middle frame) and "Great" (bottom frame).

Figure 86:
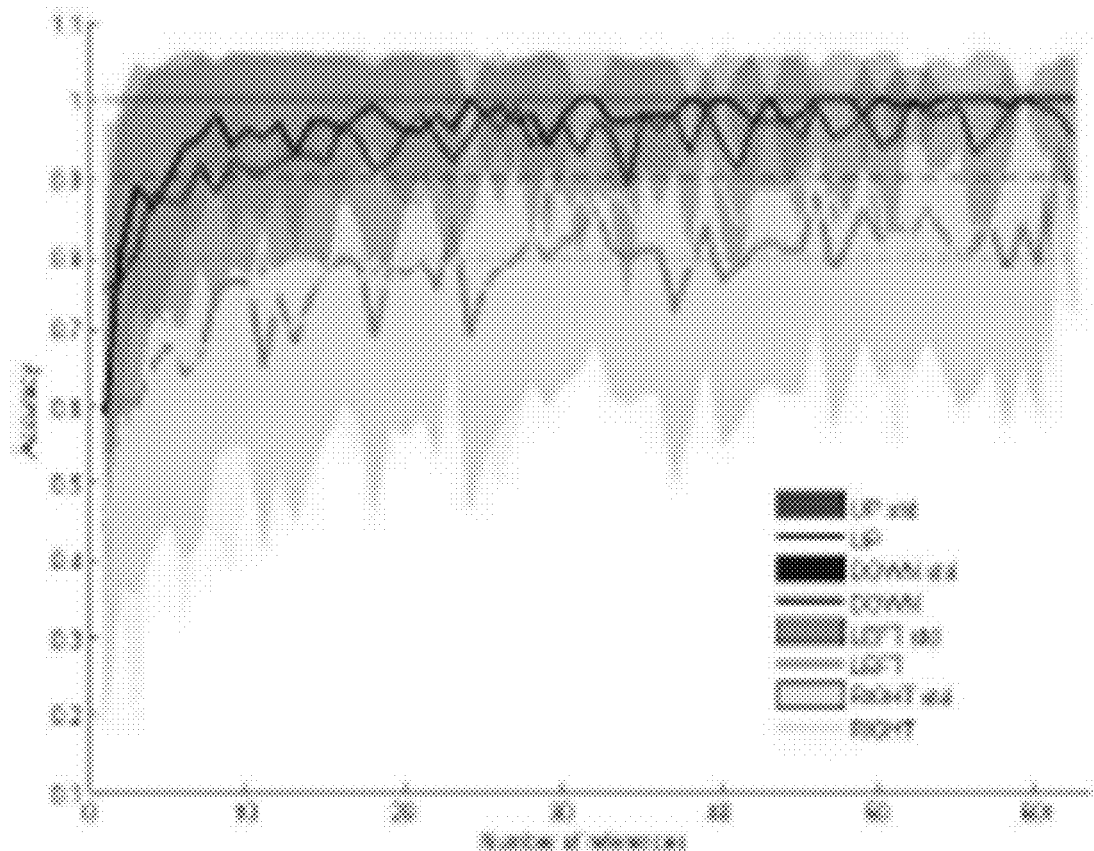

FIG. 86 provides plots showing averaged classification accuracy versus the number of reference feature vectors available for classifying each direction. Shaded areas indicate one standard deviation of the data.

Figure 87:
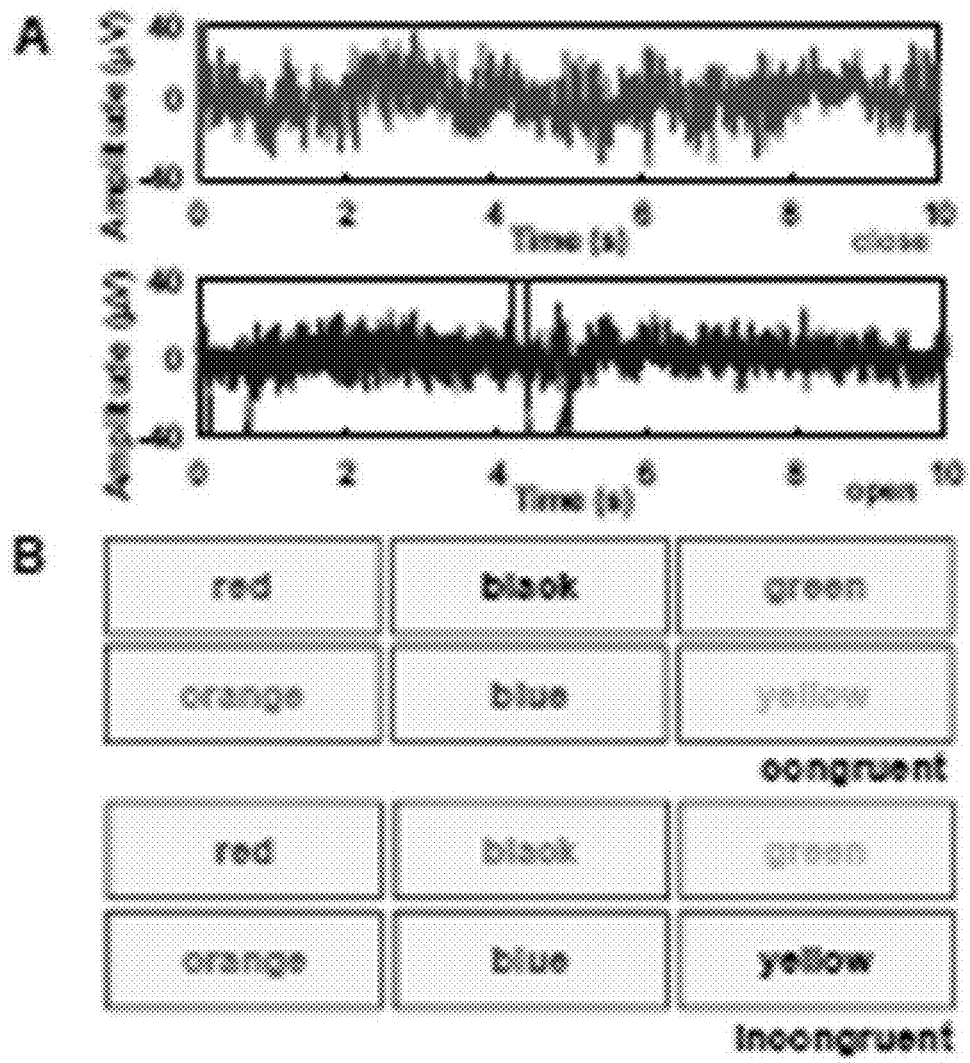

FIG. 87 provides: (A) Recorded EEG data using passive EES sensor while eyes closed (top frame) and eyes open (bottom frame). (B) Experiment setup for Stroop test. When the target letter matches with its color (congruent case) the response speed is faster than the unmatched (incongruent) case.

Figure 88:
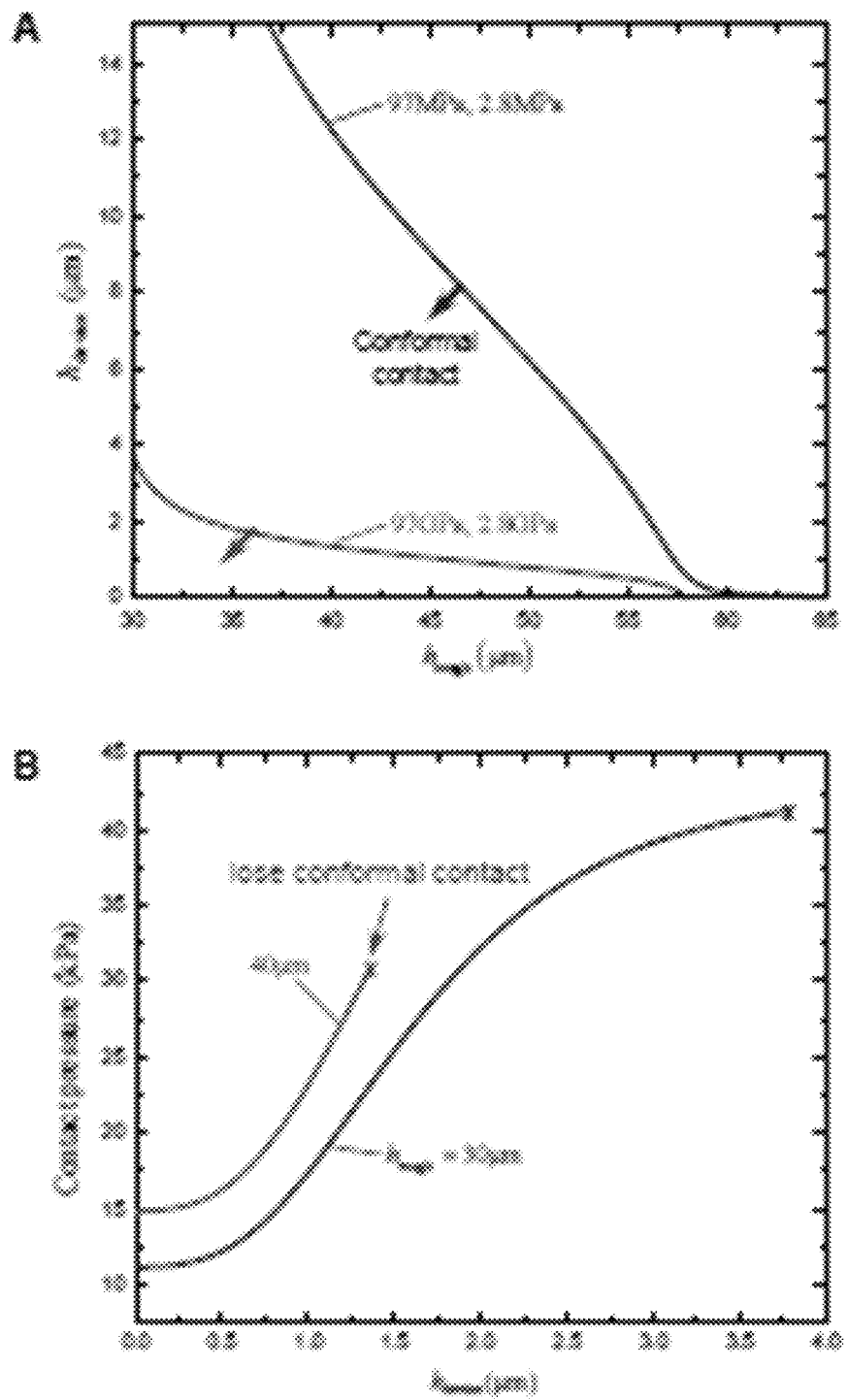

FIG. 88 provides: (A) Conformal contact requirement for filamentary serpentine EES with devices of different thickness and modulus. (B) The contact pressure between the filamentary serpentine EES and skin of different roughnesses.

Figure 89:
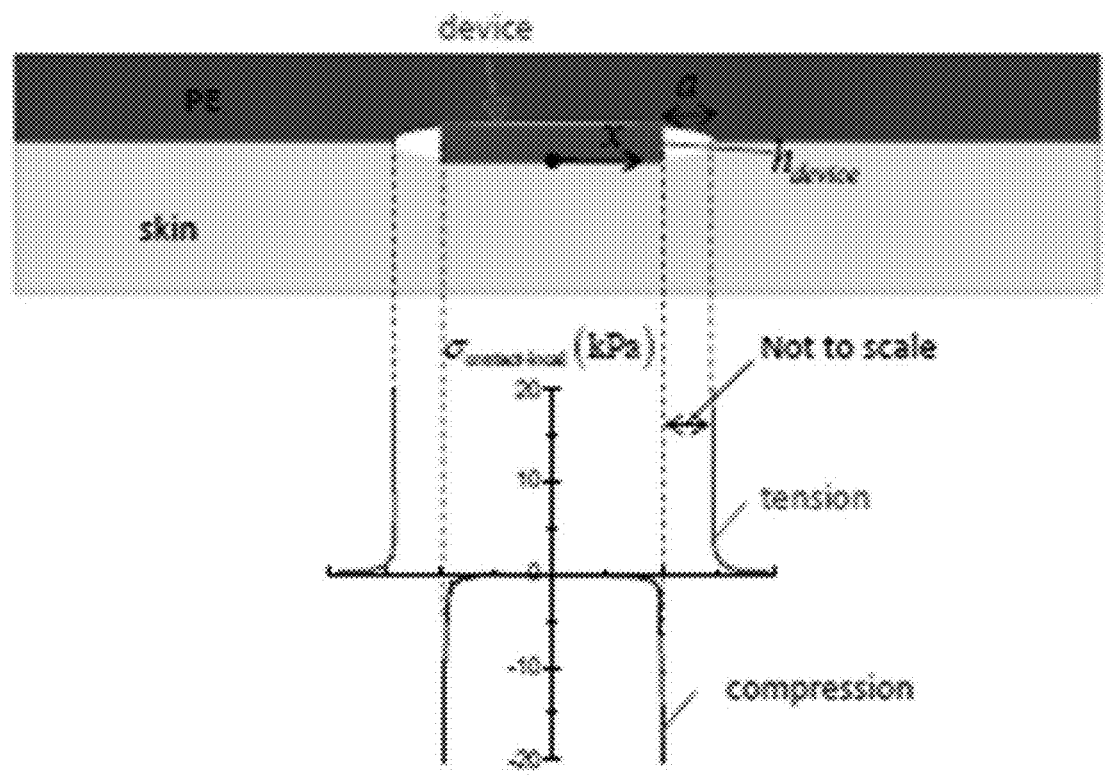

FIG. 89 provides a schematic cross-sectional view of EES at the interface between skin and PE (top) and local stress distribution along the FS-EES/skin interface (bottom).

Figure 90:
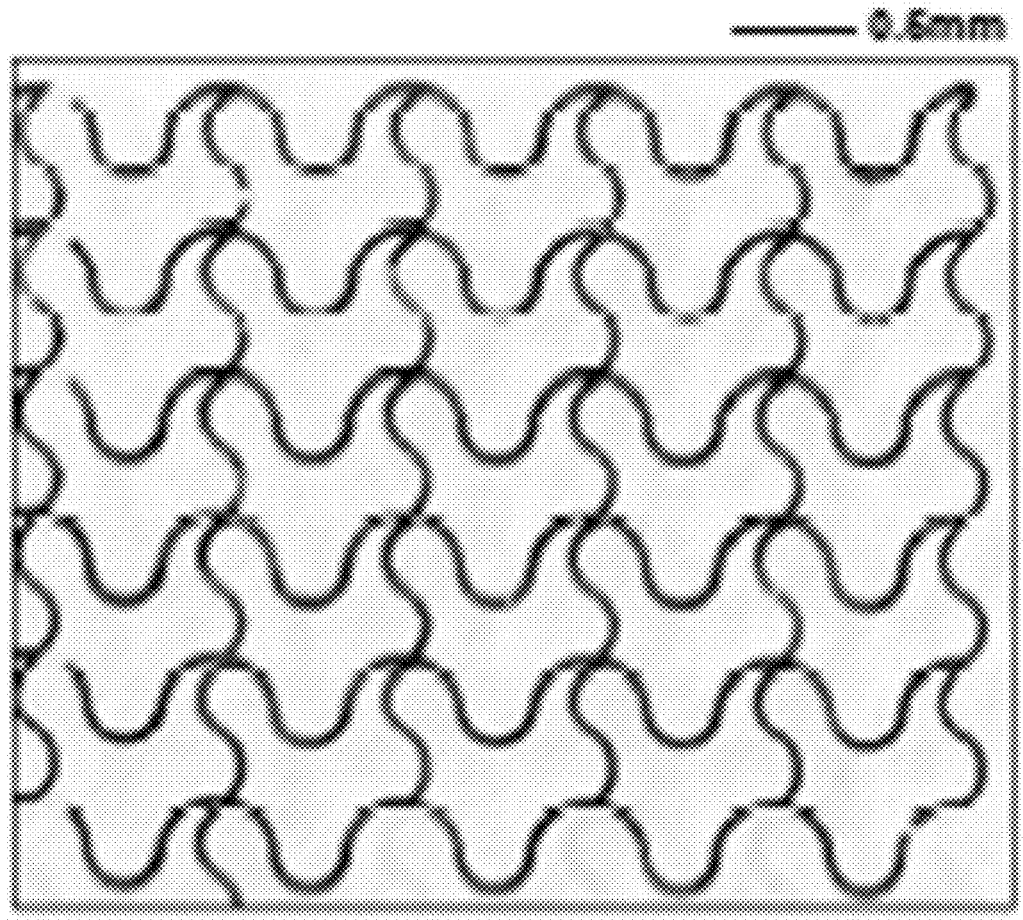

FIG. 90 provides an image of an FS-EES EP sensor on PE/PVA substrate.

Figure 91:
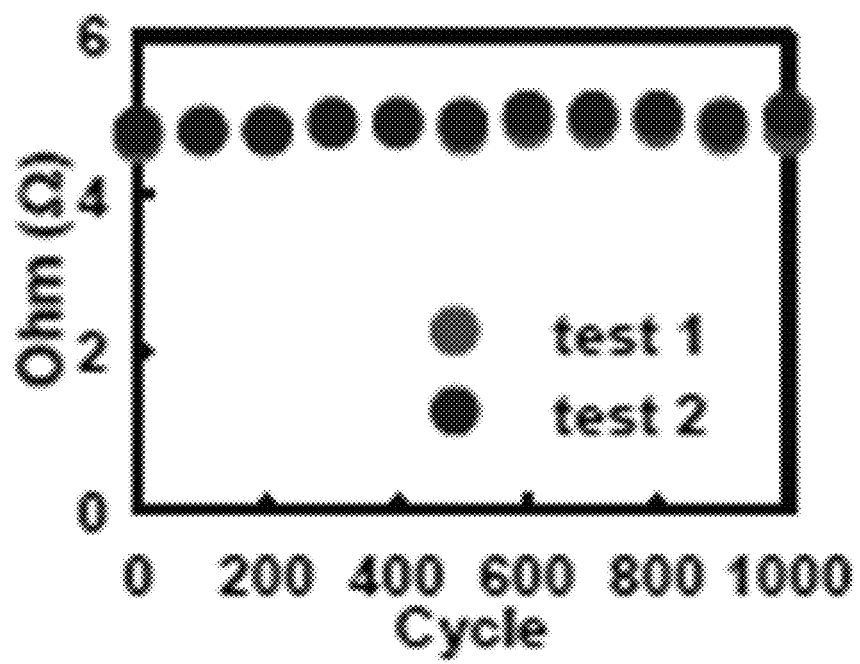

FIG. 91 provides fatigue test results for an FS-EES device under repetitive 20% tensile stretching.

FIG. 92. Principle of hydration sensor based on impedance measurement.

FIG. 93. Schematic of the differential hydration sensor, (a) sensor layout and (b) equivalent model.

Figure 94:
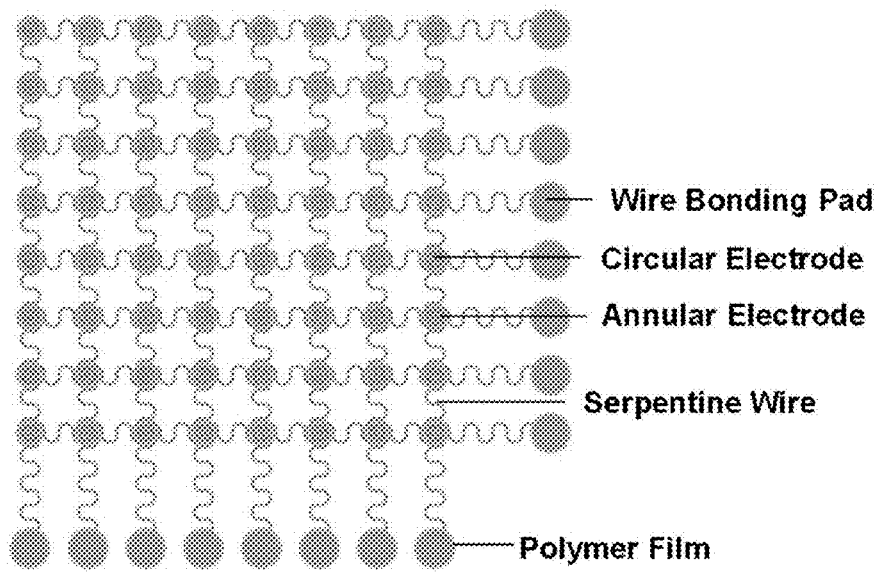

FIG. 94. Schematic of the hydration mapping sensor.

Figure 95:
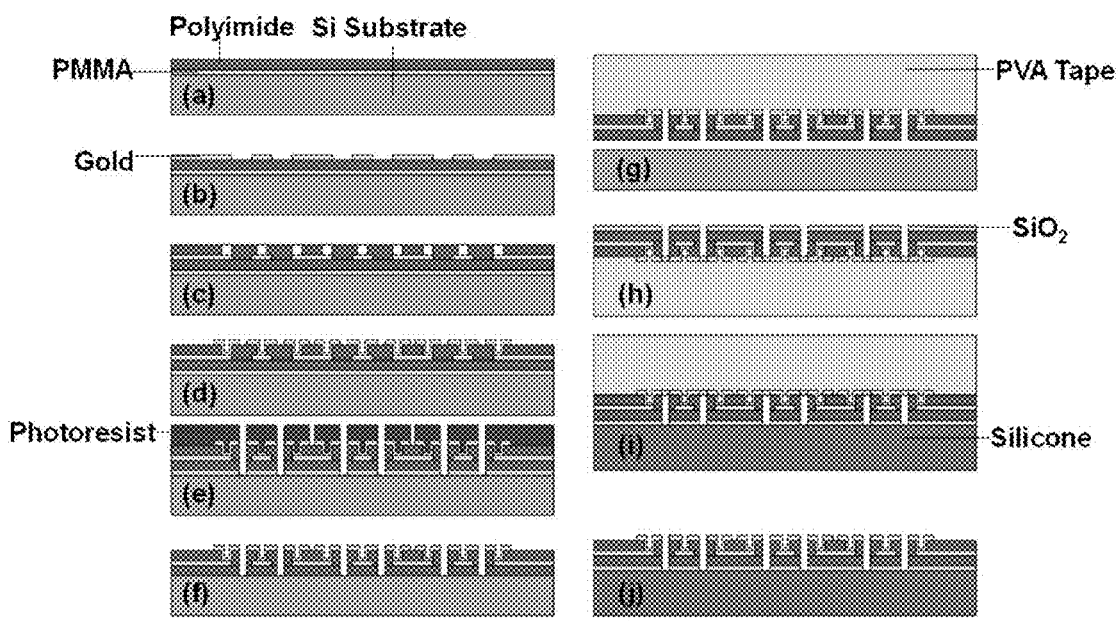

FIG. 95. Fabrication process of hydration sensors: (a) spin-coating of sacrificial PMMA layer and the polyimide supporting layer; (b) deposition and patterning of gold to form serpentine interconnections; (c) spin-coating of additional polyimide layer and opening of vias; (d) deposition and patterning of gold to form electrodes; (e) spin-coating and patterning of photoresist as a mask to define the outline of the device; (f) Removal of PMMA layer and release of the device; (g) Device pickup from Si wafer through PVA tape; (h) Deposition of $Ti/SiO_2$ layer; (i) Transfer printing of the device to a silicone substrate; (j) Removal of PVA tape in water.

Figure 96:
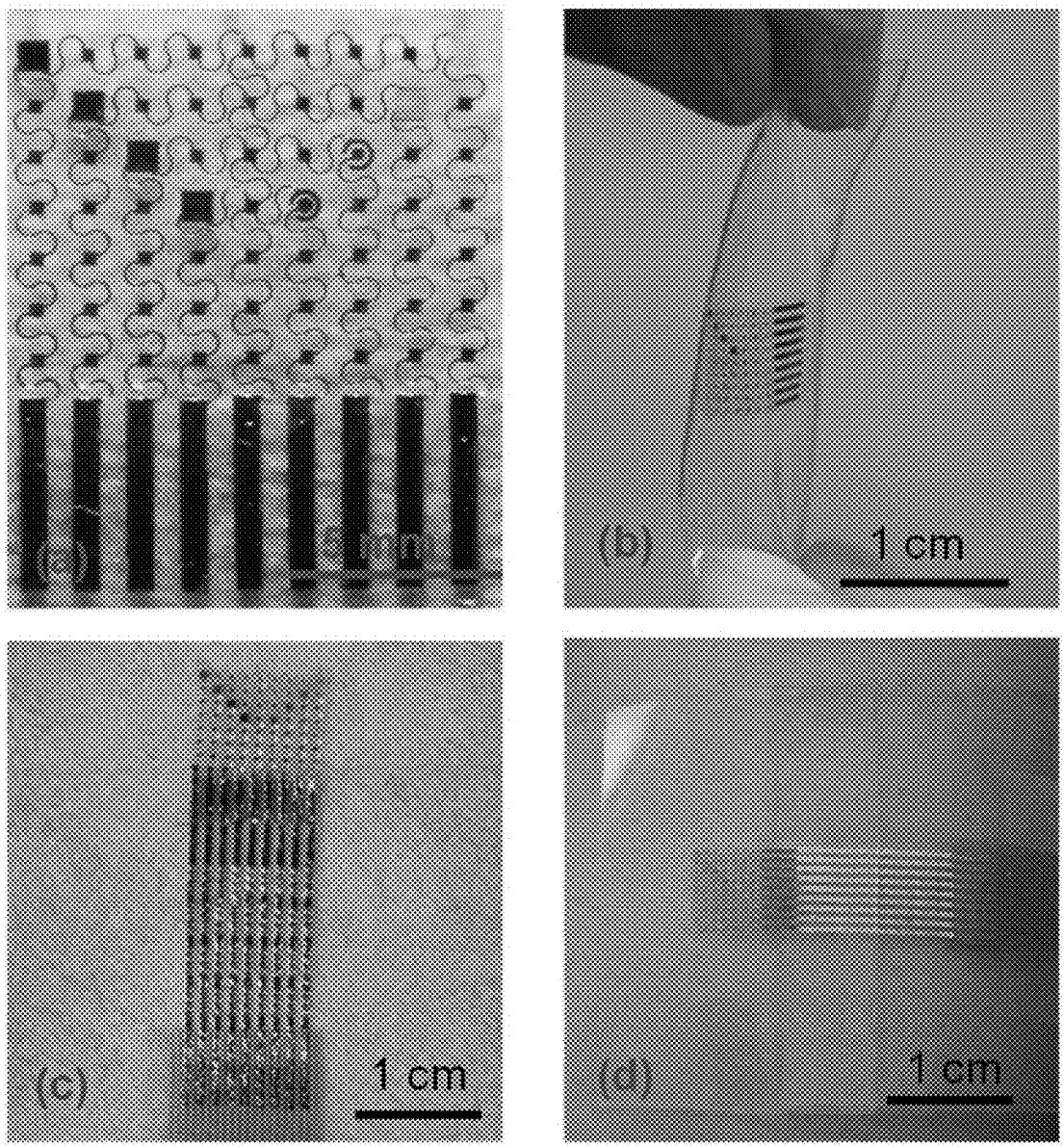

FIG. 96. Images of differential hydration sensors: (a) a fabricated differential hydration sensor on solaris substrate; (b) bending and twisting of the hydration sensor; (c) hydration sensor connected with releasable cable bonded with ACF cable; (d) hydration sensor on skin.

Figure 97:
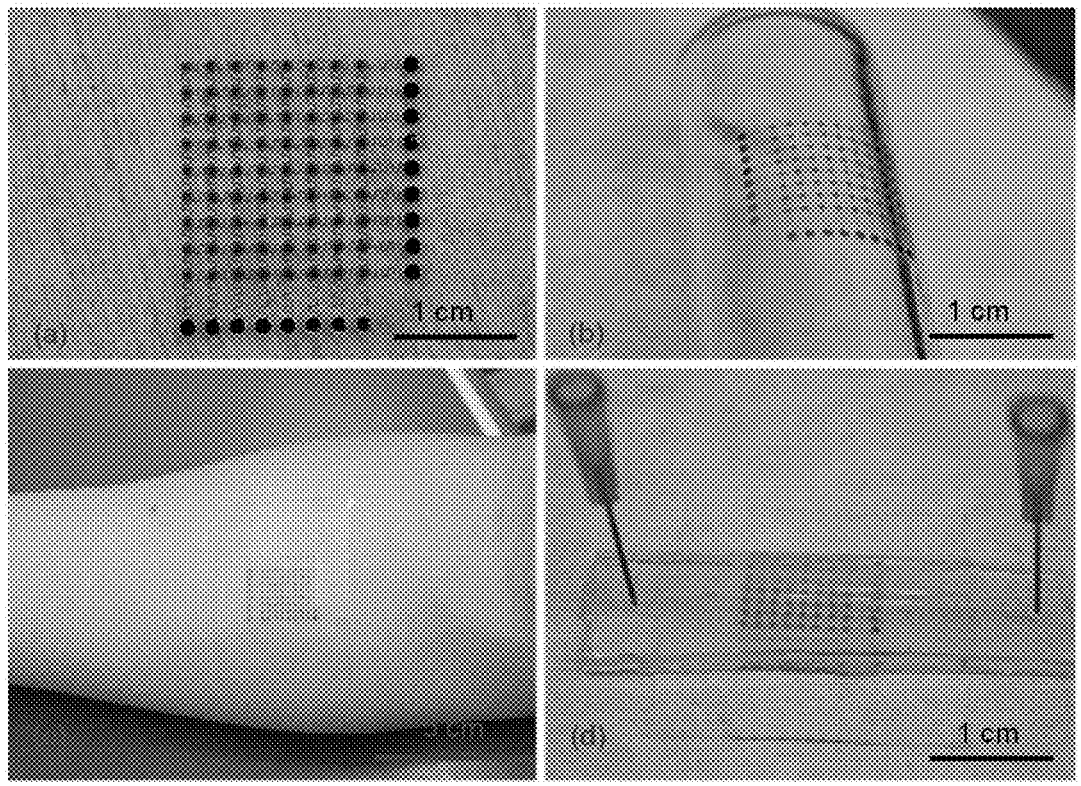

FIG. 97. Images of hydration mapping and depth profiling sensors: (a) a fabricated hydration mapping sensor on solaris substrate; (b) sensors attached to a glass tube; (c) Sensor on skin; (d) microchamber and sensors used to assess the effective measurement depth of electrodes.

Figure 98:
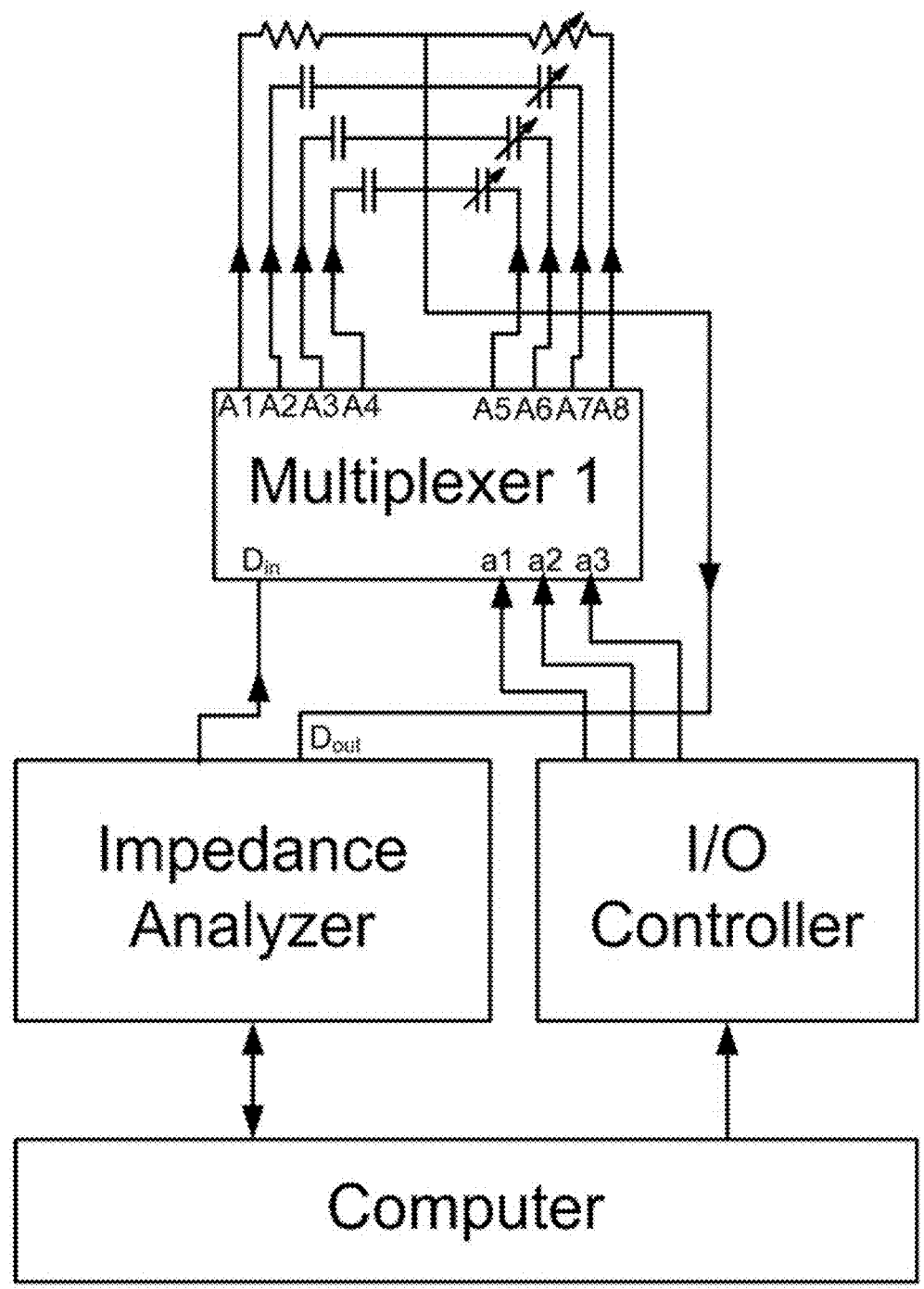

FIG. 98. Experimental setup for differential hydration sensor.

Figure 99:
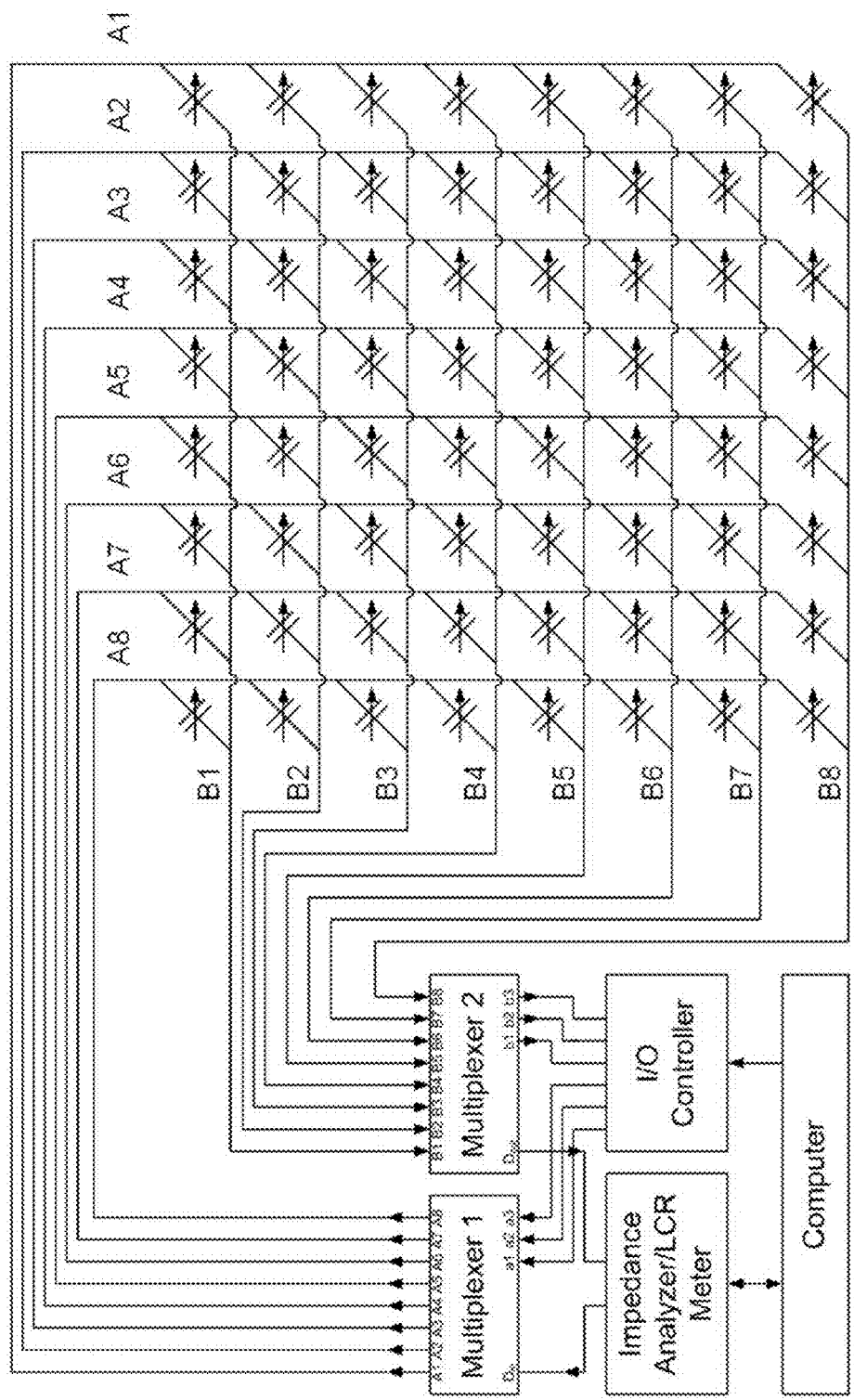

FIG. 99. Experimental setup for 8×8 hydration depth profiling and mapping sensors.

Figure 100:
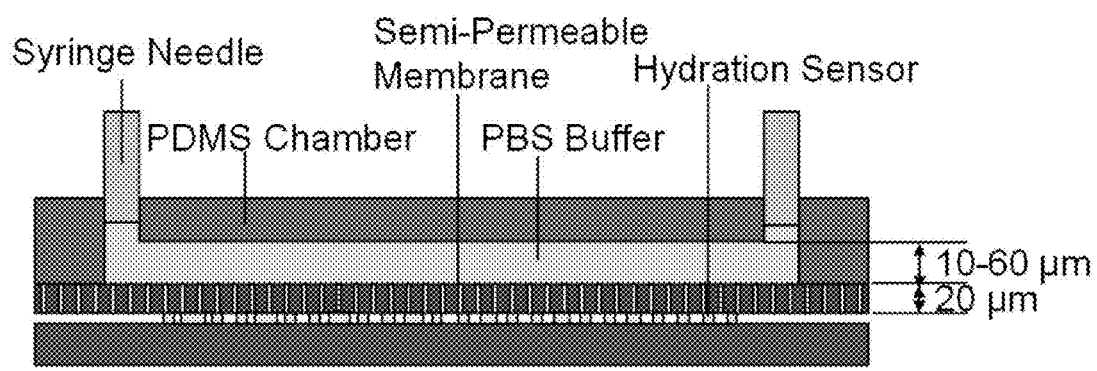

FIG. 100. Setup for in-vitro characterization of depth profiling device.

Figure 101:
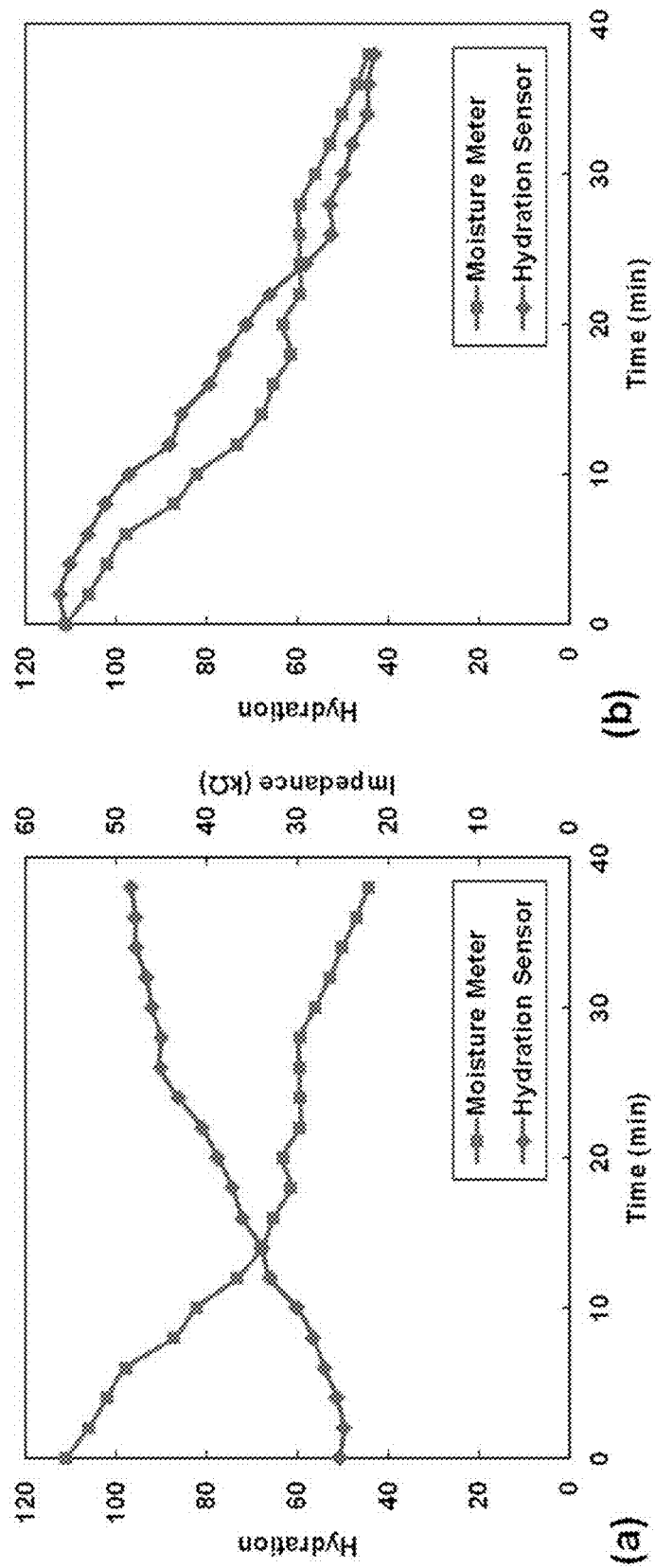

FIG. 101. The relation between the hydration levels with the impedance. (a) Before and (b) after calibration.

Figure 102:
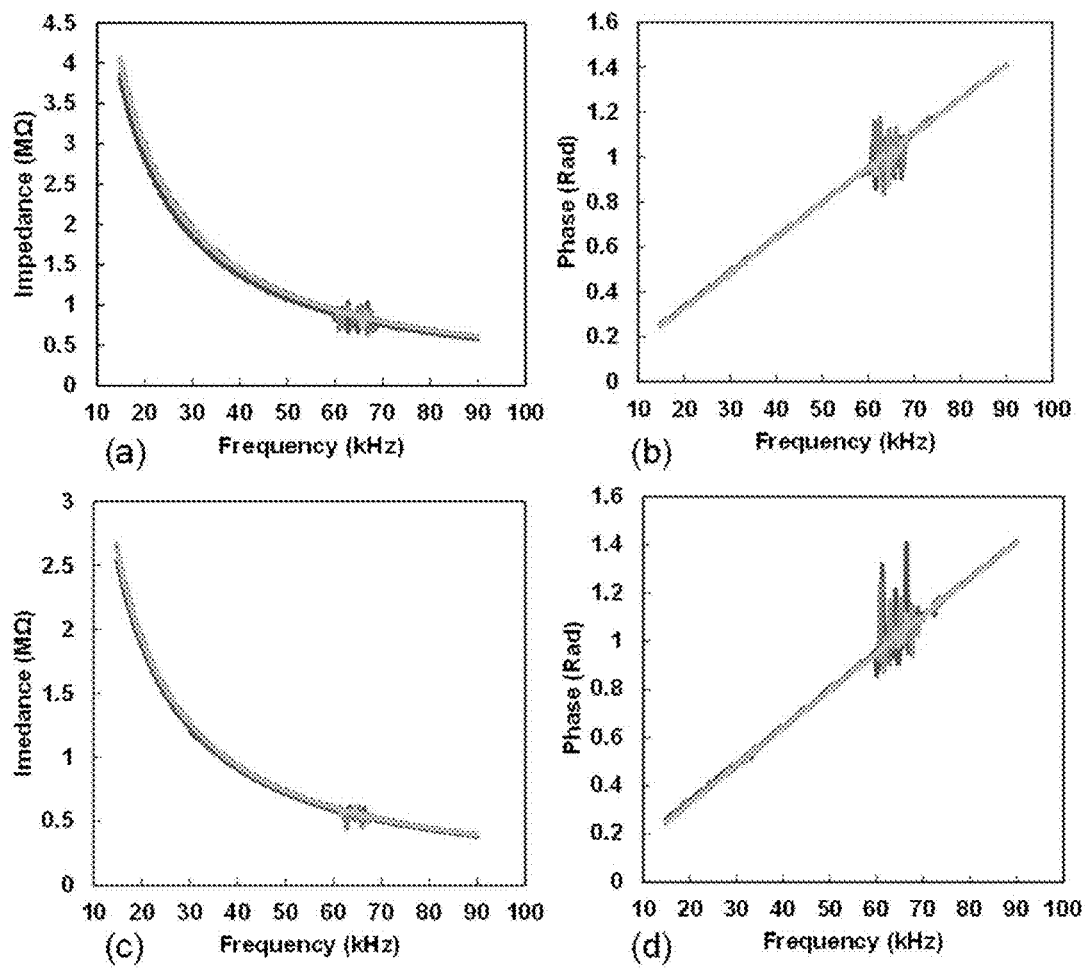

FIG. 102. Impedance variation by repeatedly attached the hydration sensor onto the skin at a stable hydration level: Impedance (a) amplitude and (b) phase of channel 4 and impedance (c) amplitude and (d) phase of channel 5.

Figure 103:
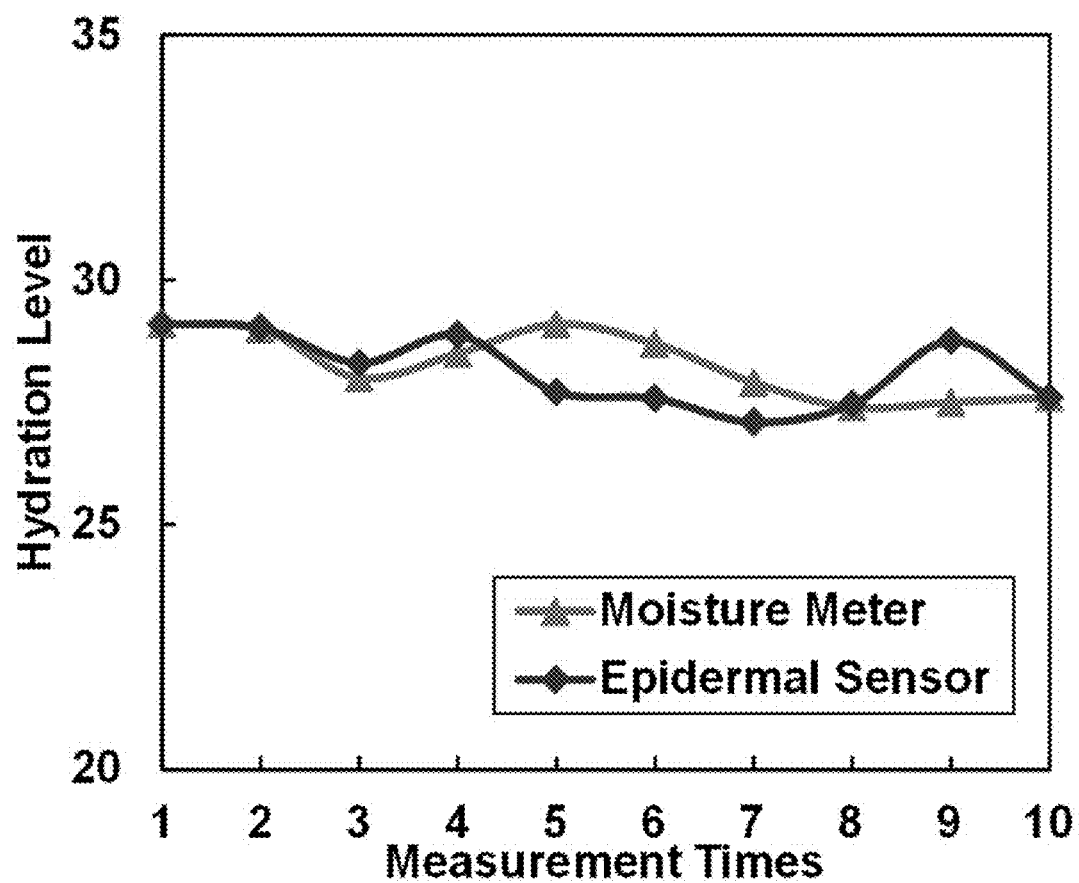

FIG. 103. Stability of the hydration sensor as compared with the moisture meter.

Figure 104:
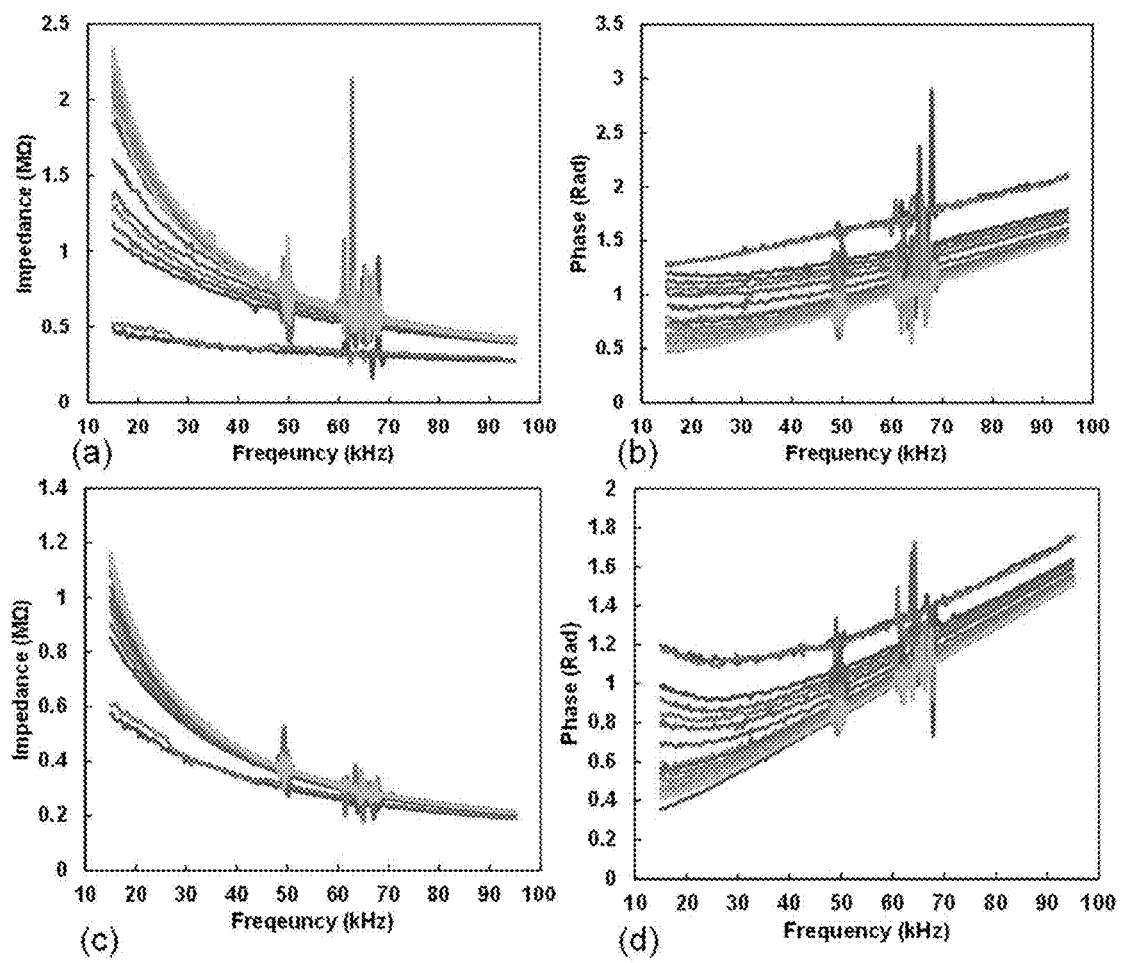

FIG. 104. Sensor response to hydration changes at various frequencies (channel 3 and channel 6): (a) impedance amplitude and (b) phase changes of channel 3 at varying hydration levels; (c) impedance amplitude and (d) phase changes of channel 4 at varying hydration levels.

Figure 105:
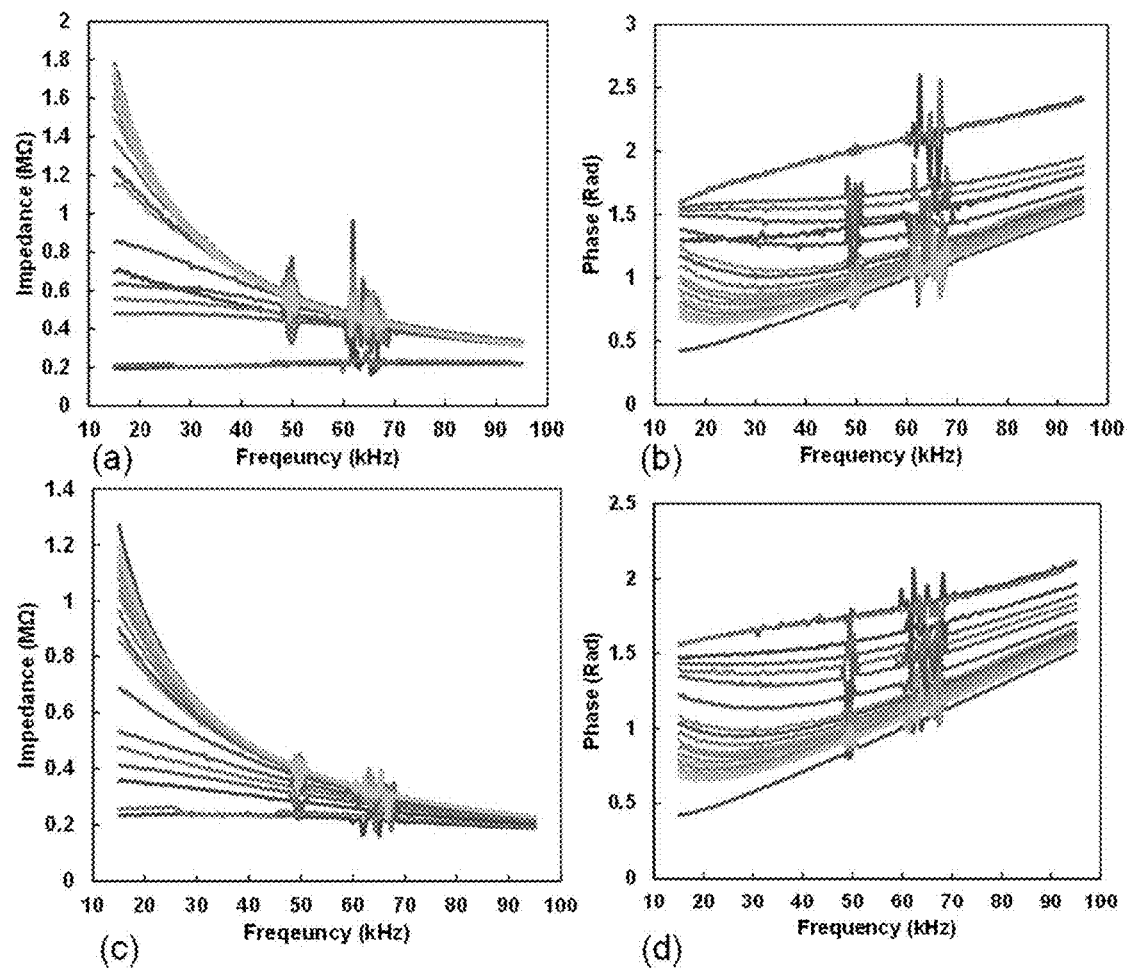

FIG. 105. Sensor response to hydration changes at various frequencies (channel 4 and channel 5): (a) impedance amplitude and (b) phase changes of channel 4 at varying hydration levels; (c) impedance amplitude and (d) phase changes of channel 5 at varying hydration levels.

Figure 106:
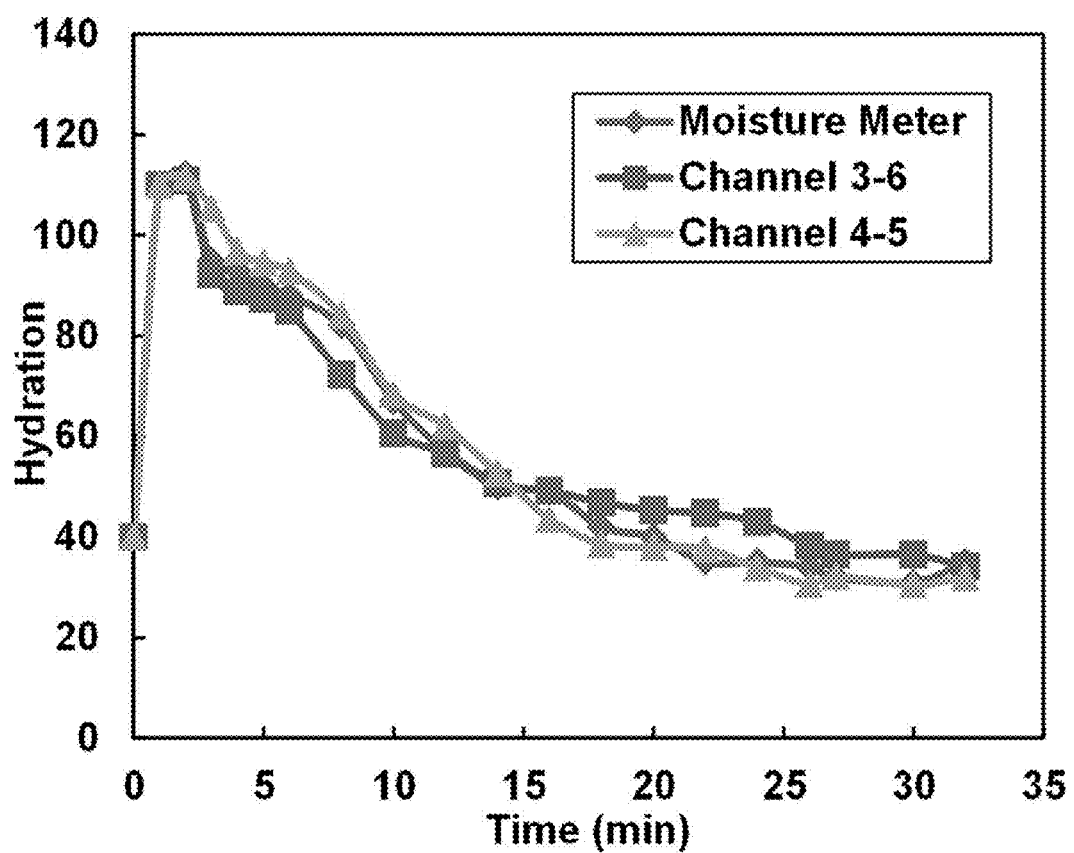

FIG. 106. Hydration measured by the differential epidermal sensor as compared with the moisture meter.

Figure 107:
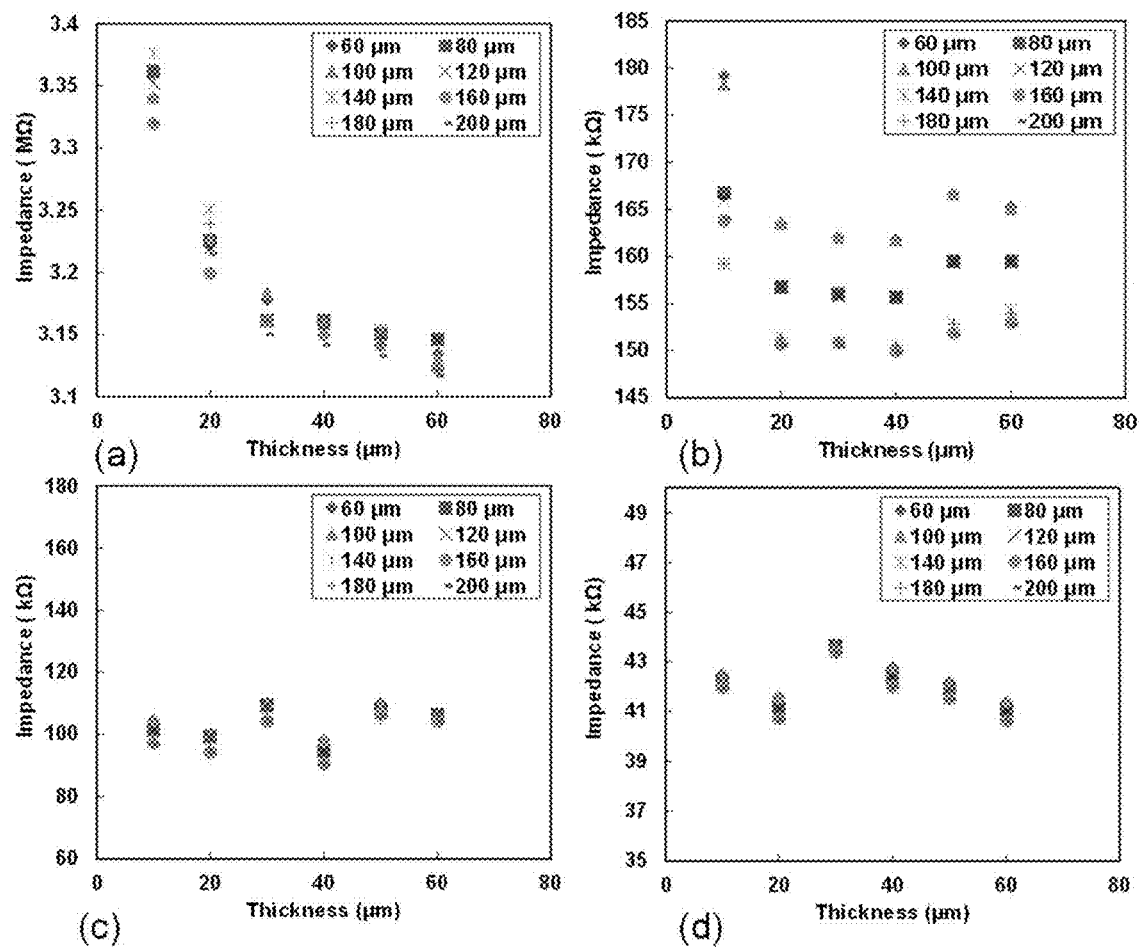

FIG. 107. Impedance of electrodes with spacing ranging from 60 to 200 µm at measurement frequencies of (a) 15 kHz, (b) 250 KHz, (c) 500 kHz, and (d) 1.25 MHz.

Figure 108:
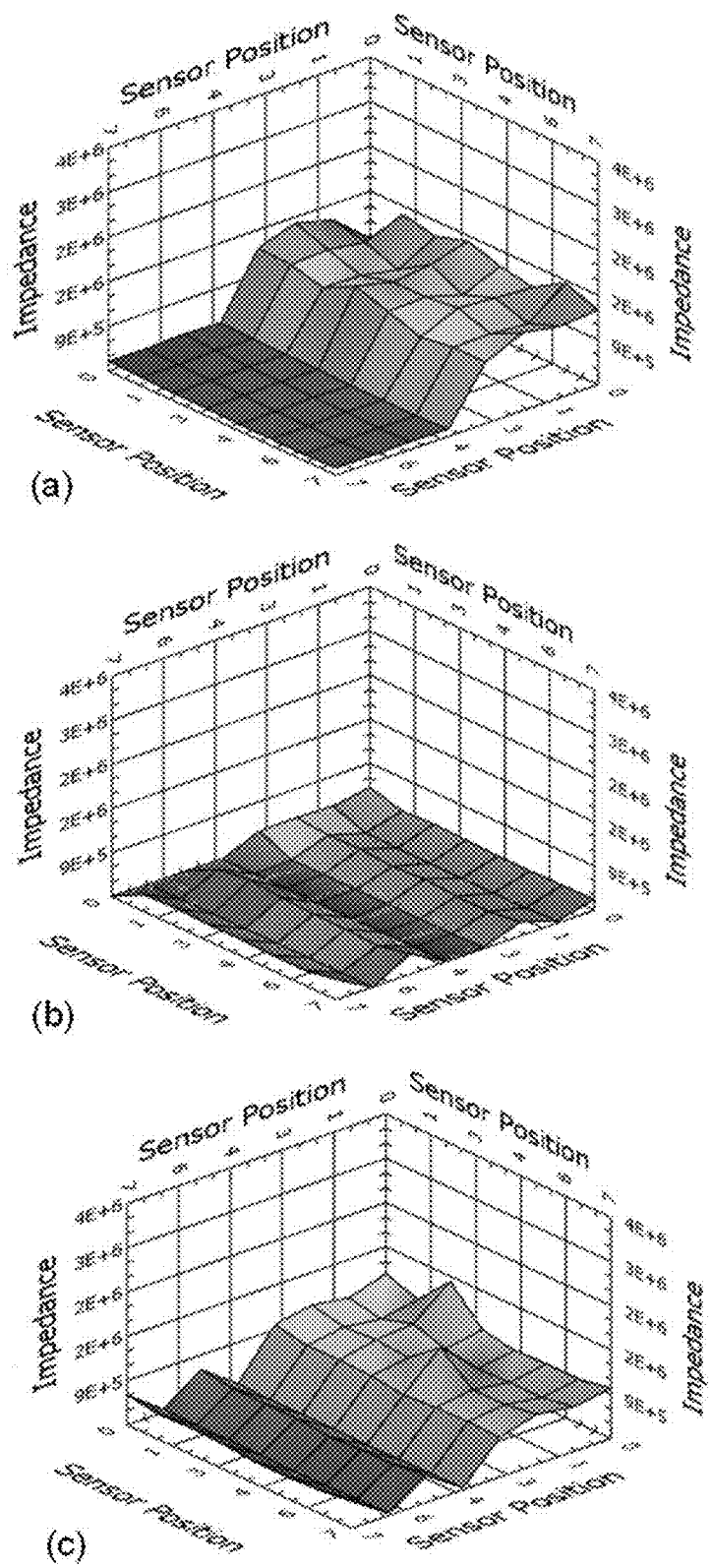

FIG. 108. Impedance of hydration sensor for depth-profile mapping at 15 kHz at hydration levels of (a) 64, (b) 117, and (c) 96.

Figure 109:
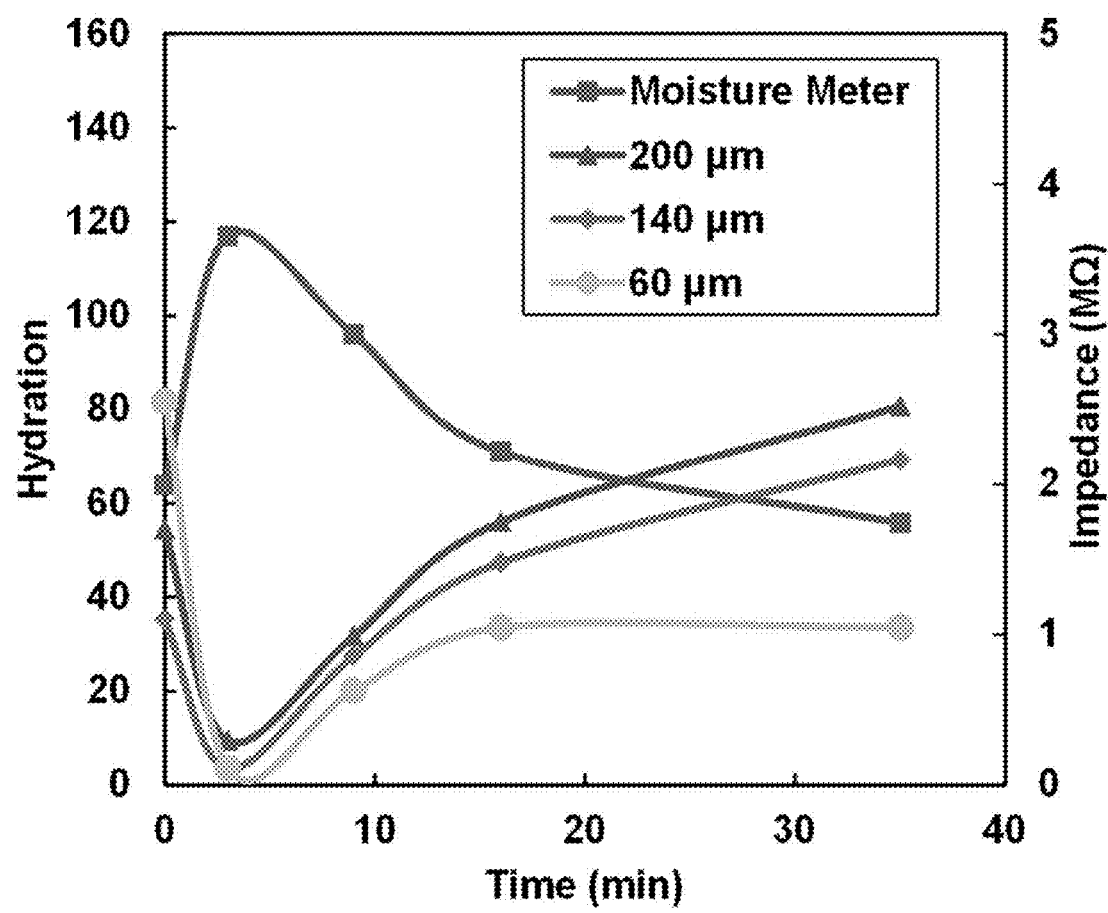

FIG. 109. Impedance of hydration sensor with different electrode spacing at 15 kHz at various hydration levels.

Figure 110:
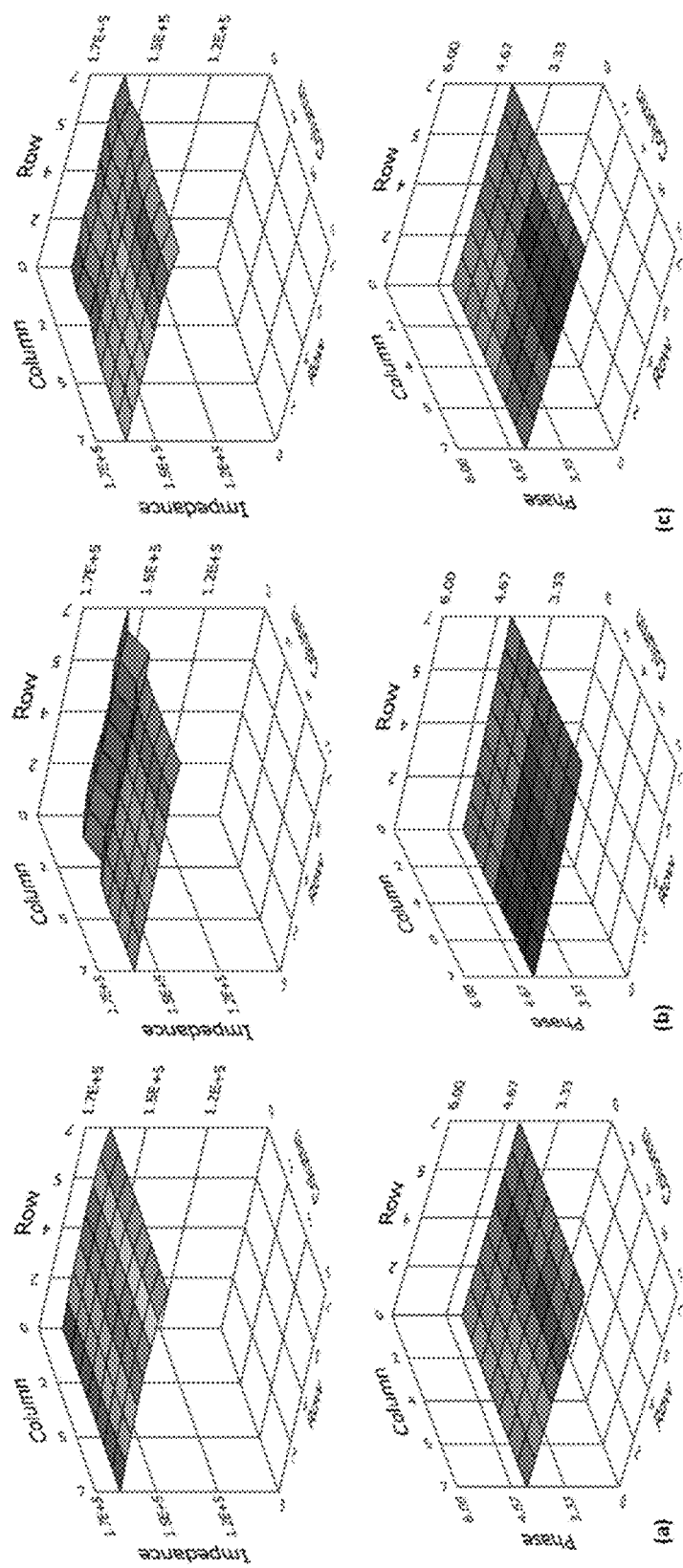

FIG. 110. Impedance amplitude and phase of hydration mapping sensor at 1.25 MHz at hydration levels of (a) 40, (b) 114, and (c) 77.

Figure 111:
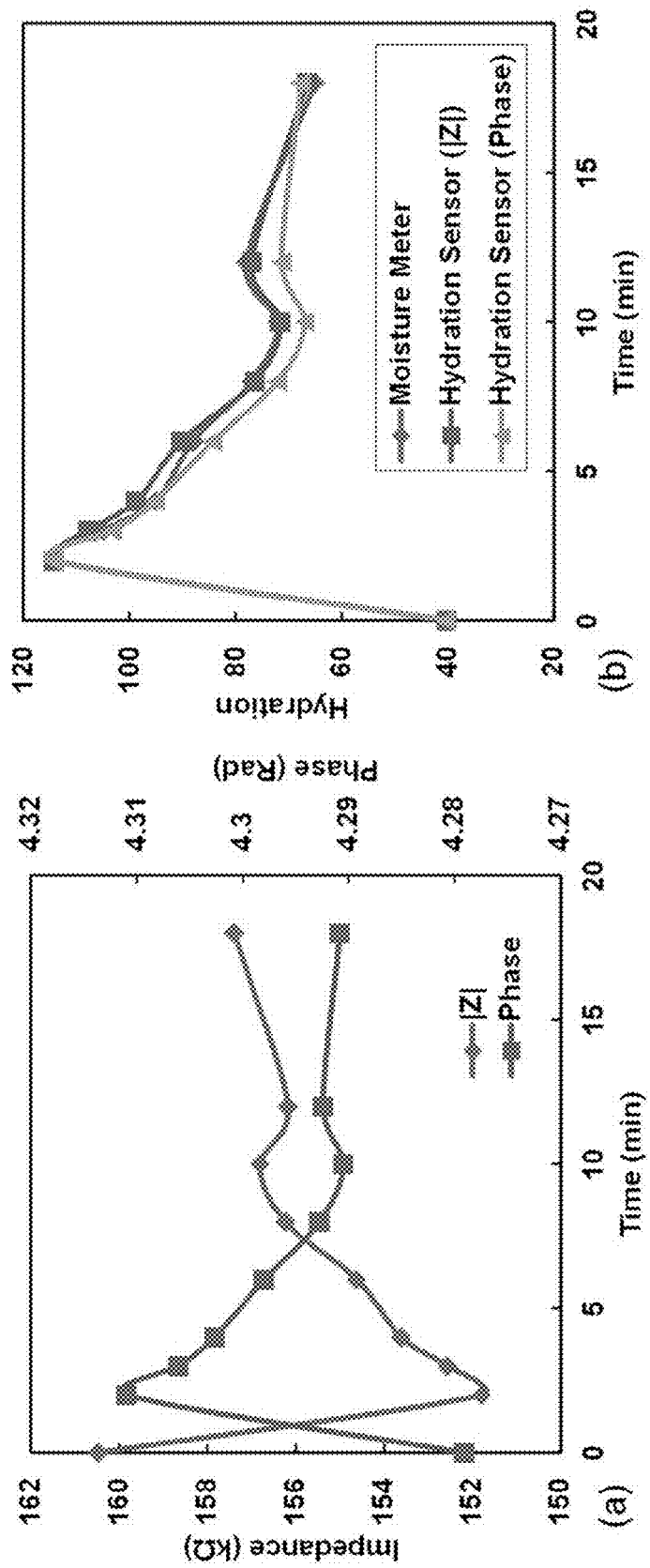

FIG. 111. Time course of (a) electrode impedance and (b) calibrated hydration levels of one electrode in the hydration mapping sensor before and after application of lotion at 1.25 MHz.

Figure 112:
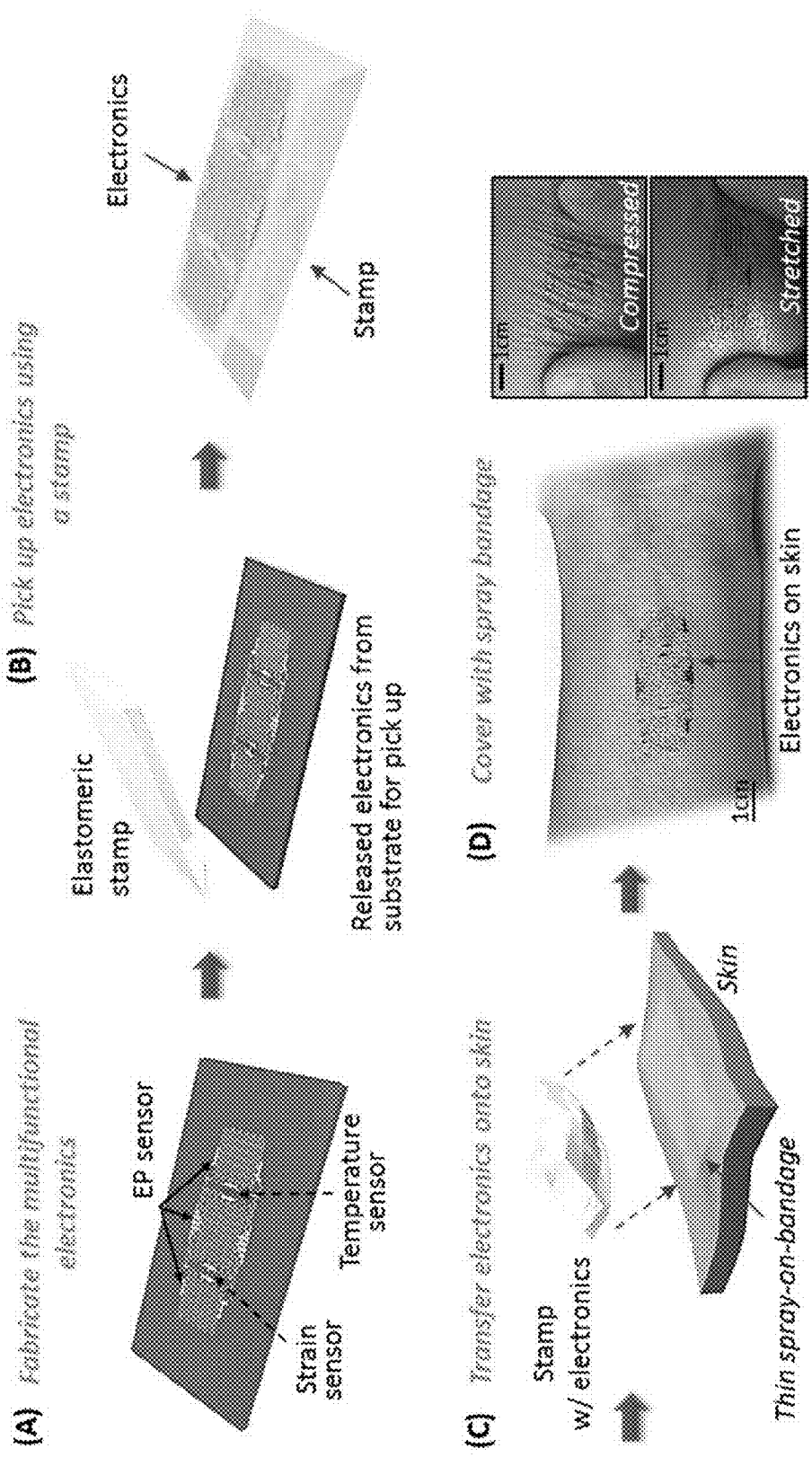

FIG. 112. Schematic illustrations of fabrication processes for multifunctional electronics and direct mounting of the electronics onto skin. (A) Fabricate the multifunctional electronics composed of EP-, strain, and temperature sensors on a Si, handling wafer. (B) Release the completed device in acetone through dissolving a sacrificial photoresist and pick up the device using a elastomeric stamp. (C) Transfer the electronics on the stamp onto the skin using a thin, sprayed glue layer. (D) Cover the electronics on the skin with a spray-on-bandage. After covering electronics with the bandage, the skin deformation is tested, which shows unnoticeable constraints in motion.

Figure 113:
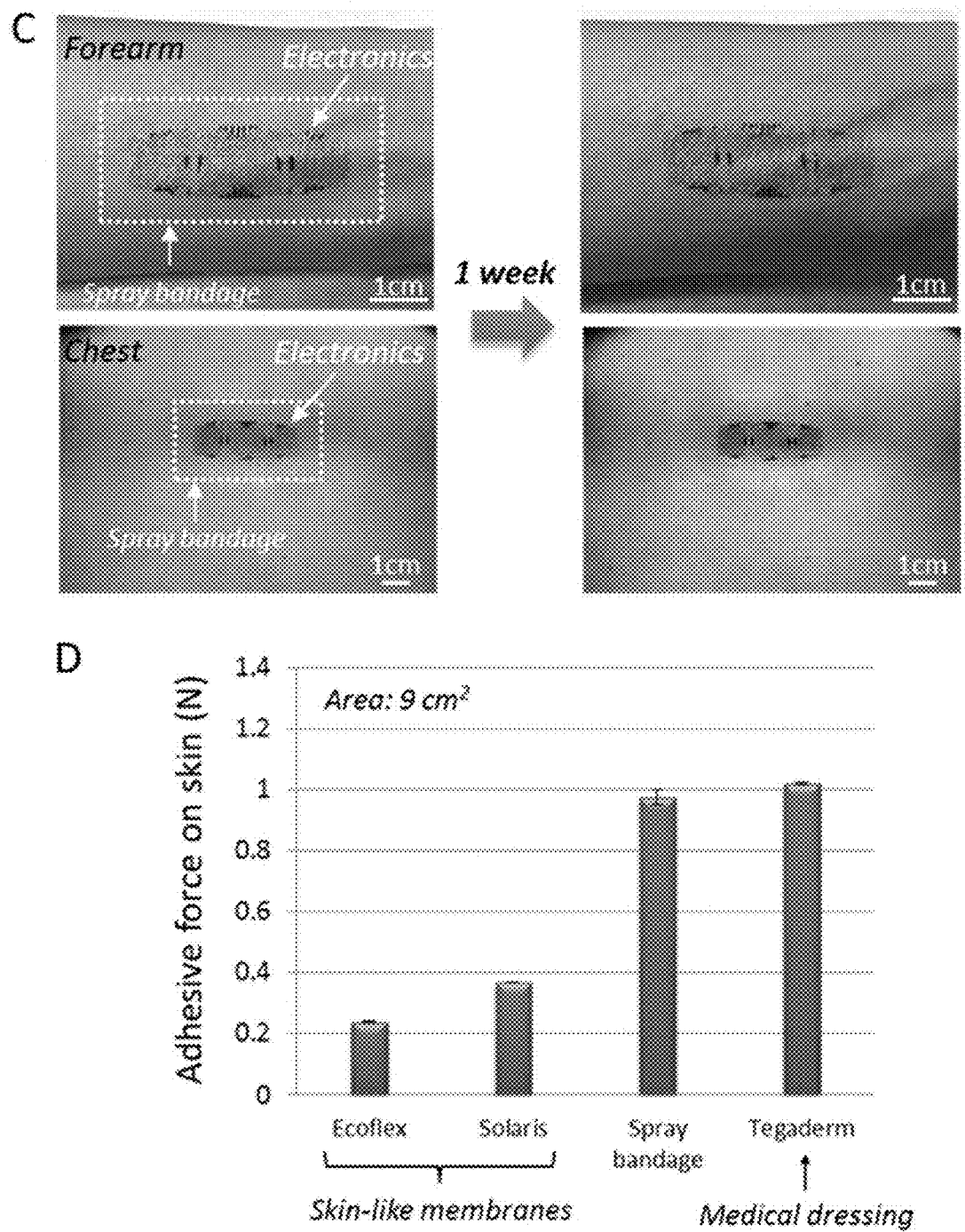

FIG. 113. Long-term wearability of an electronic device on skin with a spray bandage. (A) Characteristics of spray bandage; an optical image of spray-on-bandage on a glass slide, AFM study of the surface, and the height information from surface profilometer. (B) Cross-sectional, schematic illustration of the characteristics of the spray-on-bandage when it covers the electronic device on skin (not in scale). (C) Demonstration of long-term wearability of a skin-like device on a subject's forearm and chest for a week. (D) Comparison of adhesion force of various materials on skin (forearm) with a fixed area of 9 $cm^2$. Error bar represents the standard deviation (n=3).

Figure 114:
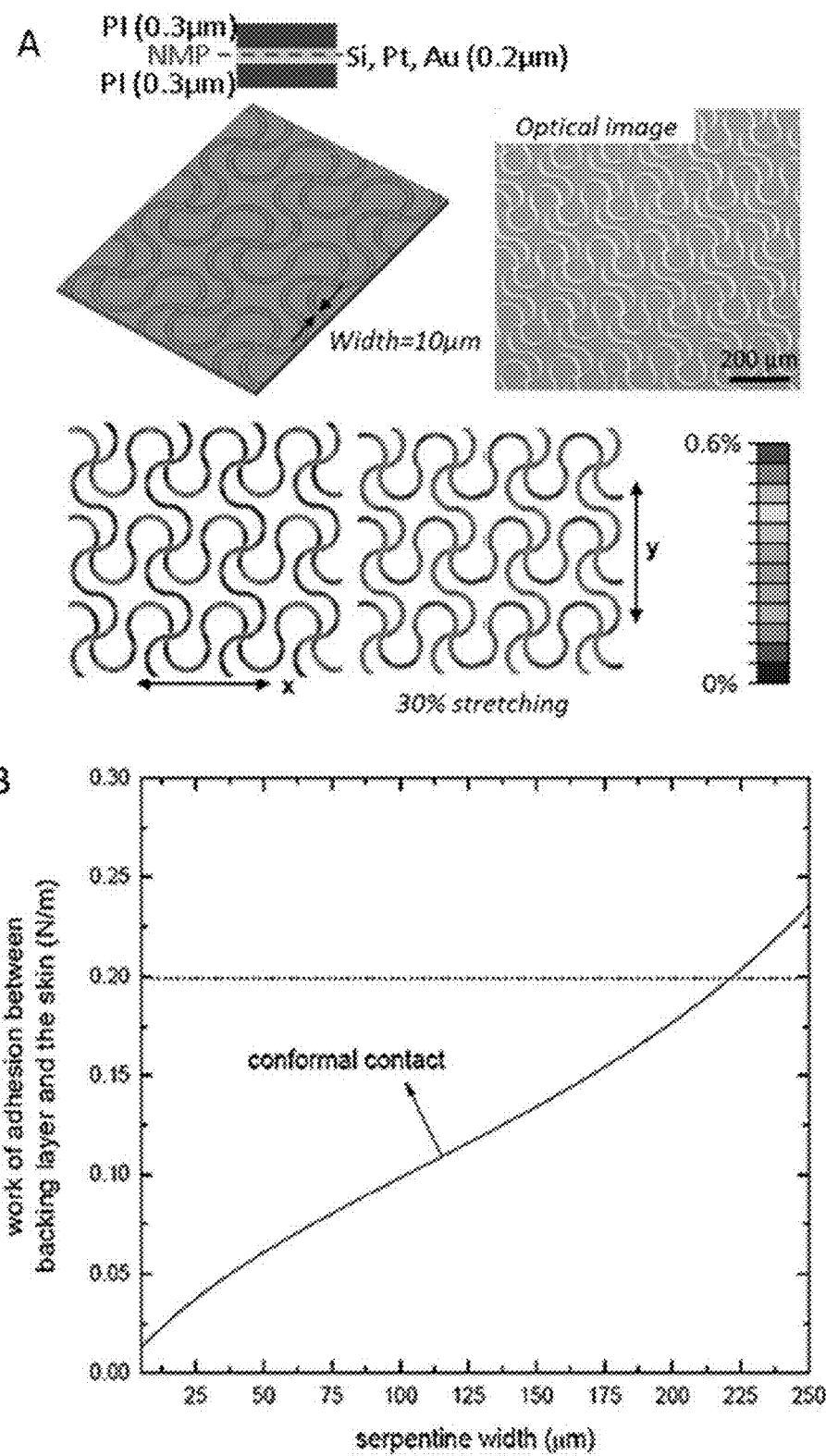

FIG. 114. FEM and experimental study of conformability of skin-like electronics on skin. (A) FEM study of mechanical stability with 10 µm-FS electrodes. (B) Scaling law between the width of FS electrode and adhesion force for conformal contact. (C) SEM study of conformal mounting of various electrode designs on the skin replicas. Inset of the bottom 10 µm-FS image shows a zoomed-out view. In the SEM images, electrodes were colorized as gold color for ease-of-viewing. (D) The comparison of skin-electrode impedance between the skin-like electronics and the conventional gel-based electrodes. Illustrations compare the conformal lamination of electrodes.

Figure 115:
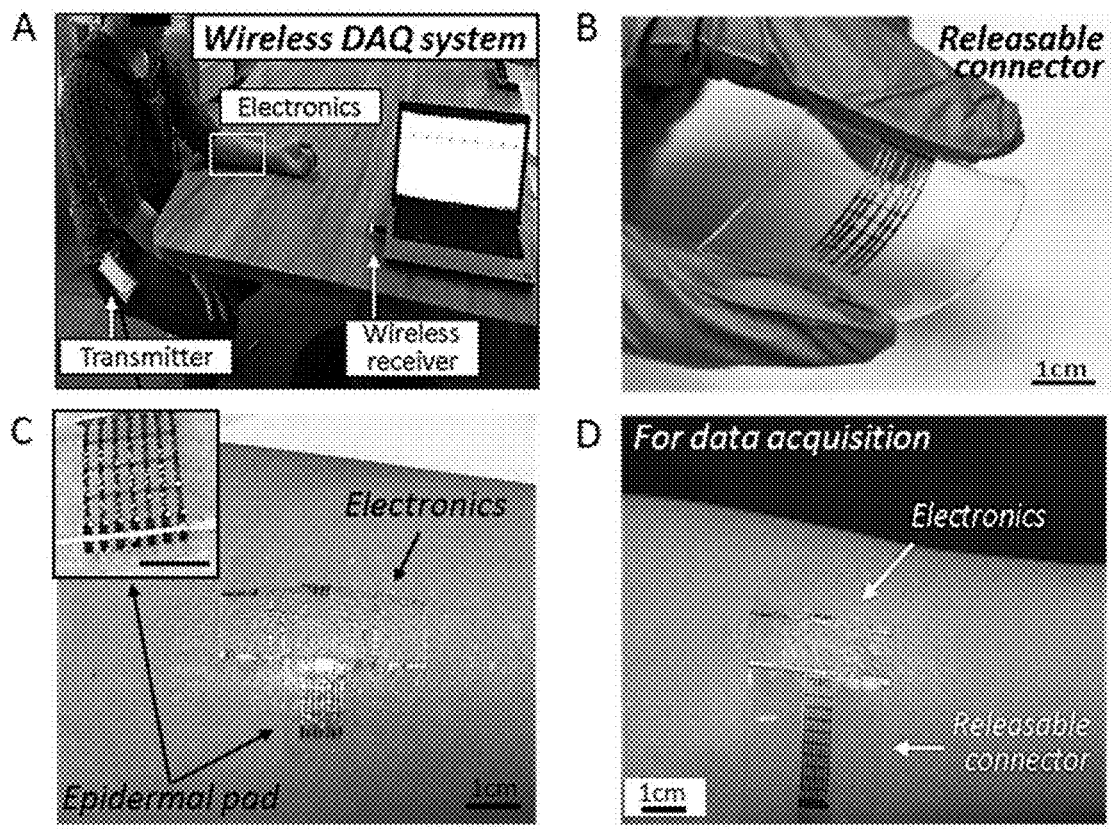

FIG. 115. Utilization of a releasable, skin-like connector with a commercial wireless data acquisition system for recording signals on skin. (A) Wireless DAQ system including a transmitter, a wireless receiver, and a laptop with data recording software. (B) A releasable connector on a stretchable, skin-like membrane. (C) The skin-like electronics sensor in conjunction with the epidermal pad. The inset shows the magnified view of the epidermal pad (scale bar: 1 mm). (D) Physically mounted releasable connector on the electronic sensor on skin for data acquisition with the wireless DAQ system.

Figure 116:
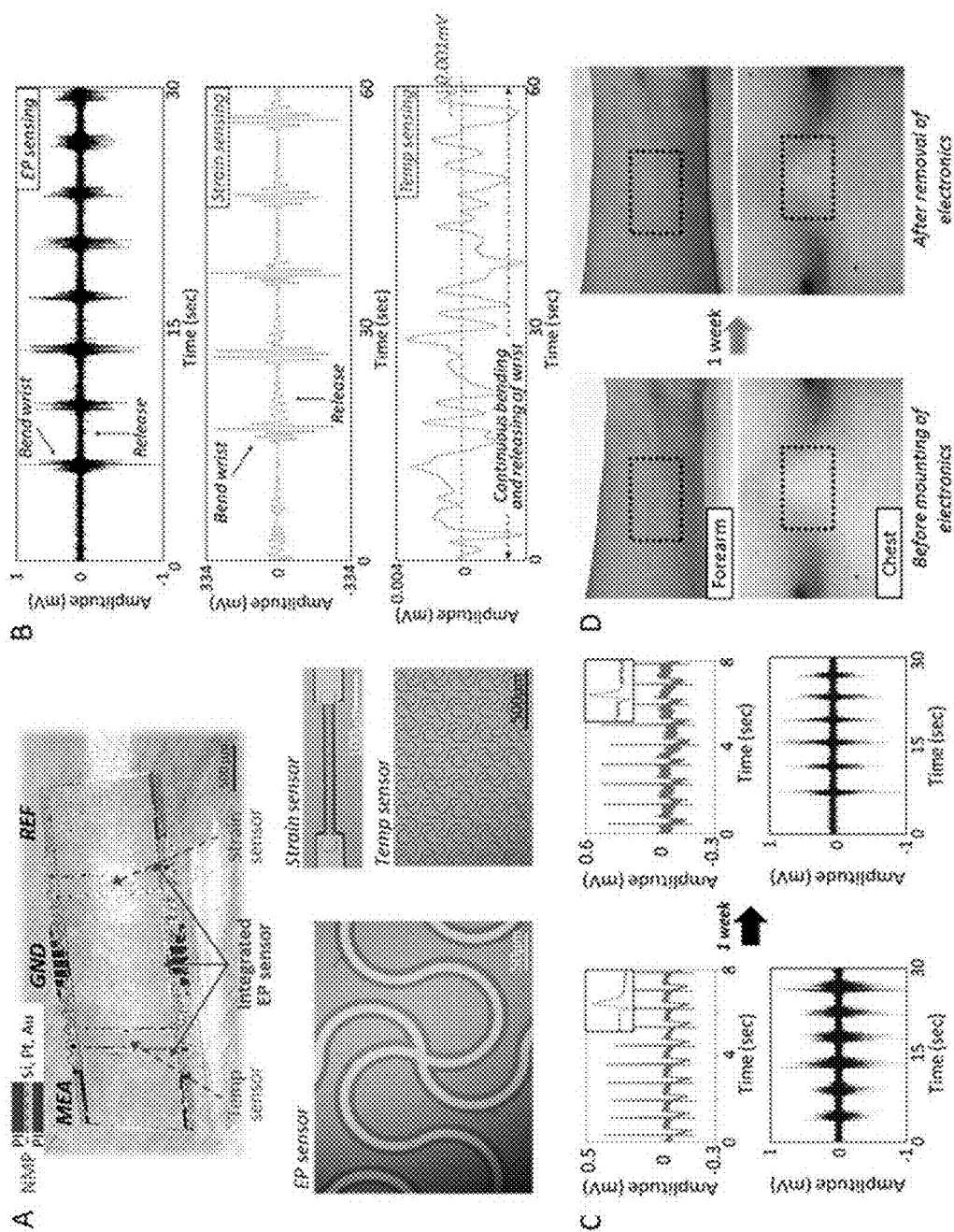

FIG. 116. Demonstration of multifunctional skin-like electronics with long-term EP measurement. (A) Multifunctional electronic device that incorporates 10 µm-FS EP sensor, Pt temperature sensor, and silicone nanomembrane strain sensor. The sensing components are placed in neutral mechanical plane. (B) Demonstration of multi-modal measurements of EMG, strain, and temperature signals on a subject's forearm. (C) Long-term (a week) measurement of ECG and EMG signals on a subject's chest and forearm, respectively. (D) Skin irritation test of wearing the skin-like electronics for a week.

DETAILED DESCRIPTION OF THE INVENTION

In general the terms and phrases used herein have their art-recognized meaning, which can be found by reference to standard texts, journal references and contexts known to those skilled in the art. The following definitions are provided to clarify their specific use in the context of the invention.

The terms "flexible" and "bendable" are used synonymously in the present description and refer to the ability of a material, structure, device or device component to be deformed into a curved or bent shape without undergoing a transformation that introduces significant strain, such as strain characterizing the failure point of a material, structure, device or device component. In an exemplary embodiment, a flexible material, structure, device or device component may be deformed into a curved shape without introducing strain larger than or equal to 5%, for some applications larger than or equal to 1%, and for yet other applications larger than or equal to 0.5% in strain-sensitive regions. A used herein, some, but not necessarily all, flexible structures are also stretchable. A variety of properties provide flexible structures (e.g., device components) of the invention, including materials properties such as a low modulus, bending stiffness and flexural rigidity; physical dimensions such as small average thickness (e.g., less than 100 microns, optionally less than 10 microns and optionally less than 1 micron) and device geometries such as thin film and mesh geometries.

"Stretchable" refers to the ability of a material, structure, device or device component to be strained without undergoing fracture. In an exemplary embodiment, a stretchable material, structure, device or device component may undergo strain larger than 0.5% without fracturing, for some applications strain larger than 1% without fracturing and for yet other applications strain larger than 3% without fracturing. A used herein, many stretchable structures are also flexible. Some stretchable structures (e.g., device components) are engineered to be able to undergo compression, elongation and/or twisting so as to be able to deform without fracturing. Stretchable structures include thin film structures comprising stretchable materials, such as elastomers; bent structures capable of elongation, compression and/or twisting motion; and structures having an island—bridge geometry. Stretchable device components include structures having stretchable interconnects, such as stretchable electrical interconnects.

"Functional layer" refers to a device-containing layer that imparts some functionality to the device. For example, the functional layer may be a thin film such as a semiconductor layer. Alternatively, the functional layer may comprise multiple layers, such as multiple semiconductor layers separated by support layers. The functional layer may comprise a plurality of patterned elements, such as interconnects running between device-receiving pads or islands. The functional layer may be heterogeneous or may have one or more properties that are inhomogeneous. "Inhomogeneous property" refers to a physical parameter that can spatially vary, thereby effecting the position of the neutral mechanical surface (NMS) within the multilayer device.

"Semiconductor" refers to any material that is an insulator at a low temperature, but which has an appreciable electrical conductivity at a temperatures of about 300 Kelvin. In the present description, use of the term semiconductor is intended to be consistent with use of this term in the art of microelectronics and electronic devices. Useful semiconductors include those comprising element semiconductors, such as silicon, germanium and diamond, and compound semiconductors, such as group IV compound semiconductors such as SiC and SiGe, group III-V semiconductors such as AlSb, AlAs, Aln, AlP, BN, GaSb, GaAs, GaN, GaP, InSb, InAs, InN, and InP, group III-V ternary semiconductors alloys such as $Al_xGa_{1-x}As$, group II-VI semiconductors such as CsSe, CdS, CdTe, ZnO, ZnSe, ZnS, and ZnTe, group I-VII semiconductors CuCl, group IV-VI semiconductors such as PbS, PbTe and SnS, layer semiconductors such as $PbI_2$, $MoS_2$ and GaSe, oxide semiconductors such as CuO and $Cu_2O$. The term semiconductor includes intrinsic semiconductors and extrinsic semiconductors that are doped with one or more selected materials, including semiconductor having p-type doping materials and n-type doping materials, to provide beneficial electronic properties useful for a given application or device. The term semiconductor includes composite materials comprising a mixture of semiconductors and/or dopants. Specific semiconductor materials useful for in some embodiments include, but are not limited to, Si, Ge, SiC, AlP, AlAs, AlSb, GaN, GaP, GaAs, GaSb, InP, InAs, GaSb, InP, InAs, InSb, ZnO, ZnSe, ZnTe, CdS, CdSe, ZnSe, ZnTe, CdS, CdSe, CdTe, HgS, PbS, PbSe, PbTe, AlGaAs, AlInAs, AlInP, GaAsP, GaInAs, GaInP, AlGaAsSb, AlGaInP, and GaInAsP. Porous silicon semiconductor materials are useful for applications of aspects described herein in the field of sensors and light emitting materials, such as light emitting diodes (LEDs) and solid state lasers. Impurities of semiconductor materials are atoms, elements, ions and/or molecules other than the semiconductor material(s) themselves or any dopants provided to the semiconductor material. Impurities are undesirable materials present in semiconductor materials which may negatively impact the electronic properties of semiconductor materials, and include but are not limited to oxygen, carbon, and metals including heavy metals. Heavy metal impurities include, but are not limited to, the group of elements between copper and lead on the periodic table, calcium, sodium, and all ions, compounds and/or complexes thereof.

"Semiconductor element", "semiconductor structure" and "semiconductor circuit element" are used synonymously in the present description and broadly refer to any semiconductor material, composition or structure, and expressly includes high quality single crystalline and polycrystalline semiconductors, semiconductor materials fabricated via high temperature processing, doped semiconductor materials, organic and inorganic semiconductors and composite semiconductor materials and structures having one or more additional semiconductor components and/or non-semiconductor components, such as dielectric layers or materials, electrodes and/or conducting layers or materials.

"Coincident" refers to refers to the relative position of two or more objects, planes or surfaces, for example a surface such as a NMS or NMP that is positioned within or is adjacent to a layer, such as a functional layer, substrate layer, or other layer. In an embodiment, a NMS or NMP is positioned to correspond to the most strain-sensitive layer or material within the layer.

"Proximate" refers to the relative position of two or more objects, planes or surfaces, for example a NMS or NMP that closely follows the position of a layer, such as a functional layer, substrate layer, or other layer while still providing desired flexibility or stretchability without an adverse impact on the strain-sensitive material physical properties. In general, a layer having a high strain sensitivity, and consequently being prone to being the first layer to fracture, is located in the functional layer, such as a functional layer containing a relatively brittle semiconductor or other strain-sensitive device element. A NMS or NMP that is proximate to a layer need not be constrained within that layer, but may be positioned proximate or sufficiently near to provide a functional benefit of reducing the strain on the strain-sensitive device element when the device is folded.

"Electronic device" is used broadly herein to refer to devices such as integrated circuits, imagers or other optoelectronic devices. Electronic device may also refer to a component of an electronic device such as passive or active components such as a semiconductor, interconnect, contact pad, transistors, diodes, LEDs, circuits, etc. Devices disclosed herein may relate to the following fields: collecting optics, diffusing optics, displays, pick and place assembly, vertical cavity surface-emitting lasers (VCSELS) and arrays thereof, LEDs and arrays thereof, transparent electronics, photovoltaic arrays, solar cells and arrays thereof, flexible electronics, micromanipulation, plastic electronics, displays, pick and place assembly, transfer printing, LEDs, transparent electronics, stretchable electronics, and flexible electronics.

A "component" is used broadly to refer to a material or individual component used in a device. An "interconnect" is one example of a component and refers to an electrically conducting material capable of establishing an electrical connection with a component or between components. In particular, an interconnect may establish electrical contact between components that are separate and/or can move with respect to each other. Depending on the desired device specifications, operation, and application, an interconnect is made from a suitable material. For applications where a high conductivity is required, typical interconnect metals may be used, including but not limited to copper, silver, gold, aluminum and the like, and alloys. Suitable conductive materials further include semiconductors, such as silicon and GaAs and other conducting materials such as indium tin oxide.

An interconnect that is "stretchable" or "flexible" is used herein to broadly refer to an interconnect capable of undergoing a variety of forces and strains such as stretching, bending and/or compression in one or more directions without adversely impacting electrical connection to, or electrical conduction from, a device component. Accordingly, a stretchable interconnect may be formed of a relatively brittle material, such as GaAs, yet remain capable of continued function even when exposed to a significant deformatory force (e.g., stretching, bending, compression) due to the interconnect's geometrical configuration. In an exemplary embodiment, a stretchable interconnect may undergo strain larger than 1%, optionally 10% or optionally 30% or optionally up to 100% without fracturing. In an example, the strain is generated by stretching an underlying elastomeric substrate to which at least a portion of the interconnect is bonded. For certain embodiments, flexible or stretchable interconnects include interconnects having wavy, meandering or serpentine shapes.

A "device component" is used to broadly refer to an individual component within an electrical, optical, mechanical or thermal device. Components include, but are not limited to, a photodiode, LED, TFT, electrode, semiconductor, other light-collecting/detecting components, transistor, integrated circuit, contact pad capable of receiving a device component, thin film devices, circuit elements, control elements, microprocessors, transducers and combinations thereof. A device component can be connected to one or more contact pads as known in the art, such as metal evaporation, wire bonding, application of solids or conductive pastes, for example. Electrical device generally refers to a device incorporating a plurality of device components, and includes large area electronics, printed wire boards, integrated circuits, device components arrays, biological and/or chemical sensors, physical sensors (e.g., temperature, light, radiation, etc.), solar cell or photovoltaic arrays, display arrays, optical collectors, systems and displays.

"Sensing element" and "sensor" are used synonymously and refers to a device component useful as a sensor and/or useful for detecting the presence, absence, amount, magnitude or intensity of a physical property, object, radiation and/or chemical. Sensors in some embodiments function to transduce a biological signal into an electrical signal, optical signal, wireless signal, acoustic signal, etc. Useful sensing elements include, but are not limited to electrode elements, chemical or biological sensor elements, pH sensors, optical sensors, photodiodes, temperature sensors, capacitive sensors strain sensors, acceleration sensors, movement sensors, displacement sensors, pressure sensors, acoustic sensors or combinations of these.

"Actuating element" and "actuator" are used synonymously and refers to a device component useful for interacting with, stimulating, controlling, or otherwise affecting an external structure, material or fluid, for example a biological tissue. Useful actuating elements include, but are not limited to, electrode elements, electromagnetic radiation emitting elements, light emitting diodes, lasers and heating elements. Actuating elements include electrodes for providing a voltage or current to a tissue. Actuating elements include sources of electromagnetic radiation for providing electromagnetic radiation to a tissue. Actuating elements include ablation sources for ablating tissue. Actuating elements include thermal sources for heating tissue. Actuating elements include displacement sources for displacing or otherwise moving a tissue.

"Island" or "device island" refers to a relatively rigid device element or component of an electronic device comprising multiple semiconductor elements or active semiconductor structures. "Bridge" or "bridge structure" refers to stretchable or flexible structures interconnecting two or more device islands or one device island to another device component. Specific bridge structures include flexible semiconductor interconnects.

"Barrier layer" refers to a device component spatially separating two or more other device components or spatially separating a device component from a structure, material or fluid external to the device. In one embodiment, a barrier layer encapsulates one or more device components. In embodiments, a barrier layer separates one or more device components from an aqueous solution, a biological tissue and/or a biological environment. In some embodiments, a barrier layer is a passive device component. In some embodiments, a barrier layer is a functional, but non-active, device component. In a specific embodiment, a barrier layer is a moisture barrier. As used herein, the term "moisture barrier" refers to a barrier layer which provides protection to other device components from bodily fluids, ionic solutions, water or other solvents. In one embodiment, a moisture barrier provides protection to an external structure, material or fluid, for example, by preventing leakage current from escaping an encapsulated device component and reaching the external structure, material or fluid. In a specific embodiment, a barrier layer is a thermal barrier. As used herein, the term "thermal barrier" refers to a barrier layer which acts as a thermal insulator, preventing, reducing or otherwise limiting the transfer of heat from one device component to another or from a device component to an external structure, fluid or material. Useful thermal barriers include those comprising materials having a thermal conductivity of 0.3 W/m·K or less, such as selected over the range of 0.001 to 0.3 W/m·K. In some embodiments, a thermal barrier comprises active cooling components, such as components known in the art of thermal management, such as thermoelectric cooling devices and systems. Thermal barriers also include those barriers comprising thermal management structures, such as structures useful for transporting heat away from a portion of a device or tissue; in these and other embodiments, a thermal barrier comprises thermally conductive material, for example material having a high thermal conductivity, such as a thermal conductivity characteristic of a metal.

"Leakage current" or "leakage" refers to electric current which flows from an electronic device along an unintended path. Under certain conditions, leakage of sufficient current from an electronic device can damage the device and/or components thereof. In certain circumstances, leakage current can also or alternatively damage the material into which it flows.

"Active circuit" and "active circuitry" refers to one or more device components configured for performing a specific function. Useful active circuits include, but are not limited to, amplifier circuits, multiplexing circuits, logic circuits, CMOS circuits, processors, and current limiting circuits. Useful active circuit elements include, but are not limited to, transistor elements and diode elements.

"Selectively permeable" refers to a property of a material to allow certain substances to pass through the material while preventing other substances from being passed through. In one embodiment, a selectively permeable material allows one or more target chemicals, molecules and/or biomolecules to be passed through the material while preventing water, ionic solutions, bodily fluids, salts, proteins and other substances from being passed through the material. In an embodiment, the barrier layer of a device has spatially patterned permeable regions, impermeable regions or a combination of both permeable regions and impermeable regions. S "Substrate" refers to a material having a surface that is capable of supporting a structure, including an electronic device or electronic device component. An structure that is "bonded" to the substrate refers to a portion of the structure in physical contact with the substrate and unable to substantially move relative to the substrate surface to which it is bonded. Unbonded portions, in contrast, are capable of substantial movement relative to the substrate.

A "NMS adjusting layer" refers to a layer whose primary function is adjusting the position of the NMS in the device. For example, the NMS adjusting layer may be an encapsulating layer or an add layer such as an elastomeric material.

In the context of this description, a "bent configuration" refers to a structure having a curved conformation resulting from the application of a force. Bent structures may have one or more folded regions, convex regions, concave regions, and any combinations thereof. Useful bent structures, for example, may be provided in a coiled conformation, a wrinkled conformation, a buckled conformation and/or a wavy (i.e., wave-shaped) configuration. Bent structures, such as stretchable bent interconnects, may be bonded to a flexible substrate, such as a polymer and/or elastic substrate, in a conformation wherein the bent structure is under strain. In some embodiments, the bent structure, such as a bent ribbon structure, is under a strain equal to or less than 30%, optionally a strain equal to or less than 10%, optionally a strain equal to or less than 5% and optionally a strain equal to or less than 1% in embodiments preferred for some applications. In some embodiments, the bent structure, such as a bent ribbon structure, is under a strain selected from the range of 0.5% to 30%, optionally a strain selected from the range of 0.5% to 10%, and optionally a strain selected from the range of 0.5% to 5%. Alternatively, the stretchable bent interconnects may be bonded to a substrate that is a substrate of a device component, including a substrate that is itself not flexible. The substrate itself may be planar, substantially planar, curved, have sharp edges, or any combination thereof. Stretchable bent interconnects are available for transferring to any one or more of these complex substrate surface shapes.

"Thermal contact" refers to the ability of two or more materials and/or structures that are capable of substantial heat transfer from the higher temperature material to the lower temperature material, such as by conduction. Thermal communication refers to a configuration of two or more components such that heat can be directly or indirectly transferred from one component to another. In some embodiments, components in thermal communication are in direct thermal communication wherein heat is directly transferred from one component to another. In some embodiments, components in thermal communication are in indirect thermal communication wherein heat is indirectly transferred from one component to another via one or more intermediate structures separating the components.

"Fluid communication" refers to the configuration of two or more components such that a fluid (e.g., a gas or a liquid) is capable of transport, flowing and/or diffusing from one component to another component. Elements may be in fluid communication via one or more additional elements such as tubes, containment structures, channels, valves, pumps or any combinations of these. In some embodiments, components in fluid communication are in direct fluid communication wherein fluid is capable of transport directly from one component to another. In some embodiments, components in fluid communication are in indirect fluid communication wherein fluid is capable of transport indirectly from one component to another via one or more intermediate structures separating the components.

"Electrical contact" refers to the ability of two or more materials and/or structures that are capable of transferring charge between them, such as in the form of the transfer of electrons or ions. Electrical communication refers to a configuration of two or more components such that an electronic signal or charge carrier can be directly or indirectly transferred from one component to another. As used herein, electrical communication includes one way and two way electrical communication. In some embodiments, components in electrical communication are in direct electrical communication wherein an electronic signal or charge carrier is directly transferred from one component to another. In some embodiments, components in electrical communication are in indirect electrical communication wherein an electronic signal or charge carrier is indirectly transferred from one component to another via one or more intermediate structures, such as circuit elements, separating the components.

"Optical communication refers to a configuration of two or more components such that electromagnetic radiation can be directly or indirectly transferred from one component to another. As used herein, optical communication includes one way and two way optical communication. In some embodiments, components in optical communication are in direct optical communication wherein electromagnetic radiation is directly transferred from one component to another. In some embodiments, components in optical communication are in indirect optical communication wherein an electromagnetic radiation is indirectly transferred from one component to another via one or more intermediate structures, such as reflectors, lenses, or prisms, separating the components.

"Ultrathin" refers to devices of thin geometries that exhibit extreme levels of bendability. In an embodiment, ultrathin refers to circuits having a thickness less than 1 µm, less than 600 nm or less than 500 nm. In an embodiment, a multilayer device that is ultrathin has a thickness less than 200 µm, less than 50 µm, or less than 10 µm.

"Thin layer" refers to a material that at least partially covers an underlying substrate, wherein the thickness is less than or equal to 300 µm, less than or equal to 200 µm, or less than or equal to 50 µm. Alternatively, the layer is described in terms of a functional parameter, such as a thickness that is sufficient to isolate or substantially reduce the strain on the electronic device, and more particularly a functional layer in the electronic device that is sensitive to strain.

"Dielectric" refers to a non-conducting or insulating material. In an embodiment, an inorganic dielectric comprises a dielectric material substantially free of carbon. Specific examples of inorganic dielectric materials include, but are not limited to, silicon nitride and silicon dioxide.

"Polymer" refers to a macromolecule composed of repeating structural units connected by covalent chemical bonds or the polymerization product of one or more monomers, often characterized by a high molecular weight. The term polymer includes homopolymers, or polymers consisting essentially of a single repeating monomer subunit. The term polymer also includes copolymers, or polymers consisting essentially of two or more monomer subunits, such as random, block, alternating, segmented, graft, tapered and other copolymers. Useful polymers include organic polymers or inorganic polymers and may be in amorphous, semi-amorphous, crystalline or partially crystalline states. Cross linked polymers having linked monomer chains are particularly useful for some applications. Polymers useable in the methods, devices and device components include, but are not limited to, plastics, elastomers, thermoplastic elastomers, elastoplastics, thermostats, thermoplastics and acrylates. Exemplary polymers include, but are not limited to, acetal polymers, biodegradable polymers, cellulosic polymers, fluoropolymers, nylons, polyacrylonitrile polymers, polyamide-imide polymers, polyimides, polyarylates, polybenzimidazole, polybutylene, polycarbonate, polyesters, polyetherimide, polyethylene, polyethylene copolymers and modified polyethylenes, polyketones, poly(methyl methacrylate, polymethylpentene, polyphenylene oxides and polyphenylene sulfides, polyphthalamide, polypropylene, polyurethanes, styrenic resins, sulfone based resins, vinyl-based resins, rubber (including natural rubber, styrene-butadiene, polybutadiene, neoprene, ethylene-propylene, butyl, nitrile, silicones), acrylic, nylon, polycarbonate, polyester, polyethylene, polypropylene, polystyrene, polyvinyl chloride, polyolefin or any combinations of these.

"Elastomer" refers to a polymeric material which can be stretched or deformed and return to its original shape without substantial permanent deformation. Elastomers commonly undergo substantially elastic deformations. Useful elastomers include those comprising polymers, copolymers, composite materials or mixtures of polymers and copolymers. Elastomeric layer refers to a layer comprising at least one elastomer. Elastomeric layers may also include dopants and other non-elastomeric materials. Useful elastomers useful include, but are not limited to, thermoplastic elastomers, styrenic materials, olefenic materials, polyolefin, polyurethane thermoplastic elastomers, polyamides, synthetic rubbers, PDMS, polybutadiene, polyisobutylene, poly(styrene-butadiene-styrene), polyurethanes, polychloroprene and silicones. In some embodiments, an elastomeric stamp comprises an elastomer. Exemplary elastomers include, but are not limited to silicon containing polymers such as polysiloxanes including poly(dimethyl siloxane) (i.e. PDMS and h-PDMS), poly(methyl siloxane), partially alkylated poly(methyl siloxane), poly(alkyl methyl siloxane) and poly(phenyl methyl siloxane), silicon modified elastomers, thermoplastic elastomers, styrenic materials, olefenic materials, polyolefin, polyurethane thermoplastic elastomers, polyamides, synthetic rubbers, polyisobutylene, poly(styrene-butadiene-styrene), polyurethanes, polychloroprene and silicones. In an embodiment, a flexible polymer is a flexible elastomer.

"Elastomeric stamp" or "elastomeric transfer device" are used interchangeably and refer to an elastomeric material having a surface that can receive as well as transfer a component, such as an electronic device or component thereof. Exemplary elastomeric transfer devices include stamps, molds and masks. The transfer device affects and/or facilitates feature transfer from a donor material to a receiver material. Stamps and transfer device may be used for assembling components via transfer printing, such as dry contact transfer printing.

"Conformal contact" refers to contact established between a device and a receiving surface, which may for example be a target tissue in a biological environment. In one aspect, conformal contact involves a macroscopic adaptation of one or more surfaces (e.g., contact surfaces) of an implantable device to the overall shape of a tissue surface. In another aspect, conformal contact involves a microscopic adaptation of one or more surfaces (e.g., contact surfaces) of an implantable device to a tissue surface resulting in an intimate contact substantially free of voids. In an embodiment, conformal contact involves adaptation of a contact surface(s) of the implantable device to a receiving surface(s) of a tissue such that intimate contact is achieved, for example, wherein less than 20% of the surface area of a contact surface of the implantable device does not physically contact the receiving surface, or optionally less than 10% of a contact surface of the implantable device does not physically contact the receiving surface, or optionally less than 5% of a contact surface of the implantable device does not physically contact the receiving surface. Conformal contact includes large area conformal contact, for example, wherein conformal contact between a tissue and device component is over an area greater than or equal to 1000 $mm^2$, and optionally greater than or equal to 10,000 $mm^2$.

"Conformable" refers to a device, material or substrate which has a bending stiffness sufficiently low to allow the device, material or substrate to adopt a desired contour profile, for example a contour profile allowing for conformal contact with a surface having a pattern of relief or recessed features. In certain embodiments, a desired contour profile is that of a tissue in a biological environment, for example heart tissue.

"Low modulus" refers to materials having a Young's modulus less than or equal to 10 MPa, less than or equal to 5 MPa, or optionally less than or equal to 1 MPa and optionally for some applications less than or equal to 0.1 MPa.

"Young's modulus" and "modulus" are used interchangeably and refer to a mechanical property of a material, device or layer which refers to the ratio of stress to strain for a given substance. Young's modulus may be provided by the expression;

$$E = \frac{(\text{stress})}{(\text{strain})} = \left(\frac{L_0}{\Delta L}\right)\left(\frac{F}{A}\right), \quad (I)$$

where E is Young's modulus, $L_0$ is the equilibrium length, $\Delta L$ is the length change under the applied stress, F is the force applied and A is the area over which the force is applied. Young's modulus may also be expressed in terms of Lame constants via the equation:

$$E = \frac{\mu(3\lambda + 2\mu)}{\lambda + \mu}, \quad (II)$$

where $\lambda$ and $\mu$ are Lame constants. High Young's modulus (or "high modulus") and low Young's modulus (or "low modulus") are relative descriptors of the magnitude of Young's modulus in a given material, layer or device. In some embodiments, a high Young's modulus is larger than a low Young's modulus, preferably 10 times larger for some applications, more preferably 100 times larger for other applications and even more preferably 1000 times larger for yet other applications. "Inhomogeneous Young's modulus" refers to a material having a Young's modulus that spatially varies (e.g., changes with surface location). A material having an inhomogeneous Young's modulus may optionally be described in terms of a "bulk" or "average" Young's modulus for the entire layer of material.

"Bending stiffness" is a mechanical property of a material, device or layer describing the resistance of the material, device or layer to an applied bending moment. Generally, bending stiffness is defined as the product of the modulus and area moment of inertia of the material, device or layer. A material having an inhomogeneous bending stiffness may optionally be described in terms of a "bulk" or "average" bending stiffness for the entire layer of material.

"Adversely affect" in the context of a tissue and/or biological environment, refers to a stimulus, such as voltage, current, temperature, electric field, electromagnetic radiation or combination thereof, capable of damaging, disrupting, reducing viability and/or killing cells of the tissue in the biological environment. As will be understood by a skilled artisan, conditions that adversely affect a tissue in a biological environment depend on the specific type and composition of the tissue and biological environment of the tissue. In an embodiment, for example, a barrier layer limits the leakage current from the electronic device to the tissue to a specific amount, such as a value equal to or less than 0.1 $\mu A/cm^2$, optionally for some applications equal to or less than 0.01 $\mu A/cm^2$; and optionally for some applications equal to or less than 0.001 $\mu A/cm^2$, so as to not adversely affect the tissue. In an embodiment, for example, a barrier layer limits the thermal transfer from the electronic device to the tissue so as to provide in situ increase in temperature of the tissue equal to or less than 0.5, optionally 1, optionally 2, or optionally 5 degrees Celsius so as to not adversely affect the tissue.

"Encapsulate" refers to the orientation of one structure such that it is at least partially, and in some cases completely, surrounded by one or more other structures. "Partially encapsulated" refers to the orientation of one structure such that it is partially surrounded by one or more other structures. "Completely encapsulated" refers to the orientation of one structure such that it is completely surrounded by one or more other structures. The invention includes implantable devices having partially or completely encapsulated electronic devices, device components and/or inorganic semiconductor components and/or electrodes.

"Biocompatible" refers to a material that does not elicit an immunological rejection or detrimental effect when it is disposed within an in-vivo biological environment. For example, a biological marker indicative of an immune response changes less than 10%, or less than 20%, or less than 25%, or less than 40%, or less than 50% from a baseline value when a biocompatible material is implanted into a human or animal.

"Bioinert" refers to a material that does not elicit an immune response from a human or animal when it is disposed within an in-vivo biological environment. For example, a biological marker indicative of an immune response remains substantially constant (plus or minus 5% of a baseline value) when a bioinert material is implanted into a human or animal.

As used herein, "liquid bandage" refers to a mixture of chemicals that are capable of creating a tissue adhesive such as a polymeric layer that binds to skin, including a polymer that is dissolved in a solvent. A number of liquid bandages are commercially available including Dermabond, Band-Aid, PeriAcryl, GluStitch, Xoin, Gesika, VetGlu, 3M Vetbond, LiquiVet, Indermil, LiquiBand, Histoacryl, New-Skin and Nexcare and compositions related thereto. A thin film of polymer is formed after application when the carrier of the polymer evaporates after application. A liquid bandage is used interchangeably with the term spray bandage. A spray bandage provides an easy means for liquid application without having to physically spread liquid over the area by hand. The liquid or spray bandage may be used to make a contact layer. The liquid or spray bandage may be used to make a cover layer. As desired, multiple layers are made by repeated application, including by liquid or spray bandages of different compositions.

Described herein are conformable electrophysiology data acquisition devices and methods for acquiring electrophysiology data at high-speed and high-resolution. The conformable devices disclosed herein include devices incorporating a moisture barrier; moisture barriers, for example, are useful for preventing conductive solutions from penetrating into electronic devices and thereby producing leakage current from components thereof. The conformable devices disclosed herein include devices useful for diagnosing and treating medical conditions in real time and with high spatial precision. The disclosed devices and methods also include those suited for monitoring electrical, optical, thermal and tissue characteristics of tissues in-vivo as they undergo motion, for example the tissue of a beating heart. The disclosed devices and methods further include those especially suited for monitoring electrical characteristics of tissues having nonplanar surfaces.

The invention may be further understood by the following non-limiting examples.

EXAMPLE 1

High-Speed, High-Resolution Cardiac Electrophysiology In-Vivo Using Conformal Electronics Mapping cardiac arrhythmias with standard, clinical electrophysiology (EP) devices can be a tedious, lengthy process, particularly over the epicardial surface. Probes with small numbers (4-10) of widely spaced (2-5 mm) passive electrodes sequentially record electrical activity from small areas of heart muscle as they are moved manually, point to point, across regions of interest. Because each electrode requires a separate connection to external processors, spatial resolution and mapping speed are limited by practical constraints on the number and configuration of electrodes and wires that can fit in the device. This example describes a high resolution, high speed system that eliminates these constraints. The device uses fully integrated, conformal electronic circuits (built with >2,000 single crystal silicon nanoribbon transistors) to simultaneously record from 288 multiplexed (16:1) channels, each with its own on-board amplifier. The low bending stiffness of the device allows it to adhere to the dynamic, three dimensional (3D) surface of the beating heart via physical lamination, without pins or adhesives. This integrated system maps activity at high spatial (sub-mm) and temporal (sub-ms) resolutions over large areas in a single pass, without human intervention. This functionality is demonstrated by mapping the spread of ventricular depolarization from spontaneous and paced activation wavefronts in-vivo in a porcine animal model, thereby introducing a platform for a new generation of intelligent, implantable medical devices.

Sudden cardiac arrest is the leading cause of death in developed countries. Many patients at risk for arrhythmic death have advanced structural heart disease, and preexisting non-lethal ventricular arrhythmias. In these and other cases, cardiac electrophysiologic (EP) studies are used to aid diagnosis and guide therapy. Conventional devices for this purpose use sparse arrays of electrodes that probe potentials at the surface of cardiac tissue. During mapping, sensors are continuously maneuvered to record from discrete sites on the heart. These sequential local recordings are "stitched" together with software to render a complete representation of cardiac electrical activity over a region of interest. The iterative nature of this approach prolongs EP procedures and impedes real time mapping of transient abnormal rhythms. Despite explosive growth and innovation in the broader electronics industry, the key limitation of EP devices is that they have retained the simple electronics-tissue interface of their earliest predecessors of ~40 years ago. Sensing and stimulating electrodes are purely passive metallic contacts individually wired to separate, remote processing units that use traditional semiconductor wafer-based electronics. Rapid, high resolution EP mapping might be most effectively accomplished by embedding modern silicon-based integrated circuit (IC) technology directly at the tissue-electrode interface. Unfortunately the planar shapes and rigid, brittle mechanical properties associated with conventional ICs strictly preclude their non-destructive, intimate integration with the curvilinear, soft surfaces of biological tissues.

Recent advances in material science provide a solution to this problem through scalable routes to ICs that offer the performance of similarly designed devices on semiconductor wafers, but with the mechanical properties of thin sheets of plastic or rubber. This technology relies on established, inorganic semiconductors (e.g. Si) configured into structural forms that provide the desired mechanical properties. For example, single crystal silicon in the form of nanoscale ribbons, membranes or wires are flexible by virtue of their small thicknesses. Multilayer circuit structures that exploit such materials in neutral mechanical plane designs can accommodate bending to radii of curvature of ~50 μm without fracture or degradation in their electrical properties.

These and related strategies enable high-performance, active electrode arrays that can stretch, fold, and conform to complex, 3D dynamic surfaces, such as the epicardial surface of the beating heart. The ability to incorporate active, powered components on flexible substrates, including amplifiers and transistor-based multiplexing circuitry, enables a high density of active electrodes on an EP device, without the need for a connecting wire between each element, or for an implanted or external control unit. Below, this example further describes the successful implementation of a system of this type, at levels of integration (i.e. >2000 transistors) that significantly exceed previous reports of active biomedical or other classes of flexible devices, and in clinically relevant modes of use (i.e. high speed, high resolution EP mapping in-vivo) that provide clear advantages over existing technologies. The results are important not only to cardiac EP applications but more generally to new classes of active electronic systems that can be integrated intimately with the human body for diagnostic or therapeutic benefit.

Figure 1A:
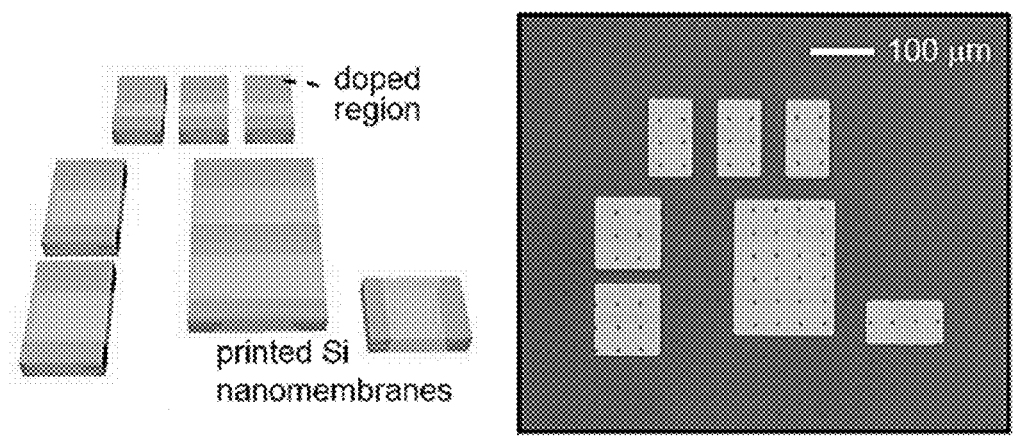
FIGS. 1a, 1, 1c, 1d and 1e provide schematic illustrations and images corresponding to steps for fabricating a device.
Figure 1B:
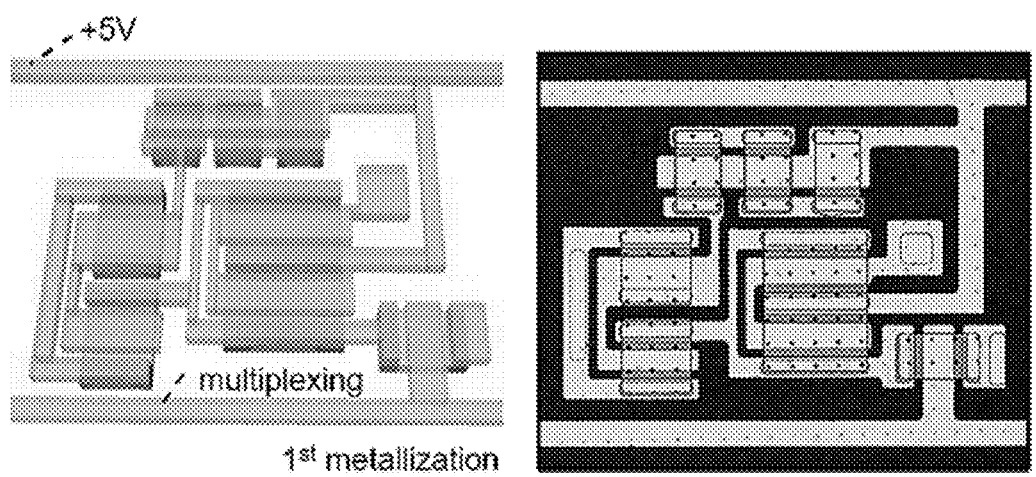
Figure 1C:
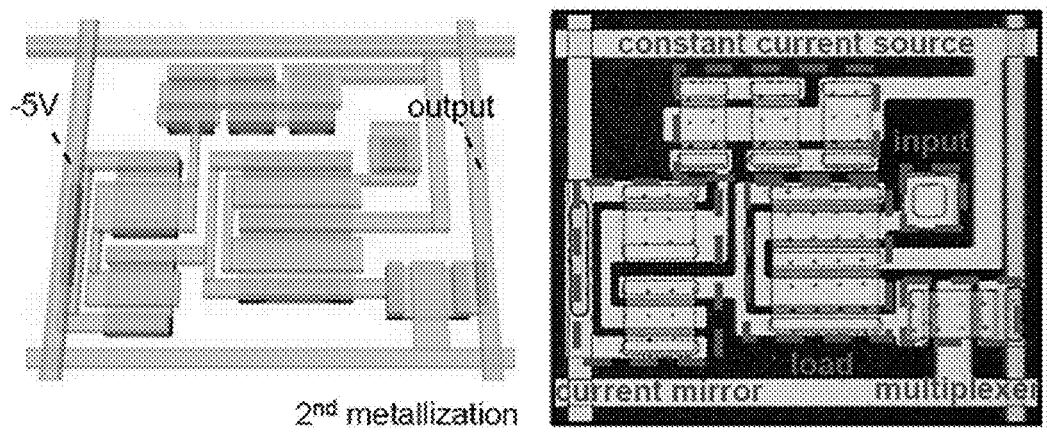
Figure 1D:
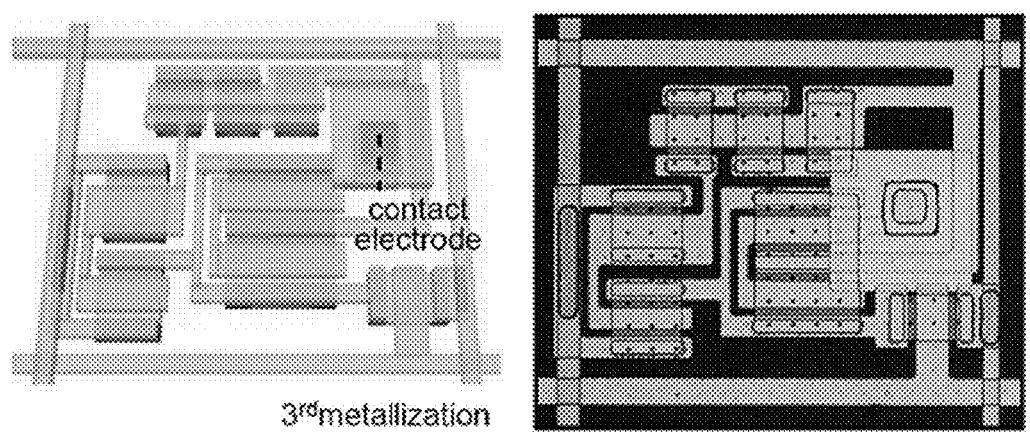
Figure 1E:
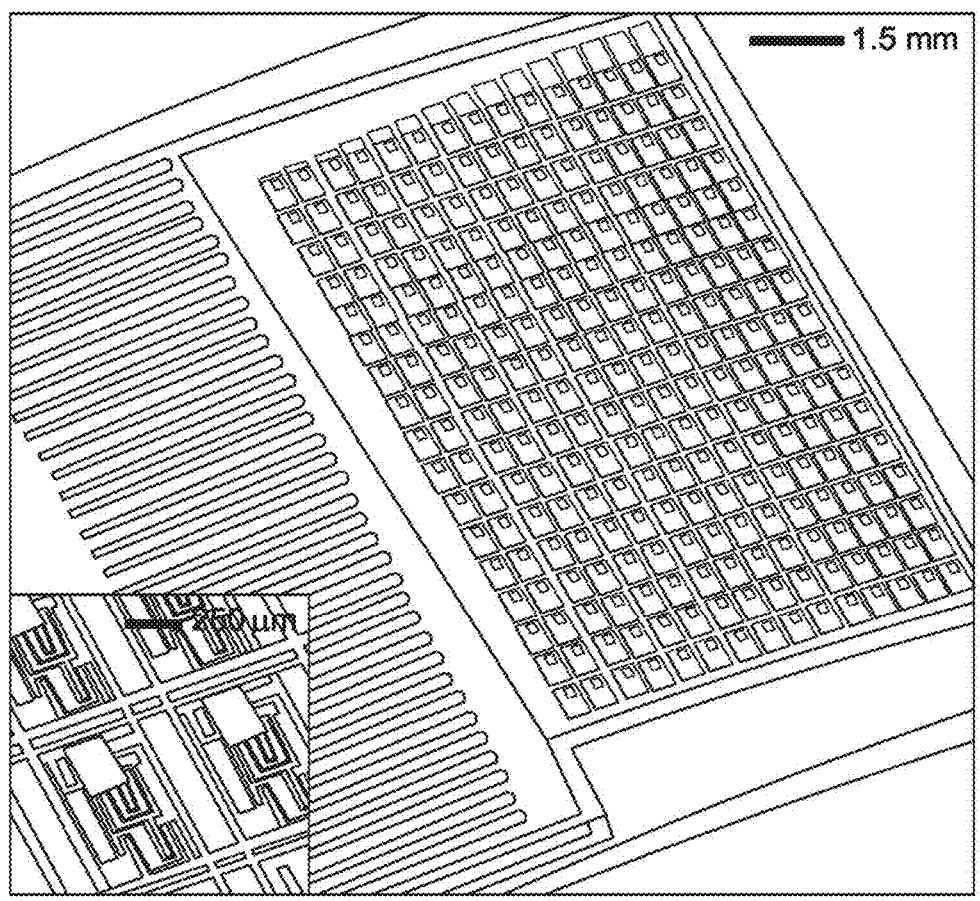

FIG. 1 shows a set of images and illustrations that detail the fabrication sequence at a single unit cell (FIGS. 1a-d), and a completed device (FIG. 1e). Each cell consists of a contact pad that serves as an electrical interface to the tissue and an associated amplifier and multiplexer. The device includes an 18 by 16 array of such amplified electrodes to provide a total of 288 measurement points, spaced by 800 μm and covering a total area of 14.4 mm by 12.8 mm. See FIG. 1. Each unit cell comprises 7 transistors for a total of 2016, representing the highest level of integration achieved in any non-display flexible electronic system. With integrated multiplexing circuitry, only 36 wires are required to connect all 288 measurement points to external data acquisition and control units.

The fabrication involves formation of transistors and interconnects in four metal layers. In the first step, transfer printing delivers to a flexible plastic substrate (polyimide; ~25 μm) an organized collection of single crystalline, semiconductor grade silicon nanomembranes (260 nm) with patterned regions of doping for ohmic contacts (FIG. 1a). Plasma enhanced chemical vapor deposition of SiO2 (~100 nm) at reduced temperatures yields a gate dielectric through which source/drain contact openings are formed by photolithography and etching in buffered oxide etchant. Electron beam evaporation, photolithography and wet etching define the first layer of metal interconnect, including source, drain and gate contacts, as shown in FIG. 1b. Similarly fabricated second and third metal layers form the column and row addressing electrodes (FIG. 1c, d) where a thin layer of spin cast polyimide (1.4 μm) with etched via holes provides the interlayer dielectric between the first and second metal layers, a trilayer organic/inorganic stack (polyimide/$Si_3N_4$/epoxy; 1.4 μm/80 nm/9 μm) and a single layer of epoxy (9 μm) forms a similar interlayer for the second and third and third and fourth metal layers, respectively. Details appear in FIGS. 5 through 9, described below. These different layers locate the circuit at the neutral mechanical plane and ensure reliable operation when immersed in saline solution, as described subsequently. The top metal layer defines surface electrodes (Au pads, 250×250 μm) that contact the cardiac tissue and connect to the underlying circuits through via holes. These electrodes, which we refer to as inputs, have impedances of 100 KOhm+10% at 1 KHz, as measured using a similarly designed passive electrode array immersed in normal saline (0.9%) solution. The entire device connects to a data acquisition system through an anisotropic conductive film (ACF) connector with 36 contacts. See the methods and FIG. 10 for details of the fabrication procedures, and dimensions of devices.

Figure 2A:
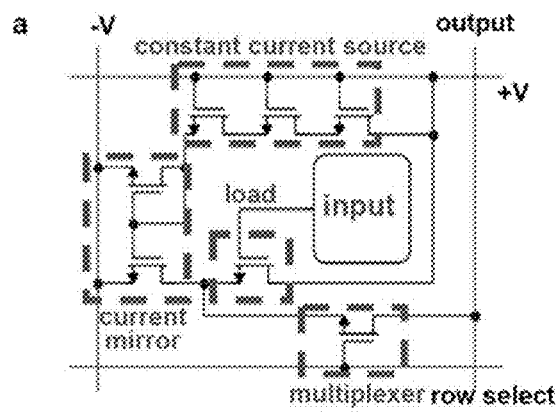
FIGS. 2a and 2b provide designs of multiplexing circuits for conformable devices.
Figure 2B:
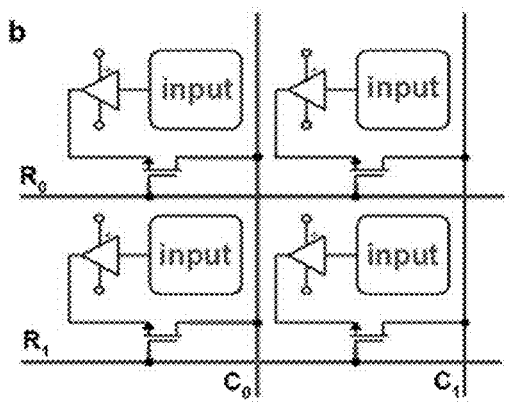
Figure 2C:
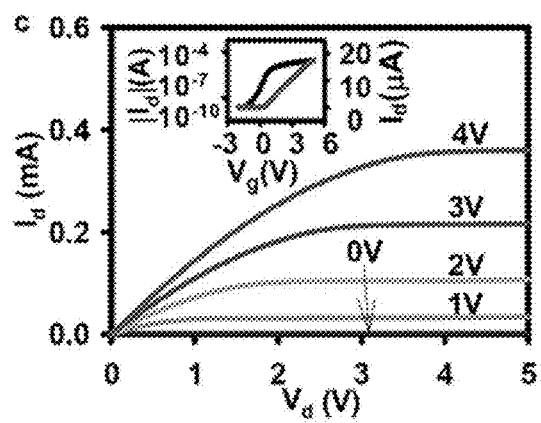
FIGS. 2c, 2d, 2e and 2f provide data showing electrical properties of conformable devices.
Figure 2D:
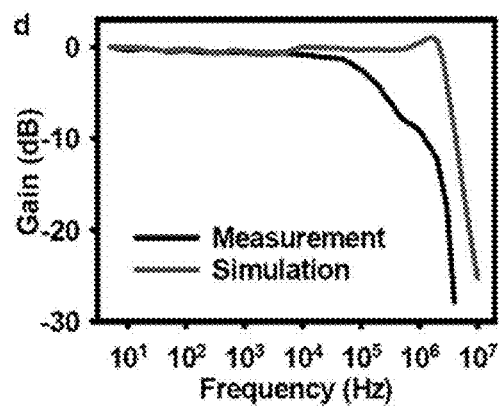
Figure 2E:
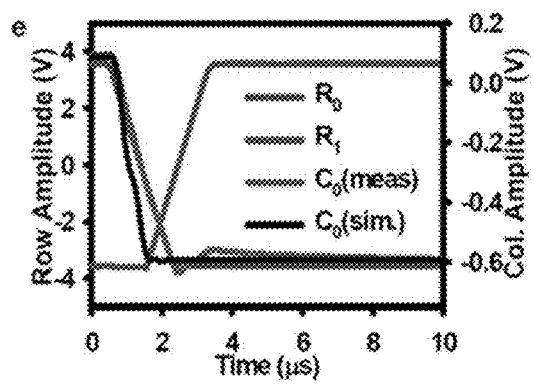
Figure 2F:
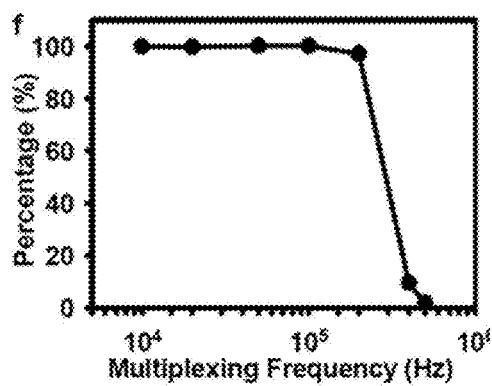

The right frames of FIG. 1c and FIG. 2a provide annotated images and circuit diagrams, respectively, of the amplifier and the multiplexing transistor. The amplifier uses a source-follower configuration with significant current gain. The multiplexing transistor enables readout of all inputs via programmed, sequential addressing of each row of electrodes, thereby providing a 16× reduction in the required number of output wires compared to a non-multiplexed electrode array. The schematic in FIG. 2b illustrates how the unit cell in FIG. 2a can be connected to other unit cells to create the multiplexed signal output. During multiplexed sampling, one row of electrodes is selected at a time by driving one of the row select signals, such as $R_0$ (highlighted in blue in FIG. 2b), high and all of the others low ($R_1 \ldots R_n$, where $R_1$ is highlighted in green). This allows the unit cells in that row to drive the column output lines ($C_0 \ldots C_n$, where $C_0$ is highlighted in red), which are connected to a high-speed analog to digital converter (see FIG. 11, National Instruments, USA). Row select signals are rapidly cycled to sample all electrodes on the array. FIG. 2c presents electrical characteristics of a representative multiplexing transistor. The transistor exhibits an on/off ratio and electron mobility of ~$10^5$ and ~490 cm$^2$/Vs, respectively. The high mobility, compared to organics or other materials for flexible electronics, enables the amplifier to have a high bandwidth, as shown in FIG. 2d, and the multiplexer to switch quickly, as shown in FIG. 2e, even for the relatively coarse dimensions of the devices reported here (i.e. channel lengths of ~40 μm). FIG. 2d shows the measured and simulated bandwidth of a single amplifier with the multiplexing disabled. The amplifier shows performance properties consistent with design targets and simulations, i.e. −3 db cutoff frequency of ~200 kHz. Simulations were obtained using commercial software (Cadence, Cadence Design Systems, USA). See methods for more details about the simulations. As shown in FIG. 2e, the multiplexer switching time was about 5 μs. The switching time was limited, however, by the slew rate of the external row select signals provided to the array, as shown in blue and green. FIG. 2f shows the percentage of the final voltage value attained during the allotted settling time, averaged across all of the electrodes, for increasing multiplexing frequency. These results demonstrate that multiplexing rates up to 200 kHz are possible, yielding sampling rates up to 12.5 kHz per electrode. FIG. 12 further shows that the signal to noise ratio (SNR) for the system remains constant up to 200 kHz multiplexing frequency. If the slew rate of the row select signals is increased, the multiplexing rate can be further increased. In experiments described below, the 16 row select signals were cycled at 10 kHz, yielding a sampling rate of 625 Hz per active electrode, with all 16 electrodes in a given row thus sampled simultaneously. The multiplexed analog signals were synchronously sampled at 50 kHz, 5 times oversampling per switch interval, to improve the signal-to-noise ratio. Data were acquired, demultiplexed, stored, and displayed using custom MATLAB software (The MathWorks™, Natick, Mass.).

Figure 2G:
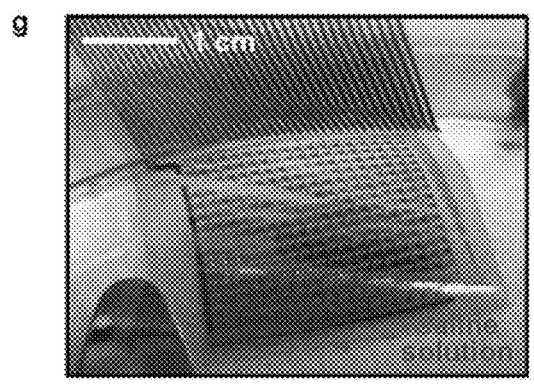
FIG. 2g shows an image of a conformable device submerged in saline solution and FIG. 2h shows a sine wave response before and after saline immersion.
Figure 2H:
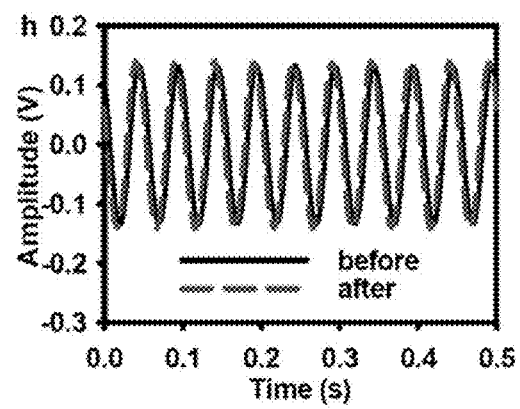

In addition to the electrical properties, mechanical flexibility and capacity to operate while immersed in a saline environment are critically important for this application. Analytical mechanics modeling elucidates the bend-induced strains in all layers of the devices used in animal experiments. The thicknesses of the layers of epoxy and the substrate were chosen to place the active circuit components near the neutral mechanical plane. As a result, for bend radii of ~5 cm, typical of those encountered in human cardiac EP studies, maximum strains in the Si and SiO$_2$ are calculated to be 0.001% and 0.0001%, respectively. These values are orders of magnitude below the fracture strains for our devices, and they are also significantly less than those expected to alter their electrical performance. Another feature of the device design is that the bending stiffness of the circuit is sufficiently low to allow conformal wrapping on the moist surface of the cardiac tissue. These mechanics can also be modeled by comparing the system energy for a circuit in a flat configuration to one in a wrapped state (see FIG. 13). The result is that wrapping is energetically favored when $\gamma > B/2R^2$, where $\gamma$ is the adhesion energy between the circuit and the tissue, R is the radius of curvature, and B is the bending stiffness of the circuit. Using R~2.5 cm and a computed value of B, one finds that wrapping is the preferred configuration for cases where $\gamma > 34.7$ mJ/m$^2$. The reported value of adhesion energy between two wet surfaces is ~75-150 mJ/m$^2$. Based upon these models and measurements from the fabricated devices, the conclusion is that the circuits will naturally wrap around the cardiac tissue without any separate mechanism to ensure adhesion. The partially wet surface of the tissue, in-vivo, facilitates this outcome. To accommodate this aspect and to enable device use in realistic clinical settings, the circuit must provide sustained operation when immersed in the body's fluids. It was found that the inorganic/organic encapsulation scheme described previously serves as an effective water barrier for this purpose. FIG. 2g shows a circuit immersed in a saline bath, to test for leakage currents by creating a conduction path from the device to a separate ground electrode in the bath. A cutoff value of 10 μA was selected, consistent with the International Electrotechnical Commission standards for medical electronic equipment (IEC 60601-1). Roughly 75% of the fabricated devices passed this test. Randomly selected samples were tested for long term reliability in the saline bath and found to operate for greater than 3 hours while maintaining a leakage current less than 10 μA. FIG. 2h presents 20 Hz sine wave response before and after saline immersion for 10 minutes, verifying negligible changes in circuit properties. 4 Hz and 40 Hz results are also displayed in FIG. 14.

Figure 3A:
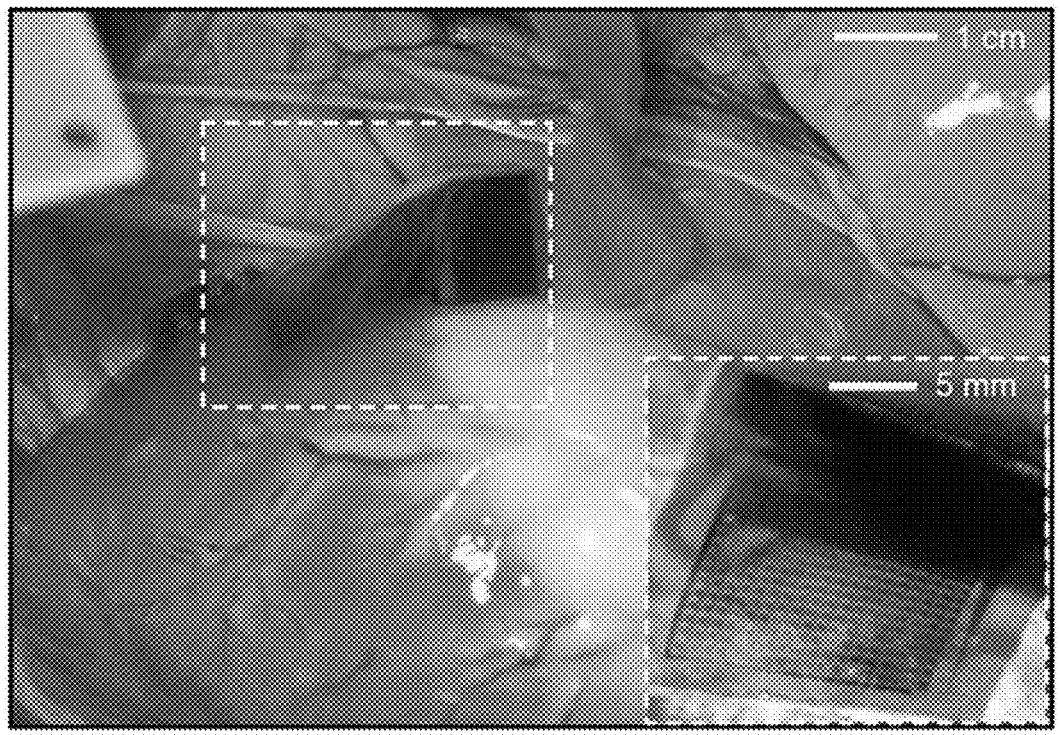
FIGS. 3a, 3b and 3c show photographs of a conformable device in vivo.
Figure 3B:
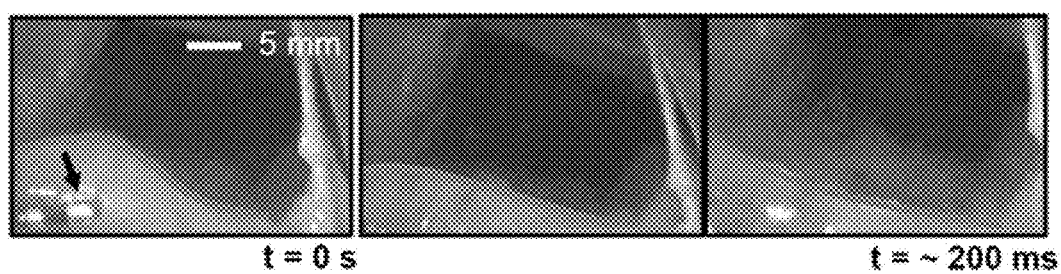
Figure 3C:
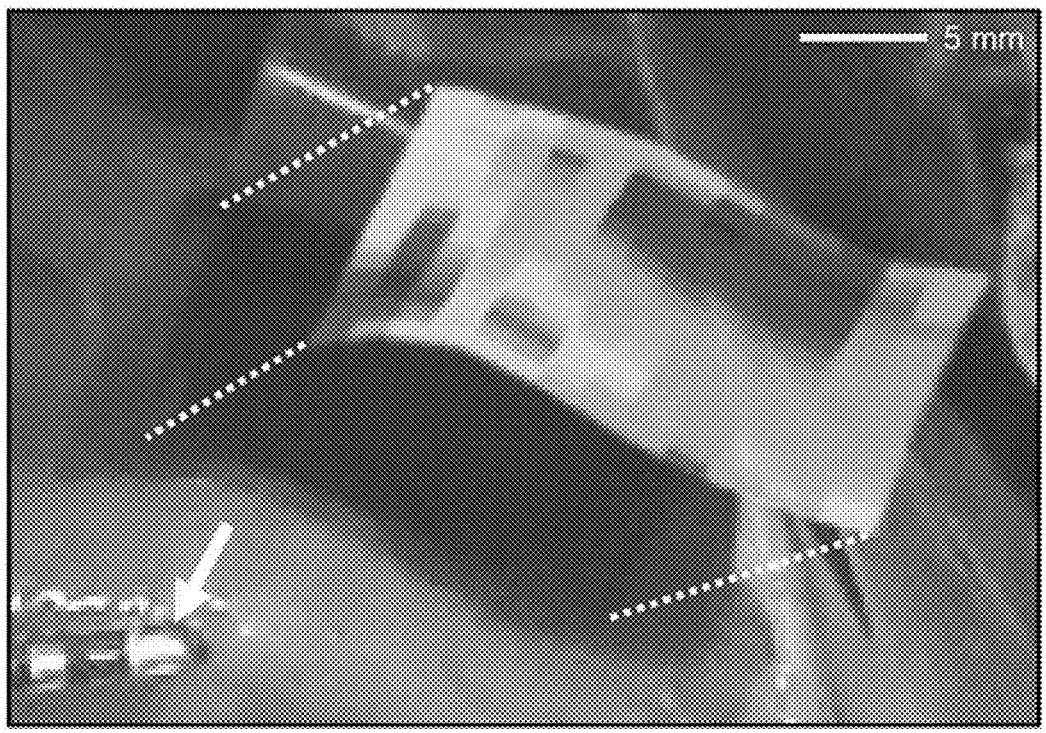

In-vivo experiments were performed in normal 80-90 pound male Yorkshire pigs. The heart was surgically exposed via a median sternotomy and a subsequent pericardiotomy. The flexible EP circuit was then placed on the epicardial surface while under direct visualization (FIG. 3a). See methodology details in FIG. 15 and FIG. 21. The device remained adhered to the curvilinear surface of the heart, even during vigorous cardiac motion. FIG. 3b shows motion snapshots at various stages of the cardiac cycle; the blue lines highlight the dynamic variations in the surface shape associated with maintaining conformal contact. Given the average heart rate of ~77 beats per minute (BPM) during in-vivo experiments and a recording duration of ~137 minutes, the device provided reliable data over the course of >10,000 bending cycles during the experiments. Unipolar voltage data were recorded from all 288 electrode elements using the sampling and multiplexing strategy described above. Baseline electrogram data were collected in sinus rhythm with the array in multiple positions and orientations on the epicardial surface. Data were also recorded while pacing the heart from multiple locations relative to the array via a standard, non-steerable decapolar electrode EP catheter (Boston Scientific, San Jose, Calif.) held in contact with the epicardial surface. FIG. 3c shows the array positioned over the left anterior descending (LAD) coronary artery, with the pacing catheter positioned just inferior to the array. The color coded map in this frame shows a visual representation of the data collected from the device, using procedures described below.

Figure 4A:
FIGS. 4a, 4b, 4c, 4d, 4e and 4f provide representative electrophysiology data recorded by a conformable device in vivo.
Figure 4B:
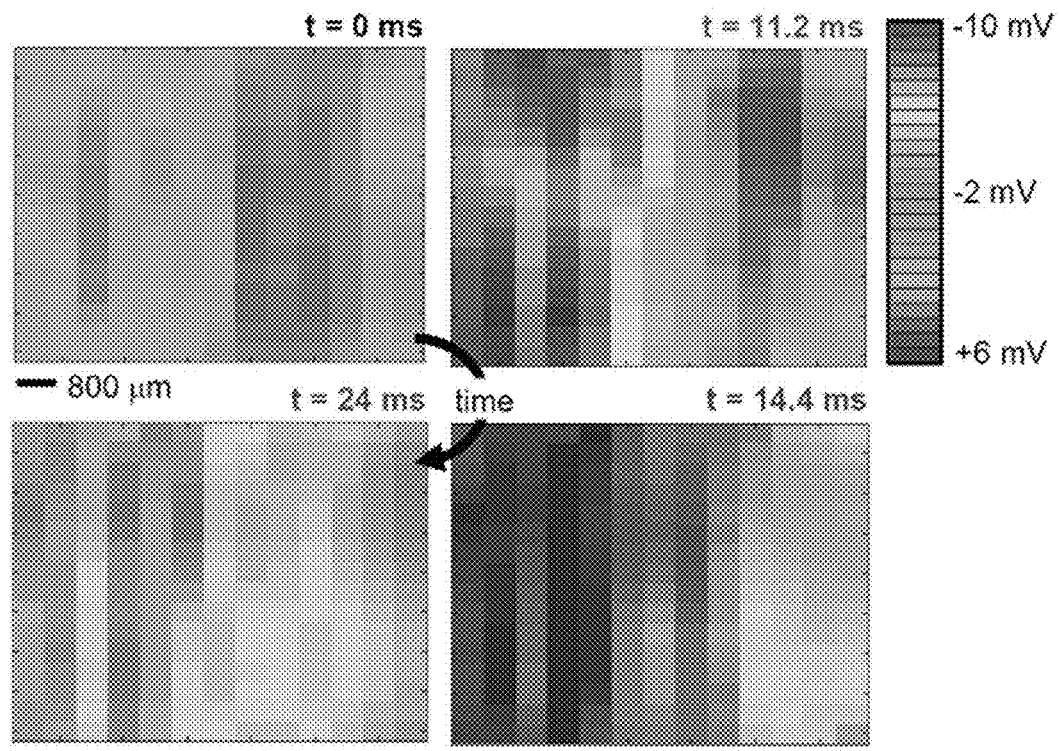
Figure 4C:
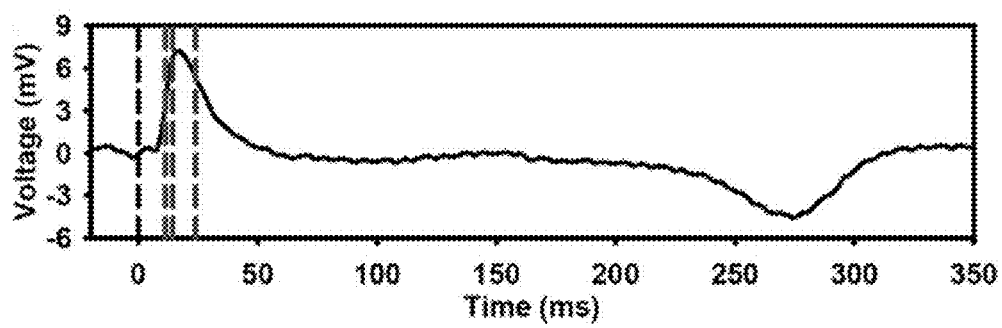
Figure 4D:
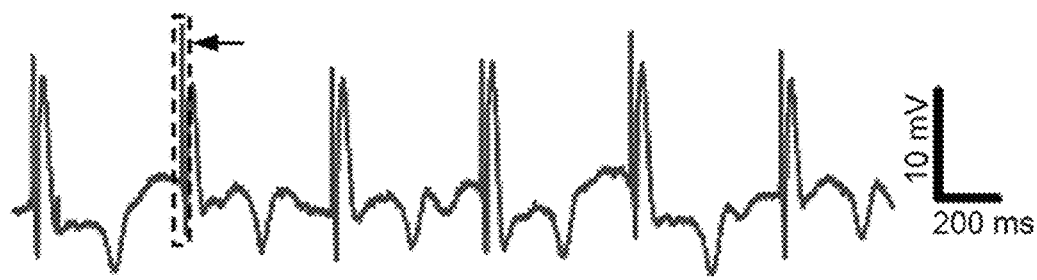
Figure 4E:
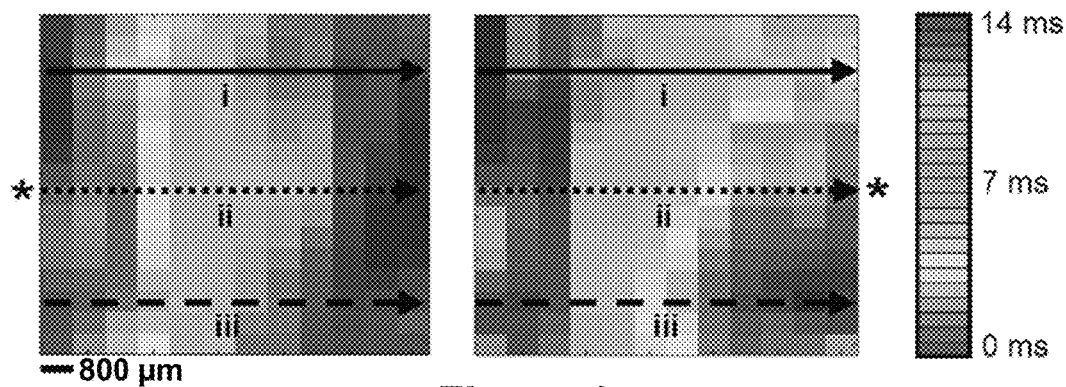
Figure 4F:
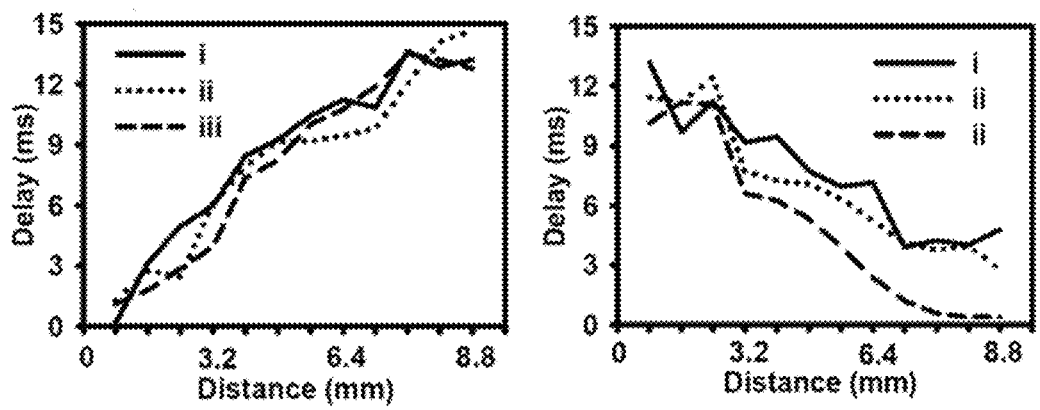
Figure 5A:
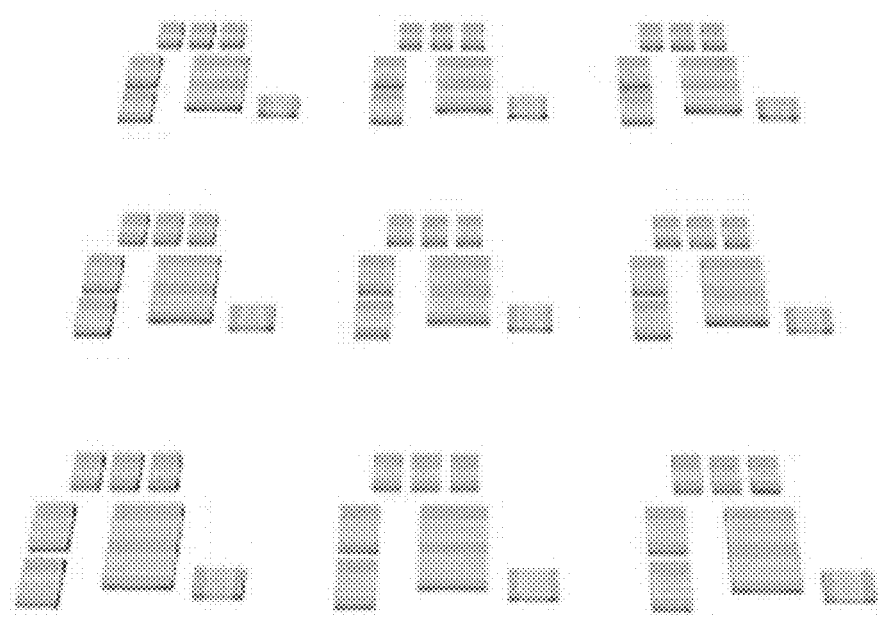
FIGS. 5a, 5b, 5c and 5d provide schematic illustration corresponding to steps for fabricating conformable devices.
Figure 5B:
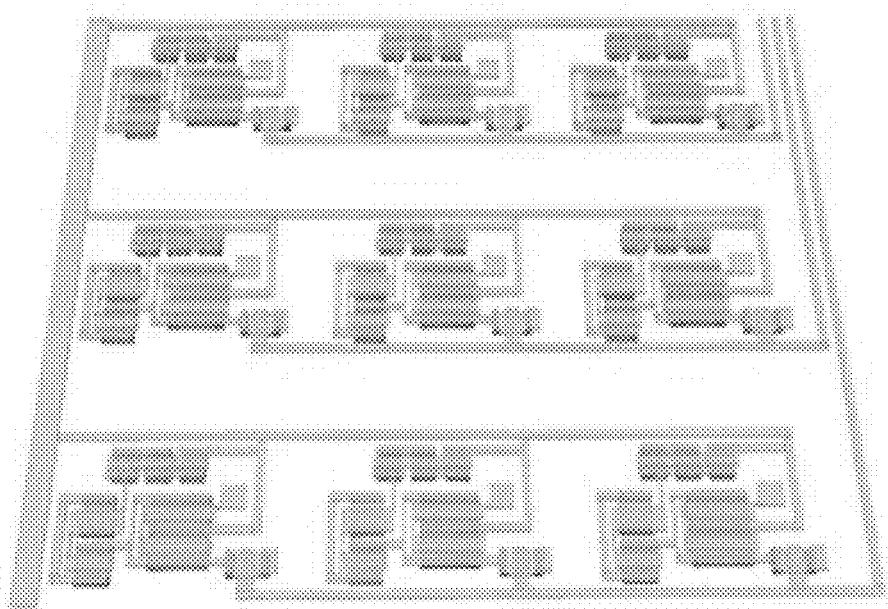
Figure 5C:
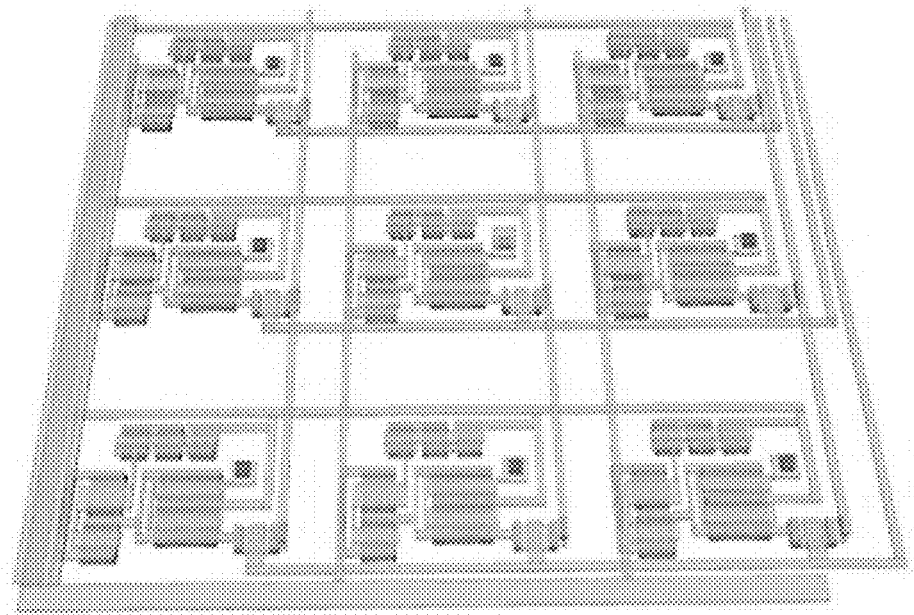
Figure 5D:
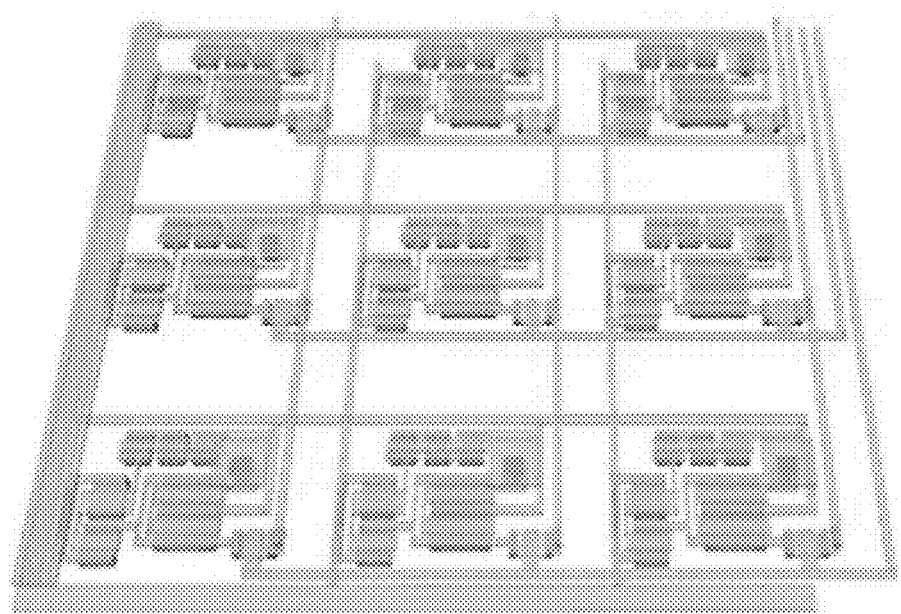
Figure 16:
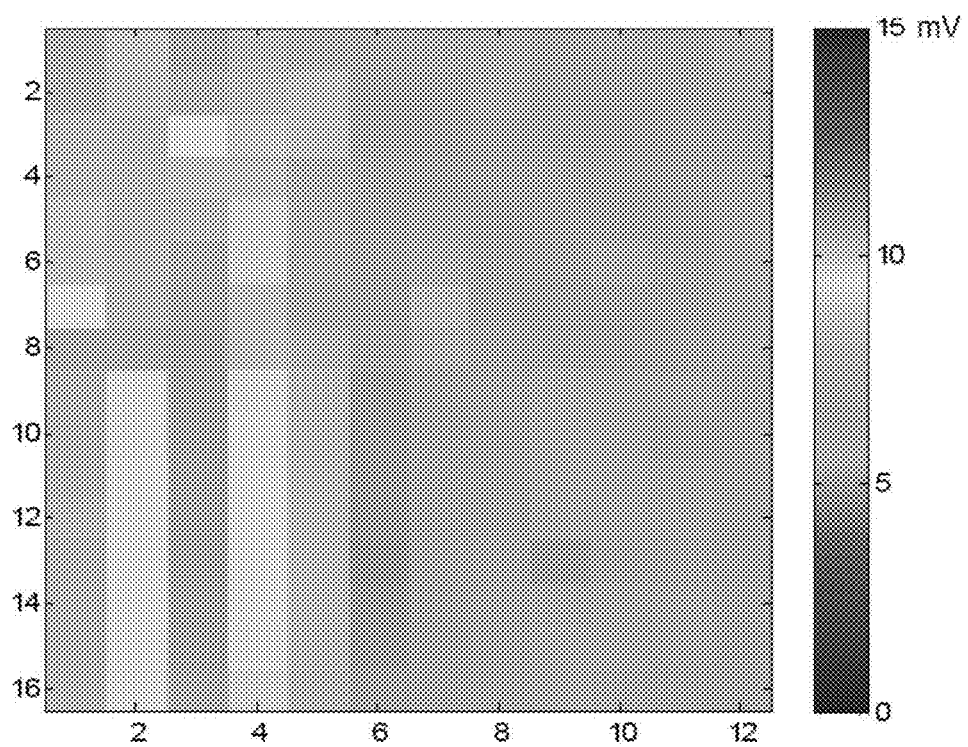
FIG. 16 shows a color map illustrating the average amplitude of electrophysiology data measured over a cardiac activation cycle.
Figure 17A:
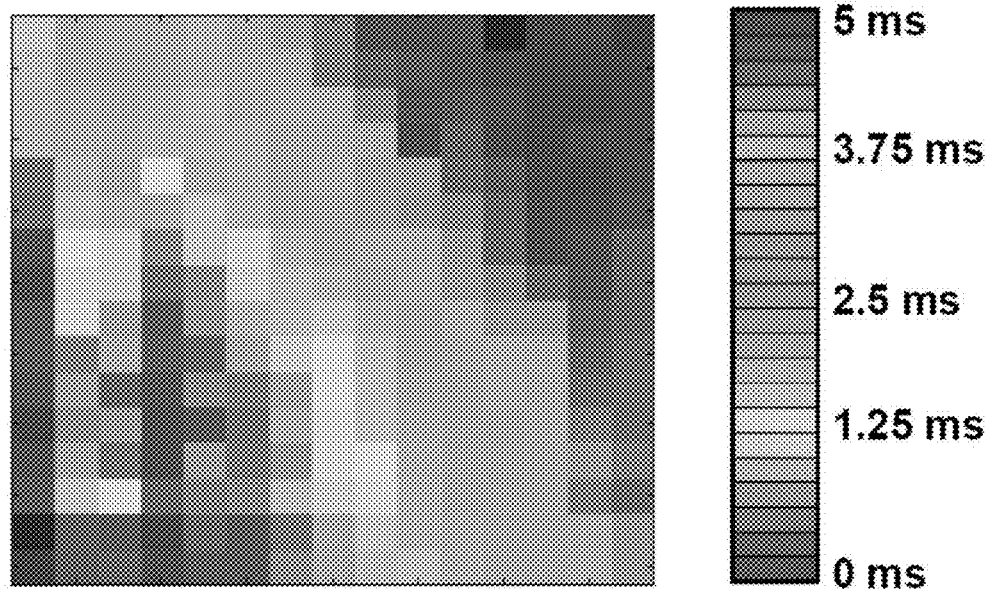
FIGS. 17a and 17b show isochronal activation maps without and with external pacing, respectively. The relative pacing electrode is indicated by an asterisk.
Figure 17B:
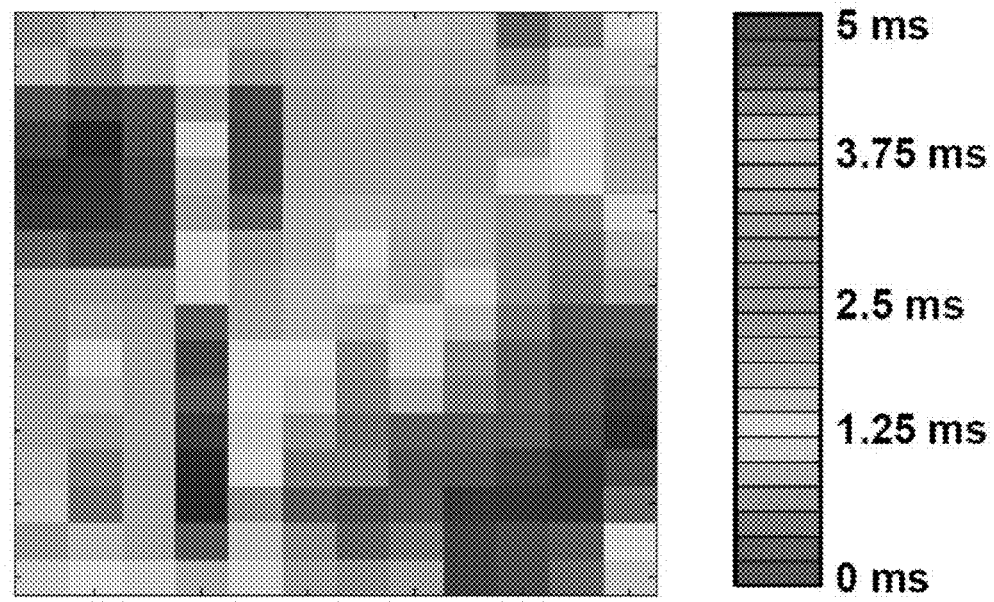
Figure 18:
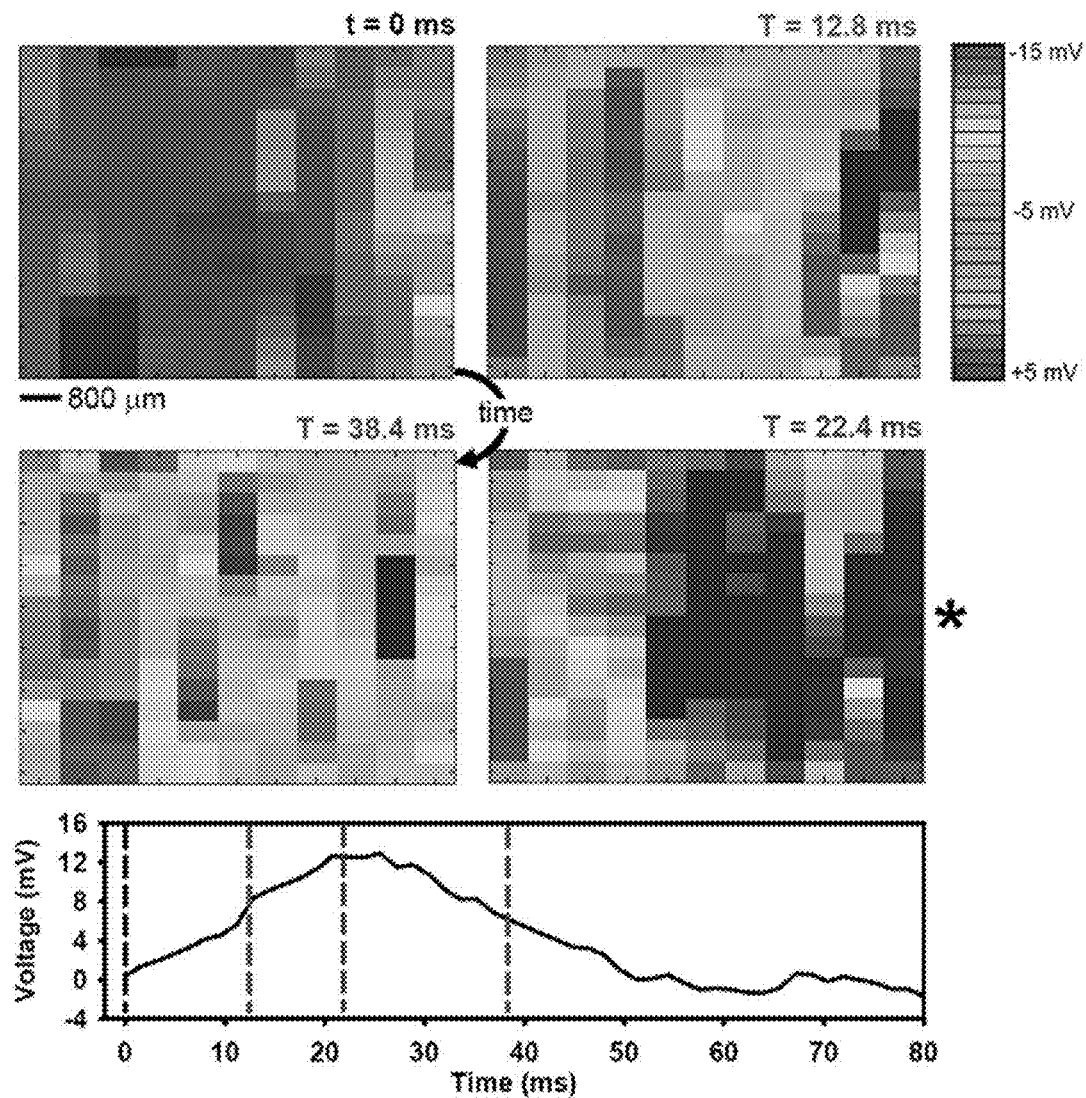
FIG. 18 shows representative voltage data for cardiac electrophysiology measurements at four points in time during a cardiac activation cycle.
Figure 22:
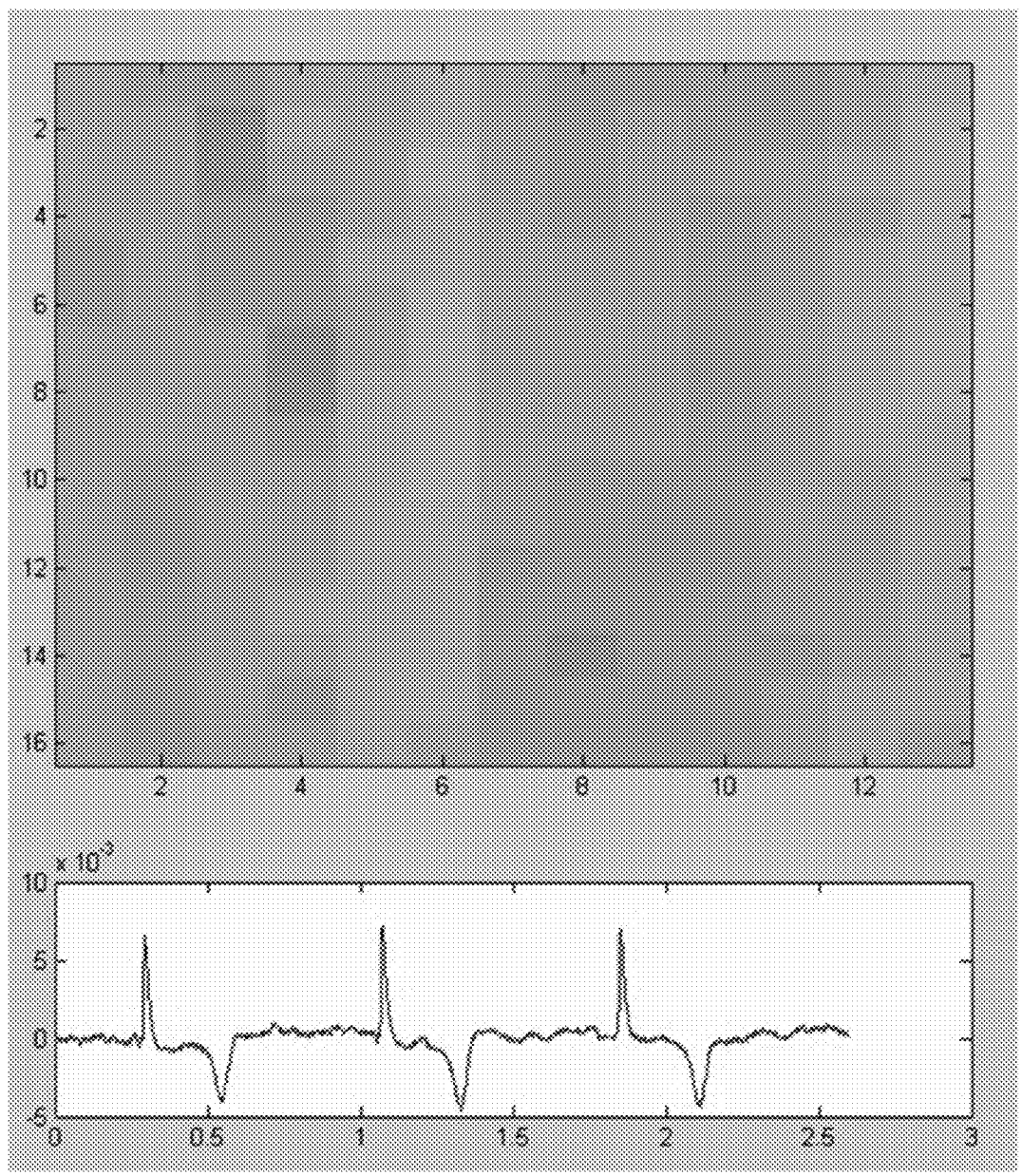
FIG. 22 shows a frame from an electrophysiology data map movie for an unpaced heart.
Figure 23:
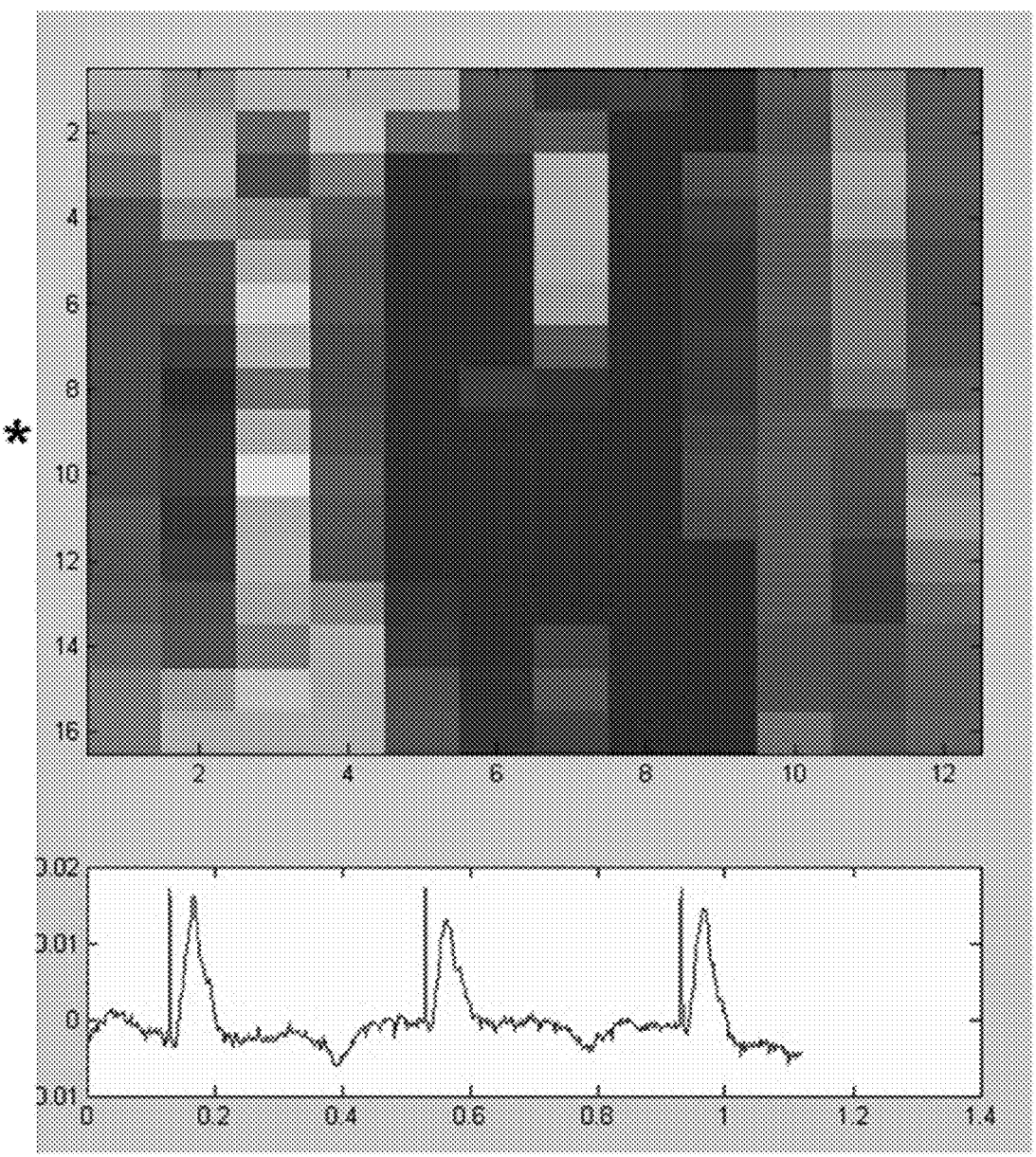
FIG. 23 shows a frame from an electrophysiology data map movie for a paced heart.
Figure 24:
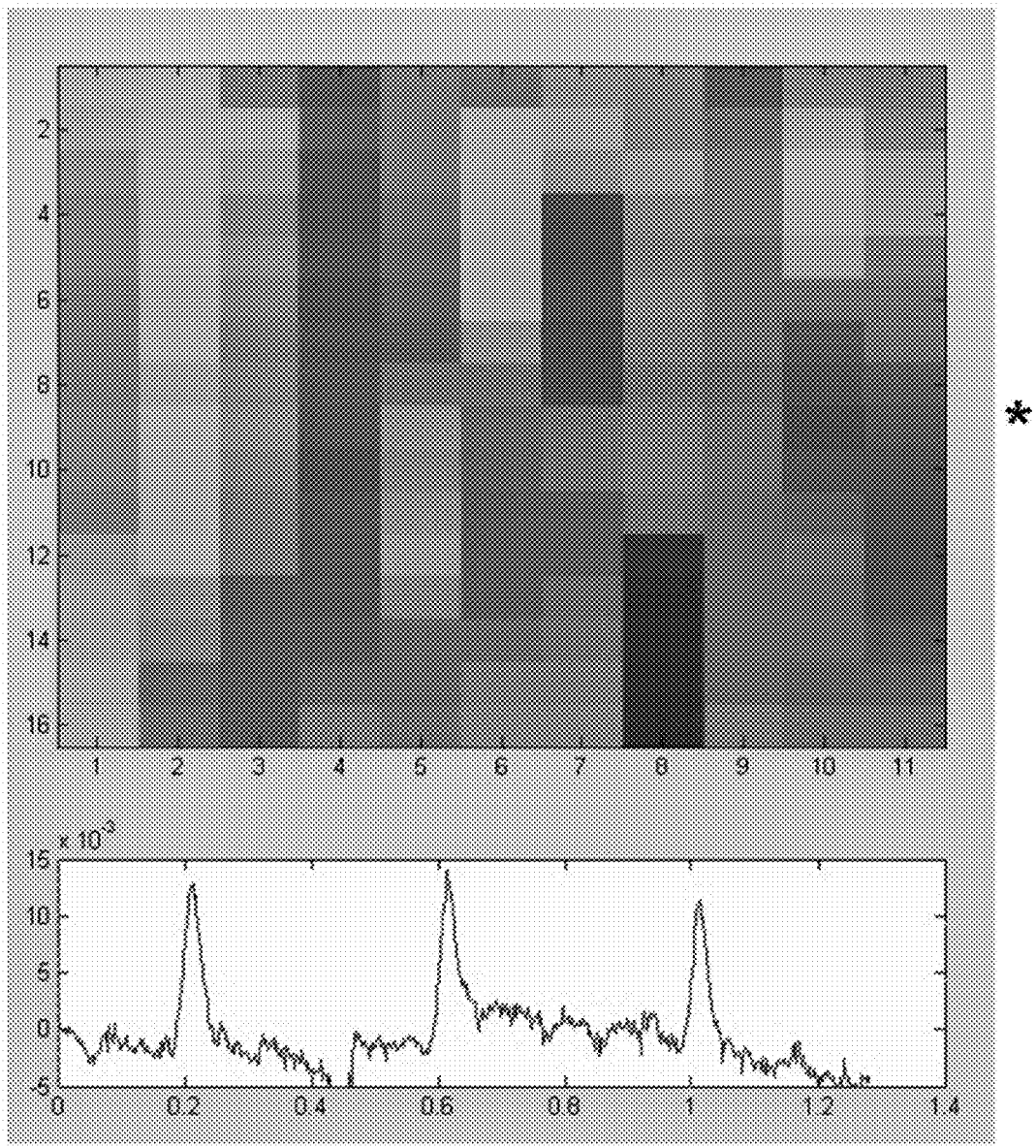
FIG. 24 shows a frame from an electrophysiology data map movie for a paced heart.

Data from all channels were filtered and processed using custom MATLAB software to determine the relative activation time at each contact by comparing the time of the maximum negative slope (dV/dt) of the unipolar electrogram to the maximum negative slope of the average electrogram of all 288 channels. These activation times were then used to generate isochronal maps showing propagation of paced and unpaced cardiac depolarization wavefronts spreading across the array for a variety of recording sites and pacing conditions (see FIG. 22 for more details). Sample voltage trace data from a single channel without remote pacing are shown in FIG. 4a. The inset at right highlights the very low noise level of the recording. The signal to noise ratio (SNR) is approximately 50. Note that negative is plotted up by convention. FIG. 4b shows voltage data for all channels taken at 4 points in time. FIG. 22 shows some of the voltage data presented in FIG. 4b. FIG. 16 illustrates the uniformity of all of the electrodes by plotting the average peak amplitude of the cardiac activation. FIG. 17a shows an isochronal activation map made from this voltage data, illustrating the natural activation pattern of the heart. Data from 5 of the 18 columns have been removed due to failures in the metal interconnections. All of the remaining channels and all rows functioned properly. FIG. 4c shows an average voltage trace collected from all of the electrodes. Dashed lines have been plotted on the trace to illustrate the instant in time that each frame in FIG. 4b was taken. Sample voltage trace data from a single channel with remote pacing are shown in FIG. 4d. FIGS. 4e and 17b show isochronal maps generated by pacing from three different locations relative to the array. Based on relative activation times, conduction velocity across the array (transverse to fiber axis) was 0.9 mm/msec (FIG. 4e); the velocity in the longitudinal direction (approximately parallel to the orientation of the LAD) was faster by a factor of 3 (FIG. 17b). These results are consistent with anisotropic conduction properties measured in previous studies. FIG. 18 shows the same paced voltage data as in the right panel of FIG. 4e for all channels taken at 4 instants in time. FIG. 23 and FIG. 24 show sample voltage data used to generate the isochronal map in the left and right panels of FIG. 4e, respectively. FIG. 4f shows sample distance vs. activation plots for selected rows of the electrode array following the arrows in FIG. 4e.

Collectively, these results represent mapping of electrical activity in the heart at unprecedented rates and levels of spatial and temporal resolution. This approach of conformal, integrated circuits for a new form of biointerfaced electronics provides a fundamentally new way to measure electrical processes in or on the body, with many clinically important implications. Specifically for the system introduced here, the high temporal and spatial resolution should improve accuracy and reduce mapping time for many cardiac arrhythmias. The more general benefit of these technologies, in the broadest sense, is the capacity to integrate the full power of silicon-based electronics technology for multiple modalities of sensing and energy delivery on a single conformable device. For example, multi-site cardiac pacing with closed-loop feedback of local ventricular contractility or cardiac output measurements via distributed arrays of active sensory and stimulation electrodes could form the basis of an entirely new class of assistive synchronization devices in cardiology. Furthermore, the mechanical properties of the circuits permit packaging in catheter-based delivery systems, with the ability to deploy on and conform to large, irregular curvilinear surfaces of the body. Pursuing these and related ideas using the materials and electronics strategies reported here has great potential to yield technologies with important benefits to human health.

Methods. Circuit design. Each unit cell incorporates an nMOS based source-follower amplifier configuration. This circuit provides significant current gain to enable fast switching of the multiplexers by supplying the current needed to charge the parasitic output capacitances. These parasitics come from several sources, including the inactive multiplexing transistors in a given column, the ~2 foot long cables that connect the electrode array to the interface circuit board, the circuit board itself and the input capacitance of its buffer amplifiers.

Circuit fabrication. The fabrication starts with the preparation of the polyimide substrate (25 μm; Kapton, Dupont, USA). For ease of handling, a sheet of this material was attached to a glass slide coated with a thin layer of poly (dimethylsiloxane) as a soft adhesive. Separately doped silicon nanoribbons were prepared through a high temperature diffusion process using a p-type silicon-on-insulator (SOI) wafer (Si(260 nm)/SiO$_2$ (1000 nm)/Si; SOITEC, France) and phosphorous spin-on-dopant (SOD) (P509, Filmtronics, USA). A 300 nm thick layer of SiO$_2$ deposited by plasma enhanced chemical vapor deposition (PECVD) served as the diffusion barrier mask. Doping regions were defined through conventional photolithography and CF$_4$/O$_2$ reactive ion etching (RIE). The diffusion was performed at 950~1000° C. in a rapid thermal annealing (RTA) system. A series of wet etching steps with HF and piranha solution (H$_2$O$_2$ and H$_2$SO$_4$ mixture) removed the SOD and SiO$_2$.

Figure 19:
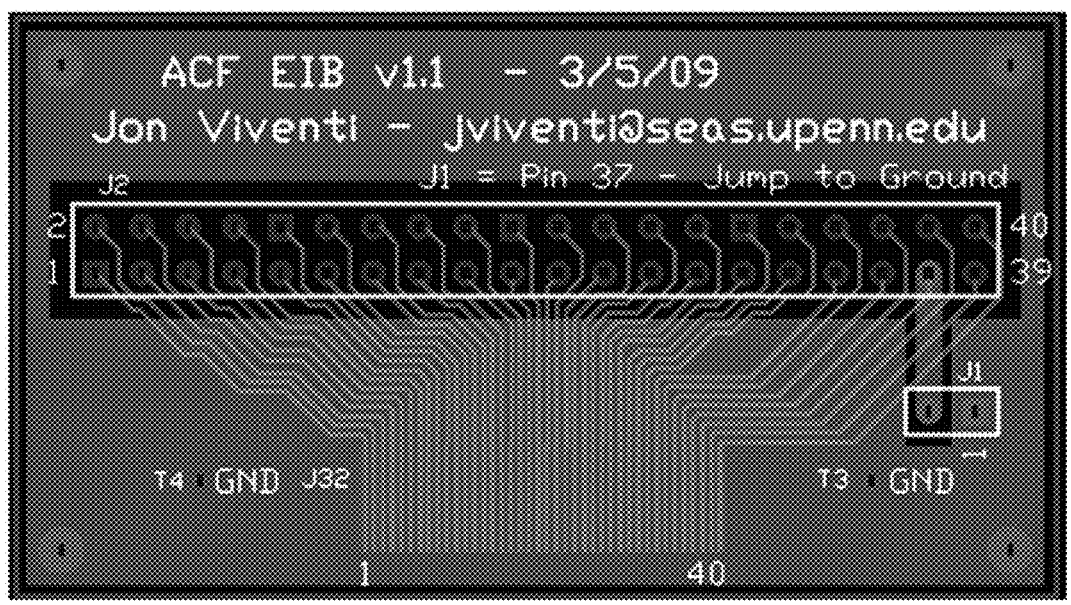
FIG. 19 shows the design of an adapter circuit board embodiment for connecting a conformable device to external circuitry through a 40 pin ribbon cable.

Doped nanomembranes derived by patterned etching of the top silicon layer of the SOI wafer were transfer printed onto the polyimide substrate using a thin, spin cast layer of a precursor to polyimide as an adhesive. To prepare the structures for transfer, the buried SiO$_2$ layer was etched away with concentrated HF solution to yield freestanding nanomembranes. The polyimide precursor was cured at 300° C. for 1 h immediately after printing. Further isolation of the active Si components, such as source, drain and channel regions, was accomplished by photolithography and reactive ion etching with SF$_6$. A thin gate oxide of SiO$_2$ (~100 nm) was then deposited by PECVD. The source/drain contact regions were opened with buffered oxide etchant through a photolithographically patterned mask. The gate electrodes and metal interconnects were deposited by electron evaporation of Cr/Au (~5 nm/~145 nm) and patterned through wet etching. Each unit cell contains 7 transistors, interconnected by wiring as described in the main text. Isolation of the metal layers was accomplished with a polyimide interlayer dielectric with thickness of 1.4 μm. Connections between layers were established through holes defined by patterned reactive ion etching with O$_2$. A stack of organic/inorganic insulation layers followed by encapsulation with a photocurable epoxy (SU8, Microchem Corp) formed a water-tight seal, as described above. The flexible heat seal connector was used to connect the electrodes with the data acquisition system. After aligning the connector to gold pads at the periphery of the circuit, the application of heat (~170° C.) and pressure (applied with clips) for 15 min. formed low resistance and strong connection between the conductive film and the electrode array. The other side of flexible conductive film was connected to an adapter circuit board. The design of this adapter board is shown in FIG. 19.

Acquisition system. The adapter circuit board was connected via a standard 40 pin ribbon cable to the main interface circuit board shown in FIG. 20. This custom circuit board provided the row select signals from to the electrode array and provided buffering of the analog output signals from the array. The buffering was accomplished by TLC2274 op-amps (Texas Instruments). This stage of buffering further reduced the output impedance to allow for longer cable runs and improved switching speed. The outputs of this circuit board were connected to National Instruments PXI-6281 and USB-6259 high-speed M Series multifunction data acquisition (DAQ) modules via standard BNC cables. The National Instruments DAQ modules were used to generate the row select signals and to sample the multiplexed analog output signals from the electrode array. In total, 18 analog input channels were used.

Circuit Simulation. Simulations were performed using Cadence's "spectreS" simulator. The "NCSU_TechLib_ami06" tech library was used for all of the transistors.

Animal experiments. The array was placed on the heart of an adult pig and conformed to the epicardial surface, including epicardial coronary vessels (FIG. 3). Initially, the array was positioned between the epicardium and parietal pericardium, where it was demonstrated to slide easily across the surface of the heart. Subsequently, the parietal pericardium was removed, and the array was left to stay in position via surface tension alone.

Supplementary Methods. Nearly all of the materials and methods relied on specialized setups specifically designed for this project, including many of the planar processing steps and transfer printing processes, the encapsulation strategies, the circuit designs and acquisition system, the methods for interconnection and readout and the mechanics analysis. The following describes additional details on certain aspects.

Fabrication sequence. The steps, outlined above, were implemented using a mask set illustrated in FIGS. 5 and 6. In FIG. 5, the green boxes correspond to the isolated silicon active regions that are connected by pink color first metal layer. After spin coating of PI interlayer dielectric and following dry etching for via, first metal layers are connected to yellow color second metal layer through purple color first via, which finishes the device fabrication process, as shown in FIG. 5.

Figure 7:
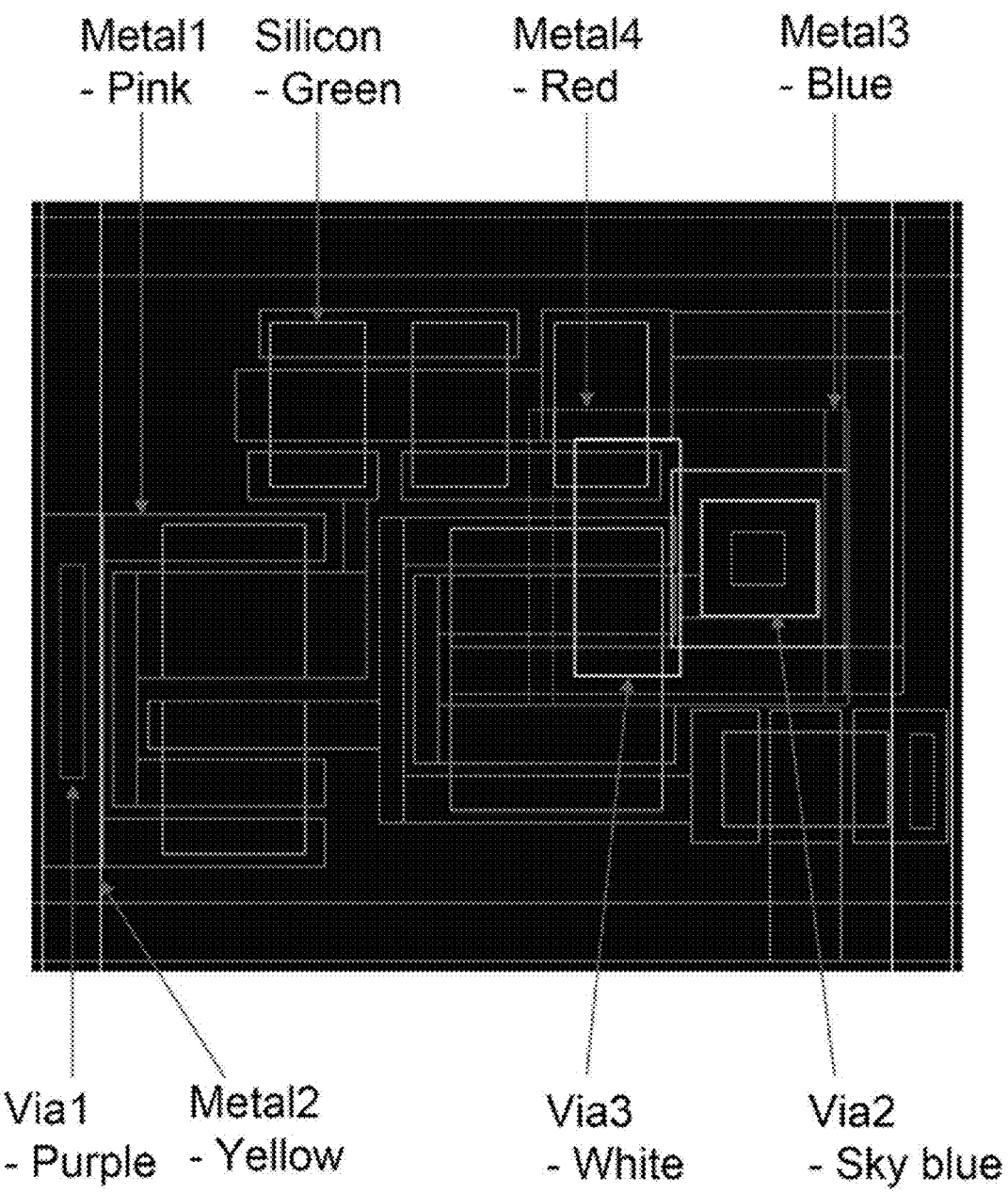
FIG. 7 shows the physical layout of a single unit cell of a conformable device embodiment.
Figure 8:
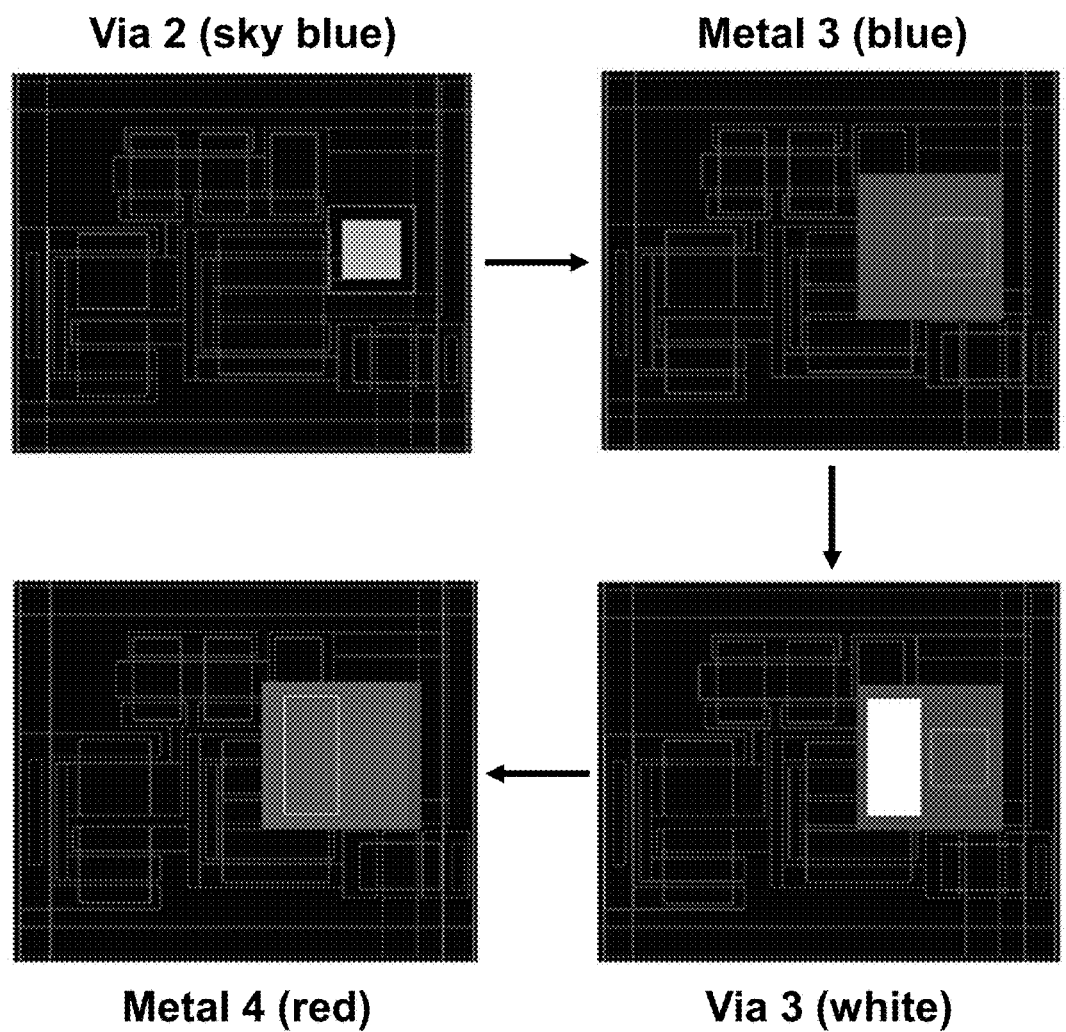
FIG. 8 shows processing steps for forming the unit cell of FIG. 7.

Since the measurement environment is wet and contains large amount of ions due to the saline solution, a multilayer insulation strategy is required to prevent the leakage current that may cause electrical shock to the test animal. The inorganic/organic multilayer and additional thick organic insulation layer were used for this passivation, as shown in FIGS. 7 and 8. FIG. 7 shows the overall design and FIG. 8 describes step by step encapsulation process. Another aspect of the encapsulation design is the misaligned via structure, between via 2 and via 3. By the intentional misalignment of the vias, the first via can be completely covered by the final epoxy layer.

Figure 10A:
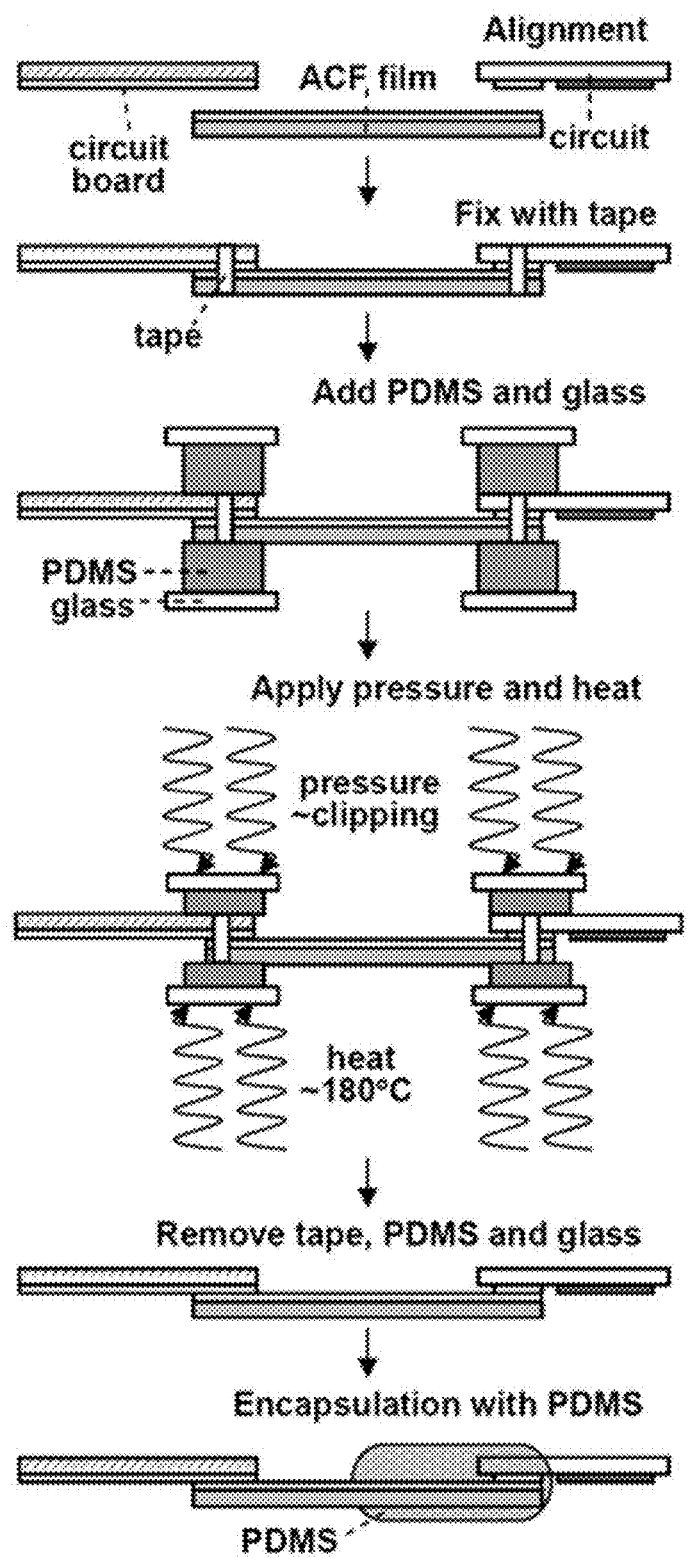
FIG. 10a shows a flow diagram for wiring a conformable device to an external circuit.
Figure 10B:
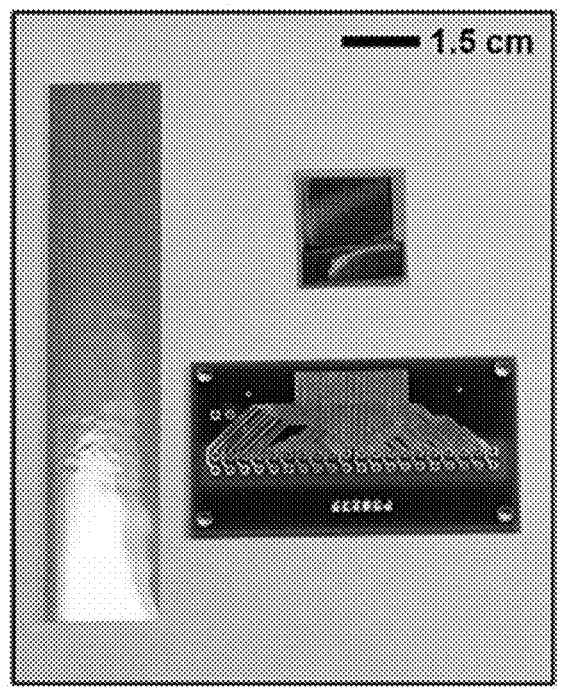
FIGS. 10b and 10c show photographs of a flexible device and external wiring components.
Figure 10C:
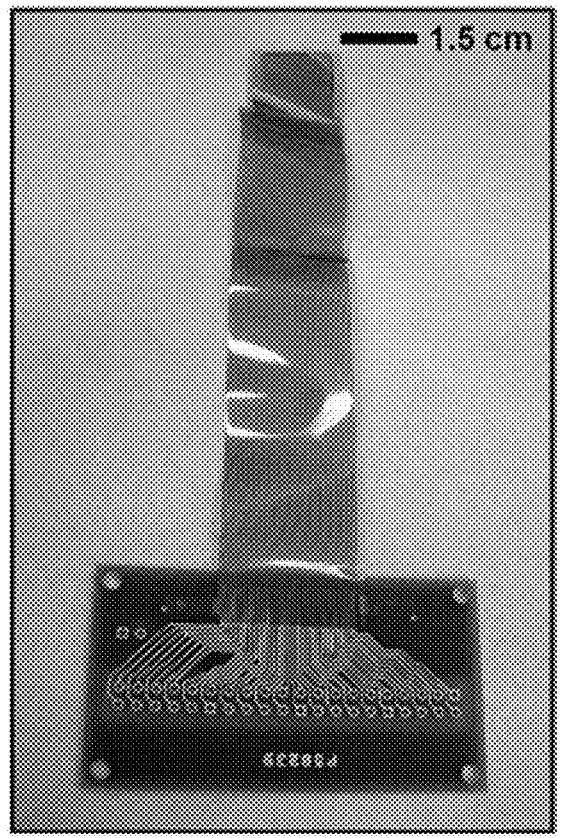

Interconnection scheme. After the device fabrication, the flexible sensor can be interconnected to the circuit board through a flexible ACF film. For this connection, heat and pressure should be applied. After alignment between ACF film and the sample, clipping with conventional metal clips provide enough pressure for the connection. To prevent mechanical failure in samples during clipping and to spread pressure over the whole connection area, a piece of PDMS and glass can be added, as shown in FIG. 10a. After clipping, heating at 180° C. for 15 min. results in a good connection between the metal and ACF film. The image before and after the heal seal connection is shown in FIGS. 10b and 10c.

Data processing. Data from all channels were high pass filtered at 1 Hz and 20 times up-sampled to 12.5 kHz sampling rate before processing. After up-sampling the data were smoothed and demeaned to remove the DC bias. An average signal was constructed and the derivative was taken to identify the relative activation times using an automatic peak search algorithm.

Figure 13A:
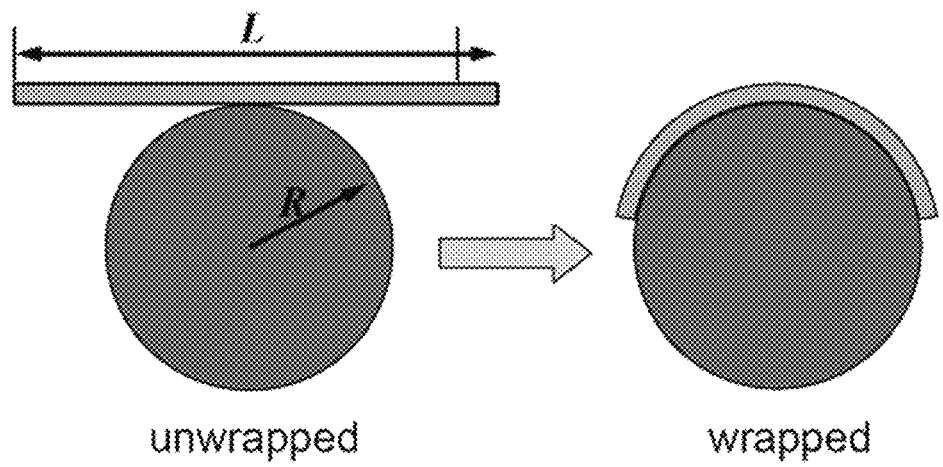
FIGS. 13a and b respectively show a schematic diagram of wrapping a conformable device on a curved surface and a cross sectional view of a conformable device embodiment.

Mechanics of the circuit wrapping on a curved surface. For a thin film of length L and bending stiffness B wrapping on a cylinder of radius R, as shown in FIG. 13a, the total energy of the wrapped state is composed of two parts, the bending energy in the thin film $U_b$ and the adhesion energy $U_a$ between the thin film and the cylinder. The bending energy in the thin film is $$\frac{1}{2}U_b = \frac{1}{2}B\kappa^2 L = \frac{B}{2R^2}L. \tag{III}$$

The adhesion energy is $$\frac{1}{2}U_a = -\gamma L, \tag{IV}$$

where γ is the adhesion energy (per unit area) between the thin film and the cylinder. If $U_b+U_a<0$ (the unwrapped state has energy of 0), the wrapped state is energetically favorable, and thus the thin film wraps around the cylinder. This gives $$\gamma > \frac{B}{2R^2}. \tag{V}$$

Figure 13B:
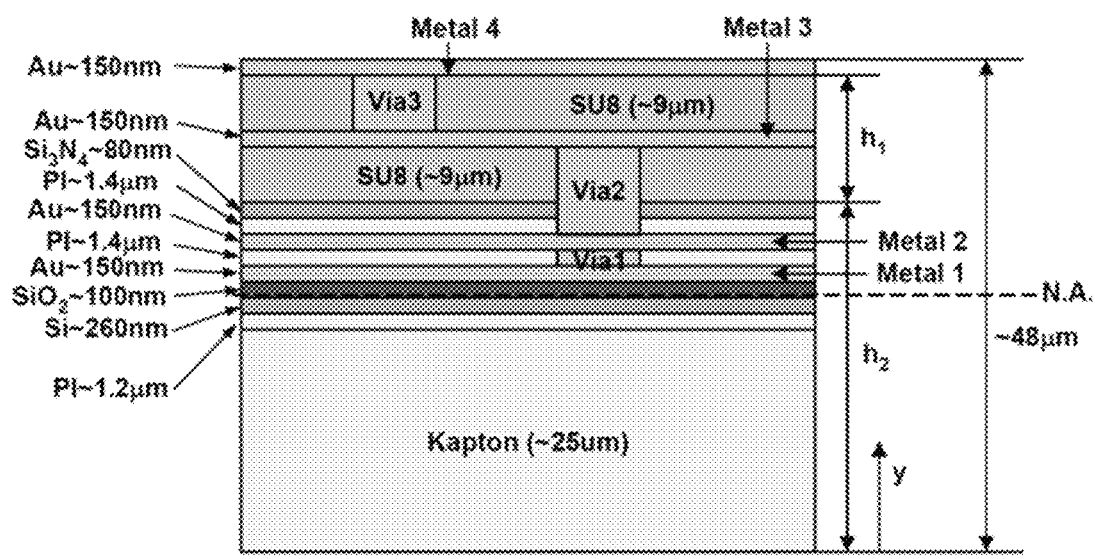

The cross sectional layout of the circuit, which will be used to determine the bending stiffness B, is shown in FIG. 13b. The top SU8 layer has a thickness $h_1$=18 μm, Young's modulus $E_{SU8}$=5.6 GPa and Poisson's ratio $V_{SU8}$=0.22. The bottom PI layer has a thickness $h_2$=25 μm, Young's modulus $E_{PI}$=3.4 GPa and Poisson's ratio $V_{PI}$=0.34. The middle layer, of thickness ~5 μm, is composed of several different components. The material and thickness of each component is shown in FIG. 13b, and their Young's moduli are: $E_{Si}$=150 GPa, $E_{SiO2}$=72 GPa, $E_{Au}$=78 GPa, $E_{Si3N4}$=194 GPa. Since each of these components only occupies a small portion of each layer of material, the position of the mechanical neutral axis can be approximately obtained as (within a few percent error)

$$y_0 = \frac{1}{2}\frac{\overline{E}_{PI}h_2^2 + \overline{E}_{SU8}h_1(2h_2 + h_1)}{\overline{E}_{PI}h_2 = \overline{E}_{SUB}h_1}, \tag{VI}$$

where $\overline{E}_{PI}=E_{PI}/(1-v_{PI}^2)$ and $\overline{E}_{SU8}=E_{SU8}/(1-v_{SU8}^2)$ are the plain strain moduli of PI and SU8, respectively. The bending stiffness of the circuit is $$B = \tag{VII}$$
$$\overline{E}_{PI}h_2\left(\frac{1}{3}h_2^2 - h_2 y_0 + y_0^2\right) + \overline{E}_{SU8}h_1\left[\frac{1}{3}h_1^2 + h_1(h_2 - y_0) + (h_2 - y_0)^2\right].$$

The strain at a point of coordinate y is given by $$\varepsilon = \frac{y - y_0}{R_b}, \qquad \text{(VIII)}$$

where Rb is the bending radius of curvature of the circuit. The position of the mechanical neutral axis is calculated as $y_0=26.5$ μm. With the bending stiffness given by Eq. (VII), Eq. (VIII) gives $\gamma > 8.7$ mJ/m². For a bending radius $R_b=5$ cm, the maximum strain in the Si is and $SiO_2$ is ~0.001% and ~0.0001%, respectively; the strains in the four Au layers are ~0.001%, 0.004%, 0.03% and 0.05%, respectively.

FIG. 1. Schematic illustration and images corresponding to steps for fabricating active, conformal electronics for cardiac electrophysiology mapping, and photograph of a completed device. FIG. 1a, Schematic illustration (left) and optical micrograph (right) of a collection of doped silicon nanomembranes at a unit cell. FIG. 1b, Configuration after fabrication of the source, drain and gate contacts, with suitable interconnects and row electrodes for multiplexed addressing. FIG. 1c, Configuration after fabrication of the second metal layer, including the column output electrodes. Annotations in the image on the right indicate the multiplexing transistor and the various components of the amplifier. FIG. 1d, Final layout after deposition of encapsulation layers and fabrication of the contact electrode that provides the interface to the cardiac tissue. FIG. 1e, Photograph of a completed device, in a slightly bent state. The inset at the bottom provides a magnified view of a pair of unit cells.

FIG. 2. Design and electrical properties of an active, flexible device for cardiac electrophysiology mapping. FIG. 2a, Circuit diagram for a unit cell, with annotations corresponding to those in FIG. 1c. FIG. 2b, Circuit diagram of four unit cells, indicating the scheme for multiplexed addressing. FIG. 2c, Current-voltage characteristics of a representative multiplexing transistor. FIG. 2d, Frequency response of a representative amplifier. FIG. 2e, Representative multiplexer switching response, showing the row select signals, column output and simulated column output. The response time is limited by the external row select signal slew rate. FIG. 2f, Average percentage settled to final value for increasing single electrode sampling rate, indicating the maximum useable multiplexing rate is approximately 200 kHz. FIG. 2g, Photograph of a completed device with ACF interconnect, immersed in a saline solution. FIG. 2h, Sine wave response (at 20 Hz) before and after saline immersion for 10 minutes.

FIG. 3. Photographs of a flexible EP mapping device in use on a porcine animal model. FIG. 3a, Photograph of flexible device conforming to the cardiac tissue via surface tension. The inset provides a magnified image at a different viewing angle. FIG. 3b, Sequence of movie frames collected at different times during the contraction cycle of the heart, illustrating the ability of the device to bend in a way that maintains intimate, conformal contact with the tissue during cardiac rhythm. Blue lines pasted on image highlights the degree of bending along the device. A conventional pacing electrode is indicated in the left frame (white arrow). FIG. 3c, Photograph of a device on the left anterior descending (LAD) coronary artery, with overlaid color map of the relative time of depolarization from paced activation. The white arrow in the lower left indicates the source of the pacing and the red colors in the activation map indicate the areas of earliest response.

FIG. 4. Representative data recorded from a porcine animal model using a flexible EP mapping device. FIG. 4a, Representative single voltage trace without external pacing. (Inset) Magnified view of the system noise. The black arrow indicates the source of the inset data. The signal to noise ratio (SNR) of the recorded signal was approximately 50. FIG. 4b, Representative voltage data for all electrodes at 4 points in time showing un-paced cardiac wave front propagation. Voltage is plotted using the colour scale in the right corner. FIG. 4c, Average voltage from all electrodes illustrating the point in time that each frame in FIG. 4b was taken. The colour of the dotted lines corresponds to the colour of the time label in FIG. 4b. FIG. 4d, Representative single voltage trace with external pacing from a standard clinical electrode. The black arrow and box highlight the pacing artifact. Note that negative is plotted up by convention in FIGS. 4a, 4c and 4d. FIG. 4e, Color map of relative activation times for two different external pacing sites. The activation times are plotted using the color bar shown at the right. Asterisks (*) indicate the relative location of the external pacing electrode. The scale bar illustrates the spacing between electrode locations. The data from the activation map at the locations marked by lines i-iii are plotted below in FIG. 4f. FIG. 4f, Distance vs. activation delay plots for selected rows of the electrode array following the arrows in FIG. 4e.

FIG. 5. Schematic illustration corresponding to steps for fabricating active, conformal electronics for cardiac electrophysiology mapping. Nine unit cells are shown to illustrate their interconnection at each metal level.

Figure 6:
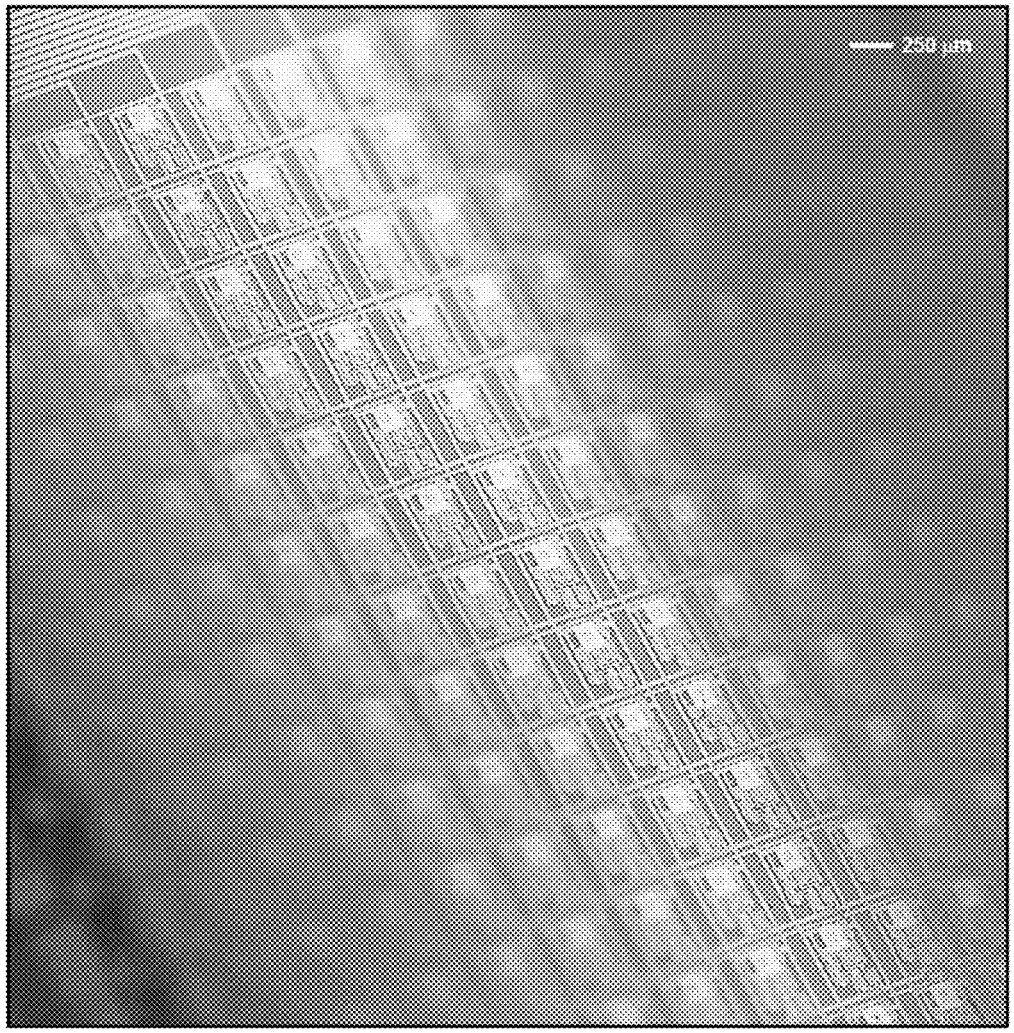
FIG. 6 provides a magnified photograph showing a conformable device in a flexed configuration.

FIG. 6. Magnified view of a completed device, in a slightly bent state to illustrate detail.

FIG. 7. Physical layout of a single unit cell showing the additional insulation layers added to prevent leakage current in saline solution.

FIG. 8. Sequential process of trilayer organic/inorganic stack fabrication.

Figure 9:
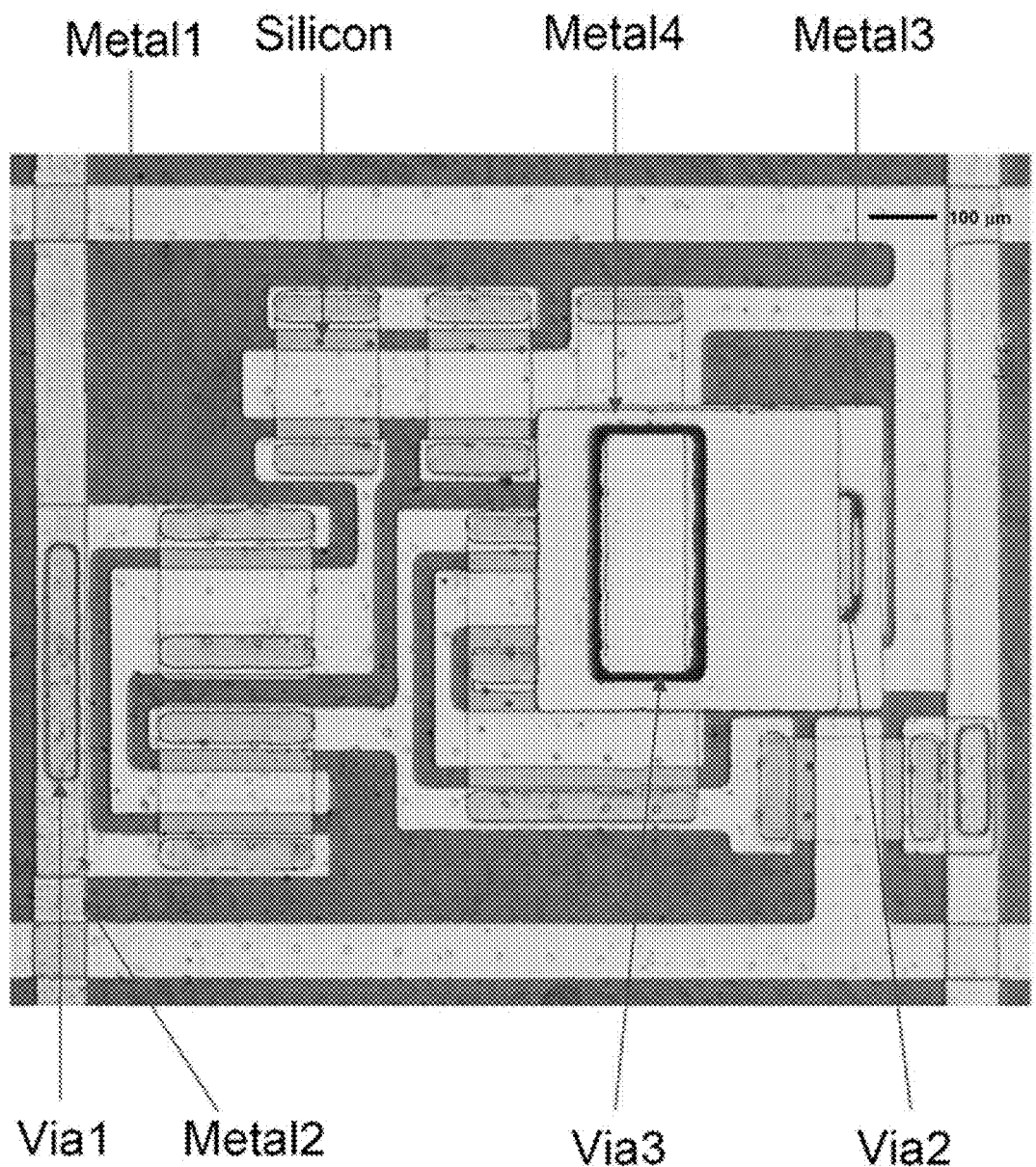
FIG. 9 shows an optical microscope image of a single unit cell of a conformable device embodiment.

FIG. 9. Optical microscope image of a single unit cell with completed insulation layers.

FIG. 10. a) Schematic diagram of ACF connection process. Image of flexible electrode array, ACF film and the circuit board before b) and after c) heat seal connection.

Figure 11A:
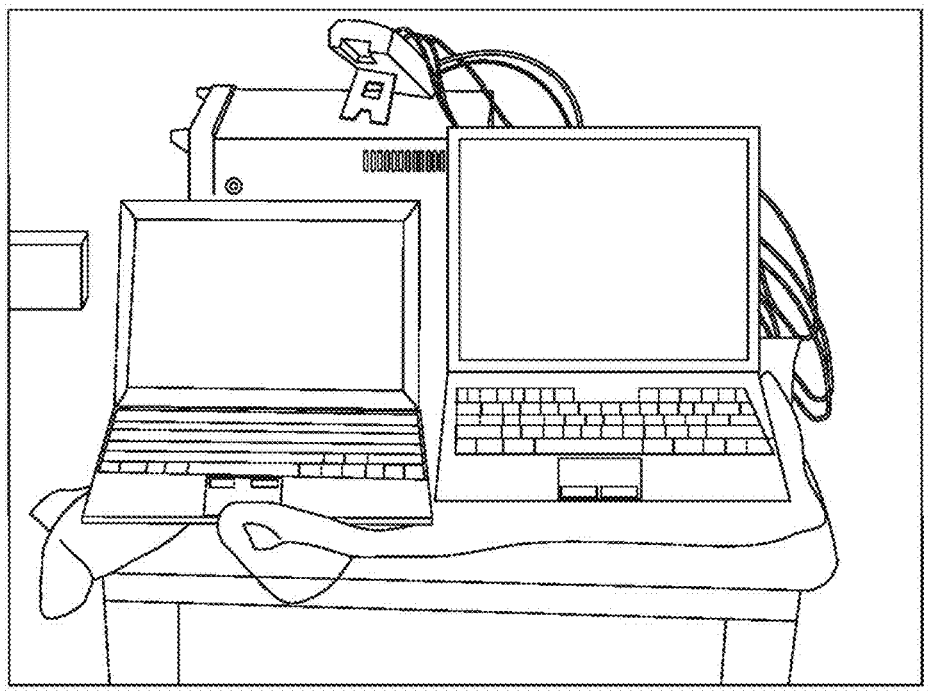
FIGS. 11a and 11b show images of the acquisition system.
Figure 11B:
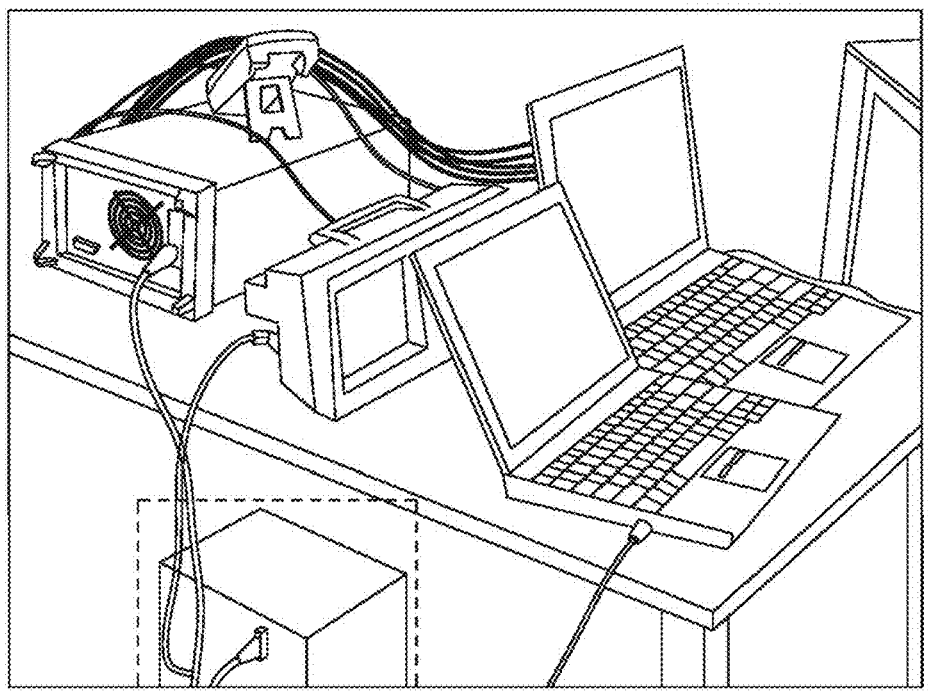
Figure 12:
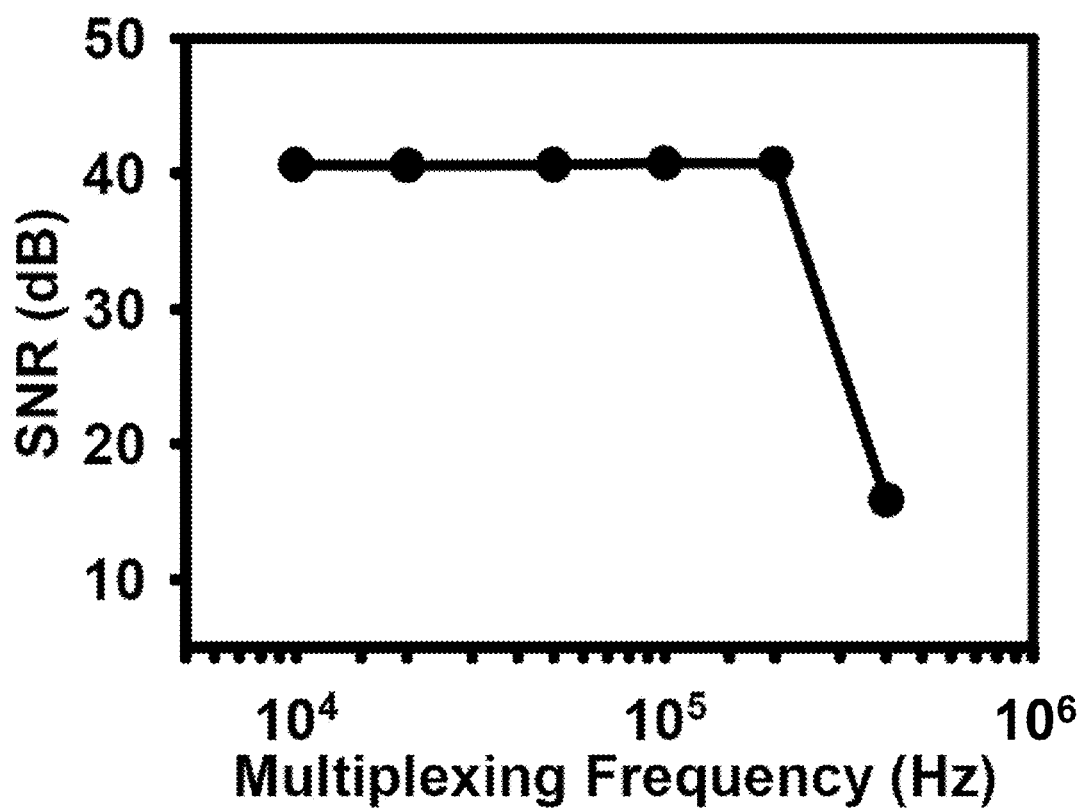
FIG. 12 provides data showing a measured signal to noise ratio dependence on multiplexing frequency.

FIG. 11. Image of acquisition system during the animal experiment: a) front view, b) side view.

FIG. 12. Signal to noise ratio dependence on multiplexing frequency for a 20 Hz test signal.

FIG. 13. Schematic diagram of wrapping model a) and cross-sectional view of sensor b).

Figure 14A:
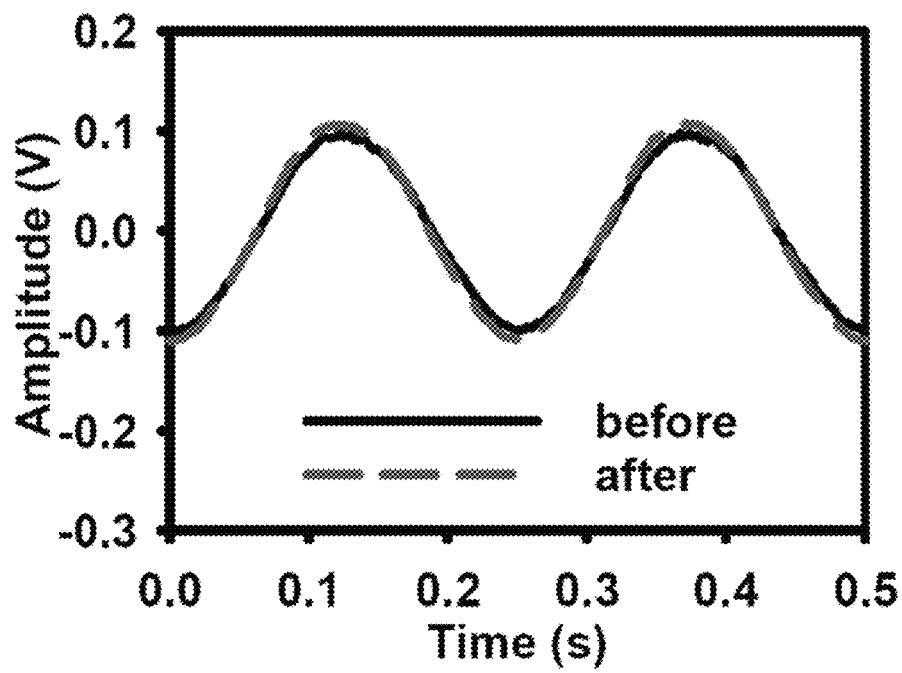
FIGS. 14a and 14b show sine wave measurements on conformable devices before and after immersion in a saline solution at frequencies of 4 and 40 Hz, respectively.
Figure 14B:
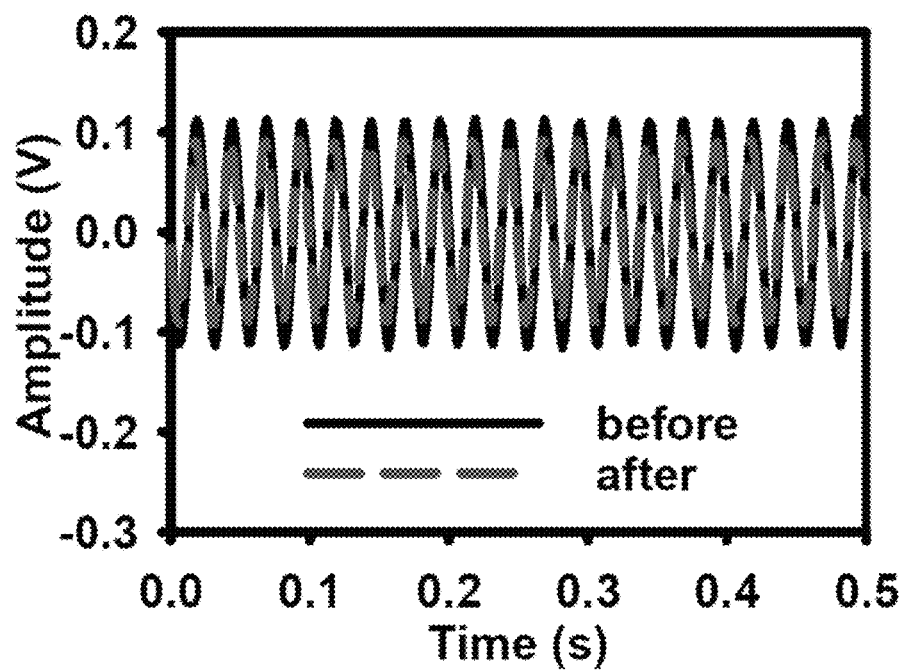

FIG. 14. Sine wave measurement before and after immersion into the saline solution: 4 Hz a) and 40 Hz b).

Figure 15A:
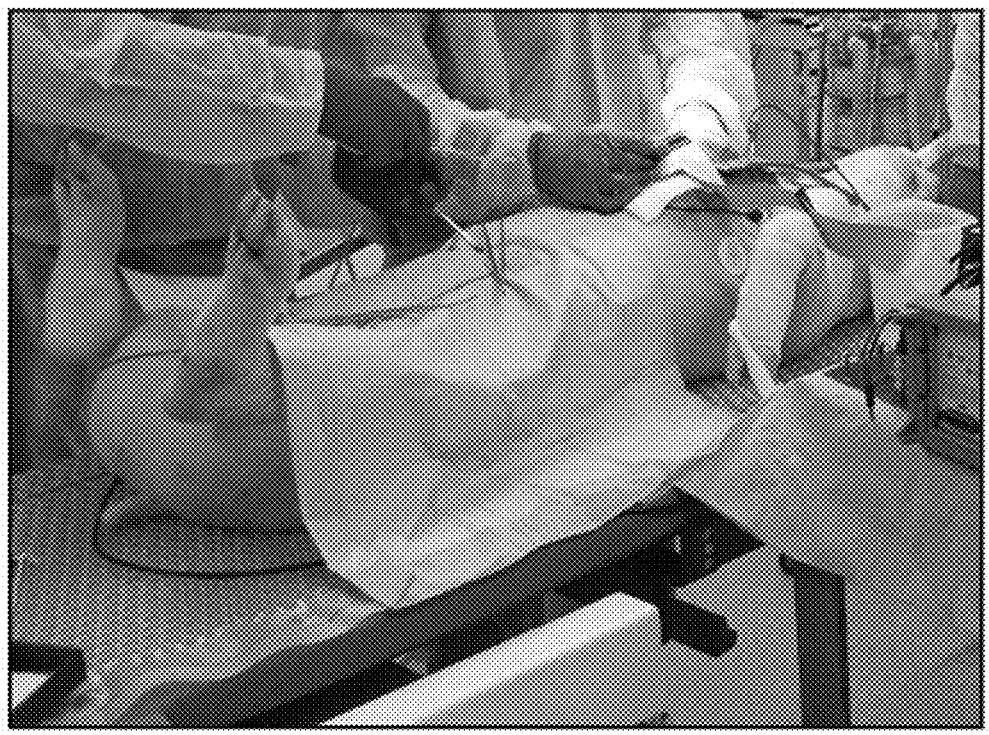
FIGS. 15a and 15b show images of an animal experiment where a conformable device is place on the surface of cardiac tissue.
Figure 15B:

FIG. 15. Image of experiment with porcine animal model a) and photograph of flexible device conforming to the cardiac tissue via surface tension b).

FIG. 16. Colour map illustrating the amplitude uniformity of all of the channels by plotting the average peak amplitude of the cardiac activation cycle.

FIG. 17. Isochronal activation map without a) and with b) pacing. The relative pacing electrode location is indicated by an asterisk (*).

FIG. 18. Representative voltage data for all electrodes at 4 points in time showing paced cardiac wave front propagation. The relative pacing electrode location is indicated by an asterisk (*). Voltage is plotted using the colour scale in the right corner. The bottom frame shows the average voltage from all electrodes. The dashed colour lines illustrate the points in time that each frame was taken. Note that negative is plotted up by convention.

FIG. 19. Design of the adapter circuit board which adapts the ACF ribbon to a 40 pin connector.

Figure 20:
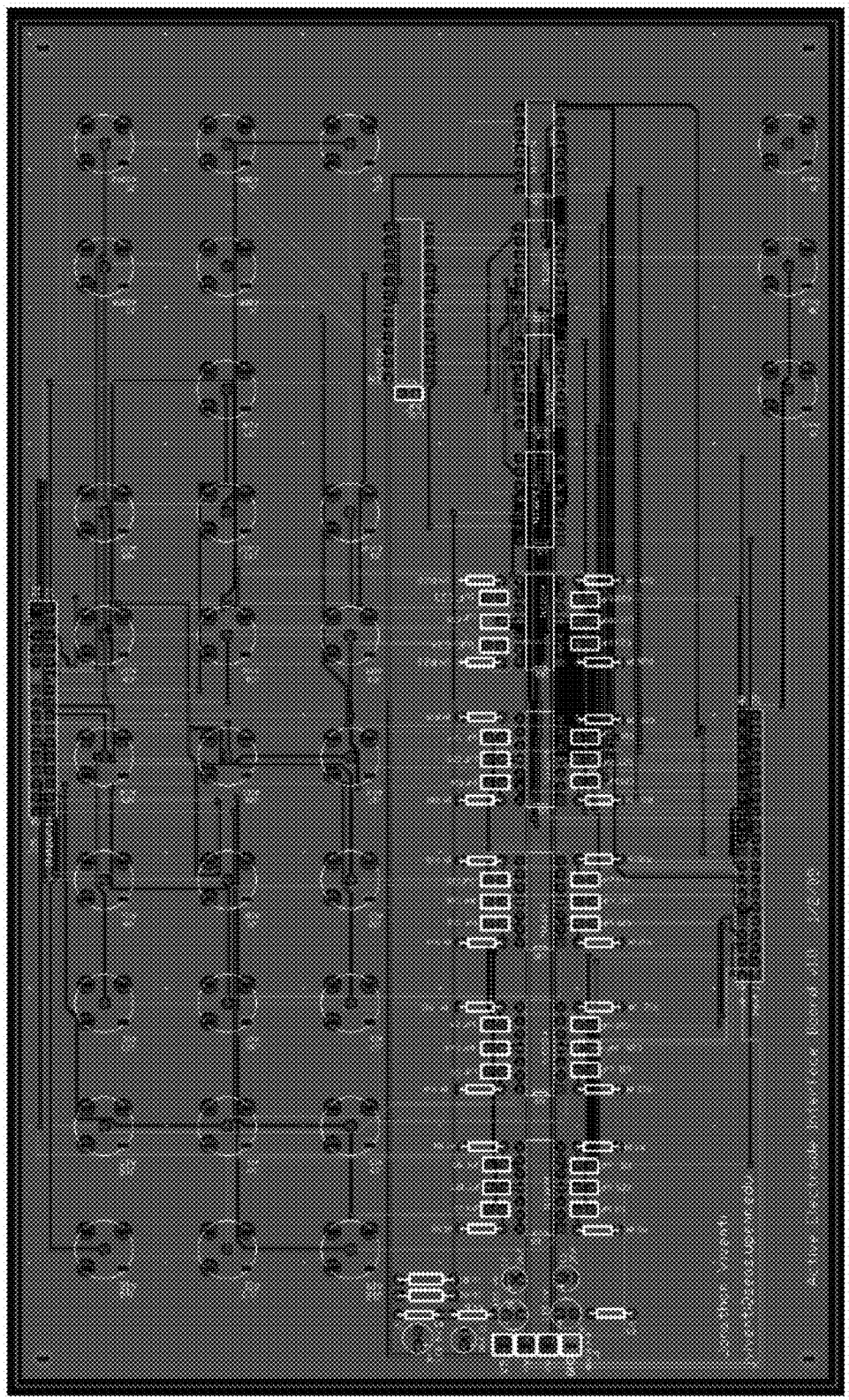
FIG. 20 shows the design of an interface circuit board embodiment.

FIG. 20. Design of the main interface circuit board which connects the 40 pin ribbon cable to the acquisition system.

Figure 21:
FIG. 21 shows an image obtained from an animal experiment.

FIG. 21. Animal experiment.

FIG. 22. Unpaced voltage data from all electrodes illustrating the natural activation pattern of the heart. The bottom frame shows an average ECG signal composed of all of the above channels along with a guide bar to show the current position in the voltage trace. Four frames from this movie are presented in FIG. 4b.

FIG. 23. Voltage data from all electrodes illustrating the paced activation pattern of the heart. The asterisk (*) indicates the relative position of the pacing electrode. The bottom frame shows an average ECG signal composed of all of the above channels along with a guide bar to show the current position in the voltage trace. Data from this interval in the recording were processed to create the isochronal map shown in the left frame of FIG. 4e.

FIG. 24. Voltage data from all electrodes illustrating the paced activation pattern of the heart. The asterisk (*) indicates the relative position of the pacing electrode. The bottom frame shows an average ECG signal composed of all of the above channels along with a guide bar to show the current position in the voltage trace. Data from this interval in the recording were processed to create the isochronal map shown in the right frame of FIG. 4e. Four frames from this movie are presented in FIG. 18.

EXAMPLE 2

Multilayer Encapsulation for Enhanced Moisture Barrier

One advantage achieved by encapsulation is prevention of leakage current from electronic circuitry to a surrounding conductive solution, such as saline solution, while the contact type metal electrode that is connected to the gate of load transistor is exposed to the surface to make a conformal and intimate contact to the curvilinear, soft cardiac tissue. This example describes a multilayer encapsulation structure to enhance prevention of leakage current.

Figure 25A:
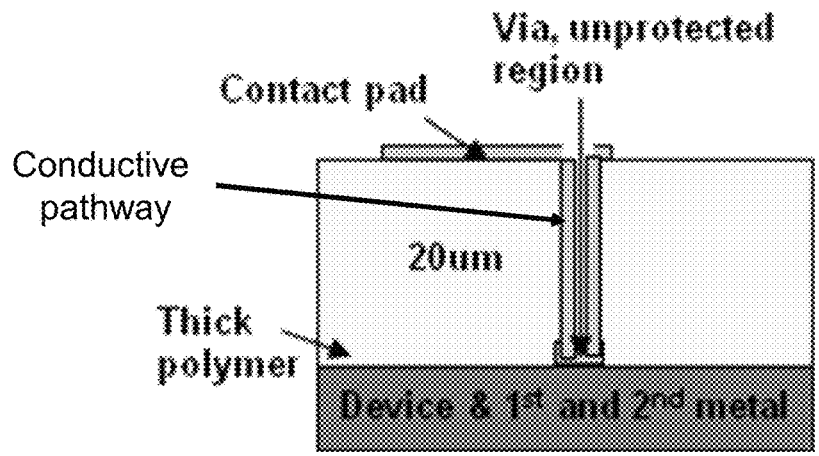
FIG. 25a shows a cross sectional image of a single layer barrier layer embodiment.

Multiple Layer Structure with Mis-aligned Via Structure. The encapsulation can be a single polymer layer or in can be a multilayer structure. If a single polymer layer (e.g., ~20 µm) is used, pinholes can form following a dry etching process for via interconnect due to incomplete masking. Such pinholes can be prevented, for example, if a photo-definable thick polymer, such as SU8, is used, since the etching process is not needed. For a one layer structure, a mis-aligned via structure is not typically use. Use of a single via structure for some device applications may increase the chance of leakage through the contact region where the metal electrode and the gate of the transistor are connected. Therefore, even though a very thick polymer layer is used, this contact region may not be thoroughly protected with a single polymer layer/via structure. FIG. 25a illustrates a single encapsulation layer with an electrode element connected to the gate of a transistor with a single via structure.

Figure 25B:
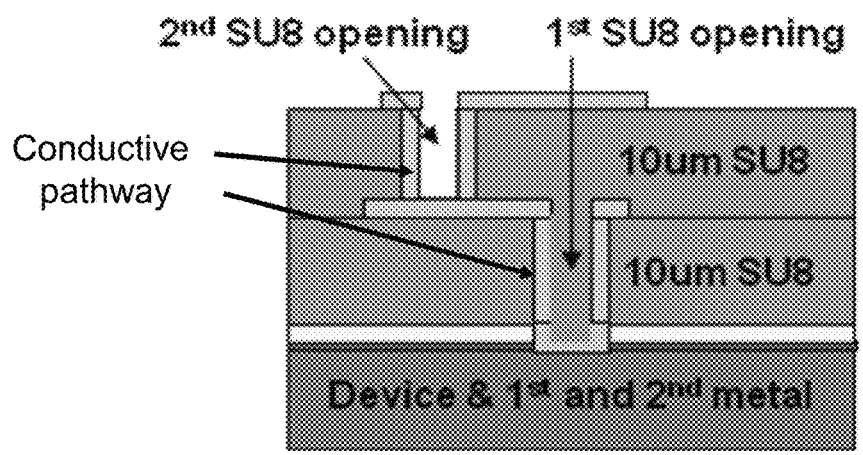
FIG. 25b shows a cross sectional image of a dual layer barrier layer embodiment.

To solve this problem, a multilayer encapsulation with a mis-aligned via structure can be used, as illustrated in FIG. 25b. In this structure, the contact region is encapsulated with another layer of polymer, leading to a reduced chance of leakage. For example, instead of thick one polymer layer (~20 µm), two layers of polymer (~10 µm each) can be used and the second layer can fill the first via and protect the contact region between the electrode and load transistor.

Even with the two layer structure described above, however, it is possible that delamination between two layers, especially between a metal and a polymer layer, can induce leakage current to flow along the interface between these two layers. To minimize this possibility, multiple mis-aligned via structure can be used. For example, three 7 µm polymer layers or four 5 µm polymer layers can be used. For any multilayer structure such as these, all vias for each layer should be misaligned.

Thickness of Encapsulation Layer (Neutral Mechanical Plane (NMP) Design. Thicker encapsulation layers generally provide better leakage prevention. However, a deformable (e.g., flexible, bendable) system needs to consider the induced strain during deformation. To reduce unwanted mechanical fracture of inorganic materials, such as silicon, the device layer should be located near the neutral mechanical plane. Therefore, the top encapsulation layer thickness can be determined depending on the substrate thickness and material property, such as modulus.

Material of Encapsulant—Inorganic/Organic multilayer. To enhance flexibility, a thinner substrate is used in some embodiments; to place the device layer at the NMP, and optionally a thinner encapsulation layer is also used. However, the thinner the polymer layer, the higher the risk for pinholes or defects and, therefore, the potential for increased leakage current. In addition, since the micro structure certain polymers is composed of fibers, the penetration of ionic fluid through gaps between each polymer fiber, in the case of a thin polymer layer, can result in increased leakage current. To prevent this kind of leakage, while maintaining thin thickness, very thin (~50 nm) inorganic layers, such as silicon nitride, can be inserted between each organic layer. This inorganic/organic multilayer effectively prevents the leakage current caused by ionic fluid penetrating through the organic polymer layers.

A further method for reducing pinholes or defects in an organic or polymer material includes reflowing during curing of the polymer.

Table 1 summarizes encapsulation considerations for some embodiments.

TABLE 1

| Factor | Exemplary Configuration or Considerations |
| --- | --- |
| Electrical leakage | <10 µA |
| Total encapsulant thickness | Encapsulation thickness/substrate thickness: 0.5~2 (0.5~2 thickness ratio in the case of the same material with the substrate.) (If different material, modulus of both materials may be considered to locate NMP near device layers.) |
| Substrate thickness | Active electronics: 5 µm~30 µm Passive electronics: 1 µm~30 µm |
| Bending stiffness | <10$^8$ GPa µm$^4$ |
| Number of misaligned vias | >1 |
| Organic/inorganic thickness | Organic: 1 µm~20 µm, Inorganic: 10 nm~500 nm |
| Modulus of organic material | 0.5 MPa~5 GPa |

Flexible vs. Stretchable. The above descriptions of this example are generally useful for flexible systems, though they can also apply to stretchable systems. An alternative approach for stretchable systems utilizes, for example, island and bridge structures, such as serpentine bridges. The encapsulation, however, should be similar, since the encapsulation layer for an island should parallel the flexible system. One additional aspect of the stretchable system is the passivation of a serpentine bridge sidewall. After dry etching to make a serpentine structure, for example, the sidewalls of serpentine metal interconnects are exposed. Even with a small amount of delamination between multi-layers of a serpentine bridge during stretching deformation, large leakage currents can be generated from the metal interconnects. To prevent leakage, the margin from the edge of the metal interconnect can be increased. Additionally, the side wall can be passivated with another layer of polymer after etching.

EXAMPLE 3

Schematic of a Conformal Electronic Device for Sensing or Actuation

FIG. 26A provides a schematic illustration of a cross sectional view of a conformal electronic device embodiment for sensing or actuation of a tissue in a biological environment. Conformable device 100 optionally comprises flexible or stretchable substrate 110 supporting a flexible or stretchable electronic circuit comprising plurality of inorganic semiconductor circuit elements 120, such as electronic device components including sensors, actuators, electrode arrays, LED arrays, optical sources, integrated circuits, multiplexing circuits and/or amplifiers. Barrier layer 130 encapsulating at least a portion of the flexible or stretchable electronic circuit may provide a moisture barrier, a thermal barrier, an electromagnetic barrier, an electrical barrier, a magnetic barrier, a selectively permeable or impermeable barrier or any combination of these. In some embodiments, the flexible substrate, the flexible or stretchable electronic circuit and the barrier layer provide a net bending stiffness or flexural rigidity of the device low enough that the device establishes conformal contact with the tissue in the biological environment. In some embodiments, conformal contact is established between external surface 135 of the device 100 and a tissue in a biological environment.

Optionally, the conformal device 100 further comprises a controller 155 in communication with the flexible or stretchable electronic circuit comprising plurality of inorganic semiconductor circuit elements 120, for example one way or two way communication as shown by the arrows indicated in FIGS. 26A and 26B. In an embodiment, controller 155 is provided in electrical communication or wireless communication, and optionally is positioned away from the tissue interface. In some embodiments, controller 155 is configured to receive input signals 156 from the electronic circuit that correspond to measurements of one or more sensed parameters, such as time information, tissue properties (e.g., position, composition, movement, electronic, chemical, optical, temperature, etc.), or other properties of the biological environment. Input signals 156 may represent raw data or processed data, optionally in the form of a measurement. In some embodiments, controller 155 is configured to provide output signals 157 to the electronic circuit that correspond to one or more control parameters, such as control signals for controlling the sensing and or actuation of the tissue, including one or more time parameter, electronic parameter, optical parameter, etc. In an embodiment, controller 155 is a processor that receives and analyzes input signals 156 and generates output signals 157 based at least in part on the input signals 156. In an embodiment, controller uses input signals 156 and output signals 157 to provide close-loop control of sensing or actuation of the tissue.

In some embodiments, the physical dimensions and material properties of flexible substrate 110 and barrier layer 130 are selected such that the semiconductor circuit elements 120 of the flexible or stretchable electronic circuit are provide proximate to the neutral mechanical plane of the device (illustrated by thick dotted line, drawing element 150). Optionally, device 100 further comprises one or more additional electronic device components 140 not encapsulated by barrier layer 130, optionally provided in physical and/or electrical contact with the target tissue in the biological environment. Additional electronic device components 140 useful in some embodiments, include sensors and actuators such as electrodes, voltage sensing or actuating elements, current sensing or actuating elements, optical sensors or actuators, temperature sensors or actuators, pH sensors, chemical or biological sensors, capacitive sensors, electrode elements, photodiodes, thermistors strain sensors, acceleration sensors, movement sensors, and displacement sensors or actuators.

FIG. 26B provides a schematic illustration of a cross sectional view of a conformal electronic device having a barrier layer comprising a multilayer structure. As shown in FIG. 26B, barrier layer 130 comprises a sequence of individual layers 130a-130e. In some embodiments, individual layers 130a-130e comprise a sequence of layer selected from the group consisting of polymer layers, inorganic layers (e.g., inorganic dielectric materials such as an oxide, carbide or nitride, etc.) and metal layers. In some embodiments, individual layers 130a-130e comprise a sequence of thin film structures, for example, thin film structures fabricated by deposition (e.g., evaporative, sputtering, etc.) or coating techniques. In some embodiments, individual layers 130a-130e comprise a sequence of thin film structures including at least one metal thin film and at least one dielectric thin film, and optionally at least one polymer thin film.

Alternatively, the circuit 120 may be free-standing without substrate 110 when applied to the biological tissue. The configuration of the circuit and transfer printing methods facilitate the placement of such free-standing structures on biological tissue, including skin. Optionally, a contact layer is provided on the skin surface to facilitate placement and transfer of the electronic circuit from the transfer substrate to the skin and barrier layers 130 that are cover layers applied to the circuit after the circuit is mounted on the skin. The cover layer(s) 130 may be polymer layers applied via a spray liquid bandage.

EXAMPLE 4

Waterproof AlInGaP Optoelectronics with Application Examples in Biomedicine and Robotics This example explores new areas and implements mechanically optimized layouts to achieve arrays of inorganic LEDs and PDs in systems that can accommodate extreme modes of mechanical deformation, for integration on substrates of diverse materials and formats. Additionally, materials and design strategies allow operation even upon complete immersion in saline solutions, biofluids, solutions of relevance to clinical medicine and soapy water, thereby opening new and unconventional opportunities for seamless integration of opotelectronics with biomedical and robotic systems. Thin implantable sheets (i.e. LED tattoos provide an example). Specifically, this example describes advances, in the following order: (1) experimental and theoretical aspects of mechanical designs that enable freely deformable, interconnected collections of LEDs and PDs on soft, elastomeric membranes, bands and coatings, (2) strategies for achieving high effective fill factors in these systems, using laminated multilayer constructs, (3) device examples on diverse substrates and in varied geometrical forms, (4) low modulus, biocompatible encapsulation materials that preserve key mechanical properties and, at the same time, enable robust operation when integrated on or implanted in living systems, (5) flexible optoelectronic components for biomedicine, with in vivo demonstrations on animal models.

For active materials, thin epitaxial semiconductor layers grown on GaAs wafers are prepared, and then vertically etched to define lateral dimensions of devices built with them. Release from the wafer via selective elimination of an underlying layer of AlAs, followed by transfer printing accomplishes integration on substrates of interest. The fabrication scheme described here uses a dual transfer process that involves first printing the semiconductor materials to a temporary substrate (glass plate coated with a trilayer of epoxy/polyimide (PI)/poly(methylmethacrylate) (PMMA)) for forming contacts, interconnections and structural bridges, and encapsulation layers. Dissolving the PMMA releases fully formed, interconnected collections of devices. A second transfer printing step achieves integration on elastomeric sheets (e.g. poly(dimethylsiloxane), PDMS) or other substrates coated with thin layers of PDMS, with strong bonding only at the locations of the devices. For all examples described in this example, the LEDs (referred to herein as µ-ILEDs to highlight the small sizes and the distinction over organic devices), and the PDs (i.e. µ-IPDs) have lateral dimensions of 100×100 µm and thicknesses of 2.5 µm, corresponding to volumes that are orders of magnitude smaller than those of commercially available devices. The thin geometries are important because they allow the use of thin film metallization for interconnect and optimized mechanical designs, described next. Details of the processing and layouts appear in FIGS. 33-35.

Figure 27A:
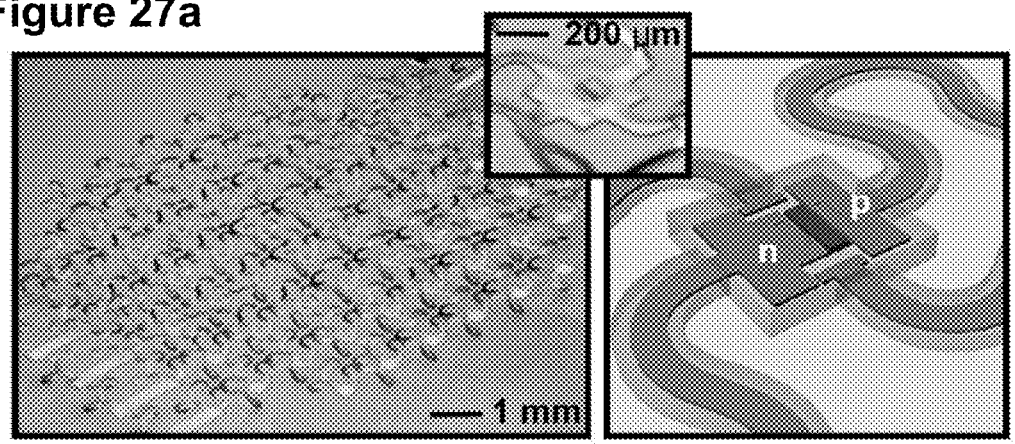
FIG. 27a, Optical image of a 6×6 array of μ-ILEDs (100 μm×100 μm, and 2.5 μm thick, in an interconnected array with a pitch of ~830 μm) with non-coplanar serpentine bridges on a thin (~400 μm) PDMS substrate (left frame). Schematic illustration (right) and corresponding photograph (inset) of a representative device, with encapsulation.
Figure 32A:
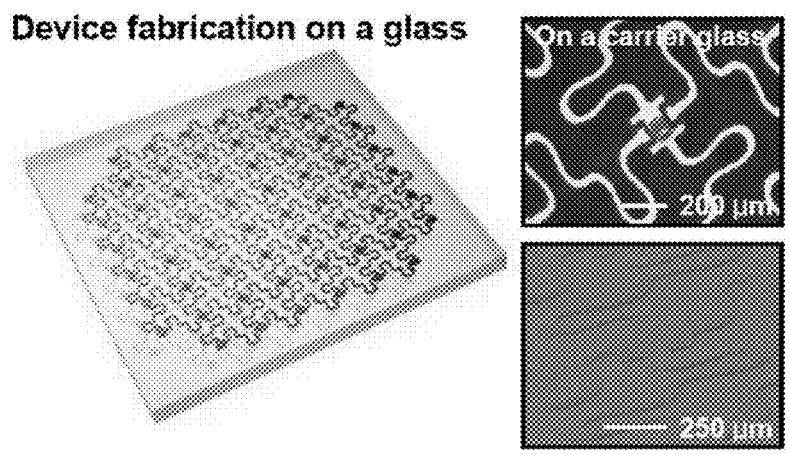
FIG. 32. (a) Schematic illustration (left frame) and corresponding microscope (top right frame) and SEM (bottom right frame) images of a 6×6 μ-ILEDs on a handle glass substrate coated with layers of polymers (epoxy/PI/PMMA).

FIGS. 27a and 36 present optical images, schematic illustrations, scanning electron microscope (SEM) images, and finite element modeling of the mechanics of arrays of µ-ILEDs connected by serpentine shaped ribbons that serve as either structural bridges or electrical interconnects, transferred to a thin, pre-strained sheet of PDMS (~400 µm thick). Here, and as described below, the devices are connected in series (FIG. 32a), such that all of them turn on and off together; a single failed device leads to failure of the entire array. The interconnects consist of thin films of metal with photodefined layers of epoxy on top and bottom to locate the metal at the neutral mechanical plane. The bridges are similar, but without the metal. Detailed geometries appear in FIG. 33. Releasing the pre-strain yields non-coplanar layouts in the serpentines via a controlled, non-linear buckling response, as shown in the left frame of FIG. 27a (~20% pre-strain). The right frame and inset of FIG. 27a present a schematic illustration and magnified optical image of a representative µ-ILED, respectively. These design choices are informed by careful studies of the mechanics through three dimensional finite element modeling (3D-FEM) of the complete systems; they represent highly optimized versions of those used for silicon circuits and µ-ILEDs. The results enable stable and robust operation during large scale uniaxial, biaxial, shear and other mixed modes of deformation, as described in the following.

Figure 27B:
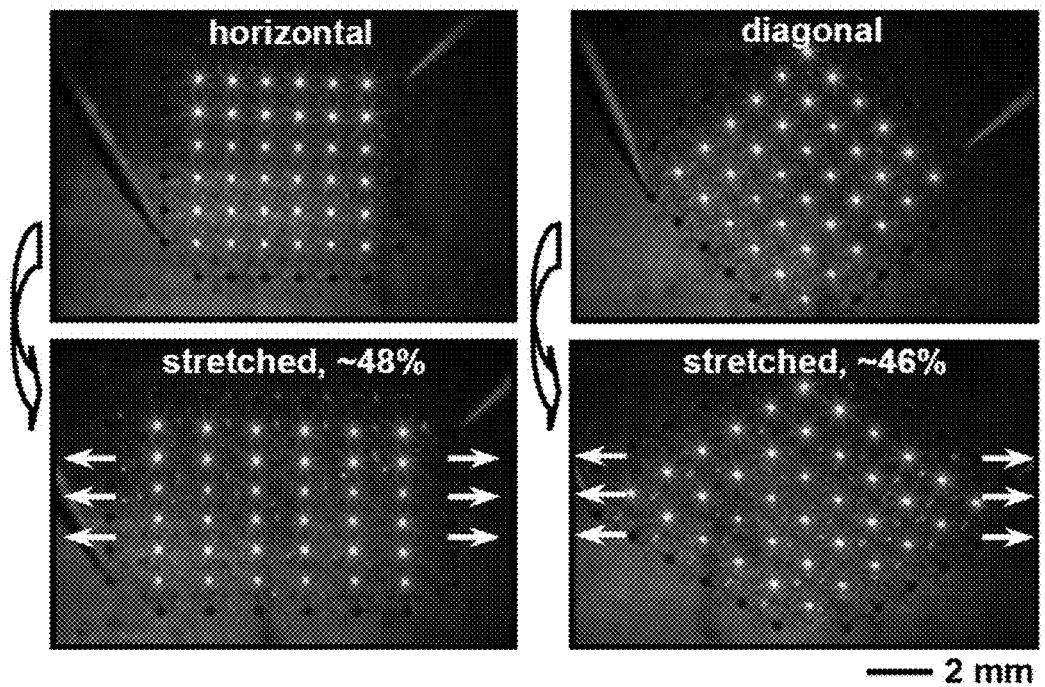
FIG. 27b, Optical images of a stretchable 6×6 array of μ-ILEDs, showing uniform emission characteristics under different uniaxial applied strains (top left: 0%, bottom left: 48% along horizontal direction, top right: 0%, bottom right: 46% along diagonal direction).

FIGS. 34a and 35a show tilted view scanning electron microscope (SEM) images and corresponding optical microscope images of adjacent µ-ILEDs and non-coplanar serpentine interconnects formed with ~20% biaxial pre-strain before (left) and after (right) uniaxial stretching (~60%), respectively. The separations between adjacent pixels change by an amount expected from the pre-strain and the applied strain, where a combination of in- and out-of-plane conformational changes in the serpentines accommodate the resulting deformations in a way that avoids any significant strains at the positions of the µ-ILEDs. In particular, 3D-FEM modeling results (FIG. 34b) reveal peak strains in the metal interconnect and the µ-ILEDs that are >300 times smaller than the applied strain (FIG. 35c shows similar results for ~59% stretching along the diagonal direction, corresponding to FIG. 35b). FIGS. 27b and 36 present two dimensional, in-plane stretching of a 6×6 array of µ-ILEDs along horizontal (left) and diagonal (right) directions. The uniform and constant operating characteristics of all devices are clearly apparent in the dark and bright (without and with external illumination) images of FIG. 27b and FIG. 36 as well as in the current-voltage (I-V) characteristics (left frame of FIG. 27c). The applied strains, calculated from the separations of inner edges of adjacent pixels before and after stretching, reach ~48% and ~46% along the horizontal and diagonal directions, respectively. The I-V characteristics are invariant even after 100000 cycles of 75% stretching along the horizontal direction (right frame of FIG. 27c).

Figure 27C:
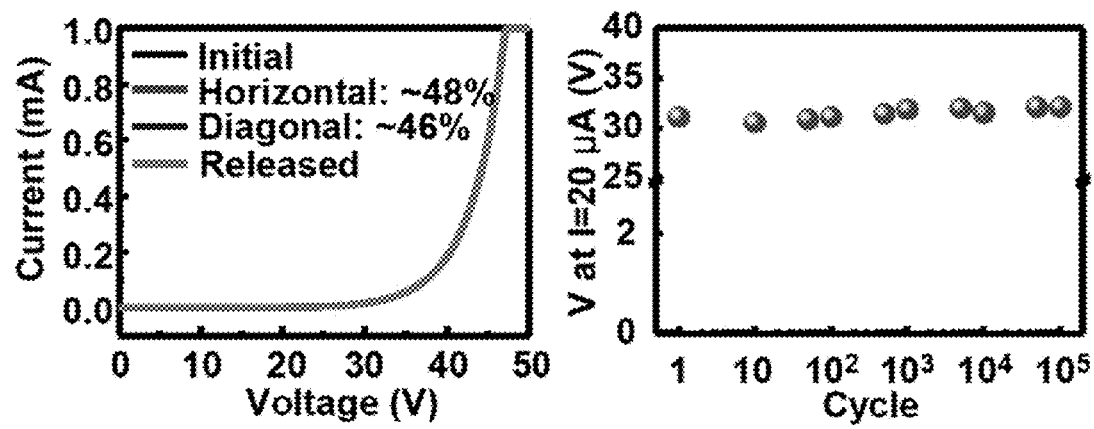
FIG. 27c, Current-voltage (I-V) characteristics of this array measured in the strained configurations shown in b (left) and voltage at 20 μA current for different cycles of stretching to 75% along the horizontal direction (right).
Figure 27D:
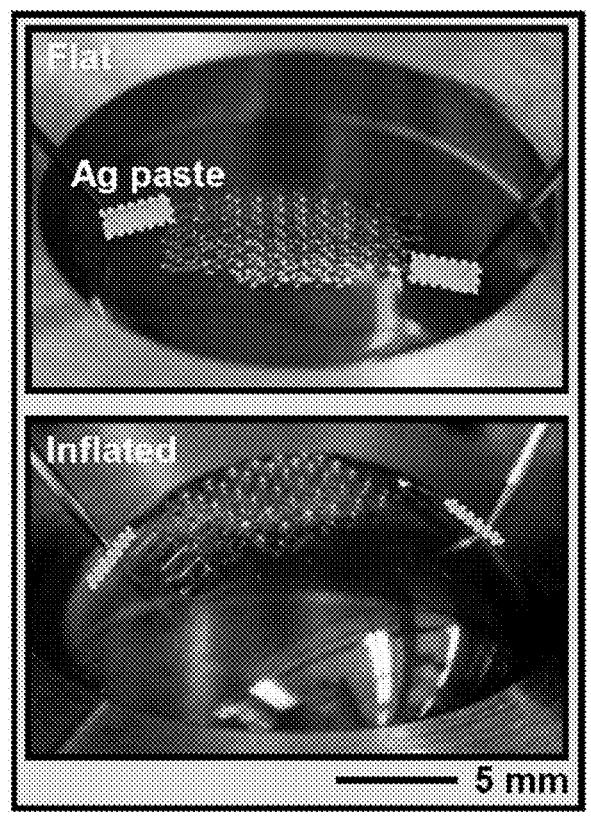
FIG. 27d, Tilted (left) view optical images of a stretchable array (6×6) of μ-ILEDs on a thin (~500 μm) PDMS membrane in a flat configuration (top) and in a hemispherical, balloon state (bottom) induced by pneumatic pressure.
Figure 27E:
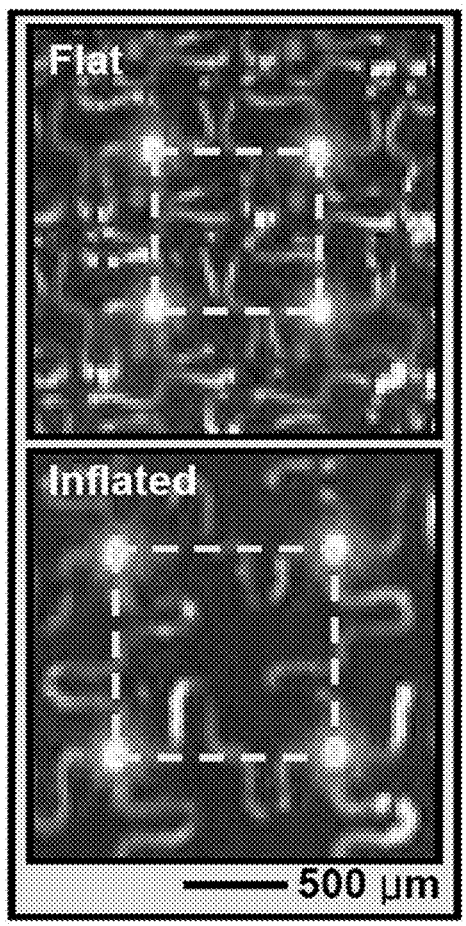
FIG. 27e, The magnified view of FIG. 27d from the top. The yellow dashed boxes highlight the dimensional changes associated with the biaxial strain.
Figure 27F:
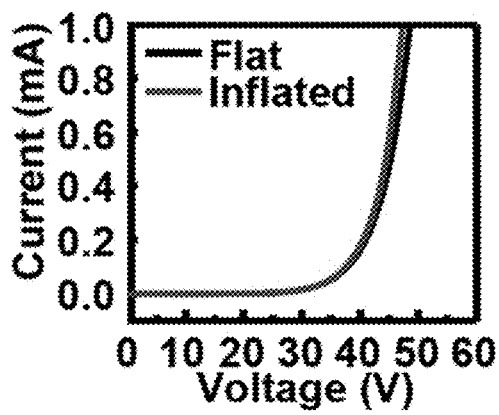
FIG. 27f, I-V characteristics of the array in its flat and inflated state.
Figure 27G:
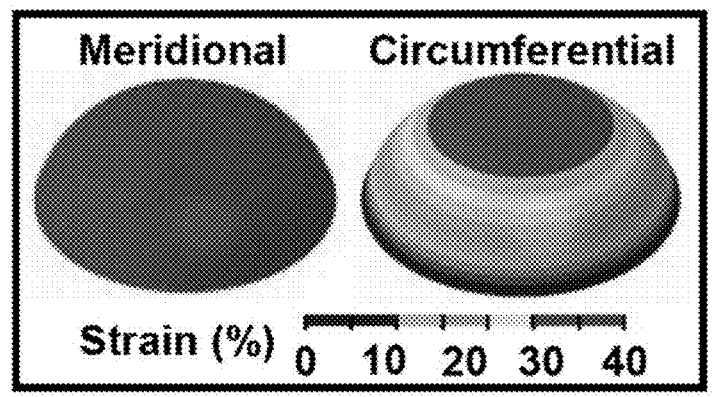
FIG. 27g, Distribution of meridional and circumferential strains determined by 3D-FEM.

Uniaxial stretching and compressing are among the simplest modes of deformation. Others of interest include biaxial, shear and related. The results of FIGS. 27d-g, and 37 demonstrate the ability of the reported designs to allow these sorts of motions, through large strains induced by pneumatic pressure, achieved by inflation of a thin (500 µm) membrane of PDMS that supports an array similar to that of FIG. 27b. Injecting air through a syringe in a specially designed cylinder that serves as a mount for the device deforms the initially flat array (top frame of FIG. 27d) into a balloon shape (bottom frame of FIG. 27d). FIG. 27e shows four pixels in the 'flat' (top) and 'inflated' states (bottom) during operation, with external illumination. The area expansion induced in this manner can reach ~85% without any device failures. The I-V characteristics also show no appreciable differences between the flat and inflated states (FIG. 27f). 3D-FEM is used to model the inflation induced deformation of a circular elastomeric membrane, with the same thickness (500 µm) and diameter (20 mm) as in experiment, but without a mounted µ-ILED array. As illustrated in FIGS. 27g and 37c, both the circumferential and meridional strains reach ~37.3% when inflated to a height of 8.3 mm, the same as in the bottom frame of FIG. 27d. Measured displacements of devices in the system of the bottom frame of FIG. 27e indicate strains of ~36%, which are comparable to values calculated by 3D-FEM. This observation suggests an important conclusion: with the designs reported here, the arrays provide negligible mechanical loading of the soft, elastomeric membrane support, consistent with the very low effective modulus provided by the optimized, non-coplanar serpentines.

Figure 28F:
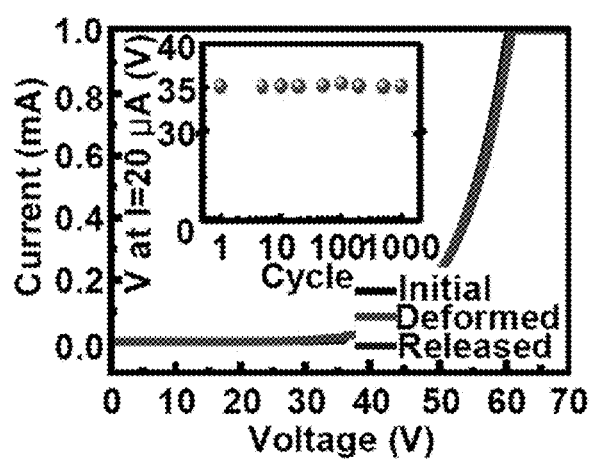
FIG. 28f, I-V characteristics of the array in FIG. 28e, before (initial), during (deformed) and after (released) deformation. The inset provides a graph of the voltage needed to generate a current of 20 μA, measured after different numbers of cycles of deformation.

Corkscrew twisting (FIG. 28a) provides another well-defined mode of deformation that is of interest. Here, large shear strains occur in addition to stretching/compressing in the axial and width directions. The device test structure in this case consists of a 3×8 array of µ-ILEDs transferred to a band of PDMS without pre-strain (see FIG. 38a for details). Optical images of flat, 360°, and 720° twisting deformations with (left) and without (right) external illumination (FIG. 28a) reveal uniform and invariant emission. These strains lead to out-of-plane motions of the serpentines, as shown in FIGS. 28b and 34b. The µ-ILEDs remain attached to the PDMS substrate due to their strong bonding. Electrical measurements indicate similar I-V characteristics with different twisting angles (FIG. 28c) and at different stages of fatigue tests, as shown in FIG. 38c. FIG. 28d presents distributions of various strain components, evaluated at the surface of a band of PDMS with thickness 0.7 mm by 3D-FEM: axial stretching (left frame), width stretching (middle frame) and shear (right frame). (For 360° twisting, see FIG. 39). The results demonstrate that the PDMS surface undergoes both extreme axial/width stretching and shear deformations, with shear dominating, and reaching values of ~40% for the 720° twist. As for the case of FIGS. 27d and 27g, the distributions of strain for the bare PDMS substrate can provide reasonably good estimates for the system. These controlled uniaxial (FIG. 27b), biaxial (FIG. 27d) and twisting (FIG. 28a) modes suggest an ability to accommodate arbitrary deformations. As two examples, FIGS. 28e and 28f show cases of stretching onto the sharp tip of a pencil and wrapped onto a cotton swab. The array of 6×6 µ-ILEDs pulled onto the pencil (red arrows indicate stretching directions) experiences local, peak strains of up to ~100%, estimated from distances between adjacent devices in this region. Similar but milder and more spatially distributed deformations occur on the cotton swab, with an 8×8 array. In both cases, observation and measurement indicate invariant characteristics, without failures, even in fatigue tests.

Figure 41B:
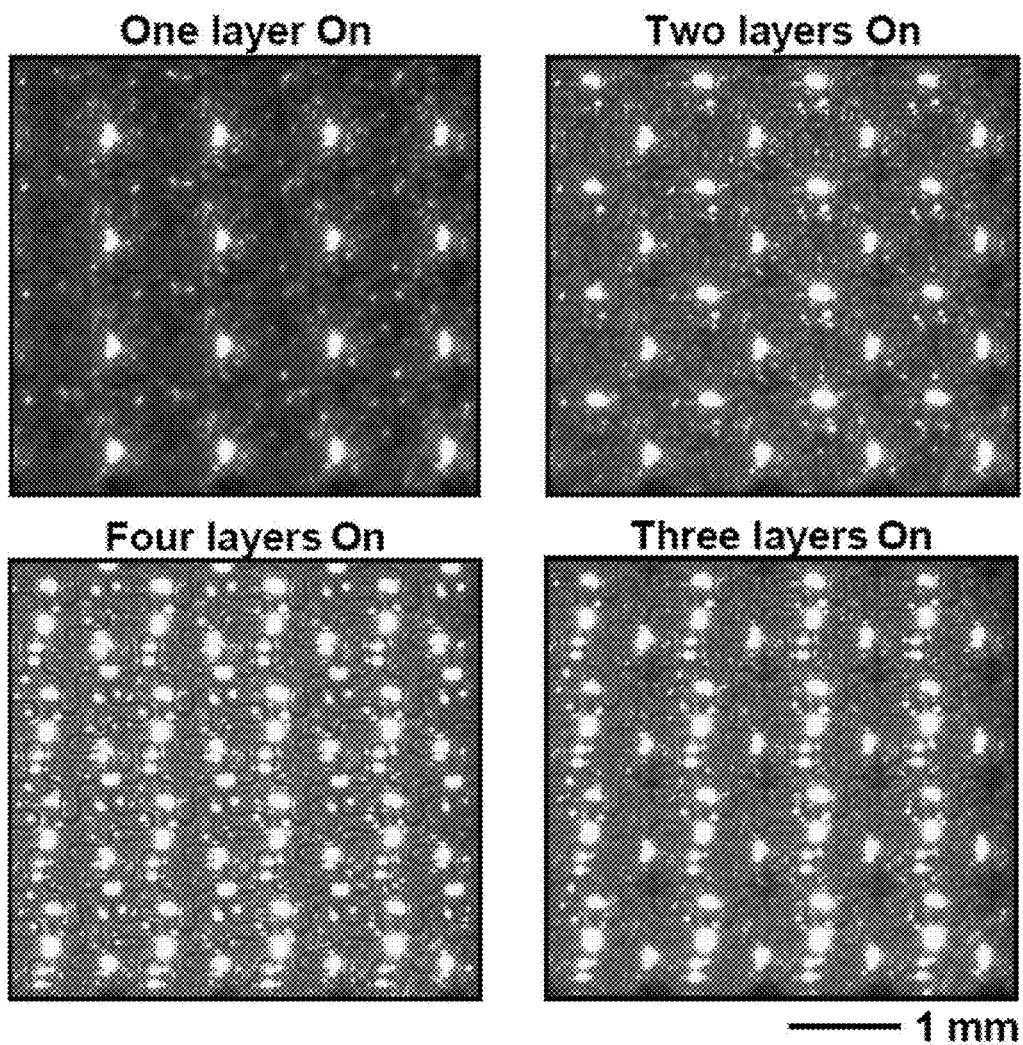

A feature of the layouts that enable these responses is the relatively small area coverage of active devices, such that the serpentine structures can absorb most of the motions associated with applied strain. An associated disadvantage, for certain applications, is that only a small part of the overall system emits light. This limitation can be circumvented with layouts that consist of multilayer stacks of devices, in laminated configurations, with suitable spatial offsets between layers. The exploded view schematic illustration in FIG. 29a shows this concept with four layers. FIG. 41 provides details. Integration is accomplished with thin coatings of PDMS (~300 µm) that serve simultaneously as elastomeric interlayer dielectrics, encapsulants and adhesives. Here, each layer consists of a substrate of PDMS (300 µm thick) and an array of LEDs (total thickness with interconnect, ~8 µm). The total thickness of the four layer system, including interlayers of PDMS, is ~1.3 mm. Optical images of emission from a four layer system appear in FIG. 29b (with external illumination) and FIG. 41b (without external illumination). FIG. 29c shows a two layer case, where each layer lights up in a different pattern. The inset on the right illustrates the same system in a bent state (bending radius=2 mm), where the maximum strain in top and bottom GaAs layers is only 0.006% and 0.007%, respectively as shown by 3D-FEM simulation (FIG. 42). The PDMS interlayers restrict the motion of the serpentines, but by an amount that reduces only slightly the overall deformability. The extent of free movement can be maximized by minimizing the modulus of the encapsulant. Here, PDMS was mixed in a ratio to yield a Young's modulus of ~0.1 MPa, to retain nearly ~90% of the stretchability of the unencapsulated case.

The favorable mechanical characteristics enable integration onto a variety of substrates that are incompatible with conventional optoelectronics. As demonstrations, µ-ILED devices were built on swatches of fabric (FIG. 43a), tree leaves (FIG. 43c), sheets of paper (FIG. 29d), and pieces of aluminum foil (FIG. 29e). In all cases, transfer printing successfully delivers the devices to these substrates with thin (~50 µm) coatings of PDMS that serve as planarizing and strain isolating layers, and as adhesives. Bending and folding tests for each case indicate robust operation under deformed states. The smallest bending radii explored experimentally were 4 mm, 2.5 mm, and 400 µm for the fabric, leaf, and paper, respectively. Theoretical modeling, using Young's moduli and thicknesses 1.2 MPa, 800 µm, 23.5 MPa, 500 µm, 600 MPa and 200 µm for the fabric, leaf and paper, respectively, shows that the fabric, leaf and paper can be completely folded, in the sense that the strain in the GaAs remains much smaller than its failure strain (~1%) even when the bend radius equals the substrate thickness. Without the strain isolation provided by the PDMS, the fabric can still be folded, but the leaf and paper can only be bent to minimal radii of 1.3 mm and 3.5 mm, respectively. This result occurs because the Young's modulus of PDMS (0.4 MPa) is much smaller than those of leaf and paper (i.e., strain isolation), while the Young's moduli of PDMS and fabric are more similar. Random wrinkling, including multi-directional folding with inward and outward bending can be accommodated, as is apparent in the devices on paper and aluminum foil (~30 µm). In images of the latter case (FIG. 29e), the number density of wrinkles reaches ~200 per $cm^2$ with approximate radii of curvature as small as 150 µm (See FIGS. 43-45 for additional images, plots of I-V characteristics, results of fatigue tests, and surface topography of these substrates).

Figure 29F:
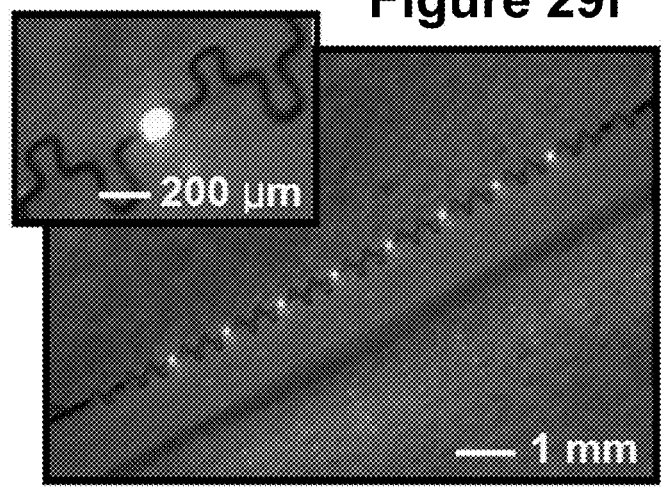
FIG. 29f, Images of a thin (~8 μm), narrow (820 μm) strip of μ-ILEDs (1×8) with serpentine interconnects on a rigid plastic tube (diameter ~2.0 mm, left). Inset shows the magnified view of a single pixel.
Figure 29G:
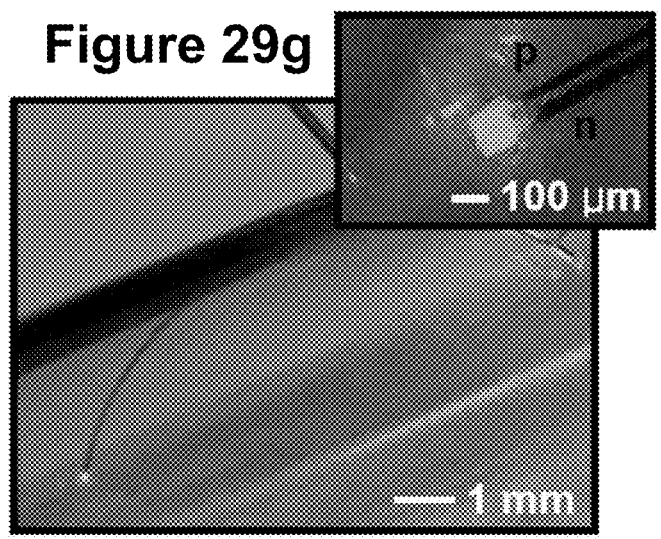
FIG. 29g, A thin strip LED device consisting of an isolated μ-ILED with straight interconnects wrapped around a glass tube (diameter ~5.0 mm, right).
Figure 30A:
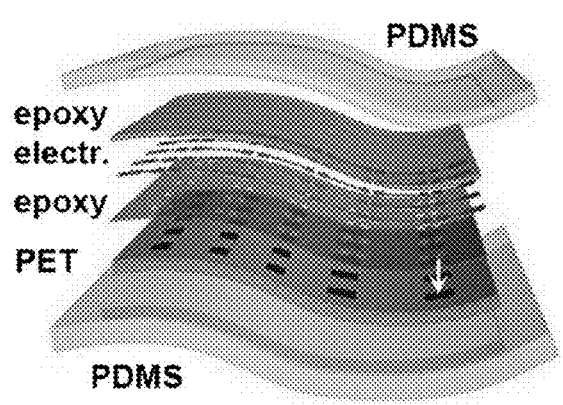
FIG. 30a, Schematic exploded view illustration of an array of μ-ILEDs (5×5) on a thin PET film (50 μm thick) coated with an adhesive. Layers of PDMS on the top and bottom provide a soft, elastomeric encapsulation that offers biocompatibility and an excellent barrier to biofluids and surrounding tissue.
Figure 30B:
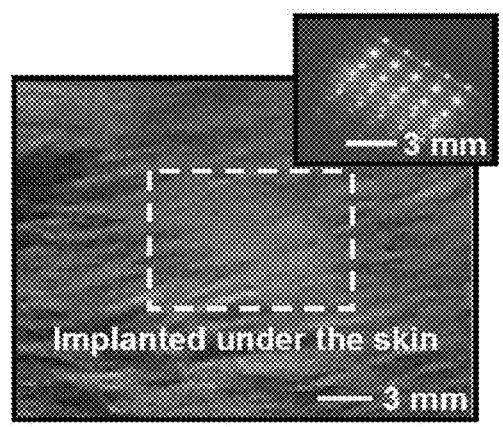
FIG. 30b, Image of an animal model with this array implanted under the skin, and on top of the muscle tissue. The inset shows the device before implantation.

FIGS. 29f and 29g present images of an array of µ-ILEDs (1×8) with serpentine metal bridges and a single µ-ILED device with long (1.25 cm×185 µm) metal interconnects, both on flexible, thin (~8 µm) ribbons mounted onto cylindrical supports. Alternatively, for longer term implantable applications, subdermal µ-ILEDs can overcome scattering limitations and bring in-vivo illumination to deep layers of tissue. This approach could yield capabilities complementary to those of fiber-optic probe-based medical spectroscopic methods, by enabling real-time evaluation of deep-tissue pathology while allowing precise delivery of radiation in programmable arrays. Such devices can be formed in geometries of strips or threads, or of sheets. As an example of the latter, the left frame of FIGS. 30a and 46 show a schematic exploded view and an illustration of fabrication procedures, respectively, for a 5×5 array of µ-ILEDs on a thin sheet of polyethylene terephthalate (PET; Grafix DURA-RAR, 50 µm thickness) film coated with an adhesive layer (epoxy) and encapsulated on top and bottom with PDMS. Thin (~500 µm) ceramic insulated gold wires that connect to metal pads at the periphery of the array provide access to external power supplies. FIG. 30b presents a picture of an animal model with the device implanted subdermally in direct contact with the underlying musculature (See methods section for details). The inset shows the same device before implantation. For continuous operation at the current levels reported here, peak increases in temperature at the tissue of a couple of degrees C. are estimated. Short pulsed mode operation could further minimize the possibility of adverse thermal effects and also, at the same time, allow the use of phase-sensitive detection techniques for increasingly sophisticated diagnostics, imaging and physiological monitoring.

In summary, the advances described here in mechanics, high fill factor multilayer layouts and biocompatible designs provide important, unusual capabilities in inorganic optoelectronics, as demonstrated by successful integration onto various classes of substrate and by use in representative devices for biomedical and robotics applications.

Figure 31A:
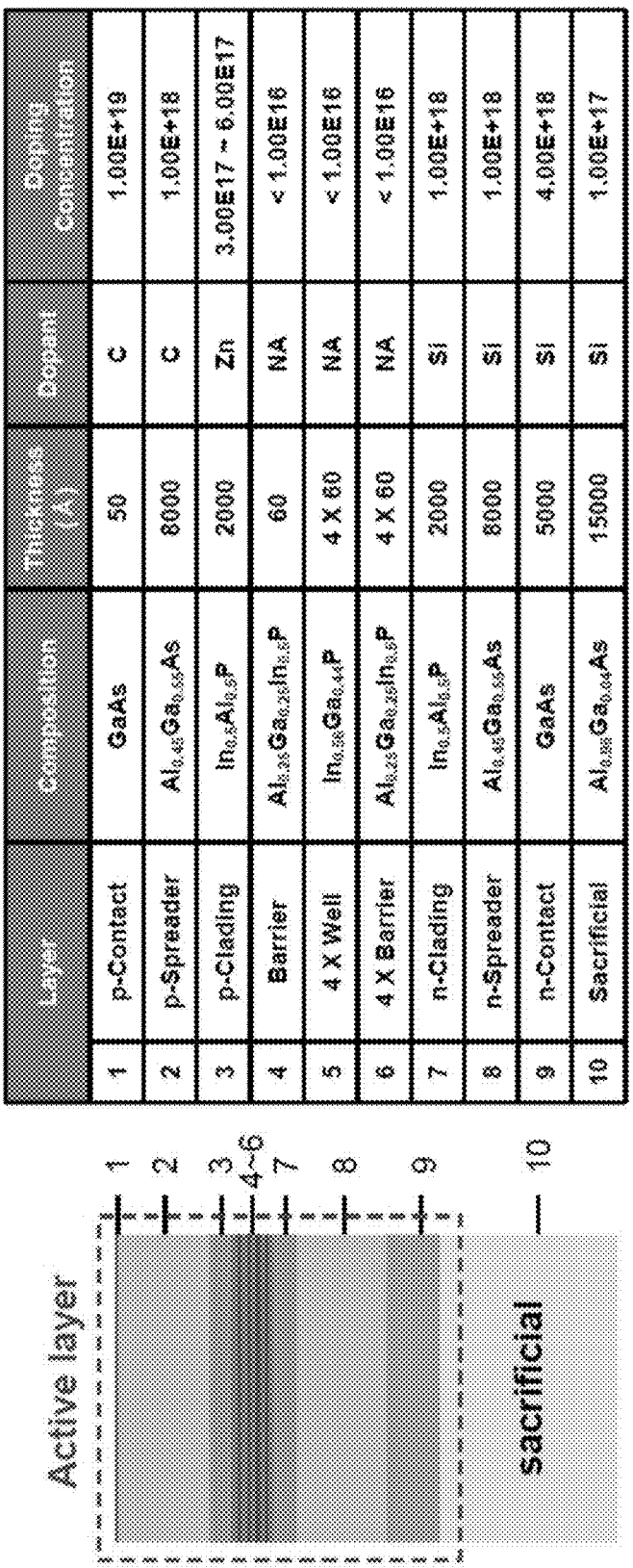
FIG. 31. Schematic illustration of epitaxial layer (a) and fabrication processes for μ-ILEDs arrays on a carrier glass substrate after transfer printing (b).
Figure 31B:
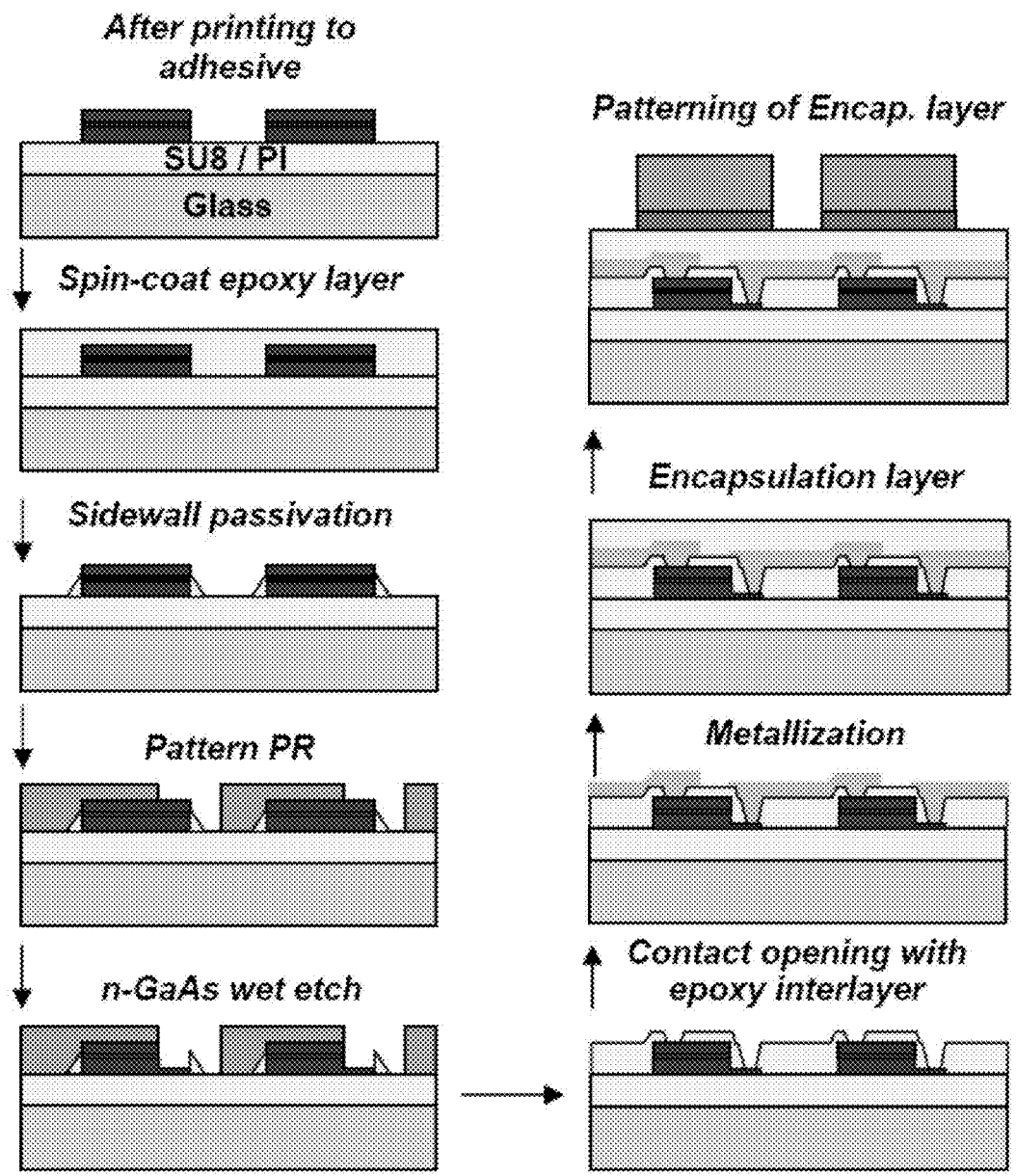

Methods. Delineating Epitaxial Semiconductor Material for µ-ILEDs and µ-IPDs. For fabrication of the µ-ILEDs and µ-IPDs, the process began with epitaxial films that included a quantum well structure (4×(6-nm-thick $Al_{0.25}Ga_{0.25}In_{0.5}P$ barriers/6-nm-thick $In_{0.56}Ga_{0.44}P$ wells)/6-nm-thick $Al_{0.25}Ga_{0.25}In_{0.5}P$ barriers) and an underlying sacrificial layer of $Al_{0.96}G_{0.04}As$ on a GaAs wafer. Details appear in FIG. 31*a*. Inductively coupled plasma reactive ion etching (ICP-RIE; Unaxis SLR 770 system) with $Cl_2/H_2$ through a hard mask of $SiO_2$ formed trenches down to the $Al_{0.96}G_{0.04}As$, to delineate active materials in 6×6 or 8×8 or 3×8 or 1×4 arrays of squares with sizes of 100 μm×100 μm. Next, photolithography defined photoresist structures at the four corners of each square to hold the epitaxial layers to the underlying GaAs wafer during removal of the $Al_{0.96}G_{0.04}As$ with diluted hydrofluoric (HF, Transene, USA) acid (deionized water (DI): 49% HF acid=1:100).

Fabricating Arrays of μ-ILEDs and μ-IPDs in Mesh Designs with Serpentine Interconnects on Glass Substrates. The released squares of epitaxial material formed according to procedures described above were transfer printed onto a glass substrate coated with layers of a photodefinable epoxy (SU8-2; Microchem.; 1.2 μm thick), polyimide (PI; Sigma-Aldrich; 1.2 μm thick), and poly(methylmethacrylate) (PMMA A2; Microchem.; 100 nm thick) from top to bottom. Next, another layer of epoxy (SU8-2, 2.0 μm) was spin-cast and then removed everywhere except from the sidewalls of the squares by reactive ion etching (RIE; PlasmaTherm 790 Series) to reduce the possibility of partial removal of the bottom n-GaAs layer during the 1st step of an etching process (1st step: $H_3PO_4:H_2O_2:DI=1:13:12$ for 25 seconds/ 2nd step: HCl:DI=2:1 for 15 seconds/3rd step: $H_3PO_4$: $H_2O_2$:DI=1:13:12 for 24 seconds) that exposed the bottom n-GaAs layer for n-contacts. Next, another layer of epoxy (1.2 μm thick) spin-cast and photopatterned to expose only certain regions of the top p-GaAs and bottom n-GaAs, provided access for metal contacts (non-Ohmic contacts) and interconnect lines (Cr/Au, 30 nm/300 nm) deposited by electron beam evaporation and patterned by photolithography and etching. These lines connected devices in a given row in series, and adjacent rows in parallel. A final layer of spin cast epoxy (2.5 μm) placed the devices and metal interconnects near the neutral mechanical plane. Next, the underlying polymer layers (epoxy/PI/PMMA) were removed in regions not protected by a masking layer of $SiO_2$ (150 nm thick) by RIE (oxygen plasma, 20 sccm, 150 mtorr, 150 W, 40 min). Wet etching the remaining $SiO_2$ with buffered oxide etchant exposed the metal pads for electrical probing, thereby completing the processing of arrays of μ-ILEDs (and/or μ-IPDs) with serpentine interconnects.

Transfer Printing of Stretchable Arrays of Devices to Substrates of Interest. Dissolving the PMMA layer of the structure described above with acetone at 75° C. for 10 minutes released the interconnected array of devices from the glass substrate. Lifting the array onto a flat elastomeric stamp and then evaporating layers of $Cr/SiO_2$ (3 nm/30 nm) selectively onto the backsides of the devices enabled strong adhesion to sheets or strips of PDMS or to other substrates coated with PDMS. For the PDMS balloon of FIG. 27*d*, prestrain was applied by partially inflating the balloon, followed by transfer printing the μ-ILEDs and then releasing (deflating) the balloon. For small substrates, roller printing techniques were used. See below for details.

Stretching Tests and Electrical Characterization. Stretching tests were performed using custom assemblies of manually controlled mechanical stages, capable of applying strains along x, y, and diagonal directions. For fatigue testing, one cycle corresponds to deformation to a certain level and then return to the undeformed state. Each fatigue test was performed up to 1000 cycles to levels of strains similar to those shown in the various figures. Electrical measurements were conducted using a probe station (4155C; Agilent), by directly contacting metal pads while stretched, bent, or twisted. The measurement was performed using a lead-out conductor line, bonded to metal pads of the arrays of μ-ILEDs. Typical voltage scan ranges for measurement of the 6×6, 8×8, and 3×8 arrays was 0~60 V, 0~80V, and 0~90V, respectively.

Animal Experiments. All procedures were performed under approved animal protocols. A female Balb/c mouse was anesthetized with an intraperitoneal injection of a mix of ketamine/xylazine. The depth of anesthesia was monitored by palpebral and withdrawal reflexes to confirm that the animal had reached "stage 3" of anesthesia. Once the animal was lightly anesthetized, the back was shaved and cleaned at the incision site with 70% ethanol, followed by a betadine surgical scrub. Previous implants were removed from the mouse and the animal was euthanized according to approved protocols. For the implants, the incision was performed on the dorsal side of the mouse and the suturing was carried out across the dermal layers (outer layers and subcutaneous tissues) above the muscle tissue.

Photographs. Images in FIGS. 27*a* and 29*e* were combined images to eliminate out-focused regions. Tens of pictures were captured at different focal depths using a Canon 1Ds Mark III with a Canon MP-E 1-5× Macro lens, and those captured pictures are merged in the software "helicon focus" to create completely focused image from several partially focused images.

Figure Captions. FIG. 27. Device layouts of μ-ILED arrays and their responses to uniaxial and balloon-shape biaxial stretching. FIG. 27*a*, Optical image of a 6×6 array of μ-ILEDs (100 μm×100 μm, and 2.5 μm thick, in an interconnected array with a pitch of ~830 μm) with non-coplanar serpentine bridges on a thin (~400 μm) PDMS substrate (left frame). Schematic illustration (right) and corresponding photograph (inset) of a representative device, with encapsulation. FIG. 27*b*, Optical images of a stretchable 6×6 array of μ-ILEDs, showing uniform emission characteristics under different uniaxial applied strains (top left: 0%, bottom left: 48% along horizontal direction, top right: 0%, bottom right: 46% along diagonal direction). FIG. 27*c*, Current-voltage (I-V) characteristics of this array measured in the strained configurations shown in b (left) and voltage at 20 μA current for different cycles of stretching to 75% along the horizontal direction (right). FIG. 27*d*, Tilted (left) view optical images of a stretchable array (6×6) of μ-ILEDs on a thin (~500 μm) PDMS membrane in a flat configuration (top) and in a hemispherical, balloon state (bottom) induced by pneumatic pressure. FIG. 27*e*, The magnified view of FIG. 27*d* from the top. The yellow dashed boxes highlight the dimensional changes associated with the biaxial strain. FIG. 27*f*, I-V characteristics of the array in its flat and inflated state.

FIG. 27*g*, Distribution of meridional and circumferential strains determined by 3D-FEM.

FIG. 28. Responses of μ-ILED arrays to twisting and stretching on sharp tips. FIG. 28*a*, Optical images of an array of μ-ILEDs (3×8) on a band of PDMS twisted to different angles (0° (flat), 360°, and 720° from top to bottom), collected with (left) and without (right) external illumination. FIG. 28*b*, SEM image of the array when twisted to 360°. The serpentine interconnects move out of the plane (red box) to accommodate the induced strains. FIG. 28*c*, I-V characteristics of the array twisted by various amounts (0 (flat), 360 and 720°). FIG. 28*d*, Distributions of axial (left), width (center) and shear (right) strain determined by 3D-FEM for twisting to 720°. FIG. 28*e*, Optical images of an array of μ-ILEDs (6×6), tightly stretched on the sharp tip of a pencil, collected with (left) and without (right) external illumination. The white arrows indicate the direction of stretching. FIG. 28f, Optical images of a stretchable 8×8 array wrapped and stretched downward on the head of a cotton swab. The inset image was obtained without external illumination. FIG. 28g, I-V characteristics of the array in FIG. 28e, before (initial), during (deformed) and after (released) deformation. The inset provides a graph of the voltage needed to generate a current of 20 µA, measured after different numbers of cycles of deformation.

FIG. 29. Multilayer laminated configurations of arrays of µ-ILEDs for high effective area coverage and integration on various unusual substrates. FIG. 29a, Schematic, exploded view illustration for a stacked device formed by multilayer lamination. FIG. 29b, Optical images of a four layer stack of 4×4 arrays with layer-to-layer offsets designed to minimize overlap of interconnect lines with positions of the µ-ILEDs. The images show emission with different numbers of layers in operation (1st layer on, 1st and 2nd layers on, 1st, 2nd and 3rd layers on, and 1st, 2nd, 3rd and 4th layers on). FIG. 29c, Optical images of a two layer stack of 8×8 arrays, with different layers in operation. The inset shows the device in a bent state (bending radius ~2 mm) with both layers on. FIG. 29d, Optical image of an array of µ-ILEDs (8×8) on a piece of paper, in a folded state (bending radius ~400 µm) during operation. The inset shows the device in its flat state. FIG. 29e, Image of a 6×6 array on a sheet of aluminum foil under crumpled state. The inset shows the device in its flat state. FIG. 29f, Images of a thin (~8 µm), narrow (820 µm) strip of µ-ILEDs (1×8) with serpentine interconnects on a rigid plastic tube (diameter ~2.0 mm, left). Inset shows the magnified view of a single pixel. FIG. 29g, A thin strip LED device consisting of an isolated µ-ILED with straight interconnects wrapped around a glass tube (diameter ~5.0 mm, right). The insets provide a magnified view. FIG. 29i, Image of a 1×8 array with serpentine metal bridges on a ~700 µm diameter fiber, wrapped around a glass tube (diameter ~1.4 mm, left frame) and, in a knotted state (inset), respectively, resting on coins (pennies) to set the scale.

Figure 47A:
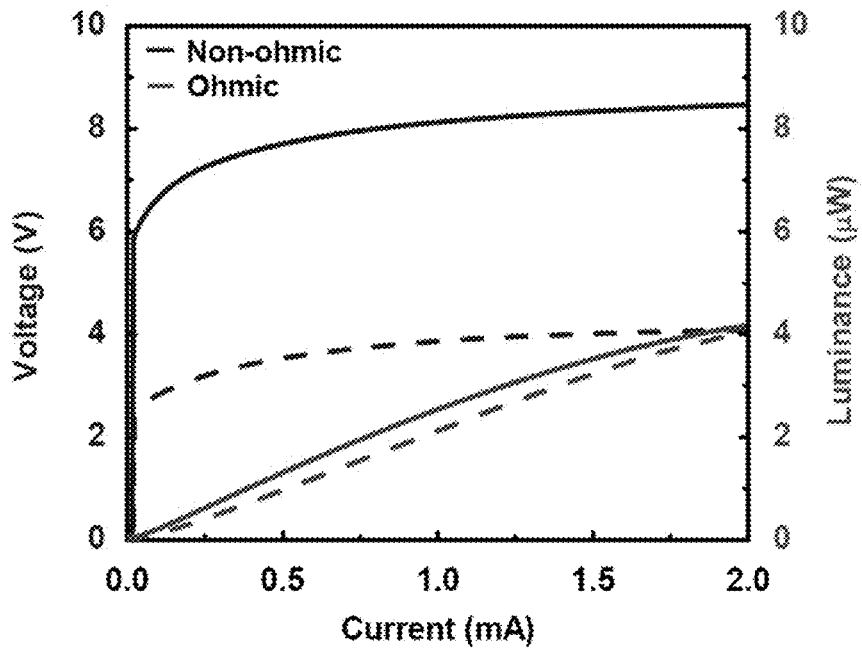

FIG. 30a, Schematic exploded view illustration of an array of µ-ILEDs (5×5) on a thin PET film (50 µm thick) coated with an adhesive. Layers of PDMS on the top and bottom provide a soft, elastomeric encapsulation that offers biocompatibility and an excellent barrier to biofluids and surrounding tissue. FIG. 30b, Image of an animal model with this array implanted under the skin, and on top of the muscle tissue. The inset shows the device before implantation. Contact Scheme. Here, simple metal (Cr/Au) to doped GaAs contacts are used instead of ohmic contacts. For improved electrical characteristics, conventional ohmic contacts of metal interconnects to GaAs can be implemented. To form the ohmic contact, a series of metal stacks followed by appropriate annealing (n ohmic contact metals: Pd/Ge/Au followed by anneal at 175° C. for 1 hour, p ohmic contact metal: Pt/Ti/Pt/Au in this paper) can be used, which results in lower take-off voltage can be obtained as shown in FIG. 47a.

Figure 47B:
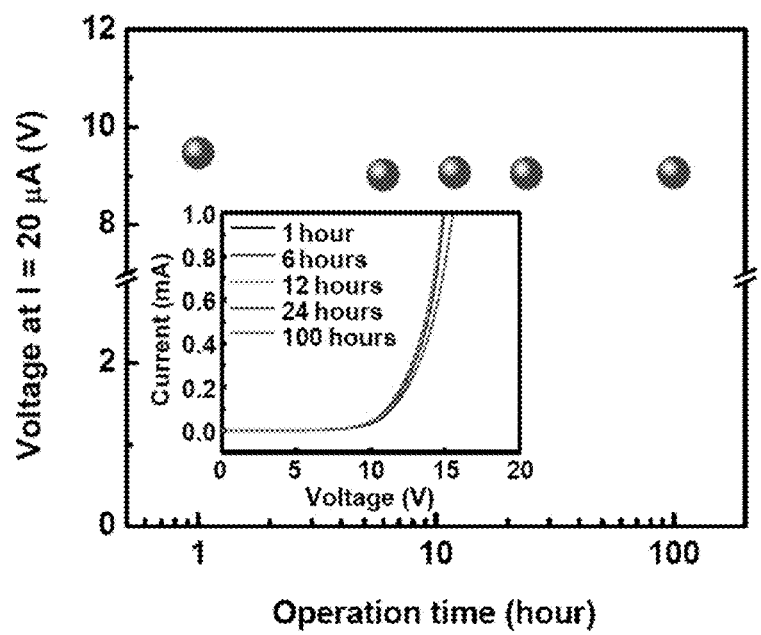

Long-term operation. Long-term operation was tested using two LED devices, connected in series, on a thin slab of PDMS was performed under the constant current mode (0.75 mA). Both devices showed robust and reliable performance during the continuous operation for 100 hours without affecting I-V characteristics as shown in FIG. 47b.

Figure 48A:
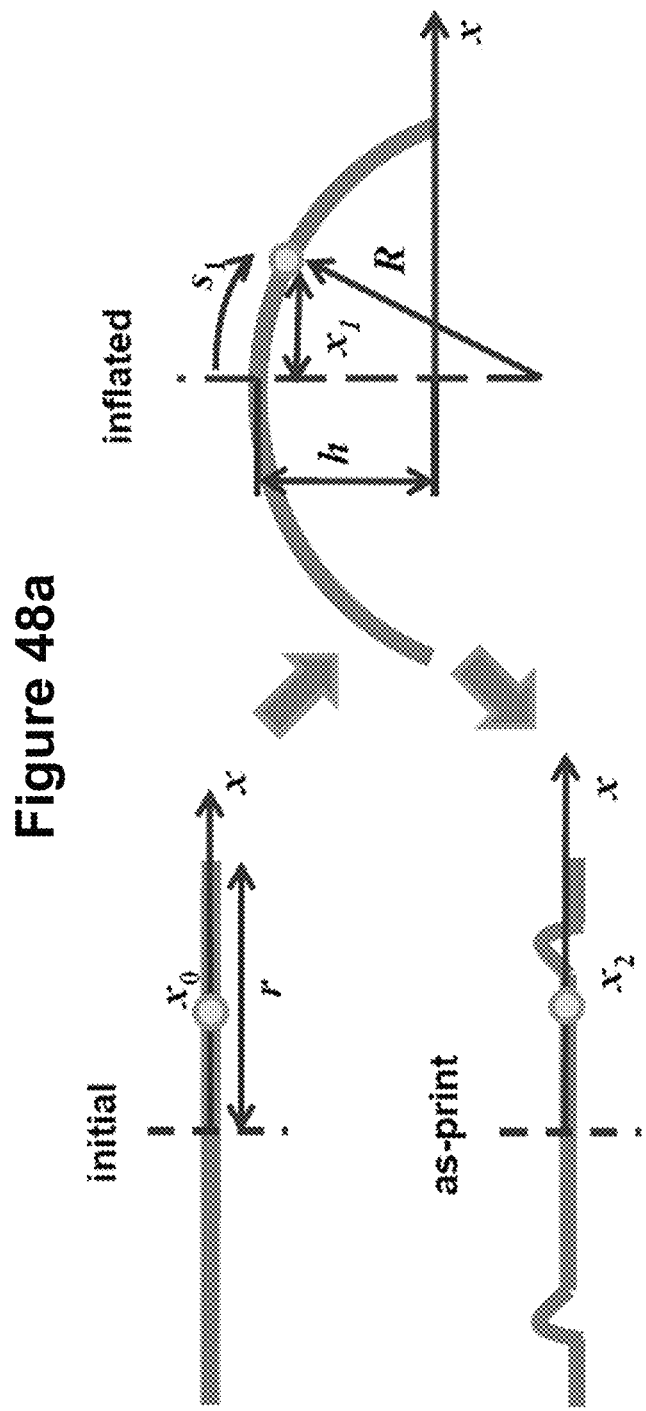
Figure 48B:
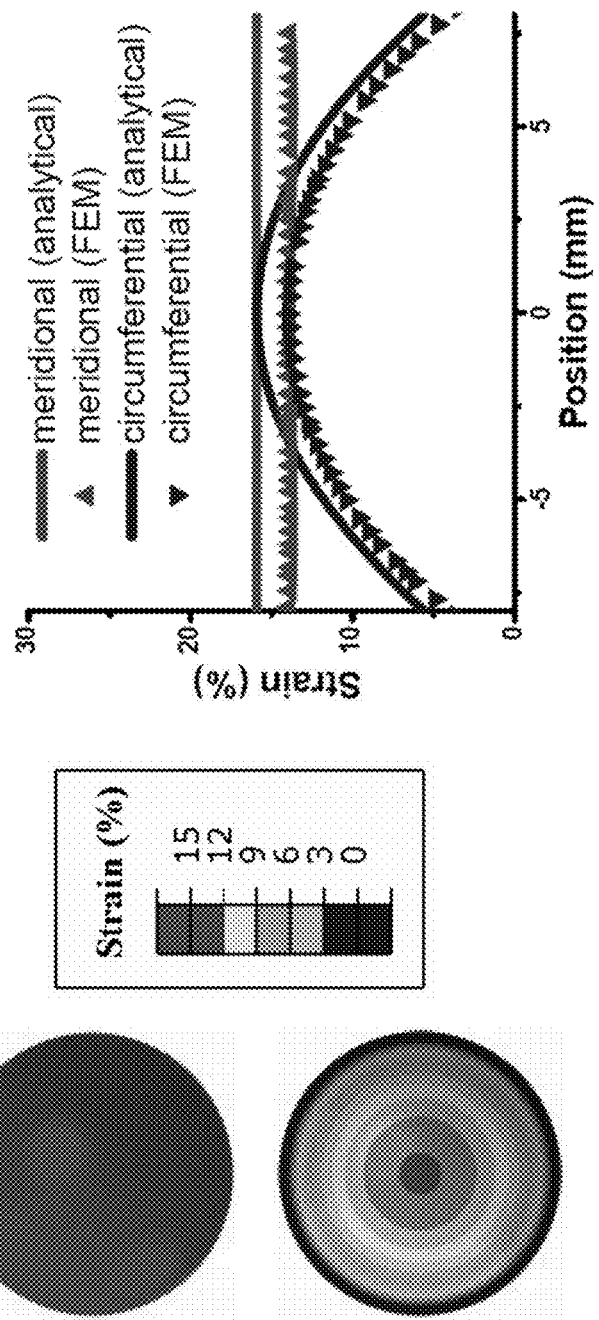

FEM Simulation of Balloon Deformation. FIG. 48a illustrates the mechanics model for inflating and transfer printing onto the PDMS balloon of FIG. 27. The initially flat, circular thin film (initial state, upper left frame of FIG. 38a) of radius r is fixed at its outer boundary, and is inflated by air to a spherical cap of height h (inflated state, right frame of FIG. 48a). The radius of the sphere is $R=(h^2+r^2)/(2h)$. The spherical cap is pressed down and flattened during transfer printing, as shown in the lower left frame of FIG. 48a (as-print state). The deformation is uniform along the meridional direction during inflation, while all material points move vertically downward during printing. Therefore, for a point of distance $x_0$ to the film center at the initial state, its position changes to $x_1$ in the inflated state with an arc distance $s_1$ to the film center, and then changes to $x_2$ in the state during printing, where $s_1=(R_{x_0}/r)\arcsin(r/R)$ and $x_1=x_2=R\sin[(x_0/r)\sin^{-1}(r/R)]$. These give the meridional and circumferential strains of the inflated state as:

$$\varepsilon_{\theta 1} = \frac{R}{r}\arcsin\frac{r}{R} - 1, \quad (S1)$$

$$\varepsilon_{\phi 1} = \frac{R}{x_0}\sin\left(\frac{x_0}{r}\arcsin\frac{r}{R}\right) - 1. \quad (S2)$$

The meridional and circumferential strains at the state during printing are given by:

$$\varepsilon_{\theta 2} = \frac{R}{r}\cos\left(\frac{x_0}{r}\sin^{-1}\frac{r}{R}\right)\sin^{-1}\frac{r}{R} - 1, \quad (S3)$$

$$\varepsilon_{\varphi 2} = \frac{R}{x_0}\sin\left(\frac{x_0}{r}\sin^{-1}\frac{r}{R}\right) - 1. \quad (S4)$$

Figure 48C:
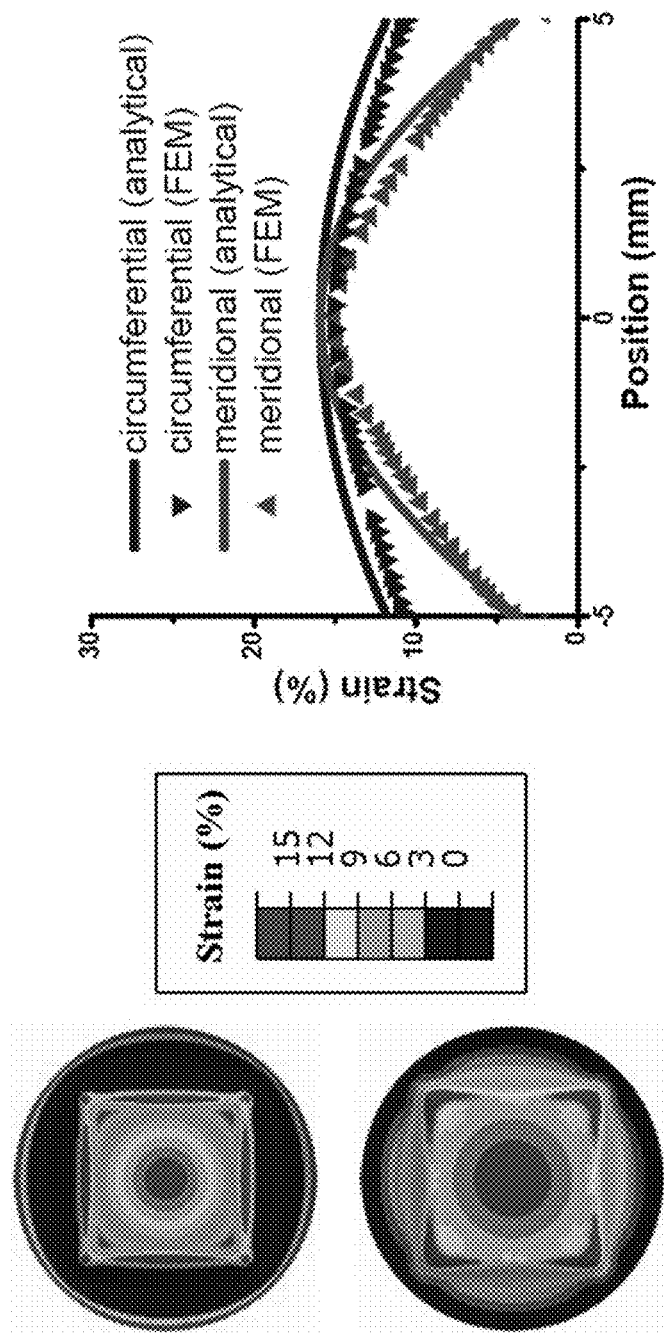

Finite element method (FEM) was used to study this process in order to validate the analytical model above. The contours of meridional and circumferential strains of the inflated state appear in the upper and lower left frames of FIG. 48b, respectively. The results are compared with analytical solutions, Equations (S1) and (S2), in the right frame of FIG. 48b, and show good agreement. Therefore, the analytical formulae, Equations (S1) and (S2), can be used to predict the PDMS strain under different inflation, and further to estimate the strain in devices on the balloon surface. FIG. 48c shows the contours of meridional (upper left frame) and circumferential (lower left frame) strains of the asprint state, and the comparison with analytical solutions from Equations (S3) and (S4) (right frame). The analytical solutions, once again, agree well with FEM simulations without any parameter fitting.

Bending of LEDs on Various Substrates. The LED, as illustrated in FIG. 49, consists of multiple layers with thicknesses $h_1=3.5$ µm, $h_2=2.5$ µm, $h_3=1.2$ µm and $h_4=1.2$ µm, and Young's moduli are $E_{SU8}=5.6$ GPa, $E_{GaAs}=85.5$ GPa and $E_{PI}=3.2$ GPa. These layers are modeled as a composite beam with equivalent tensile and bending stiffnesses. The PDMS strain isolation layer has thickness $h_5=50$ um and Young's modulus $E_{PDMS}=0.4$ MPa. The Young's modulus $E_{sub}$ and thickness H of the substrate are 1.2 MPa and 0.8 mm for the fabric, 23.5 MPa and 0.5 mm for the fallen leaf, and 600 MPa and 0.2 mm for the paper. The strain isolation model then gives very small maximum strains in GaAs, 0.043%, 0.082% and 0.23% for the completely folded fabric, leaf and paper, respectively. The minimal bend radii are the same as the corresponding substrate thicknesses H, i.e., 800 µm, 500 µm and 200 µm for the fabric, leaf and paper, respectively. For the Al foil substrate, the minimum bend radius is obtained as 139 µm when the strain in GaAs reaches 1%.

Without the PDMS strain isolation layer, the LED and substrate are modeled as a composite beam. The position of neutral axis (measured from the top surface) is given by:

$$y_0 = \frac{\left\{\begin{array}{l} E_{SU8}[(h_1+h_3)^2 + 2h_2 h_3] + E_{PI} h_4(2h_1 + 2h_2 + 2h_3 + h_4) + \\ E_{GaAs} h_2(2h_1 + h_2) + E_{sub} H(2h_1 + 2h_2 + 2h_3 + 2h_4 + H) \end{array}\right\}}{2[E_{SU8}(h_1+h_3) + E_{GaAs} h_2 + E_{PI} h_4 + E_{sub} H]}.$$

The maximum strain in GaAs is $$\varepsilon_{GaAs} = \frac{1}{R_b}\max(|y_0 - h_1|, |h_1 + h_2 - y_0|),$$

where $R_b$ is the bending radius. Therefore, the minimum bending radius of LED array on the substrate is $$R_b = \frac{1}{\varepsilon_{failure}}\min(|y_0 - h_1|, |h_1 + h_2 - y_0|),$$

where $\varepsilon_{failure}=1\%$ is the failure strain of GaAs. For the fabric substrate, the maximum strain in GaAs is only 0.34% even when it is completely folded, which gives the minimum bending radius the same as the thickness 0.8 mm. For the fallen leaf and the paper, the minimum bending radii are 1.3 mm and 3.5 mm.

Figure Captions. FIG. 33. Schematic illustration of epitaxial layer (a) and fabrication processes for μ-ILEDs arrays on a carrier glass substrate after transfer printing (b).

Figure 32B:
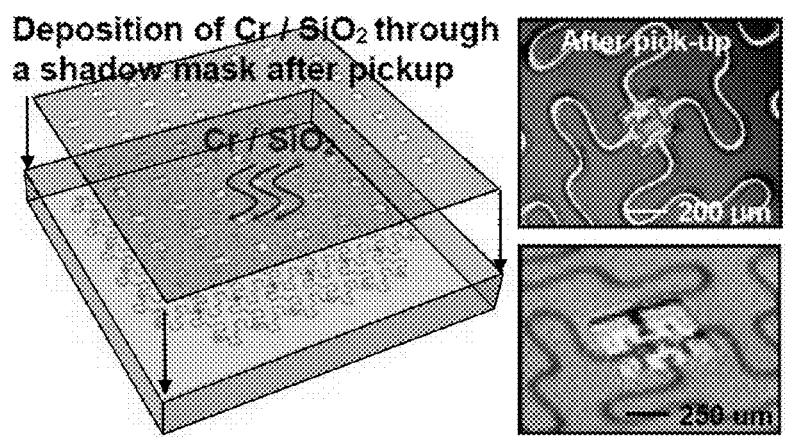
Figure 32C:
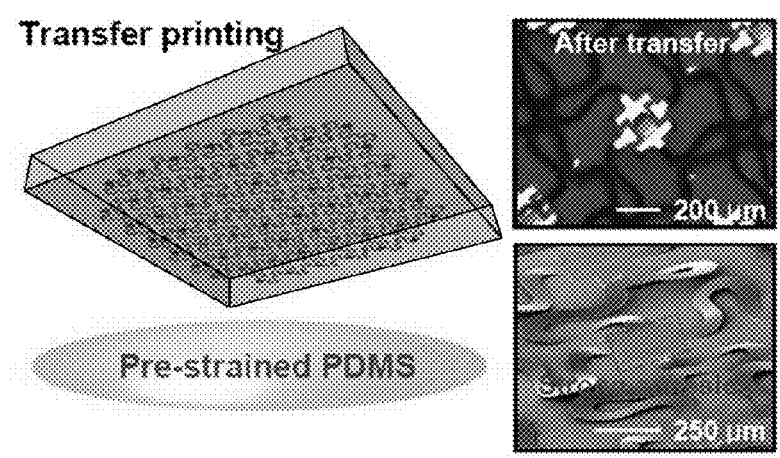

FIG. 32. (a) Schematic illustration (left frame) and corresponding microscope (top right frame) and SEM (bottom right frame) images of a 6×6 μ-ILEDs on a handle glass substrate coated with layers of polymers (epoxy/PI/PMMA). (b) Schematic illustration (left frame) and corresponding microscope (top right frame) and optical (bottom right frame) images of a 6×6 μ-ILEDs array which is picked up with a PDMS stamp for transfer printing. A shadow mask for selective deposition of Cr/SiO$_2$ (thickness: 3 nm/30 nm) covers the retrieved array on a soft elastomeric PDMS stamp. (c) Schematic illustration of transfer printing to a pre-strained thin (thickness: ~400 μm) PDMS substrate (left frame) and microscope (top right frame) and SEM (bottom right frame) images of the transferred μ-ILEDs array on a prestrained thin PDMS substrate. Prestrain value was ~20%.

FIG. 33. (a) Schematic illustration of top encapsulation layers indicating some of the key dimensions. (b) Schematic illustration of the cross sectional structure at an island, with approximate thicknesses for each layer. The inset corresponds to an SEM image of a μ-ILEDs array after transfer printing to a thin PDMS substrate with prestrain of ~20%. (c) Schematic illustration of the cross sectional structure at metal interconnection bridges, with approximate thicknesses of each layer.

FIG. 34. (a) Tilted view SEM images of adjacent μ-ILEDs (yellow dashed boxes) before (left, formed with ~20% pre-strain) and after (right) stretching along the horizontal direction (red arrows). (b) Strain distributions determined by 3D-FEM for the cases corresponding to frames in (a). The black outlines indicate the positions of the devices and the serpentines before relaxing the pre-strain.

FIG. 35. (a) Optical microscope images of two pixels in a μ-ILEDs array with a serpentine bridge design before (left frame) and after (right frame) external stretching along the horizontal direction. The upper and lower images show optical micrographs in emission light off (upper) and on (lower) states. The distance between adjacent pixels appears in the lower images and used for calculation of applied strains. The lower images were obtained without external illumination. (b) Optical micrograph images of two pixels in a μ-ILEDs array before (left frame) and after (right frame) external stretching along the diagonal direction. (c) FEM simulation under external stretching along the diagonal direction (left frame), and strain contours in the GaAs active island (top right frame) and the metal bridge (bottom right frame).

FIG. 36. Optical images of a 6×6 μ-ILEDs array with a serpentine mesh design with external illumination under the same strain circumstances as FIG. 27b.

FIG. 37. (a) Optical image of an 8×8 μ-ILEDs array on a thin PDMS substrate in its on state, which is under the same kind of deformed condition as bottom left frame of FIG. 27d. (b) Top view optical images of same array as FIG. 27d in its 'flat' (left frame) and 'inflated' state (right frame) without external illumination. (c) Spatial distribution of FEM results of the right frame of FIG. 27d and analytical solutions calculated from Equations (S1) and (S2).

FIG. 38. (a) Schematic illustrations of a 3×8 μ-ILEDs array integrated on a thin PDMS substrate with detailed dimensions (upper frame: registrations of the μ-ILEDs on a PDMS donor substrate, lower frame: entire view of the printed 3×8 μ-ILEDs array). The inset on top represents an optical microscope image of this μ-ILEDs array on a handle glass substrate before transfer printing. (b) Magnified view of the SEM image in FIG. 28b. The white dotted rectangle highlights the non-coplanar bridge structures. (c) Voltage at 20 μA current for each twisting cycle of 360°.

FIG. 39. FEM strain contours of axial (top), width (center), and shear (bottom) strains for 360° twisted PDMS substrate.

FIG. 40. Fatigue test result of a 6×6 μ-ILEDs array as shown in FIG. 28e. (a) Plot of I-V characteristics of a 6×6 μ-ILEDs array as a function of deformation cycles. (b) Plot of voltage needed to generate a current of 20 μA measured after deformation cycles up to 1000 times. Each deformed state is approximately same as shown in FIG. 28e.

FIG. 41. (a) Schematic illustration of stacked devices describing states of FIG. 29b. (b) Optical images of stacked devices as shown in FIG. 29b, collected without external illumination.

FIG. 42. (a) The strain distribution of the two-layer system in the stacked array bent to a radius of curvature 2 mm, as shown in FIG. 29c. The black dashed rectangles demonstrate the positions of μ-ILEDs. (b) The strain distribution in GaAs layers in the μ-ILEDs island.

FIG. 43. (a) Optical image of a 6×6 μ-ILEDs array with serpentine metal interconnects, integrated on fabrics, in its bent and on state (bending radius ~4.0 mm). The inset shows the device in its flat and off state. (b) Plot of I-V characteristics of this array in its bent state. Inset provides a graph of the voltage needed to generate a current of 20 μA, measured after different numbers of cycles of bending deformation. (c) Optical image of an 8×8 μ-ILEDs array with a human pattern, integrated on a fallen leaf, in its bent and on state. The inset image was collected with external illumination. (d) Plot of I-V characteristics in the bent state as shown in FIG. 43c. (e) Optical image of a μ-ILEDs array integrated on a paper in its folded and on state. (f) Optical image of the same μ-ILEDs array as shown in FIG. 29e in its mildly crumbled state. Inset represents microscope image of adjacent four pixels in their on states.

FIG. 44. (a) Plot of I-V characteristics of a 6×6 μ-ILEDs array integrated on paper in its flat (FIG. 29d inset) and folded (FIG. 29d) state. (b) Plot of I-V characteristics of a 6×6 μ-ILEDs array integrated on aluminum foil in its flat (FIG. 29e inset) and crumbled (the center frame of FIG. 29e) state. (c) Fatigue tests of arrays of 6×6 μ-ILEDs as shown in FIG. 43e. Plot of I-V characteristics of a μ-ILEDs array integrated on paper as a function of deformation cycles (left frame). Plot of voltage needed to generate a current of 20 μA measured after deformation cycles up to 1000 times (right frame). (d) Fatigue tests of arrays of 6×6 μ-ILEDs as shown in FIG. 43f. Plot of I-V characteristics of a μ-ILEDs array integrated on aluminum foil as a function of deformation cycles (left frame). Plot of voltage needed to generate a current of 20 μA measured after deformation cycles up to 1000 times (right frame).

FIG. 45. SEM images of various substrate such as fabrics (a), Al foils (b), paper (c), and fallen leaves (d) before (left frame) and after (right frame) coating of thin layer of PDMS.

FIG. 46. Schematic illustration of the encapsulation of an implantable array of μ-ILEDs as described in FIGS. 30a and 30b.

FIG. 47. (a) Result of Luminance (L)-Current (I)-Voltage (V) measurement of an individual pixel with and without applied ohmic contacts. (b) Applied voltage to generate a current of 20 μA, measured after different operation time. The inset provides I-V characteristics with different operation time.

FIG. 48. (a) Schematic illustration of analytical model for the inflation and printing-down of PDMS film. (b) FEM contours of meridional (upper left) and circumferential (lower left) strains of the inflated state and its comparison with analytical solutions calculated from Equations (S1) and (S2). (c) FEM contours of meridional (upper left) and circumferential (lower left) strains of the as-printed state and its comparison with analytical solutions Equations (S3) and (S4) (right frame).

FIG. 49. Schematic illustration of the cross section of μ-ILEDs on a substrate.

EXAMPLE 5

System for Biological Sensing and Stimulating Applications Using High Density Array Devices The capacity to intimately integrate the full power of modern semiconductor technology with the soft, fluid-bathed, curvilinear and moving surfaces of an animal, e.g., a human, has major implications for human health, for diagnostic, therapeutic and surgical applications. In general, current forms of high performance electronic devices are built on the hard, rigid and brittle surfaces of semiconductor wafers, in formats that are inherently incompatible with establishing intimate, large area interfaces with a biological tissue. Electronic platforms that are flexible and stretchable have the potential to avoid these limitations. An example of a flexible high-density active electrode array fabricated particularly for biological applications is disclosed in commonly assigned International Patent Application Publication No. WO 2009/114689, published on Sep. 17, 2009, and entitled "Flexible and Scalable Sensor Arrays for Recording and Modulating Physiologic Activity," the entirety of which is incorporated herein by reference.

One example of a biological therapeutic application is cardiac resynchronization therapy (CRT). CRT refers to the simultaneous application of multiple pacing stimuli to different areas of a failing heart in order to improve cardiac function. In patients with heart failure due to myocardial infarction or other causes, the ability of the ventricle to pump blood is compromised by dyssynchronous activity in various walls of the ventricle. By promoting more organized mechanical contraction via two or more electrical stimuli that are carefully timed and positioned on or in the heart, more synchronous and thus more efficient ventricular function can be restored. Unlike basic pacemaker therapy, in which a single electrical stimulus is applied to the ventricle for each heartbeat purely to treat abnormally slow heart rhythms, CRT is designed to effectively replace the electrical system of the failing heart and improve the organization of ventricular contraction at all heart rates.

Another application is to map conditions across the surface of a biological tissue, e.g., the heart, to determine an appropriate stimulation scheme to be applied, e.g., pacing or ablating. Cardiac mapping is useful to isolate failing areas and to use that information to determine where to focus treatment, such as ablation treatment. There are numerous biological sensing and stimulating applications that would benefit from a highly flexible and yet miniaturized device that supports an array of elements useful for sensing a variety of conditions from the tissue and/or for applying different types of energy to the tissue.

In an embodiment, the invention provides a thin and highly flexible device having an array of elements that can be used for sensing or stimulating is used as a platform from which numerous biological sensing, mapping and stimulating applications are provided. There are numerous applications described herein that exploit the spatial arrangement of elements on the device, and in so doing, provide a mechanism to deliver treatments that would not otherwise be possible without more invasive procedures, such as surgery.

Referring first to FIG. 55, a system 10 is shown that is designed for biological sensing and therapeutic treatment applications. The system 10 comprises a flexible high-density micro-array device (array device) 100 that connects or interfaces with a control system 200. The array device 100 is configured to be placed in operational contact or communication with a biological tissue shown at reference numeral 20 for monitoring and/or therapeutic treatment of the biological tissue. Examples of biological tissue for which the array device 100 may be used include heart tissue, brain or other nervous system organs, muscles, retinas, ear drums, circulatory system structures, tumor tissues, and digestive system structures.

Examples of specific structures and fabrication techniques for the array device 100 are described in the aforementioned co-pending application. FIGS. 68-74, described hereinafter, illustrate additional electrical circuit configurations for the array device 100. The array device 100 comprises an array of elements 110 that may be sensors and/or effectors on a thin and highly flexible substrate 115. The array device 100 is fabricated using silicon-based circuit fabrication techniques. It is highly flexible and stretchable and well suited to flex with the natural movement of a biological tissue.

The elements 110 on the array device 100 may serve as sensors and/or effectors. As used herein, an effector is any device that takes a signal and introduces an intervention to modulate biological (e.g., brain or heart) activity. Examples of effectors include electrical stimulators, photo/light-emitters (e.g., for activating brain tissues impregnated with a light responsive compound), chemical releasing/infusion devices, devices that change temperature, pressure, and/or acceleration, and devices that introduce electrical, magnetic or other fields, etc. Illumination sources such as a light source or other source that can activate tissue for diagnostic or monitoring purposes may also be used. For example, such illumination sources may be used to activate brain tissue to interrogate its function but not necessarily to modulate its activity.

Similarly, a sensor is any element that can be used to transduce a biological signal into an electrical or other signal. Examples of sensors include: electrical contacts for recording electrophysiological signals, optical detectors for recording light correlates of biological activity, chemical sensors for detecting changes in chemical concentrations or PH (e.g., chloride, neurotransmitters, lactate, glucose, other metabolites, neuro-active compounds, medications, biological substances such as tumor-secreted factors, etc.), devices for measuring temperature, force, acceleration, movement, pressure, etc.

A sensor may also include functionality of the effector as defined above.

The control system 200 interfaces with the electrode array device 100 through one or more direct wired connections, or optionally though a wireless connection. The control system 200 comprises a signal analysis subsystem 300 and a treatment application subsystem 400. One or both of these subsystems may be employed for a particular application. Some of the functions of these subsystems may be incorporated on-board the array device 100. The signal analysis subsystem analyzes signals obtained from individual elements 110 of the array device 100 for those elements configured as sensor elements. An example of an application of the signal analysis subsystem is to analyze local ventricular contraction parameters derived from sensor elements 110 in the form of strain gauge micro-sensors. The treatment application subsystem 400 takes input from the signal analysis subsystem or some other source in order to determine parameters for a therapy to be applied, via the array device 100, or some other device. For example, the treatment application subsystem 400 may determine pacing parameters to be employed when the array device 100 is configured to apply multiple spatially diverse pacing stimuli. These are only examples of the possible functions of the signal analysis subsystem 300 and treatment application subsystem 400. Other examples are described hereinafter. In addition, while signal analysis subsystem 300 and therapy application subsystem 400 are shown as separate blocks, they be implemented within a single block, i.e., by a microprocessor, microcontroller, digital signal processor, or other programmable or fixed logic device.

Turning to FIG. 56, a diagram is provided to show that the array device 100 can be collapsed (wrapped or rolled on itself) for introduction into a body of an animal for deployment at the biological tissue site of interest. To this end, as shown in FIG. 57, the array device 100, when collapsed, rolled or wrapped on itself, may be inserted into a catheter or other introducer sheath device 30 for guidance and delivery to the biological tissue site.

Example Application: Cardiac Resynchronization

One application described herein relates to cardiac resynchronization.

Referring to FIGS. 58 and 59, an example application is shown in which the array device 100 is introduced inside the pericardium of the heart of an animal using the introducer sheath 30. Once the introducer sheath 30 reaches into the pericardium, the array device 100 is allowed to unroll or unwrap by being pushed outward from the sheath 30, such as by a guide wire, in order to make contact with an area of the heart of interest as shown in FIG. 59. Suitable electrical (and/or physical) contact between the array elements 110 of the array device and the heart tissue is enhanced by the pericardial fluid around the surface of the heart inside the pericardial sac.

Thus, FIGS. 58 and 59 show that the array device 100 is a thin, ultra-flexible device platform supporting an array of active electronics that can be introduced into or around the heart via standard catheter delivery techniques in a traditional electrophysiology laboratory. It is collapsed (e.g., retracted, rolling, or folded), moved to within or around the heart and related structures (with the assistance of a combination of fluid and air injected in the pericardial space), and re-deployed at a separate location.

In one form, the device 100 is initially introduced into the body on a biodegradable backing platform (e.g. silk). This biodegradable platform will provide additional support for implantation and initial manipulation, then dissolve and facilitate close adherence of the device 100 to cardiac and heart-related tissues.

In an alternative form, the array device 100 may be directly placed on the epicardium via surgical techniques.

Turning to FIGS. 60 and 61, an example of a closed-loop application of the array device 100 is now described. In this example, the array device 100 is secured to the epicardium and connected to an implantable electronics unit 500 within which the control system 200 resides. The electronics unit 500 connects to the array device via a tunneled lead 510 and also connects to transvenous right atrial and right ventricular pacing electrodes 530 and 535 via leads 520 and 525.

In the configuration shown in FIG. 61, pacing stimuli can be delivered in a programmable fashion with high spatial and temporal adaptability that is well suited for cardiac resynchronization therapy (CRT). As explained herein, CRT involves the simultaneous application of multiple pacing stimuli to different areas of the heart. Since the array device 100 has numerous spatially arranged elements 110, which can be configured as active effector elements, the array device 100 is well suited to provide a fully implantable system that is capable of delivering CRT.

In particular, the array device 100 provides for the ability to pace the heart from essentially any location, sequence of locations, or combination of locations on the ventricles. This allows for customization and optimization of pacing for each individual patient, with the goal of increasing both the number of patients for whom CRT will be indicated and the proportion of patients that experience a positive response.

FIGS. 62 and 63 illustrate the flexibility in spatially controlling pacing stimuli to the heart. FIG. 62 is a simplified diagram of the active area of the array device, showing effector elements 110 of the array device 100 arranged in rows A-D and columns 1-4. FIG. 63 illustrates a variety of spatial and timing schemes that may be employed with respect to the effector elements on the array device. In addition to the schemes depicted in FIG. 63, individual effector elements 110 may be addressed for delivering a stimulus at a particular time instant. Thus, there are numerous spatial and timing schemes that can be employed in connection with the array device 100 for delivering pacing stimuli to the heart. Furthermore, the array device 100 makes feasible a multitude of additional applications and advantages over existing resynchronization devices and systems. Incorporation of sensors such as strain gauges at select array elements 110 can provide information on local ventricular contraction parameters that enable a closed-loop system in which the control system 200 can adjust and optimize pacing parameters in real-time. Such a system may be crucial in improving the response rate to resynchronization therapy, as current optimization techniques focus on adjusting parameters at one point in time and maintaining those parameters as the "permanent" settings.

Further still, using appropriate sensors (described above) for the elements of the array device 100, the array device 100 may be employed with integrated active circuitry for measuring cardiac contractility, myocardial wall displacement, myocardial wall stress, and movement in real-time, with high spatial and temporal resolution. Similarly, the array device 100 may be employed with integrated active circuitry for modulating, that is, actively controlling, cardiac contractility, myocardial wall displacement, myocardial wall stress, and movement in real-time, with high spatial and temporal resolution, through appropriate stimuli. As described above, the array device 100 may be employed with integrated active circuitry for measuring and improving myocardial contractile function in a real-time, closed-loop system.

FIG. 64 illustrates a flow chart for a continuously adjustable stimulation process 600 that may be performed by the control system 200. At 610, local ventricular contraction is sensed from suitably configured sensor elements on the array device 100. At 620, the contraction data obtained from the sensor elements on the array device 100 is analyzed to continuously characterize (e.g., on a beat-by-beat basis) the ventricular contraction behavior of the heart. At 630, pacing parameters associated with CRT or other pacing schemes for pacing stimuli delivered via effector elements of the array device 100 (or via other pacing electrodes positioned in or on the heart) are continuously adjusted based on the ventricular contraction behavior of the heart.

Some real-time adjustment in heart rate and atrioventricular timing can be effected by incorporation of various activity sensors in current devices. However, these changes are based on preset algorithms rather than concurrently measured individual patient data. It is likely that ideal atrioventricular and interventricular timing varies significantly with changing hemodynamic conditions. Consequently, the ability to integrate instantaneous feedback on a beat-by-beat basis may improve a patient's response to CRT.

In addition, an implanted electrode array can be used to record information about spontaneous arrhythmias that may develop. Heart failure with diminished left ventricular ejection fraction (EF) is associated with an increased risk of sudden cardiac death, and large randomized trials have demonstrated mortality benefit from prophylactic ICD implant in patients both with and without prior myocardial infarction (MI). As such, many patients for whom CRT is indicated also qualify for implantable cardioverter-defibrillator (ICD) implantation. A significant portion of patients with an ICD will eventually develop a life-threatening tachyarrhythmia that will require an ICD shock; a subgroup of those patients may have multiple episodes requiring multiple shocks, a painful and psychologically stressful therapy. Catheter ablation procedures for eliminating ventricular tachycardia are becoming increasingly common to prevent further arrhythmias and ICD shocks in such patients, and localization of the clinically important arrhythmia can at times be difficult. The more extensive and detailed spatial information recorded by an implanted array of electrodes during an arrhythmia prior to hospitalization, compared with the limited information recorded by the two or three leads in conventional devices, will help in planning a more efficient and effective ablation procedure. It will also provide more data with which to compare arrhythmias induced during an EP study, facilitating more rapid identification of those arrhythmias that are clinically relevant.

Another scheme that may be employed with the use of the device 100 is to electrically silence regions of the heart that are responsible for generating life threatening arrhythmias through timed depolarization. Using correctly timed stimulations from the array device 100 to the heart, arrhythmogenic foci or areas of myocardium can be maintained in a constant state of depolarization, and thus be unable to participate in arrhythmogenesis. The array device 100 can be configured, functionally, in size, to act on regions of the heart (e.g. the entirety of a myocardial infarction) that are too large to be treated with conventional ablation techniques. Similar concepts may apply to treatment of epilepsy, with brain stimulation to prevent the development of seizure activity. A different but related technique is use of the array device 100 for "electrical silencing" through stimulation of neural inputs to the heart, i.e., the sympathetic trunk or ganglionated plexi that innervate the heart. A closed-loop mechanism may be employed to modify the spatial and temporal pattern of stimulation in real-time based on the effectiveness of arrhythmia suppression.

It is possible that the array device 100, once implanted, could additionally provide mechanical support to the failing heart. Passive constraint of the ventricles against chronic dilation via an implanted synthetic mesh-like device was previously studied in randomized trials of the CorCap™ Cardiac Support Device (CSD) (Acorn Cardiovascular, Inc., St. Paul, Minn.).

FIG. 65 illustrates a configuration of the array device 100 that may be suitable to provide mechanical support to a failing heart. The array device 100, equipped to operate as both a pacing device and a recording device, can provide active, mechanical systolic support analogous to cardiomyoplasty. The array device 100 is constructed of a size suitable to be wrapped around a region of the heart to provide passive mechanical support for facilitating ventricular diastole or active mechanical support to augment systolic function.

The device serves as a flexible, active, multi-scale array with adjustable spatial and temporal resolution capable of high-density recording and stimulation from the epicardium or endocardium. The pacing configurations and schemes that are available through the use of the array device 100 are numerous, from single-site pacing to multiple-site pacing. In addition, the array device 100 can be used in a system to treat arrhythmias that cannot be safely or effectively ablated. Moreover, the array device 100 can be used to detect the early stages of a cardiac event and to treat it with a suitable stimulation scheme to stop it.

Example Application: Anatomic and Physiologic Mapping and Ablation

Anatomic and physiologic mapping of the surface of a biological tissue has important applications. For example, mapping the epicardial surface via percutaneous pericardial puncture, as first demonstrated in patients with Chagas' disease and ventricular tachycardia (VT), has proven useful in ablation of VT circuits with crucial portions of the reentrant circuits located in subepicardial muscle. Surgical data suggests that at least 15% of post-myocardial infarction VT is dependent on such subepicardial circuits, a proportion that is likely much higher in patients with non-ischemic cardiomyopathy and VT.

One advantage to the aforementioned percutaneous procedure is the ability to access the epicardium without the need for surgical exposure. However, the lack of surgical exposure creates several obstacles, including inability to easily visualize the location and course of epicardial coronary arteries and the phrenic nerve, as well as difficulties distinguishing epicardial fat from scarred myocardium. The appearance of multi-component and late electrograms has been primarily used to distinguish an area of scar from fat.

A method for direct visualization of epicardial landmarks using real-time video pericardioscopy has been described in the literature. Multiple fluoroscopic techniques have also been used to localize the coronary arteries at the time of epicardial mapping, including simultaneous catheter-based coronary angiography and fusion of a 3D electroanatomical map with previously acquired computed tomography (CT) angiograms. Both methods require exposure to intravenous (IV) contrast material, and both are limited by the precision of merging two sets of images, whether by eye or using a computer-assisted technique. In contrast, during traditional epicardial mapping via a surgical approach, both coronary arteries and epicardial fat are easily distinguished visually by the operator.

The availability of a single instrument that can be used to reliably map both the structures and electrical properties of the heart with exquisite spatial resolution, despite the absence of direct visualization, is very desirable. Such an instrument would ideally take advantage of traditional endovascular approaches or a percutaneous pericardial approach.

Reference is now made to FIG. 66 for an application of the system 10 (FIG. 55) adapted for a simultaneous anatomic and physiologic mapping and ablation application. In this application, the body organ to be mapped and treated is the heart, but this is only by way of example. The array device 100 is delivered to the endocardium or epicardium via traditional endovascular techniques or by a modified version of the nonsurgical transthoracic approach now commonly used, e.g., as depicted and described above in connection with FIGS. 58 and 59. The array device 100 is configured to have a large number of electrodes over an array of spatial locations that are configured as sensors for recording electrograms and also elements that are configured as effectors for delivering radiofrequency (RF) or other ablation energy. In addition, some of array elements may be configured as one or more of a variety of sensors (optical, chemical or other) for detection of epicardial coronary artery blood flow and discrimination of tissue properties.

The array device 100 is connected via a suitable lead 540 to a control system shown at reference numeral 200' that is external to the patient. The control system 200' comprises a signal generator 310, a controller 320, a display 330 and a signal processor 410. The signal processor 410 analyzes output of the sensor array elements on the array device 100 and generates data suitable for displaying mapping images on the display 330, such as shown at the mapping image 335. In one example, the mapping image 335 may be a three-dimensional (3D) map of electrophysiologic properties (e.g., voltage activation), anatomic properties (e.g., muscle, epicardial vessels, or fat), and ablation sites. In the mapping image 335, there is a region 335a (dark purple) that represents healthy muscle, a region 335b (rainbow range of colors) that represents varying degrees of scared myocardium a region 335c (light purple) that represents an area of epicardial fat. The bold dashed lines shown at 337 represent epicardial coronary arteries and the dots (red in color) 339 represent ablation sites. The mapping image 335 thus illustrates, through color or other visual indications, all of these anatomic and physiologic properties identified by a single multimodal array device 100 employing the techniques described herein.

Technologies that may be integrated on the flexible array and adapted for sensing conditions of coronary arteries include optical sensors, pressure or strain measurements, acoustic sensors, and chemical sensors. These sensors may also be used to detect ischemic changes and other abnormalities associated with tissue compromise and disease. Relatively simple measurements of tissue conductivity and impedance may be sufficient for distinguishing epicardial fat from muscle.

The signal processor 410 may also generate data that is useful to the controller 320 to control the signal generator 310. The controller 320 may be an automated controller, e.g., microprocessor suitably programmed with control logic, or a manual control apparatus. In either case, the controller 320 is configured to modify the ablation energy produced by the signal generator 310 for application via any combination of effector elements on array device 100.

The ability to include active circuitry on the array device 100 enables minimization of electrical connections between the array and the operator, thereby promoting the primary goal of an adaptable yet small device that can be delivered percutaneously or endovascularly. Moreover, the ability to record and store localized cardiac electrograms from multiple spatially diverse sites simultaneously during ventricular arrhythmias enables faster and more accurate localization of those arrhythmias in the electrophysiology laboratory.

The spatial arrangement of sensors on the array device 100 allows for creation of a 3D electroanatomic map-analogous to the functionality of the CARTO XP (BiosenseWebster) and EnSite NavX™ (St. Jude Medical) mapping systems. Depending upon the array size and density of the array device 100, all electrodes could be localized in 3D space using only a select subset of elements (electrodes) on the array device, with interpolation of the remaining point locations. More specifically, the array device 100 is placed in or on the heart (only) during a mapping and/or ablation procedure, and it may be moved around in or on the heart in order to map as large an area as possible of the heart. This is indicated by the arrows in FIG. 66. The select subset of electrodes is used as select points on the array device that are localized (relative to other structures or catheters in the heart) using, for example, magnetic-based 3D localization techniques such as those of the CARTO XP or impedance-based 3D localization NavX systems. Using interpolation of the localization data for the select subset of elements, the exact position of every element on the array device 100 is localized.

This position tracking technique is useful to create a virtual 3D map of where the array device 100 has been on or in the heart and some representation of the data collected at those locations on or in the heart. One example is a voltage map. A 3D "shell" of the surface is generated from the voltage measurements made at elements of the array device and the voltage levels at every measurement point may be color-coded. With numerous sensor modalities on the array device 100, the array device 100 may be used to superimpose multiple 3D maps at the same time, such as for voltage measurements, blood flow measurements and strain (pressure) measurements. Alternatively, given the 3D deformability of the array device 100, emitters of different types can be linked to each electrode contact to compute the location of all the elements of the array device with higher resolution.

Thus, the array device 100 serves as a flexible, active, multi-scale device with adjustable spatial and temporal resolution capable of high-density recording from and stimulation to the heart, delivered both through standard endovascular techniques to the endocardium and minimally invasively to the epicardium.

The device 100 is an implantable flexible electronic device with integrated active circuitry useful for both anatomic and electrical mapping of the heart surface and surrounding structures with high spatial and temporal resolution. Information gathered from a variety of sensor modalities integrated on the device can be used to distinguish myocardial tissue, epicardial fat, coronary arteries, large nerves, and other structures underlying the device.

The device 100 can deliver ablation energy via RF or other modality and effect a clinically significant lesion with high spatial resolution. Ablation can be spatially tuned in closed-loop fashion at the resolution of individual electrodes on the array.

In addition to mapping and ablating arrhythmias directly, the cardiac applications for such a device are wide-ranging. Mapping other cardiac and mediastinal structures, including ganglionated plexi and other components of the cardiac autonomic nervous system, are examples of such future direction in the treatment of arrhythmias. The highly adaptable nature of the array device 100 in terms of size, shape, and the type of electronic components included also lends itself to incorporation with existing long-term monitoring devices, such as the Chronicle® implantable hemodynamic monitor or long-term arrhythmia event monitors.

The foregoing concepts related to cardiac mapping have been demonstrated in live animal experiments, together with the ability to record useful electrical signals and reliably pace the heart from an array device with passive circuitry placed on the epicardial surface of the ventricle under direct visualization. In addition, an array device with active circuitry has been used to record electrograms from 288 array sensor elements of the array device 100 covering a 2.2 square centimeter area of the left ventricular epicardium using only 36 separate connecting wires between the array and the recording apparatus. A much higher degree of multiplexing is envisioned to allow for the use of a single USB 2.0, Firewire™ or similar connector providing input and output access to and from the array device.

Example In-Vivo Experiments

With reference to FIGS. 67A, 67B and 67C, data from in-vivo experiments are now described. In-vivo experiments were performed in two normal 80-90 pound male Yorkshire pigs. The heart was surgically exposed via a median sternotomy and subsequent pericardiotomy. An array device 100 was placed on the epicardial surface while under direct visualization as shown in FIG. 67A. The device adhered to the curvilinear surface of the heart, even during vigorous cardiac motion and during rapid pacing. FIG. 67B shows motion snapshots at various stages of the cardiac cycle and it is seen that the array device adapts to the dynamic variations in the surface shape of the heart in order to maintain conformal contact. Given the average heart rate of approximately 77 beats per minute (BPM) during in-vivo experiments and a recording duration of approximately 137 minutes, the device provided reliable data over the course of more than 10,000 bending cycles during our experiments.

Unipolar voltage data were recorded from all 288 sensors on the array device 100 using a multiplexing and sampling scheme. Baseline electrogram data were collected in sinus rhythm with the array in multiple positions and orientations on the epicardial surface. Data were also recorded while pacing the heart from multiple locations relative to the array device via a standard, non-steerable decapolar electrode EP catheter held in contact with the epicardial surface. FIG. 67C shows the array device 100 positioned over the left anterior descending (LAD) coronary artery, with the pacing catheter shown at 32 positioned just inferior to the array. The color coded map 340 in this frame shows a visual representation of the data collected from the array device 100, using procedures described below.

Data from all 288 sensors on the array device 100 were filtered and processed using custom MATLAB software to determine the relative activation time at each contact by comparing the time of the maximum negative slope (dV/dt) of the unipolar electrogram to the maximum negative slope of the average electrogram of all 288 sensor channels. These activation times were then used to generate isochronal maps showing propagation of paced and unpaced cardiac depolarization wavefronts spreading across the array for a variety of sensor sites and pacing conditions.

Sample voltage trace data from a single channel without remote pacing are shown in FIG. 4a. The inset at right highlights the very low noise level of the recording, with a signal-to-noise ratio (SNR) of approximately 50. Note that negative is plotted up in the figure, by convention.

FIG. 4b shows voltage data for all channels taken at 4 points in time and showing paced cardiac wavefront propagation. Voltage is plotted using the color scale in the right corner. FIG. 4c illustrates a plot of average voltage from sensing elements and illustrating the point in time that each frame in FIG. 4b was taken. The color of the dotted lines corresponds to the color of the time label in FIG. 4b.

FIG. 4d illustrates a representative single voltage trace with external pacing from a standard clinical electrode. The black arrow and box highlight the pacing artifact. Note that negative is plotted up by convention in FIGS. 4a, 4c, and 4d.

FIG. 4e illustrates isochronal color maps of relative activation times for two different external pacing sites. The activation times are plotted using the color bar shown at the right. Asterisks (*) indicate the relative location of the external pacing electrode. The scale bar illustrates the spacing between electrode locations. The data from the activation map at the locations marked by lines i-iii are plotted in FIG. 4f in distance vs. activation delay plots for selected rows of the sensor array following the arrows in FIG. 4e.

These results clearly establish this technology as the basis for devices with advanced capabilities. With straightforward additions to the circuits and external control, the same systems could provide multi-site cardiac pacing with closed-loop feedback of local ventricular contractility or cardiac output measurements via distributed arrays of active sensory and stimulation electrodes. Furthermore, the mechanical properties of the circuits permit packaging in catheter-based delivery systems, with the ability to deploy on and conform to large and small, irregular curvilinear surfaces of the body. Pursuing these possibilities and other biomedical devices with other functionality using the materials and electronics strategies reported here has great potential to yield technologies with important benefits to human health.

Example Array Device and Circuit Configurations

FIG. 68 illustrates an example of the array device 100. The array device comprises an array of elements 110 that, in the example shown in FIG. 68, are electrodes, each of which is coupled to an associated preamplifier 120. The output of each preamplifier is coupled to a column line 130 through an analog switch 140. By activating a specific row signal 145 and de-activating the other (N−1) row signals, the output of the selected row amplifier will be allowed to drive the column line 130. In this manner, any one of the N rows can be selected to drive the column amplifier 150. This column amplifier 150 provides additional gain to match the range of the signal to the input range of the column analog to digital converter 160. The column analog to digital converter 160 converts the analog signals from the electrode channels to digital values. The digital output of the column analog to digital converter 160 is connected to a digital buffer 170, and the outputs of all N digital buffers 170 (one for each column)

are connected together. Each column signal 120 can be individually selected via the N column select signals 180. In this way, the data from the N column analog to digital converters 160 can be combined down to one digital input on the integrated microprocessor 190.

With reference to FIGS. 69-70, schematic diagrams are shown for various configurations of sensing and stimulation selection control of elements in the array device 100. These configurations are useful in connection with various sensing and stimulation applications, examples of which are described above.

Turning to FIG. 69, a schematic diagram is shown that illustrates how unit cells connect to other unit cells to create a multiplexed signal output, for example for sensing from one of the elements 110 that is configured to operate as a sensor electrode. During multiplexed sampling, one row of electrodes is selected at a time by driving one of the row select signals (such as $R_0$) high, and all of the other row select signals low. This allows the elements in that row to drive the column output lines labeled C0, C1, . . . , to a high-speed analog-to-digital converter. The row select signals are rapidly cycled to sample all elements 110 on the array device 100.

FIG. 70 is similar to FIG. 69, but adds stimulation control capability. In this example, the stimulation input lines STIM0, STIM1, etc., are provided. When a stimulation voltage is driven onto one of the stimulation input lines while any or all of the row select lines are enabled, the elements 110 (electrodes) will deliver stimulation energy to the local tissue area. The configuration shown in FIG. 70 adds a minimal amount of extra wiring and complexity, but is tied to the recording multiplexing rate due to the sharing of the row select signals.

FIG. 71 illustrates a schematic diagram that is similar to FIG. 70, but uses independent stimulation row select signals. Like the configuration of FIG. 69, when a stimulation voltage is driven onto one of the stimulation input lines while any or all of the row select lines are enabled, the elements 110 (electrodes) will deliver a stimulation energy to the local tissue area. However, stimulation row selection signals STIM R0, STIM R1, . . . , are provided. These signals are used to selectively enable stimulation at any or all of the rows. This configuration adds more external wires but provides for a stimulation capability that is time independent of sensing multiplexing.

FIG. 72 shows an example transistor level schematic for an element 110 in a sensing configuration. There is a constant current source 112, a current mirror 114 and a multiplexer 116.

FIG. 73 shows an example transistor level layout for an element 110 with stimulation control according to that described above in connection with FIG. 70. In this configuration, there is a stimulation control demultiplexing transistor 118 that is connected to the stimulation control line, e.g., STIM0. FIG. 74 shows an example transistor level layout for an element 110 with row independent selectable stimulation control according to that described above in connection with FIG. 71. In the configuration of FIG. 74, there is a demultiplexing transistor 118 that is connected to both the stimulation control line, STIM0, and to the stimulation row select control line STIM R0.

The devices, configurations and techniques described herein are meant to be by way of example only. Other applications for the array device 100 include ablation for treatment of neurological maladies and pain treatment in muscle and other tissues. In addition, ablation techniques may be performed with different types of energies and modalities. Ablation modalities that could be applied include: RF energy (whether single frequency or phased), cryoablation (freezing), laser energy, and high-intensity focused ultrasound (HIFU). Additionally, high voltage electrical stimulation can be used as an ablation technique. In this application, the cells are destroyed through electroporation, which is a mechanism by which high voltage electrical fields create pores or the breakdown of the cell membrane. With enough energy, this causes irreversible damage and cell death, achieving the goal of ablation.

EXAMPLE 6

Conformable Skin—Mounted Electronic Devices for Interfacing with Tissue

The invention provides skin-mounted electronic devices for electrophysiological mapping and sensing various other characteristics from the body and/or tissue of a subject. A major difference, however, from other implantable devices, such as a conventional cardiac sensors, is that this skin-mounted electronic device of the invention is non-invasive. For example, even though it positioned on skin, i.e. non-invasive, the device of this aspect is capable of making electrocardiography, electromyography, electroencephalography (EKG, EMG and EEG) measurements, from the heart, muscle and brain tissue, respectively.

An important issue of invasiveness with respect to medical devices is post-surgery recovery. For example, many surgical procedures require large incision that causes post-surgery trauma. The present skin-mounted non-invasive device does not require recovery since it is attached to skin, like a bandage, rather than implanted or surgically administered as in some conventional medical device. Another important advantage of the present skin-mounted devices is that they can be used for long periods of time, which is not feasible with conventional implantable and even non-invasive devices. For example, many invasive medical devices have issues of long time biocompatibility in the human body. Also some conventional non-invasive sensors, such as commercial EEG electrodes, require use of conductive gel to reduce impedance and provide higher signal to noise ratios. Such conventional devices, however, cannot be used for long periods of time as the conductive gel is prone to drying out. In addition, the conductive gel can be uncomfortable and cause skin irritation. The present skin-mounted electronic devices do not require a conductive gel, for example because it is capable of using active capacitance coupled devices for electrophysiological mapping.

In an embodiment, the invention provides a device for establishing an interface with a skin of a subject, the device comprising: (1) a flexible or stretchable substrate having an average modulus less than or equal to 1 MPa; (2) a flexible or stretchable electronic circuit comprising one or more inorganic semiconductor circuit elements, said flexible or stretchable electronic circuit supported by the flexible or stretchable substrate; and (3) a barrier layer encapsulating at least a portion of the flexible or stretchable electronic circuit, the flexible or stretchable substrate or both flexible or stretchable electronic circuit and the substrate; wherein the substrate, barrier layer and the electronic circuit provide a net bending stiffness of the device low enough that the device establishes conformal contact with the skin of the subject. Devices of this aspect of the invention include skin mounted tissue sensors, tissue actuators and arrays of tissue sensors and actuators. In come embodiments, for example, matching of the modulii of components of the device (e.g., substrate, electronic circuit or barrier layer) and the skin is useful for establishing robust conformal contact at the interface with the skin. In an embodiment, the device does not include an adhesive layer between the skin and the electronic circuit component.

The composition, physical dimensions and properties of the flexible or stretchable substrate is important in devices of this aspect of the invention. In an embodiment, for example, flexible or stretchable substrate has an average modulus less than or equal to 500 KPa, optionally for some applications less than or equal to 100 KPa, and optionally for some applications less than or equal to 50 KPa. In an embodiment, for example, the flexible or stretchable substrate has an average modulus selected over the range of 0.5 KPa to 100 KPa. In an embodiment, for example, the flexible or stretchable substrate has an average modulus equal to or less than 50 times the average modulus of the skin of the subject at the interface. In an embodiment, for example, the flexible or stretchable substrate has a thickness less than or equal to 500 microns, optionally for some applications less than or equal to 100 microns and optionally for some applications less than or equal to 50 microns. In an embodiment, for example, the flexible or stretchable substrate has a thickness selected over the range of 1 to 500 microns, and optionally selected over the range of 1 to 100 microns, and selected over the range of 1 to 50 microns. In an embodiment, for example, the flexible or stretchable substrate is a low modulus polymer, such as a low modulus rubber or a low modulus silicone material. In an embodiment, for example, the flexible or stretchable substrate is Ecoflex®. In an embodiment, for example, the flexible or stretchable substrate is a bioinert or biocompatible material.

The composition, physical dimensions and properties of the flexible or stretchable substrate is important in devices of this aspect of the invention. In an embodiment, the flexible or stretchable electronic circuit comprises one or more sensors or actuators and/or one or more amplifiers or multiplex circuits. For example, devices of this aspect include a flexible or stretchable electronic circuit comprising one or more electrodes, transistors, light emitting diodes, photodiodes, temperature sensors, electrocardiography sensors, electromyography sensors, electroencephalography sensors, thermistors, diodes, capacitive sensors, or any combinations of these. In an embodiment, the flexible or stretchable electronic circuit comprises one or more single crystalline inorganic semiconductor structures. In an embodiment, the flexible or stretchable electronic circuit is assembled on the flexible or stretchable substrate via contact printing.

In an embodiment, a device of this aspect further comprises a transfer substrate supporting the flexible or stretchable substrate, the flexible or stretchable electronic circuit or both, for example a transfer substrate in physical contact with the flexible or stretchable substrate. In an embodiment, for example, the transfer substrate is a removable substrate, wherein the transfer substrate is partially or completely removed upon providing the device in contact with the skin of the subject. In an embodiment, for example, the removable substrate is a dissolvable substrate, wherein the removable substrate is partially or completely dissolved after the device is provided in contact with the skin of the subject. In an embodiment, the transfer substrate is a polymer such as polyvinyl acetate.

In an aspect, the invention provides a method of interfacing an electronic device with skin of a subject, the method comprising: (1) providing the skin of the subject; (2) providing a conformable electronic device, the device comprising: (i) a flexible or stretchable substrate having an average modulus less than or equal to 1 MPa; (ii) a flexible or stretchable electronic circuit comprising one or more inorganic semiconductor circuit elements, said flexible or stretchable electronic circuit supported by the flexible or stretchable substrate; (iii) a barrier layer encapsulating at least a portion of the flexible or stretchable electronic circuit; and (iv) a transfer substrate supporting said flexible or stretchable substrate, said flexible or stretchable electronic circuit or both; (3) contacting the conformable electronic device to a receiving surface of the skin, wherein upon contact the flexible or stretchable electronic circuit is positioned between the skin and the a flexible or stretchable substrate; and (4) at least partially removing the transfer substrate, wherein the flexible or stretchable substrate, barrier layer and the flexible or stretchable electronic circuit provide a net bending stiffness of the device low enough that the device establishes conformal contact with the skin of the subject upon at least partial removal of the transfer substrate, thereby interfacing the electronic device with the skin of the subject. In an embodiment, the step of at least partially removing the transfer substrate comprises entirely removing the transfer substrate. In an embodiment, the step of at least partially removing the transfer substrate comprises dissolving the transfer substrate after the step of contacting the conformable electronic device to a receiving surface of the skin.

Methods of this aspect of the invention may further comprising sensing and/or actuating a tissue of the subject, for example wherein the tissue of the subject is a heart, muscle or brain of the subject. In an embodiment, for example, the method further comprises making electrocardiography measurements, electromyography measurements or electroencephalography measurements of the subject. In an embodiment, for example, the method further comprises providing electromagnetic radiation to the tissue of the subject. In an embodiment, for example, the method further comprises measuring the temperature of the tissue of the subject. In an embodiment, for example, the method further comprises making one or more voltage measurements, current measurements, electromagnetic radiation intensity or power measurements, temperature measurements, pressure measurements, tissue acceleration measurements, or tissue movement measurements of the tissue of the subject.

In some embodiments, a transfer substrate is a PVA backing layer that is able to be dissolved with water. Benefits of the use of a PVA backing layer include that it is biocompatible and does not result in problems with the skin. Use of a low modulus flexible or stretchable substrate is beneficial for providing very good conformal contact to the skin, which is important in some sensing applications for providing a low impedance and high signal to noise ratio. Also good conformal contact enables very strong lamination for long periods of time without the need for additional chemical adhesive.

In the case of active skin electronic device, for example, active EKG/EMG sensors, the electronic circuit component may comprise an electrode. The electrode of this aspect may be in physical contact with the skin or may not be in physical contact with the skin at the interface. Embodiments of this aspect include, for example, use of capacitance type circuit that do not require physical contact. In some embodiments, for example, the device is passivated with one or more thin layer of polyimide.

Figure 50A:
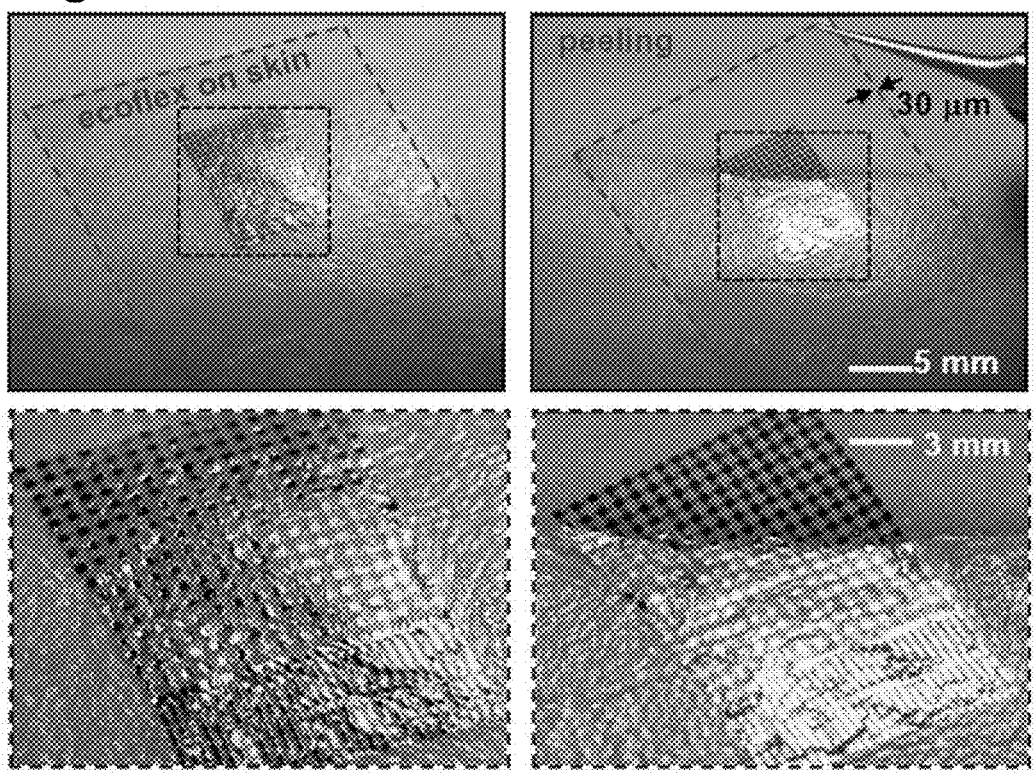
Figure 50B:
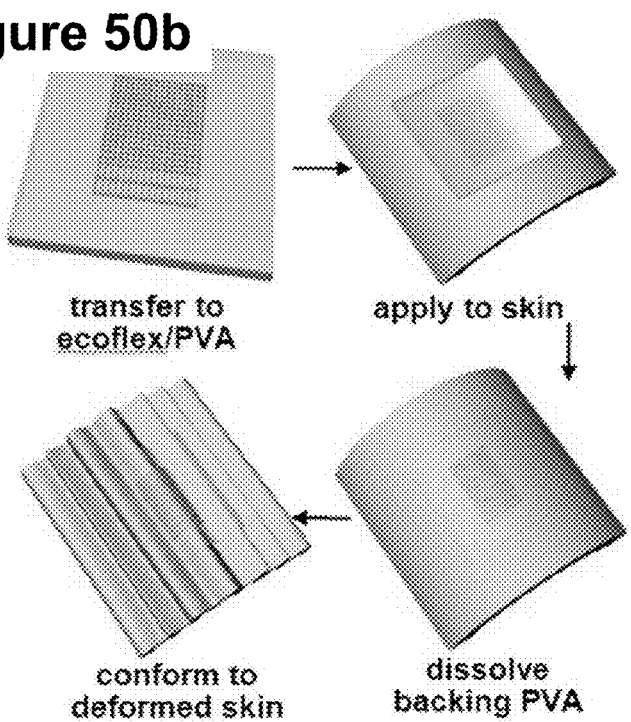
Figure 50C:
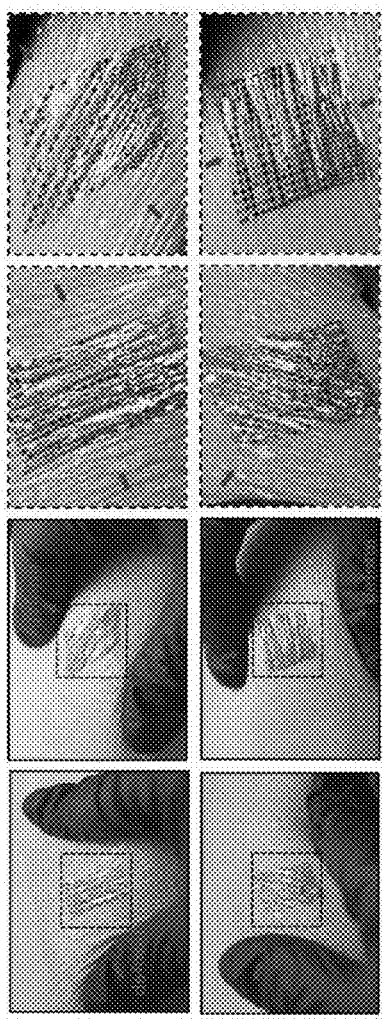
Figure 50D:
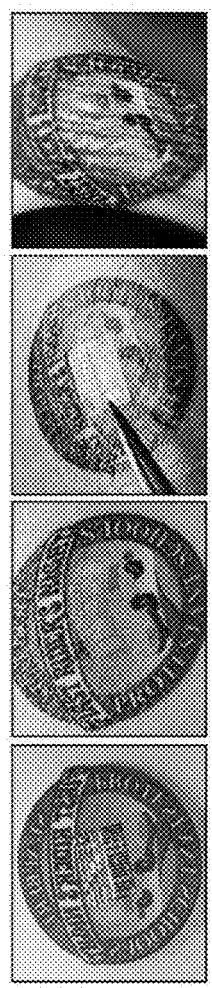
Figure 50E:
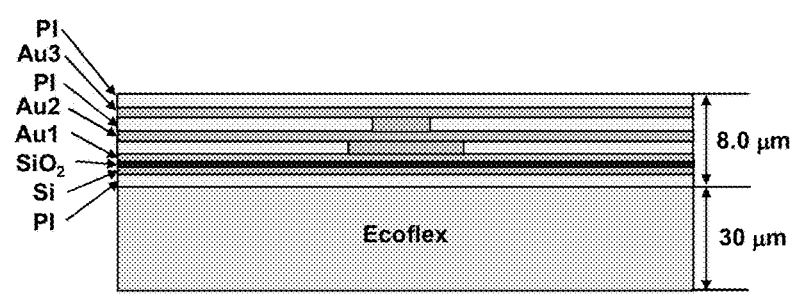

FIG. 50e provides a schematic diagram illustrating a cross-sectional view of a skin-mounted conformal device of the invention having an encapsulating barrier layer. As illustrated in FIG. 50e the device comprises a flexible or stretchable Ecoflex® substrate supporting a flexible or stretchable electronic circuit having a multilayer device geometry. The electronic circuit component comprises a series of layers including encapsulating polyimide layers (PI), and functional silicon (Si) layer, silicon oxide layer (SiO$_2$) and gold layers (AU1, AU2, and AU3). The invention includes, however, skin-mounted devices having one or more electrodes directly exposed and/or in physical contact with the skin, for example, without polyimide encapsulation.

To demonstrate the applicability of this aspect of the invention for a range of biomedical applications, the skin-mounted electronic devices were fabricated and interfaced with skin in the context of tissue sensing and actuation applications. FIGS. 50-54 provide device schematics, images and experimental results describing this aspect of the invention.

FIG. 50 provides: (a) Four frames of the electrode array transfer printed onto thin, low modulus ecoflex. On skin (left top), partially peeled off state (right top), magnified view of each top frame (bottom). Blue dotted boxes correspond to the magnified images at the bottom frame. The modulus and thickness of ecoflex substrate is ~50 kPa and ~30 um, respectively. The electrode array is facing down to skin, sandwiched by the skin and ecoflex substrate. (b) Schematic view of application procedures of skin patch to the skin. The electrode array is transfer printed onto ecoflex, coated on the PVA film, an water dissolvable and biocompatible film. The transferred electrode array is positioned onto the right location of skin. Some water can be applied to the backside of PVA film to dissolve it away. Thin, low modulus skin patch conforms very well to skin, like a tattoo. (c) Deformed images of skin patch on skin to four different directions and their magnified views. The highly conformal skin patch follows the wrinkles on skin very well. (d) Electrode array transfer printed at the backside of the commercial temporary tattoo. It is applied to the skin. Instead of ecoflex thin film, a temporary tattoo can be used for the purpose of camouflage or cover-up.

FIG. 51 provides (a) Mechanically optimized fully serpentine electrode array (left). The right frame shows the stress-strain relationship from which the modulus in the plot was calculated. The optimized design shows comparable modulus with the bare skin. (b) Debonding experiment results under tension (left) and compression (right). As the modulus and thickness decrease, the debonding happens at larger strain. (c) Cross-sectional image (X-ray) of skin electronic devices located on the pig skin.

FIG. 52 provides (a) Serpentine shape active EMG/EKG sensor. Left top frame shows source, drain and gate of nmos transistor and silicon drain to gate feedback resistor. Inset shows conventional shape active EMG/EKG sensor. Left bottom image shows the final device image for serpentine shape device and its magnified view (inset). Right top and bottom frame shows transfer and IV curve for the transistor. (b) Circuit diagram for active EMG/EKG sensor and the frequency response of active sensor (common source amplifier). (c) Microscope image of temperature sensor using platinum resistor and gold serpentine wires. Right frame shows the calibration curve, showing different resistances of temperature sensor at different temperatures. (d) Microscope image of strain gauge using conductive PDMS (CPDMS). Right frame shows the calibration curve of the strain gauge. (e) Microscope images of proximity sensor using forward and reverse biased LED array. Forward biased LED array radiates light and reverse biased LED array detects the reflected light from the object. As the distance between the object and LED array decreases, the reflectance increases and thereby the photocurrent increases, as shown in the right frame. (f) A single LED pixel powered by wireless power transmission coil. Right frame shows the IV curve of LED pixel. (g) Microscope image of PN diodes (left) and it S21 value measured at different frequencies in radio frequency range. (h) Microscope image of inductor and capacitor pair (left top). Right top plot shows S21 value of capacitor at various RF frequencies and left bottom plot shows S21 and S11 values of inductor at RF frequencies. Right bottom plot shows the estimated oscillation frequencies for different capacitors.

FIG. 53 provides (a) Passive electrode array on forehead for undeformed (left top) and deformed (right top and bottom) state. Left bottom image shows the partially peeled off state. (b) EEG measurement results for Stroop test. When the target letter matches with the highlighted letter (congruent case) the response speed is faster than unmatched (incongruent case) case. (c) EEG measurement results for eye open and eye close case. Left plot shows raw EEG and right plot shows results after Fourier transformation.

FIG. 54 provides (a) EKG measurement result measured with active EKG sensor (left) and magnified view of single heartbeat (right). (b) EMG measurement result from a right leg during walking (from 0 sec to 10 sec) and standing (from 10 sec to 20 sec) measured with active EMG sensor (left) and conventional passive EMG sensor with conductive gel (right). (c) Magnified view of EMG signal of (b). (d) Corresponding spectrogram for each electrode. (e) EMG measurement result from neck for four different words, "up", "down", "left" and "right". (f) Corresponding spectrogram for four words. (g) Video game control using recorded EMG signal.

References

Reuss, R. H. et al. Macroelectronics: perspectives on technology and applications. Proc. IEEE. 93, 1239-1256 (2005).

Forrest, S. R. The path to ubiquitous and low cost organic electronic appliances on plastic. Nature 428, 911-918 (2004).

Menard, E. et al. Micro- and nanopatterning techniques for organic electronic and optoelectronic systems. Chem. Rev. 107, 1117-1160 (2007).

Loo, Y.-L. & McCulloch, I. Progress and challenges in commercialization of organic electronics, MRS Bull. 33, 653-662 (2008).

So, F., Kido, J. & Burrows, P. Organic light-emitting devices for solid-state lighting, MRS Bull. 33, 663-669 (2008).

Razavi, F. H. et al. Three dimensional nanopillar array photovoltaics on low cost and flexible substrates. Nature Materials 8, 648-653 (2009).

Ko, H. et al. Flexible Carbon Nanofiber Connectors with Anisotropic Adhesion Properties. Small 6, 22-26 (2010).

Cohen-Karni, T., Timko, B. P., Weiss, L. E., & Lieber, C. M. Flexible electrical recording from cells using nanowire transistor arrays. Proc. Natl. Acad. Sci. USA 106, 7309-7313 (2009).

Timko, B. P., Cohen-Karni, T., Yu, G., Qing, Q., Tian, B., & Lieber, C. M. Electrical Recording from Hearts with Flexible Nanowire Device Arrays Nano Lett. 9, 914-918 (2009).

Siegel, A. C., Philips, S. T., Wiley, B. J., & Whitesides, G. M. Thin, lightweight, foldable thermochromic displays on paper. Lab Chip 9, 2775-2781 (2009).

Siegel, A. C. et al. Foldable Printed Circuit Boards on Paper Substrates. Adv. Funct. Mater. 20, 28-35 (2010).

Hu, L. et al. Highly conductive paper for energy-storage devices. Proc. Natl. Acad. Sci. USA 106, 21490-21494 (2009).

Hu, L. et al. Stretchable, Porous, and Conductive Energy Textiles. Nano Lett. 10, 708-714 (2010)

Sekitani, T. et al. Stretchable active-matrix organic light-emitting diode display using printable elastic conductors. Nature Mater. 8, 494-499 (2009).

Jacobs, H. O. & Whitesides, G. M. Submicrometer Patterning of Charge in Thin-Film Electrets. Science 291, 1763-1766 (2001).

Cole, J., Wang, X. & Jacobs, H. O. Patterned Growth and Transfer of ZnO Micro- and Nanocrystals with Size and Location Control. Adv. Mater. 20, 1474-1478 (2008).

Leong, T. G. et al. Tetherless thermobiochemicall actuated microgrippers. Proc. Natl. Acad. Sci. USA 106, 703-709 (2009).

Park, S.-I. et al. Printed assemblies of inorganic light-emitting diodes for deformable and semitransparent displays, Science 325, 977-981 (2009).

Dupuis, D. R. & Krames, M. R. History, developrnent, and applications of high-brightness visible light-emitting diodes, IEEE J. Lightwave Tech. 26, 1154-1171 (2008).

Kim, D.-H. et al. Materials and noncoplanar mesh designs for integrated circuits with linear elastic responses to extreme mechanical deformations, Proc. Natl. Acad. Sci. USA 105, 18675-18680 (2008).

Brown, X. Q., Ookawa, K. & Wong, J. Y. Evaluation of polydimethylsiloxane scaffolds with physiologically-relevant elastic moduli: interplay of substrate mechanics and surface chemistry effects on vascular smooth muscle cell response, Biomaterials 26, 3123-3129 (2005).

Kim, D.-H. et al. Optimized structural designs for stretchable silicon integrated circuits, Small 5, 2841-2847 (2009).

Kim, D.-H. et al., Ultrathin silicon circuits with strain-isolation layers and mesh layouts for high-performance electronics on fabric, vinyl, leather, and paper, Adv. Mater. 21, 3703-3707 (2009).

Jeon, B. S., Chun, S. Y. & Hong, C. J. Structural and mechanical properties of woven fabrics employing peirce's model, Textile Research Journal, 73, 929-933 (2003).

Gardner, W. R. & Ehlig, C. F. Physical aspects of the irnternal water relations of plant leaves, Plant Physiol. 40, 705-710 (1965).

Cox, H. L., The elasticity and strength of paper and other fibrous materials, Br. J. Appl. Phys. 3, 72-79 (1952).

Hayase, M. et al. Photoangioplasty with local motexafin lutetium delivery reduces macrophages in a rabbit post-balloon injury model, Cardiovascular Research 49, 449-455 (2001).

Waksman, R. et al. Photopoint photodynamic therapy promotes stabilization of atherosclerotic plaques and inhibits plaque progression, J. Am. Coll. Cardiol. 52, 1024-1032 (2008).

Woodburn, K. W. et al. Phototherapy of cancer and atheromatous plaque with texaphyrins. J. Clin. Laser Med. Surg. 14, 343-348 (1996).

Overholt, B. F., Panjehpour, M., Denovo, R. C. & Petersen, M. G., Photodynamic therapy for esophageal cancer using a 180° windowed esophageal balloon, Lasers in Surg. Med. 14, 27-33 (2005).

Sum, S., Madden, S., Hendricks, M., Chartier, S. & Muller, J. Near-infrared spectroscopy for the detection of lipid core coronary plaques. Current Cardiovascular Imaging Reports 2, 307-315 (2009).

Waxman, S. et al. In vivo validation of a catheter-based near-infrared spectroscopy system for detection of lipid core coronary plaques: initial results of the spectacl study. J. Am. Coll. Cardiol. Img. 2, 858-868 (2009).

Waxman, S, Near-Infrared Spectroscopy for Plaque Characterization, J Intery Cardiol. 21, 452-458 (2008).

Corazza, A. V., Jorge, J., Kurachi, C. & Bagnato, V. S., Photobiomodulation on the angiogenesis of skin wounds in rats using different light sources, Photomedicine and Laser Surgery 25, 102-106 (2007).

Wong-Riley, M. T. T. et al. Photobiomodulation directly benefits primary neurons functionally inactivated by toxins, J. Biol. Chem. 280, 4761-4771 (2005).

Vinck, E. M., Cagnie, B. J., Cornelissen, M. J., Declercq, H. A. & Gambier, D. C., Increased fibroblast proliferation induced by light emitting diode and low power laser irradiation, Lasers Med. Sci. 18, 95-99 (2003).

Schindl, A. et al. Direct stimulatory effect of low-intensity 670-nm laser irradiation on human endothelial cell proliferation, Br. J. Dermatol. 148, 334-336 (2003).

Amir, A. et al. The influence of helium-neon irradiation on the viability of skin flaps in the rat, Br. J. Plast. Surg. 53, 58-62 (2000).

Yao, J. et al. Functional nanostructured Plasmonic materials, Adv. Mater. 22, 1102-1110 (2010).

Yao, J. et al. Seeing molecules by eye: Surface plasmon resonance imaging at visible wavelengths with high spatial resolution and submonolayer sensitivity, Angew. Chem. 47, 5013-5017 (2008).

Aliot, E. M. et al. EHRA/HRS Expert Consensus on Catheter Ablation of Ventricular Arrhythmias Developed in a partnership with the European Heart Rhythm Association (EHRA), a Registered Branch of the European Society of Cardiology (ESC), and the Heart Rhythm Society (HRS); in collaboration with the American College of Cardiology (ACC) and the American Heart Association (AHA). Europace 11, 771-817 (2009).

Zheng, Z.-J. et al. Sudden cardiac death in the United States, 1989 to 1998. Circulation 104, 2158-2163 (1998).

Zipes, D. P. et al. ACC/AHA/ESC 2006 Guidelines for Management of Patients With Ventricular Arrhythmias and the Prevention of Sudden Cardiac Death: A Report of the American College of Cardiology/American Heart Association Task Force and the European Society of Cardiology Committee for Practice Guidelines (Writing Committee to Develop Guidelines for Management of Patients With Ventricular Arrhythmias and the Prevention of Sudden Cardiac Death. Circulation 114, 385-484 (2006).

Scherlag, B. J., Lau, S. H., Helfant, R. H., Berkowitz, W. D., Stein, E. & Damato, A.N. Catheter technique for recording His bundle activity in man. Circulation, 39, 13-18 (1969).

Khang, D. Y., Jiang, H., Huang, Y. & Rogers, J. A. A Stretchable form of single crystal silicon for high performance electronics on rubber substrates. Science 311, 208-212 (2006).

Kim, D.-H. & Rogers, J. A. Stretchable electronics: materials strategies and devices, Adv. Mater. 20, 4887-4892 (2008).

Ko, N. C. et al. A hemispherical electronic eye camera based on compressible silicon optoelectronics. Nature 454, 748-753 (2008).

Kim, D.-H. et al. Materials and noncoplanar mesh designs for integrated circuits with linear elastic responses to extreme mechanical deformations. Proc. Nat. Acad. Sci. USA 105, 18675-18680 (2008).

Baca, A. J. et al. Semiconductor wires and ribbons for high-performance flexible electronics. Angew. Chem. 47, 5524-5542 (2008).

Patolsky, F. et al. Stimulation, and Inhibition of Neuronal Signals with High-Density Nanowire Transistor Arrays, Science, 313, 1100-1104 (2006).

Timko, B. P. et al. Electrical Recording from Hearts with Flexible Nanowire Device Arrays, Nano Lett. 9, 914-918 (2009).

Chaudhury, M. K. & Whitesides, G.M. Direct measurement of interfacial interactions between semispherical lenses and flat sheets of poly(dimethylsiloxane) and their chemical derivatives. Langmuir 7, 1013-1025 (1991).

Qian, J. & Gao, H. Scaling effects of wet adhesion in biological attachment systems. Acta Biomaterialia 2, 51-58 (2006).

Michalske, T. A. & Fuller, E. R. Closure and repropagation of healed cracks in silicate glass. J. Am. Ceram. Soc. 68, 586-590 (1985).

Kadish, A., Shinnar, M., Moore, E. N., Levine, J. H., Balke, C. W. & Spear, J. F. Interaction of fiber orientation and direction of impulse propagation with anatomic barriers in anisotropic canine myocardium. Circulation. 78, 1478-1494 (1988).

Clerc, L. Directional differences of impulse spread in trabecular muscle from mammalian heart. J. Physiol. 255, 335-346 (1976).

Al-Halhouli, A.T., Kampen, I., Krah, T. & Buttgenbach, S, Nanoindentation testing of SU-8 photoresist mechanical properties. Microelectronic Engineering 85, 942-944 (2008).

Yu, D. Y. W. & Spaepen, F. The yield strength of thin copper films on Kapton. J. Appl. Phys. 95, 2991-2997 (2004).

U.S. Patent Application Publication Nos. US 2003/0149456, US 2006/0173364, US 2007/0043416, US 2008/0157235, US 2010/0002402.

U.S. Pat. Nos. 5,678,737, 6,666,821.

International Patent Application Publication Nos. WO 98/49936 and WO 2009/114689.

EXAMPLE 7

Epidermal Electronics

Disclosed herein are materials, mechanics principles and designs layouts for electronic systems that achieve thicknesses (~30 μm), effective elastic moduli (<150 kPa), bending stiffnesses (<1 nN·m) and areal mass densities (<3.8 mg/cm$^2$) matched to the epidermis. Laminating such devices onto the skin leads to conformal contact, intimate integration and adequate adhesion based on van der Waals interactions alone, in a manner that is mechanically invisible to the user. We describe a diverse collection of devices in this format, ranging from elecrophysiological (EP), temperature and strain sensors, to transistors, light emitting diodes, photodetectors and a variety of components capable of radio frequency operation, including inductors, capacitors, oscillators and rectifying diodes. Silicon solar cells and wireless inductive coils provide options for power supply. As systems-level demonstrators of this technology, this Example discloses skin-mounted, amplified monitors of EP activity produced by the heart, brain and skeletal muscles. Data collected with such devices contain sufficient information for meaningful human/machine interfaces, for example, as illustrated herein with an unusual type of computer game controller.

Physiological measurement and stimulation techniques that exploit interfaces to the skin have been of interest for more than 40 years, the former beginning in 1966 with electromyography of laryngeal muscles [1-3]. Despite much progress over this time, nearly all associated device technologies continue to rely on conceptually old designs. Typically, small numbers of bulk electrodes mount on the skin via adhesive tapes, mechanical clamps/straps and/or penetrating needles, often mediated by conductive gels, with terminal connections to separate boxes that house collections of rigid circuit boards, power supplies and communication components [4-9]. These systems have many important capabilities, but they are poorly suited for practical application outside of research labs or clinical settings, due to difficulties in establishing long-lived, robust electrical contacts that do not irritate the skin, and in achieving integrated systems with overall sizes, weights and shapes that do not cause discomfort during prolonged use [8,9]. Illustrated in this Example is a different approach, in which the electrodes, electronics, sensors, power supply and communication components are configured together into ultrathin, low modulus, lightweight, stretchable 'skin-like' membranes that conformally laminate onto the surface of the skin by soft contact, in a manner that is mechanically invisible to the user, much like a temporary transfer tattoo.

FIG. 75 shows a demonstration platform for the individual components of such a technology, including a collection of multifunctional sensors (e.g. temperature, strain, electrophysiological), microscale light emitting diodes (LEDs), active/passive circuit elements (e.g. transistors, diodes, resistors), wireless power coils and devices for radio frequency (RF) communications (e.g. high frequency inductors, capacitors, oscillators and antennae), all integrated on the surface of a thin (~30 μm), gas-permeable elastomeric sheet based on a modified polyester (PE; BASF, Germany) with low Young's modulus (~60 kPa, as shown in FIG. 79 A). The devices and interconnects exploit ultrathin layouts (<7 μm), neutral mechanical plane (NMP) configurations and optimized geometrical designs. The active elements use established electronic materials such as silicon and gallium arsenide, in the form of filamentary serpentine nanoribbons and micro/nanomembranes. The result is a high performance system that offers reversible, elastic responses to large strain deformations with effective moduli, bending stiffnesses and areal mass densities that are orders of magnitude smaller than those possible with conventional electronics, or even with recently explored flexible/stretchable device technologies [10-19]. These and other key physical properties are, in fact, comparable to those of the skin itself. Water-soluble polymer sheets (polyvinyl alcohol; PVA, Aicello, Japan; Young's modulus ~1.9 GPa, thickness ~50 μm (as shown in FIG. 79 B)), serve as temporary supports for manual mounting of these systems on the skin, in an overall construct that is directly analogous to that of a temporary transfer tattoo. The top frame of FIG. 75 B provides an image of a device like the one in FIG. 75 A, after integrating it onto the skin by washing away the PVA and then partially peeling it back using a pair of tweezers. When completely removed, the system collapses on itself due to its extreme deformability and 'skin-like' physical properties, as shown in the bottom frame of FIG. 75 B. The schematic illustration in the inset shows an approximate cross sectional layout.

These mechanical characteristics lead to robust adhesion to the skin via van der Waals forces alone, without any mechanical fixturing hardware or adhesive tapes. The devices impose negligible mechanical or mass loading, as is evident from the images of FIG. 75 C, which show the skin deforming freely and reversibly, without any apparent constraints in motion due to the devices. Electronics in this form can even be integrated directly with commercial temporary transfer tattoos, as a substrate alternative to PE/PVA. The result, shown in FIG. 75 D, is of possible interest as a way to conceal the active components and/or to exploit low cost materials (i.e. substrate, adhesives, backing layers) already developed for temporary transfer tattoos. Potential uses include physiological status monitoring, wound measurement/treatment, biological/chemical sensing, human-machine interfaces, covert communications and others.

Understanding the mechanics of this kind of device, the mechanophysiology of the skin, and the behavior of the coupled abiotic-biotic system, are all critically important. For present purposes, the skin can be approximated as a bilayer, consisting of the epidermis (modulus: 140-600 kPa; thickness 0.05-1.5 mm) and the dermis (modulus: 2-80 kPa; thickness 0.3-3 mm) [20-23]. This bilayer exhibits linear elastic response to tensile strains <~15%, which transitions to non-linear behavior at higher strains, with adverse, irreversible effects beyond 30% [24]. The surface of the skin typically has natural wrinkles, creases and pits with amplitudes and feature sizes of 15-100 µm [25] and 40-1000 µm [26], respectively. The devices described here (i.e. FIG. 75) have moduli, thicknesses and other physical properties that are well matched to the epidermis itself, with the ability to conform to the relief on its surface. We therefore refer to this class of technology as an 'epidermal electronic system' (EES).

Macroscopically, EES on skin can be treated as a thin film on an epidermis/dermis bilayer substrate. Microscopically, the sizes of the individual electronic components and interconnects are comparable to those of relief features on the skin, and therefore must be considered explicitly. Multiscale analysis and experimental measurements can capture the detailed behaviors. We begin by considering aspects of adhesion, in the macroscopic limit. Globally, detachment can occur in either tension or compression, due to interfacial cracks that initiate at the edges or the central regions of the EES, respectively. Low effective moduli and small thicknesses minimize the deformation-induced stored elastic energy that drives both of these failure modes. Analytical calculation discussed in this Example shows that compared to silicon chips (thickness ~1 mm) and sheets of polyimide (thickness ~75 µm), the driving forces for delamination of the EES/skin interface are reduced by more than five orders of magnitude. The values are so small, in fact, that adequate adhesion is possible, immediately upon lamination, due simply to van der Waals interactions. FIG. 76 A shows measurements and theoretical calculations discussed in this Example that explore the relevant scaling behaviors, in structures that provide simplified, macroscopic models of EES/skin. The experiments use sheets of PE (~2 mm thick) for the skin and films of poly(dimethylsiloxane) (PDMS, Dow Corning, USA) for the EES. FIG. 76 A plots the critical delamination strain as a function of PDMS thickness, for two different formulations: one with a modulus of 19 kPa (50:1) and the other 145 kPa (30:1, FIG. 79 C). The results confirm that reducing the modulus and thickness lowers the forces that drive interface delamination, for a given applied strain (bending or stretching), without lower bound.

To explore the limits, consider that the mechanical properties of the EES depend on the effective modulus and thickness of both the circuits/sensors and the substrate. In samples like those in FIG. 75, the properties of the active components and interconnects can dominate the mechanics of the overall system. The in-plane layouts and materials of this layer are, therefore, key design parameters. Recent work in stretchable electronics establishes that the overall range of deformability can be optimized in systems composed of active devices joined together in open mesh structures by non-coplanar interconnects in NMP configurations, where elastomers with relatively large modulus (2-10 MPa) and thickness (mm's to cm's) serve as substrates [13, 14]. For EES, the effective modulus ($E_{EES}$) and bending stiffness ($\overline{EI}_{EES}$), rather than the range of stretchability, are paramount. These requirements demand alternative designs and choices of materials. If we assume that the moduli of the individual devices (e.g. ~160 GPa for Si and ~90 GPa for GaAs) are much higher than the compliance of the interconnects, then we can write the approximate expression $E_{EES}=E_{int}(1+L_d/L_s)$, which has been verified by the finite element method (FEM), where $E_{int}$ is the effective modulus of the interconnects, $L_d$ is the characteristic device size, and $L_s$ is the distance between devices, as illustrated in FIG. 79 D. The value of $E_{EES}$ can be minimized by reducing $E_{int}$ and $L_d/L_s$. For the former, thin, narrow interconnect lines, formed into large-amplitude, 'filamentary serpentine' (FS) shapes represent effective designs. For the latter, ultrathin active devices that adopt similar FS layouts and continuously integrate with FS interconnects reduce the effective value of $L_d$ to zero. The value of $\overline{EI}_{EES}$ decreases rapidly with the thicknesses of the devices, interconnects and substrate. FIG. 76 B (left frame) shows an ultrathin FS construct, with a cross sectional schematic illustration as an inset. Results of tensile testing (right frame of FIG. 76 B) indicate that such FS-EES samples (left frame of FIG. 76 B) achieve $E_{EES}$ (~140 kPa) and $\overline{EI}_{EES}$ (~0.3 nN·m, calculation shown in SOM) that are comparable to the epidermis, and more than one and five orders of magnitude smaller than previously reported stretchable electronic devices, respectively [27]. Furthermore, highly repeatable loading and unloading stress-strain curves up to strains of 30% demonstrate the pure elastic response of the FS-EES, with a range of stretchability that is much larger than that of the epidermis. Such highly elastic FS layouts can maintain nearly 20% areal contact of active elements with the skin, for effective electrical interfaces. FEM captures quantitatively the strains and stresses in FS-EES, as a function of induced deformation, as shown in FIG. 76 C for stretching to ~30% strain along the x (left) and y (right) directions. In both cases, the maximum principal strains in the metal are less than ~0.2%. The same calculations yield effective tensile moduli (FIG. 76 B, right frame), with excellent correspondence to experiment. In certain applications, layouts that involve some combination of FS geometries and device islands (i.e. $L_d$ not equal to zero) connected by FS interconnects (e.g. FIG. 75 and FIG. 79 E) can be used, with expected consequences on the local mechanics (FIG. 79 F). In both options, suitable designs lead to mechanical and adhesive properties that allow conformal adhesion to the skin and minimal loading effects (FIG. 76 D). Without optimized layouts, we observe delamination under similar conditions of deformation, consistent with the fracture modes illustrated in FIG. 76 A.

For many uses of EES, physical coupling of electrodes to the surface of the skin is important. Microscopic characterization and modeling of the skin-EES interface provides some insights. Confocal micrographs of EES mounted on pig skin appear in FIG. 76 E, F as well as FIG. 80 C. With FS structures, the results show remarkably conformal contact, not only at the PE regions of the EES, but also at the FS elements (FIG. 76 E, F). Similar behavior obtains, but in a less ideal fashion (FIG. 80 C), with layouts that incorporate large device islands. These observations are consistent with analytical mechanics treatments that use macroscopic models of the EES and account for microscopic structures on the skin. Here, it can be shown discussed in this Example that contact will occur spontaneously, without an applied pressure, when $$\frac{\pi \overline{E}_{skin} h_{rough}^2}{\gamma \lambda_{rough}} < 16 + \frac{\overline{E}_{skin} \lambda_{rough}^3}{\pi^3 \overline{EI}_{EES}}, \quad (1)$$

where $\gamma$, $\overline{E}_{skin}$, $h_{rough}$ and $\lambda_{rough}$ are the effective work of adhesion, and the plane-strain modulus, roughness amplitude and wavelength of the skin, respectively. The scaling law in Eq. (1), which involves two dimensionless combinations of EES and skin properties, shows that EES with low bending stiffness, on smooth and soft skin with strong adhesion all promote conformal contact. Using experimental data and a measured value of $\gamma$~0.16 N/m as discussed in this Example, this criterion implies that the FS-EES can conform to the skin, without applied pressure, when $h_{rough}$ is <~50 μm (FIG. 76 G) for $\lambda_{rough}$=140 μm, consistent with observation in FIG. 76 F where the roughness amplitude is 5~20 μm. Related calculations indicate that the contact pressure created by surface interactions is ~10 kPa (FIG. 88 B), which is below the sensitivity of human skin (~20 kPa, [28]) but still sufficient to offer reasonable adhesion. (Improved bonding can be achieved by using adhesives that are built into platforms for temporary transfer tattoos, as in FIG. 75D). From a microscopic point of view, the soft, conformal nature of the EES helps to drive adhesion to the skin, with strongest effects in regions away from the devices and interconnects, where the local effective modulus is lowest. These interfacial forces assist in bringing neighboring FS structures into contact with the skin as well. Narrow, thin FS geometries facilitate this process. For materials and layouts explored here, the result is a total compressive force (per unit length) of ~–0.1 N/m for each FS strip. Calculations show that these interactions reduce the widths of the gaps between the PE and skin that exist proximal to the edges of the FS elements to <0.2 μm, even for the thickest device structure (~3 μm) in experiments (FIG. 79 E).

A key capability of EES is in monitoring electrophysiological (EP) processes related to activity of the brain (electroencephalograms; EEG), the heart (electrocardiograms; ECG) and muscle tissue (electromyograms; EMG). Amplified sensor electrodes that incorporate silicon metal oxide semiconductor field effect transistors (MOSFETs) in circuits where all components adopt FS designs provide devices for this purpose. Here, the gate of a FS-MOSFET connects to an extended FS electrode for efficient coupling to the body potential (FIG. 77 A; the inset shows an analogous design based on a rectangular device island and FS interconnects), via contact with the skin, in a common-source amplifier configuration (FIG. 77 B, left frame). FIG. 77 B (right frame) indicates the measured frequency response at different input capacitances ($C_{IN}$), in quantitative agreement with circuit simulations (FIGS. 81A and B). The value of $C_{IN}$ is determined by the sum of capacitances of gate electrode, the encapsulating PI and junction between the gate electrode and the body surface. The bandwidth matches requirements for high performance EP recording. A typical layout for this purpose includes four amplified channels, each comprised of a FS-MOSFET, a silicon-based FS resistor and an FS electrode. One channel provides a reference, while the others serve as sites for measurement. Results of demonstration experiments appear subsequently.

Many other classes of semiconductor devices and sensors are also possible in EES, including resistance-based temperature sensors built with meander electrodes of Pt (FIG. 81C left and FIG. 813C), in-plane strain gauges based on carbon-doped silicones (FIG. 81C right frame and FIG. 81D), LEDs and photodetectors based on AlInGaP (FIG. 77 D left frame and FIG. 81E-G; for possible use in optical characterization of the skin/biofluids), and silicon FS photovoltaic cells (FIG. 77 D right frame). Such cells can generate of a few tens of μW (FIG. 81H); increasing the areas or areal coverages can improve the output, but not without compromises in size and mechanics. Wireless powering via inductive effects represents an appealing alternative. FIG. 77 E shows an example of an FS inductive coil connected to a microscale InGaN LED, and electromagnetic modeling of its RF response. The resonance frequency (~35 MHz) matches that of a separately located transmission coil powered by an external supply. Voltage and current outputs in the receiver are sufficient to operate the microscale LEDs remotely, as shown in FIG. 77 E. Such coils provide power directly in this example; they can also, conceivably, be configured to charge future classes of EES-integrated storage capacitors or batteries.

FIGS. 77 F and G present examples of various RF components, of the type needed for wireless communications or for scavenging RF energy. FIG. 77 F shows an optical image of silicon PIN diode (left frame) and its small-signal scattering parameters (right frame), indicating insertion loss (S21 in forward condition) of <6 dB and isolation (S21 in reverse condition) of >15 dB for frequencies up to 2 GHz. Examples of FS inductors and capacitors and their RF responses appear in FIG. 77 F. Connecting pairs of such devices yields oscillators with expected resonant frequencies (FIG. 77 F, lower right frame). A notable behavior is that the response varies with state of deformation, due the dependence of the RF inductance on geometry. For example, at tensile strains of ~12%, the resonance frequency shifts by ~30%. (FIG. 81 I and J). Such effects, which also appear in the wireless power coils but not in the other devices of FIG. 77, will influence the behavior of antenna structures and certain related RF components. These issues must be considered explicitly in EES design and modes of operation.

EES configured for measuring ECG, EMG and EEG, in conformal, skin-mounted modes without conductive gels or penetrating needles provide important, system-level demonstrations of the ideas. ECG recordings from the chest reveal high quality signals with information on all phases of the heartbeat, including rapid depolarization of the cardiac wave, and the associated QRS complex (FIG. 78 A, right frame)[29]. EMG measured on the leg, with muscle contractions to simulate walking and resting are presented in FIG. 78 B, left frame. The measurements agree remarkably well with signals simultaneously collected using commercial, bulk tin electrodes that require conductive gels, mounted with tapes at the same location (FIG. 78 B, right frame; FIG. 82). FIG. 78 C shows an alternative way to view the data (spectrogram), where the spectral content appears in a color contour plot with frequency and time along the y and x axes, respectively. Each muscle contraction corresponds to a red, vertical stripe that spans from 10 Hz to 300 Hz [29].

To demonstrate EMG recording in a mode where conventional devices are particularly ill-suited, an EES mounted on the throat can monitor muscle activity, non-invasively, during speech (FIG. 83 A). Here, recordings collected during vocalization of four words ("up", "down", "left" and "right"), repeated 10 times each (FIG. 846) exhibit distinctive patterns, as in FIG. 78 D. Measurements from another set of words ("go", "stop" and "great"; FIGS. 83 B and 85) suggest sufficient structure in the signals for recognizing a vocabulary of words. These capabilities create opportunities for EES-based human/machine interfaces. As an example, dynamic time warping pattern recognition algorithms applied to throat-based EMG data (FIG. 78 D) enable control of a computer strategy game (Sokoban), as illustrated in FIG. 78 E. The classifications occur in less than 3 s on a dual-core PC running codes in MATLAB, with an accuracy >90% (FIG. 86). Significant increases in speed are possible via optimized software and hardware implementations.

As a human/machine interface, EEG data offer additional promise, for use separately or together with EMG signals. EES mounted on a region of the forehead that is first prepared by exfoliating the stratum corneum using Scotch tape, yields reproducible, high quality results, as demonstrated in alpha rhythms recorded from awake subjects with their eyes closed (FIG. 87 A). The expected feature at ~10 Hz appears clearly in the Fourier transformed data of FIG. 78 F (left frame). The spectrogram of FIG. 78 F (center) shows similar signatures during an experiment in which the subject's eyes are closed for first 10 seconds and then open for the next 10 seconds. The responses at ~10 and ~14 seconds correspond to eye opening and blinking, respectively. This activity disappears when the eyes are held open. The signal-to-noise ratios are comparable to those obtained in otherwise identical experiments using conventional, rigid bulk electrodes applied to the skin with conducting, coupling gels. In further demonstrations, EEG measured by EES reveal well-known cognitive phenomena such as the Stroop effect [30, 31]. In these experiments, subjects randomly presented with congruent or incongruent (FIG. 87 B) colored words, whisper the color (not the word) as quickly as possible. The data show that the motor responses pertaining to the whispering are manifested by two peaks at ~650 ms (congruent case) and ~1000 ms (incongruent case) in the right frame of FIG. 78 F. The time delay implies that the congruent stimuli require fewer cognitive resources and are quicker to process than the incongruent ones, consistent with the literature [30, 31].

The materials and mechanics ideas presented here enable intimate, mechanically 'invisible', integration of high performance electronic functionality with the surface of the skin, in ways that bypass limitations of previous approaches. Integration of the individual components exemplified here with one another and with additional ones such as power storage devices, may provide systems with expanded capabilities in sensing, computation, communication and others, for both healthcare and non-healthcare related applications. An important perspective is that many of the EES concepts are fully compatible with small-scale integrated circuits that can be released from ultrathin body silicon-on-wafer substrates. For long-term use, materials and device strategies may be employed to accommodate the continuous efflux of dead cells from the surface of the skin, and the processes of transpiration will also be needed.

Estimation of Driving Forces for Interfacial Delamination Between Devices and Skin Fracture mechanics of a linear elastic bilayer system [32] gives the steady-state driving force $$G = \frac{1}{2}Eh\varepsilon^2$$

for interface delamination between a thin film of Young's modulus E and thickness h and a thick substrate under uniform tensile strain ε. For tensile strain of 1%, the driving forces for interface delamination of 1 mm-thick silicon (E=180 GPa) and 75 μm-thick polyimide (E=4 GPa) are $9\times10^3$ J/m$^2$ and 15 J/m$^2$, respectively. For EES (E=150 kPa, h=30 μm), the driving force is only $2.25\times10^{-4}$ J/m$^2$, which is more than five orders of magnitude lower than silicon or polyimide based devices.

Sample Preparation for Confocal Microscopy

To prepare samples for confocal microscopy, we stained the polymers and the pig skin with fluorescent dyes having distinct excitation and emission bands, as shown in FIG. 80 A. Alexa 488 (Invitrogen) was used to stain the PE substrate. Ten grams of Alexa 488 powder was first dissolved in 300 μl DMSO (Dimethyl sulfoxide). Next, 1 μl of the 488-DMSO solution was diluted by 1 ml toluene and 100 μl of the resulting 488-DMSO-toluene solution was added to 2 ml Part A pre-polymer of 0030 Ecoflex. A magnetic stir bar was used to facilitate mixing, for 1 hour. We next added 2 ml Part B pre-polymer of Ecoflex and further mixed for 5 minutes. Spin coating this pre-polymer mixture at 3000 rpm onto a water-soluble PVA substrate and curing at room temperature for 4 hours and then at 70° C. for 2 hours completed the preparation of PE. Alexa 647 was used to stain a film of polyimide, patterned into the shape of electronic circuitry. For the polyimide we dissolved ten grams of Alexa 647 powder into 300 μl DMSO. We then added 1 μl 647-DMSO to 1 ml NMP (N-Methylpyrrolidone) and mixed 10 μl of the resulting 647-DMSO-NMP solution into 1 ml of polyimide pre-polymer. As before, we used a magnetic stir bar to mix for 1 hour. Spin coating at 4000 rpm onto a PMMA coated Si wafer and bake at 250° C. in glove box for 1 hour completed the preparation. Patterning the PI into desired structures of island-plus-serpentine and filamentary serpentine was accomplished by photolithography and dry etching. The final step involved transfer-printing the polyimide structure onto the PE(Ecoflex)-coated PVA substrate.

To stain the pig skin, we first mixed 10 gram FM 1-43FX into 300 μl DMSO. We then diluted 1 μl FM-DMSO solution with 1 ml 1×PBS (Phosphate Buffered Saline). We rinsed a the pig skin in 1×PBS thoroughly. Applying a drop of the 1 ml FM-DMSO-PBS solution onto the skin surface and waiting for 10 minutes produced the desired stain. Rinsing with 1×PBS removed excess dye. Fluorescent EES was then applied to stained pig skin sample by placing the device side against the surface of the skin and the gently spraying 1×PBS to dissolve away the PVA backing layer.

During imaging, a 488 nm laser was used to excite both Alexa 488 as well as FM 1-43. Alexa 647 was excited by a 639 nm laser. Three tracks were created for the PE substrate (Alexa 488, blue), polyimide (Alexa 647, red), and pig skin (FM 1-43FX, blue and green) respectively. In-plane as well as thickness direction resolution was ~1 μm. Three dimensional confocal scanning results from bare pig skin and island-plus-serpentine EES on pig skin appear in FIGS. 80 B and 80 C, respectively.

Macroscopic Mechanics Models for Interfacial Delamination Under Tension/compression The driving force for interfacial delamination between a PDMS film and a PE sheet subject to tensile strain ε in the PE can be obtained analytically as $$G = \frac{\bar{E}_{PDMS} h_{PDMS} \bar{E}_{PE} h_{PE} \varepsilon^2}{2\left(1 - \frac{\bar{E}_{PDMS} h_{PDMS}}{\bar{E}_{PDMS} h_{PDMS} + \bar{E}_{PE} h_{PE}} \frac{L_{PDMS}}{L_{PE}}\right)^2} \qquad (S2)$$

-continued $$\frac{(\overline{E}_{PDMS}h_{PDMS}^3 + \overline{E}_{PE}h_{PE}^3)}{(\overline{E}_{PDMS}h_{PDMS}^2 - \overline{E}_{PE}h_{PE}^2)^2 +} \\ 4\overline{E}_{PDMS}h_{PDMS}\overline{E}_{PE}h_{PE}(h_{PDMS} + h_{PE})^2 \quad (5)$$

where $\overline{E}$, h and L are the plane-strain modulus, thickness and length of the corresponding layers. Equation (S2) is an extension of the steady-state driving force for interfacial delamination of a linear elastic bilayer to account for the finite lengths of PDMS film and PE sheet. FEM has been used to calculate the interfacial crack tip energy release rate. For relatively long delamination (much larger than $h_{PDMS}$ and $h^{PE}$), FEM validates Eq. (S2) for a wide range of PDMS and PE elastic moduli and layer thickness. For short interfacial delamination ($\sim h^{PE}$), the numerical results show similar dependence on the layer thickness as Eq. (S2), but are 2~2.5 times larger than Eq. (S2). The critical delamination strain is obtained once the driving force for interfacial delamination reaches the adhesion energy $\gamma_{PDMS/PE}$ between PDMS and PE. For 50:1 and 30:1 PDMS, the adhesion energy is 250 mJ/m² and 50 mJ/m², respectively.

For compression in the PE, initiation of interfacial delamination is more challenging to determine the case of tension because of compression on the interface. The large pre-stretch in the PE, as performed in experiments, prevents Euler-type buckling (to an arch shape). Therefore, increasing the compression induced in this manner eventually leads to wrinkling of the PDMS on PE. This behavior is similar to surface wrinkling of a semi-infinite solid subject to compression parallel to the surface [33], but it is different in the following three aspects:

It involves two materials (PDMS and PE) such that the continuity of displacements and stress tractions must be enforced;

Both layers have finite thickness, and cannot be modeled as semi-infinite solids;

PE has large prestretch, which is not completely released during compression.

These features give the critical strain for wrinkling determined from the eigenvalue of a 8*8 matrix. The critical strain for wrinkling degenerates to [33] a semi-infinite solid.

Microscopic Mechanics Models for Contact Between EES and Skin

Microscopic mechanics models are developed to study contact between EES and skin, particularly on the effects of skin roughness, and device thickness and size. The skin morphology can be represented by a sinusoidal form $y(x)=h_{rough}[1+\cos(2\pi x/\lambda_{rough})]/2$ with skin roughness amplitude $h_{rough}$ and wavelength $\lambda_{rough}$. For non-conformal contact between EES and skin, EES does not follow the skin morphology and remains flat, which gives the total energy $\overline{U}_{non-conformal}=0$. For conformal contact, both EES and skin deform such that the total displacement is y(x). The displacements of EES and skin surface can be represented by $w(x)=h[1+\cos(2\pi x/\lambda_{rough})]/2$ and $u_z(x)=(h_{rough}-h)[1+\cos(2\pi x/\lambda_{rough})]/2$, respectively, where the maximum deflection h of EES is to be determined.

The total energy (per unit length along the wavelength direction) for conformal contact is $\overline{U}_{conformal}=\overline{U}_{bending}+\overline{U}_{skin}+\overline{U}_{adhesion}$, where the bending energy of EES is $\overline{U}_{bending}=(1/\lambda_{rough})\int_0^{\lambda_{rough}}(\overline{EI}_{EES}/2)(w'')^2dx=\pi^4 \overline{EI}_{EES}h^2/\lambda_{rough}^4$, the elastic energy of skin is $\overline{U}_{skin}\approx\pi \overline{E}_{skin}(h_{rough}-h)^2/(16\lambda_{rough})$, and the interfacial adhesion energy is $\overline{U}_{adhesion}=-\gamma\int_0^{\lambda_{rough}}\sqrt{1+(w')^2}dx\approx-\gamma[1+\pi^2h^2/(4\lambda_{rough}^2)]$. Minimization of the total energy then gives analytically the maximum deflection of EES $h=\overline{E}_{skin}h_{rough}/(16\pi^3\overline{EI}_{EES}/\lambda_{rough}^3+\overline{E}_{skin})$.

Conformal contact requires $\overline{U}_{conformal}<\overline{U}_{non-conformal}$, which gives $$\frac{4\pi^2 \overline{EI}_{EES}}{\gamma \lambda_{rough}^2} < \frac{4\lambda_{rough}^2}{h_{rough}^2 \pi^2}\left(\frac{16\pi^3 \overline{EI}_{EES}}{\overline{E}_{skin}\lambda_{rough}^3}+1\right) + \frac{1}{\frac{16\pi^3 \overline{EI}_{EES}}{\overline{E}_{skin}\lambda_{rough}^3}+1}. \quad (S3)$$

Since $\lambda_{rough} \sim 7 h_{rough}$ in experiments (FIG. 76 F), the second term on the right hand side is negligible and the above equation becomes $$\frac{\pi \overline{E}_{skin}h_{rough}^2}{\gamma \lambda_{rough}} < 16 + \frac{\overline{E}_{skin}\lambda_{rough}^3}{\pi^3 \overline{EI}_{EES}}. \quad (S4)$$

For the FS-EES (FIG. 76 B), $\overline{EI}_{EES}\approx0.27\times10^{-9}$ N-m (see Section S5), $\overline{E}_{skin}\approx130$ kPa, $\lambda_{rough}\approx140$ μm, $\gamma\approx0.16$ N/m (see Section S5), the above criterion implies that EES can have conformal contact with skin when the skin roughness is smaller than ~56 μm (FIG. 76 G). This result is consistent with conformal contact observed in FIG. 76 F (roughness in the range of 5~20 μm, as marked by the color bar in FIG. 76 G).

For the island-plus-serpentine EES (FIG. 79 D), the device is much thicker (Au 0.5 μm-PI 1.2 μm-Au 0.2 μm-PI 1.2 μm) and larger (500 μm×500 μm) than the FS strips (0.5 μm thick, 100 μm wide). For 400 μm spacing between adjacent islands (FIG. 79 D), the effective bending stiffness is $\overline{EI}_{EES}\approx1.6\times10^{-9}$ N-m from FEM, and the effective work of adhesion is $\gamma\approx0.14$ N/m (see Section S5). The criterion above implies that EES loses conformal contact once the skin roughness exceeds 27 μm, which is consistent with partial contact observed in the experiments for the range of skin roughness 20~50 μm (FIG. 80 C).

For the FS-EES design, the effect of device thickness is studied by changing thicknesses of all layers proportionally. Let $h_{device}$ denote the total thickness of device. FIG. 88 A shows that, for FS made of Au-PI as in experiments (red curve), the skin roughness for conformal contact decreases from ~56 μm to ~30 μm as the device thickness increases by 8 times. If all elastic moduli are proportionally reduced by 1000 times (blue curve), FS-EES would have conformal contact with much rougher skin. Therefore, thinner, softer devices promote conformal contact between EES and skin.

The thickness and modulus of the device and the skin roughness also play important roles on the comfort, or 'wearability', of EES. The contact pressure at the EES-skin interface is obtained analytically as [34]

$$\sigma_{contact-global} = \frac{8\pi^4 \overline{E}_{skin}h_{rough}}{16\pi^3 \lambda_{rough} + \frac{\overline{E}_{skin}\lambda_{rough}^4}{\overline{EI}_{EES}}}\cos\frac{2\pi x}{\lambda_{rough}}. \quad (S5)$$

FIG. 88 B (blue curve) shows the contact pressure between the FS-EES and skin of average roughness ($h_{rough}=30$ μm) for EES with device thickness of 0.5 μm. The maximum contact pressure is only 12.5 kPa, which is below the human skin sensitivity (~20 kPa [28]) and therefore would not induce discomfort; devices thicker than 1.2 μm give a contact pressure higher than 20 kPa, while devices thicker than 3.8 μm lose conformal contact to the skin. Larger skin roughness of 40 μm (red curve) results in higher interfacial pressure, and the device thickness to lose conformal contact becomes much smaller (~1.5 μm). From Eq. (S5), it is obvious that softer device materials will give smaller contact pressure.

FIG. 89 illustrates the mechanics model to determine the gap width a along the edges of EES. Since FS thickness $h_{device}$ (~1 μm) is much smaller than that of the skin (~1 mm) and the PE (~30 μm) and the FS strip width (~100 μm), the FS between the skin and PE is analogous to inserting a rigid wedge of uniform thickness $h_{device}$ at the skin/PE interface, leading to an interfacial crack [35]. The interfacial crack tip energy release rate is [36]

$$G \approx \frac{(\overline{E}_{skin} + \overline{E}_{PE})h_{device}^2}{16\pi a}. \quad (S6)$$

The gap width a is obtained by G reaching the adhesion energy $\gamma_{PE/skin}$ as $$a \approx \frac{(\overline{E}_{skin} + \overline{E}_{PE})h_{device}^2}{16\pi \gamma_{PE/skin}}, \quad (S7)$$

which has been verified by FEM for the range of FS thickness in experiments.

The stress distribution $\sigma_{contact-local}$ over FS width is obtained analytically (Huang et el., Langmuir, 2005), and is shown schematically in FIG. 89. The total force on FS strip is the integration of this $\sigma_{contact-local}$ and $\sigma_{contact-global}$ in Eq. (S4) over FS strip width, $$F_{total} = \int_{FS\ width} (\sigma_{contact-global} + \sigma_{contact-local}) dx,$$

which has an average of −0.1 N/m for skin with $h_{rough}$=15 μm and $\lambda_{rough}$=140 μm.

Effective work of adhesion between EES and skin, and effective bending stiffness of EES The effective work of adhesion between EES and skin is given by $$\gamma = \alpha\gamma_{device-skin} + (1-\alpha)\gamma_{PE-skin}, \quad (S8)$$

where α is the area fraction of devices, and $\gamma_{device-skin}$ and $\gamma_{PE-skin}$ are the work of adhesion for device-skin and PE-skin interfaces, respectively. Since adhesion between device (Au) and skin is very weak, Eq. (S8) is simplified to $\gamma \approx (1-\alpha)\gamma_{PE-skin}$. For the experimental value of $\gamma_{PE-skin}$=0.2N/m measured by rod-rolling set-up described in [37], the effective work of adhesion is $\gamma \approx 0.16$ N/m for the FS-EES ($\alpha \approx 22.5\%$) and $\gamma \approx 0.14$ N/m for the island-plus-serpentine EES ($\alpha \approx 30.9\%$).

Similarly, for FS strips distributed over the entire surface of FS-EES electronics, the effective bending stiffness of EES is given by $$\overline{EI}_{EES} = \alpha \overline{EI}_{device} + (1-\alpha)\overline{EI}_{PE}, \quad (S9)$$

where $\overline{EI}_{PE} = \overline{E}_{PE} h_{PE}^3/12$ is the bending stiffness of PE ($\overline{E}_{PE}$=65 kPa and $h_{PE}$=30 μm are the plane-strain modulus and thickness of PE, respectively), and the bending stiffness for PE with device is $$\overline{EI}_{device} = \sum_{i=1}^{3} \overline{E}_i h_i \left[ \left(b - \sum_{j=1}^{i} h_j\right)^2 + \left(b - \sum_{j=1}^{i} h_j\right) h_i + \frac{1}{3} h_i^2 \right]$$

$$\left( \text{where } b = \sum_{i=1}^{3} \overline{E}_i h_i \left( \sum_{j=1}^{i} h_j - \frac{1}{2} h_i \right) \bigg/ \sum_{i=1}^{3} \overline{E}_i h_i; \right.$$

$\overline{E}_1 = \overline{E}_{PE}$, $h_1 = h_{PE}$; $\overline{E}_2 = 2.8$ GPa, $h_2 = 0.3$ μm are the plane-strain modulus and thickness for PI, respectively; and $\overline{E}_3 = 97$ GPa, $h_3 = 0.2$ μm for Au). For $\alpha \approx 22.5\%$ from FIG. 76B, Eq. (S9) gives the effective bending stiffness $0.27 \times 10^{-9}$ N-m, which agrees reasonably well with $0.30 \times 10^{-9}$ N-m obtained by FEM.

Sample Fabrication of an FS-EES EP Sensor

The sample fabrication begins with high temperature diffusion doping to define low resistance source and drain area for Ohmic contacts. Phosphorous spin-on-dopant (P509, Filmtronics, USA) was diffused at 950° C. with constant supply of gas mixture (nitrogen:oxygen, 8:2). Transfer printing the resulting doped silicon nanomembrane to a handle wafer coated with PMMA/PI, followed by dry etching for isolation active regions, defined silicon areas on thin PI, as shown in FIG. 77 A left frame. Electron-beam evaporation of metal (Cr/Au, 50/1500A) interconnects ground and output to the sensor and defines source, drain and gate electrodes (FIG. 77 A right frame and its inset for a magnified view). Additional metallization for larger area sensor electrode, connection different layers through vias and second transfer printing to PE/PVA results in final sensor, as shown in FIG. 90.

S7. ECG Measurement

The body ground electrode was a tin electrode filled with conductive gel, attached to the bony area on the right side of the subject's right ankle. The EES was attached to the lower-left edge of the rib cage, near the left side of the midline of the chest. Usually one of the electrodes on the EES was used as reference electrode, while another was recording electrode. The negative end of the AA battery that powered the EES was also tied to the body ground. The gain of the main amplifier was 10000, with a high-pass frequency (HPF) of 0.1 Hz, and a low-pass-frequency (LPF) of 100 Hz. The sampling frequency was 1000 Hz. A notch filter was applied in software to eliminate 60 Hz power line interference.

EMG Measurement from Leg

The EES was attached at about ⅓ the distance from the knee to the ankle, on the interior side of the left leg. Other parameters were the same as those for ECG, but with HPF=0.01 Hz and LPF=300 Hz. Passive measurements were done separately after recording with the EES, with otherwise exactly the same configurations. Two tin electrodes were attached in close vicinity of the EES, one on each side of it, vertically along the axis of extension of the muscle. The voltage differences between them were reported as the passive EMG.

EMG Measurement from Neck

The EES was attached at the skin overlying the cricothyroid muscle. The measurement parameters were the same as those for EMG on the leg.

EEG Measurement from Forehead (Alpha Rhythms and Stroop Effects)

The body ground and reference electrodes were gold electrodes IN EES FORMAT without using conductive gel, attached to the subject's left and right earlobes respectively.

The passive EES was attached the center of the subject's forehead without applying conductive gel. If the EES has multiple channels, then usually one of the electrodes on it would be used as reference electrode, while another would be recording electrode. The gain of the main amplifier was 10000, HPF=0.01 Hz, LPF=300 Hz. Sampling frequency was 1000 Hz. A notch filter was applied in software to eliminate 60 Hz power line interference.

Simulated Computer Game Control Via Neck EMG Measured by EES

All computations were done in Matlab®. After eliminating 60 Hz interference from the raw data using an offline notch filter, the feature vector associated with each utterance was generated from the spectrogram of the data, using sliding window length of 256, overlap size of 250, and the fast-fourier transform (FFT) length of 512. Spectrograms were generated for an entire trial first, and then sliced into 750 ms intervals that correspond to the utterances of words, according to EMG onset times. These onset times were determined by an energy detecting procedure, where raw data were first sent through a high pass filter (Chebyshev type I, cutoff 70 Hz, high-pass 80 Hz), concatenated by a matched filter, and the signals were then squared. Whenever the power crossed a threshold value, a pair of onset and offset times of EMG activity was recorded.

In the original labeled dataset, there were 63 feature vectors for each of the 4 words. The metric of distance between any two feature vectors was the L1-norm, and dynamic time warping (DTW) was used to calculate the similarity score between them. In the computer game control demonstration, the user manipulated an avatar that can move in 4 directions in the game called Sokoban. In a simulated demonstration, when the user presses a key to signify the intended direction for the avatar, a candidate feature vector is randomly drawn from the EMG feature pool for that direction, and compared with all the rest of the feature vectors in all four pools as references, in terms of DTW scores. As a result, a nearest neighbor can be found for the candidate from one of the four pools, and it will be classified as a member from this nearest neighbor's group.

The classification accuracy depends on the number of reference feature vectors available for each direction (FIG. 86). We have simulated (by resampling the data pool without replacement in 100 trials) the situation where various numbers of references were randomly available from each of the four pools, and found that the classification accuracy estimated across 100 trials increased with the number of references. When 62 references in each pool were used, the averaged accuracy could be higher than 95% for "up" and "down", and higher than 85% for "left" and "right". Thereby, the intended directions can be accurately classified and conveyed to the avatar, and gaming can thus be accomplished.

DFT (Discrete Fourier Transform) Coefficient

Given a vector of length N, x[1], . . . , x[N] the definition of the DFT coefficients, X(k), is as follows.

$$X(k) = \sum_{j=1}^{N} x[j] \cdot \exp\left\{-\frac{2\pi i}{N}(j-1)(k-1)\right\}$$

Where k=1, . . . , N

Fatigue Test

Repetitive stretching up to 1000 times with 30% tensile strain at 20 rpm shows no performance (resistance) degradation of FS electrodes, as shown in FIG. 91.

References

1. H. Berger, Arch Psychiatr Nervenkr 87, 527 (1929).
2. C. Hardyck, L. Petrinovich, D. Elsworth, Science 154, 1467 (1966).
3. E. J. Fox, R. Melzack, Pain 2, 141 (1976).
4. J. G. Webster, in Medical Instrumentation: Application and Design (John Wiley & Sons, Inc., New York, 2009) p. 189-240.
5. A. Searle, L. Kirkup, Physiol. Meas. 21, 271 (2001).
6. P. Griss, H. K. Tolvanen-Laakso, P. Meriläinen, G. Stemme, IEEE Trans. Biomed. Eng. 49, 597 (2002).
7. L. M. Yu, F. E. H. Tay, D. G. Guo, L. Xu, K. L. Yap, Sens. Actuators A 151, 17 (2009).
8. B. Gerdle, S. Karlsson, S. Day, M. Djupsjöbacka, in Acquisition, Processing and Analysis of the Surface Electromyogram. Modern Techniques in Neuroscience, U. Windhorst, H. Johansson Eds. (Springer Verlag, Berlin, 1999) p. 705-755.
9. J. R. Ives, S. M. Mirsattari, D. Jones, Clinical Neurophysiol. 118, 1633 (2007).
10. T. Sekitani et al., Science 321, 1468 (2008).
11. S. C. B. Mannsfeld et al., Nat. Mater. 9, 859 (2010).
12. K. Takei et al., Nat. Mater. 9, 821 (2010).
13. D.-H. Kim et al., Science 320, 507 (2008).
14. R.-H. Kim et al., Nat. Mater. 9, 929 (2010).
15. M. Kubo et al., Adv. Mater. 22, 2749, (2010).
16. M. Gonzalez et al., Microelectronics Reliability 48, 825 (2008).
17. S. P. Lacour, J. Jones, S. Wagner, T. Li, Z. Suo, Proc. IEEE. 93, 1459 (2005).
18. C. Keplinger, M. Kaltenbrunner, N. Arnold, S. Bauer, Proc. Natl. Acad. Sci. USA. 107, 4505 (2010).
19. L. Hu et al., Nano Letters 10, 708 (2010).
20. Kuwazuru et al., Med. Eng. Physics 30, 516 (2008).
21. M. Geerligs, J. Biomech., In press (2011).
22. C. Pailler-Mattei et al., Med. Eng. Phy. 30, 599 (2008).
23. http://dermatology.about.com/cs/skinanatomy/a/anatomy.htm.
24. V. Arumugam, J. Biosci. 19, 307 (1994).
25. L. Tchvialeva et al., in Skin Roughness Assessment. New Developments in Biomedical Engineering, D. Campolo Eds. (InTech, http://www.intechopen.com/download/pdf/pdfs_id/9090, 2010) p. 346.
26. K.-P. Wilhelm, P. Elsner, E. Berardesca, in Bioengineering of the Skin: Skin Surface Imaging and Analysis, (CRC Press, Boca Raton, 1997) p. 154.
27. D.-H. Kim et al., Proc. Natl. Acad. Sci. USA. 105, 18675 (2008).
28. A. Kaneko, N. Asai, T. Kanda, J. Hand Ther. 18, 421 (2005).
29. L. Sömmo, P. Laguna, in Bioelectrical Signal Processing in Cardiac and Neurological Applications, (Elsevier, Amsterdam, 2005) p. 337-452.
30. J. R. Stroop, J. Experimental Psychology 18, 643 (1935).
31. O. Spreen, E. A. Strauss, in Compendium of Neuropsychological Tests: Administration, Norms and Commentary, (Oxford University Press, New York, 2006) p. 477-499.
32. J. W. Hutchinson, Z. Suo, Advances in Applied Mechanics 29, 63 (1992).
33. M. A. Biot., Appl. Sci. Res. A 12, 168 (1963).

34. H. Jiang, Y. Sun, J. A. Rogers, Y. Huang, Int. J. Solids Struct. 45, 2014 (2008).

35. Huang et al., Langmuir 21, 8058 (2005).

36. H. Tada, P. C. Paris, G. R. Irwin, in The Stress Analysis of Cracks Handbook, (ASME Press, New York, 2000).

37. M. A. Meitl et al., Nat. Mater. 5, 33 (2006).

EXAMPLE 8

Epidermal Skin Hydration Sensors

Skin hydration monitoring is important for dermatology to analyze several diseases and evaluate the effectiveness of medical therapies [1-4]. Aesthetically speaking, hydration measurement is also important for cosmetology to assess the effectiveness of anti-aging and moisturization treatments. Skin hydration levels have been characterized through measurement of skin electrical impedance [5-7], mechanical [8-10], thermal conductivity, spectroscopy [5, 11, 12] and reflectivity [13]. Among these methods, the electrical impedance detection is most convenient and is represented by several commercial products [14-17]. However, these commercial sensors generally realize hydration detection by bulky electrodes [14], whose accuracies are subjective to the inconsistency of contact force between the electrode and the skin. In addition, these sensors measure skin hydration at a fixed frequency, lacking the flexibility to probe the hydration level at different skin depths with various clinic and cosmetic interests.

We have demonstrated epidermal electronics circuits that can be conformably attached to the skin as tattoos [18]. Integrated with multiple functions, these epidermal circuits allow non-invasive detection of physiological parameters with maximized stretchability and flexibility. This example presents three types of epidermal hydration sensors based on impedance detection. These sensors effectively resolve the requirement of precise contact force and provide improved flexibility to bio-impedance measurement applications [19, 20]. One sensor conducts differential hydration measurement, which compensates for temperature variation, human activity, and other disturbances that may lead to unexpected impedance changes. In addition, these sensors allow for measurement of hydration level at different depths of the skin and conduct large area hydration mapping through multiplexing techniques. The experimental results demonstrate that these sensors possess comparable accuracy and stability to commercial moisture meter (CMM) and can integrate with other sensing or actuating elements to realize multifunctional epidermal applications.

Principle and Designs: Epidermal skin hydration sensors are based on impedance measurement of the hydration induced changes in the electrical properties of the skin. Varied moisture levels can alter the electrical conductance as well as permittivity of the skin, leading to different skin impedance [21]. As shown in FIG. 92, by applying an alternative changing voltage to the skin through the central electrode, and measuring the attenuation of this voltage during the transportation within the skin through peripheral electrodes, the impedance along the path that the electrical field has passed can be determined.

Three types of epidermal sensors that can realize differential hydration sensing, skin hydration depth profiling and hydration mapping in large area have been developed. The sensor that is used for differential hydration measurement contains four pairs of electrodes that explore capacitive and resistive hydration measurement (FIG. 93(a)). These electrodes, which are named by channel 1 to 8 when counted from right to left, include two pairs of circular electrodes, one pair of interdigitated electrodes, and one pair of meander electrodes, The circular electrodes and interdigitated electrodes measure skin hydration through capacitive detection, while the meander electrode measures the hydration-induced resistive changes or can be used as a temperature sensor. All channels of the sensor share a common ground, which is located at the center of the device. The sensing electrodes (sensing module) are exposed and directly contact with the skin, while the reference electrodes are embedded in a polymer film and blocked by solid metal films that act as flowing ground. These sensors are connected with serpentine metallic wires, which are used for the communication between the sensor and a measurement setup while maintaining the stretchability and flexibility of the entire device. The entire device is passivated in a polymer film that is bond to a silicone substrate through covalent bonding. The differential measurement provides excellent rejection to common mode disturbances in the measurement system and eliminates the impedance changes caused by serpentine interconnections.

The device used for skin hydration depth profiling contains 8×8 electrodes connected with serpentine wires (FIG. 94). Each of the electrodes is formed by concentric circular and annular electrodes. The annular electrodes have fixed inner and outer diameters, while the diameter of circular electrodes on the same row steadily increases, resulting in different spacing between the circular electrodes and annular electrodes on the same row. The circular electrodes on the same row share the same serpentine connections, while the annular electrodes on the same column are connected with the same serpentine wires. This configuration facilitates measurement of 64 sensors through 16 channels using multiplexing technique. Anisotropic conductive films (ACF) cable can be bond with the wire bonding pads to connect the device with a measurement setup. The device is passivated in a polymer film with all 64 electrode pairs exposed. The entire device is supported by a silicone substrate that is flexible and stretchable. The device used for hydration mapping also contains 8×8 electrode pairs and share common features as the hydration depth profiling sensor (FIG. 94). Differently, these electrodes have the same spacing between the inner circular electrodes and outer annular electrodes.

Fabrication processes: All epidermal hydration sensors are fabricated using similar processes. The fabrication starts with spin-coating a sacrificial PMMA layer (500 nm) and a supporting polyimide film (1 µm) on silicon (Si) substrate (panel (a) of FIG. 95). Cr (5 nm) and Au (400 nm) layers are then deposited and patterned to form the serpentine interconnections (panel (b) of FIG. 95), which are then passivated by another polyimide film (1 µm). A patterned photoresist layer (AZ4620, 10 µm) then define the area for vias, which are later formed by etching polyimide film through reactive ion etching (RIE) (panel (c) of FIG. 95). Following the removal of the photoresist layer, an addition Cr/Au (5 nm/200 nm) layer were deposited and patterned to form the electrodes (panel (d) of FIG. 95). Afterwards, a photoresist layer (AZ4620, 20 µm) that defines the device outline is used as a mask layer to etch through the polyimide film and PMMA film by RIE. The photoresist on the device as well as the PMMA underneath the device is then stripped in acetone for 5 minutes at 100° C. The resulting device collapses onto the Si substrate and is picked up by water-soluble PVA tape. Ti/SiO$_2$ layers (5/40 nm) are then deposited as an adhesion layer to bond the device with silicone substrate (500 um PDMS or Solaris) (panel (i) of FIG. 95). Finally, the entire device is put into water to remove the PVA tape, resulting in a flexible and stretchable hydration sensor (panel (j) of FIG. 95). FIG. 96 shows a fabricated differential hydration sensor (panel (a)), which has excellent flexibility (panel (b) of FIG. 96). This differential hydration sensor can be further connected with a releasable connector that contains serpentine wires (panel (c) of FIG. 96). The releasable connector provides a flexible interface between the hydration sensor and ACF and is fabricated using similar fabrication processes as the hydration sensors. The device as well as the releasable connector is finally put on the skin for hydration detection (panel (d) of FIG. 96). A hydration mapping device is shown in panel (a) of FIG. 97, which also has excellent flexibility (panel (b) of FIG. 97) and can be put on to the skin for hydration measurement (panel (c) of FIG. 97). The device used for skin hydration depth profiling is similar to the hydration mapping device (panel (d) of FIG. 97).

Experimental Setup: The impedance of the differential hydration sensor can be measured using a setup as shown in FIG. 98. An impedance analyzer chip (AD5933, Analog Devices) is used to measure the impedance changes of the differential hydration sensor at sweeping frequencies ranging from 10 kHz to 100 kHz. The impedance analyzer provided an excitation AC voltage ($D_{in}$) at the sweeping frequencies to each channel of the hydration sensor through a multiplexer (ADG 708, Analog Devices). By changing the combination of voltage supplies to a1, a2, and a3 in the multiplexer through a computer controlled I/O controller, 8 channels of the sensor (labeled from A1 to A8) can be individually selected. The amplitude and phase of $D_{in}$ changed with the impedance of each channel. As a result, the attenuated signal from all electrodes is read through $D_{out}$, which is shared by all sensor channels in a time-sequence.

The experimental setup (FIG. 99) for skin hydration depth profiling and mapping shares the various features as the one used for differential measurements (FIG. 98). In addition to the impedance analyzer chip, a LCR meter that provides sweeping frequency ranging from 20 Hz to 2 MHz is used to provide more sophisticated impedance measurement at higher frequency. To sweep both columns and rows of the high density hydration sensors, an additional multiplexer is added into the system to allow the selection of the channel of $D_{out}$. The computer controls the I/O controller to send out 6 bits digital signal that selects one column and one row of the hydration sensor at a time. As a result, impedance from one of the 64 electrode pairs is read out each time. The LCR meter, multiplexer, and the I/O controller are fast enough to complete the sweeping of 64 electrodes in 1 second.

Experimental Methods: The hydration sensors are attached to the ventral forearm for convenience of self-monitoring of skin impedance. The hydration sensor is compatible with any other skin location as desired. The skin hydration is manipulated by application of body lotion. The sensor response of all three types of devices to various hydration levels is characterized, while a CMM (MoistureMeterSC Compact, Delfin Inc) measures the skin hydration levels as references, which re then used to calibrate the impedance from the hydration sensor. The repeatability of device output is assessed by repeatedly peeling off and reattaching the sensor to the skin at a stable hydration level. In addition, the stability of the epidermal hydration sensor is compared with the CMM at a fixed hydration level.

The effective measurement depth of the hydration sensors is characterized using molded PDMS chambers with height varied from 10 to 60 μm (FIG. 100). During the measurement, the PDMS chambers are filled with PBS buffer and sealed with a regenerated cellulose semi-permeable membrane with a thickness of 20 μm. As a result, if the electrode is capable of measuring the PBS in the chamber, height-dependent impedance changes can be observed. Otherwise, the sensor impedance will become leveled above certain height of the chambers. Thus, we can determine the sensors' effective measurement depth from impedance measurement. Using a hydration sensor with various electrode spacing from 60 to 200 um and measured at varying frequencies ranging from 15 kHz to 2 MHz, we obtain the frequency [22] and geometry dependence of effective measurement depth of hydration sensors.

Hydration sensors presented in this example are mostly characterized at a frequency ranging from 15 kHz to 2 MHz. The relatively low frequencies allow measurement deeper into the skin and offer larger response to hydration changes, while the high frequencies limit the effective depth of the measurement and are less subjective to the influence from electrolyte. In addition, the selection of measurement frequencies also allows electrode polarization minimization, which is most prominent at low frequency (below 10 kHz). Furthermore, this frequency range covers the frequency used by the CMM, providing direct comparison between the measured impedance and hydration levels obtained by CMM.

Experimental Results and Discussions: Comparison between hydration measured by moisture meter and impedance measured by hydration sensor of the present example. The relation between hydration levels measured by the CMM and the impedance of a differential hydration sensor is first characterized. The time course of the skin impedance and hydration is obtained in turn through a differential hydration sensor and the CMM after application of body lotion to the forearm of the volunteer. At a fixed frequency of 15 kHz, the impedance of the channel 4 of the hydration sensor is obtained and compared with hydration levels from the CMM with an arbitrary unit (FIG. 101(a)). The impedance values are inversely proportional to the hydration levels. As sensor impedance difference changed from 25 kΩ to 48 kΩ, the skin hydration level decreases from 110 to 22. This result indicates that higher hydration levels lead to increase of electrical conductivity as well as decrease in the permittivity of the skin. The impedance values are converted into hydration levels using a first order linear equation, whose coefficients are calculated using two reference hydration levels and the corresponding electrode impedance. FIG. 101(b) shows the results after converting the sensor impedance into hydration levels. The converted results show excellent consistency with the CMM, indicating that the epidermal hydration sensor is a good alternative to the CMM.

Repeatability: The repeatability of the epidermal sensor is assessed at varying frequencies at a stable skin hydration level. During the measurement, the sensor is repeatedly attached onto and retrieved from the skin. The data from channel 4 and 5 of the hydration sensor is recorded (FIG. 102). As can be seen from FIG. 102 panels (a) and (b), both the amplitude and phase of the impedance are very stable with the exception that significant noise and fluctuations are observed at frequencies around 60 kHz. This may be due to the harmonic frequency from the supply power. At 15 kHz, the impedance amplitude of channel 4 varies by 7.4%, while the phase varies within 8.3%. The impedance of channel 5 also shows similar repeatability with an impedance amplitude change within 5.15% and a phase change within 5.52%. These results indicate that the hydration sensor has excellent reliability and repeatability, and is suitable for applications were repeated attachment and removal is required.

The stability of the hydration sensor is compared with the CMM. Both the hydration sensor and the CMM are used to measure the skin hydration at a stable level without application of lotion. The impedance difference between channel 4 and 5 are converted into hydration levels using the first two reference points from the CMM. Among the ten measured points (FIG. 103), the hydration sensor exhibits comparable stability as the CMM. The hydration levels from the hydration sensor are stable at approximately 28.15 with a standard deviation of 0.74, while the CMM shows an average hydration value of 28.28 and a standard deviation of 0.68. Note that the relatively smaller deviation of the CMM is achieved by manually controlling the contact force between the electrode and the skin in a designated range. The operation of the epidermal hydration sensor is more convenient without the concern of contact force, while allowing comparable stability as the CMM.

Differential hydration sensor response to hydration changes. The sensor responses at varying hydration level are measured at frequencies ranging from 15 kHz to 95 kHz. The impedance amplitude and phase of all sensor channels changes with skin hydration levels (FIGS. 104 and 105). But the impedance of sensing modules changed larger than the impedance from the reference modules. For example, as the hydration levels changes from 40 to 110, the impedance amplitude of channel 4 changed by 1.58 M$\Omega$, while the impedance amplitude of channel 5 changed by 1.04 M$\Omega$. The change of the impedance in the reference module with the hydration levels can be mostly attributed to the parasitic capacitance and resistance from the serpentine wires, and is effectively compensated by subtracting the impedance from the sensing module. The results again exhibit some noise at frequencies ranging from 50 to 60 kH due to the harmonic frequency from the power supply. In addition, the impedance amplitude and phase of channel 4 change by 89% and 73% when hydration levels change from 40 to 110. The percentage change of impedance is 10 times larger than the percentage changes in repeatability measurements, indicating that the epidermal hydration sensor is practically applicable in hydration level monitoring that requires repeated sensor reattachment.

The impedance differences between channel 3 and 6 as well as channel 4 and 5 are converted into hydration levels using two reference values from the CMM (FIG. 106). The converted results exhibit excellent consistency between CMM and epidermal sensors. At a measurement period of approximately 35 minutes, the maximum deviation between the measured hydration levels from CMM and converted values from epidermal sensor is only 10%. These results indicate that the epidermal hydration sensor is readily used for skin hydration monitoring with comparable performance as the CMM and improved convenience.

In-vitro characterization of depth profiling sensor. The frequency and geometry dependence on electrode impedance are conducted at various frequencies from 15 kHz to 2 MHz. Using the test chamber that simulates the structure of human skin as shown in FIG. 97($d$) and FIG. 100, electrode impedance with respect to chamber heights can be obtained to determine the effective measurement depth of the hydration sensors. As shown in FIG. 107, the electrodes respond to changes in chamber height differently. The capability of electrode in measuring PBS buffer in chambers of different height is determined by both measurement frequencies and the electrode spacing. However, frequency changes produce more significant influence as compared to the electrode spacing. For example, at a frequency of 15 kHz, all electrodes exhibit decreasing impedance with the chamber height up to 40 µm (FIG. 107($a$)). Considering the thickness of the semi-permeable membrane, the electrodes are capable of measuring a depth that is larger than 60 µm. However, this capability decreased quickly with frequencies. At 250 kHz, most electrode impedance became leveled at a chamber height of 20 µm, equivalent to a 40 µm effective measurement depth (FIG. 107($b$)). Ignoring the fluctuation caused by sensing errors, electrode impedance does not change with chamber height at 500 kHz and 1.25 MHz, indicating an effective measurement depths lower than 20 µm.

Compared to the influence from the measurement frequency, the influence of the electrode spacing is more prominent at low frequency. For example, at 15 kHz, impedance of the electrode with 80 µm spacing becomes gradually leveled at approximately 35 µm, while impedance of electrode with 200 µm spacing decreases steadily up to 60 µm. This observation indicates that electrodes with larger spacing have a deeper skin depth. The results of frequency and geometry dependence of effective measurement depth is used to assess the electrodes used in the differential hydration sensor having electrode spacing of 50 or 80 µm. This spacing indicates an effective measurement depth lower than 55 µm at 15 kHz, which is comparable to the thickness of stratum corneum. These in-vitro depth profiling results demonstrate the ability to measure hydration at different skin depths by changing the measurement frequency and electrode spacing.

Depth profiling hydration sensor response to hydration changes. The depth profiling sensor can be in-vivo characterized at a low frequency, at which the effects of measurement frequencies and electrode spacing are most prominent. Here, 8×8 depth profiling sensor is used to measure the hydration level at different depths of the skin. FIG. 108 demonstrates the electrode impedance exhibits an impedance gradient related to the electrode spacing. Impedance decreases with increasing hydration levels. Impedance of electrodes with three different spacing (200, 140 and 60 µm) are selected to compare with hydration levels obtained by the CMM. As shown in FIG. 109, the skin hydration changes from 64 to 114 after the lotion application, and then decreases back to 56. The electrodes with spacing of 200 and 140 µm follow the trend well. In contrast, the electrode with 60 µm spacing has initial impedance that is larger than terminated impedance. These results are consistent with the in-vitro experiments and indicate that electrodes with 200 and 140 µm spacing can follow the hydration levels changes in the stratum corneum, while the electrode with 60 µm may capture the hydration level changes beyond the layer of stratum corneum.

Hydration mapping sensor response to hydration changes. An 8×8 hydration mapping sensor is used to obtain the hydration levels over a relatively large skin surface area. Results from both the hydration sensor and the CMM are obtained at a fixed frequency of 1.25 MHz, at which the hydration measurements are constrained in the region of straturm corneum according to the experiments above. As shown by FIG. 110 (a) and (b), the electrode impedance is very uniform on the dry skin due to the same electrode spacing. After application of the lotion, both impedance amplitude and phase changes with the hydration levels on the skin. The initial hydration level of the skin is 40, corresponding to an average electrode impedance at about 161 k$\Omega$ (FIG. 110 (a)). After application of the lotion, the skin hydration changes to 114 (FIG. 110 (b)), corresponding to an average impedance of 155 k$\Omega$. At a hydration level of 77, the impedance changes back to 158 kΩ (FIG. 110(c)). Selecting one of the electrodes on the center of the device, the time course of electrode impedance and phase is obtained before and after the lotion application (FIG. 111(a)). During the measurement, the hydration level changes from 40 to 114 then back to 65. This corresponds to an electrode impedance change from 160 kΩ to 151 kΩ and then to 157 kΩ. Corresponding changes also occur in the phase of the electrode impedance. The impedance amplitude and phase are converted back to hydration levels and compared with the hydration levels obtained by the CMM (FIG. 111(b)). The results demonstrate excellent consistency between the bulky electrode from the CMM and miniaturized electrodes from the hydration sensor, indicating that both the impedance amplitude and phase can be used to obtain skin hydration levels. This result is obtained at the same frequency as the CMM to facilitate direct performance comparison. However, this sacrifices the sensitivity of the miniaturized electrodes. By appropriately decreasing the measurement frequency, a more sensitive hydration measurement is achieved with performance that outweighs the CMM.

In this example, three types of epidermal hydration sensors are presented that can conformally attach to the skin and have demonstrated their ability to measure hydration in non-invasive manner. These sensors use miniaturized electrodes to achieve performance that is comparable to CMM. More importantly, these hydration sensors provide improved simplicity and convenience in operation, making these sensors ideal alternatives to CMM. Sensor characterizations conducted under different frequencies and sensor geometry demonstrate excellent reliability, repeatability, and stability of these sensors in hydration measurements. These sensors can be readily integrated with wireless components to realize wireless hydration monitoring. In addition, by integrating with multiple sensing elements or using different sensing parameters (e.g. frequency, spacing), these sensors can be used in other biophysical and biomedical sensing applications.

References

[1] C. Blichmann and J. Serup, "Hydration studies on scaly hand eczema," *Contact Dermatitis*, 16: 155-159, 1987.

[2] M. Boguniewicz, et al., "A Multidisciplinary Approach to Evaluation and Treatment of Atopic Dermatitis," *Seminars in Cutaneous Medicine and Surgery*, 27: 115-127, 2008.

[3] V. M. Sharma, et al., "Influence of heat-stress induced dehydration on mental functions," *Ergonomics*, 29: 791-9, 1986.

[4] S. M. Kleiner, "Water: An Essential But Overlooked Nutrient," *Journal of the American Dietetic Association*, 99: 200-206, 1999.

[5] T. Frodin, et al., "Hydration of human stratum corneum studied in vivo by optothermal infrared spectrometry, electrical capacitance measurement, and evaporimetry," *Acta Derm Venereol*, 68: 461-7, 1988.

[6] H. Tagami, et al., "Evaluation of the Skin Surface Hydration in Vivo by Electrical Measurement," *J Investig Dermatol*, 75: 500-507, 1980.

[7] M. Paye, et al., "Corneometiy measurements to evaluate skin dryness in the modified soap chamber test*," *Skin Research and Technology*, 1: 123-127, 1995.

[8] H. Dobrev, "Use of Cutometer to assess epidermal hydration," Skin *Research and Technology*, 6: 239-244, 2000.

[9] F. M. Hendriks, et al., "Influence of hydration and experimental length scale on the mechanical response of human skin in vivo, using optical coherence tomography," *Skin Research and Technology*, 10: 231-241, 2004.

[11] E. M. Attas, et al., "Near-IR spectroscopic imaging for skin hydration: The long and the short of it," *Biopolymers*, 67: 96-106, 2002.

[12] F. Kadlec, et al., "Assessing skin hydration status in haemodialysis patients using terahertz spectroscopy: a pilot/feasibility study," *Physics in Medicine and Biology*, 53: 7063, 2008.

[13] S. I. Alekseev, et al., "Millimeter wave reflectivity used for measurement of skin hydration with different moisturizers," *Skin Res Technol*, 14: 390-6, 2008.

[14] E. Alanen, et al., "Measurement of hydration in the stratum corneum with the MoistureMeter and comparison with the Corneometer," *Skin Research and Technology*, 10: 32-37, 2004.

[15] J. W. Fluhr, et al., "Comparative study of five instruments measuring stratum corneum hydration (Corneometer CM 820 and CM 825, Skicon 200, Nova DPM 9003, DermaLab). Part I. In vitro," *Skin Research and Technology*, 5: 161-170, 1999.

[16] A. O. Barel and P. Clarys, "In vitro calibration of the capacitance method (Corneometer CM 825) and conductance method (Skicon-200) for the evaluation of the hydration state of the skin," *Skin Research and Technology*, 3: 107-113, 1997.

[17] P. Clarys, et al., "Non-invasive electrical measurements for the evaluation of the hydration state of the skin: comparison between three conventional instruments—the Comeometer®, the Skicon® and the Nova DPW®," *Skin Research and Technology*, 5: 14-20, 1999.

[18] D.-H. Kim, et al., "Epidermal Electronics," *Science*, 333: 838-843, 2011.

[19] J. R. Matthie, "Bioimpedance measurements of human body composition: critical analysis and outlook," *Expert Rev Med Devices*, 5: 239-61, 2008.

[20] A. Guimerà, et al., "Method and device for bio-impedance measurement with hard-tissue applications," *Physiological Measurement*, 29:S279, 2008.

[21] S. H. Hamed, et al., "Construction, in vitro and in vivo evaluation of an in-house conductance meter for measurement of skin hydration," *Medical Engineering & Physics*.

[22] Ø. G. Martinsen, et al., "Measuring depth depends on frequency in electrical skin impedance measurements," *Skin Research and Technology*, 5: 179-181, 1999.

EXAMPLE 9

Direct and Conformal Lamination of Multifunctional Electronics on Skin for Long-Term Health Monitoring Fabrication and mounting of skin-like electronics: The multifunctional, skin-like electronics incorporates filamentary serpentine (FS) shaped sensing components such as electrophysiological (EP)-, strain-, and temperature sensors (FIG. 112A, detail layout in FIG. 116A). Gold (Au) EP sensors integrate measurement, ground and reference electrodes together for EP recording on skin, while strain and temperature sensors are based on silicon nanomembrane and platinum, respectively. The FS shapes of the skin-like electronics are designed to ensure the mechanical stability upon skin motion of stretching and compression to which the device is attached.

Fabrication of the skin-like sensor begins with high temperature diffusion doping of silicon (Si) nano-ribbons (260 nm in thickness) on a silicon-on-insulator wafer. The doped nano-ribbons are transfer-printed on a polyimide (PI) coated handling wafer. The remaining fabrication processes on a Si wafer follow conventional microelectronic techniques. Photolithography and dry etching process isolate the active region of nano-ribbons, to construct a silicon nano-membrane-strain sensor. A temperature sensor made of platinum (Pt, 40 nm in thickness) is prepared through electron-beam evaporation. Au-EP sensors including measurement (MEA), ground (GND), and reference (REF) electrodes and contact electrical pads are defined by photolithography after metallization, to complete the multifunctional device on a handling Si wafer (FIG. 112A). The completed device is immersed in acetone to dissolve a sacrificial photoresist layer on the wafer. The released electronics from the wafer are picked up by an elastomeric stamp (FIG. 112B). Afterwards, the electronics on the stamp is directly transfer-printed onto the skin using a thin glue layer (~200 nm) of spray-on-bandage ("liquid bandage"; in this example Nexcare™) as shown in FIG. 112C. Finally, the electronics on the skin is covered by multiple layers (in this example: four) of spray bandages ("liquid bandages") to ensure long-term wearability (FIG. 112D).

Long-term wearability and adhesion force. As discussed above (see, e.g., Example 7), and in [1], an epidermal electronic device can be mounted on skin with van der Waals force alone. That method provides robust adhesion of the light weight, ultrathin device on the skin. However, the use of the epidermal device is limited for long-term (seven days) wearing because the thin, skin-like membrane can be damaged or peeled off with hand contact, fluid contact such as from showering, bathing or sweating, or physical abrasion arising from exercise and other day-to-day activity. For long-term use of the skin-like electronics, this example provides a new method that utilizes commercial skin products such as medical spray bandage, thin medical dressing, or silicone tapes. The advantages of these medical products lie on their pre-approved ingredients for skin application and proven characteristics such as water proof and breathability, which are crucial factors for long-term use on skin.

We exploit spray-type liquid bandages (Walgreen® and Nexcare™) that provide a thin shielding layer on skin along with breathability and waterproof protection. After direct mounting of electronics on skin, Walgreen spray bandage made first coating layer, then Nexcare bandage was sprayed over the first layer. Through sequential repetition, a total of four layers shield the electronics on skin for long-term wearability. The reason for use of two products is to take advantage of their unique properties; Walgreen spray bandage provides more robust coating layer, while Nexcare has better water proofing characteristics. The sprayed shielding layer on skin was measured to be about 1.1±0.3 µm in thickness (n=3). The assessment of the thickness and roughness is conducted by using a surface profilometer (Dektak) and atomic force microscopy (AFM; Asylum) as shown in FIG. 113A. This ultrathin polymer layer ensures conformal coverage on curvy, wavy skin surface since the amplitudes of the skin are about 15 to 100 µm and the feature sizes are about 40 to 1000 µm [2, 3].

The medical spray bandage is a polymer dissolved in solvents. Thus, when it is sprayed on skin, solvents are evaporated, such that it forms a thin polymer layer sheet on skin. The major ingredient of the spray bandage is Hexamethyldisiloxane, which is a solvent. Among other ingredients, acrylate terpolymer forms the transparent polymer on skin and polyphenylmethylsiloxane provides water proof characteristics. The schematic illustration in FIG. 113B represents the characteristics of the spray-on-bandage when it covers the electronics on the skin. The breathable polymer layer allows oxygen onto the skin, penetration of moisture out of the membrane, and blocks water, dirt and other particles. Referring to FIG. 113B, the flexible and stretchable electronic circuit 900 is mounted to skin 910, optionally by a contact layer 930 that may be a spray or liquid bandage. After mounting, spray or liquid bandage is used as a cover layer 920 to cover the flexible and stretchable electronic circuit from surrounding environment. For comfort and to minimize adverse biological event to the skin, layers 920 and 930 are preferably a commercially-approved spray or liquid bandage approved for biological use. In this embodiment, the electronic circuit 900 comprises an array of sensors or actuators 901 that are interconnected by serpentine interconnects 902. The cover layer 920 may be applied in multiple layers. In an aspect, at least one of the cover layers is chemically or materially different than another cover layer. Such a cover layer configuration is referred herein as a "composite" cover layer and is advantageous for tailoring functional attributes of the cover layer to the application of interest (e.g., waterproofing, heat resistance, chemical resistance, durability, coloring, and the like) via independent selection and ordering of the layers.

For demonstration of long-term wearability, some of skin-like electronic devices are mounted on a subject's forearm and chest with the coverage of spray bandages (FIG. 113C). The wearing test for a week with five volunteers (age: 21~32) showed good wearability and robustness against motions, water and sweat from normal life without damaging or fracturing the electronics. Note that a subject sprayed Walgreen bandage on the device once a day before going to bed.

For quantitative study of the bandage robustness, adhesion forces of various materials on skin were measured by using a digital force meter (WeiHeng). Following the similar measurement setup of the reported study [4], adhesion forces of skin-like membranes, spray bandage and typical medical dressing are measured on a subject's forearm (FIG. 113D). Low modulus, skin-like membranes (Ecoflex, Solaris; Smooth-On) have an adhesive force less than 0.4 N at the fixed area (9 cm$^2$) on the skin. The spray-on-bandage (liquid bandage) showed a much higher adhesion force (0.98 N) than the skin-like membrane (Ecoflex; 0.24 N) used in our previous study [1]. A typical medical dressing (Tegaderm, Nexcare) is selected for comparison because it is widely used in hospitals and known to stay on the skin more than a week. When the adhesion force of spray bandage is compared to that of Tegaderm, the force magnitude was very similar. Thus, this study illustrates that the spray-on-bandage has a strong binding force to keep the electronics on the skin for long time. It should be noted that the adhesion force of Tegaderm with this measurement setup was consistent with the reported value [4]. The measured Young's modulus of the spray-on-bandage is 84.5 MPa and the elongation is 131%. Even though the modulus shows a larger value than the modulus range of epidermis (140~600 kPa), the spray-on-bandage only imposed little constraints on skin motion in normal life (FIG. 112D). Compared to other medical bandages or tapes (GPa range of moduli) on skin, the spray-on-bandage does not show discomfort of wearability. In addition, the extreme elongation provides enough stretchability of the bandage without fracture upon skin motion. Note that our unique transfer printing technology allow the placement of the electronics on various commercial medical products such as micropore tape (3M), Tegaderm (Nexcare), and silicone medical tape (3M).

Conformability of skin-like electronics on skin: The skin-like electronic sensor is designed with FS layout to follow the skin morphology. The finite element modeling (FEM) computation is conducted to study the mechanical stability of the skin-like electronics. The study considered 30% stretching of electronics in x- and y-orientations since the strain on skin beyond 30% results in nonlinear and irreversible effects [5]. The total thickness of electronics is 0.8 µm from two layers of PI (0.3 µm) and silicon nanomembrane, Pt and Au layers (0.2 µm). The sensing components are placed in neutral mechanical plane (NMP) as shown in FIG. 114A. The FEM study of 10 µm-width FS electrode results in the maximum principal strain as 0.6%, which shows mechanical stability (fracture strain: 1%) of the electronics upon repeated motion and stretching of skin.

We also conduct quantitative mechanical study on the conformal contact of electronics on skin as the relationship between the width of FS electrode and the required adhesion force of a backing layer (FIG. 114B). The skin surface is modeled by a sinusoidal form, $y(x)=h_{rough}[1+\cos(2\pi x/\lambda_{rough})]/2$ with skin roughness amplitude ($h_{rough}$) and wavelength ($\lambda_{rough}$). Low bending stiffness from a thin, soft and compliant material provides conformal contact on the skin [6], which means that the thickness and modulus of the electronic device can change the conformability on the skin. In this mechanical study, the scaling law represented that as FS width increases, more adhesion force from a backing layer is required for conformal contact (FIG. 114B). Hence, assuming the same adhesion force from the same backing layer, the narrower FS electrode can show better conformal contact than that of wider FS electrode.

To demonstrate the relationship between the conformal contact and width of FS electrode, skin replicas are prepared by using commercial silicone products, Dragon Skin® (Smooth-On), and polydimethylsiloxane (PDMS, Dow Corning). First mold is made using Dragon skin-kit by curing it on a subject's forearm, particularly on a smooth and hairless surface. Based on the first mold, the second mold for a skin replica is fabricated with PDMS. Following the same skin-mounting process of electronics (FIG. 112), three types of FS-based electrodes are mounted on skin replicas, and they are investigated by scanning electron microscopy (SEM) as shown in FIG. 114C. For better SEM imaging of non-conductive silicone molds, the skin replicas with electronics are coated with 10 nm of palladium/gold. In the SEM images, electronics are colorized as gold for ease of viewing, while black background with various features and amplitudes represent the skin replica. The first pattern (500 µm-IS) is made of 500 µm²-square island and 100 µm-FS interconnects show that the big island and serpentines are not conformally mounted on the fine, skin geometry. When the second pattern (100 µm-FS) is used, it mostly followed the skin morphology, but could not entirely cover the deep creases and pits of the skin. It can be explained that the 100 µm-width is at the outer range of the fine skin amplitudes and feature sizes [2, 3] as described earlier. Thereafter, when the width of FS electrode is reduced 10-fold to 10 µm, the 10 µm-FS electrode demonstrates extreme conformal lamination on the skin.

With the 10 µm-FS shaped electronics, a quantitative study of the conformal adhesion on skin is conducted. The impedance between skin and electrode is measured using a pre-amplifier (James Long Co.) and compared with the conventional gel-based metal electrodes. For the impedance measurement, the applied frequency and amplitude of the sinusoidal inputs are 37 Hz and 0.5 $V_{rms}$ (root-mean-square voltage). As shown in FIG. 114D, even with about 20% areal contact coverage of FS-patterns, it showed the similar impedance value of ~50 kΩ as the conductive-gel based electrodes (~56 kΩ). It can be simply explained considering that the skin-like electronics can be conformally mounted on the skin unlike the conventional electrode that needs gels to compensate the geometry mismatch between the planar electrode and curvy skin (illustrations in FIG. 114D). As expected, the conventional rigid electrode without applying gels shows much higher impedance of ~180 kΩ than that with gels. Note that the dimension of each electrode for both skin-like device and conventional electrode is about 1 cm in diameter, and the three electrodes (measurement, ground, and reference) are placed sequentially with the interdistance of ~2.5 cm for the direct comparison with integrated EP sensors of a skin-device.

Releasable connector and wireless data acquisition: To measure and record physiological signals on skin, a commercial wireless data acquisition (DAQ) system is utilized (BioRadio 150, Cleveland Medical Devices; 2.4 GHz RF band, 100 feet light of sight transmission range). FIG. 115A shows the experimental setup that includes the skin-like electronics on a subject's forearm, a transmitter, a wireless receiver, and a laptop with data recording software. The portable transmitter acquires the signals from the skin-like electronics using a releasable, skin-like connector, and then amplifies, digitizes and transmits the signals to the USB receiver for real-time monitoring or recording. To avoid wearing many electrical wires on the sensors like the conventional rigid electrodes, a releasable, skin-like connector that is configured on a stretchable, skin-like membrane (500 µm-thick sheet; Solaris, Smooth-On) is provided. The stretchable connector on a thin membrane is fabricated by using the transfer-printing technology (FIG. 115B). The releasable connector is repeatedly contacted with the sensor through a simple, mount-release process. For the connection of the skin-sensor with the releasable connector, an epidermal pad is embedded onto the skin-like electronics (FIG. 115C). The releasable connector makes physical contact with the epidermal pads for data acquisition with the help of sticky membranes and van der Waals interaction between gold pads (FIG. 115D). With this class of data recording strategy, a subject can avoid wearing wires and attendant discomfort for long-term continuous measurement of signals.

Multifunctionality and long-term EP measurement: The skin-like electronics is compatible with a plurality of sensing elements and actuators as well as different types of sensors and actuators depending on the application of interest. In this example different sensors are used: EP sensor, temperature, and strain sensing gauges in the stretchable system for multimodal functionality. FIG. 116A shows the multifunctional electronic device that is encapsulated in top and bottom polymer (PI) layers, which locate the silicon nanomembrane, Pt and Au electrodes/serpentine interconnectors at NMP. For EP measurement, FS shaped Au electrodes including MEA, GND, and REF are configured into one passive-type device that does not include signal amplifiers or power supply on the device (FIG. 116A). The dry electrodes without conductive gels record EP signals on skin through direct electrode-skin contact. The GND electrode define the common zero potential when placed at the center between the MEA and REF electrodes (5 cm apart). The EP signal is recorded by the potential difference measured from the MEA and REF electrodes on skin. All measured signals are transmitted in a wireless system and analyzed in a commercial software (BioRadio 150, Cleveland Medical Devices) having data filters. The strain sensor to measure the mechanical motion on skin is made of ultra-thin sheet of silicon nanomembrane in a longitudinal direction. The rectangular nanomembrane sensor (width: 30 μm, length: 510 μm) is made by microfabrication and is anchored with Au-serpentine pads to record resistance change from the mechanical strain on skin (FIG. 116A). The gauge factor (GF) of this piezoresistor based on Si semiconductor is: $GF=(\Delta R/R_0)/\varepsilon$, where $\Delta R$ is the resistance change, $R_0$ is the initial state, and $\varepsilon$ is the strain deformation. Even though GF of single crystalline silicon is ~100, the GF of the skin-like electronics is measured to be 5 under uniaxial in-plane strain of 10%. It can be originated from the elastic mismatch between the nanomembrane resistor and the substrate. The temperature sensor made of Pt electrode has the meander or serpentine pattern for structure stability against mechanical stretching and for conformability on skin. The serpentine array composed of Ti/Pt is connected with Au pads for electrical connection and data acquisition, which read the resistance change according to the temperature variation. The width of serpentine is 10 μm. To calibrate the temperature sensor, the resistance ($\Omega$) change is recorded following the temperature change (° C.). The sensitivity of the sensor is ~1 $\Omega/°$ C., which shows good temperature reading as a resistor.

FIG. 116B demonstrates the multimodal measurements of electromyography (EMG), strain, and temperature signals on a forearm when a subject is bending his wrist. For EMG measurement, the skin-like electronics is mounted on a skeletal muscle on the front end of the interior side of a subject's left forearm. The subject repeated the bending and releasing motion of a wrist for 30 seconds. The differential voltage potential from the skeletal muscle is recorded after filtering the signal with 60 Hz notch filter. In the EMG graph, the high frequency triangle-shaped waveforms show the voltage amplitude from 500 pV to 1 mV. Upon the skin movement during wrist bending, the strain resistor in the sensor detects the strain change as voltage amplitude that reached to 334 mV. The recorded signal went through 60 Hz notch and bandpass (butterworth) filters for 60 seconds. In addition, the repetition of bending-releasing of a wrist causes the temperature change, which is detected by the temperature resistor for 60 seconds. The signal amplitude recorded through 60 Hz notch and lowpass (Bessel) filters. Even though the signal fluctuates, after 60 seconds ~0.001 mV difference is recorded, corresponding to a temperature increase of ~1° C.

For demonstration of long-term health monitoring using the skin-like electronics, electrocardiography (ECG) on chest and EMG on forearm are recorded for seven days. As shown in FIG. 116C, the skin-like devices showed high quality ECG over time on the subject's chest near the left side of the midline of the chest. The sampling frequency is 960 samples/seconds with 16 bit resolution. The 60 Hz notch filter is applied to eliminate the power line noise on the signal. The ECG signals reveal high quality data with information of all phases of heartbeats with QRS complex (insets in the graphs). The signal-to-noise ratios of those ECG signals are favorably comparable to the conventional gel-based electrode system. In addition, EMG signals are recorded on a subject's forearm through bending and releasing of a wrist for a week. The recorded muscle activity on forearm demonstrate consistent signal quality over time, even the frequency spectrum and recorded voltage amplitude are changed slightly. In the measurement, the sampling frequency and filters are the same as ECG measurement. Note that after a week wearing of the device, the device shows consistent ECG signals even though the background noise increases slightly, which may be caused by accumulated dead cells on the skin surface.

FIG. 116D demonstrates the skin irritation test for a week with the skin-like electronics on a subject's forearm and chest. As photos show the skin conditions before mounting and after removal of electronics, there are no negative influence on skin such as itching, allergy or erythema.

The multifunctional electronics that are directly and conformally mounted on skin introduce a new class of 'skin-like' electronic system for long-term health monitoring. The spray-on-bandage that cover the electronics make a breathable, water proof shielding layer on skin without noticeable constraints in motion. The quantitative mechanical study supports a 10 μm-width serpentine design for extreme conformability and high quality EP recording without use of conductive gels. A skin-like, releasable connector in conjunction with a wireless DAQ system can benefit wearing of a skin-like device with high quality data acquisition on the skin. When this multifunctional electronics is integrated with fully embedded wireless communication system, this class of technology as an 'instrumented' medical patch can enable ubiquitous, long-term wearable health monitoring system at home settings.

References

1. Kim, D. H.; Lu, N. S.; Ma, R.; Kim, Y. S.; Kim, R. H.; Wang, S. D.; Wu, J.; Won, S. M.; Tao, H.; Islam, A.; Yu, K. J.; Kim, T. I.; Chowdhury, R.; Ying, M.; Xu, L. Z.; Li, M.; Chung, H. J.; Keum, H.; McCormick, M.; Liu, P.; Zhang, Y. W.; Omenetto, F. G.; Huang, Y. G.; Coleman, T.; Rogers, J. A., *Science* 2011, 333 (6044), 838-843. DOI DOI 10.1126/science.1206157.

2. Tchvialeva, L.; Zeng, H.; Markhvida, I.; D., M.; Lui, H.; Lee, T., *New Developments in Biomedical Engineering* 2010.

3. Wilhelm, K. P.; Elsner, P.; Berardesca, E., *Bioengineering of the Skin: Skin Surface Imaging and Analysis.* CRC: Boca Raton, 1997.

4. Klode, J.; Schottler, L.; Stoffels, I.; Korber, A.; Schadendorf, D.; Dissemond, J., *J Eur Acad Dermatol* 2011, 25 (8), 933-939. DOI DOI 10.1111/j.1468-3083.2010.03886.x.

5. Arumugam, V.; Naresh, M. D.; Sanjeevi, R., *J Bioscience* 1994, 19 (3), 307-313.

6. Wang, S. D.; Li, M.; Wu, J.; Kim, D. H.; Lu, N. S.; Su, Y. W.; Kang, Z.; Huang, Y. G.; Rogers, J. A., *J Appl Mech-T Asme* 2012, 79 (3). DOI Artn 031022
Doi 10.1115/1.4005963.

STATEMENTS REGARDING INCORPORATION BY REFERENCE AND VARIATIONS

All references cited throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The following references relate generally to flexible and/or stretchable electronic devices, systems and related methods for biomedical applications, and are hereby incorporated by reference to the extent not inconsistent with the disclosure herein: (1) U.S. patent application Ser. No. 12/968,637, filed on Dec. 15, 2010, (2) PCT International Patent Application No. PCT/US10/60425, filed on Dec. 15, 2010, (3) U.S. patent application Ser. No. 12/892,001, Sep. 28, 2010, (4) PCT International Patent Application No. PCT/US10/50468, Sep. 28, 2010; (5) U.S. patent application Ser No. 12/916,282 and PCT App. PCT/US12/40482, both filed Jun. 1, 2012.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

When a group of substituents is disclosed herein, it is understood that all individual members of that group and all subgroups, including any isomers, enantiomers, and diastereomers of the group members, are disclosed separately. When a Markush group or other grouping is used herein, all individual members of the group and all combinations and subcombinations possible of the group are intended to be individually included in the disclosure. When a compound is described herein such that a particular isomer, enantiomer or diastereomer of the compound is not specified, for example, in a formula or in a chemical name, that description is intended to include each isomers and enantiomer of the compound described individual or in any combination. Additionally, unless otherwise specified, all isotopic variants of compounds disclosed herein are intended to be encompassed by the disclosure. For example, it will be understood that any one or more hydrogens in a molecule disclosed can be replaced with deuterium or tritium. Isotopic variants of a molecule are generally useful as standards in assays for the molecule and in chemical and biological research related to the molecule or its use. Methods for making such isotopic variants are known in the art. Specific names of compounds are intended to be exemplary, as it is known that one of ordinary skill in the art can name the same compounds differently.

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably. The expression "of any of claims XX-YY" (wherein XX and YY refer to claim numbers) is intended to provide a multiple dependent claim in the alternative form, and in some embodiments is interchangeable with the expression "as in any one of claims XX-YY."

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. Nothing herein is to be construed as an admission that the invention is not entitled to antedate such disclosure by virtue of prior invention.

Whenever a range is given in the specification, for example, a temperature range, a time range, or a composition or concentration range, all intermediate ranges and subranges, as well as all individual values included in the ranges given are intended to be included in the disclosure. As used herein, ranges specifically include the values provided as endpoint values of the range. For example, a range of 1 to 100 specifically includes the end point values of 1 and 100. It will be understood that any subranges or individual values in a range or subrange that are included in the description herein can be excluded from the claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

We claim:

1. A device for establishing an interface with a skin of a subject, the device comprising:
   a flexible substrate having an effective Young's modulus less than or equal to 10 MPa;
   a flexible electronic circuit supported by the flexible substrate, wherein the flexible electronic circuit comprises a plurality of electrophysiological sensors provided in an array; wherein each of said electrophysiological sensors independently comprises an inorganic thin film layer, an electrode thin film layer or a combination of these; including one or more inorganic semiconductor circuit elements or electrodes, or a combination of inorganic semiconductor circuit elements and electrodes, wherein the plurality of electrophysiological sensors are connected with filamentary serpentine wires; and a barrier layer encapsulating at least a portion of the flexible electronic circuit; wherein said barrier layer is a multilayer structure comprising a plurality of polymer layers; wherein said barrier layer provides an electrical, physical, chemical, and thermal barrier;

said device having a multilayer geometry wherein said flexible substrate, said flexible electronic circuit and said barrier layer are provided as a series of stacked layers wherein said flexible electronic circuit is provided between said flexible substrate and said barrier layer;

wherein the flexible substrate, barrier layer and the electronic circuit provide a net bending stiffness less than or equal to $1 \times 10^8$ GPa $\mu m^4$ so as to allow for conformal contact to be established with the skin of the subject.

2. The device of claim 1, wherein the device is a skin mountable tissue sensor, a skin mountable tissue actuator, or an array of skin mountable tissue sensors or skin mountable tissue actuators.

3. The device of claim 1, wherein the device does not include an adhesive layer between the skin of the subject and the flexible electronic circuit.

4. The device of claim 1, wherein the device has an effective Young's modulus and a thickness within a factor of 2 of a modulus and a thickness of an epidermal layer of the skin of the subject at the interface during use.

5. The device of claim 1, wherein the device has an effective Young's modulus less than or equal to 500 kPa.

6. The device of claim 1, wherein the device has an effective Young's modulus equal to or less than 50 times an effective Young's modulus of the skin of the subject at the interface during use.

7. The device of claim 1, wherein the device has an average thickness less than or equal to 500 microns.

8. The device of claim 1, wherein the device has a net bending stiffness that is less than or equal to 1 nN m.

9. The device of claim 1, wherein the device has an areal mass density less than or equal to 10 mg $cm^{-2}$.

10. The device of claim 1, wherein the flexible substrate is a low modulus polymer.

11. The device of claim 1, wherein the flexible substrate effective Young's modulus is less than or equal to 500 kPa.

12. The device of claim 1, wherein the flexible substrate is a low modulus rubber material or a low modulus silicone material.

13. The device of claim 1, wherein the flexible substrate is a bioinert or biocompatible material.

14. The device of claim 1, wherein the flexible substrate comprises a gas-permeable elastomeric sheet.

15. The device of claim 1, wherein the flexible electronic circuit comprises one or more electrodes transistors, inducers, LEDs, capacitors, oscillators, photodiodes, diodes or any combinations of these.

16. The device of claim 1, wherein the flexible electronic circuit comprises one or more amplifiers, strain gauges, temperature sensors, wireless power coils, solar cells, inductive coils, high frequency inductors, high frequency capacitors, high frequency oscillators, high frequency antennae, multiplex circuits, electrocardiography sensors, electromyography sensors, electroencephalography sensors, electrophysiological sensors, thermistors, transistors, diodes, resistors, capacitive sensors, light emitting diodes, or any combinations of these.

17. The device of claim 1, wherein the flexible electronic circuit has an average thickness less than or equal to 100 microns.

18. The device of claim 1, wherein the flexible electronic circuit comprises one or more single crystalline inorganic semiconductor structures.

19. The device of claim 1, wherein the flexible electronic circuit is positioned within 10 μm of a neutral mechanical plane of the device.

20. The device of claim 1, wherein the flexible electronic circuit comprises a plurality of stretchable electronic devices or device components.

21. The device of claim 20, wherein the flexible electronic circuit comprises one or more electronic devices or device components having a curved, serpentine, bent, wavy or buckled geometry.

22. The device of claim 21, wherein the flexible electronic circuit comprises one or more electronic devices or device components comprising structures having a curved geometry, wherein the one or more electronic devices or device components exhibit one or more curves positioned within a plane parallel to a receiving surface of the flexible substrate supporting the flexible electronic circuit.

23. The device of claim 21, wherein the flexible electronic circuit comprises one or more electronic devices or device components having the wavy geometry comprising structures characterized by a plurality of maxima and minima, wherein the maxima and minima are positioned within a plane parallel to a receiving surface of the flexible substrate supporting the flexible electronic circuit.

24. The device of claim 21, wherein the flexible electronic circuit comprises one or more nanoribbons, micromembranes or nanomembranes.

25. The device of claim 24, wherein the nanoribbons, micromembranes or nanomembranes are provided in a wavy geometry characterized by a plurality of maxima and minima.

26. The device of claim 25, wherein adjacent maxima and minima of the wavy geometry are separated by a distance less than or equal to 10 microns.

27. The device of claim 25, wherein the wavy geometry is characterized by a periodic structure.

28. The device of claim 25, wherein the wavy geometry is characterized by an amplitude of less than 10 microns.

29. The device of claim 25, wherein the wavy geometry is characterized by a radius of curvature less than or equal to 1 mm.

30. The device of claim 25, wherein the wavy geometry is a serpentine geometry.

31. The device of claim 30, wherein the serpentine geometry is characterized by a repeating s-shaped feature.

32. The device of claim 24, wherein local displacement of the nanoribbons, micromembranes or nanomembranes within a plane parallel to the receiving surface of the flexible substrate supporting the flexible electronic circuit reduces an overall state of strain of the device.

33. The device of claim 24, wherein the nanoribbons, micromembranes or nanomembranes comprise metallic structures, single crystalline semiconductor structures, or hybrid structures comprising one or more metallic structures connected to one or more single crystalline semiconductor structures.

34. The device of claim 1, wherein the flexible electronic circuit comprises one or more island and bridge structures.

35. The device of claim 34, wherein the island structures comprise one or more semiconductor circuit elements.

36. The device of claim 34, wherein the bridge structures comprise one or more flexible electrical interconnections.

37. The device of claim 1, wherein the flexible electronic circuit is assembled on the flexible substrate via contact printing.

38. The device of claim 1, further comprising a transfer substrate supporting the flexible substrate, the flexible electronic circuit, or both the flexible substrate and the flexible electronic circuit.

39. The device of claim 38, wherein the transfer substrate is in physical contact with the flexible substrate.

40. The device of claim 38, wherein the transfer substrate is a removable substrate and wherein the transfer substrate is configured to be partially or completely removed upon providing the device in contact with the skin of the subject or a dissolvable substrate and wherein the transfer substrate is configured to be partially or completely dissolved after the device is provided in contact with the skin of the subject.

41. The device of claim 38, wherein the transfer substrate is a polymer or polyvinyl acetate.

42. The device of claim 1, wherein the flexible substrate, the electronic circuit and the barrier layer provide a net flexural rigidity of the device less than or equal to $1 \times 10^{-4}$ N m.

43. The device of claim 1, wherein the barrier layer further comprises a material selected from the group consisting of: an inorganic polymer, an organic polymer, an elastomer, a biopolymer, a ceramic, and any combination of these.

44. The device of claim 1, wherein the barrier layer comprises an elastomer.

45. The device of claim 1, wherein the barrier layer comprises PDMS, polyimide, SU-8, parylene, parylene C, silicon carbide (SiC), or $Si_3N_4$.

46. The device of claim 1, wherein the barrier layer is a biocompatible material or a bioinert material.

47. The device of claim 1 that is a hydration sensor, wherein the flexible electronic circuit comprises a plurality of electrodes for determining impedance of underlying skin of a subject.

48. The device of claim 47, wherein the plurality of electrodes is selected from the group consisting of: meander electrodes; interdigitated electrodes, circular electrodes and annular electrodes.

49. The device of claim 47, further comprising sensing electrodes configured to be in contact with skin and reference electrodes embedded in said flexible substrate.

50. The device of claim 47, wherein said hydration sensor maps hydration level over a surface area, maps hydration level as a function of depth from skin surface, or maps hydration level over both a surface area and depth.

51. The device of claim 50, wherein said hydration level map is generated for a depth that is up to about 60 to 100 micrometers from the skin surface.

52. The device of claim 1, wherein the flexible substrate, the barrier layer and the electronic circuit provide said net bending stiffness, an average thickness, an effective Young's modulus, and an areal mass density that are matched to the epidermal layer during use.

53. The device of claim 1, wherein the flexible substrate, barrier layer and the electronic circuit provide a net bending stiffness less than 1 nN m, average thickness less than or equal to 500 microns, average Young's modulus less 150 kPa, and areal mass density less than 3.8 mg $cm^{-2}$.

54. The device of claim 1, wherein said substrate is additionally stretchable.

55. The device of claim 1, wherein said electronic circuit is additionally stretchable.

56. The device of claim 1, wherein said substrate is stretchable and said electronic circuit is additionally stretchable.

57. The device of claim 1, wherein said barrier layer has a thermal conductivity of 0.3 W/m·K or less.

58. The device of claim 1, wherein said barrier layer limits leakage current from the electronic device to the tissue to amount equal to or less than 0.1 µA/$cm^2$.

* * * * *